US011384060B2

(12) United States Patent
Chung et al.

(10) Patent No.: US 11,384,060 B2
(45) Date of Patent: *Jul. 12, 2022

(54) AMIDE COMPOUNDS AND USE THEREOF

(71) Applicant: ALPHALA CO., LTD., Taipei (TW)

(72) Inventors: Cheng-Ho Chung, Taipei (TW);
Shi-Liang Tseng, Taipei (TW);
Yung-Ning Yang, Taipei (TW); Yen-Fu Chen, Taipei (TW)

(73) Assignee: ALPHALA CO., LTD., Taipei (TW)

( * ) Notice: Subject to any disclaimer, the term of this patent is extended or adjusted under 35 U.S.C. 154(b) by 7 days.

This patent is subject to a terminal disclaimer.

(21) Appl. No.: 16/477,072

(22) PCT Filed: Jan. 22, 2018

(86) PCT No.: PCT/US2018/014632
§ 371 (c)(1),
(2) Date: Jul. 10, 2019

(87) PCT Pub. No.: WO2018/140339
PCT Pub. Date: Aug. 2, 2018

(65) Prior Publication Data
US 2019/0337915 A1 Nov. 7, 2019

Related U.S. Application Data

(60) Provisional application No. 62/449,620, filed on Jan. 24, 2017.

(51) Int. Cl.
*C07D 233/92* (2006.01)
*C07D 257/04* (2006.01)
*C07D 277/66* (2006.01)
*C07D 471/04* (2006.01)
*C07D 417/04* (2006.01)
*C07D 307/81* (2006.01)
*C07D 405/04* (2006.01)
*C07D 405/12* (2006.01)
*C07D 405/14* (2006.01)
(Continued)

(52) U.S. Cl.
CPC ............. *C07D 307/79* (2013.01); *A61P 3/10* (2018.01); *C07C 233/92* (2013.01); *C07D 209/08* (2013.01); *C07D 213/56* (2013.01); *C07D 213/90* (2013.01); *C07D 231/18* (2013.01); *C07D 237/14* (2013.01); *C07D 239/34* (2013.01); *C07D 257/04* (2013.01); *C07D 263/57* (2013.01); *C07D 271/06* (2013.01); *C07D 271/07* (2013.01); *C07D 271/10* (2013.01); *C07D 271/113* (2013.01); *C07D 277/66* (2013.01); *C07D 307/81* (2013.01); *C07D 333/60* (2013.01); *C07D 401/04* (2013.01); *C07D 401/12* (2013.01); *C07D 403/04* (2013.01); *C07D 405/04* (2013.01); *C07D 405/12* (2013.01); *C07D 405/14* (2013.01); *C07D 413/04* (2013.01); *C07D 413/12* (2013.01); *C07D 417/04* (2013.01); *C07D 471/04* (2013.01); *C07D 491/04* (2013.01)

(58) Field of Classification Search
CPC .. C07C 233/92; C07D 257/04; C07D 277/66; C07D 471/04; C07D 417/04; C07D 307/81; C07D 405/04; C07D 405/12; C07D 405/14; C07D 413/04; C07D 413/12; C07D 263/57; C07D 213/56; C07D 491/04; C07D 271/06; C07D 271/10; C07D 271/113; C07D 401/04; C07D 401/12; C07D 231/18; C07D 403/04; C07D 239/34; C07D 237/14; C07D 333/60; A61K 31/16; A61K 31/395; A61K 31/41; A61P 3/10
See application file for complete search history.

(56) References Cited

U.S. PATENT DOCUMENTS 8,309,580 B2 * 11/2012 Banno .................. C07D 405/14
514/336
8,436,043 B2 * 5/2013 Banno .................. C07D 405/12
514/469
(Continued)

OTHER PUBLICATIONS

Cecil Textbook of Medicine, edited by Bennet, J.C., and Plum F., 20th edition, vol. 1, 1004-101 O, 1996.*
(Continued)

*Primary Examiner* — Laura L Stockton
(74) *Attorney, Agent, or Firm* — Bacon & Thomas, PLLC

(57) ABSTRACT

Disclosed are compounds of formula (I) below and pharmaceutically acceptable salts thereof: (I), in which each of variables $R_1$, $R_2$, $R_3$, $R_4$, $R_5$, $A_1$, $A_2$, $A_3$, $A_4$, X and Y is defined herein. Also disclosed are methods for reducing the glycemic level and treating glucagon-associated disorders with a compound of formula (I) or a salt thereof and a pharmaceutical composition containing same.

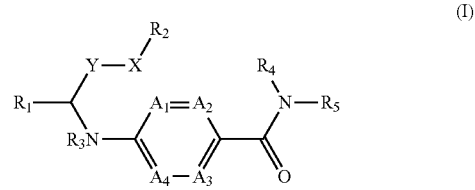

(I)

10 Claims, No Drawings

| (51) | Int. Cl. | |
|---|---|---|
| | *C07D 413/04* | (2006.01) |
| | *C07D 413/12* | (2006.01) |
| | *C07D 263/57* | (2006.01) |
| | *C07D 213/56* | (2006.01) |
| | *C07D 491/04* | (2006.01) |
| | *C07D 271/06* | (2006.01) |
| | *C07D 271/10* | (2006.01) |
| | *C07D 271/113* | (2006.01) |
| | *C07D 401/04* | (2006.01) |
| | *C07D 401/12* | (2006.01) |
| | *C07D 231/18* | (2006.01) |
| | *C07D 403/04* | (2006.01) |
| | *C07D 239/34* | (2006.01) |
| | *C07D 237/14* | (2006.01) |
| | *C07D 333/60* | (2006.01) |
| | *A61P 3/10* | (2006.01) |
| | *C07D 307/79* | (2006.01) |
| | *C07C 233/92* | (2006.01) |
| | *C07D 209/08* | (2006.01) |
| | *C07D 213/90* | (2006.01) |
| | *C07D 271/07* | (2006.01) |

(56) References Cited

U.S. PATENT DOCUMENTS 8,710,236 B2 * 4/2014 Gomez-Galeno ......... A61P 9/00
548/224
2002/0061870 A1 5/2002 Pearson et al.
2004/0197380 A1 10/2004 Wolf et al.
2005/0009892 A1 1/2005 Kuwabara et al.

OTHER PUBLICATIONS

Freshney et al., Culture of Animal Cells, A Manual of Basic Technique, Alan R. Liss, Inc., 1983, New York, p. 4.*
Dermer et al., Bio/Technology, 1994, 12:320.*
Bruno et al., Expert Opinion Emerging Drugs, (2005), 10(4), pp. 747-771. (Year: 2005).*
Park, Diabetes Research and Clinical Practice 66S (2004), S33-S35. (Year: 2004).*
Curtis et al., The Journal of the American Board of Family Practice, vol. 18, pp. 37-43, (2005). (Year: 2005).*
Colagiuri et al., American Journal of Public Health, Sep. 2006, vol. 96, No. 9, pp. 1562-1569. (Year: 2006).*
Gupta et al., American Journal of Alzheimer's Disease & Other Dementias, vol. 35, pp. 1-17, 2020. (Year: 2020).*

* cited by examiner

AMIDE COMPOUNDS AND USE THEREOF

This application claims the benefit of filing date of U.S. Provisional Application Ser. No. 62/449,620, filed Jan. 24, 2017, which is hereby incorporated by reference.

FIELD OF THE DISCLOSURE

The present disclosure relates to compounds that act as antagonists or inverse agonists of the glucagon receptor, pharmaceutical compositions comprising the compounds, and the uses of the compounds or compositions.

BACKGROUND

Diabetes is a major public health issue and affects millions of people in the world. The two major hormones, insulin and glucagon, which regulate blood sugar homeostasis, play important roles in diabetes. The glucagon is secreted by pancreatic alpha cells and can stimulate glycogenolysis and gluconeogenesis. Moreover, the glucagon signaling might also affect lipid metabolism, food intake, cardiovascular system and adipose tissue mass. The antagonism of glucagon signaling has been pursued as a potential therapy for diabetes for a long time. Many of them were done through interfering the receptor-ligand binding. The glucagon receptor is a class B G-protein coupled receptor and is mainly expressed in liver and less in other tissues.

Antagonism of glucagon receptor by small molecules reduces the downstream secondary messengers including cAMP and calcium ion which lead to gluconeogenic genes expression and subsequent blood sugar elevation. Glucagon receptor –/– mice exhibit resistance to diet-induced obesity and streptozotocin-induced diabetes. Currently several small molecules glucagon receptor antagonists have entered clinical trials and showed significant blood sugar reduction versus placebo. Glucagon receptor antagonism also may have benefit in cardiovascular disease through cardiomyocytes protection. In glucagon receptor inactivated mouse model, animals showed higher survival rate and lower heart failure after myocardial infarction.

There is a need to develop new glucagon receptor modulators that have fewer and less deterious side effects for therapeutic use.

SUMMARY

The present disclosure relates to certain amide compounds as glucagon receptor modulators for treating glucagon-associated disorders. Unexpectedly, these compounds, acting as antagonists or inverse agonists of the glucagon receptor, produce higher efficacy in modulating the glucagon receptor for reducing the glycemic level, as compared to known therapeutic agents.

An aspect of this disclosure is drawn to the compounds of formula (I) below and pharmaceutically acceptable salts thereof:

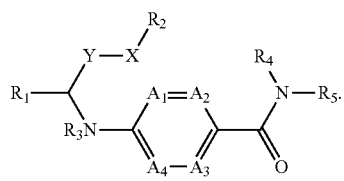

(I)

In this formula, each of $A_1$, $A_2$, $A_3$ and $A_4$ independently is $CR_6$ or N, with the proviso that no more than two of $A_1$, $A_2$, $A_3$, and $A_4$ are N. X is —$CH_2$—, —NH—, —O—, —S— or a direct bond. Y is —(C=O)—, —$CH_2$— or a direct bond. $R_1$ is $C_{1-6}$ alkyl, $C_{1-6}$ alkoxy, aryl, heteroaryl, $C_{3-12}$ cycloalkyl, $C_{1-12}$ heterocycloalkyl, or —($C_{1-6}$ alkyl)-($C_{3-12}$ Cycloalkyl); the $C_{1-6}$ alkyl being optionally substituted with one to three moieties selected from the group consisting of halo, hydroxyl, $C_{1-6}$ alkoxy, aryl and heteroaryl; each of the $C_{1-6}$ alkoxy, aryl, heteroaryl, $C_{3-12}$ cycloalkyl, and $C_{1-12}$ hetarocycloalkyl being optionally substituted with one to three moieties selected from the group consisting of halo, aryl, $C_{1-6}$ alkyl optionally substituted with one to three halo and $C_{1-6}$ alkoxy optionally substituted with one to three halo; the heteroaryl being optionally fused with one aryl moiety; and the aryl being optionally substituted with heteroaryl or heteroaryl fused with one aryl moiety. $R_2$ is $C_{1-6}$ alkyl,

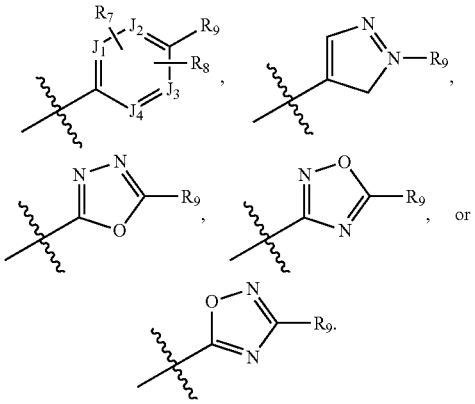

$R_3$ is H, methyl or ethyl. $R_4$ is H, $C_{1-6}$ alkyl, or $C_{1-6}$ alkoxy, each of the $C_{1-6}$ alkyl and $C_{1-6}$ alkoxy being optionally substituted with one to three halo. $R_5$ is tetrazolyl, —$CH_2$-tetrazolyl, —$CH_2CH_2CO_2R_{10}$, —$CH_2CH(OH)CO_2H$, or —$(CH_2)_2SO_3H$. $R_6$ is H, halo, $C_{1-6}$ alkyl, or $C_{1-6}$ alkoxy, each of the $C_{1-6}$ alkyl and $C_{1-6}$ alkoxy being optionally substituted with one to three halo. $R_7$ is H, halo, $C_{1-6}$ alkyl or $C_{1-6}$ alkoxy. $R_8$ is H, halo, $C_{1-6}$ alkyl or $C_{1-6}$ alkoxy. $R_9$ is H, halo, $C_{1-6}$ alkyl, $C_{1-6}$ alkoxy, $C_{3-12}$ cycloalkyl, aryl or heteroaryl; the $C_{1-6}$ alkyl being optionally substituted with one to three halo; each of the $C_{1-6}$ alkoxy, $C_{3-12}$ cycloalkyl, aryl and heteroaryl being optionally substituted with one to three moiety selected from the group consisting of halo, aryl, $C_{1-6}$ alkyl optionally substituted with one to three halo, $C_{1-6}$ alkoxy optionally substituted with one to three halo, amino, and CN; and the heteroaryl being optionally fused with one aryl moiety or one heteroaryl moiety. $R_{10}$ is H or $C_{1-6}$ alkyl. And, each of $J_1$, $J_2$, $J_3$, $J_4$ independently is C or N, with the proviso that no more than two of $J_1$, $J_2$, $J_3$ and $J_4$ are N.

The term "alkyl" herein refers to a straight or branched hydrocarbon group, containing 1-6 carbon atoms. Examples include methyl, ethyl, n-propyl, i-propyl, n-butyl, i-butyl, and t-butyl.

The term "cycloalkyl" refers to a saturated and partially unsaturated monocyclic, bicyclic, tricyclic, or tetracyclic hydrocarbon group having 3-12 (e.g., 3-10 and 3-7) carbon atoms. Examples include cyclopropyl, cyclobutyl, cyclopentyl, cyclopentenyl, cyclohexyl, cyclohexenyl, cycloheptyl, and cyclooctyl.

The term "heterocycloalkyl" refers to a nonaromatic 5-8 membered monocyclic, 8-12 membered bicyclic, or 11-14 membered tricyclic ring system having one or more heteroatoms (e.g., O, N, P, and S). Examples include piperazinyl, imidazolidinyl, azepanyl, pyrrolidinyl, dihydrothiadiazolyl, dioxanyl, morpholinyl, tetrahydropuranyl, and tetrahydrofuranyl.

The term "alkoxy" refers to an —O-alkyl group. Examples include methoxy, ethoxy, propoxy, and isopropoxy.

The term "halo" refers to a fluoro, chloro, bromo, or iodo radical.

The term "amino" refers to a radical derived from amine, which is unsubstituted or mono-/di-substituted with alkyl, aryl, cycloalkyl, heterocycloalkyl, or heteroaryl.

The term "aryl" refers to a 6-carbon monocyclic, 10-carbon bicyclic, 14-carbon tricyclic aromatic ring system. Examples of aryl groups include phenyl, naphthyl, and anthracenyl.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl.

Alkyl, cycloalkyl, heterocycloalkyl, alkoxy, aryl, and heteroaryl mentioned herein include both substituted and unsubstituted moieties. Possible substituents on cycloalkyl, heterocycloalkyl, alkoxy, aryl, and heteroaryl include, but are not limited to, $C_{1-6}$ alkyl, $C_{2-6}$ alkenyl, $C_{2-6}$ alkynyl, $C_{3-12}$ cycloalkyl, $C_{3-12}$ cycloalkenyl, $C_{1-12}$ heterocycloalkyl, $C_{1-12}$ heterocycloalkenyl, $C_{1-6}$ alkoxy, aryl, aryloxy, heteroaryl, heteroaryloxy, amino, $C_{1-6}$ alkylamino, $C_{1-20}$ dialkylamino, arylamino, diarylamino, $C_{1-6}$ alkylsulfonamino, arylsulfonamino, $C_{1-6}$ alkylimino, arylimino, $C_{1-6}$ alkylslfonimino, arylsulfonimino, hydroxyl, halo, thio, $C_{1-6}$ alkylthio, arylthio, $C_{1-6}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl include all of the above-recited substituents except $C_{1-6}$ alkyl. Cycloalkyl, heterocycloalkyl, aryl, and heteroaryl can also be fused with each other.

In addition to the compounds of formula (I) described above, their pharmaceutically acceptable salts and solvates, where applicable, are also covered by this disclosure. A salt can be formed between an anion and a positively charged group (e.g., amino) on a compound. Examples of a suitable anion include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. A salt can also be formed between a cation and a negatively charged group. Examples of a suitable cation include sodium ion, potassium ion, magnesium ion, calcium ion, and an ammonium cation such as tetramethylammonium ion. A salt further includes those containing quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine.

Another aspect of this disclosure is a pharmaceutical composition for treating disorders associated with glucagon, such as a metabolic disorder associated with glucagon (e.g., type I diabetes and type II diabetes).

The pharmaceutical composition contains one of the compounds of formula (I) described above or its pharmaceutically acceptable salt and a pharmaceutically acceptable carrier, excipient or diluent.

This disclosure also covers use of such a composition for the manufacture of a medicament for treating disorders (for example, a metabolic disorder) associated with glucagon.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters, fluorocarbons, and/or other solubilizing or dispersing agents known in the art. A composition having an active compound can also be administered in the form of suppositories for rectal administration.

The carrier, the excipient and the diluent in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

Still within the scope of the present disclosure is a method of treating disorders (for example, a metabolic disorder) associated with glucagon.

The method includes administering to a subject in need thereof an effective amount of a compound of formula (I) or a pharmaceutically acceptable salt thereof.

The above-described compounds or a pharmaceutical composition containing one or more of them can be administered to a subject orally, parenterally, by inhalation spray, topically, rectally, nasally, buccally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

The term "treating", "treat" or "treatment" refers to application or administration of the compound to a subject with the purpose to cure, alleviate, relieve, alter, remedy, improve, or affect the disease, the symptom, or the predisposition. "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of other active agents.

The details of one or more embodiments of the disclosure are set forth in the description below. Other features, objects, and advantages of the disclosure will be apparent from the description and from the claims.

DETAILED DESCRIPTION

A first embodiment of the present disclosure is the compounds of formula (I) or pharmaceutically acceptable salts thereof:

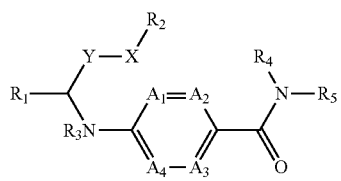
(I)

in which each of variables each of variables $R_1$, $R_2$, $R_3$, $R_4$, $R_5$, $A_1$, $A_2$, $A_3$, $A_4$, X and Y is defined as in the SUMMARY section.

A second embodiment of the present disclosure is the compound of the first embodiment or a pharmaceutically acceptable salt thereof wherein $R_3$ is H, and $R_4$ is H.

A third embodiment of the present disclosure is the compound of the first or second embodiments or a pharmaceutically acceptable salt thereof, wherein

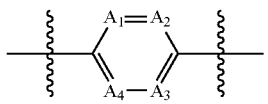

is

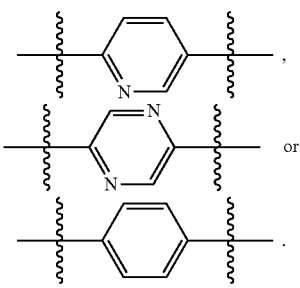

A fourth embodiment of the present disclosure is the compound of any one of the first to third embodiments or a pharmaceutically acceptable salt thereof wherein X is —O— or —S—, Y is —CH$_2$—, $R_2$ is

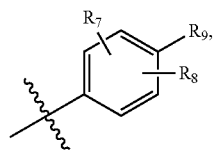

$R_3$ is H, and $R_4$ is H.

A fifth embodiment of the present disclosure is the compound of the fourth embodiment or a pharmaceutically acceptable salt thereof, wherein $R_2$ is

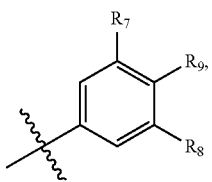

$R_7$ is H, halo, $C_{1-6}$ alkyl or $C_{1-6}$ alkoxy, and $R_8$ is H, halo or $C_{1-6}$ alkyl.

A sixth embodiment of the present disclosure is the compound of the fourth or fifth embodiments or a pharmaceutically acceptable salt thereof, wherein $R_7$ and $R_8$ are the same, and $R_7$ and $R_8$ are H, methyl, ethyl, propyl, isopropyl, butyl t-butyl, F or Cl.

A seventh embodiment of the present disclosure is the compound of the fourth or fifth embodiments or a pharmaceutically acceptable salt thereof; wherein $R_7$ is F, Cl, methoxy, ethoxy, propoxy or isobutoxy, and $R_8$ is H.

An eighth embodiment of the present disclosure is the compound of the fourth embodiment or a pharmaceutically acceptable salt thereof; wherein $R_2$ is

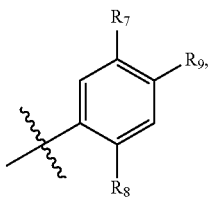

$R_7$ is F or Cl, $R_8$ is H, F or Cl.

A ninth embodiment of the present disclosure is the compound of any one of the first to third embodiments or a pharmaceutically acceptable salt thereof; wherein $R_2$ is

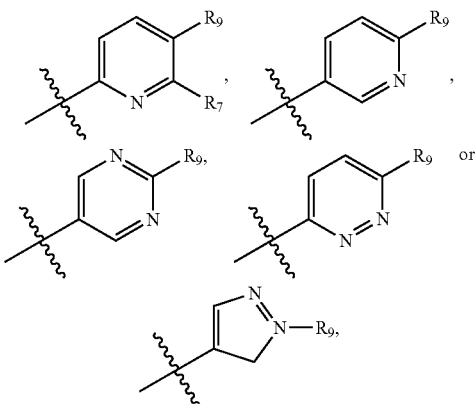

and $R_7$ is $C_{1-6}$ alkyl.

A tenth embodiment of the present disclosure is the compound of the third or ninth embodiments or a pharmaceutically acceptable salt thereof, wherein $R_7$ is methyl or ethyl.

An eleventh embodiment of the present disclosure is the compound of any one of the first to third embodiments or a pharmaceutically acceptable salt thereof; wherein X is —CH$_2$—, Y is a direct bond, $R_2$ is

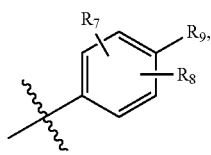

$R_3$ is H, and $R_4$ is H.

A twelfth embodiment of the present disclosure is the compound of any one of the first to third and eleventh embodiments or a pharmaceutically acceptable salt thereof, wherein $R_7$ and $R_8$ are H.

A thirteenth embodiment of the present disclosure is the compound of any one of the first to third embodiments or a pharmaceutically acceptable salt thereof; wherein X is —$CH_2$—, Y is a direct bond, $R_2$ is

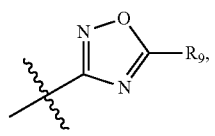

$R_3$ is H, and $R_4$ is H.

A fourteenth embodiment of the present disclosure is the compound of any one of the first to third embodiments or a pharmaceutically acceptable salt thereof; wherein X and Y are direct bonds, $R_2$ is

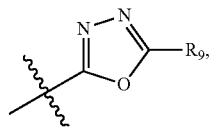

$R_3$ is H, and $R_4$ is H.

A fifteenth embodiment of the present disclosure is the compound of any one of the first to third embodiments or a pharmaceutically acceptable salt thereof; wherein X is —O—, Y is —$CH_2$—, $R_2$ is

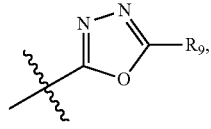

$R_3$ is H, and $R_4$ is H.

A sixteenth embodiment of the present disclosure is the compound of any one of the first to third embodiments or a pharmaceutically acceptable salt thereof; wherein X is —NH—, Y is —(C=O)—, $R_2$ is

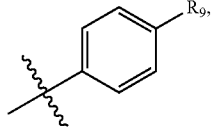

$R_3$ is H, and $R_4$ is H.

A seventeenth embodiment of the present disclosure is the compound of any one of the first to sixteenth embodiments or a pharmaceutically acceptable salt thereof, wherein $R_1$ is methyl, ethyl, n-propyl, i-propyl, 2-butyl, n-butyl, i-butyl, t-butyl, n-pentyl, isopentyl, methoxy, ethoxymethyl, 1-methoxypropyl, 1-methoxy-2methylpropyl, ethoxy, n-propoxy, i-propoxy, 3-isobutoxypropan-2-yl, 2-butoxy, n-butoxy, i-butoxy, t-butoxy, phenyl, benzyl, biphenyl, naphthyl, benzofuranyl or indolyl; each of the methyl, ethyl, n-propyl, i-propyl, 2-butyl, n-butyl, i-butyl, t-butyl, n-pentyl and isopentyl, is optionally substituted with one to three moieties selected from the group consisting of F, Cl, methoxy, ethoxy, n-propoxy, i-propoxy, 2-butoxy, n-butoxy, i-butoxy, t-butoxy, phenyl, biphenyl and naphthyl; each of the methoxy, ethoxy, n-propoxy, i-propoxy, 2-butoxy, n-butoxy, i-butoxy and t-butoxy is optionally substituted with one to three F or Cl; each of the phenyl, biphenyl, naphthyl and indolyl is optionally substituted with one to three moieties selected from the group consisting of F, Cl, methyl, ethyl, n-propyl, i-propyl, 2-butyl, n-butyl, i-butyl, t-butyl, trifluoromethyl, benzofuranyl and methoxy substituted pyrimidyl.

An eighteenth embodiment of the present disclosure is the compound of any one of the first to seventeenth embodiments or a pharmaceutically acceptable salt thereof, wherein $R_5$ is tetrazolyl, —$CH_2$-tetrazolyl, —$CH_2CH_2CO_2H$, —$CH_2CH_2CO_2Et$, —$CH_2CH_2CO_2Me$, —$CH_2CH(OH)CO_2H$, or —$(CH_2)_2SO_3H$.

A nineteenth embodiment of the present disclosure is the compound of any one of the first to eighteenth embodiments or a pharmaceutically acceptable salt thereof, wherein $R_9$ is methyl, ethyl, n-propyl, i-propyl, 2-butyl, n-butyl, i-butyl, t-butyl, methoxy, ethoxy, n-propoxy, i-propoxy, 2-butoxy, n-butoxy, i-butoxy, t-butoxy, phenyl, benzyl, biphenyl, naphthyl, pyridinyl, pyridazinyl, benzofuranyl, benzothiazolyl, imidazopyridinyl, oxadiazol, benzooxazol, pyrazol or indolyl; each of the methyl, ethyl, n-propyl, i-propyl, 2-butyl, n-butyl, i-butyl and t-butyl is optionally substituted with one to three moieties selected from the group consisting of F, Cl, methoxy, ethoxy, n-propoxy, i-propoxy, 2-butoxy, n-butoxy, i-butoxy, t-butoxy, phenyl, biphenyl and naphthyl; each of the methoxy, ethoxy, n-propoxy, i-propoxy, 2-butoxy, n-butoxy, i-butoxy and t-butoxy is optionally substituted with one to three F, Cl or amino; each of the phenyl, benzyl, biphenyl, naphthyl, pyridinyl, pyridazinyl, benzofuranyl, benzothiazolyl, imidazopyridinyl, oxadiazol, benzooxazol, pyrazol and indolyl is optionally substituted with one to three moieties selected from the group consisting of F, Cl, methyl, ethyl, n-propyl, i-propyl, 2-butyl, n-butyl, i-butyl, t-butyl, methoxy, ethoxy, n-propoxy, i-propoxy, 2-butoxy, n-butoxy, i-butoxy, t-butoxy, —$CF_3$, —$OCF_3$ and phenyl.

A twentieth embodiment of the present disclosure is the compound of any one of the first to nineteenth embodiments or a pharmaceutically acceptable salt thereof, wherein $R_6$ is H, or $C_{1-6}$ alkyl.

A twenty first embodiment of the present disclosure is the compound of any one of the first to nineteenth embodiments or a pharmaceutically acceptable salt thereof, wherein the compound of formula (I) can be the compound of the following formula (II):

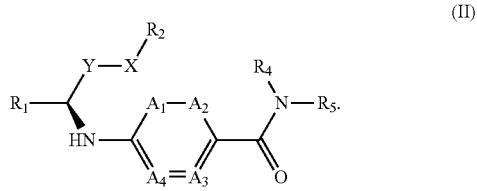

(II)

A twenty first embodiment of the present disclosure is a compound selected from the group consisting of Compounds 1-1 to 1-54, Compounds 2-1 to 2-13, Compounds 3-1 to 3-24, Compounds 4-1 to 4-5, Compounds 5-1 to 5-3, Compounds 6-1 to 6-3, Compounds 7-1 to 7-11, Compounds 8-1 to 8-25, Compounds 9-1 to 9-6, Compounds 10-1 to 10-19, Compounds 11-1 to 11-2, Compounds 12-1 to 12-11, Compounds 13-1 to 13-14, Compounds 14-1 and 14-2, Compounds 15-1 to 15-37, Compounds 16-1 and 16-2, Compounds 17-1 to 17-12, Compounds 18-1 to 18-9, Compounds 19-1 to 19-34, Compounds 20-1 to 20-7, Compounds 21-1 to 21-3, Compounds 22-1 to 22-20, Compounds 23-1 to 23-35 and Compounds 24-1 to 24-28, which are listed in the following Tables 1 to 24.

In one aspect of the present disclosure, the compound can be any one selected from the group consisting of Compound 1-2, Compound 1-8, Compound 1-9, Compound 1-12, Compound 1-16, Compound 1-17, Compound 1-18, Compound 1-19, Compound 1-20, Compound 1-22, Compound 1-25, Compound 1-30, Compound 1-32, Compound 1-48, Compound 1-52, Compound 1-54, Compound 2-4, Compound 2-6, Compound 2-9, Compound 2-10, Compound 3-2, Compound 3-3, Compound 3-4, Compound 3-5, Compound 3-8, Compound 3-9, Compound 3-10, Compound 3-12, Compound 3-43, Compound 3-14, Compound 3-15, Compound 3-19, Compound 3-20, Compound 3-22, Compound 3-24, Compound 4-2, Compound 7-1, Compound 7-5, Compound 7-8, Compound 7-11, Compound 8-3, Compound 8-5, Compound 8-8, Compound 8-11, Compound 8-13, Compound 8-15, Compound 8-16, Compound 8-20, Compound 8-22, Compound 8-23, Compound 8-25, Compound 9-1, Compound 11-1, Compound 11-2, Compound 13-1, Compound 13-2, Compound 13-3, Compound 13-4, Compound 13-6, Compound 13-7, Compound 13-8, Compound 13-9, Compound 13-10, Compound 13-11, Compound 13-14, Compound 14-2, Compound 15-3, Compound 15-7, Compound 15-9, Compound 15-10, Compound 15-13, Compound 15-22, Compound 15-28, Compound 15-29, Compound 18-2, Compound 18-3, Compound 18-7, Compound 18-8, Compound 19-5, Compound 22-1, Compound 22-18, Compound 23-1, Compound 23-5 and Compound 23-10.

The compounds of the present disclosure may contain asymmetric or chiral centers, and exist in different stereoisomeric forms. Unless specified otherwise, all stereoisomeric forms of the compounds of the present disclosure as well as mixtures thereof including racemic mixtures are within the scope of the present disclosure. In addition, the compounds of the present disclosure may also exist in different geometric and positional isomers. For example, both the cis- and trans-forms, as well as mixtures of the compound with a double bond or a fused ring, are also within the scope of the present disclosure.

Diastereomeric mixtures can be separated into their individual diastereoisomers by any methods, such as by chromatography and/or fractional crystallization. Enantiomers can be separated by use of a chiral HPLC column or by converting the enantiomeric mixture into a diastereomeric mixture by reaction with an appropriate optically active compound to separate the diastereoisomers and convert the individual diastereoisomers into pure enantiomers. The specific stereoisomers may be synthesized by converting one stereoisomer into the other by asymmetric transformation, by using an optically active starting material or by asymmetric synthesis using optically active reagents, catalysts, substrates or solvents.

In the compounds of the present disclosure, the carbon attached to both $NR_3$ and Y can have a stereoisomeric configuration of R or S, and such compounds can have an enantiomeric excess of 90% or higher (e.g., ≥95% and ≥99%).

Also within the present disclosure is a pharmaceutical composition comprising: (1) the compound of the present disclosure or the pharmaceutically acceptable salt thereof, and (2) a pharmaceutically acceptable carrier, excipient or diluent. The composition may also comprise at least one additional pharmaceutical agent such as anti-obesity agents and/or anti-diabetic agent. The compound or the pharmaceutically acceptable salt thereof or the composition of the present disclosure may be used in the manufacture of a medicament of treating diseases, conditions or disorders associated with glucagon.

Also within the present disclosure is a method for reducing the glycemic level in a subject, which includes the step of administering to the subject in need thereof an effective amount of the compound of the present disclosure or the pharmaceutically acceptable salt thereof.

Further covered by the present disclosure a method of treating diseases, conditions or disorders associated with glucagon, which includes the step of administering to a subject in need thereof an effective amount of the compound of the present disclosure or the pharmaceutically acceptable salt thereof.

In the present disclosure, the aforesaid subject can be mammal, for example, human.

In the present disclosure, the diseases, conditions or disorders associated with glucagon can be, for example, hyperglycemia, Type II diabetes, metabolic syndrome, impaired glucose tolerance, glucosuria, diabetic nephropathy, diabetic neuropathy, diabetic retinopathy, hyperinsulinemia, insulin resistance syndrome, cataracts, obesity, dyslipidemia, hypertension and myocardial infarction. However, the present disclosure is not limited thereto, and the compounds or the pharmaceutically acceptable salt thereof of the present disclosure can be applied to any other diseases, conditions or disorders associated with the glucagon signaling pathway. In one aspect of the present disclosure, the diseases, conditions or disorders associated with glucagon is hyperglycemia, Type II diabetes, impaired glucose tolerance, insulin resistance syndrome and obesity. In another aspect of the present disclosure, the diseases, conditions or disorders associated with glucagon is Type II diabetes.

The compounds or the pharmaceutically acceptable salt thereof of the present disclosure may be administered in combination with at least one additional pharmaceutical agent such as anti-obesity agents and/or anti-diabetic agent. The administration formulation can be, for example, (a) a single formulation comprising the compound of the present disclosure or the pharmaceutically acceptable salt thereof a pharmaceutically acceptable carrier, excipient or diluent and at least one additional pharmaceutical agent; or (b) two formulations administered simultaneously or sequentially and in any order, wherein one comprises the compound of the present disclosure or the pharmaceutically acceptable salt thereof, a pharmaceutically acceptable carrier, excipient or diluent and the other one comprises at least one additional pharmaceutical agent.

Suitable anti-diabetic agents may include an acetyl-CoA carboxylase-2 (ACC-2) inhibitor, an A2 antagonist, a biguanide (e.g., metformin), a diacylglycerol O-acyltransferase 1 (DGAT-1) inhibitor, a dipeptidyl peptidase IV (DPP-IV) inhibitor (e.g., alogliptin, sitagliptin, saxagliptin and vildagliptin), a fatty acid oxidation inhibitor, a glucagon-like peptide 1 (GLP-1) agonist (e.g., exendin-3 and exendin-4), a glycogen phosphorylase inhibitor, insulin, an insulin mimetic, an insulin secreatagogue, a meglitinide, a phosphodiesterase (PDE)-10 inhibitor, a protein tyrosine phosphatase-1B (PTP-1B) inhibitor (e.g., hyrtiosal extract and trodusquemine), a sulfonylurea (e.g., acetohexamide, chlorpropamide, diabinese, glibenclamide, gliclazide, glimepiride, glipentide, glipizide, gliquidone, glisolamide, glyburide, tolazamide, and tolbutamide), an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), SIRT-1 inhibitor (e.g., resveratrol), an SGLT1 inhibitor, an SGLT2 inhibitor (e.g. dapagliflozin, remogliflozin, sergliflozin and AVE2268), a c-jun amino-terminal kinase (JNK) inhibitor, and a VPAC2 receptor agonist. In one embodiment of the present disclosure, suitable anti-diabetic agents may include metformin, SGLT2 inhibitors and/or DPP-IV inhibitors.

Suitable anti-obesity agents may include a 11β-hydroxy steroid dehydrogenase-1 (11β-HSD type 1) inhibitor, a 5HT2c agonist (e.g., lorcaserin), an anorectic agent (such as a bombesin agonist), a ciliary neurotrophic factor (such as Axokine™), a cholecystokinin-A (CCK-A) agonist (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide), a dehydroepiandrosterone or an analog thereof, a dopamine agonist (such as bromocriptine), a galanin antagonist, a ghrelin antagonist, a glucagon-like peptide-1 agonist, a glucocorticoid agonist or antagonist, a histamine 3 antagonist or inverse agonist, a human agouti-related protein (AGRP) inhibitor, a leptin analogs, a leptin agonists, a lipase inhibitors (such as tetrahydrolipstatin, i.e. orlistat and cetilistat), a MCR-4 agonist, a melanin concentrating hormone antagonist, a leptin (the OB protein), a melanocyte-stimulating hormone analog, a monoamine reuptake inhibitor (such as sibutramine), a MTP/ApoB inhibitor (e.g., a gut-selective MTP inhibitor, such as dirlotapide, mitratapide and implitapide, R56918 (CAS No. 403987) and CAS No. 913541-47-6), a neuropeptide-Y antagonist (e.g., a NPY Y5 antagonist), a neuromedin U agonist, an opioid antagonist (e.g., naltrexone), an orexin antagonist, an orexin antagonist, a $PYY_{3-36}$ or an analog thereof, a stearoyl-CoA desaturase-1 (SCD-1) inhibitor, a sympathomimetic agents, a thyromimetic agent, and a $β_3$ adrenergic agonist. In one embodiment of the present disclosure, suitable anti-obesity agents may include a 5HT2c agonist, a CCK-A agonists, a gut-selective MTP inhibitor, a lipase inhibitor, a MCR-4 agonist, $PYY_{3-36}$, an opioid antagonist, bromocriptine, exenatid, leptin, liraglutide, obinepitide, odistat, oleoyl-estrone, pramlintide, tesofensine, sibutramine and AOD-9604.

Methods for synthesizing the compounds of formula (I) are well known in the art. See, for example, R. Larock, Comprehensive Organic Transformations ($2^{nd}$ Ed., VCH Publishers 1999); P. G. M. Wuts and T. W. Greene, Greene's Protective Groups in Organic Synthesis ($4^{th}$ Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis ($2^{nd}$ ed., John Wiley and Sons 2009); P. Roszkowski, J. K. Maurin, Z. Czarnocki "Enantioselective synthesis of (R)-(−)-praziquantel (PZQ)" Tetrahedron: Asymmetry 17 (2006) 1415-1419; and L. Hu, S. Magesh, L. Chen, T. Lewis, B. Munoz, L. Wang "Direct inhibitors of keap1-nrf2 interaction as antioxidant inflammation modulators," WO2013/067036.

The compounds of formula (I) thus prepared can be initially screened using in vitro assays, e.g., the glucagon cAMP inhibition assay and $I^{125}$-glucagon binding assay both described below, for their potency in binding to glucagon receptor and inhibiting downstream cAMP. They can be subsequently evaluated using in vivo assays known in the field. The selected compounds can be further tested to verify their efficacy in disease related efficacy and adverse effects models. Based on the results, an appropriate dosage range and administration route can be determined.

The following embodiments are made to clearly exhibit the above-mentioned and other technical contents, features and/or effects of the present disclosure. Through the exposition by means of the specific embodiments, people would further understand the technical means and effects the present disclosure adopts to achieve the above-indicated objectives. Moreover, as the contents disclosed herein should be readily understood and can be implemented by a person skilled in the art, all equivalent changes or modifications which do not depart from the concept of the present disclosure should be encompassed by the appended claims.

EXAMPLE

Without further elaboration, it is believed that one skilled in the art can, based on the above description, utilize the present disclosure to its fullest extent. The following specific examples, i.e., EXAMPLES 1-26, are therefore to be construed as merely illustrative, and not limitative of the remainder of the disclosure in any way whatsoever. All publications cited herein are incorporated by reference in their entirety.

Among the specific examples, EXAMPLES 1-24 set forth the procedures for preparing certain intermediates and 390 exemplary compounds of formula (I), as well as the analytical data for the compounds thus prepared; and EXAMPLES 25 and 26 set forth the protocols for testing these compounds.

Described below are the procedures used to synthesize the exemplary compounds of the present disclosure.

Unless otherwise stated, all starting materials used were commercially available and used as supplied. Reactions requiring anhydrous conditions were performed in flame-dried glassware and cooled under an argon or nitrogen atmosphere. Unless otherwise stated, reactions were carried out under argon or nitrogen and monitored by analytical thin-layer chromatography performed on glass-backed plates (5 cm_10 cm) precoated with silica gel 60 F254 as supplied by Merck. Visualization of the resulting chromatograms was done by looking under an ultraviolet lamp (λ=254 nm), followed by dipping in an nBuOH solution of Ninhydrin (0.3% w/v) containing acetic acid (3% v/v) or ethanol solution of phosphomolybdic acid (2.5% w/v) and carring by heat gun. Solvents for reactions were dried under an argon or nitrogen atmosphere prior to use as follows. THF, Toluene, and DCM were dried by the column of Dried molecular Sieve 5A (LC technology solution Inc). DMF dried by calcium hydride or anhydrous is commercial available. Flash chromatography was used routinely for purification and separation of product mixtures using RediSep Rf Silica Gel Disposable Flash Columns, Gold® 20-40/40-60 microns silica gel and Reusable RediSep Rf Gold® C18 Reversed Phase columns, 20-40 microns supplied by RediSep. Eluent systems are given in volume/volume concentrations. $^{13}$C and $^{1}$H NMR spectra were recorded on Bruker AVIII (400 MHz). Chloroform-d or dimethyl sulfoxido-d6 and CDsOD was used as the solvent and TMS (δ 0.00 ppm) as an internal standard. Chemical shift values are reported in ppm relative to the TMS in delta (δ) units. Multiplicities are recorded as s (singlet), br s (broad singlet), d (doublet), t (triplet), q (quartet), dd (doublet of doublet), dt (doublet of triplet), m (multiplet). Coupling constants (J) are expressed in Hz. Electrospray mass spectra (ESMS) were recorded using a Thermo LTQ XL mass spectrometer. Spectral data were recorded as m/z values.

In the preparation of compounds of the present invention, protection of remote functionality (e.g., primary or secondary amine) of intermediates may be necessary. The need for such protection may vary depending on the nature of the remote functionality and the conditions of the preparation methods. Suitable amino protecting groups (NHPg) include, for example, acetyl, trifluoroacetyl, tbutoxycarbonyl (BOC), 9-fluorenylmethyleneoxycarbonyl (Fmoc) and benzyloxycarbonyl (CBz). Similarly, a "hydroxyl protecting group" refers to a substituent of a hydroxy group that blocks or protects the hydroxy functionality. Suitable hydroxyl protecting groups (OPg) include, for example, allyl, acetyl, silyl, benzyl, paramethoxy benzyl, trityl, and the like. The need for such protection is readily determined by one skilled in the art.

Reaction Schemes I and II illustrate the general procedures that can be used to synthesize the following compounds of the formula (I) of the present disclosure.

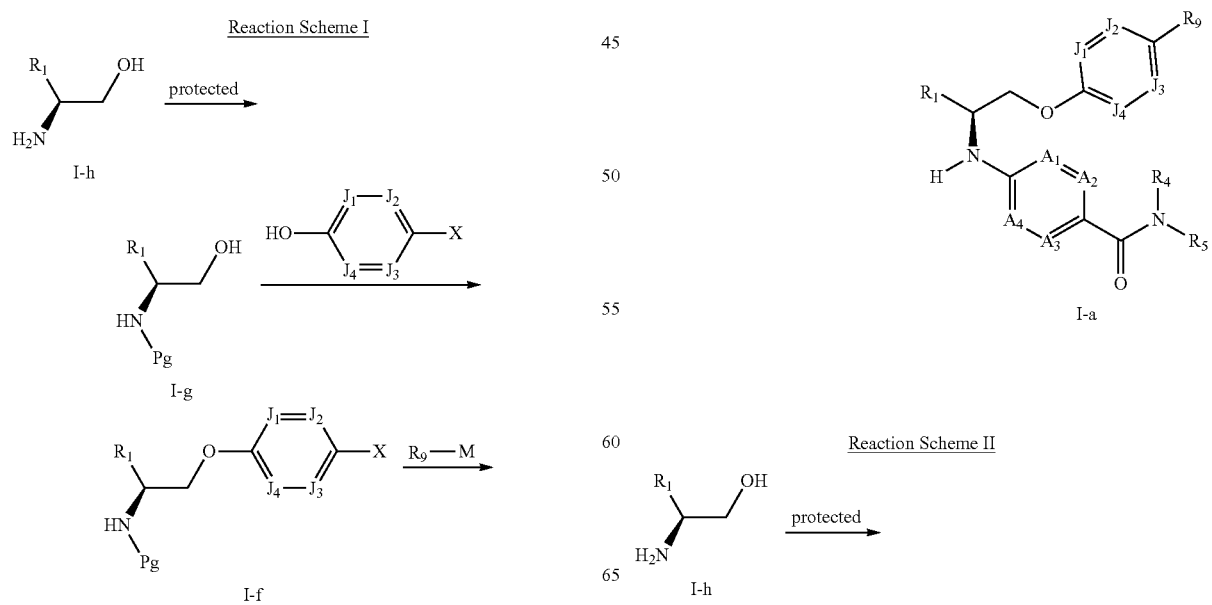

-continued

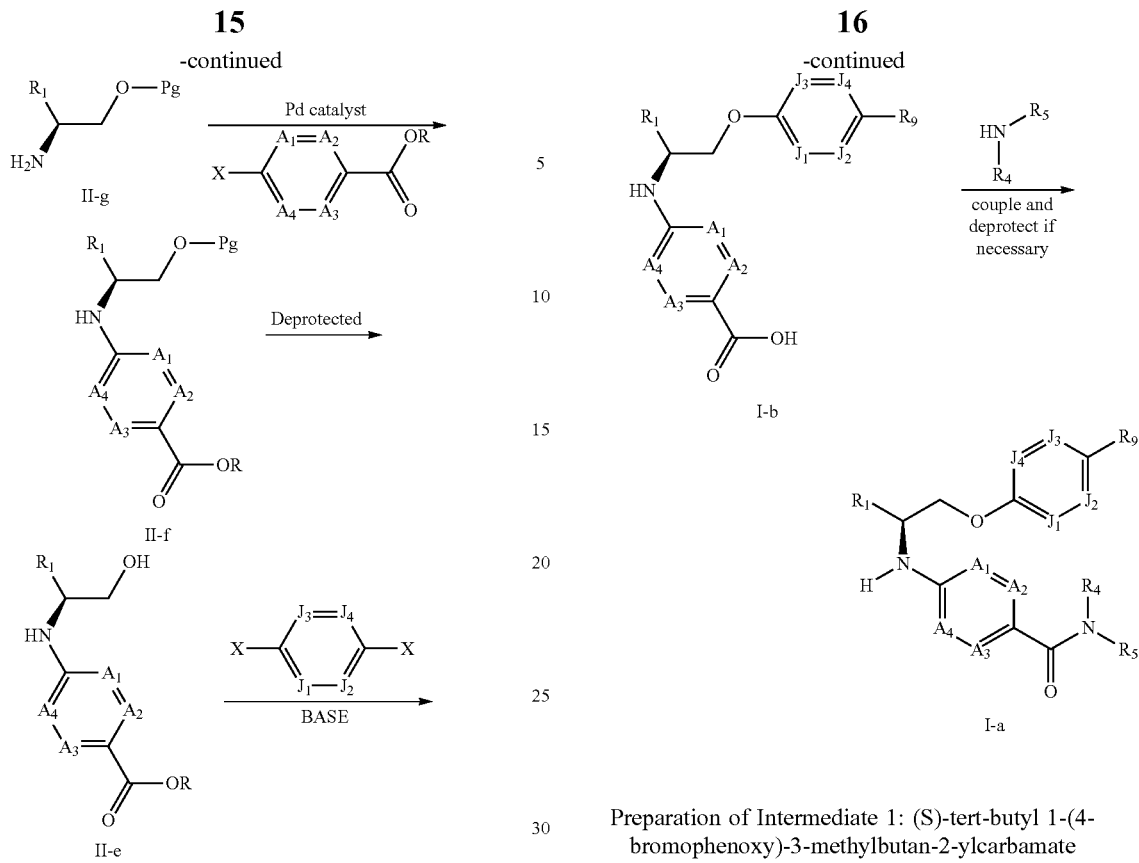

I-b

I-a

Preparation of Intermediate 1: (S)-tert-butyl 1-(4-bromophenoxy)-3-methylbutan-2-ylcarbamate

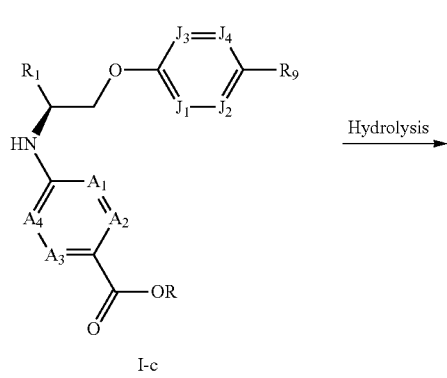

Intermediate 1

Step I: Mesiylation (S)-tert-butyl 1-hydroxy-3-methylbutan-2-ylcarbamate (4.26 g, 21.1 mmol) was dissolved in anhydrous DCM (80 mL) and $Et_3N$ (3.52 mL, 25.29 mmol) was added to the solution. A solution of methanesulfonyl chloride (1.96 mL, 25.3 mmol) in anhydrous DCM (10 mL) was added dropwise to the mixture. The reaction mixture was stirred for 3 h. The mixture was poured to the cold water and white solid was precipitated to give crude (S)-2-(tert-butoxycarbonylamino)-3-methylbutyl methanesulfonate (5.91 g, in qualitatively yield), which was of suitable purity to use directly in next reaction.

Step II: $SN_2$

To a 500 mL round-bottomed flask, cesium carbonate (15.6 g, 48 mmol) was dried with nitrogen at 100° C. then added DMF into the flask. 4-bromophenol (2.77 g, 16 mmol) in 90 mL DMF was added at 60° C. and the mixture was

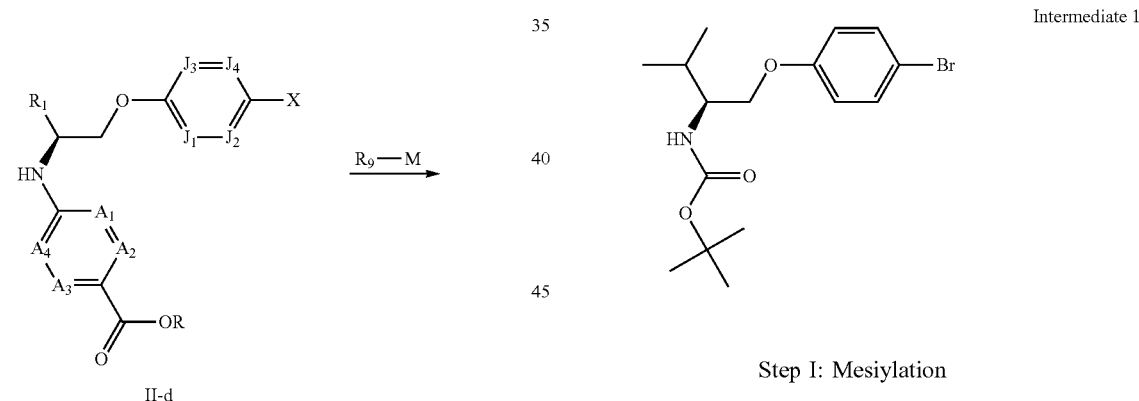

stirred at 60-70° C. under nitrogen condition for 18 h. (S)-2-(tert-butoxycarbonylamino)-3-methylbutyl methanesulfonate (5.91 g, 21 mmol) were added. After another 40 h it was partitioned between EtOAc and H₂O, the aqueous phase extracted twice with EtOAc and the combined organic phase washed with NaHCO₃ solution. Drying (MgSO₄) and concentration afforded an oily residue that was purified by column chromatography on silica gel to give (S)-tert-butyl 1-(4-bromophenoxy)-3-methylbutan-2-ylcarbamate (2.86 g, 50%) as a white solid. $^1$H NMR (400 MHz, CDCl₃): δ7.30-7.38 (m, 2H), 6.71-6.79 (m, 2H), 4.74 (d, J=8.8 Hz, 1H), 3.85-4.02 (m, 2H), 3.67 (t, J=8.3 Hz, 1H), 1.97 (dq, J=13.7, 6.8 Hz, 1H), 1.43 (s, 9H), 0.93-0.99 (m, 6H).

Preparation of Intermediate 2: (S)-tert-butyl 1-(4-(benzofuran-2-yl)phenoxy)-3-methylbutan-2-ylcarbamate

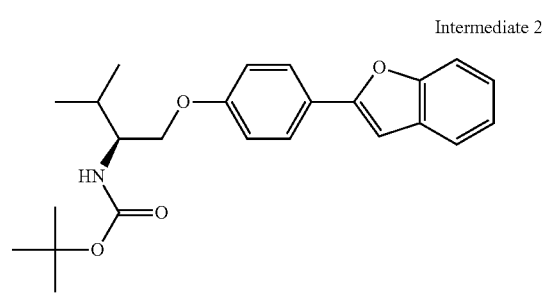 [SMILES: CC(C)[C@@H](COc1ccc(-c2cc3ccccc3o2)cc1)NC(=O)OC(C)(C)C]

Intermediate 2

Step II: Suzuki Coupling

A solution of (S)-tert-butyl 1-(4-bromophenoxy)-3-methylbutan-2-ylcarbamate (2.86 g, 8 mmol), 2-benzofuranylboronic acid (1.61 g, 10 mmol), palladium acetate(II) (66 mg, 0.8 mmol), triphenylphosphine (420 mg, 1.6 mmol) and 2M K₂CO₃ (14 mL, 28 mmol) in EtOH/PhMe (2 mL/12 mL) was heated at 90° C. for 18 h. The reaction mixture was cooled, poured into half-saturated NaHCO₃(aq) and extracted with EtOAc. The combined organic layers were dried over MgSO₄ and concentrated in vacuo. The residue was purified by silica gel chromatography to afford(S)-tert-butyl 1-(4-(benzofuran-2-yl)phenoxy)-3-methylbutan-2-ylcarbamate. (2.21 g, 70%). $^1$H NMR (400 MHz, CDCl₃): δ 7.74-7.80 (m, 2H), 7.50-7.56 (m, 1H), 7.47 (d, J=8.3 Hz, 1H), 7.16-7.24 (m, 2H), 6.91-7.00 (m, 2H), 6.87 (d, J=1.0 Hz, 1H), 4.79 (d, J=8.8 Hz, 1H), 4.08 (dd, J=9.3, 2.9 Hz, 1H), 4.00 (dd, J=9.3, 3.9 Hz, 1H), 3.71 (br. s., 1H), 1.94-2.07 (m, 1H), 1.44 (s, 9H), 0.94-1.02 (m, 6H).

Preparation of Intermediate 3: 4-(benzofuran-2-yl)phenol

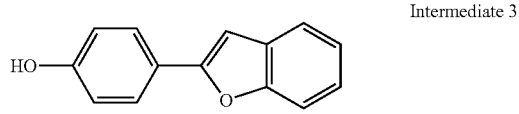 [SMILES: Oc1ccc(-c2cc3ccccc3o2)cc1]

Intermediate 3

To a 1 L round-bottomed flask, potassium carbonate (28 g, 203 mol) was added and dissolved in 102 mL water and benzofuran-2-ylboronic acid (11.3 g, 70 mmol) 4-bromophenol (10 g, 58 mmol) was added followed by toluene (232 ml), EtOH (58 ml) and PPh₃ (3.04 g, 11.6 mmol). The mixture was bubbled with nitrogen for 30 min then added Pd(OAc)₂ (1.3 g, 5.8 mmol) and raised temperature to reflux. The reaction was stirred for overnight quenched with Japanese acid spray and purified through celite. The mixture was extracted with EA and dried with MgSO₄ purified through column chromatography and got 4-(benzofuran-2-yl)phenol (8.8 g, 72%) as white solid. $^1$H NMR (400 MHz, CDCl₃): δ7.71-7.77 (m, 2H), 7.51-7.56 (m, 1H), 7.45-7.50 (m, 1H), 7.16-7.26 (m, 2H), 6.87-6.92 (m, 2H), 6.85-6.87 (m, 1H), 4.90 (s, 1H).

Preparation of Intermediate 4: (S)-tert-butyl 1-(4-(benzofuran-2-yl)phenoxy)-3-methylbutan-2-ylcarbamate

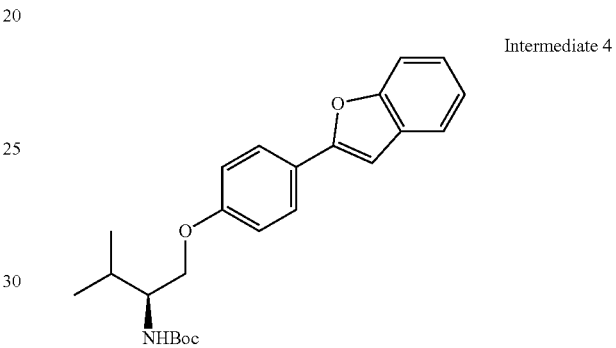

Intermediate 4

Deprotonation flask: To a 500 mL round-bottomed flask, cesium carbonate (37 g, 113 mmol) was dried with nitrogen at 100° C. then added DMF into the flask. 4-(benzofuran-2-yl)phenol (8.74 g, 42 mmol) was added at 60° C. and the mixture was stirred at 60-70° C. under nitrogen condition for 18 h.

To a 250 mL round-bottomed flask, (S)-tert-butyl 1-hydroxy-3-methylbutan-2-ylcarbamate (11.4 g, 56 mmol) was dissolved in 110 mL anhydrous DCM and cooled to 5° C. by ice bath was added TEA (11.33 g, 112 mmol) and MsCl (7.7 g, 67.2 mmol) was added dropwise over 10 min, the reaction was stirred at room temperature for 2 h. The reaction was quenched with water and extracted with DCM, dried with MgSO₄. The organic layer was combined and removed solvent by vacuo and ready for the next reaction. The (S)-2-(tert-butoxycarbonylamino)-3-methylbutyl methanesulfonate was dissolved in 40 mL DMF and poured into the deprotonation flask, the reaction was stirred at 60-70° C. for 24 h. The mixture was removed salt by filter and removed solvent by rotavapor, extracted with EA and water. The organic layer was washed with water and dried with MgSO₄. Crude compound was purified through column chromatography and got (S)-tert-butyl 1-(benzofuran-2-yl)phenoxy)-3-methylbutan-2-ylcarbamate (8.31 g, 50%). $^1$H NMR (400 MHz, CDCl₃): δ7.74-7.80 (m, 2H), 7.50-7.56 (m, 1H), 7.47 (d, J=8.3 Hz, 1H), 7.16-7.24 (m, 2H), 6.91-7.00 (m, 2H), 6.87 (d, J=1.0 Hz, 1H), 4.79 (d, J=8.8 Hz, 1H), 4.08 (dd, J=9.3, 2.9 Hz, 1H), 4.00 (dd, J=9.3, 3.9 Hz, 1H), 3.71 (br. s., 1H), 1.94-2.07 (m, 1H), 1.44 (s, 9H), 0.94-1.02 (m, 6H).

Preparation of Intermediate 5: (S)-1-(4-(benzofuran-2-yl)phenoxy)-3-methylbutan-2-amine

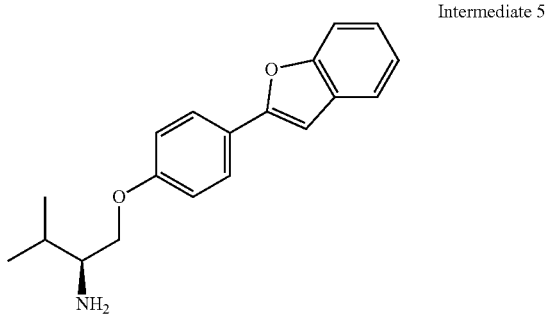 [SMILES: CC(C)[C@H](N)COc1ccc(-c2cc3ccccc3o2)cc1]

Intermediate 5

The compound (S)-tert-butyl 1-(4-(benzofuran-2-yl)phenoxy)-3-methylbutan-2-ylcarbamate (574 mg, 13.4 mmol) was suspended in trifluoroacetic acid (15 mL, 200 mmol) in anhydrous dichloromethane (150 mL) at room temperature for overnight. After reaction, excess trifluoroacetic acid was neutralized by dropwised addition of $Na_2CO_{3(aq)}$ until pH=10. Then it was extracted with $CH_2Cl_2$. The combined organic layer was dried with anhydrous $MgSO_4$ and concentrated in vacuo to give crude product. It was further purified by silica gel flash column chromatography using dichloromethane and methanol as eluent to give compound white solid. $^1$H NMR (400 MHz, $CDCl_3$): δ 7.74-7.80 (m, 2H), 7.51-7.56 (m, 1H), 7.46-7.50 (m, 1H), 7.21 (m, 2H), 6.94-6.99 (m, 2H), 6.87 (d, J=1.0 Hz, 1H), 4.03 (dd, J=8.8, 3.9 Hz, 1H), 3.83 (dd, J=9.3, 7.8 Hz, 1H), 2.97 (ddd, J=7.8, 5.9, 3.9 Hz, 1H), 1.80 (dq, J=13.1, 6.7 Hz, 1H), 1.34 (s, 2H), 0.99 (m, 6H).

Example 1: Synthesis of Compounds 1-1 to 1-54

Compound 1-1: Ethyl(S)-3-(4-((1-(4-(benzofuran-2-yl)phenoxy)-3-methylbutan-2-yl)amino)benzamido)propanoate

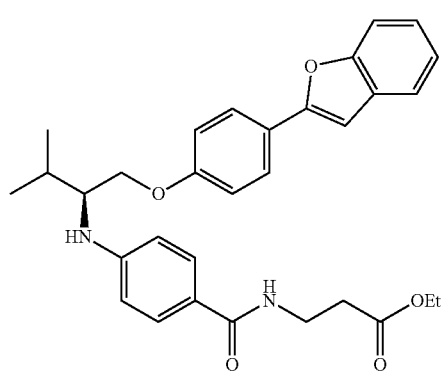 [SMILES: CCOC(=O)CCNC(=O)c1ccc(N[C@H](COc2ccc(-c3cc4ccccc4o3)cc2)C(C)C)cc1]

A solution of (S)-1-(4-(benzofuran-2-yl)phenoxy)-3-methylbutan-2-amine (7.40 g, 25 mmol) and ethyl 3-(4-iodobenzamido)propanoate (10 g, 29 mmol) and 2-isobutyrylcyclohexan-1-one (0.84 g, 5 mmol), Cesium carbonate (16.3 g, 50 mmol) in 25 ml DMF (dried), and bubbled the solution with $N_{2(g)}$ for 10 min then added copper iodide (0.48 g, 2.5 mmol). The reaction was stirred at room temperature for 5 days. The reaction was then diluted with ethyl acetate (100 mL), filtered through Celite and extracted with ethyl acetate (2×100 mL). The combined organics were washed with brine, dried over sodium sulfate, filtered and concentrated to give crude product, and purification via column chromatography (0-70% ethyl acetatein hexanes) gave ethyl (S)-3-(4-((1-(4-(benzofuran-2-yl)phenoxy)-3-methylbutan-2-yl)amino)benzamido) propanote (5.20 g 40%) as white solid. $^1$H NMR (400 MHz, $CDCl_3$): δ 7.72-7.79 (m, 2H), 7.56-7.63 (m, 2H), 7.51-7.55 (m, 1H), 7.43-7.49 (m, 1H), 7.16-7.24 (m, 2H), 6.89-6.96 (m, 2H), 6.87 (s, 1H), 6.57-6.65 (m, 3H), 4.10-4.21 (m, 3H), 4.07 (dd, J=4.4, 2.0 Hz, 2H), 3.67 (q, J=6.2 Hz, 2H), 3.55-3.63 (m, 1H), 2.56-2.64 (m, 2H), 2.09-2.21 (m, 1H), 1.24 (t, J=7.1 Hz, 3H), 1.04 (d, J=6.4 Hz, 3H), 1.05 (d, J=6.8 Hz, 3H). MS (M+1): 515.

Compound 1-2: (S)-3-(4-((1-(4-(benzofuran-2-yl)phenoxy)-3-methylbutan-2-yl)amino)benzamido)propanoic Acid

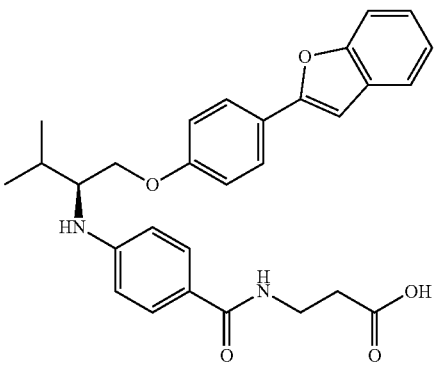

To a solution of ethyl (S)-3-(4-((1-(4-(benzofuran-2-yl)phenoxy)-3-methylbutan-2-yl)amino)benzamido)propanoate (5.15 g, 10 mmol) in THF (50 mL) was added 2 N aqueous lithium hydroxide (20 mL, 40 mmol). The reaction was stirred at room Temperature for 3 hours. The THF was then removed in vacuo and the residue was extracted with dichloromethane. The aqueous phase was acidified to pH=4 with 3 N aqueous hydrochloric acid and extracted with ethyl acetate (2×100 mL). The combined organics were washed with brine, dried over sodium sulfate, filtered and concentrated to give (S)-3-(4-((1-(4-(benzofuran-2-yl)phenoxy)-3-methylbutan-2-yl) amino)benzamido)propanoic acid as a white solid (4.47 g, 92%). $^1$H NMR (400 MHz, DMSO-$d_6$): δ 12.14 (s, 1H), 8.05-8.02 (m, 1H), 7.81-7.85 (m, 2H), 7.57-7.62 (m, 4H), 7.21-7.30 (m, 3H), 7.04-7.07 (m, 2H), 6.66 (d, J=8.8 Hz, 1H), 6.11 (d, J=8.9 Hz, 1H), 4.02-4.14 (m, 2H), 3.64-3.70 (m, 1H), 3.38-3.43 (m, 2H), 2.45-2.47 (m, 2H), 2.01-2.09 (m, 1H), 1.01 (d, J=6.8 Hz, 3H), 0.98 (d, J=6.8 Hz, 3H). MS (M+1): 487.

Compound 1-3: 3-(4-(((2S,3S)-1-((4'-(tert-butyl)-[1,1'-biphenyl]-4-yl)oxy)-3-methylpentan-2-yl)amino)benzamido)propanoic Acid

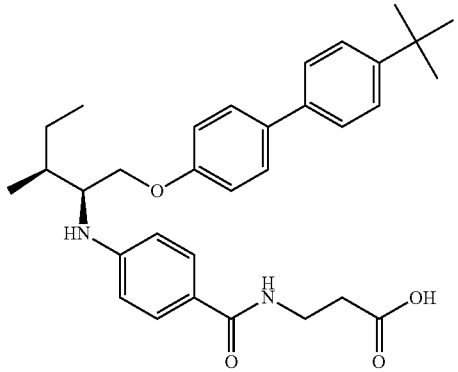 [SMILES: CC[C@H](C)[C@@H](COc1ccc(-c2ccc(C(C)(C)C)cc2)cc1)Nc1ccc(C(=O)NCCC(=O)O)cc1]

¹H NMR (400 MHz, CDCl₃): δ 7.58 (d, J=7.8 Hz, 2H), 7.36-7.52 (m, 6H), 6.90 (d, J=8.8 Hz, 2H), 6.63-6.72 (m, 1H), 6.57 (d, J=8.3 Hz, 2H), 4.05 (br. s., 2H), 3.58-3.72 (m, 3H), 2.57-2.70 (m, 2H), 1.79-1.92 (m, 1H), 1.56-1.71 (m, 1H), 1.16-1.29 (m, 1H), 0.99 (d, J=6.8 Hz, 3H), 0.93 (t, J=7.3 Hz, 3H). MS (M+1): 517.

Compound 1-5: 3-(4-(((2S)-3-methyl-1-((4'-(trifluoromethyl)-[1,1'-biphenyl]-4-yl)oxy)pentan-2-yl)amino)benzamido)propanoic Acid

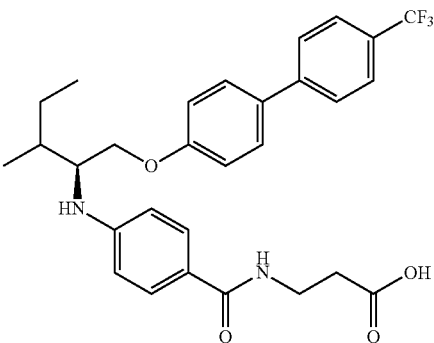

¹H NMR (400 MHz, CDCl₃): δ 7.55-7.64 (m, 6H), 7.48 (d, J=8.8 Hz, 2H), 6.90-6.93 (d, J=8.8 Hz, 2H), 6.58 (d, J=8.3 Hz, 2H), 4.02-4.10 (m, 2H), 3.60-3.70 (m, 3H), 2.61-2.67 (m, 2H), 1.80-1.92 (m, 1H), 1.64 (ddd, J=13.1, 7.5, 3.9 Hz, 1H), 1.18-1.28 (m, 1H), 0.99 (d, J=6.8 Hz, 3H), 0.93 (t, J=7.3 Hz, 3H). MS (M+1): 529.

Compound 1-4: 3-(4-(((2S,3S)-1-(4-(benzofuran-2-yl)phenoxy)-3-methylpentan-2-yl)amino)benzamido)propanoic Acid

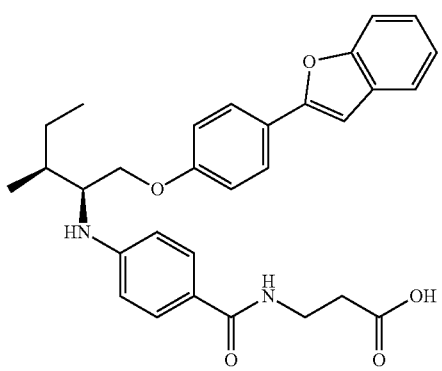 [SMILES: CC[C@H](C)[C@@H](COc1ccc(-c2cc3ccccc3o2)cc1)Nc1ccc(C(=O)NCCC(=O)O)cc1]

¹H NMR (400 MHz, CDCl₃): δ 7.74 (d, J=8.8 Hz, 2H), 7.58 (d, J=8.8 Hz, 2H), 7.50-7.54 (m, 1H), 7.46 (d, J=8.3 Hz, 1H), 7.16-7.23 (m, 2H), 6.90 (d, J=8.8 Hz, 2H), 6.85 (s, 1H), 6.74 (t, J=5.6 Hz, 1H), 6.57 (d, J=8.3 Hz, 2H), 4.00-4.09 (m, 2H), 3.59-3.70 (m, 3H), 2.65 (t, J=5.6 Hz, 2H), 1.79-1.90 (m, 1H), 1.63 (ddd, J=13.2, 7.3, 3.9 Hz, 1H), 1.18-1.28 (m, 1H), 0.98 (d, J=6.8 Hz, 3H), 0.93 (t, J=7.3 Hz, 3H). MS (M+1): 501.

Compound 1-6: 3-(4-(((2S,3S)-3-methyl-1-((4'-(trifluoromethoxy)-[1,1'-biphenyl]-4-yl)oxy)pentan-2-yl)amino)benzamido)propanoic Acid

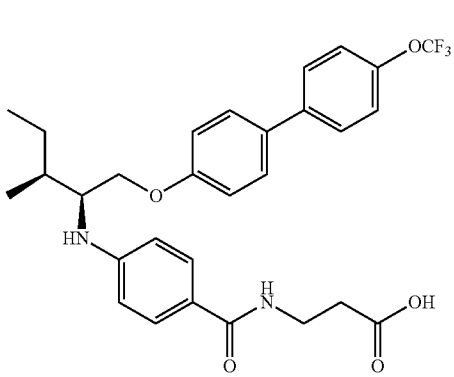 [SMILES: CC[C@H](C)[C@@H](COc1ccc(-c2ccc(OC(F)(F)F)cc2)cc1)Nc1ccc(C(=O)NCCC(=O)O)cc1]

¹H NMR (400 MHz, DMSO-d₆): δ 8.26 (t, J=5.2 Hz, 1H), 7.71 (d, J=8.8 Hz, 2H), 7.57 (t, J=8.8 Hz, 4H), 7.39 (d, J=8.3 Hz, 2H), 7.01 (d, J=8.8 Hz, 2H), 6.64 (d, J=8.8 Hz, 2H), 6.14 (d, J=8.8 Hz, 1H), 4.06-4.15 (m, 1H), 3.96-4.05 (m, 1H), 3.61-3.72 (m, 1H), 2.13 (t, J=6.8 Hz, 2H), 1.72-1.83 (m, 1H), 1.54-1.66 (m, 1H), 1.18-1.34 (m, 1H), 0.94 (d, J=6.8 Hz, 3H), 0.89 (t, J=7.4 Hz, 3H). MS (M+1): 545.

Compound 1-7: 3-(4-(((2S,3S)-1-((2',4'-dichloro-[1,1'-biphenyl]-4-yl)oxy)-3-methylpentan-2-yl)amino)benzamido)propanoic Acid

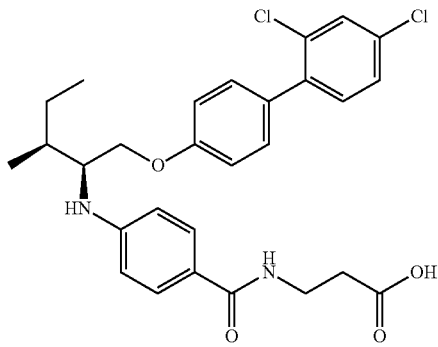 [SMILES: CC[C@H](C)[C@@H](COc1ccc(-c2ccc(Cl)cc2Cl)cc1)Nc1ccc(C(=O)NCCC(=O)O)cc1]

¹H NMR (400 MHz, CDCl₃): δ 7.57 (d, J=8.3 Hz, 2H), 7.44 (d, J=2.0 Hz, 1H), 7.18-7.32 (m, 4H), 6.90 (d, J=8.3 Hz, 2H), 6.79-6.86 (m, 1H), 6.57 (d, J=8.3 Hz, 2H), 4.02-4.09 (m, 2H), 3.60-3.70 (m, 3H), 2.64 (t, J=5.6 Hz, 2H), 1.81-1.92 (m, 1H), 1.57-1.70 (m, 1H), 1.18-1.30 (m, 1H), 0.99 (d, J=6.8 Hz, 3H), 0.93 (t, J=7.3 Hz, 3H). MS (M+1): 529.

Compound 1-8: N-((1H-tetrazol-5-yl)methyl)-4-((2S,3S)-1-(4-(benzofuran-2-yl)phenoxy)-3-methylpentan-2-yl)amino)benzamide

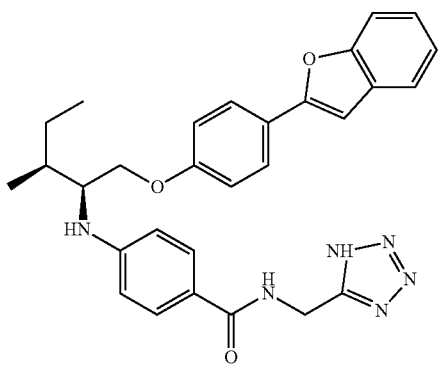 [SMILES: CC[C@H](C)[C@@H](COc1ccc(-c2cc3ccccc3o2)cc1)Nc1ccc(C(=O)NCc2nnn[nH]2)cc1]

¹H NMR (400 MHz, DMSO-d₆): δ 8.70 (t, J=5.4 Hz, 1H), 7.83 (d, J=8.8 Hz, 2H), 7.67 (d, J=8.3 Hz, 2H), 7.52-7.64 (m, 2H), 7.18-7.32 (m, 3H), 7.05 (d, J=8.8 Hz, 2H), 6.67 (d, J=8.8 Hz, 2H), 6.26 (d, J=8.8 Hz, 1H), 4.68 (d, J=5.9 Hz, 2H), 4.15 (dd, J=10.0, 3.7 Hz, 1H), 3.99-4.08 (m, 1H), 3.66-3.75 (m, 1H), 1.72-1.87 (m, 1H), 1.61 (ddd, J=13.1, 7.5, 3.9 Hz, 1H), 1.19-1.32 (m, 1H), 0.96 (d, J=6.8 Hz, 3H), 0.90 (t, J=7.3 Hz, 3I). MS (M+1): 511.

Compound 1-9: (R)-3-(4-(((2S,3S)-1-(4-(benzofuran-2-yl)phenoxy)-3-methylpentan-2-yl)amino)benzamido)-2-hydroxypropanoic Acid

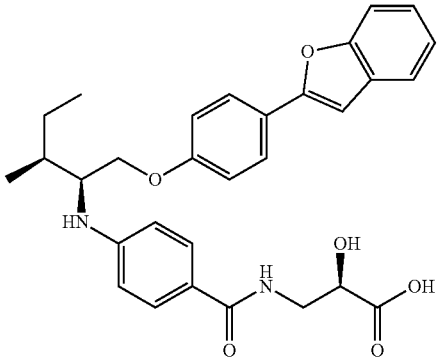 [SMILES: CC[C@H](C)[C@@H](COc1ccc(-c2cc3ccccc3o2)cc1)Nc1ccc(C(=O)NC[C@@H](O)C(=O)O)cc1]

¹H NMR (400 MHz, DMSO-d₆): δ 8.02 (t, J=5.4 Hz, 1H), 7.83 (d, J=8.3 Hz, 2H), 7.54-7.69 (m, 4H), 7.18-7.31 (m, 3H), 7.05 (d, J=8.8 Hz, 2H), 6.66 (d, J=8.8 Hz, 2H), 6.19 (d, J=8.8 Hz, 1H), 4.09-4.17 (m, 2H), 4.04 (dd, J=10.0, 6.1 Hz, 1H), 3.70 (br. s., 1H), 3.48-3.60 (m, 1H), 3.34-3.45 (m, 1H), 1.69-1.85 (m, 1H), 1.51-1.69 (m, 1H), 1.26 (dt, J=13.8, 8.0 Hz, 1H), 0.95 (d, J=6.8 Hz, 3H), 0.90 (t, J=7.3 Hz, 3H). MS (M+1): 517.

Compound 1-10: (S)-3-(4-((1-(4-(benzofuran-2-yl)phenoxy)hexan-2-yl)amino)benzamido) propanoic Acid

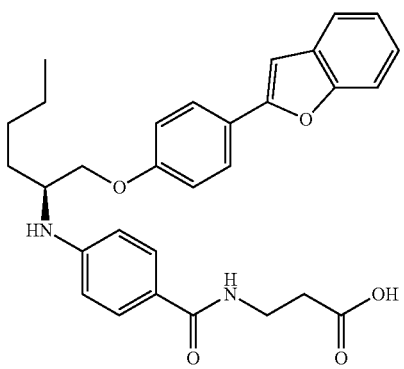 [SMILES: CCCC[C@@H](COc1ccc(-c2cc3ccccc3o2)cc1)Nc1ccc(C(=O)NCCC(=O)O)cc1]

¹H NMR (400 MHz, CDCl₃): δ 7.49-7.65 (m, 4H), 7.32-7.46 (m, 3H), 7.13 (q, J=7.4, 1.2 Hz, 2H), 6.64-6.82 (m, 3H), 6.29-6.45 (m, 2H), 3.61-3.80 (m, 2H), 3.41-3.55 (m, 3H), 2.39-2.51 (m, 2H), 1.49-1.61 (m, 1H), 1.32-1.42 (m, 1H), 1.03-1.20 (m, 4H), 0.71 (t, J=6.9 Hz, 3H). MS (M+1): 501.

Compound 1-11: (S)-3-(4-((1-((4'-(tert-butyl)-[1,1'-biphenyl]-4-yl)oxy)hexan-2-yl)amino)benzamido) propanoic Acid

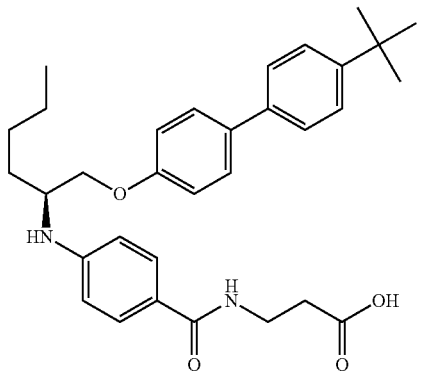 [SMILES: CCCC[C@@H](COc1ccc(-c2ccc(C(C)(C)C)cc2)cc1)Nc1ccc(C(=O)NCCC(=O)O)cc1]

¹HNMR (400 MHz, CDCl₃): δ 7.59 (d, J=8.8 Hz, 2H), 7.39-7.52 (m, 6H), 6.91 (d, J=8.3 Hz, 2H), 6.69-6.77 (m, 1H), 6.58 (d, J=8.8 Hz, 2H), 3.93-4.06 (m, 2H), 3.71-3.79 (m, 1H), 3.62-3.72 (m, 2H), 2.63-2.69 (m, 2H), 1.76-1.87 (m, 1H), 1.54-1.69 (m, 1H), 1.26-1.44 (m, 4H), 0.89 (t, J=7.1 Hz, 3H). MS (M+1): 517.

Compound 1-12: (S)-3-(4-((1-((4'-(dimethylamino)-[1,1'-biphenyl]-4-yl)oxy)-3-methylbutan-2-yl)amino) benzamido)propanoic Acid

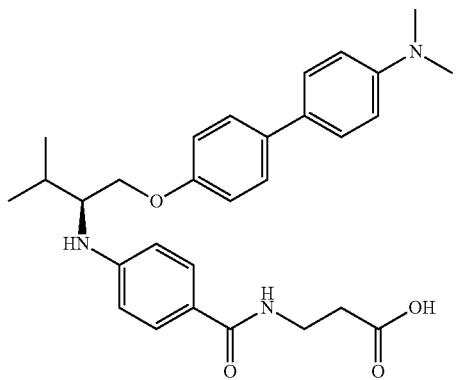 [SMILES: CC(C)[C@@H](COc1ccc(-c2ccc(N(C)C)cc2)cc1)Nc1ccc(C(=O)NCCC(=O)O)cc1]

White solid. ¹H NMR (400 MHz, DMSO-d₆): δ 8.04 (t, J=5.4 Hz, 1H), 7.59 (d, J=8.8 Hz, 2H), 7.48-7.42 (m, 4H), 6.94 (d, J=8.8 Hz, 2H), 6.76 (d, J=8.8 Hz, 2H), 6.66 (d, J=8.8 Hz, 2H), 6.11 (d, J=8.8 Hz, 1H), 4.07-3.96 (m, 2H), 3.66-3.63 (m, 1H), 3.43-3.38 (m, 2H), 2.47 (t, J=7.3 Hz, 2H), 2.08-2.02 (m, 1H), 1.01-0.96 (m, 6H). MS (M+1): 490.

Compound 1-13: Preparation of N-((1H-tetrazol-5-yl)methyl)-4-(((2S,3S)-1-((2',4'-dichloro-[1,1'-biphenyl]-4-yl)oxy)-3-methylpentan-2-yl)amino)benzamide

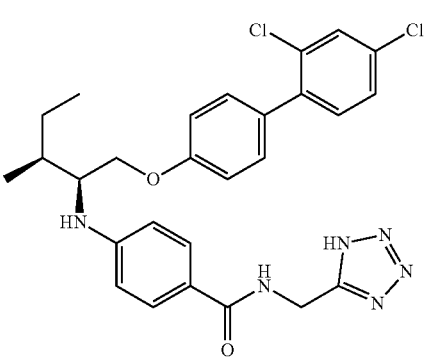 [SMILES: CC[C@H](C)[C@@H](COc1ccc(-c2ccc(Cl)cc2Cl)cc1)Nc1ccc(C(=O)NCc2nnn[nH]2)cc1]

¹H NMR (400 MHz, DMSO-d₆): δ 8.74 (t, J=5.6 Hz, 1H), 7.61-7.73 (m, 3H), 7.44-7.50 (m, 1H), 7.36-7.42 (m, 1H), 7.34 (d, J=8.3 Hz, 2H), 7.01 (d, J=8.3 Hz, 2H), 6.68 (d, J=8.8 Hz, 2H), 6.26 (d, J=8.8 Hz, 1H), 4.69 (d, J=5.4 Hz, 2H), 4.09-4.17 (m, 1H), 4.03 (dd, J=9.8, 5.9 Hz, 1H), 3.65-3.78 (m, 1H), 1.74-1.86 (m, 1H), 1.53-1.68 (m, 1H), 1.27 (dt, J=13.8, 8.0 Hz, 1H), 0.96 (d, J=6.8 Hz, 3H), 0.90 (t, J=7.3 Hz, 3H). MS (M+1): 539.

Compound 1-14: (R)-3-(4-(((2S,3S)-1-((2',4'-dichloro-[1,1'-biphenyl]-4-yl)oxy)-3-methylpentan-2-yl)amino)benzamido)-2-hydroxypropanoic Acid

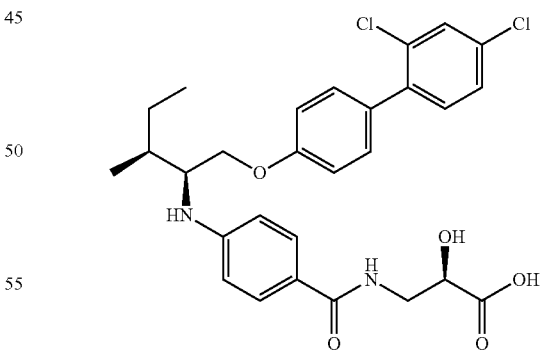

¹H NMR (400 MHz, DMSO-d₆): δ 8.05 (br. s., 1H), 7.57-7.68 (m, 3H), 7.42-7.49 (m, 1H), 7.37 (d, J=8.3 Hz, 1H), 7.32 (d, J=8.8 Hz, 2H), 7.00 (d, J=8.8 Hz, 2H), 6.66 (d, J=8.8 Hz, 2H), 6.17 (d, J=8.8 Hz, 1H), 4.06-4.16 (m, 1H), 3.97-4.06 (m, 1H), 3.89 (br. s., 1H), 3.68 (br. s., 1H), 3.42 (br. s., 2H), 1.72-1.85 (m, 1H), 1.60 (ddd, J=13.1, 7.5, 3.9 Hz, 1H), 1.19-1.34 (m, 1H), 0.94 (d, J=6.8 Hz, 3H), 0.89 (t, J=7.3 Hz, 3H). MS (M+1): 545.

Compound 1-15: (S)-3-(4-((1-((4'-(trifluoromethyl)-[1,1'-biphenyl]-4-yl)oxy)hexan-2-yl)amino)benzamido)propanoic Acid

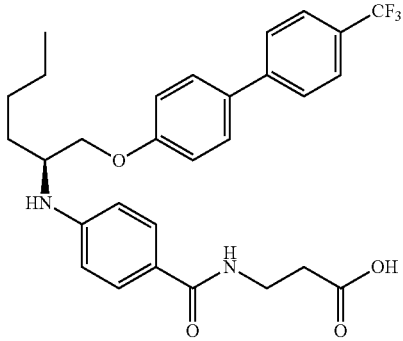 [SMILES: CCCC[C@@H](COc1ccc(-c2ccc(C(F)(F)F)cc2)cc1)Nc1ccc(C(=O)NCCC(=O)O)cc1]

¹H NMR (400 MHz, DMSO-d₆): δ 8.06 (t, J=5.4 Hz, 1H), 7.82 (d, J=8 Hz, 2H), 7.75 (d, J=8 Hz, 2H), 7.66 (d, J=8.8 Hz, 2H), 7.60 (d, J=8.8 Hz, 2H), 7.04 (d, J=8.8 Hz, 2H), 6.64 (d, J=8.8 Hz, 2H), 6.13 (d, J=8.8 Hz, 1H), 3.95-4.06 (m, 2H), 3.73-3.86 (m, 1H), 3.38-3.42 (m, 2H), 2.45-2.49 (m, 2H), 1.65-1.79 (m, 1H), 1.57 (td, J=8.9, 5.1 Hz, 1H), 1.25-1.48 (m, 4H), 0.87 (t, J=7.3 Hz, 3H). MS (M+1): 529.

Compound 1-17: (S)-3-(4-((1-((2',4'-dichloro-[1,1'-biphenyl]-4-yl)oxy)hexan-2-yl)amino)benzamido)propanoic Acid

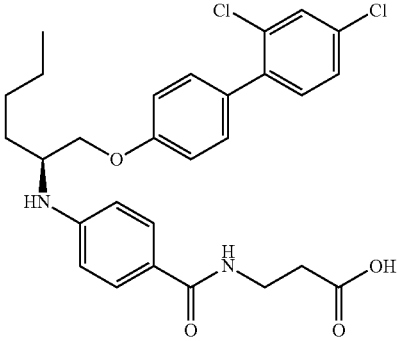

¹H NMR (400 MHz, CDCl₃): δ 7.61 (d, J=8.8 Hz, 2H), 7.46 (d, J=2.0 Hz, 1H), 7.32 (d, J=8.8 Hz, 2H), 7.21-7.28 (m, 3H), 6.93 (d, J=8.8 Hz, 2H), 6.69 (t, J=5.9 Hz, 1H), 6.60 (d, J=8.8 Hz, 2H), 3.97-4.09 (m, 2H), 3.74-3.82 (m, 1H), 3.69 (q, J=5.9 Hz, 2H), 2.68 (t, J=5.9 Hz, 2H), 1.77-1.91 (m, 1H), 1.57-1.72 (m, 1H), 1.30-1.54 (m, 4H), 0.91 (t, J=7.1 Hz, 3H); MS (M+1): 529.

Compound 1-16: Preparation of (S)—N-((1H-tetrazol-5-yl)methyl)-4-((1-((4'-(trifluoromethyl)-[1,1'-biphenyl]-4-yl)oxy)hexan-2-yl)amino)benzamide

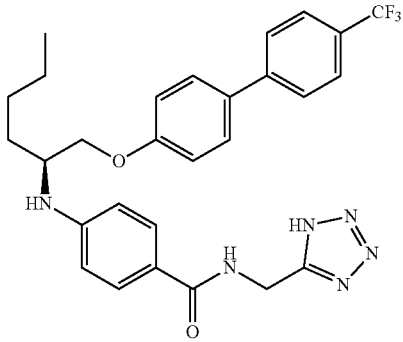 [SMILES: CCCC[C@@H](COc1ccc(-c2ccc(C(F)(F)F)cc2)cc1)Nc1ccc(C(=O)NCc2nnn[nH]2)cc1]

¹H NMR (400 MHz, DMSO-d₆): δ 8.73-8.80 (m, 1H), 7.81-7.85 (m, 2H), 7.74-7.79 (m, 2H), 7.63-7.69 (m, 4H), 7.05 (d, J=8.8 Hz, 2H), 6.67 (d, J=9.3 Hz, 2H), 6.20-6.27 (m, 1H), 4.69 (d, J=5.4 Hz, 2H), 4.01 (d, J=4.9 Hz, 2H), 3.76-3.88 (m, 1H), 1.68-1.78 (m, 1H), 1.49-1.64 (m, 1H), 1.32 (br. s., 4H), 0.84-0.90 (m, 3H); MS (M+1): 539.

Compound 1-18: (S)—N-((1H-tetrazol-5-yl)methyl)-4-((1-((2',4'-dichloro-[1,1'-biphenyl]-4-yl)oxy)hexan-2-yl)amino)benzamide

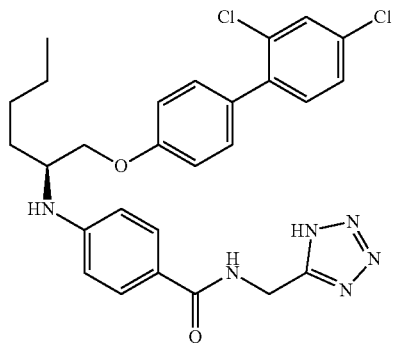 [SMILES: CCCC[C@@H](COc1ccc(-c2ccc(Cl)cc2Cl)cc1)Nc1ccc(C(=O)NCc2nnn[nH]2)cc1]

¹H NMR (400 MHz, DMSO-d₆): δ 8.75 (t, J=5.4 Hz, 1H), 7.68 (d, J=2.4 Hz, 1H), 7.65 (d, J=8.8 Hz, 2H), 7.47 (dd, J=8.3, 2.0 Hz, 1H), 7.39 (d, J=83 Hz, 1H), 7.34 (d, J=8.8 Hz, 2H), 7.00 (d, J=8.8 Hz, 2H), 6.66 (d, J=8.8 Hz, 2H), 6.21 (d, J=8.3 Hz, 1H), 4.68 (d, J=5.4 Hz, 2H), 4.00 (d, J=5.4 Hz, 2H), 3.75-3.86 (m, 1H), 1.66-1.80 (m, 1H), 1.51-1.64 (m, 1H), 1.27-1.48 (m, 4H), 0.87 (t, J=7.1 Hz, 3H); MS (M+1): 539.

Compound 1-19: (S)-3-(4-((1-((2'-chloro-4'-(trifluoromethyl)-[1,1'-biphenyl]-4-yl)oxy)hexan-2-yl)amino)benzamido)propanoic Acid

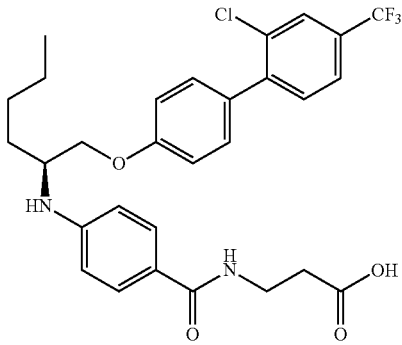

$^1$H NMR (400 MHz, DMSO-d$_6$): δ 7.70 (d, J=1.0 Hz, 3H), 7.59 (d, J=8.8 Hz, 2H), 7.52 (dd, J=8.1, 1.2 Hz, 1H), 7.40 (d, J=7.8 Hz, 1H), 7.32-7.35 (m, 2H), 6.90-6.98 (m, 2H), 6.77 (t, J=5.9 Hz, 1H), 6.58 (d, J=8.8 Hz, 2H), 3.97-4.06 (m, 2H), 3.73-3.81 (m, 1H), 3.67 (q, J=5.9 Hz, 2H), 2.65 (t, J=5.9 Hz, 2H), 1.76-1.88 (m, 1H), 1.58-1.69 (m, 1H), 1.29-1.50 (m, 4H), 0.89 (t, J=7.1 Hz, 3H). MS (M+1): 563.

Compound 1-20: (S)—N-((1H-tetrazol-5-yl)methyl)-4-((1-((2'-chloro-4'-(trifluoromethyl)-[1,1'-biphenyl]-4-yl)oxy)hexan-2-yl)amino)benzamide

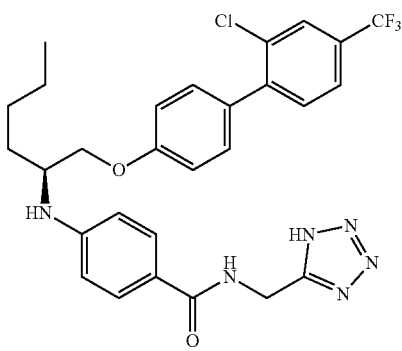 [SMILES: CCCC[C@@H](COc1ccc(-c2ccc(C(F)(F)F)cc2Cl)cc1)Nc1ccc(C(=O)NCc2nnn[nH]2)cc1]

$^1$H NMR (400 MHz, DMSO-d$_6$): δ 8.76 (t, J=5.6 Hz, 1H), 7.94 (d, J=1.0 Hz, 1H), 7.76 (dd, J=8.1, 1.2 Hz, 1H), 7.66 (d, J=8.8 Hz, 2H), 7.60 (d, J=7.8 Hz, 1H), 7.41 (d, J=8.8 Hz, 2H), 7.04 (d, J=8.8 Hz, 2H), 6.67 (d, J=8.8 Hz, 2H), 6.23 (d, J=8.3 Hz, 1H), 4.69 (d, J=5.4 Hz, 2H), 4.02 (d, J=5.4 Hz, 2H), 3.77-3.88 (m, 1H), 1.69-1.81 (m, 1H), 1.53-1.64 (m, 1H), 1.26-1.50 (m, 4H), 0.88 (t, J=7.1 Hz, 3H). MS (M+1): 573.

Compound 1-21: (R)-3-(4-(((S)-1-((4'-(dimethylamino)-[1,1'-biphenyl]-4-yl)oxy)-3-methylbutan-2-yl)amino)benzamido)-2-hydroxypropanoic Acid

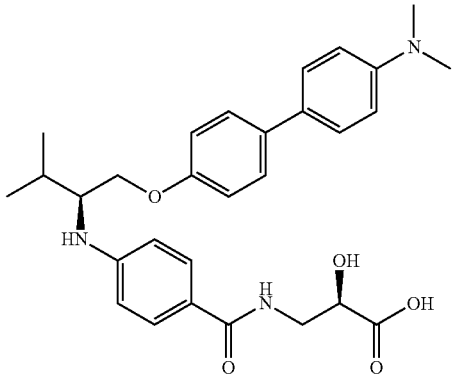 [SMILES: CC(C)[C@@H](COc1ccc(-c2ccc(N(C)C)cc2)cc1)Nc1ccc(C(=O)NC[C@@H](O)C(=O)O)cc1]

White solid. $^1$H NMR (400 MHz, DMSO-d$_6$): δ 8.10 (dd, J=8.8, 3 Hz, 1H), 7.90 (d, J=8.8 Hz, 1H), 7.69 (d, J=8, 1H), 7.62-7.56 (m, 3H), 7.43 (d, J=1.5 Hz, 1H), 7.34 (dt, J=8, 1.5 Hz, 1H), 7.27 (dt, J=8.8, 1.5 Hz, 1H), 7.22 (d, J=3 Hz, 1H), 7.09 (dd, J=8.8, 3 Hz, 1H), 6.67 (d, J=8.8 Hz, 2H), 6.13 (d, J=8.8 Hz, 1H), 4.17-4.05 (m, 2H), 3.69-3.60 (m, 2H), 3.44-3.38 (m, 1H), 3.21-3.17 (m, 1H), 2.06-2.01 (m, 1H), 1.02-0.97 (m, 6H). MS (M+1): 506.

Compound 1-22: (S)-3-(4-((1-((2'-chloro-4'-(trifluoromethyl)-[1,1'-biphenyl]-4-yl)oxy)-3-methylbutan-2-yl)amino)benzamido)propanoic Acid

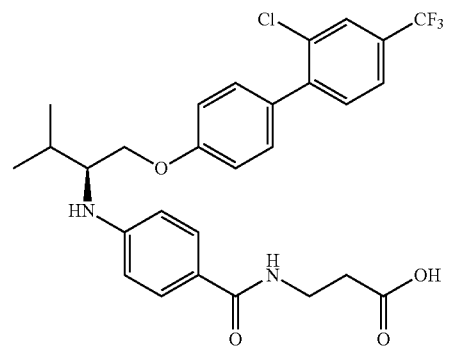

$^1$H NMR (400 MHz, DMSO-d$_6$): δ 8.08 (br. s., 1H), 7.94 (s, 1H), 7.76 (d, J=7.8 Hz, 1H), 7.53-7.63 (m, 3H), 7.35-7.45 (m, 2H), 6.99-7.08 (m, 2H), 6.66 (d, J=8.8 Hz, 2H), 6.10 (d, J=8.8 Hz, 1H), 4.00-4.14 (m, 2H), 3.61-3.72 (m, 2H), 3.39 (d, J=5.4 Hz, 3H), 2.40 (t, J=7.1 Hz, 2H), 1.98-2.11 (m, 1H), 0.94-1.06 (m, 6H). MS (M+1): 549.

Compound 1-23: 3-(4-((2-(4-(benzofuran-2-yl)phenoxy)-1-phenylethyl)amino)benzamido) propanoic Acid

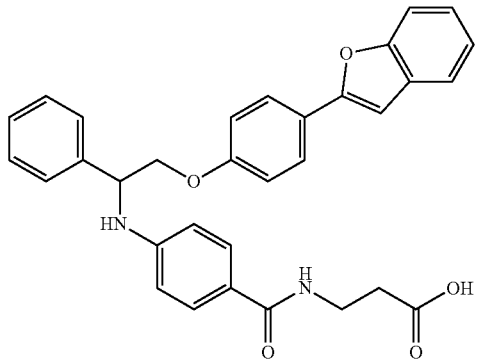 [SMILES: O=C(O)CCNC(=O)c1ccc(NC(COc2ccc(-c3cc4ccccc4o3)cc2)c2ccccc2)cc1]

¹H NMR (400 MHz, CDCl₃): δ 7.77 (d, J=8.8 Hz, 3H), 7.28-7.54 (m, 13H), 7.17-7.26 (m, 9H), 6.96 (d, J=9.3 Hz, 3H), 6.88 (s, 1H), 6.54 (d, J=8.8 Hz, 4H), 4.72-4.89 (m, 1H), 4.22-4.37 (m, 1H), 3.63-3.77 (m, 6H), 2.66 (t, J=5.9 Hz, 2H). MS (M+1): 521.

Compound 1-25: (S)-3-(4-((1-((2'-fluoro-4'-(trifluoromethyl)-[1,1'-biphenyl]-4-yl)oxy)-3-methylbutan-2-yl)aminobenzamido)propanoic Acid

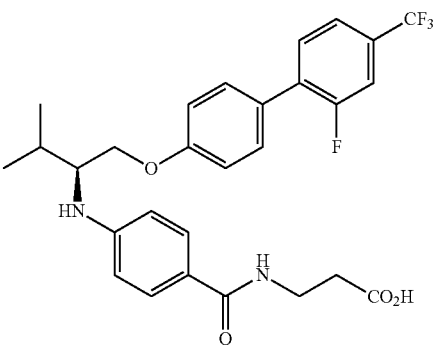

White solid. ¹H NMR (400 MHz, DMSO-d₆): δ 8.03 (t, J=5.4 Hz, 1H), 7.74-7.71 (m, 2H), 7.64-7.59 (m, 3H), 7.54-7.52 (m, 2H), 7.06 (d, J=8.8 Hz, 2H), 6.67 (d, J=8.8 Hz, 2H), 6.10 (d, J=8.8 Hz, 1H), 4.13-4.02 (m, 2H), 3.70-3.63 (m, 1H), 3.44-3.39 (m, 2H), 2.47 (t, J=6.8 Hz, 2H), 2.09-2.01 (m, 1H), 1.02-0.97 (m, 6H). MS (M+1): 533.

Compound 1-24: (S)-3-(4-((3-methyl-1-(4-(5-(trifluoromethyl)pyridin-2-yl)phenoxy)butan-2-yl)amino)benzamido)propanoic Acid

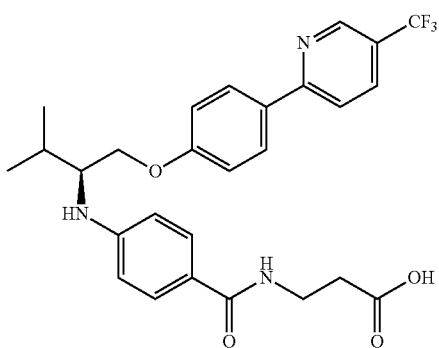 [SMILES: CC(C)[C@@H](COc1ccc(-c2ccc(C(F)(F)F)cn2)cc1)Nc1ccc(C(=O)NCCC(=O)O)cc1]

¹H NMR (400 MHz, DMSO-d₆): δ 8.96 (s, 1H), 8.16-8.22 (m, 1H), 8.11 (d, J=8.8 Hz, 3H), 7.49-7.63 (m, 2H), 7.03-7.11 (m, 2H), 6.66 (d, J=8.8 Hz, 2H), 6.10 (d, J=8.8 Hz, 1H), 4.01-4.17 (m, 3H), 3.62-3.72 (m, 2H), 3.36 (br. s., 2H), 2.20-2.32 (m, 2H), 2.05 (dq, J=13.0, 6.6 Hz, 1H), 0.99 (d, J=5.9 Hz, 3H), 0.99 (d, J=19.1 Hz, 3H). MS (M+1): 516.

Compound 1-26: 3-(4-(((2S,3S)-1-((2,4'-difluoro-[1,1'-biphenyl]-4-yl)oxy)-3-methylpentan-2-yl)amino)benzamido)propanoic Acid

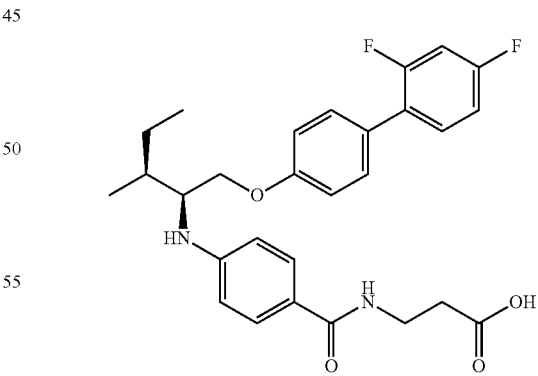

¹H NMR (400 MHz, CDCl₃): δ 7.58 (d, J=8.8 Hz, 2H), 7.35-7.39 (m, 2H), 7.31 (td, J=8.8, 6.4 Hz, 1H), 6.81-6.93 (m, 4H), 6.77 (t, J=5.9 Hz, 1H), 6.57 (d, J=8.8 Hz, 2H), 4.00-4.08 (m, 2H), 3.60-3.70 (m, 3H), 2.64 (t, J=5.9 Hz, 2H), 1.79-1.92 (m, 1H), 1.58-1.69 (m, 1H), 1.17-1.27 (m, 1H), 0.98 (d, J=6.8 Hz, 3H), 0.93 (t, J=7.3 Hz, 3H). MS (M+1): 497.

Compound 1-27: (S)-3-(4-((1-((2'-fluoro-4'-(trifluoromethyl)-[1,1'-biphenyl]-4-yl)oxy)hexan-2-yl)amino)benzamido)propanoic Acid

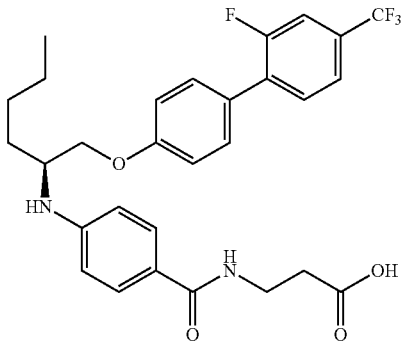 [SMILES: CCCC[C@@H](COc1ccc(-c2ccc(C(F)(F)F)cc2F)cc1)Nc1ccc(C(=O)NCCC(=O)O)cc1]

$^1$H NMR (400 MHz, CDCl$_3$): δ 7.59 (d, J=8.8 Hz, 2H), 7.34-7.52 (m, 5H), 6.94 (d, J=8.8 Hz, 2H), 6.79 (t, J=5.9 Hz, 1H), 6.58 (d, J=8.8 Hz, 2H), 4.01 (tt, J=9.5, 4.6 Hz, 2H), 3.72-3.80 (m, 1H), 3.66 (q, J=5.9 Hz, 2H), 2.64 (t, J=5.6 Hz, 2H), 1.76-1.86 (m, 1H), 1.57-1.68 (m, 1H), 1.29-1.49 (m, 4H), 0.89 (t, J=7.1 Hz, 3H). MS (M+1): 547.

Compound 1-29: (S)-3-(4-((3-methyl-1-(4-(6-(trifluoromethyl)pyridazin-3-yl)phenoxy)butan-2-yl)amino)benzamido)propanoic Acid

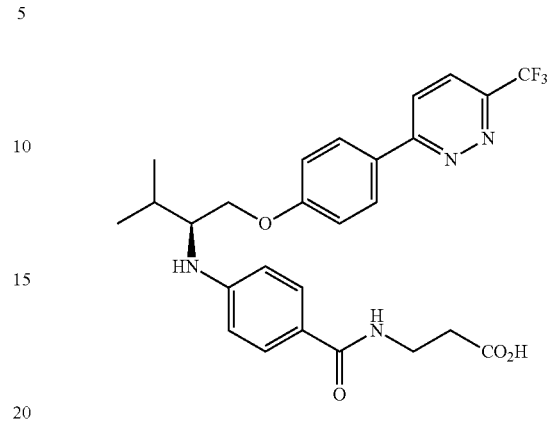

White solid. $^1$H-NMR (400 MHz, DMSO-d$_6$): δ 8.46 (d, J=8.8 Hz, 1H), 8.26-8.20 (m, 3H), 8.03 (t, J=5.4 Hz, 1H), 7.59 (d, J=8.8 Hz, 2H), 7.14 (d, J=8.8, 3 Hz, 2H), 6.67 (d, J=8.8 Hz, 2H), 6.12 (d, J=8.8 Hz, 1H), 4.18-4.06 (m, 2H), 3.72-3.65 (m, 1H), 3.43-3.39 (m, 2H), 2.46 (t, J=6.8 Hz, 2H), 2.09-1.98 (m, 1H), 1.02-0.98 (m, 6H). MS (M+1): 517.

Compound 1-28: 3-(4-((1-phenyl-2-((4'-(trifluoromethyl)-[1,1'-biphenyl]-4-yl)oxy)ethyl)amino) benzamido)propanoic Acid

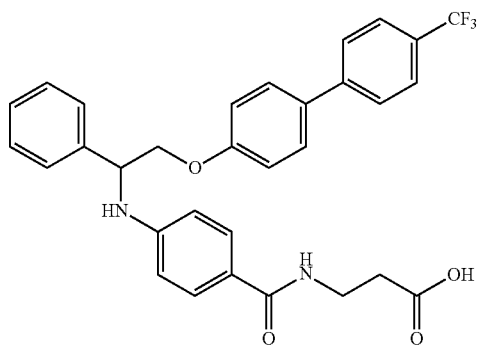 [SMILES: O=C(O)CCNC(=O)c1ccc(NC(COc2ccc(-c3ccc(C(F)(F)F)cc3)cc2)c2ccccc2)cc1]

$^1$H NMR (400 MHz, CDCl$_3$): δ 7.58-7.65 (m, 4H), 7.48-7.53 (m, 4H), 7.24-7.43 (m, 5H), 6.86-7.08 (m, 2H), 6.69 (t, J=5.9 Hz, 1H), 6.52 (d, J=8.8 Hz, 2H), 4.79 (dd, J=7.8, 3.9 Hz, 1H), 4.27 (dd, J=9.8, 3.9 Hz, 1H), 4.04-4.15 (m, 1H), 3.62 (q, J=5.9 Hz, 2H), 2.61 (t, J=5.9 Hz, 2H).

Compound 1-30: Ethyl (S)-3-(4-((1-(4-(benzo[d]thiazol-2-yl)phenoxy)-3-methylbutan-2-yl)amino)benzamido)propenoate

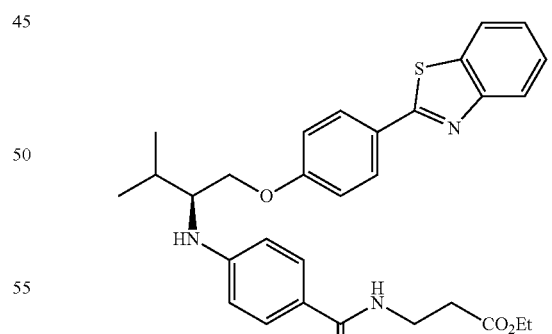

$^1$H NMR (400 MHz, CDCl$_3$): δ 7.97-8.03 (m, 3H), 7.86 (d, J=7.3 Hz, 1H), 7.57-7.64 (m, 2H), 7.41-7.48 (m, 1H), 7.30-7.37 (m, 1H), 6.91-6.98 (m, 2H), 6.56-6.65 (m, 3H), 4.07-4.20 (m, 5H), 3.68 (q, J=5.9 Hz, 2H), 3.56-3.64 (m, 1H), 2.56-2.63 (m, 2H), 2.09-2.21 (m, 1H), 1.21-1.28 (m, 3H), 1.04 (d, J=6.8 Hz, 3H), 1.05 (d, J=6.8 Hz, 3H). MS (M+1): 532.

Compound 1-31: Methyl (S)-3-(4-((1-(4-(benzo[d]thiazol-2-yl)phenoxy)-3-methylbutan-2-yl)amino)benzamido)propanoate

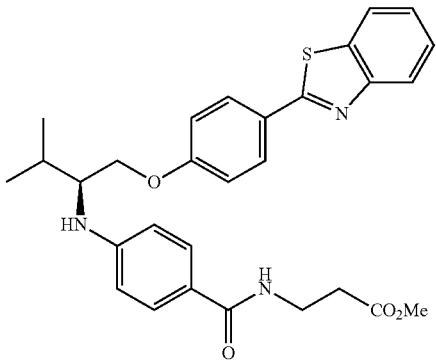 [SMILES: COC(=O)CCNC(=O)c1ccc(N[C@H](COc2ccc(-c3nc4ccccc4s3)cc2)C(C)C)cc1]

¹H NMR (DMSO-d₆): δ 8.04-8.13 (m, 2H), 7.96-8.04 (m, 3H), 7.55-7.65 (m, 2H), 7.52 (td, J=7.6, 1.5 Hz, 1H), 7.39-7.45 (m, 1H), 7.07-7.14 (m, 2H), 6.67 (d, J=8.8 Hz, 2H), 6.14 (d, J=8.8 Hz, 1H), 4.04-4.20 (m, 2H), 3.64-3.74 (m, 1H), 3.57-3.63 (m, 3H), 3.39-3.48 (m, 2H), 2.55 (t, J=7.1 Hz, 2H), 2.05 (dq, J=13.2, 6.5 Hz, 1H), 0.98 (d, J=6.8 Hz, 3H), 1.01 (d, J=6.8 Hz, 3H). MS (M+1): 518.

Compound 1-33: (S)-2-(4-((1-((2'-fluoro-4'-(trifluoromethyl)-[1,1'-biphenyl]-4-yl)oxy)-3-methylbutan-2-yl)amino)benzamido)ethane-1-sulfonic Acid

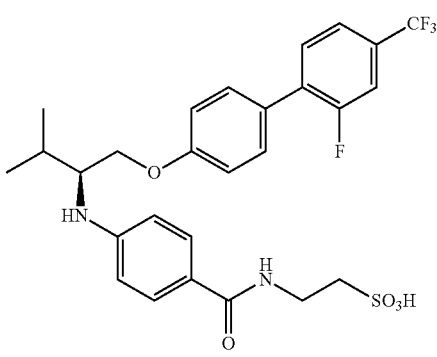 [SMILES: CC(C)[C@@H](COc1ccc(-c2ccc(C(F)(F)F)cc2F)cc1)Nc1ccc(C(=O)NCCS(=O)(=O)O)cc1]

White solid. ¹H-NMR (400 MHz, DMSO-d₆): δ 8.09 (t, J=5.4 Hz, 1H), 7.75-7.71 (m, 2H), 7.64-7.62 (m, 1H), 7.54-7.52 (m, 4H), 7.07 (d, J=8.8 Hz, 2H), 6.67 (d, J=8.8 Hz, 2H), 6.12 (d, J=8.8 Hz, 1H), 4.13-4.02 (m, 2H), 3.70-3.63 (m, 1H), 3.50-3.45 (m, 2H), 2.64 (t, J=6.8 Hz, 2H), 2.10-1.99 (m, 1H), 1.02-0.97 (m, 6H). MS (M+1): 569.

Compound 1-32: (S)-3-(4-((1-(4-(benzo[d]thiazol-2-yl)phenoxy)-3-methylbutan-2-yl)amino)benzamido)propanoic Acid

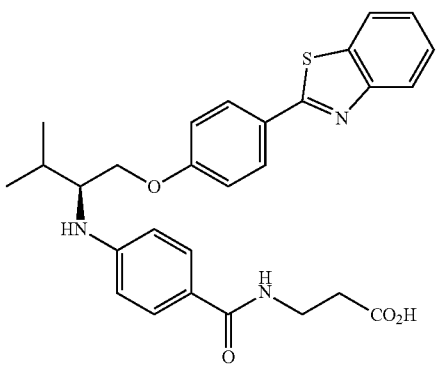

¹H NMR (400 MHz, DMSO-d₆): δ 8.06-8.15 (m, 2H), 7.97-8.05 (m, 3H), 7.55-7.63 (m, J=8.3 Hz, 2H), 7.47-7.54 (m, 1H), 7.38-7.46 (m, 1H), 7.11 (d, J=9.3 Hz, 2H), 6.61-6.71 (m, J=8.8 Hz, 2H), 6.12 (d, J=8.8 Hz, 1H), 4.15 (dd, J=10.0, 4.2 Hz, 1H), 4.07 (dd, J=10.0, 6.1 Hz, 1H), 3.64-3.72 (m, 2H), 3.34-3.42 (m, 2H), 2.35-2.44 (m, 2H), 2.05 (dq, J=12.8, 6.6 Hz, 1H), 1.00 (d, J=5.4 Hz, 3H), 1.00 (d, J=19.1 Hz, 3H). MS (M+1): 504.

Compound 1-34: (R)-3-(4-((1-(4-(benzofuran-2-yl)phenoxy)-3-methylbutan-2-yl)amino)benzamido)propanoic Acid

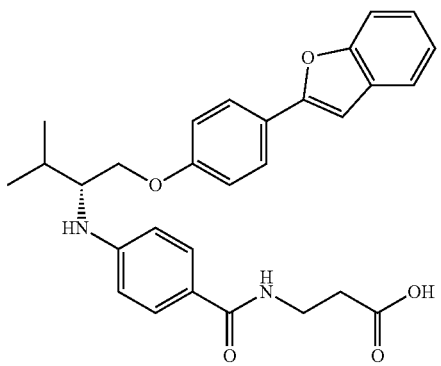 [SMILES: CC(C)[C@H](COc1ccc(-c2cc3ccccc3o2)cc1)Nc1ccc(C(=O)NCCC(=O)O)cc1]

¹HNMR (400 MHz, DMSO-d₆): δ 12.14 (s, 1H), 8.05-8.02 (m, 1H), 7.81-7.85 (m, 2H), 7.57-7.62 (m, 4H), 7.21-7.30 (m, 3H), 7.04-7.07 (m, 2H), 6.66 (d, J=8.8 Hz, 1H), 6.11 (d, J=8.9 Hz, 1H), 4.02-4.14 (m, 2H), 3.64-3.70 (m, 1H), 3.38-3.43 (m, 2H), 2.45-2.47 (m, 2H), 2.01-2.09 (m, 1H), 1.01 (d, J=6.8 Hz, 3H), 0.98 (d, J=6.8 Hz, 3H). MS (M+1): 487.

Compound 1-35: (R)-3-(4-((1-((2'-chloro-4'-(trifluoroethyl)-[1,1'-biphenyl]-4-yl)oxy)-3-methylbutan-2-yl)amino)benzamido)propanoic Acid

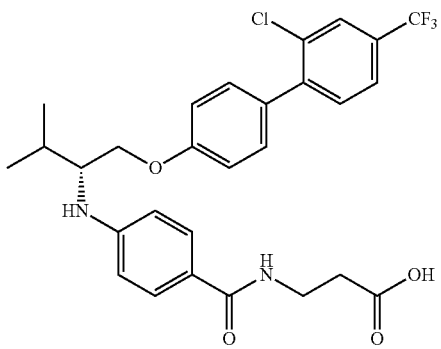 [SMILES: CC(C)[C@H](COc1ccc(-c2ccc(C(F)(F)F)cc2Cl)cc1)Nc1ccc(C(=O)NCCC(=O)O)cc1]

$^1$H NMR (400 MHz, DMSO-d$_6$): δ 8.08 (br. s., 1H), 7.94 (s, 1H), 7.76 (d, J=7.8 Hz, 1H), 7.53-7.63 (m, 3H), 7.35-7.45 (m, 2H), 6.99-7.08 (m, 2H), 6.66 (d, J=8.8 Hz, 2H), 6.10 (d, J=8.8 Hz, 1H), 4.00-4.14 (m, 2H), 3.61-3.72 (m, 2H), 3.39 (d, J=5.4 Hz, 3H), 2.40 (t, J=7.1 Hz, 2H), 1.98-2.11 (m, 1H), 0.94-1.06 (m, 6H). MS (M+1): 549.

Compound 1-37: (S)-3-(4-((1-((2'-chloro-4'-(dimethylamino)-[1,1'-biphenyl]-4-yl)oxy)-3-methylbutan-2-yl)amino)benzamido)propanoic Acid

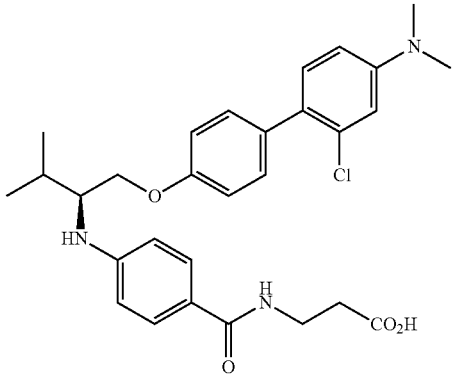

White solid. $^1$H-NMR (400 MHz, DMSO-d$_6$): δ 8.04 (t, J=5.6 Hz, 1H), 7.58 (d, J=8.8 Hz, 2H), 7.26 (d, J=8.8 Hz, 2H), 7.15 (d, J=8.8 Hz, 1H), 6.94 (d, J=8.8 Hz, 2H), 6.76-6.71 (m, 2H), 6.66 (d, J=8.8 Hz, 2H), 6.09 (d, J=8.8 Hz, 1H), 4.06-3.97 (m, 2H), 3.67-3.62 (m, 1H), 2.46 (t, J=6.8 Hz, 2H), 2.08-2.02 (m, 1H), 1.01-0.96 (m, 6H). MS (M+1): 524.

Compound 1-36: (S)-3-(4-((1-((2',4'-dichloro-[1,1'-biphenyl]-4-yl)oxy)-3,3-dimethylbutan-2-yl)amino)benzamido)propanoic Acid

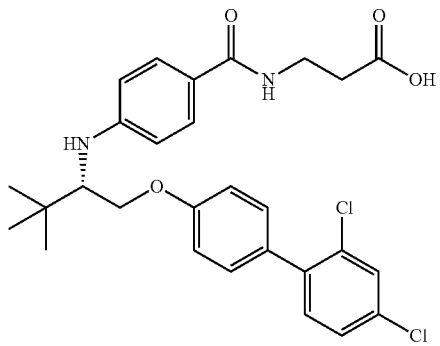 [SMILES: CC(C)(C)[C@@H](COc1ccc(-c2ccc(Cl)cc2Cl)cc1)Nc1ccc(C(=O)NCCC(=O)O)cc1]

$^1$H NMR (400 MHz, DMSO-d$_6$): δ 8.02 (t, 1H), 7.68 (d, J=2.4 Hz, 1H), 7.56 (d, J=8.8 Hz, 2H), 7.43-7.50 (dd, 1H), 7.27-7.42 (d, 3H), 6.91-6.99 (dt, 2H), 6.70 (d, J=8.8 Hz, 2H), 5.99 (d, J=9.8 Hz, 1H), 4.22-4.35 (dd, 1H), 3.88-4.09 (m, 2H), 3.62-3.71 (m, 1H), 2.46 (t, J=7.1 Hz, 2H), 1.02 (s, 9H). MS (M+1): 529.

Compound 1-38: 3-(4-(((2S,3S)-1-((2'-chloro-4'-methoxy-[1,1'-biphenyl]-4-yl)oxy)-3-methylpentan-2-yl)amino)benzamido)propanoic Acid

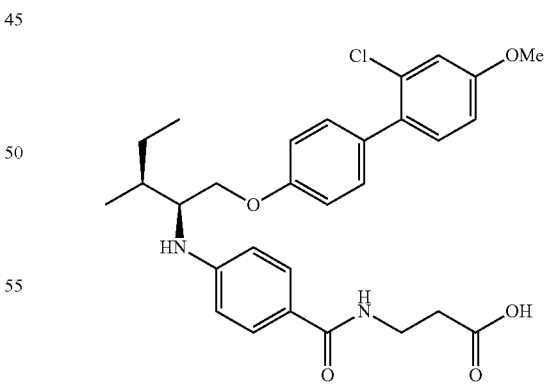

$^1$H NMR (400 MHz, Acetone-d$_6$): δ 7.68 (d, J=8.3 Hz, 2H), 7.45-7.50 (m, 1H), 7.25-7.33 (m, 3H), 7.05 (d, J=2.4 Hz, 1H), 6.92-7.01 (m, 3H), 6.73 (d, J=8.8 Hz, 2H), 5.48-5.56 (m, 1H), 4.18 (dd, J=16.9, 4.6 Hz, 2H), 3.85 (s, 3H), 3.59 (d, J=5.9 Hz, 2H), 2.61 (t, J=6.6 Hz, 2H), 1.88-1.95 (m, 1H), 1.68-1.80 (m, 1H), 1.28-1.41 (m, 1H), 1.05 (d, J=6.8 Hz, 3H), 0.96 (t, J=7.6 Hz, 3H). MS (M+1): 525.

Compound 1-39: (S)-3-(4-((1-(4-(imidazo[1,2-a]pyridin-2-yl)phenoxy)-3-methylbutan-2-yl)amino)benzamido)propanoic Acid

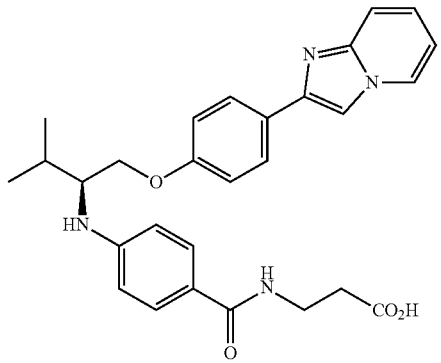 [SMILES: CC(C)[C@@H](COc1ccc(-c2cn3ccccc3n2)cc1)Nc1ccc(C(=O)NCCC(=O)O)cc1]

White solid. ¹H-NMR (400 MHz, DMSO-d₆): δ 8.48 (d, J=7.8 Hz, 1H), 8.26 (s, 1H), 8.03 (t, J=5.6 Hz, 1H), 7.86 (d, J=8.8 Hz, 2H), 7.59 (d, J=8.8 Hz, 2H), 7.53 (d, J=7.8 Hz, 1H), 7.23-7.19 (m, 1H), 6.98 (d, J=8.8 Hz, 2H), 6.86 (t, J=7.8 Hz, 1H), 6.66 (d, J=8.8 Hz, 2H), 6.09 (d, J=8.8 Hz, 1H), 4.11-3.99 (m, 2H), 3.67-3.63 (m, 1H), 2.47 (t, J=6.8 Hz, 2H), 2.08-2.03 (m, 1H), 1.01-0.97 (m, 6H). MS (M+1): 487.

Compound 1-41: (S)-3-(4-((1-(4-(furo[3,2-b]pyridin-2-yl)phenoxy)-3-methylbutan-2-yl)amino)benzamido)propanoic Acid

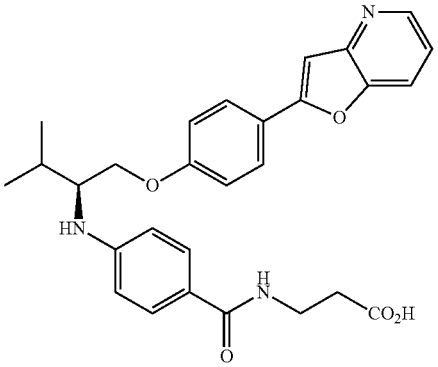

¹H NMR (400 MHz, DMSO-d₆): δ 8.46 (dd, 1H), 8.02-8.09 (m, 1H), 7.98 (d, 1H), 7.91 (dt, 2H), 7.58 (d, 2H), 7.47 (s, 1H), 7.28 m (q, 1H), 7.09 (dt, 2H), 6.66 (d, 2H), 6.12 (d, 1H), 4.01-4.17 (m, 2H), 3.62-3.73 (m, 2H), 2.45 (t, 2H), 2.00-2.11 (m, 1H), 1.24 (s, 1H), 0.99 (m, 6H). MS (M+1): 488.

Compound 1-40: (S)-3-(4-((1-(4-(benzofuran-2-yl)phenoxy)-3,3-dimethylbutan-2-yl)amino)benzamido)propanoic Acid

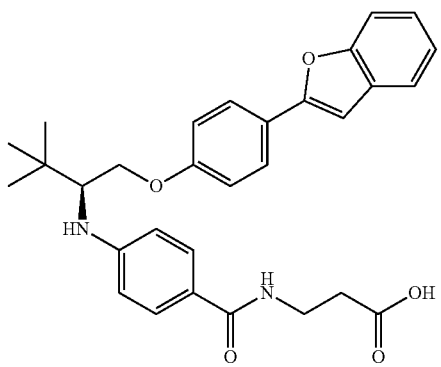 [SMILES: CC(C)(C)[C@@H](COc1ccc(-c2cc3ccccc3o2)cc1)Nc1ccc(C(=O)NCCC(=O)O)cc1]

¹H NMR (400 MHz, DMSO-d₆): δ 8.00-8.07 (m, 1H), 7.81 (d, J=8.8 Hz, 1H), 7.54-7.63 (m, 3H), 7.20-7.31 (m, 2H), 7.00 (d, J=8.8 Hz, 1H), 6.70 (d, J=8.8 Hz, 1H), 5.97-6.03 (m, 1H), 4.27-4.34 (m, 1H), 3.94-4.01 (m, 1H), 3.64-3.72 (m, 1H), 3.40 (d, J=5.4 Hz, 2H), 2.42-2.48 (m, 2H), 1.03 (s, 9H). MS (M+1): 501.

Compound 1-42: (S)-3-(4-((1-((2'-chloro-4'-(trifluoromethyl)-[1,1'-biphenyl]-4-yl)oxy)-3,3-dimethylbutan-2-yl)amino)benzamido)propanoic aid

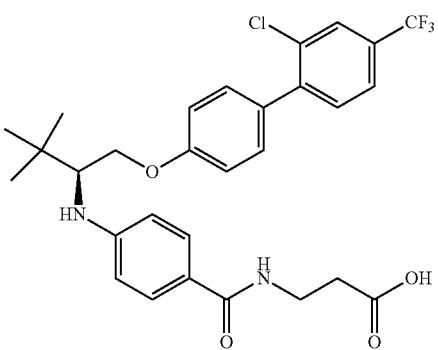 [SMILES: CC(C)(C)[C@@H](COc1ccc(-c2ccc(C(F)(F)F)cc2Cl)cc1)Nc1ccc(C(=O)NCCC(=O)O)cc1]

¹H NMR (400 MHz, CDCl₃): δ 7.69 (s, 1H), 7.58 (d, J=8.3 Hz, 2H), 7.52 (d, J=8.3 Hz, 1H), 7.39 (d, J=7.8 Hz, 1H), 7.32 (d, J=8.8 Hz, 2H), 6.89 (d, J=8.3 Hz, 2H), 6.63 (d, J=8.3 Hz, 3H), 4.20 (dd, J=9.5, 4.2 Hz, 1H), 4.03 (dd, J=9.3, 4.9 Hz, 1H), 3.68 (d, J=4.4 Hz, 2H), 3.57 (t, J=4.6 Hz, 1H), 2.68 (br. s., 2H), 1.07 (s, 9H). MS (M+1): 563.

Compound 1-43: 3-(4-((3-methyl-1-(4-(5-(trifluoromethyl)-1,3,4-oxadiazol-2-yl)phenoxy)butan-2-yl)amino)benzamido)propanoic Acid

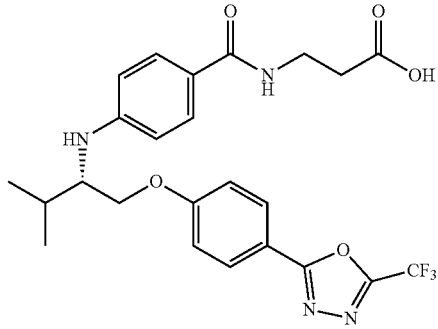 [SMILES: CC(C)[C@@H](COc1ccc(-c2nnc(C(F)(F)F)o2)cc1)Nc1ccc(C(=O)NCCC(=O)O)cc1]

¹H NMR (400 MHz, CDCl₃): δ 7.98 (d, J=8.0 Hz, 2H), 7.58 (d, J=8.8 Hz, 2H), 6.96 (d, J=8.0 Hz, 2H), 6.80 (t, J=5.9 Hz, 1H), 6.58 (d, J=8.8 Hz, 2H), 4.09 (d, J=4.0 Hz, 2H), 3.60-3.72 (m, 2H), 2.64 (t, J=5.6 Hz, 2H), 2.11 (dq, J=13.4, 6.8 Hz, 1H), 0.95-1.09 (m, 6H). MS (M+1): 507.

Compound 1-45: 3-(4-(((2S,3S)-1-(4-(5-(tert-butyl)-1,3,4-oxadiazol-2-yl)phenoxy)-3-methylpentan-2-yl)amino)benzamido)propanoic Acid

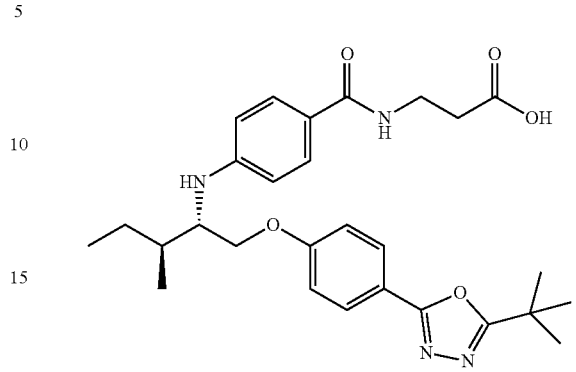

¹H NMR (400 MHz, CDCl₃): δ 7.90 (d, J=8.8 Hz, 2H), 7.58 (d, J=8.8 Hz, 2H), 6.91 (d, J=8.8 Hz, 2H), 6.88-6.81 (m, 1H), 6.56 (d, J=8.3 Hz, 2H), 4.14-4.01 (m, 2H), 3.69-3.58 (m, 3H), 2.67-2.58 (m, 2H), 1.89-1.78 (m, 1H), 1.68-1.57 (m, 1H), 1.44 (s, 9H), 1.30-1.18 (m, 1H), 0.98 (d, J=6.8 Hz, 3H), 0.92 (t, J=7.3 Hz, 3H). MS (M+1): 509.

Compound 1-44: 3-(4-((3-methyl-1-(4-(5-(trifluoromethyl)-1,3,4-oxadiazol-2-yl)phenoxy) pentan-2-yl)amino)benzamido)propanoic Acid

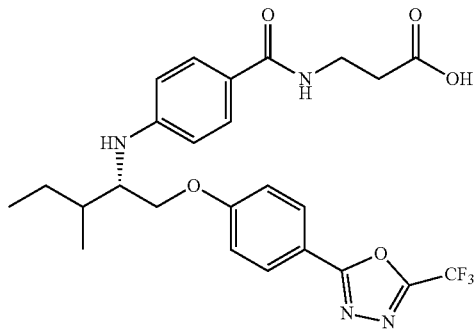 [SMILES: CCC(C)[C@@H](COc1ccc(-c2nnc(C(F)(F)F)o2)cc1)Nc1ccc(C(=O)NCCC(=O)O)cc1]

¹H NMR (400 MHz, CDCl₃): δ 7.97 (d, J=8.0 Hz, 2H), 7.58 (d, J=8.4 Hz, 2H), 6.96 (d, J=8.8 Hz, 2H), 6.85 (t, J=5.4 Hz, 1H), 6.57 (d, J=8.8 Hz, 2H), 4.03-4.15 (m, 2H), 3.59-3.70 (m, 3H), 2.62 (t, J=5.6 Hz, 2H), 1.79-1.89 (m, 1H), 1.51-1.70 (m, 1H), 1.10-1.31 (m, 2H), 0.98 (d, J=6.8 Hz, 3H), 0.88-0.95 (t, J=8.0 Hz, 3H). MS (M+1): 521.

Compound 1-46: 3-(4-(((2S,3S)-3-methyl-1-(4-(5-phenyl-1,3,4-oxadiazol-2-yl)phenoxy)pentan-2-yl)amino)benzamido)propanoic Acid

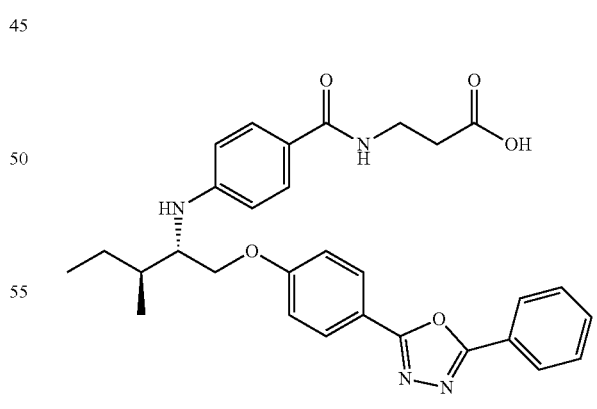

¹H NMR (400 MHz, CDCl₃): δ 8.16-8.05 (m, 2H), 8.04-7.96 (m, 2H), 7.59 (d, J=8.3 Hz, 2H), 7.53-7.42 (m, 3H), 6.95 (d, J=8.8 Hz, 2H), 6.83-6.69 (m, 1H), 6.58 (d, J=8.3 Hz, 2H), 4.16-4.03 (m, 2H), 3.72-3.59 (m, 3H), 2.72-2.60 (m, 2H), 1.91-1.78 (m, 1H), 1.72-1.57 (m, 1H), 1.30-1.19 (m, 1H), 1.00 (d, J=6.8 Hz, 3H), 0.93 (t, J=7.3 Hz, 3H). MS (M+1): 529. HPLC 99%.

Compound 1-47: Ethyl (S)-3-(4-((1-(4-(benzo[d]oxazol-2-yl)phenoxy)-3-methylbutan-2-yl)amino)benzamido)propanoate

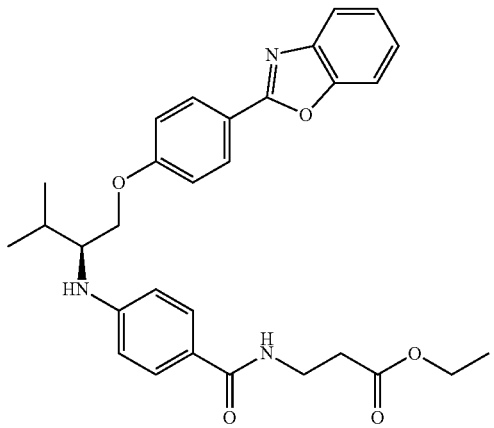 [SMILES: CCOC(=O)CCNC(=O)c1ccc(N[C@H](COc2ccc(-c3nc4ccccc4o3)cc2)C(C)C)cc1]

$^1$H NMR (400 MHz, DMSO-d$_6$): δ 8.09-8.16 (m, 2H), 8.05 (t, J=5.4 Hz, 1H), 7.71-7.79 (m, 2H), 7.54-7.62 (m, 2H), 7.34-7.42 (m, 2H), 7.11-7.18 (m, 2H), 6.61-6.71 (m, J=8.8 Hz, 2H), 6.13 (d, J=9.3 Hz, 1H), 4.14-4.22 (m, 1H), 4.01-4.12 (m, 3H), 3.65-3.75 (m, 1H), 3.38-3.47 (m, 2H), 2.52-2.55 (m, 2H), 2.05 (dq, J=13.2, 6.7 Hz, 1H), 1.17 (t, J=7.1 Hz, 3H), 0.98 (d, J=6.8 Hz, 3H), 1.01 (d, J=6.8 Hz, 3H), MS (M+1): 516. HPLC 95%.

Compound 1-48: (S)-3-(4-((1-(4-(benzo[d]oxazol-2-yl)phenoxy)-3-methylbutan-2-yl)amino)benzamido)propanoic Acid

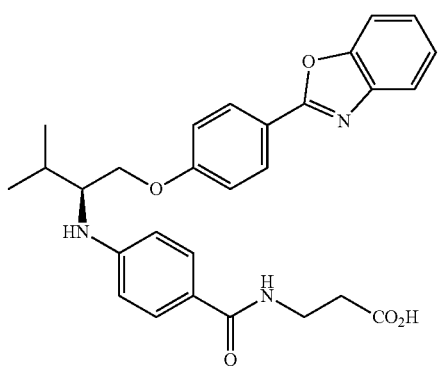 [SMILES: CC(C)[C@@H](COc1ccc(-c2nc3ccccc3o2)cc1)Nc1ccc(C(=O)NCCC(=O)O)cc1]

$^1$H NMR (400 MHz, DMSO-d$_6$): δ 12.16 (br. s., 1H), 8.09-8.15 (m, 2H), 8.04 (t, J=5.6 Hz, 1H), 7.71-7.78 (m, 2H), 7.56-7.63 (m, J=8.8 Hz, 2H), 7.35-7.42 (m, 2H), 7.11-7.18 (m, 2H), 6.67 (d, J=9.3 Hz, 2H), 6.13 (d, J=9.3 Hz, 1H), 4.17 (dd, J=10.0, 4.2 Hz, 1H), 4.08 (dd, J=10.0, 6.1 Hz, 1H), 3.63-3.74 (m, 1H), 3.37-3.45 (m, 2H), 2.42-2.48 (m, 2H), 2.05 (dq, J=12.9, 6.8 Hz, 1H), 1.01 (d, J=6.8 Hz, 3H), 0.98 (d, J=6.8 Hz, 3H). MS (M+1): 488.

Compound 1-49: (S)-3-(4-((1-(4-(5-(tert-butyl)-1,3,4-oxadiazol-2-yl)phenoxy)hexan-2-yl)amino)benzamido)propanoic Acid

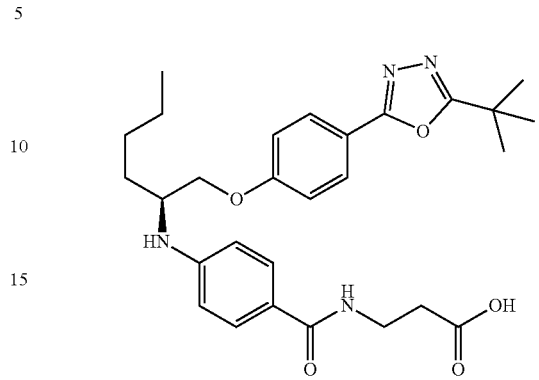

$^1$H NMR (400 MHz, CDCl$_3$): δ 7.91 (d, J=8.8 Hz, 2H), 7.59 (d, J=8.3 Hz, 2H), 6.92 (d, J=9.3 Hz, 2H), 6.83-6.71 (m, 1H), 6.57 (d, J=8.8 Hz, 2H), 4.04-4.00 (m, 2H), 3.81-3.73 (m, 1H), 3.71-3.61 (m, 2H), 2.71-2.59 (m, 2H), 1.87-1.72 (m, 1H), 1.70-1.56 (m, 1H), 1.45 (s, 9H), 1.41-1.28 (m, 4H), 0.89 (t, J=6.6 Hz, 3H). MS (M+1): 509.

Compound 1-50: (S)-3-(4-((1-(4-(5-phenyl-1,3,4-oxadiazol-2-yl)phenoxy)hexan-2-yl)amino) benzamido)propanoic Acid

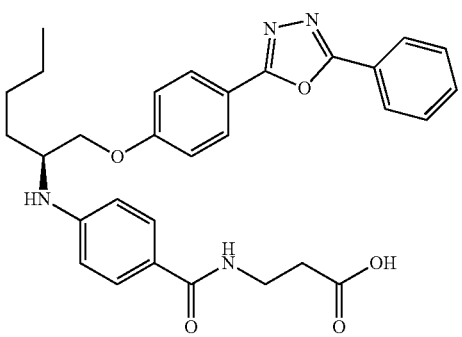 [SMILES: CCCC[C@@H](COc1ccc(-c2nnc(-c3ccccc3)o2)cc1)Nc1ccc(C(=O)NCCC(=O)O)cc1]

$^1$H NMR (400 MHz, CDCl$_3$): δ 8.07 (td, J=2.3, 5.1 Hz, 2H), 8.02-7.95 (m, 2H), 7.59 (d, J=8.3 Hz, 2H), 7.53-7.44 (m, 3H), 6.97-6.81 (m, 3H), 6.60-6.53 (m, 2H), 4.04-3.96 (m, 2H), 3.80-3.72 (m, 1H), 3.69-3.61 (m, 2H), 2.67-2.60 (m, 2H), 1.85-1.73 (m, 1H), 1.60 (d, J=4.9 Hz, 1H), 1.47-1.28 (m, 4H), 0.87 (t, J=7.1 Hz, 3H). MS (M+1): 529.

Compound 1-51: Ethyl (R)-3-(4-((1-(4-(benzo[d]thiazol-2-yl)phenoxy)-3-methylbutan-2-yl)amino)benzamido)propanoate

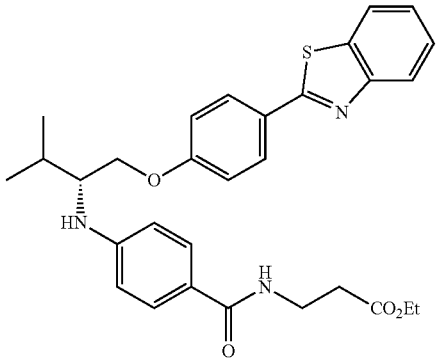

¹H NMR (400 MHz, DMSO-d₆): δ 7.96-8.13 (m, 5H), 7.56-7.64 (m, J=8.8 Hz, 2H), 7.51 (d, J=1.0 Hz, 1H), 7.43 (d, J=8.3 Hz, 1H), 7.06-7.16 (m, 2H), 6.67 (d, J=8.8 Hz, 2H), 6.12 (s, 1H), 4.06 (q, J=6.8 Hz, 4H), 3.64-3.75 (m, 1H), 3.44 (d, J=5.4 Hz, 2H), 2.52-2.56 (m, 2H), 2.05 (dq, J=13.3, 6.7 Hz, 1H), 1.17 (t, J=7.1 Hz, 3H), 1.00 (d, J=4.9 Hz, 3H), 1.00 (d, J=18.6 Hz, 3H). MS (M+1): 532.

Compound 1-53: Ethyl (R)-3-(4-((1-(4-benzo[d]oxazol-2-yl)phenoxy)-3-methylbutan-2-yl)amino)benzamido)propanoate

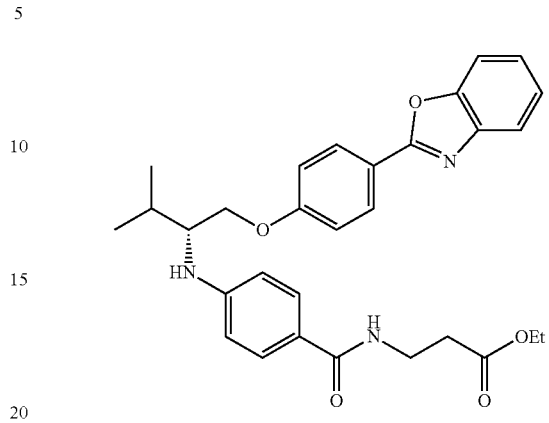

¹H NMR (400 MHz, DMSO-d₆): δ 8.08-8.16 (m, J=8.8 Hz, 2H), 8.00-8.08 (m, 1H), 7.68-7.77 (m, 2H), 7.59 (d, J=8.3 Hz, 2H), 7.33-7.42 (m, 2H), 7.14 (d, J=7.3 Hz, 2H), 6.63-6.72 (m, J=8.8 Hz, 2H), 6.13 (d, J=8.8 Hz, 1H), 4.13-4.22 (m, 1H), 3.98-4.13 (m, 3H), 3.64-3.74 (m, 1H), 3.38-3.48 (m, 2H), 2.52-2.57 (m, 2H), 2.05 (dq, J=13.3, 6.7 Hz, 1H), 1.17 (t, J=7.1 Hz, 3H), 1.00 (dd, J=12.2, 6.8 Hz, 6H). MS (M+1): 516.

Compound 1-52: (R)-3-(4-((1-(4-(benzo[d]thiazol-2-yl)phenoxy)-3-methylbutan-2-yl)amino)benzamido)propanoic Acid

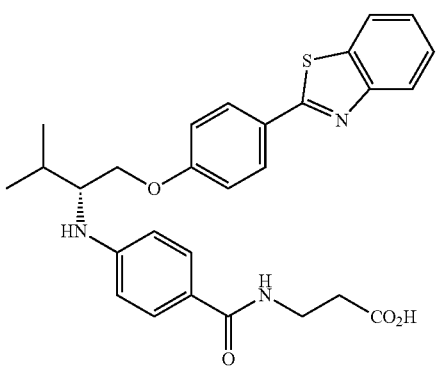 [SMILES: CC(C)[C@H](COc1ccc(-c2nc3ccccc3s2)cc1)Nc1ccc(C(=O)NCCC(=O)O)cc1]

¹H NMR (400 MHz, DMSO-d₆): δ 7.97-8.12 (m, 5H), 7.56-7.63 (m, J=8.8 Hz, 2H), 7.51 (td, J=7.7, 1.2 Hz, 1H), 7.38-7.46 (m, 1H), 7.04-7.14 (m, 2H), 6.67 (d, J=8.8 Hz, 2H), 6.12 (d, J=8.8 Hz, 2H), 4.01-4.18 (m, 2H), 3.63-3.73 (m, 1H), 3.35-3.44 (m, 2H), 2.44 (t, J=7.1 Hz, 2H), 2.05 (dq, J=13.1, 6.7 Hz, 1H), 0.99 (d, J=5.4 Hz, 3H), 0.99 (d, J=19.1 Hz, 3H). MS (M+1): 504.

Compound 1-54: (R)-3-(4-((1-(4-(benzo[d]oxazol-2-yl)phenoxy)-3-methylbutan-2-yl)amino)benzamido)propanoic Acid

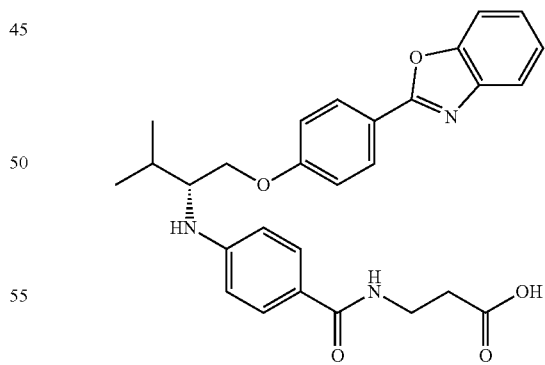

¹H NMR (400 MHz, DMSO-d₆): δ 8.12 (d, J=8.3 Hz, 2H), 8.01-8.08 (m, 1H), 7.70-7.79 (m, 2H), 7.60 (dd, J=8.8, 1.5 Hz, 2H), 7.34-7.42 (m, 2H), 7.14 (dd, J=8.8, 1.5 Hz, 2H), 6.67 (d, J=8.8 Hz, 2H), 6.13 (d, J=8.8 Hz, 1H), 4.16 (d, J=6.8 Hz, 1H), 4.08 (dd, J=9.8, 6.4 Hz, 1H), 3.63-3.73 (m, 1H), 3.36-3.44 (m, 2H), 2.40-2.48 (m, 2H), 2.05 (dq, J=13.3, 6.7 Hz, 1H), 1.01 (d, J=6.4 Hz, 3H), 0.98 (d, J=6.8 Hz, 3H). MS (M+1): 488.

Example 2: Synthesis of Compounds 2-1 to 2-13

Compound 2-1: (R)-3-(4-((1-((2,6-dimethyl-4'-(trifluoromethyl)-[1,1'-biphenyl]-4-yl)oxy)-3-phenylpropan-2-yl)amino)benzamido)propanoic Acid

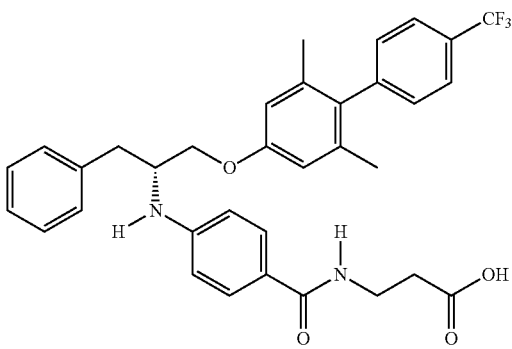 [SMILES: Cc1cc(OC[C@@H](Cc2ccccc2)Nc2ccc(C(=O)NCCC(=O)O)cc2)cc(C)c1-c1ccc(C(F)(F)F)cc1]

¹H NMR (400 MHz, DMSO-d₆): δ 8.03-8.12 (m, 1H), 7.78 (d, J=7.8 Hz, 2H), 7.60 (dd, J=8.8, 2.0 Hz, 2H), 7.23-7.42 (m, 6H), 7.14-7.23 (m, 1H), 6.68-6.76 (m, 2H), 6.65 (d, J=8.8 Hz, 2H), 6.27 (d, J=7.8 Hz, 1H), 3.91-4.09 (m, 3H), 3.40 (d, J=6.4 Hz, 3H), 3.02 (dd, J=13.7, 5.9 Hz, 1H), 2.91 (dd, J=13.7, 7.3 Hz, 1H), 2.40-2.48 (m, 2H), 1.85-1.94 (m, 6H). MS (M+1): 591.

Compound 2-2: (R)-3-(4-((1-((2,6-dimethyl-4'-trifluoromethoxy)-[1,1'-biphenyl]-4-yl)oxy)-3-phenylpropan-2-yl)amino)benzamido)propanoic Acid

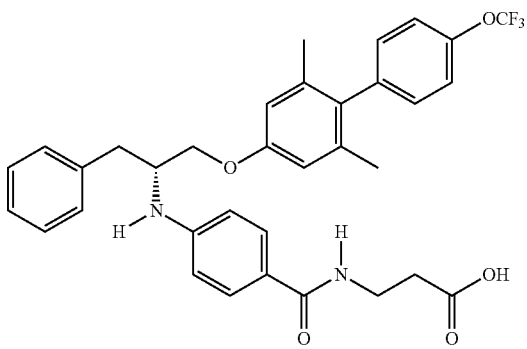 [SMILES: Cc1cc(OC[C@@H](Cc2ccccc2)Nc2ccc(C(=O)NCCC(=O)O)cc2)cc(C)c1-c1ccc(OC(F)(F)F)cc1]

¹H NMR (400 MHz, CDCl₃): δ 7.56-7.64 (m, J=8.8 Hz, 2H), 7.15-7.31 (m, 8H), 7.06-7.13 (m, 2H), 6.80-6.91 (m, 1H), 6.59-6.65 (m, 2H), 6.52-6.59 (m, 2H), 3.86-4.01 (m, 4H), 3.63 (d, J=5.4 Hz, 2H), 3.02 (d, J=6.4 Hz, 2H), 2.59 (br. s., 2H), 1.95 (s, 6H). MS (M+1): 591.

Compound 2-3: (S)-3-(4-((1-((2,6-dimethyl-4'-(trifluoromethoxy)-[1,1'-biphenyl]-4-yl)oxy)-4-methylpentan-2-yl)amino)benzamido)propanoic Acid

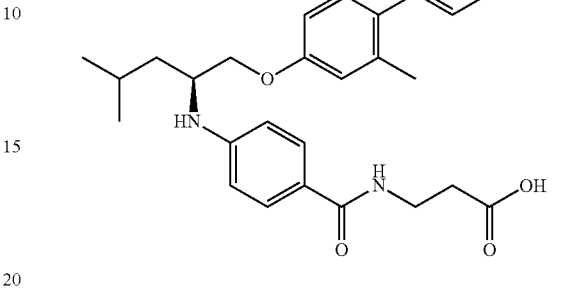

¹H NMR (400 MHz, CDCl₃): δ 7.59 (d, J=7.8 Hz, 2H), 7.36 (br. s., 1H), 7.15-7.21 (m, 2H), 7.01-7.09 (m, 2H), 6.56-6.65 (m, 2H), 6.40-6.48 (m, 2H), 3.93-4.04 (m, 1H), 3.76-3.93 (m, 2H), 3.71 (br. s., 1H), 3.48 (br. s., 2H), 3.28-3.43 (m, 1H), 2.40 (br. s., 2H), 1.88-1.93 (m, 6H), 1.62-1.75 (m, 1H), 0.82-0.92 (m, 6H). MS (M+1): 573.

Compound 2-4: (S)-3-(4-((1-((2,6-dimethyl-4'-(trifluoromethyl)-[1,1'-biphenyl]-4-yl)oxy)-3-methylbutan-2-yl)amino)benzamido)propanoic Acid

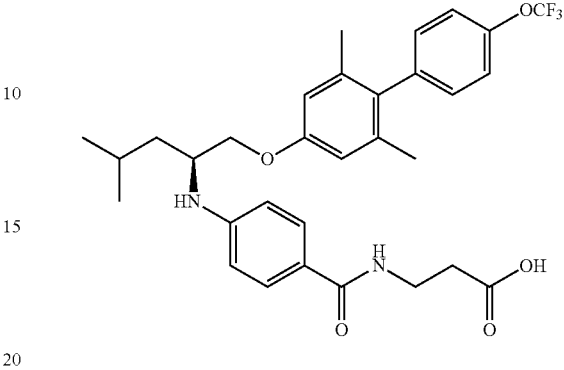

¹H NMR (400 MHz, CDCl₃): δ 7.60 (d, J=8.3 Hz, 2H), 7.63 (d, J=7.8 Hz, 2H), 7.21 (d, J=7.3 Hz, 2H), 6.87 (br. s., 1H), 6.47-6.74 (m, 4H), 5.47 (br. s., 1H), 3.89-4.18 (m, 2H), 3.65 (br. s., 2H), 3.56 (br. s., 1H), 2.64 (br. s., 2H), 2.15 (m, 1H), 1.94 (br. s., 6H), 0.91-1.14 (m, 6H). MS (M+1): 543.

Compound 2-5: (S)-3-(4-((1-((4'-(tert-butyl)-2,6-dimethyl-[1,1'-biphenyl]-4-yl)oxy)-3-methylbutan-2-yl)amino)benzamido)propanoic Acid

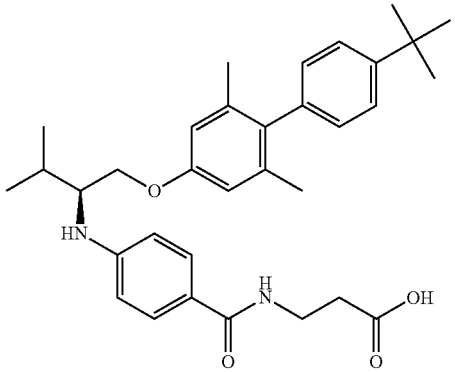 [SMILES: Cc1cc(OC[C@@H](Nc2ccc(C(=O)NCCC(=O)O)cc2)C(C)C)cc(C)c1-c1ccc(C(C)(C)C)cc1]

¹H NMR (400 MHz, CDCl₃): δ 7.59 (d, J=8.8 Hz, 2H), 7.30-7.43 (m, J=7.8 Hz, 2H), 6.93-7.06 (m, J=7.8 Hz, 2H), 6.74-6.84 (m, 1H), 6.49-6.68 (m, 4H), 3.95-4.09 (m, 2H), 3.67 (q, J=5.7 Hz, 2H), 3.48-3.60 (m, 1H), 2.66 (t, J=5.6 Hz, 2H), 2.14 (dq, J=13.4, 6.8 Hz, 1H), 1.98 (s, 6H), 1.34 (s, 9H), 1.03 (dd, J=6.8, 2.0 Hz, 6H). MS (M+1): 531.

Compound 2-7: 3-(4-(((2S,3S)-1-(4-(benzofuran-2-yl)-3,5-dimethylphenoxy)-3-methylpentan-2-yl)amino)benzamido)propanoic Acid

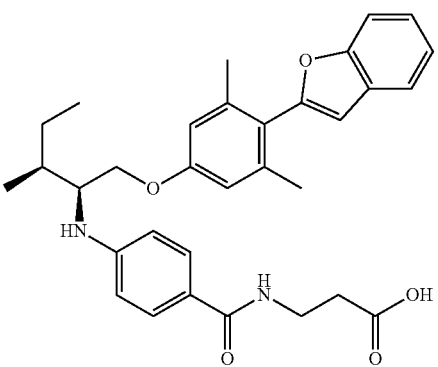

¹H NMR (400 MHz, CDCl₃): δ 7.56-7.62 (m, 3H), 7.47 (d, J=7.8 Hz, 1H), 7.20-7.29 (m, 2H), 6.71 (t, J=6.1 Hz, 1H), 6.63 (s, 2H), 6.56-6.60 (m, 3H), 4.01-4.19 (m, 2H), 3.58-3.72 (m, 3H), 2.66 (t, J=5.9 Hz, 2H), 2.19 (s, 6H), 1.81-1.91 (m, 1H), 1.59-1.71 (m, 1H), 1.19-1.31 (m, 1H), 1.00 (d, J=6.8 Hz, 3H), 0.94 (t, J=7.3 Hz, 3H). MS (M+1): 529.

Compound 2-6: 3-(4-(((2S,3S)-1-((4'-(tert-butyl)-2,6-dimethyl-[1,1'-biphenyl]-4-yl)oxy)-3-methylpentan-2-yl)amino)benzamido)propanoic Acid

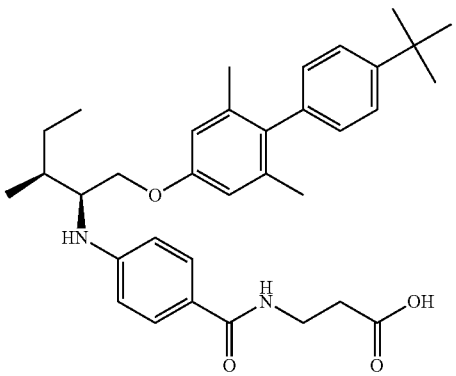 [SMILES: CC[C@H](C)[C@@H](COc1cc(C)c(-c2ccc(C(C)(C)C)cc2)c(C)c1)Nc1ccc(C(=O)NCCC(=O)O)cc1]

¹H NMR (400 MHz, Acetone-d₆): δ 7.66-7.72 (m, 2H), 7.45-7.48 (m, 2H), 7.01-7.06 (m, 2H), 6.73 (d, J=8.8 Hz, 2H), 6.67 (s, 2H), 4.13 (dd, J=12.0, 4.6 Hz, 2H), 3.71-3.82 (m, 1H), 3.59 (t, J=6.8 Hz, 2H), 2.61 (t, J=6.8 Hz, 2H), 1.95 (s, 6H), 1.36 (s, 9H), 1.05 (d, J=6.8 Hz, 3H), 0.93-0.99 (m, 3H).

Compound 2-8: 3-(4-(((2S,3S)-1-((2,6-dimethyl-4'-(trifluoromethoxy)-[1,1'-biphenyl]-4-yl)oxy)-3-methylpentan-2-yl)amino)benzamido)propanoic Acid

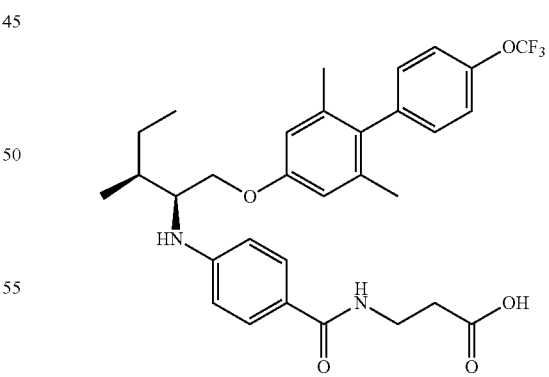

¹H NMR (400 MHz, CDCl₃): δ 7.59 (d, J=8.8 Hz, 2H), 7.22 (d, J=8.3 Hz, 2H), 7.1 (d, J=8.8 Hz, 2H), 6.70-6.82 (m, 1H), 6.62 (s, 2H), 6.58 (d, J=8.3 Hz, 2H), 4.04 (d, J=4.4 Hz, 2H), 3.57-3.71 (m, 3H), 2.65 (t, J=5.6 Hz, 2H), 1.6 (s, 6H), 1.80-1.88 (m, 1H), 1.58-1.74 (m, 1H), 1.19-1.31 (m, 1H), 1.00 (d, J=6.8 Hz, 3H), 0.94 (t, J=7.3 Hz, 3H). MS (M+1): 573.

Compound 2-9: 3-(4-(((2S,3S)-1-((2',4'-dichloro-2,6-dimethyl-[1,1'-biphenyl]-4-yl)oxy)-3-methylpentan-2-yl)amino)benzamido)propanoic Acid

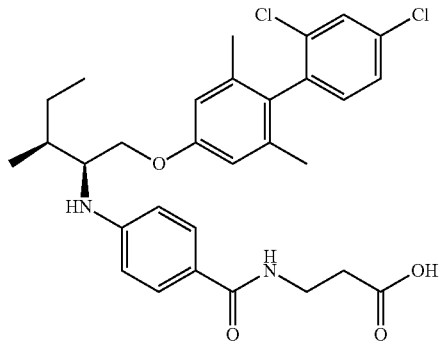 [SMILES: CC[C@H](C)[C@@H](COc1cc(C)c(-c2ccc(Cl)cc2Cl)c(C)c1)Nc1ccc(C(=O)NCCC(=O)O)cc1]

¹H NMR (400 MHz, CDCl₃): δ 7.53-7.60 (m, 2H), 6.76 (br. s., 1H), 6.53-6.64 (m, 4H), 6.48 (s, 2H), 3.98 (d, J=4.4 Hz, 2H), 3.65 (q, J=5.4 Hz, 2H), 3.58 (d, J=6.4 Hz, 1H), 2.63 (t, J=5.6 Hz, 2H), 2.24 (s, 6H), 1.77-1.88 (m, 1H), 1.57-1.68 (m, 1H), 1.15-1.25 (m, 1H), 0.97 (d, J=6.8 Hz, 3H), 0.89-0.94 (m, 3H). MS (M+1): 557.

Compound 2-10: 3-(4-(((2S,3S)-1-((2,6-dimethyl-4'-(trifluoromethyl)-[1,1'-biphenyl]-4-yl)oxy)-3-methylpentan-2-yl)amino)benzamido)propanoic Acid

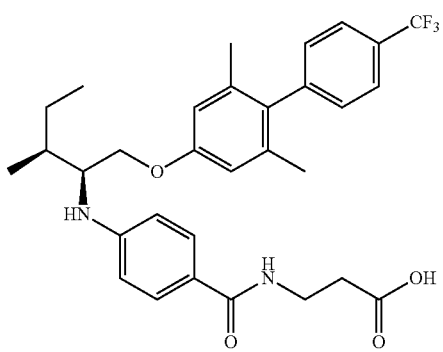 [SMILES: CC[C@H](C)[C@@H](COc1cc(C)c(-c2ccc(C(F)(F)F)cc2)c(C)c1)Nc1ccc(C(=O)NCCC(=O)O)cc1]

¹H NMR (400 MHz, DMSO-d₆): δ 8.00-8.12 (m, 1H), 7.78 (d, J=7.8 Hz, 2H), 7.59 (d, J=8.8 Hz, 2H), 7.35 (d, J=7.8 Hz, 2H), 6.71 (s, 2H), 6.64 (d, J=8.8 Hz, 2H), 6.04-6.19 (m, 1H), 3.94-4.11 (m, 2H), 3.61-3.72 (m, 1H), 3.39 (q, 2H), 2.45 (t, 2H), 1.91 (s, 6H), 1.73-1.84 (m, 1H), 1.56-1.67 (m, 1H), 1.20-1.34 (m, 1H), 0.96 (d, 3H). 0.91 (t, 3H). MS (M+1): 557.

Compound 2-11: (S)-3-(4-((1-((2'-chloro-2,6-dimethyl-4'-(trifluoromethyl)-[1,1'-biphenyl]-4-yl)oxy)-3-methylbutan-2-yl)amino)benzamido)propanoic Acid

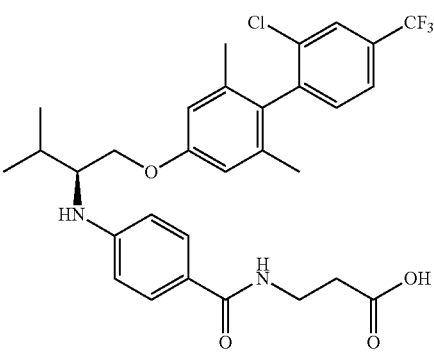 [SMILES: Cc1cc(OC[C@@H](Nc2ccc(C(=O)NCCC(=O)O)cc2)C(C)C)cc(C)c1-c1ccc(C(F)(F)F)cc1Cl]

¹H NMR (400 MHz, DMSO-d₆): δ 8.02 (t, J=5.4 Hz, 1H), 7.53-7.63 (m, 2H), 6.78 (s, 1H), 6.64 (d, J=8.8 Hz, 2H), 6.47-6.57 (m, 1H), 6.03 (dd, J=8.8, 4.9 Hz, 1H), 3.88-4.07 (m, 2H), 3.54-3.68 (m, 1H), 3.38-3.45 (m, 2H), 2.46 (t, J=7.1 Hz, 2H), 2.30 (s, 3H), 2.20 (s, 3H), 1.97-2.07 (m, 1H), 0.90-1.03 (m, 6H).

Compound 2-12: (S)-3-(4-((1-(4-(benzofuran-2-yl)-3,5-dimethylphenoxy)hexan-2-yl)amino)benzamido) propanoic Acid

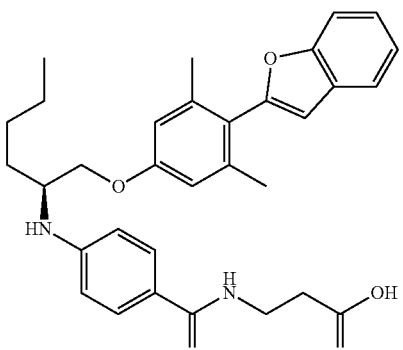

¹H NMR (400 MHz, CDCl₃): δ 7.55-7.65 (m, 3H), 7.47 (d, J=7.8 Hz, 1H), 7.17-7.31 (m, 2H), 6.77-6.88 (m, 1H), 6.53-6.70 (m, 4H), 3.99 (dd, J=8.3, 4.4 Hz, 2H), 3.75 (br. s., 1H), 3.62-3.71 (m, 2H), 2.66 (t, J=5.6 Hz, 2H), 2.20 (s, 6H), 1.72-1.88 (m, 1H), 1.54-1.70 (m, 1H), 1.29-1.51 (m, 4H), 0.90 (t, J=6.8 Hz, 3H); MS (M+1): 529.

Compound 2-13: (S)—N-((1H-tetrazol-5-yl)methyl)-4-((1-(4-(benzofuran-2-yl)-3,5-dimethylphenoxy)hexan-2-yl)amino)benzamide

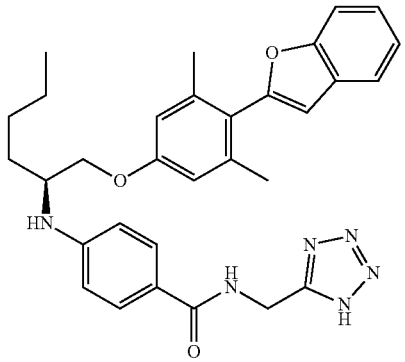 [SMILES: CCCC[C@@H](COc1cc(C)c(-c2cc3ccccc3o2)c(C)c1)Nc1ccc(C(=O)NCc2nnn[nH]2)cc1]

¹H NMR (400 MHz, DMSO-d₆): δ 8.77 (t, J=5.6 Hz, 1H), 7.62-7.70 (m, 3H), 7.56 (d, J=8.3 Hz, 1H), 7.22-7.32 (m, 2H), 6.86 (s, 1H), 6.76 (s, 2H), 6.67 (d, J=8.8 Hz, 2H), 6.22 (d, J=8.3 Hz, 1H), 4.70 (d, J=5.9 Hz, 2H), 3.95-4.03 (m, 2H), 3.74-3.86 (m, 1H), 2.15 (s, 6H), 1.68-1.80 (m, 1H), 1.50-1.64 (m, 1H), 1.27-1.50 (m, 4H), 0.88 (t, J=7.1 Hz, 3H); MS (M+1): 539.

Compound 3-2: (R)-3-(4-(((S)-1-((2,2'-dichloro-4'-(trifluoromethyl)-[1,1'-biphenyl]-4-yl)oxy)-3-methylbutan-2-yl)amino)benzamido)-2-hydroxypropanoic Acid

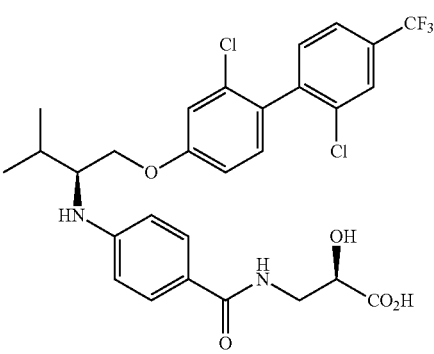

White solid. ¹H NMR (400 MHz, DMSO-d₆): δ 8.10-8.07 (m, 1H), 7.98 (s, 1H), 7.79 (d, J=7.8 Hz, 1H), 7.59-7.53 (m, 3H), 7.27 (d, J=8.8 Hz, 1H), 7.23-7.19 (m, 1H), 7.04-7.01 (m, 1H), 6.68-6.63 (m, 2H), 6.15-6.07 (m, 1H), 4.15-3.98 (m, 3H), 3.67-3.60 (m, 3H), 2.06-2.01 (m, 1H), 1.02-0.94 (m, 6H). MS (M+1): 599.

Example 3: Synthesis of Compounds 3-1 to 3-24

Compound 3-1: N-((1H-tetrazol-5-yl)methyl)-4-(((2S,3S)-1-(4-(benzofuran-2-yl)-3-chlorophenoxy)-3-methylpentan-2-yl)amino)benzamide

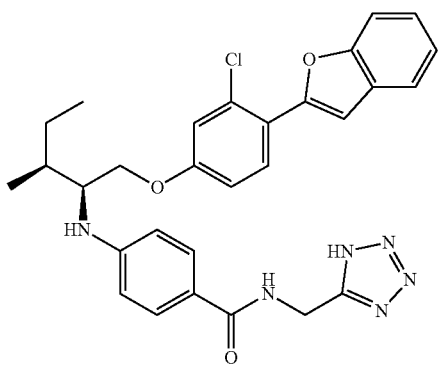 [SMILES: CC[C@H](C)[C@@H](COc1ccc(-c2cc3ccccc3o2)c(Cl)c1)Nc1ccc(C(=O)NCc2nnn[nH]2)cc1]

White solid. ¹H NMR (400 MHz, DMSO-d₆): δ 8.68 (t, J=5.9 Hz, 1H), 7.91 (d, J=8.8 Hz, 1H), 7.70-7.60 (m, 4H), 7.43 (s, 1H), 7.34 (t, J=8.3 Hz, 1H), 7.27 (t, J=8.3 Hz, 1H), 7.22 (d, J=2.5 Hz, 1H), 7.09 (dd, J=8.8, 2.5 Hz, 1H), 6.67 (d, J=8.8 Hz, 2H), 6.26 (d, J=8.8 Hz, 1H), 4.67 (d, J=5.9 Hz, 2H), 4.21-4.07 (m, 2H), 3.75-3.68 (m, 1H), 1.78-1.70 (m, 1H), 1.64-1.59 (m, 1H), 1.30-1.26 (m, 1H), 0.96 (d, J=6.9 Hz, 3H), 0.90 (t, J=7.3 Hz, 3H). MS (M+1): 545.

Compound 3-3: (S)—N-((1H-tetrazol-5-yl)methyl)-4-((1-((2,2'-dichloro-4'-(trifluoromethyl)-[1,1'-biphenyl]-4-yl)oxy)-3-methylbutan-2-yl)amino)benzamide

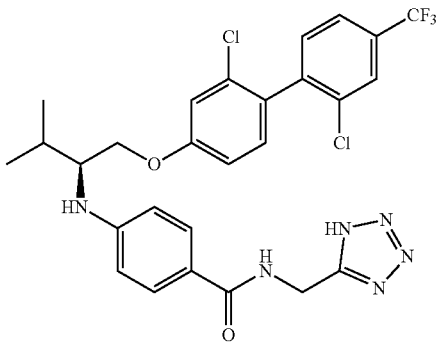 [SMILES: CC(C)[C@@H](COc1ccc(-c2ccc(C(F)(F)F)cc2Cl)c(Cl)c1)Nc1ccc(C(=O)NCc2nnn[nH]2)cc1]

White solid. ¹H NMR (400 MHz, DMSO-d₆): δ 8.72-8.69 (m, 1H), 7.99 (s, 1H), 7.79 (d, J=7.8 Hz, 1H), 7.67-7.55 (m, 3H), 7.29-7.18 (m, 2H), 7.05-7.00 (m, 1H), 6.69 (d, J=8.8 Hz, 2H), 6.20 (d, J=8.8 Hz, 1H), 4.67 (d, J=4.9 Hz, 2H), 4.17-4.06 (m, 2H), 3.71-3.65 (m, 1H), 2.06-2.03 (m, 1H), 1.02-0.98 (m, 6H). MS (M+1): 593.

Compound 3-4: (S)-3-(4-((1-((2,2'-dichloro-4'-(trifluoromethyl)-[1,1'-biphenyl]-4-yl)oxy)-3-methylbutan-2-yl)amino)benzamido)propanoic Acid

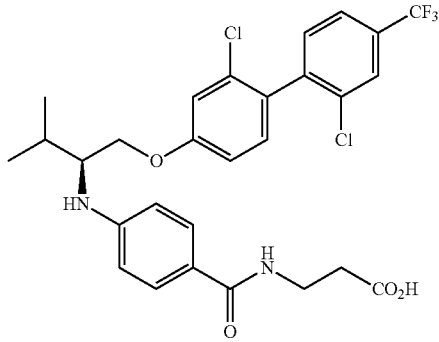 [SMILES: CC(C)[C@@H](COc1ccc(-c2ccc(C(F)(F)F)cc2Cl)c(Cl)c1)Nc1ccc(C(=O)NCCC(=O)O)cc1]

White solid. ¹HNMR (400 MHz, DMSO-$d_6$): δ 8.17 (pseudo-brs, 1H), 7.99 (d, J=1.5 Hz, 1H), 7.79 (dd, J=8, 1.5 Hz, 1H), 7.61-7.55 (m, 3H), 7.28-7.18 (m, 2H), 7.01 (dt, J=8, 3 Hz, 1H), 6.66 (d, J=8.8 Hz, 2H), 6.10 (d, J=8.8 Hz, 1H), 4.12-4.05 (m, 2H), 3.38-3.35 (m, 3H), 3.42-3.37 (m, 2H), 2.29 (t, J=8.8 Hz, 2H), 2.09-2.00 (m, 1H), 1.02-0.97 (m, 6H). MS (M+1): 583.

Compound 3-6: (R)-3-(4-(((S)-1-(4-(benzofuran-2-yl)-3-chlorophenoxy)-3-methylbutan-2-yl)amino)benzamido)-2-hydroxypropanoic Acid

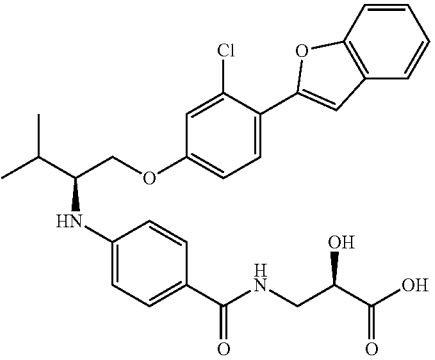

White solid. ¹H NMR (400 MHz, DMSO-$d_6$): δ 8.10 (dd, J=8.8, 3 Hz, 1H), 7.90 (d, J=8.8 Hz, 1H), 7.69 (d, J=8, 1H), 7.62-7.56 (m, 3H), 7.43 (d, J=1.5 Hz, 1H), 7.34 (dt, J=8, 1.5 Hz, 1H), 7.27 (dt, J=8.8, 1.5 Hz, 1H), 7.22 (d, J=3 Hz, 1H), 7.09 (dd, J=8.8, 3 Hz, 1H), 6.67 (d, J=8.8 Hz, 2H), 6.13 (d, J=8.8 Hz, 1H), 4.17-4.05 (m, 2H), 3.69-3.60 (m, 2H), 3.44-3.38 (m, 1H), 3.21-3.17 (m, 1H), 2.06-2.01 (m, 1H), 1.02-0.97 (m, 6H). MS (M+1): 537.

Compound 3-5: (S)—N-((1H-tetrazol-5-yl)methyl)-4-((1-(4-(benzofuran-2-yl)-3-chlorophenoxy)-3-methylbutan-2-yl)amino)benzamide

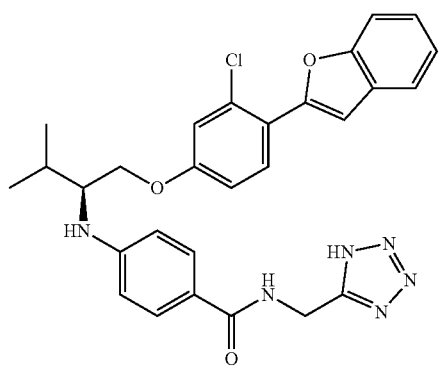 [SMILES: CC(C)[C@@H](COc1ccc(-c2cc3ccccc3o2)c(Cl)c1)Nc1ccc(C(=O)NCc2nnn[nH]2)cc1]

White solid. ¹H NMR (400 MHz, DMSO-$d_6$): δ 8.64 (t, J=5.9 Hz, 1H), 7.90 (d, J=8.8 Hz, 1H), 7.70-7.60 (m, 4H), 7.43 (s, 1H), 7.34 (t, J=8.3 Hz, 1H), 7.27 (t, J=8.3 Hz, 1H), 7.22 (d, J=2.5 Hz, 1H), 7.09 (dd, J=8.8, 2.5 Hz, 1H), 6.69 (d, J=8.8 Hz, 2H), 6.19 (d, J=8.8 Hz, 1H), 4.67 (d, J=5.9 Hz, 2H), 4.19-4.06 (m, 2H), 3.72-3.65 (m, 1H), 2.08-2.01 (m, 1H), 1.02-0.97 (m, 6H). MS (M+1): 531.

Compound 3-7: (S)-3-(4-((1-(4-(benzofuran-2-yl)-3-chlorophenoxy)-3-methylbutan-2-yl)amino)benzamido)propanoic Acid

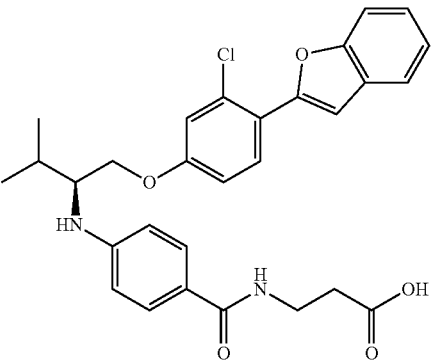 [SMILES: CC(C)[C@@H](COc1ccc(-c2cc3ccccc3o2)c(Cl)c1)Nc1ccc(C(=O)NCCC(=O)O)cc1]

White solid. ¹H NMR (400 MHz, DMSO-$d_6$): δ 8.12 (t, J=5.9 Hz, 1H), 7.89 (d, J=8.8 Hz, 1H), 7.69 (d, J=7.8 Hz, 1H), 7.62-7.58 (m, 3H), 7.42 (s, 1H), 7.33 (dt, J=8.3 Hz, 1H), 7.27 (t, J=8 Hz, 1H), 7.21 (d, J=3 Hz, 1H), 7.08 (dd, J=8.8, 2.5 Hz, 1H), 6.66 (d, J=8.8 Hz, 2H), 6.10 (d, J=8.8 Hz, 1H), 4.17-4.05 (m, 2H), 3.68-3.64 (m, 1H), 3.40-3.35 (m, 2H), 2.31 (t, J=8.8 Hz, 2H), 2.05-2.00 (m, 1H), 1.02-0.96 (m, 6H). MS (M+1): 521.

Compound 3-8: (S)-3-(4-((1-((2,2'-dichloro-4'-(trifluoromethyl)-[1,1'-biphenyl]-4-yl)oxy)hexan-2-yl)amino)benzamido)propanoic Acid

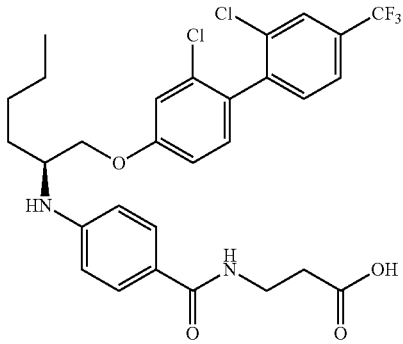 [SMILES: CCCC[C@@H](COc1ccc(-c2ccc(C(F)(F)F)cc2Cl)c(Cl)c1)Nc1ccc(C(=O)NCCC(=O)O)cc1]

¹H NMR (400 MHz, CDCl₃): δ 7.71 (d, J=1.0 Hz, 1H), 7.60 (d, J=8.3 Hz, 2H), 7.54 (d, J=8.1, 1.2 Hz, 1H), 7.35 (d, J=7.8 Hz, 1H), 7.12 (d, J=8.8 Hz, 1H), 7.01 (d, J=2.4 Hz, 1H), 6.84 (dd, J=8.6, 2.7 Hz, 1H), 6.70 (t, J=6.1 Hz, 1H), 6.59 (d, J=8.8 Hz, 2H), 3.96-4.04 (m, 2H), 3.74-3.81 (m, 1H), 3.68 (q, J=5.9 Hz, 2H), 2.67 (t, J=5.9 Hz, 2H), 1.76-1.86 (m, 1H), 1.57-1.68 (m, 1H), 1.31-1.49 (m, 4H), 0.90 (t, J=7.1 Hz, 3H). MS (M+1): 597.

Compound 3-10: (S)-3-(4-((1-(4-(benzofuran-2-yl)-3-chlorophenoxy)hexan-2-yl)amino)benzamido)propanoic Acid

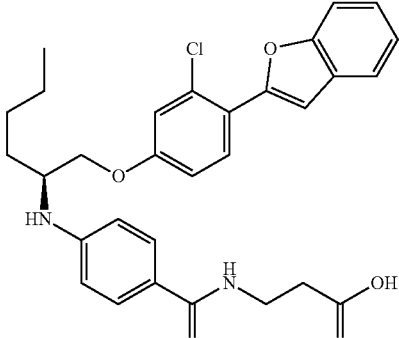

¹H NMR (400 MHz, CDCl₃): δ 7.90 (d, J=8.8 Hz, 1H), 7.55-7.62 (m, 2H), 7.47 (d, J=8.3 Hz, 1H), 7.34 (s, 1H), 7.17-7.29 (m, 2H), 6.98 (d, J=2.4 Hz, 1H), 6.86 (dd, J=8.8, 2.4 Hz, 1H), 6.78 (t, J=5.9 Hz, 1H), 6.57 (d, J=8.8 Hz, 2H), 3.90-4.01 (m, 2H), 3.70-3.77 (m, 1H), 3.66 (q, J=5.9 Hz, 2H), 2.65 (t, J=5.6 Hz, 2H), 1.72-1.83 (m, 1H), 1.53-1.65 (m, 1H), 1.30-1.45 (m, 4H), 0.88 (t, J=7.1 Hz, 3H). MS (M+1): 535.

Compound 3-9: (S)—N-((1H-tetrazol-5-yl)methyl)-4-((1-((2,2'-dichloro-4'-(trifluoromethyl)-[1,1'-biphenyl]-4-yl)oxy)hexan-2-yl)amino)benzamide

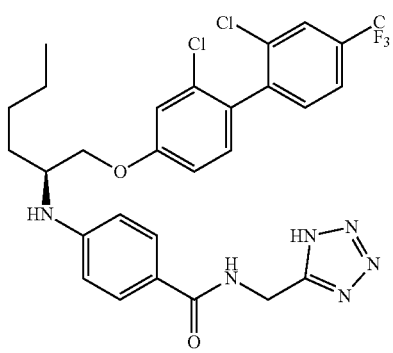 [SMILES: CCCC[C@@H](COc1ccc(-c2ccc(C(F)(F)F)cc2Cl)c(Cl)c1)Nc1ccc(C(=O)NCc2nnn[nH]2)cc1]

¹H NMR (400 MHz, DMSO-d₆): δ 8.77 (t, J=5.6 Hz, 1H), 7.99 (d, J=1.0 Hz, 1H), 7.79 (dd, J=8.1, 1.2 Hz, 1H), 7.67 (d, J=8.8 Hz, 2H), 7.56 (d, J=7.8 Hz, 1H), 7.28 (d, J=8.8 Hz, 1H), 7.16-7.20 (m, 1H), 6.99-7.05 (m, 1H), 6.67 (d, J=8.8 Hz, 2H), 6.24 (d, J=8.3 Hz, 1H), 4.69 (d, J=5.9 Hz, 2H), 4.05 (d, J=5.4 Hz, 2H), 3.77-3.87 (m, 1H), 1.67-1.79 (m, 1H), 1.53-1.64 (m, 1H), 1.27-1.50 (m, 4H), 0.88 (t, J=7.1 Hz, 3H). MS (M+1): 606.

Compound 3-11: (S)—N-((1H-tetrazol-5-yl)methyl)-4-((1-(4-(benzofuran-2-yl)-3-chlorophenoxy) hexan-2-yl)amino)benzamide

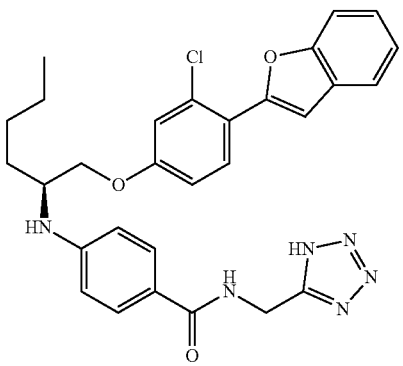 [SMILES: CCCC[C@@H](COc1ccc(-c2cc3ccccc3o2)c(Cl)c1)Nc1ccc(C(=O)NCc2nnn[nH]2)cc1]

¹H NMR (400 MHz, DMSO-d₆): δ 8.69 (t, J=5.4 Hz, 1H), 7.91 (d, J=8.8 Hz, 1H), 7.64-7.71 (m, 3H), 7.61 (d, J=8.3 Hz, 1H), 7.43 (s, 1H), 7.24-7.37 (m, 2H), 7.21 (d, J=2.4 Hz, 1H), 7.09 (dd, J=8.8, 2.4 Hz, 1H), 6.66 (d, J=8.8 Hz, 2H), 6.22 (d, J=8.3 Hz, 1H), 4.67 (d, J=5.4 Hz, 2H), 4.06 (d, J=4.9 Hz, 2H), 3.77-3.86 (m, 1H), 1.66-1.79 (m, 1H), 1.58 (td, J=8.7, 4.6 Hz, 1H), 1.28-1.49 (m, 4H), 0.87 (t, J=7.1 Hz, 3H); MS (M+1): 545.

Compound 3-12: (S)-3-(4-((1-((2,2',4'-trichloro-[1,1'-biphenyl]-4-yl)oxy)hexan-2-yl)amino) benzamido)propanoic Acid

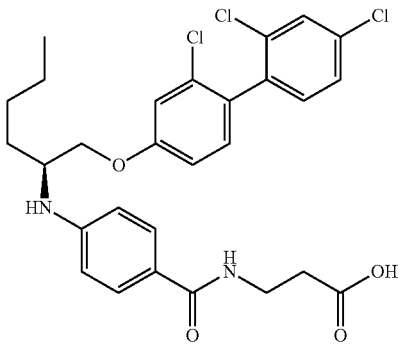 [SMILES: CCCC[C@@H](COc1ccc(-c2ccc(Cl)cc2Cl)c(Cl)c1)Nc1ccc(C(=O)NCCC(=O)O)cc1]

¹H NMR (400 MHz, CDCl₃): δ 7.59 (d, J=8.8 Hz, 2H), 7.46 (d, J=2.0 Hz, 1H), 7.26 (dd, J=8.3, 2.0 Hz, 1H), 7.09-7.17 (m, 2H), 6.98 (d, J=2.4 Hz, 1H), 6.82 (dd, J=8.3, 2.4 Hz, 1H), 6.72 (t, J=5.9 Hz, 1H), 6.58 (d, J=8.8 Hz, 2H), 3.95-4.03 (m, 2H), 3.73-3.80 (m, 1H), 3.67 (q, J=5.9 Hz, 2H), 2.66 (t, J=5.9 Hz, 2H), 1.75-1.87 (m, 1H), 1.57-1.68 (m, 1H), 1.31-1.48 (m, 4H), 0.89 (t, J=7.1 Hz, 3H); MS (M+1): 563.

Compound 3-13: (S)—N-((1H-tetrazol-5-yl)methyl)-4-((1-((2,2',4'-trichloro-[1,1'-biphenyl]-4-yl)oxy)hexan-2-yl)amino)benzamide

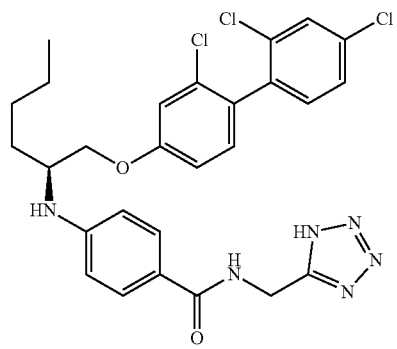 [SMILES: CCCC[C@@H](COc1ccc(-c2ccc(Cl)cc2Cl)c(Cl)c1)Nc1ccc(C(=O)NCc2nnn[nH]2)cc1]

¹H NMR (400 MHz, DMSO-d₆): δ 8.76 (t, J=5.4 Hz, 1H), 7.73 (d, J=2.0 Hz, 1H), 7.67 (d, J=8.3 Hz, 2H), 7.49 (dd, J=8.3, 2.4 Hz, 1H), 7.33 (d, J=8.4 Hz, 1H), 7.21-7.27 (m, 1H), 7.15 (d, J=2.0 Hz, 1H), 6.97-7.01 (m, 1H), 6.67 (d, J=8.8 Hz, 2H), 6.22 (d, J=8.3 Hz, 1H), 4.69 (d, J=5.4 Hz, 2H), 4.04 (d, J=4.9 Hz, 2H), 3.76-3.86 (m, 1H), 1.72 (td, J=9.2, 5.1 Hz, 1H), 1.51-1.63 (m, 1H), 1.26-1.49 (m, 4H), 0.88 (t, J=7.1 Hz, 3H); MS (M+1): 573.

Compound 3-14: (S)-3-(4-((1-(4-(benzofuran-2-yl)-2,5-dichlorophenoxy)-3-methylbutan-2-yl)amino)benzamido)propanoic Acid

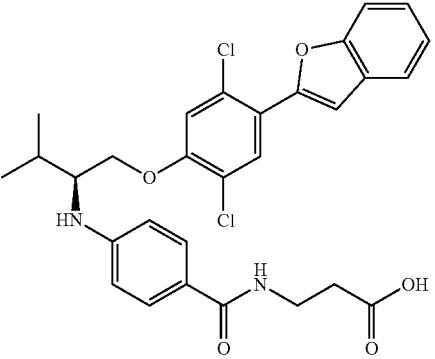 [SMILES: CC(C)[C@@H](COc1cc(Cl)c(-c2cc3ccccc3o2)cc1Cl)Nc1ccc(C(=O)NCCC(=O)O)cc1]

¹H NMR (400 MHz, DMSO-d₆): δ 7.98 (s, 1H), 7.57-7.76 (m, 4H), 7.50 (d, J=6.8 Hz, 2H), 7.24-7.39 (m, 2H), 6.69 (d, J=8.8 Hz, 2H), 6.03 (d, J=8.8 Hz, 1H), 4.10-4.31 (m, 2H), 3.66-3.74 (m, 1H), 3.36-3.47 (m, 2H), 2.44-2.48 (m, 1H), 2.02-2.16 (m, 1H), 1.01 (dd, J=8.8, 6.8 Hz, 6H). MS (M+1): 521.

Compound 3-15: 3-(4-((2-((2'-chloro-4'-(trifluoromethyl)-[1,1'-biphenyl]-4-yl)oxy)-1-phenylethyl)amino)benzamido)propanoic Acid

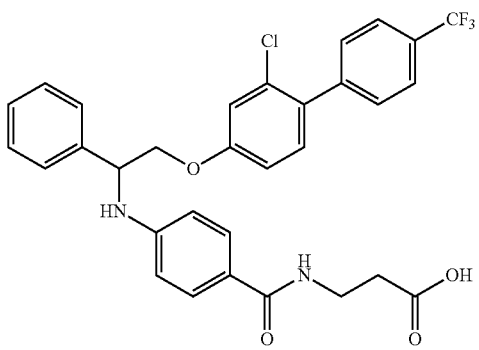 [SMILES: O=C(O)CCNC(=O)c1ccc(NC(COc2ccc(-c3ccc(C(F)(F)F)cc3)c(Cl)c2)c2ccccc2)cc1]

¹H NMR (400 MHz, CDCl₃): δ 7.69-7.72 (m, 1H), 7.48-7.54 (m, 3H), 7.24-7.44 (m, 8H), 6.94-6.98 (m, 2H), 6.64 (t, J=6.1 Hz, 1H), 6.49-6.56 (m, 2H), 4.80 (dd, J=7.8, 3.9 Hz, 1H), 4.29 (dd, J=9.8, 3.9 Hz, 1H), 4.01-4.19 (m, 1H), 3.63 (q, J=5.9 Hz, 2H), 2.62 (t, J=5.9 Hz, 2H). MS (M+1): 583.

Compound 3-16: (S)-3-(4-((1-((2-chloro-4'-(trifluoromethyl)-[1,1'-biphenyl]-4-yl)oxy)hexan-2-yl)amino)benzamido)propanoic Acid

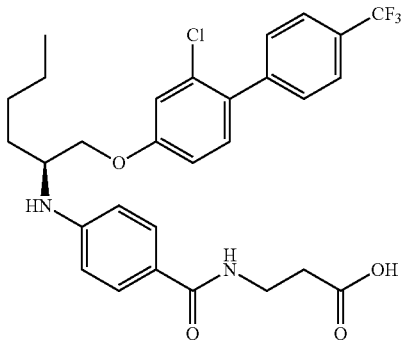 [SMILES: CCCC[C@@H](COc1ccc(-c2ccc(C(F)(F)F)cc2)c(Cl)c1)Nc1ccc(C(=O)NCCC(=O)O)cc1]

¹H NMR (400 MHz, CDCl₃): δ 7.60 (d, J=8.8 Hz, 2H), 7.36-7.41 (m, 2H), 7.16-7.25 (m, 3H), 6.96-7.00 (m, 1H), 6.86 (t, J=5.9 Hz, 1H), 6.82 (dd, J=8.8, 2.4 Hz, 1H), 6.58 (d, J=8.8 Hz, 2H), 3.93-4.03 (m, 2H), 3.71-3.80 (m, 1H), 3.66 (q, J=5.9 Hz, 2H), 2.64 (t, J=5.9 Hz, 2H), 1.73-1.86 (m, 1H), 1.55-1.67 (m, 1H), 1.30-1.48 (m, 4H), 0.89 (t, J=7.1 Hz, 3H). MS (M+1): 563.

Compound 3-17: (S)—N-((1H-tetrazol-5-yl)methyl)-4-((1-((2-chloro-4'-(trifluoromethyl)-[1,1'-biphenyl]-4-yl)oxy)hexan-2-yl)amino)benzamide

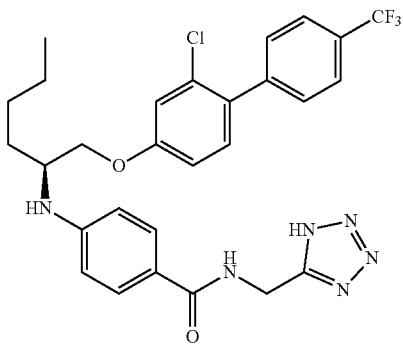 [SMILES: CCCC[C@@H](COc1ccc(-c2ccc(C(F)(F)F)cc2)c(Cl)c1)Nc1ccc(C(=O)NCc2nnn[nH]2)cc1]

¹H NMR (400 MHz, DMSO-d₆): δ 8.76 (t, J=5.6 Hz, 1H), 7.64-7.71 (m, 2H), 7.47-7.56 (m, 2H), 7.39-7.45 (m, 2H), 7.30-7.38 (m, 1H), 7.09-7.16 (m, 1H), 6.96-7.06 (m, 1H), 6.67 (d, J=8.8 Hz, 2H), 6.21 (d, J=8.8 Hz, 1H), 4.69 (d, J=5.9 Hz, 2H), 4.03 (d, J=4.9 Hz, 2H), 3.73-3.87 (m, 1H), 1.63-1.79 (m, 1H), 1.51-1.63 (m, 1H), 1.20-1.45 (m, 4H), 0.88 (t, J=7.1 Hz, 3H). MS (M+1): 573.

Compound 3-18: (S)-2-(4-((1-(4-(benzofuran-2-yl)-3-chlorophenoxy)-3-methylbutan-2-yl)amino)benzamido)ethane-1-sulfonic Acid

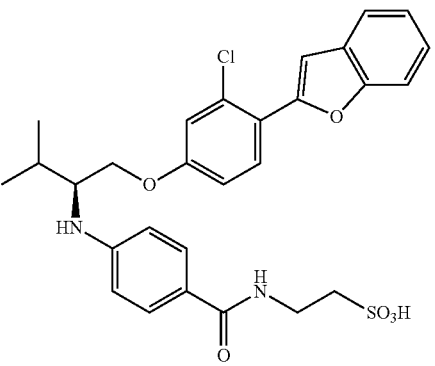 [SMILES: CC(C)[C@@H](COc1ccc(-c2cc3ccccc3o2)c(Cl)c1)Nc1ccc(C(=O)NCCS(=O)(=O)O)cc1]

White solid. ¹HNMR (400 MHz, DMSO-d₆): δ 8.13 (t, J=5.4 Hz, 1H), 7.89 (d, J=8.8 Hz, 1H), 7.68 (d, J=8.3 Hz, 1H), 7.61-7.55 (m, 3H), 7.41 (s, 1H), 7.32 (dt, J=8, 1.5 Hz, 1H), 7.27-7.24 (m, 1H), 7.19 (d, J=2.4 Hz, 1H), 7.07 (dd, J=8.8, 3 Hz, 1H), 6.67 (d, J=8.8 Hz, 2H), 6.16 (d, J=8 Hz, 1H), 4.15-4.06 (m, 2H), 3.64 (brs, 1H), 3.53-3.48 (m, 2H), 2.69 (t, J=6.8 Hz, 2H), 2.05-2.00 (m, 1H), 1.00-0.95 (m, 6H). MS (M+1): 558.

Compound 3-19: 3-(4-(((2S,3S)-1-(4-(benzofuran-2-yl)-2,5-dichlorophenoxy)-3-methylpentan-2-yl)amino)benzamido)propanoic Acid

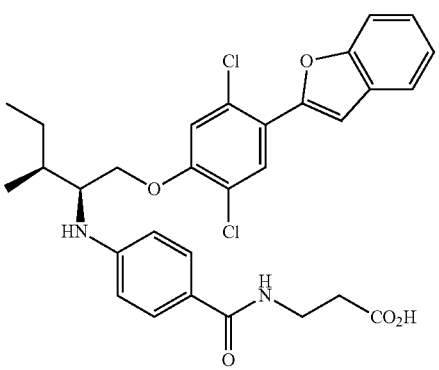 [SMILES: CC[C@H](C)[C@@H](COc1cc(Cl)c(-c2cc3ccccc3o2)cc1Cl)Nc1ccc(C(=O)NCCC(=O)O)cc1]

¹H NMR (400 MHz, CDCl₃): δ 7.85-8.12 (m, 2H), 7.55-7.67 (m, 2H), 7.28-7.52 (m, 2H), 6.91-7.04 (m, 1H), 6.54-6.68 (m, 3H), 3.99-4.21 (m, 3H), 3.63-3.78 (m, 2H), 2.69 (t, J=5.6 Hz, 1H), 1.93 (dd, J=7.3, 3.4 Hz, 1H), 1.64-1.72 (m, 1H), 1.20-1.28 (m, 2H), 0.87-1.10 (m, 6H). MS (M+1): 569.

Compound 3-20: 3-(4-(((2S,3S)-3-methyl-1-((2,2',5-trichloro-4'-(trifluoromethyl)-[1,1'-biphenyl]-4-yl)oxy)pentan-2-yl)amino)benzamido)propanoic Acid

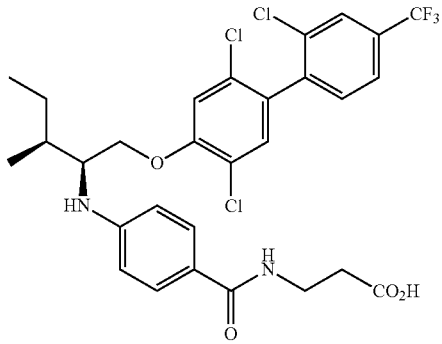 [SMILES: CC[C@H](C)[C@@H](COc1cc(Cl)c(-c2ccc(C(F)(F)F)cc2Cl)cc1Cl)Nc1ccc(C(=O)NCCC(=O)O)cc1]

¹H NMR (400 MHz, CDCl₃): δ 7.72-7.77 (m, 1H), 7.55-7.65 (m, 3H), 7.33-7.40 (m, 1H), 7.01 (s, 1H), 6.61-6.68 (m, 3H), 4.10-4.22 (m, 2H), 3.71 (q, J=6.0 Hz, 3H), 2.71 (t, J=6.0 Hz, 2H), 1.95 (ddd, J=12.4, 7.2, 3.6 Hz, 1H), 1.72 (ddd, J=12.4, 7.2, 3.6 Hz, 1H), 1.07 (d, J=7.2 Hz, 3H), 0.99 (t, J=7.2 Hz, 3H). MS (M+1): 631.

Compound 3-22: (S)-3-(4-((1-((2-chloro-2'-fluoro-4'-(trifluoromethyl)-[1,1'-biphenyl]-4-yl)oxy)hexan-2-yl)amino)benzamido)propanoic Acid

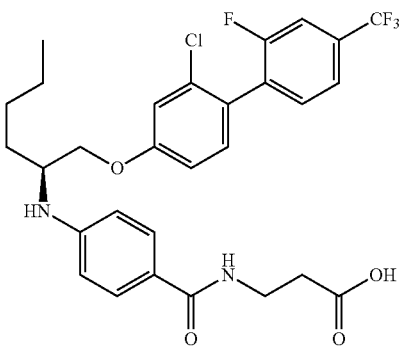

¹H NMR (400 MHz, CDCl₃): δ7.60 (d, J=8.8 Hz, 2H), 7.34-7.47 (m, 3H), 7.14-7.21 (m, 1H), 6.97-7.03 (m, 1H), 6.76-6.88 (m, 2H), 6.58 (d, J=8.8 Hz, 2H), 3.99 (tt, J=9.0, 4.6 Hz, 2H), 3.70-3.81 (m, 1H), 3.59-3.70 (m, 2H), 2.65 (t, J=5.9 Hz, 2H), 1.71-1.86 (m, 1H), 1.56-1.66 (m, 1H), 1.29-1.47 (m, 4H), 0.89 (t, J=6.8 Hz, 3H). MS (M+1): 581.

Compound 3-21: 3-(4-(((2S,3S)-1-((2,5-dichloro-2'-fluoro-4'-(trifluoromethyl)-[1,1'-biphenyl]-4-yl)oxy-3-methylpentan-2-yl)amino)benzamido)propanoic Acid

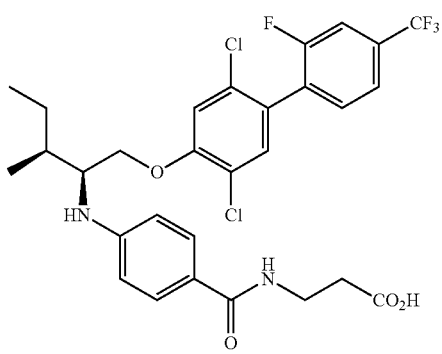 [SMILES: CC[C@H](C)[C@@H](COc1cc(Cl)c(-c2ccc(C(F)(F)F)cc2F)cc1Cl)Nc1ccc(C(=O)NCCC(=O)O)cc1]

¹H NMR (400 MHz, CDCl₃): δ 7.55-7.65 (m, 3H), 7.36-7.51 (m, 2H), 6.94-7.03 (m, 1H), 6.57-6.72 (m, 3H), 4.02-4.22 (m, 3H), 3.63-3.76 (m, 3H), 2.70 (t, J=5.6 Hz, 2H), 1.84-2.01 (m, 1H), 1.61-1.78 (m, 1H), 1.05 (dd, J=13.2, 7.2 Hz, 3H), 0.97 (q, J=7.2 Hz, 3H). MS (M+1): 615.

Compound 3-23: (S)-3-(4-((1-(4-(benzofuran-2-yl)-3-chlorophenoxy)-3,3-dimethylbutan-2-yl)amino)benzamido)propanoic Acid

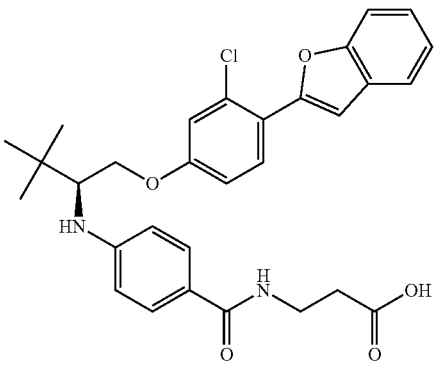 [SMILES: CC(C)(C)[C@@H](COc1ccc(-c2cc3ccccc3o2)c(Cl)c1)Nc1ccc(C(=O)NCCC(=O)O)cc1]

¹H NMR (400 MHz, Acetone-d₆): δ 7.93 (d, J=8.8 Hz, 1H), 7.67 (d, J=8.8 Hz, 3H), 7.54 (d, J=1.0 Hz, 1H), 7.41 (s, 1H), 7.33 (td, 1H), 7.26 (td, 1H), 7.12 (d, J=2.4 Hz, 1H), 7.03 (dd, 1H), 6.78 (d, J=8.8 Hz, 2H), 4.45 (q, 1H), 4.18 (q, 1H), 3.76-3.84 (m, 1H), 3.58 (t, 2H), 2.62 (t, J=6.6 Hz, 2H), 1.12 (s, 9H). MS (M+1): 535.

Compound 3-24: (S)-3-(4-((1-((2-chloro-2'-fluoro-4'-(trifluoromethyl)-[1,1'-biphenyl]-4-yl)oxy)-3,3-dimethylbutan-2-yl)amino)benzamido)propanoic Acid

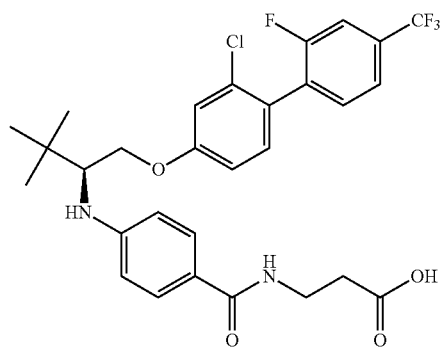 [SMILES: CC(C)(C)[C@@H](COc1ccc(-c2ccc(C(F)(F)F)cc2F)c(Cl)c1)Nc1ccc(C(=O)NCCC(=O)O)cc1]

¹H NMR (400 MHz, Acetone-d₆): δ 7.84 (s, 1H), 7.70-7.75 (m, 1H), 7.67 (d, J=8.3 Hz, 2H), 7.60 (d, J=7.8 Hz, 1H), 7.41 (d, 2H), 7.01 (d, 2H), 6.78 (d, J=8.3 Hz, 2H), 4.39 (dd, J=10.0, 3.7 Hz, 1H), 4.12 (dd, J=9.8, 6.8 Hz, 1H), 3.75-3.83 (m, 1H), 3.59 (q, 2H), 2.62 (t, J=6.8 Hz, 2H), 1.13 (s, 9H). MS (M+1): 581.

Compound 4-2: (S)-3-(6-((1-(4-(benzofuran-2-yl)phenoxy)-3-methylbutan-2-yl)amino)nicotinamido) propanoic Acid

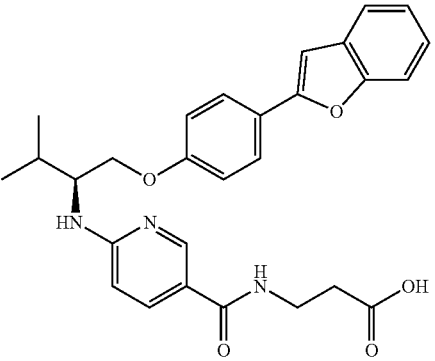

¹H NMR (400 MHz, DMSO-d₆): δ 8.48 (d, J=2.4 Hz, 1H), 8.23 (t, J=5.4 Hz, 1H), 7.80-7.86 (m, 2H), 7.78 (dd, J=8.8, 2.4 Hz, 1H), 7.55-7.64 (m, 2H), 7.20-7.31 (m, 3H), 7.00-7.14 (m, 3H), 6.59 (d, J=8.8 Hz, 1H), 4.29 (br. s., 1H), 4.05-4.15 (m, 2H), 3.33-3.46 (m, 2H), 2.39-2.47 (m, 3H), 2.07 (dq, J=13.4, 6.8 Hz, 1H), 0.98 (t, J=6.8 Hz, 6H); MS (M+1): 488.

Example 4: Synthesis of Compounds 4-1 to 4-5

Compound 4-1: (S)-3-(6-((3-methyl-1-((4'-(trifluoromethyl)-[1,1'-biphenyl]-4-yl)oxy)butan-2-yl)amino)nicotinamido)propanoic Acid

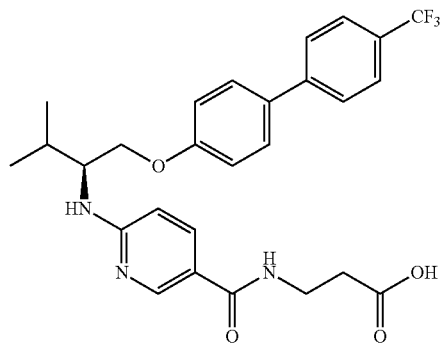 [SMILES: CC(C)[C@@H](COc1ccc(-c2ccc(C(F)(F)F)cc2)cc1)Nc1ccc(C(=O)NCCC(=O)O)cn1]

White solid. ¹H NMR (400 MHz, DMSO-d₆): δ 8.48 (d, J=4 Hz, 1H), 8.20 (t, J=4 Hz, 1H), 7.83-7.74 (m, 5H), 7.66 (d, J=8 Hz, 2H), 7.08-7.04 (m, 3H), 6.59 (d, J=8 Hz, 1H), 4.30-4.28 (m, 1H), 4.13-4.06 (m, 2H), 3.74-3.71 (m, 1H), 3.42 (quartet, J=8 Hz, 2H), 2.48 (t, J=8 Hz, 2H), 2.10-1.98 (m, 1H), 0.99-0.96 (m, 6H). MS (M+1): 516.

Compound 4-3: 3-(6-(((2S,3S)-1-((2',4'-dichloro-[1,1'-biphenyl]-4-yl)oxy)-3-methylpentan-2-yl)amino)nicotinamido)propanoic Acid

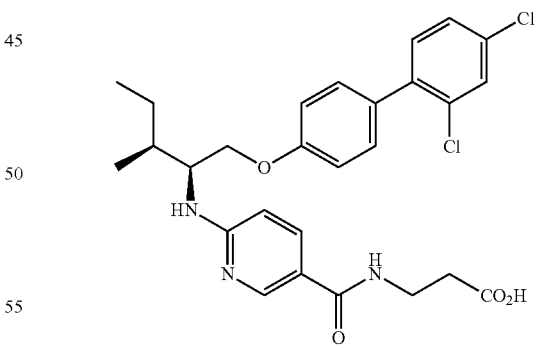

White solid. ¹HNMR (400 MHz, DMSO-d₆): δ 8.46 (d, J=1.9 Hz, 1H), 8.18 (t, J=5.4 Hz, 1H), 7.76 (dd, J=8.4, 1.9 Hz, 1H), 7.68 (d, J=1.9 Hz, 1H), 7.47 (dd, J=8.4, 1.9 Hz, 1H), 7.39 (d, J=8.8 Hz, 1H), 7.33 (d, J=8.8 Hz, 2H), 7.10 (d, J=8.8 Hz, 1H), 7.02 (d, J=8.8 Hz, 2H), 6.56 (d, J=8.8 Hz, 2H), 4.31 (brs, 1H), 4.10 (d, J=4.9 Hz, 1H), 3.35-3.32 (m, 2H), 2.47 (t, J=7 Hz, 2H), 1.85-1.82 (m, 1H), 1.59-1.56 (m, 1H), 1.27-1.22 (m, 1H), 0.95 (d, J=6.8 Hz, 3H), 0.88 (t, J=6.8 Hz, 3H). MS (M+1): 530.

Compound 4-4: 3-(6-(((2S,3S)-1-(4-(5-(tert-butyl)-1,3,4-oxadiazol-2-yl)phenoxy)-3-methylpentan-2-yl)amino)nicotinamido)propanoic Acid

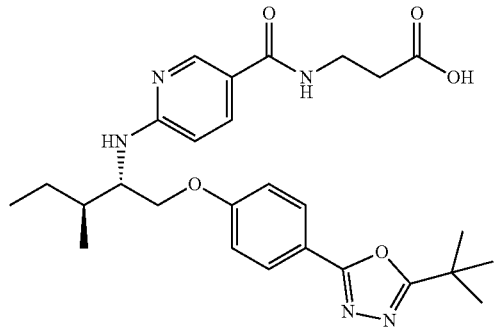 [SMILES: CC[C@H](C)[C@@H](COc1ccc(-c2nnc(C(C)(C)C)o2)cc1)Nc1ccc(C(=O)NCCC(=O)O)cn1]

¹H NMR (400 MHz, CDCl₃): δ 8.25-8.18 (d, J=9.3 Hz, 1H), 8.16-8.09 (m, 1H), 7.90 (d, J=8.8 Hz, 2H), 7.77-7.69 (m, 1H), 6.90 (d, J=9.3 Hz, 2H), 6.79-6.69 (d, J=9.3 Hz, 1H), 4.24-4.14 (m, 1H), 4.13-4.07 (m, 1H), 3.89-3.78 (m, 1H), 3.75-3.60 (m, 2H), 2.58-2.48 (m, 2H), 1.94-1.82 (m, 1H), 1.66-1.56 (m, 1H), 1.43 (s, 9H), 1.37-1.30 (m, 1H), 1.03 (d, J=6.8 Hz, 3H), 0.93 (t, J=7.3 Hz, 3H). MS (M+1): 510.

Example 5: Synthesis of Compounds 5-1 to 5-3

Compound 5-1: (S)-3-(4-((1-((4-(benzofuran-2-yl)phenyl)thio)-3-methylbutan-2-yl)amino)benzamido)propanoic Acid

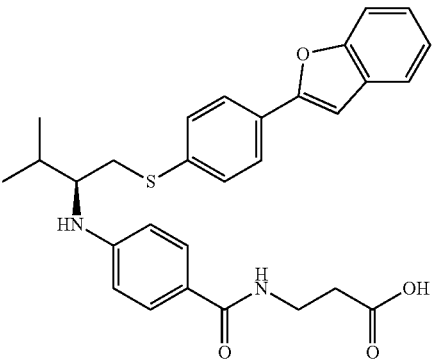 [SMILES: CC(C)[C@@H](CSc1ccc(-c2cc3ccccc3o2)cc1)Nc1ccc(C(=O)NCCC(=O)O)cc1]

¹H NMR (400 MHz, DMSO-d₆): δ 8.03 (t, J=5.4 Hz, 1H), 7.78-7.88 (m, 2H), 7.55-7.71 (m, 4H), 7.36-7.44 (m, 3H), 7.23-7.36 (m, 2H), 6.50-6.65 (m, 2H), 6.12 (d, J=9.3 Hz, 1H), 3.46-3.70 (m, 1H), 3.36-3.46 (m, 2H), 3.30 (dd, J=12.7, 4.4 Hz, 1H), 3.08 (dd, J=12.7, 8.3 Hz, 1H), 2.43-2.49 (m, 2H), 1.91-2.03 (m, 1H), 0.84-1.02 (m, 6H). MS (M+1): 503.

Compound 4-5: 3-(6-(((2S,3S)-3-methyl-1-(4-(5-phenyl-1,3,4-oxadiazol-2-yl)phenoxy)pentan-2-yl)amino)nicotinamido)propanoic Acid

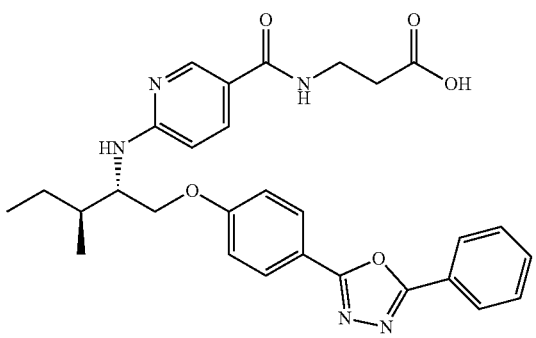

¹H NMR (400 MHz, CDCl₃): δ 8.19 (s, 1H), 8.15 (d, J=8.8 Hz, 1H), 8.04 (dd, J=2.0, 7.3 Hz, 2H), 7.96 (d, J=8.8 Hz, 2H), 7.73-7.65 (m, 1H), 7.50-7.42 (m, 3H), 6.91 (d, J=8.8 Hz, 2H), 6.70 (d, J=9.3 Hz, 1H), 4.21-4.14 (m, 1H), 4.14-4.08 (m, 1H), 3.85 (br. s., 1H), 3.70-3.60 (m, 2H), 2.53 (dd, J=4.2, 6.6 Hz, 2H), 1.92-1.81 (m, 1H), 1.61 (ddd, J=3.9, 7.6, 13.4 Hz, 1H), 1.35-1.25 (m, 1H), 1.02 (d, J=6.8 Hz, 3H), 0.95-0.87 (m, 3H). MS (M+1): 530.

Compound 5-2: 3-(4-(((2S,3S)-3-methyl-1-((4'-(trifluoromethyl)-[1,1'-biphenyl]-4-yl)thio)pentan-2-yl)amino)benzamido)propanoic Acid

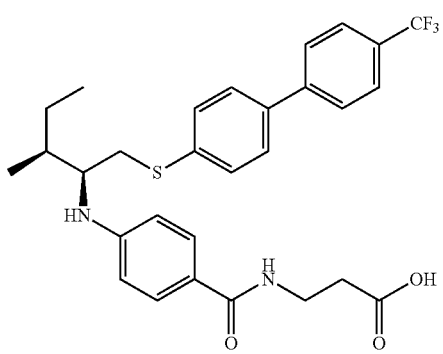 [SMILES: CC[C@H](C)[C@@H](CSc1ccc(-c2ccc(C(F)(F)F)cc2)cc1)Nc1ccc(C(=O)NCCC(=O)O)cc1]

¹H NMR (400 MHz, CDCl₃): δ 7.51-7.68 (m, 6H), 7.45 (d, J=8.8 Hz, 2H), 7.32-7.41 (m, 2H), 7.24 (s, 1H), 6.73 (br. s., 1H), 6.38-6.50 (m, 2H), 5.06 (br. s., 1H), 3.65 (q, J=5.9 Hz, 2H), 3.56 (q, J=5.9 Hz, 1H), 3.21 (dd, J=13.2, 4.4 Hz, 1H), 3.04 (dd, J=13.2, 6.8 Hz, 1H), 2.64 (t, J=5.9 Hz, 2H), 1.69-1.84 (m, 1H), 1.37-1.61 (m, 1H), 1.04-1.31 (m, 1H), 0.78-0.98 (m, 6H). MS (M+1): 545.

Compound 5-3: 3-(4-(((2S,3S)-1-((4-(benzofuran-2-yl)phenyl)thio)-3-methylpentan-2-yl)amino)benzamido)propanoic Acid

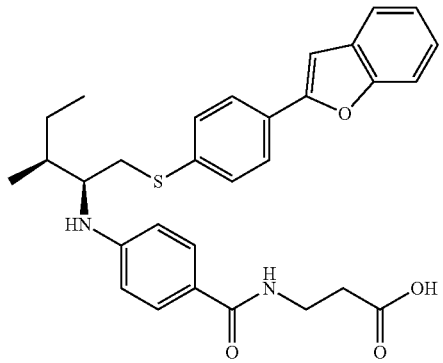 [SMILES: CC[C@H](C)[C@@H](CSc1ccc(-c2cc3ccccc3o2)cc1)Nc1ccc(C(=O)NCCC(=O)O)cc1]

¹H NMR (400 MHz, CDCl₃): δ 7.67-7.73 (m, 2H), 7.46-7.57 (m, 4H), 7.18-7.34 (m, 5H), 6.96 (d, J=1.0 Hz, 1H), 6.65 (t, J=5.6 Hz, 1H), 6.44 (d, J=8.8 Hz, 2H), 3.65 (d, J=5.9 Hz, 1H), 3.65 (d, J=16.6 Hz, 1H), 3.49-3.60 (m, 1H), 3.20 (dd, J=13.2, 4.9 Hz, 1H), 3.02 (dd, J=13.2, 6.8 Hz, 1H), 2.65 (br. s., 2H), 1.72-1.82 (m, 1H), 1.47-1.59 (m, 1H), 1.04-1.30 (m, 1H), 0.80-0.96 (m, 6H). MS (M+1): 517.

Compound 6-2: (S)-3-(4-((1-(4-(benzofuran-2-yl)phenoxy)-3-methylbutan-2-yl)(ethyl)amino)benzamido)propanoic Acid

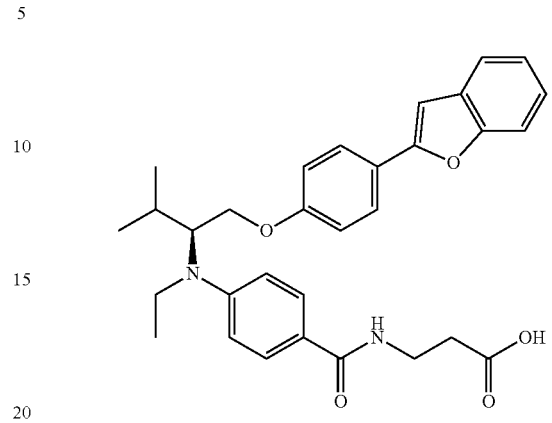

White solid. ¹HNMR (400 MHz, DMSO-d₆): δ 8.10 (t, J=5.4 Hz, 1H), 7.82 (d, J=8.8 Hz, 2H), 7.66 (d, J=8.8 Hz, 2H), 7.62-7.57 (m, 2H), 7.29-7.21 (m, 3H), 7.01 (d, J=8.8, 2H), 6.80 (d, J=8.8 Hz, 2H), 4.27-4.25 (m, 2H), 4.04-3.97 (m, 1H), 3.45-3.40 (m, 4H), 2.83 (s, 3H), 2.48 (t, J=6.8, 2H), 2.15-2.12 (m, 1H), 1.08-1.01 (m, 6H), 0.84 (d, J=6.4 Hz, 3H); MS (M+1): 515.

Example 6: Synthesis of Compounds 6-1 to 6-3

Compound 6-1: (S)-3-(4-((1-(4-(benzofuran-2-yl)phenoxy)-3-methylbutan-2-yl)(methyl) amino)benzamido)propanoic Acid

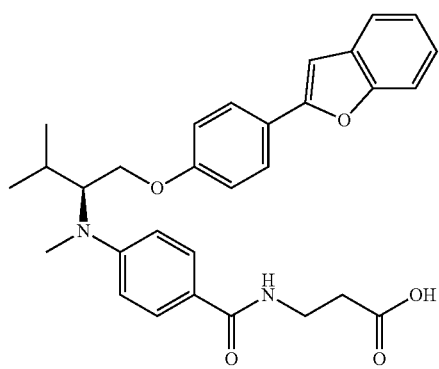 [SMILES: CC(C)[C@@H](COc1ccc(-c2cc3ccccc3o2)cc1)N(C)c1ccc(C(=O)NCCC(=O)O)cc1]

White solid. ¹H-NMR (400 MHz, DMSO-d₆): δ 8.11 (t, J=5.4 Hz, 1H), 7.80 (d, J=8.8 Hz, 2H), 7.67 (d, J=8.8 Hz, 2H), 7.61-7.57 (m, 2H), 7.29-7.21 (m, 3H), 6.98 (d, J=8.8, 2H), 6.80 (d, J=8.8 Hz, 2H), 4.27-4.42 (m, 2H), 4.01-3.96 (m, 1H), 3.45-3.40 (m, 2H), 2.83 (s, 3H), 2.48 (t, J=6.8, 2H), 2.15-2.10 (m, 1H), 1.07 (d, J=6.4 Hz, 3H), 0.84 (d, J=6.4 Hz, 3H); MS (M+1): 501.

Compound 6-3: (S)-3-(4-((1-(4-(benzofuran-2-yl)phenoxy)-3-ethoxypropan-2-yl)amino) benzamido) propanoic Acid

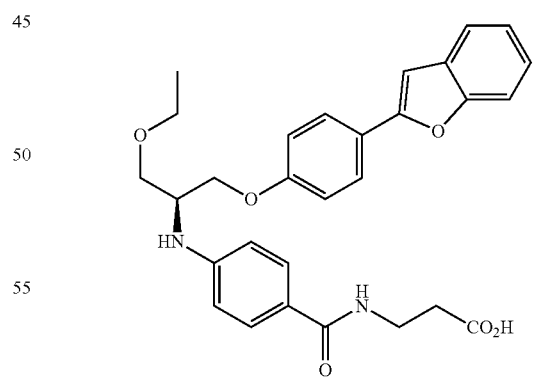

¹H-NMR (400 MHz, DMSO-d₆): δ 12.14 (s, 1H), 8.08-8.06 (t, 1H), 7.87-7.84 (d, 1H), 7.63-7.61 (d, 2H), 7.48-7.47 (d, 1H), 7.43-7.40 (d, 2H), 7.30-7.22 (m, 2H), 7.04-7.01 (d, 2H), 6.70-6.68 (d, 2H), 6.21-6.19 (d, 1H), 4.17-4.08 (m, 2H), 4.04-3.98 (m, 1H), 3.59-3.57 (d, 2H), 3.54-3.46 (m, 2H), 3.43-3.38 (q, 2H), 2.47-2.45 (t, 2H), 1.14-1.10 (t, 3H), MS (M+1): 503.

Example 7: Synthesis of Compounds 7-1 to 7-11

Compound 7-1: (S)-3-(4-((1-(4-(benzofuran-2-yl)-3,5-difluorophenoxy)-3-methylbutan-2-yl)amino)benzamido)propanoic Acid

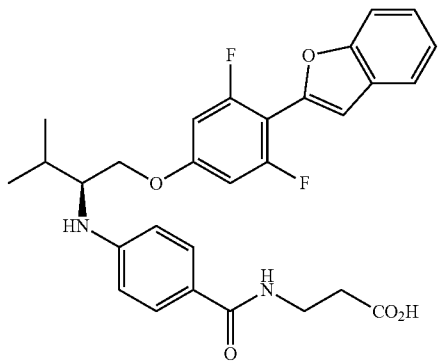 [SMILES: CC(C)[C@@H](COc1cc(F)c(-c2cc3ccccc3o2)c(F)c1)Nc1ccc(C(=O)NCCC(=O)O)cc1]

White solid. $^1$H-NMR (400 MHz, DMSO-$d_6$): δ 8.04 (t, J=5.4 Hz, 1H), 7.70 (d, J=8.8 Hz, 1H), 7.64-7.58 (m, 3H), 7.35 (dt, J=7, 1.4 Hz, 1H), 7.31-7.27 (m, 1H), 7.18 (d, J=1 Hz, 1H), 6.94 (dd, J=8.8 Hz, 2H), 6.65 (d, J=8.8 Hz, 2H), 6.12 (d, J=8 Hz, 1H), 4.19-4.06 (m, 2H), 3.70-3.64 (m, 1H), 3.43-3.38 (m, 2H), 2.46 (t, J=6.8 Hz, 2H), 2.05-1.98 (m, 1H), 1.01-0.96 (m, 6H). MS (M+1): 523.

Compound 7-2: (S)-3-(4-((1-((2'-chloro-2,6-difluoro-4'-(trifluoromethyl)-[1,1'-biphenyl]-4-yl)oxy)-3-methylbutan-2-yl)amino)benzamido)propanoic Acid

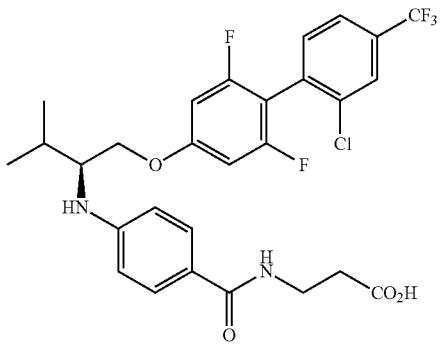

White solid. $^1$H-NMR (400 MHz, DMSO-$d_6$): δ 8.06-8.02 (m, 2H), 7.83 (d, J=8.3 Hz, 1H), 7.70 (d, J=8.3 Hz, 1H), 7.60-7.57 (m, 2H), 7.69-7.70 (m, 2H), 7.12-7.07 (m, 2H), 6.08 (d, J=8.8 Hz, 1H), 4.17-4.01 (m, 2H), 3.69-3.64 (m, 1H), 3.43-3.37 (m, 2H), 2.47 (t, J=7 Hz, 2H), 2.05-1.97 (m, 1H), 1.02-0.97 (m, 6H). MS (M+1): 585.

Compound 7-3: (S)-3-(4-((1-((2,6-difluoro-4'-(trifluoromethyl)-[1,1'-biphenyl]-4-yl)oxy)-3-methylbutan-2-yl)amino)benzamido)propanoic Acid

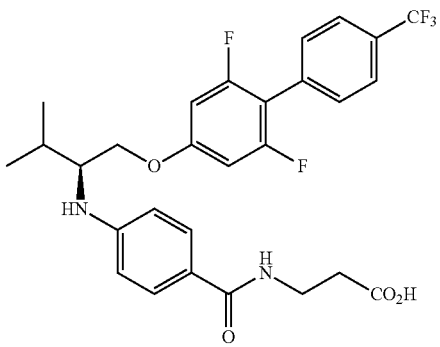 [SMILES: CC(C)[C@@H](COc1cc(F)c(-c2ccc(C(F)(F)F)cc2)c(F)c1)Nc1ccc(C(=O)NCCC(=O)O)cc1]

White solid. $^1$H-NMR (400 MHz, DMSO-$d_6$): δ 8.04 (t, J=5.4 Hz, 1H), 7.83 (d, J=8.8 Hz, 2H), 7.64 (d, J=8.8 Hz, 2H), 7.59 (d, J=8.8 Hz, 2H), 6.89 (d, J=8.8 Hz, 2H), 6.65 (d, J=8.8 Hz, 2H), 6.10 (d, J=8.8 Hz, 1H), 4.38-4.34 (m, 1H), 4.16-4.04 (m, 2H), 3.68-3.63 (m, 1H), 3.43-3.37 (m, 2H), 2.46 (t, J=7 Hz, 2H), 2.05-1.96 (m, 1H), 1.01-0.96 (m, 6H). MS (M+1): 551.

Compound 7-4: (S)-3-(4-((3-methyl-1-((2,2',6-trifluoro-4'-(trifluoromethyl)-[1,1'-biphenyl]-4-yl)oxy)butan-2-yl)amino)benzamido)propanoic Acid

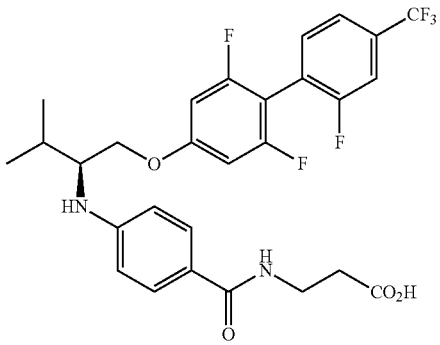 [SMILES: CC(C)[C@@H](COc1cc(F)c(-c2ccc(C(F)(F)F)cc2F)c(F)c1)Nc1ccc(C(=O)NCCC(=O)O)cc1]

White solid. $^1$H-NMR (400 MHz, DMSO-$d_6$): δ 8.03 (t, J=5.4 Hz, 1H), 7.85 (d, J=8.4 Hz, 1H), 7.71-7.70 (m, 2H), 7.60-7.57 (m, 2H), 6.93 (d, J=8.8 Hz, 2H), 6.65 (d, J=8.8 Hz, 2H), 6.11 (d, J=8.8 Hz, 1H), 4.17-4.05 (m, 2H), 3.68-3.65 (m, 1H), 3.34-3.38 (m, 2H), 2.47 (t, J=7 Hz, 2H), 1.81-1.74 (m, 1H), 2.05-1.91 (m, 1H), 1.01-0.97 (m, 6H). MS (M+1): 569.

Compound 7-5: (S)-3-(4-((1-((2'-chloro-2,6-difluoro-4'-(trifluoromethyl)-[1,1-biphenyl]-4-yl)oxy)-4-methylpentan-2-yl)amino)benzamido)propanoic Acid

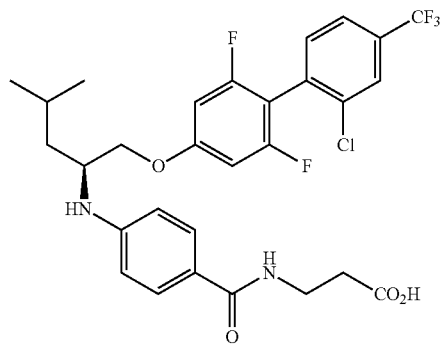 [SMILES: CC(C)C[C@@H](COc1cc(F)c(-c2ccc(C(F)(F)F)cc2Cl)c(F)c1)Nc1ccc(C(=O)NCCC(=O)O)cc1]

White solid. ¹HNMR (400 MHz, DMSO-d$_6$): δ 8.07 (t, J=5.4 Hz, 1H), 8.02 (s, 1H), 7.80 (d, J=7.8 Hz, 1H), 7.69-7.61 (m, 3H), 6.87 (d, J=8.8 Hz, 2H), 6.66 (d, J=8.8 Hz, 2H), 6.10 (d, J=8.8 Hz, 1H), 4.04-4.01 (m, 2H), 3.87-3.83 (m, 1H), 3.45-3.41 (m, 2H), 2.48 (t, J=7 Hz, 2H), 1.80-1.75 (m, 1H), 1.56-1.52 (m, 2H), 0.94 (d, J=6.8 Hz, 3H), 0.86 (d, J=6.8 Hz, 3H). MS (M+1): 599.

Compound 7-7: (S)-3-(4-((4-methyl-1-((2,2',6-trifluoro-4'-(trifluoromethyl)-[1,1'-biphenyl]-4-yl)oxy)pentan-2-yl)amino)benzamido)propanoic Acid

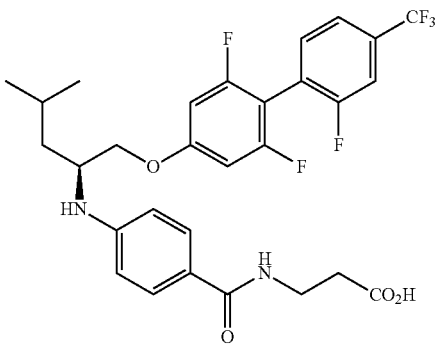

¹H NMR (400 MHz, DMSO-d$_6$): δ 12.2 (s, 1H), 8.07-8.06 (m, 1H), 7.82-7.61 (m, 4H), 6.88 (d, J=8.8 Hz, 2H), 6.67-6.61 (m, 2H), 6.10-6.04 (m, 1H), 4.04-3.95 (m, 2H), 3.86-3.81 (m, 1H), 3.44-3.38 (m, 2H), 2.48 (t, J=7 Hz, 2H), 1.80-1.73 (m, 1H), 1.56-1.46 (m, 2H), 0.93 (t, J=6.8 Hz, 3H), 0.87 (t, J=6.8 Hz, 3H). MS (M+1): 583.

Compound 7-6: (S)-3-(4-((1-((2,6-difluoro-4'-(trifluoromethyl)-[1,1'-biphenyl]-4-yl)oxy)-4-methylpentan-2-yl)amino)benzamido)propanoic Acid

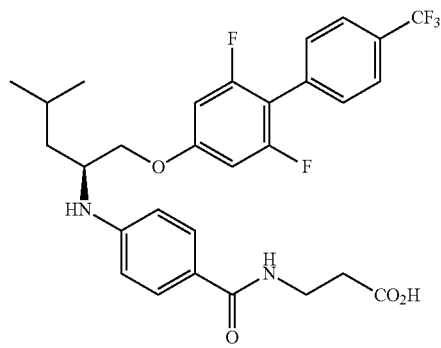 [SMILES: CC(C)C[C@@H](COc1cc(F)c(-c2ccc(C(F)(F)F)cc2)c(F)c1)Nc1ccc(C(=O)NCCC(=O)O)cc1]

¹H NMR (400 MHz, DMSO-d$_6$): δ 8.06 (t, J=5.4 Hz, 1H), 7.81 (d, J=7.8 Hz, 1H), 7.63-7.60 (m, 4H), 6.85 (d, J=8.8 Hz, 2H), 6.64 (d, J=8.8 Hz, 2H), 6.09 (d, J=8.8 Hz, 1H), 4.02-4.01 (m, 2H), 3.87-3.82 (m, 1H), 3.44-3.39 (m, 2H), 2.47 (t, J=7 Hz, 2H), 1.80-1.74 (m, 1H), 1.56-1.47 (m, 2H), 0.94 (d, J=6.8 Hz, 3H), 0.86 (d, J=6.8 Hz, 3H). MS (M+1): 565.

Compound 7-8: (S)-3-(4-((1-((2',4'-dichloro-2,6-difluoro-[1,1'-biphenyl]-4-yl)oxy)-4-methylpentan-2-yl)amino)benzamido)propanoic Acid

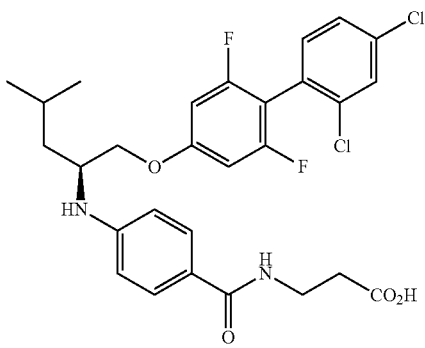 [SMILES: CC(C)C[C@@H](COc1cc(F)c(-c2ccc(Cl)cc2Cl)c(F)c1)Nc1ccc(C(=O)NCCC(=O)O)cc1]

White solid. ¹HNMR (400 MHz, DMSO-d$_6$): δ 8.05 (t, J=5.4 Hz, 1H), 7.78 (d, J=1.9 Hz, 1H), 7.61 (d, J=8.8 Hz, 2H), 7.54-7.44 (m, 2H), 6.85 (d, J=8.8 Hz, 2H), 6.55-6.59 (m, 2H), 6.09 (d, J=8.8 Hz, 1H), 4.05-4.00 (m, 1H), 3.87-3.82 (m, 1H), 3.44-3.39 (m, 2H), 2.47 (t, J=7 Hz, 2H), 1.79-1.74 (m, 1H), 1.57-1.48 (m, 2H), 0.94 (d, J=6.8 Hz, 3H), 0.87 (d, J=6.8 Hz, 3H). MS (M+1): 565.

Compound 7-9: (S)-3-(4-((1-((3',5'-dichloro-2,6-difluoro-[1,1'-biphenyl]-4-yl)oxy)-4-methylpentan-2-yl)amino)benzamido)propanoic Acid Compound 7-11: (S)-3-(4-((1-((2',4'-dichloro-2,6-difluoro-[1,1'-biphenyl]-4-yl)oxy)-3-methylbutan-2-yl)amino)benzamido)propanoic Acid

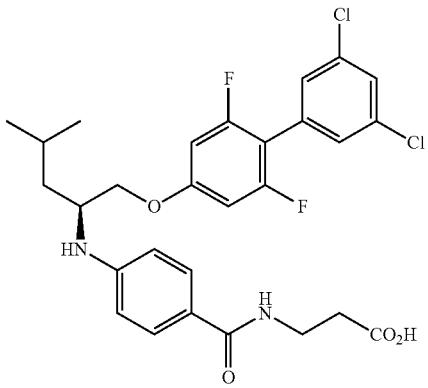 [SMILES: CC(C)C[C@@H](COc1cc(F)c(-c2cc(Cl)cc(Cl)c2)c(F)c1)Nc1ccc(C(=O)NCCC(=O)O)cc1]

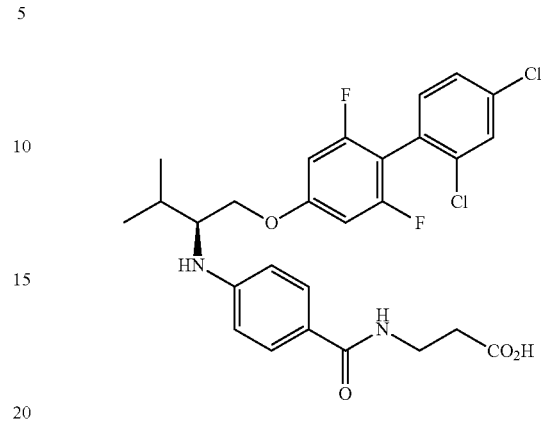

White solid. $^1$HNMR (400 MHz, DMSO-$d_6$): δ 8.05 (t, J=5.4 Hz, 1H), 7.65-7.59 (m, 3H), 7.47-7.415 (m, 2H), 6.84 (d, J=8.8 Hz, 2H), 6.64 (d, J=8.8 Hz, 2H), 6.08 (d, J=8.8 Hz, 1H), 4.03-4.00 (m, 2H), 3.87-3.82 (m, 1H), 3.44-3.39 (m, 2H), 2.47 (t, J=7 Hz, 2H), 1.79-1.74 (m, 1H), 1.56-1.47 (m, 2H), 0.94 (d, J=6.8 Hz, 3H), 0.86 (d, J=6.8 Hz, 3H). MS (M+1): 565.

White solid. $^1$HNMR (400 MHz, DMSO-$d_6$): δ 8.05 (t, J=5.6 Hz, 1H), 7.78 (d, J=2.4 Hz, 1H), 7.58 (d, J=8.8 Hz, 2H), 7.54-7.51 (m, 1H), 7.45 (d, J=8.8 Hz, 1H), 6.86 (d, J=8.8 Hz, 2H), 6.65 (d, J=8.8 Hz, 2H), 6.11 (d, J=8.8 Hz, 1H), 4.14-4.03 (m, 2H), 3.68-3.62 (m, 1H), 2.47 (t, J=6.8 Hz, 2H), 2.04-2.00 (m, 1H), 1.00-0.95 (m, 6H). MS (M+1): 551.

Compound 7-10: (S)-3-(4-((1-(4-(benzofuran-2-yl)-3,5-difluorophenoxy)-4-methylpentan-2-yl)amino)benzamido)propanoic Acid

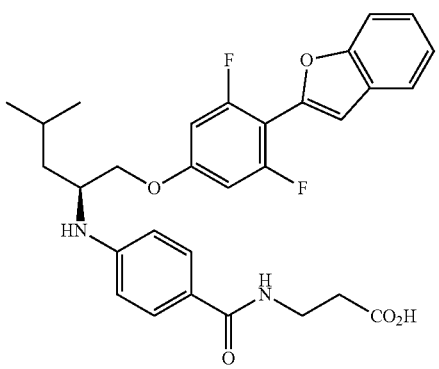 [SMILES: CC(C)C[C@@H](COc1cc(F)c(-c2cc3ccccc3o2)c(F)c1)Nc1ccc(C(=O)NCCC(=O)O)cc1]

White solid. $^1$HNMR (400 MHz, DMSO-$d_6$): δ 8.06 (t, J=5.4 Hz, 1H), 7.69 (d, J=7.8 Hz, 1H), 7.62-7.58 (m, 3H), 7.36-7.26 (m, 2H), 7.17 (s, 1H), 6.90 (d, J=8.8 Hz, 2H), 6.64 (d, J=8.8 Hz, 2H), 6.09 (d, J=8.8 Hz, 1H), 4.04-3.95 (m, 2H), 3.88-3.79 (m, 1H), 3.42-3.39 (m, 2H), 2.47 (t, J=7 Hz, 2H), 1.79-1.74 (m, 1H), 1.57-1.46 (m, 2H), 0.94 (d, J=6.8 Hz, 3H), 0.86 (d, J=6.8 Hz, 3H). MS (M+1): 537.

Example 8: Synthesis of Compounds 8-1 to 8-25

Compound 8-1: (S)-3-(4-((1-((2,2'-difluoro-4'-(trifluoromethyl)-[1,1'-biphenyl]-4-yl)oxy)-3-methylbutan-2-yl)amino)benzamido)propanoic Acid

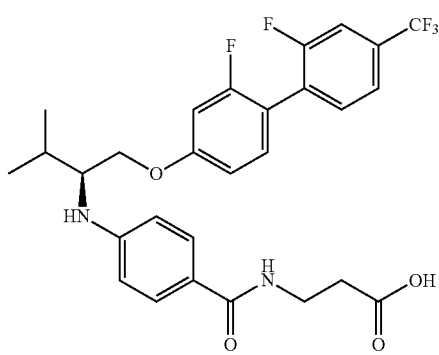 [SMILES: CC(C)[C@@H](COc1ccc(-c2ccc(C(F)(F)F)cc2F)c(F)c1)Nc1ccc(C(=O)NCCC(=O)O)cc1]

$^1$H NMR (400 MHz, CDCl$_3$): δ 7.59 (d, J=8.3 Hz, 2H) (m, 2H), 7.36-7.48 (m, 3H), 7.21-7.27 (m, 1H), 6.65-6.78 (m, 3H), 6.59 (d, J=8.3 Hz, 2H), 4.00-4.05 (m, 2H), 3.66 (q, J=5.9 Hz, 2H), 3.54-3.60 (m, 1H), 2.62-2.67 (m, 2H), 2.06-2.15 (m, 1H), 0.99-1.06 (m, 6H). MS (M+1): 551.

Compound 8-2: (S)-2-(4-((1-((2,2'-difluoro-4'-(trifluoromethyl)-[1,1'-biphenyl]-4-yl)oxy)-3-methylbutan-2-yl)amino)benzamido)ethane-1-sulfonic Acid

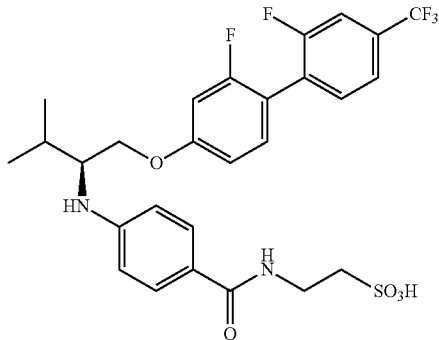 [SMILES: CC(C)[C@@H](COc1ccc(-c2ccc(C(F)(F)F)cc2F)c(F)c1)Nc1ccc(C(=O)NCCS(=O)(=O)O)cc1]

$^1$H NMR (400 MHz, DMSO-d$_6$): δ 8.11 (t, J=4.9 Hz, 1H), 7.78 (d, J=9.3 Hz, 1H), 7.64-7.71 (m, 2H), 7.54 (d, J=8.8 Hz, 2H), 7.35-7.43 (m, 1H), 7.00 (dd, J=11.5, 2.2 Hz, 1H), 6.92 (dd, J=8.8, 2.4 Hz, 1H), 6.64-6.70 (m, 2H), 6.13 (d, J=8.8 Hz, 1H), 4.10-4.16 (m, 1H), 4.02-4.08 (m, 1H), 3.62-3.71 (m, 1H), 3.46-3.54 (m, 2H), 2.68 (t, J=6.1 Hz, 2H), 1.99-2.09 (m, 1H), 0.99 (m, 6H). MS (M+1): 587.

Compound 8-4: (S)-2-(4-((1-(4-(benzofuran-2-yl)-3-fluorophenoxy)-3-methylbutan-2-yl)amino)benzamido)ethane-1-sulfonic Acid

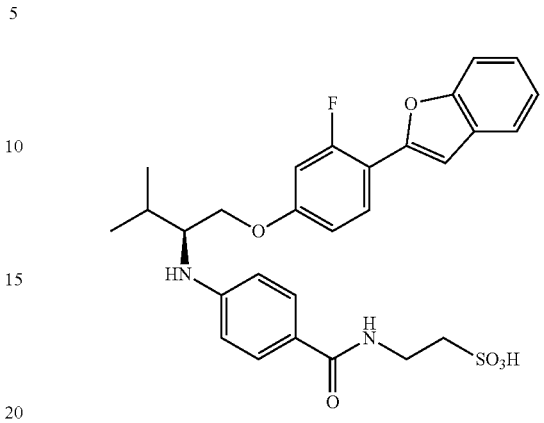

$^1$H NMR (400 MHz, DMSO-d$_6$): δ 8.11 (t, J=5.1 Hz, 1H), 7.87 (t, J=9.0 Hz, 1H), 7.59-7.68 (m, 2H), 7.54 (d, J=8.3 Hz, 2H), 7.23-7.34 (m, 2H), 7.16 (d, J=2.9 Hz, 1H), 7.04 (dd, J=13.7, 2.4 Hz, 1H), 6.94 (dd, J=8.8, 2.4 Hz, 1H), 6.67 (d, J=8.8 Hz, 2H), 6.14 (d, J=8.8 Hz, 1H), 4.00-4.20 (m, 2H), 3.67 (dd, J=8.6, 4.6 Hz, 1H), 3.44-3.55 (m, 2H), 2.68 (t, J=6.8 Hz, 2H), 1.94-2.08 (m, 1H), 0.93-1.08 (m, 6H). MS (M+1): 541.

Compound 8-3: (S)-3-(4-((1-(4-(benzofuran-2-yl)-3-fluorophenoxy)-3-methylbutan-2-yl)amino)benzamido)propanoic Acid

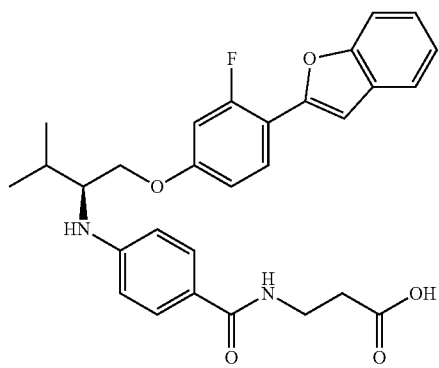

$^1$H NMR (400 MHz, CDCl$_3$): δ 7.87 (t, J=8.8 Hz, 1H), 7.53-7.62 (m, 3H), 7.47 (d, J=7.8 Hz, 1H), 7.16-7.28 (m, 2H), 7.05 (d, J=2.9 Hz, 1H), 6.81 (t, J=5.9 Hz, 1H), 6.72 (dd, J=8.8, 2.4 Hz, 1H), 6.66 (dd, J=12.7, 2.4 Hz, 1H), 6.57 (d, J=8.8 Hz, 2H), 3.99 (d, J=4.4 Hz, 2H), 3.66 (q, J=5.5 Hz, 2H), 3.52-3.58 (m, 1H), 2.64 (t, J=5.9 Hz, 2H), 2.02-2.13 (m, 1H), 0.96-1.03 (m, 6H). MS (M+1): 505.

Compound 8-5: (S)-3-(4-((1-((2'-chloro-2-fluoro-4'-(trifluoromethyl)-[1,1'-biphenyl]-4-yl)oxy)-3-methylbutan-2-yl)amino)benzamido)propanoic Acid

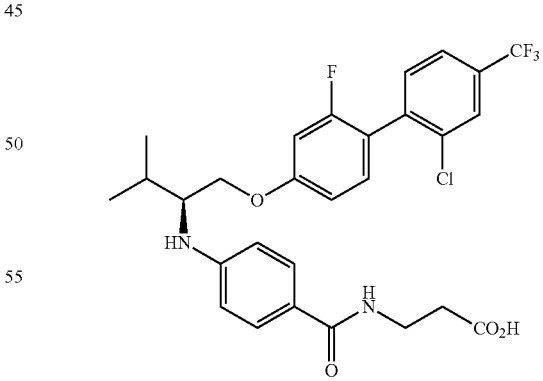

$^1$H NMR (400 MHz, CDCl$_3$): δ 7.71 (d, J=1.0 Hz, 1H), 7.59 (d, J=8.8 Hz, 2H), 7.53 (dd, J=7.8, 1.0 Hz, 1H), 7.39 (d, J=7.8 Hz, 1H), 7.16 (t, J=8.6 Hz, 1H), 6.76-6.85 (m, 1H), 6.64-6.76 (m, 2H), 6.59 (d, J=8.8 Hz, 2H), 4.00-4.06 (m, 2H), 3.66 (q, J=5.9 Hz, 2H), 3.54-3.61 (m, 1H), 2.65 (t, J=5.6 Hz, 2H), 2.08-2.16 (m, 1H), 1.02 (d, J=6.8 Hz, 3H), 1.03 (d, J=6.8 Hz, 3H). MS (M+1): 567.

Compound 8-6: (S)-3-(4-((1-((2,2'-difluoro-4'-(trifluoromethyl)-[1,1'-biphenyl]-4-yl)oxy)-4-methylpentan-2-yl)amino)benzamido)propanoic Acid

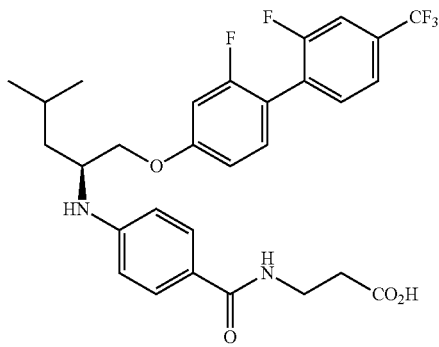 [SMILES: CC(C)C[C@@H](COc1ccc(-c2ccc(C(F)(F)F)cc2F)c(F)c1)Nc1ccc(C(=O)NCCC(=O)O)cc1]

$^1$H NMR (400 MHz, DMSO-d$_6$): δ 7.54-7.64 (m, 2H), 7.35-7.49 (m, 3H), 6.49-6.80 (m, 5H), 3.79-4.03 (m, 3H), 3.63-3.73 (m, 2H), 2.67 (t, J=5.6 Hz, 2H), 1.44-1.88 (m, 3H), 0.85-1.05 (m, 6H). MS (M+1): 565.

Compound 8-7: 3-(4-(((2S,3S)-1-(4-(benzofuran-2-yl)-3-fluorophenoxy)-3-methylpentan-2-yl)amino)benzamido)propanoic Acid

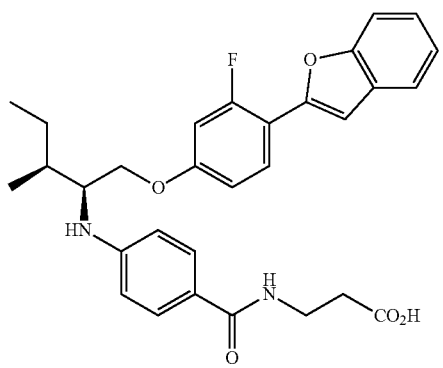 [SMILES: CC[C@H](C)[C@@H](COc1ccc(-c2cc3ccccc3o2)c(F)c1)Nc1ccc(C(=O)NCCC(=O)O)cc1]

$^1$H NMR (400 MHz, CDCl$_3$): δ 7.87 (t, J=8.6 Hz, 1H), 7.52-7.62 (m, 3H), 7.47 (d, J=7.8 Hz, 1H), 7.34 (t, J=8.3 Hz, 1H), 7.15-7.28 (m, 2H), 7.05 (d, J=3.4 Hz, 1H), 6.72-6.75 (m, 1H), 6.67 (dd, J=13.0, 2.2 Hz, 1H), 6.62 (dd, J=10.3, 2.9 Hz, 1H), 6.55 (d, J=8.8 Hz, 2H), 3.98-4.07 (m, 1H), 3.89-3.97 (m, 11H), 3.54-3.70 (m, 3H), 2.64 (t, J=5.4 Hz, 2H), 1.74-1.90 (m, 11H), 1.53-1.66 (m, 1H), 1.18-1.28 (m, 11H), 0.90-0.99 (m, 6H). MS (M+1): 519.

Compound 8-8: 3-(4-(((2S,3S)-1-((2'-chloro-2-fluoro-4'-(trifluoromethyl)-[1,1'-biphenyl]-4-yl)oxy)-3-methylpentan-2-yl)amino)benzamido)propanoic Acid

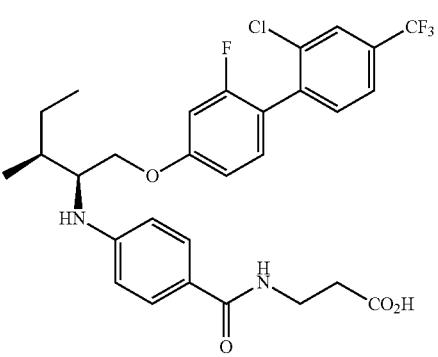 [SMILES: CC[C@H](C)[C@@H](COc1ccc(-c2ccc(C(F)(F)F)cc2Cl)c(F)c1)Nc1ccc(C(=O)NCCC(=O)O)cc1]

$^1$H NMR (400 MHz, CDCl$_3$): δ 7.71 (s, 1H), 7.59 (d, J=8.3 Hz, 2H), 7.53 (d, J=8.3 Hz, 1H), 7.39 (d, J=−8.3 Hz, 1H), 7.16 (t, J=8.6 Hz, 1H), 6.63-6.82 (m, 3H), 6.58 (d, J=8.8 Hz, 2H), 4.01-4.11 (m, 2H), 3.59-3.72 (m, 3H), 2.65 (t, J=5.9 Hz, 2H), 1.80-1.90 (m, 1H), 1.55-1.69 (m, 1H), 1.16-1.23 (m, 1H), 1.00 (d, J=6.4 Hz, 3H), 0.94 (t, J=7.3 Hz, 3H). MS (M+1): 581.

Compound 8-9: (S)-3-(4-((1-((2',4'-dichloro-2-fluoro-[1,1'-biphenyl]-4-yl)oxy)-3-methylbutan-2-yl)amino)benzamido)propanoic Acid

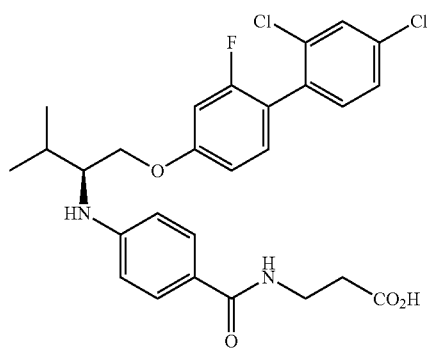 [SMILES: CC(C)[C@@H](COc1ccc(-c2ccc(Cl)cc2Cl)c(F)c1)Nc1ccc(C(=O)NCCC(=O)O)cc1]

$^1$H NMR (400 MHz, CDCl$_3$): δ 7.58 (d, J=8.8 Hz, 2H), 7.44-7.46 (m, 1H), 7.23-7.27 (m, 1H), 7.19 (d, J=8.3 Hz, 1H), 7.10-7.16 (m, 1H), 6.77-6.89 (m, 1H), 6.62-6.72 (m, 2H), 6.57 (dd, J=8.6, 1.2 Hz, 2H), 3.97-4.05 (m, 2H), 3.66 (d, J=3.4 Hz, 2H), 3.56 (q, J=4.6 Hz, 1H), 2.61-2.67 (m, 2H), 2.11 (ddd, J=13.2, 6.8, 1.5 Hz, 1H), 0.99-1.05 (m, 6H). MS (M+1): 533.

Compound 8-10: 3-(4-(((2S,3S)-1-((2,2'-difluoro-4'-(trifluoromethyl)-[1,1'-biphenyl]-4-yl)oxy)-3-methylpentan-2-yl)amino)benzamido)propanoic Acid

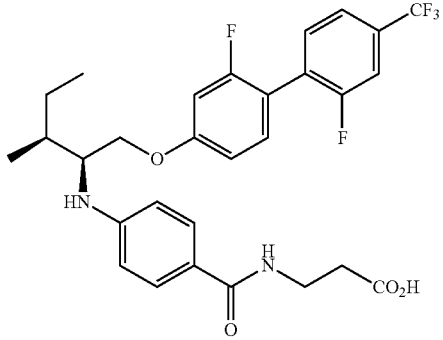 [SMILES: CC[C@H](C)[C@@H](COc1ccc(-c2ccc(C(F)(F)F)cc2F)c(F)c1)Nc1ccc(C(=O)NCCC(=O)O)cc1]

$^1$H NMR (400 MHz, CDCl$_3$): δ 7.59 (d, J=8.8 Hz, 2H), 7.42-7.46 (m, 2H), 7.38 (d, J=9.8 Hz, 1H), 7.21-7.28 (m, 1H), 6.77-6.87 (m, 1H), 6.65-6.76 (m, 2H), 6.57 (d, J=8.8 Hz, 2H), 4.01-4.07 (m, 2H), 3.60-3.69 (m, 3H), 2.64 (t, J=4.9 Hz, 2H), 1.79-1.89 (m, 1H), 1.63 (ddd, J=13.1, 7.5, 3.9 Hz, 1H), 1.18-1.29 (m, 1H), 0.98 (d, J=6.8 Hz, 3H), 0.93 (t, J=7.3 Hz, 2H). MS (M+1): 565.

Compound 8-12: (S)-3-(4-((1-((3',5'-dichloro-2-fluoro-[1,1'-biphenyl]-4-yl)oxy)-3-methylbutan-2-yl)amino)benzamido)propanoic Acid

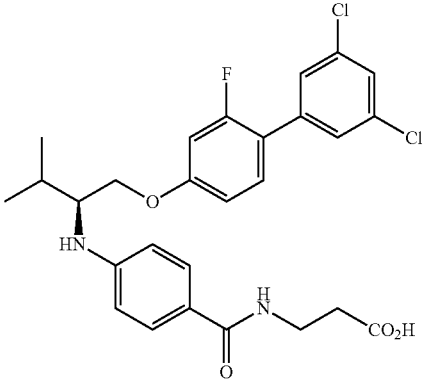

$^1$H NMR (400 MHz, CDCl$_3$): δ 7.58 (d, J=8.8 Hz, 2H), 7.34 (t, J=1.5 Hz, 2H), 7.27-7.30 (m, 1H), 7.21-7.27 (m, 1H), 6.77 (d, J=5.4 Hz, 1H), 6.62-6.71 (m, 2H), 6.58 (d, J=8.8 Hz, 2H), 3.98-4.03 (m, 2H), 3.66 (q, J=5.4 Hz, 2H), 3.53-3.59 (m, 1H), 2.64 (t, J=5.6 Hz, 2H), 2.05-2.14 (m, 1H), 1.01 (dd, J=6.6, 4.6 Hz, 6H). MS (M+1): 533.

Compound 8-11: 3-(4-(((2S,3S)-1-((2',4'-dichloro-2-fluoro-[1,1'-biphenyl]-4-yl)oxy)-3-methylpentan-2-yl)amino)benzamido)propanoic Acid

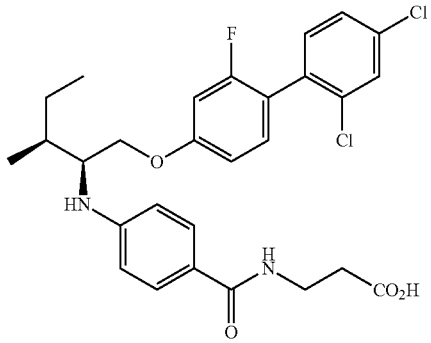 [SMILES: CC[C@H](C)[C@@H](COc1ccc(-c2ccc(Cl)cc2Cl)c(F)c1)Nc1ccc(C(=O)NCCC(=O)O)cc1]

$^1$H NMR (400 MHz, CDCl$_3$): δ 7.58 (d, J=8.8 Hz, 2H), 7.45 (d, J=2.0 Hz, 1H), 7.23-7.27 (m, 1H), 7.16-7.20 (m, 1H), 7.13 (t, J=8.3 Hz, 1H), 6.79 (t, J=5.4 Hz, 1H), 6.62-6.72 (m, 2H), 6.57 (d, J=8.3 Hz, 2H), 3.98-4.07 (m, 2H), 3.59-3.70 (m, 3H), 2.64 (t, J=5.4 Hz, 2H), 1.79-1.90 (m, 1H), 1.64 (ddd, J=13.3, 7.5, 3.7 Hz, 1H), 1.17-1.28 (m, 1H), 0.99 (d, J=6.8 Hz, 3H), 0.93 (t, J=7.6 Hz, 3H). MS (M+1): 547.

Compound 8-13: (S)-3-(4-((1-(4-(benzofuran-2-yl)-3-fluorophenoxy)hexan-2-yl)amino)benzamido) propanoic Acid

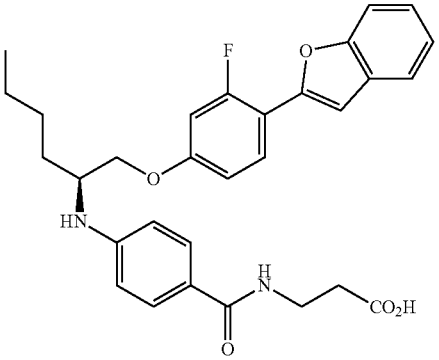 [SMILES: CCCC[C@@H](COc1ccc(-c2cc3ccccc3o2)c(F)c1)Nc1ccc(C(=O)NCCC(=O)O)cc1]

$^1$H NMR (400 MHz, CDCl$_3$): δ 7.87 (t, J=8.6 Hz, 1H), 7.57 (dd, J=15.9, 7.6 Hz, 3H), 7.47 (d, J=8.3 Hz, 1H), 7.17-7.27 (m, 2H), 7.05 (d, J=3.4 Hz, 1H), 6.58-6.76 (m, 3H), 6.55 (d, J=8.3 Hz, 2H), 3.84-3.99 (m, 2H), 3.60-3.74 (m, 3H), 2.62 (t, J=5.6 Hz, 2H), 1.66-1.82 (m, 1H), 1.49-1.64 (m, 1H), 1.23-1.42 (m, 4H), 0.88 (t, J=6.9 Hz, 3H). MS (M+1): 519.

Compound 8-14: 3-(4-(((2S,3S)-1-((2-fluoro-4'-(trifluoromethyl)-[1,1'-biphenyl]-4-yl)oxy)-3-methylpentan-2-yl)amino)benzamido)propanoic Acid

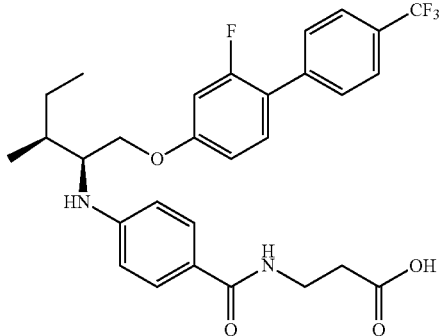 [SMILES: CC[C@H](C)[C@@H](COc1ccc(-c2ccc(C(F)(F)F)cc2)c(F)c1)Nc1ccc(C(=O)NCCC(=O)O)cc1]

¹H NMR (400 MHz, CDCl₃): δ 7.51-7.68 (m, 6H), 7.30 (t, J=8.8 Hz, 1H), 6.82 (t, J=5.9 Hz, 1H), 6.64-6.76 (m, 2H), 6.52-6.61 (m, 2H), 4.00-4.08 (m, 2H), 3.60-3.68 (m, 3H), 2.63 (t, J=5.6 Hz, 2H), 1.78-1.90 (m, 1H), 1.57-1.69 (m, 1H), 1.21-1.27 (m, 1H), 0.90-1.00 (m, 6H). MS (M+1): 547. HPLC: 97%.

Compound 8-16: (S)-3-(4-((1-((2',4'-dichloro-2-fluoro-[1,1'-biphenyl]-4-yl)oxy)hexan-2-yl)amino)benzamido)propanoic Acid

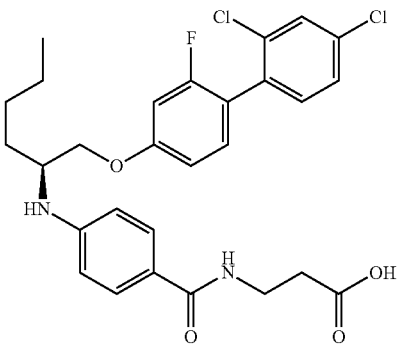

¹H NMR (400 MHz, CDCl₃): δ 7.59 (d, J=8.3 Hz, 2H), 7.43-7.46 (m, 1H), 7.23-7.27 (m, 1H), 7.17-7.21 (m, 1H), 7.13 (t, J=8.3 Hz, 1H), 6.80-6.91 (m, 1H), 6.63-6.73 (m, 2H), 6.56 (d, J=8.3 Hz, 2H), 3.91-4.02 (m, 2H), 3.71-3.80 (m, 1H), 3.61-3.69 (m, 2H), 2.59-2.66 (m, 2H), 1.73-1.85 (m, 1H), 1.55-1.66 (m, 1H), 1.29-1.47 (m, 4H), 0.88 (t, J=7.1 Hz, 3H). MS (M+1): 547.

Compound 8-15: (S)-3-(4-((1-((2'-chloro-2-fluor-4'-(trifluromethyl)-[1,1'-biphenyl]-4-yl)oxy)hexan-2-yl)amino)benzamido)propanoic Acid

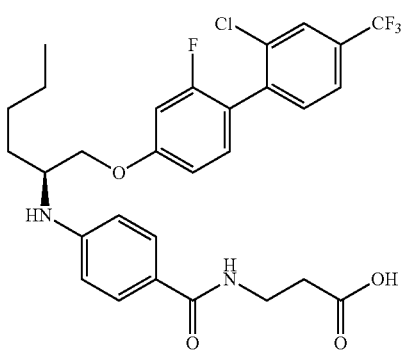 [SMILES: CCCC[C@@H](COc1ccc(-c2ccc(C(F)(F)F)cc2Cl)c(F)c1)Nc1ccc(C(=O)NCCC(=O)O)cc1]

¹H NMR (400 MHz, CDCl₃): δ 7.71 (d, J=1.0 Hz, 1H), 7.60 (d, J=8.3 Hz, 2H), 7.52 (dd, J=8.1, 1.2 Hz, 1H), 7.39 (d, J=8.3 Hz, 1H), 7.14-7.20 (m, 1-), 6.89 (t, J=5.6 Hz, 1H), 6.66-6.76 (m, 2H), 6.58 (d, J=8.8 Hz, 2H), 3.95-4.03 (m, 2H), 3.73-3.80 (m, 1H), 3.65 (q, J=5.9 Hz, 2H), 2.63 (t, J=5.6 Hz, 2H), 1.75-1.84 (m, 1H), 1.56-1.67 (m, 1H), 1.31-1.49 (m, 4H), 0.89 (t, J=7.1 Hz, 3H). MS (M+1): 581.

Compound 8-17: (S)-3-(4-((1-((2,2'-difluoro-4'-(trifluoromethyl)-[1,1'-biphenyl]-4-yl)oxy)hexan-2-yl)amino)benzamido)propanoic Acid

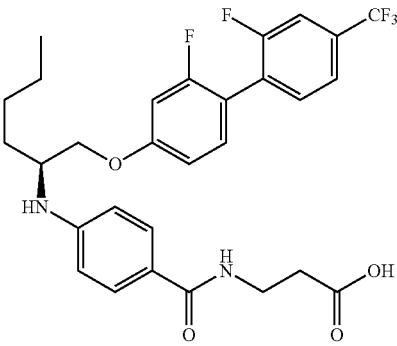 [SMILES: CCCC[C@@H](COc1ccc(-c2ccc(C(F)(F)F)cc2F)c(F)c1)Nc1ccc(C(=O)NCCC(=O)O)cc1]

¹H NMR (400 MHz, CDCl₃): δ 7.59 (d, J=8.3 Hz, 2H), 7.41-7.48 (m, 2H), 7.38 (d, 3=9.8 Hz, 1H), 7.21-7.27 (m, 1H), 6.81-6.96 (m, 1H), 6.66-6.77 (m, 2H), 6.57 (d, J=8.8 Hz, 2H), 3.93-4.02 (m, 2H), 3.72-3.80 (m, 1H), 3.65 (q, J=5.4 Hz, 2H), 2.63 (t, J=5.4 Hz, 2H), 1.74-1.85 (m, 1H), 1.56-1.67 (m, 1H), 1.29-1.49 (m, 4H), 0.88 (t, J=6.8 Hz, 3H). MS (M+1): 565.

Compound 8-18: (S)-3-(4-((1-((2-fluoro-4'-(trifluoromethyl)-[1,1'-biphenyl]-4-yl)oxy)hexan-2-yl)amino)benzamido)propanoic Acid

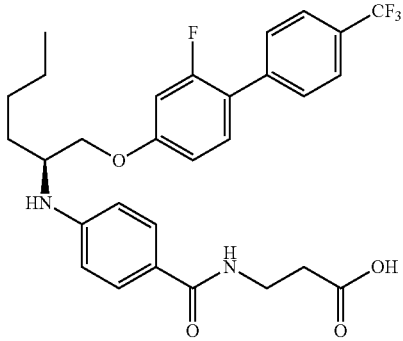 [SMILES: CCCC[C@@H](COc1ccc(-c2ccc(C(F)(F)F)cc2)c(F)c1)Nc1ccc(C(=O)NCCC(=O)O)cc1]

$^1$H NMR (400 MHz, CDCl$_3$): δ 7.54-7.65 (m, 6H), 7.30 (t, J=8.8 Hz, 1H), 6.86 (d, J=4.9 Hz, 1H), 6.64-6.76 (m, 2H), 6.51-6.62 (m, 2H), 3.88-4.02 (m, 2H), 3.57-3.80 (m, 3H), 2.61 (br. s., 2H), 1.71-1.86 (m, 1H), 1.51-1.66 (m, 1H), 1.27-1.46 (m, 4H), 0.88 (t, J=6.8 Hz, 3H). MS (M+1): 547.

Compound 8-19: (S)-3-(4-((1-((2',4'-dichloro-2-fluoro-[1,1'-biphenyl]-4-yl)oxy)-4-methylpentan-2-yl)amino)benzamido)propanoic Acid

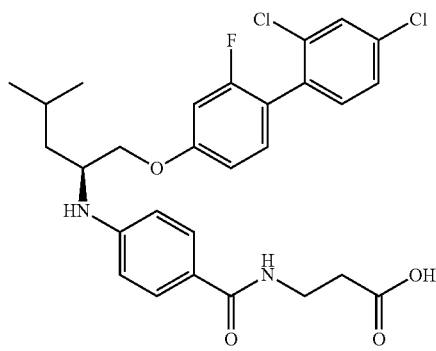 [SMILES: CC(C)C[C@@H](COc1ccc(-c2ccc(Cl)cc2Cl)c(F)c1)Nc1ccc(C(=O)NCCC(=O)O)cc1]

$^1$H NMR (400 MHz, DMSO-d$_6$): δ 8.06 (t, J=5.4 Hz, 1H), 7.73 (d, J=2.0 Hz, 1H), 7.56-7.62 (m, J=8.8 Hz, 2H), 7.48-7.52 (m, 1H), 7.39 (d, J=8.8 Hz, 1H), 7.21-7.29 (m, 1H), 6.92 (dd, J=11.7, 2.4 Hz, 1H), 6.86 (dd, J=8.8, 2.4 Hz, 1H), 6.61-6.67 (m, J=8.8 Hz, 2H), 6.09 (d, J=8.8 Hz, 1H), 3.99 (d, J=4.9 Hz, 2H), 3.79-3.90 (m, 1H), 3.36-3.43 (m, 2H), 2.45 (t, J=7.2 Hz, 2H), 1.72-1.84 (m, 1H), 1.50-1.57 (m, 2H), 0.95 (d, J=6.8 Hz, 3H), 0.88 (d, J=6.8 Hz, 3H). MS (M+1): 547.

Compound 8-20: (S)-3-(4-((1-(4-(benzofuran-2-yl)-3-fluorophenoxy)-4-methylpentan-2-yl)amino)benzamido)propanoic Acid

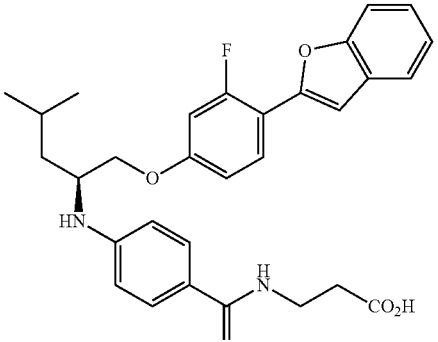

$^1$H NMR (400 MHz, DMSO-d$_6$): δ 8.08 (br. s., 1H), 7.88 (t, J=9.0 Hz, 1H), 7.67 (dd, J=7.2, 1.2 Hz, 1H), 7.56-7.63 (m, 3H), 7.32 (td, J=7.6, 1.6 Hz, 1H), 7.23-7.29 (m, 1H), 7.14-7.18 (m, 1H), 7.02 (dd, J=13.6, 2.4 Hz, 1H), 6.94 (dd, J=8.8, 2.4 Hz, 1H), 6.64 (d, J=8.8 Hz, 2H), 6.09 (d, J=8.4 Hz, 1H), 4.02 (d, J=5.4 Hz, 2H), 3.80-3.91 (m, 1H), 3.36-3.43 (m, 3H), 2.43 (t, J=7.2 Hz, 2H), 1.72-1.83 (m, 1H), 1.48-1.58 (m, 2H), 0.95 (d, J=6.8 Hz, 4H), 0.88 (d, J=6.8 Hz, 4H). MS (M+1): 518.

Compound 8-21: (S)-3-(4-((1-(4-(benzofuran-2-yl)-3-fluorophenoxy)-3,3-dimethylbutan-2-yl)amino)benzamido)propanoic Acid $^1$H NMR (400 MHz, DMSO-d$_6$): δ 7.99-8.10 (m, 1H), 7.85 (s, 1H), 7.57 (d, J=8.8 Hz, 4H), 7.22-7.38 (m, 2H), 7.12-7.18 (m, 1H), 6.97-7.05 (m, 1H), 6.82-6.91 (m, 1H), 6.70 (d, J=8.8 Hz, 2H), 5.97-6.05 (m, 1H), 4.27-4.39 (m, 1H), 3.96-4.06 (m, 1H), 3.60-3.78 (m, 2H), 2.39-2.48 (m, 2H), 1.02 (s, 9H). MS (M+1): 519.

Compound 8-22: (S)-3-(4-((1-((2',4'-dichloro-2-fluoro-[1,1'-biphenyl]-4-yl)oxy)-3,3-dimethylbutan-2-yl)amino)benzamido)propanoic Acid

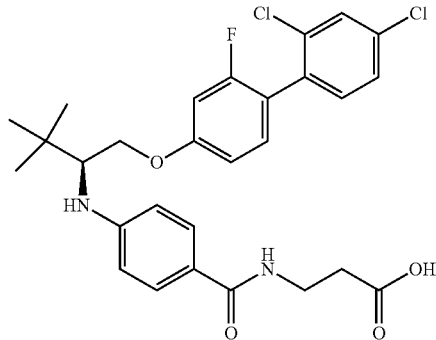 [SMILES: CC(C)(C)[C@@H](COc1ccc(-c2ccc(Cl)cc2Cl)c(F)c1)Nc1ccc(C(=O)NCCC(=O)O)cc1]

$^1$H NMR (400 MHz, Acetone-d$_6$): δ 7.67 (d, J=8.8 Hz, 2H), 7.60 (d, J=2.0 Hz, 1H), 7.41-7.47 (m, 2H), 7.38 (d, 1H), 7.22 (t, 1H), 6.74-6.84 (m, 4H), 5.38 (d, 1H), 4.41 (dd, J=9.8, 3.9 Hz, 1H), 4.13 (dd, J=10.0, 7.1 Hz, 1H), 3.75-3.83 (m, 1H), 3.54-3.63 (q, 2H), 2.61 (t, J=6.8 Hz, 3H), 1.12 (s, 9H). MS (M+1): 547.

Compound 8-24: (S)-3-(4-((1-(3-fluoro-4-(5-(trifluoromethyl)-1,3,4-oxadiazol-2-yl)phenoxy)hexan-2-yl)amino)benzamido)propanoic Acid

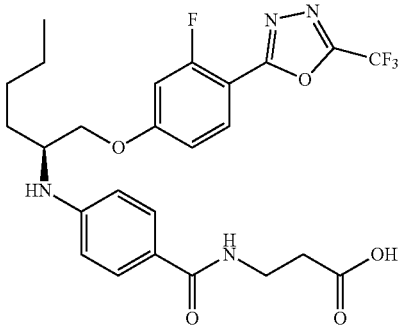

$^1$H NMR (400 MHz, DMSO-d$_6$): δ 8.04 (t, J=6.0 Hz, 1H), 8.00 (t, J=8.8 Hz, 1H), 7.59 (d, J=8.8 Hz, 2H), 7.16 (dd, J=13.2, 2.4 Hz, 1H), 7.02 (dd, J=9.0, 2.2 Hz, 1H), 6.63 (d, J=8.8 Hz, 2H), 6.01-6.24 (m, 1H), 4.10 (d, J=5.4 Hz, 2H), 3.74-3.89 (m, 1H), 3.37-3.42 (m, 2H), 2.44-2.48 (m, 2H), 1.51-1.78 (m, 2H), 1.23-1.47 (m, 5H), 0.85-0.87 (t, J=8.0 Hz, 3H). MS (M+1): 539.

Compound 8-23: (S)-3-(4-((1-((2,2'-difluoro-4'-(trifluoromethyl)-[1,1'-biphenyl]-4-yl)oxy)-3,3-dimethylbutan-2-yl)amino)benzamido)propanoic Acid

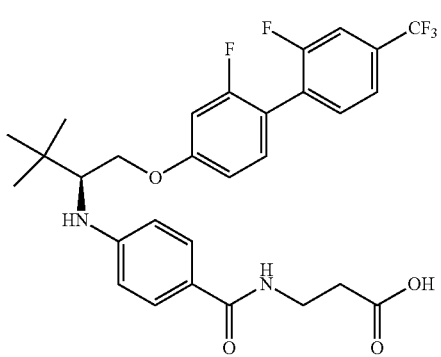 [SMILES: CC(C)(C)[C@@H](COc1ccc(-c2ccc(C(F)(F)F)cc2F)c(F)c1)Nc1ccc(C(=O)NCCC(=O)O)cc1]

$^1$H NMR (400 MHz, Acetone-d$_6$): δ 7.84-7.91 (m, 1H), 7.56-7.80 (m, 4H), 7.42-7.52 (m, 1H), 7.23-7.33 (m, 1H), 6.74-6.90 (m, 4H), 5.31-5.44 (m, 1H), 4.38-4.45 (m, 1H), 4.09-4.20 (m, 1H), 3.75-3.87 (m, 1H), 3.53-3.65 (m, 2H), 2.56-2.62 (m, 3H), 1.12 (s, 9H). MS (M+1): 565.

Compound 8-25: (S)-3-(4-((1-(4-(benzo[d]thiazol-2-yl)-3-fluorophenoxy)-3-methylbutan-2-yl)amino)benzamido)propanoic Acid

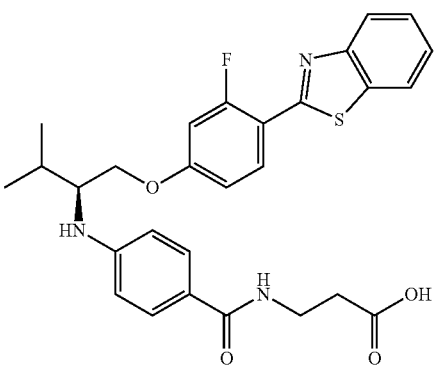 [SMILES: CC(C)[C@@H](COc1ccc(-c2nc3ccccc3s2)c(F)c1)Nc1ccc(C(=O)NCCC(=O)O)cc1]

$^1$H NMR (400 MHz, DMSO-d$_6$): δ 12.16 (br. s., 1H), 8.48 (d, J=2.4 Hz, 1H), 8.23-8.31 (m, 1H), 8.20 (t, J=5.4 Hz, 1H), 8.14 (d, J=7.8 Hz, 1H), 8.06 (d, J=7.8 Hz, 1H), 7.78 (dd, J=8.8, 2.4 Hz, 1H), 7.51-7.61 (m, 1H), 7.41-7.51 (m, 1H), 7.17 (d, J=13.7 Hz, 1H), 7.03 (d, J=8.8 Hz, 1H), 7.07 (d, J=8.3 Hz, 1H), 6.59 (d, J=8.8 Hz, 1H), 4.31 (br. s., 1H), 4.09-4.23 (m, 2H), 3.38-3.46 (m, 2H), 2.43-2.48 (m, 2H), 1.99-2.13 (m, 1H), 0.98 (d, J=6.6 Hz, 6H). MS (M+1): 522.

Example 9: Synthesis of Compounds 9-1 to 9-6

Compound 9-1: (S)-3-(5-((1-(4-(benzofuran-2-yl)phenoxy)-3-methylbutan-2-yl)amino)pyrazino-2-carboxamido)propanoic Acid

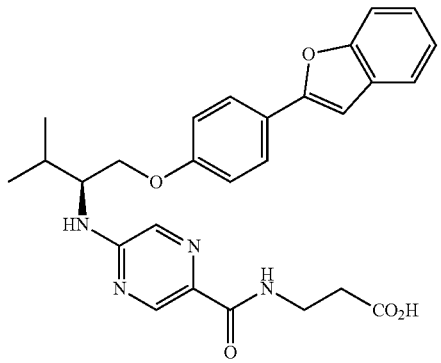 [SMILES: CC(C)[C@@H](COc1ccc(-c2cc3ccccc3o2)cc1)Nc1cnc(C(=O)NCCC(=O)O)cn1]

White solid. $^1$HNMR (400 MHz, DMSO-$d_6$): δ 8.51 (d, J=1.0 Hz, 1H), 8.27 (t, J=5.8 Hz, 1H), 8.00 (d, J=1.0 Hz, 1H), 7.83 (d, J=8.8 Hz, 2H), 7.74 (d, J=8.8 Hz, 1H), 7.62-7.57 (m, 2H), 7.30-7.21 (m, 3H), 7.07 (d, J=8.8 Hz, 2H), 4.32-4.27 (m, 1H), 4.16-4.12 (m, 2H), 3.48-3.43 (m, 2H), 2.48 (t, J=8.8 Hz, 2H), 2.13-2.06 (m, 1H), 1.00-0.97 (m, 6H). MS (M+1): 489.

Compound 9-2: 3-(5-(((2S,3 S)-1-((2',4'-dichloro-[1,1'-biphenyl]-4-yl)oxy)-3-methylpentan-2-yl)amino)pyrazine-2-carboxamido)propanoic Acid

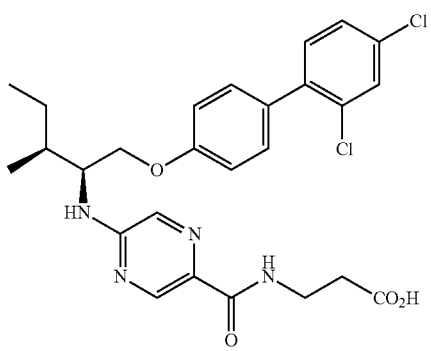

White solid. $^1$HNMR (400 MHz, DMSO-$d_6$): δ 8.50 (d, J=1.9 Hz, 1H), 8.25 (t, J=5.4 Hz, 1H), 7.98 (d, J=1.9 Hz, 1H), 7.78 (d, J=8.4 Hz, 1H), 7.68 (d, J=1.9 Hz, 1H), 7.47 (d, J=8.8, 1.9 Hz, 1H), 7.39 (d, J=8.8 Hz, 1H), 7.33 (d, J=8.8 Hz, 2H), 7.02 (d, J=8.8 Hz, 2H), 4.32 (brs, 1H), 4.17-4.12 (m, 1H), 3.48-3.43 (m, 2H), 2.48 (t, J=7 Hz, 2H), 1.87-1.84 (m, 1H), 1.59-1.55 (m, 1H), 1.28-1.22 (m, 1H), 0.97 (d, J=6.8 Hz, 3H), 0.89 (t, J=6.8 Hz, 3H). MS (M+1): 531.

Compound 9-3: (S)-3-(5-((3-methyl-1-((4'-(trifluoromethyl)-[1,1'-biphenyl]-4-yl)oxy)butan-2-yl)amino)picolinamido)propanoic Acid

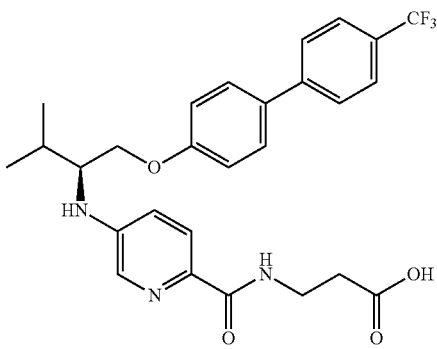 [SMILES: CC(C)[C@@H](COc1ccc(-c2ccc(C(F)(F)F)cc2)cc1)Nc1ccc(C(=O)NCCC(=O)O)nc1]

White solid. $^1$HNMR (400 MHz, DMSO-$d_6$): δ 8.31 (t, J=6 Hz, 1H), 8.06 (d, J=1.5 Hz, 1H), 7.82 (d, J=8 Hz, 2H), 7.76-7.73 (m, 3H), 7.66 (d, J=8 Hz, 2H), 7.11 (dd, J=8, 4 Hz, 1H), 7.04 (d, J=8 Hz, 1H), 6.50 (d, J=10 Hz, 1H), 4.15 (dd, J=10, 6 Hz, 1H), 4.04 (dd, J=10.6 Hz, 1H), 3.74-3.71 (m, 1H), 3.46 (quartet, J=6.8 Hz, 2H), 2.48 (t, J=6.8 Hz, 2H), 2.09-2.01 (m, 1H), 1.02-0.99 (m, 6H). MS (M+1): 516.

Compound 9-4: (S)-3-(6-((1-((2,6-difluoro-4'-(trifluoromethyl)-[1,1'-biphenyl]-4-yl)oxy)-4-methylpentan-2-yl)amino)nicotinamido)propanoic Acid

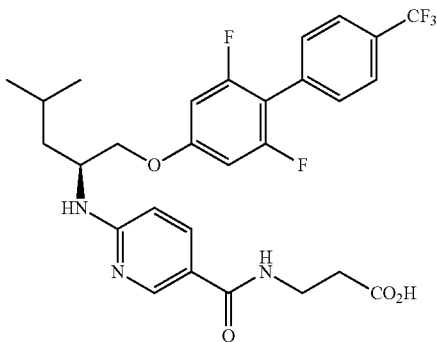 [SMILES: CC(C)C[C@@H](COc1cc(F)c(-c2ccc(C(F)(F)F)cc2)c(F)c1)Nc1ccc(C(=O)NCCC(=O)O)cn1]

White solid. $^1$HNMR (400 MHz, DMSO-$d_6$): δ 8.50 (d, J=2.4 Hz, 1H), 8.22 (t, J=5.6 Hz, 1H), 7.83-7.77 (m, 3H), 7.64 (d, J=8.3 Hz, 2H), 7.06 (d, J=7.8 Hz, 1H), 6.94 (d, J=8.8 Hz, 2H), 6.53 (d, J=8.8 Hz, 1H), 4.44 (brs, 1H), 4.12-3.95 (m, 2H), 3.44-3.39 (m, 2H), 2.47 (t, J=6.8 Hz, 2H), 1.73-1.71 (m, 1H), 1.58-1.50 (m, 2H), 0.92 (d, J=6.4 Hz, 3H), 0.85 (d, J=6.4 Hz, 3H). MS (M+1): 566.

Compound 9-5: (S)-3-(6-((1-(4-(benzo[d]thiazol-2-yl)-3-fluorophenoxy)-3-methylbutan-2-yl)amino)nicotinamido)propanoic Acid

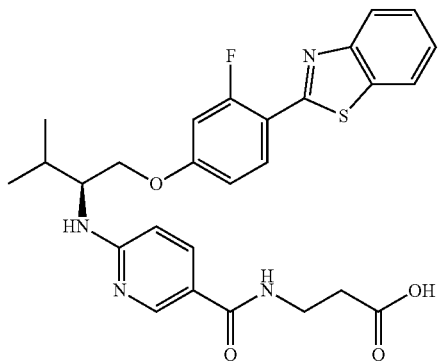 [SMILES: CC(C)[C@@H](COc1ccc(-c2nc3ccccc3s2)c(F)c1)Nc1ccc(C(=O)NCCC(=O)O)cn1]

$^1$H NMR (400 MHz, DMSO-$d_6$): δ12.16 (br. s., 1H), 8.48 (d, J=2.4 Hz, 1H), 8.23-8.31 (m, 1H), 8.20 (t, J=5.4 Hz, 1H), 8.14 (d, J=7.8 Hz, 1H), 8.06 (d, J=7.8 Hz, 1H), 7.78 (dd, J=8.8, 2.4 Hz, 1H), 7.51-7.61 (m, 1H), 7.41-7.51 (m, 1H), 7.17 (d, J=13.7 Hz, 1H), 7.03 (d, J=8.8 Hz, 1H), 7.07 (d, J=8.3 Hz, 1H), 6.59 (d, J=8.8 Hz, 1H), 4.31 (br. s., 1H), 4.09-4.23 (m, 2H), 3.38-3.46 (m, 2H), 2.43-2.48 (m, 2H), 1.99-2.13 (m, 1H), 0.98 (t, J=6.6 Hz, 6H). MS (M+1): 523.

Compound 9-6: (S)-3-(4-((1-((1-(2,4-difluorophenyl)-1H-pyrazol-4-yl)oxy)-4-methylpentan-2-yl)amino)benzamido)propanoic Acid

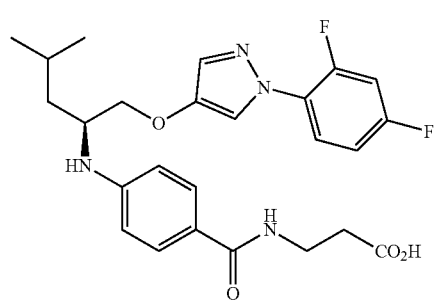 [SMILES: CC(C)C[C@@H](COc1cnn(-c2ccc(F)cc2F)c1)Nc1ccc(C(=O)NCCC(=O)O)cc1]

White solid. $^1$HNMR (400 MHz, DMSO-$d_6$): δ 8.04 (t, J=5.4 Hz, 1H), 7.89 (d, J=1.9 Hz, 1H), 7.76-7.70 (m, 1H), 7.59-7.57 (m, 3H), 7.52-7.47 (m, 1H), 7.24-7.20 (m, 1H), 6.61 (d, J=8.8 Hz, 2H), 6.07 (d, J=8.8 Hz, 1H), 3.92-3.85 (m, 2H), 3.84-3.76 (m, 1H), 2.46 (t, J=6.8 Hz, 2H), 1.77-1.73 (m, 1H), 1.52-1.48 (m, 2H), 0.93 (d, J=6.8 Hz, 3H), 0.85 (d, J=6.8 Hz, 3H). MS (M+1): 487.

Example 10: Synthesis of Compounds 10-1 to 10-19

Compound 10-1: (S)-3-(4-((3-methyl-1-((6-(4-(trifluoromethyl)phenyl)pyridin-3-yl)oxy)butan-2-yl)amino)benzamido)propanoic Acid

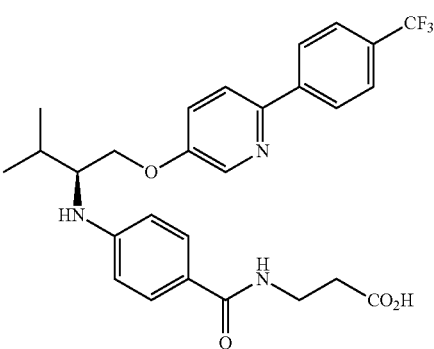 [SMILES: CC(C)[C@@H](COc1ccc(-c2ccc(C(F)(F)F)cc2)nc1)Nc1ccc(C(=O)NCCC(=O)O)cc1]

White solid. $^1$HNMR (400 MHz, DMSO-$d_6$): δ 8.38 (d, J=3 Hz, 1H), 8.21 (d, J=8.8 Hz, 2H), 8.05 (t, J=5.4 Hz, 1H), 7.99 (d, J=8.8 Hz, 1H), 7.78 (d, J=8.8 Hz, 2H), 7.61 (d, J=8.8 Hz, 2H), 7.50 (dd, J=8.8, 2.5 Hz, 1H), 6.67 (d, J=8.8 Hz, 2H), 6.13 (d, J=8.8 Hz, 1H), 4.42-4.10 (m, 2H), 3.71-3.65 (m, 1H), 3.44-3.39 (m, 2H), 2.48 (t, J=7 Hz, 2H), 2.07-2.02 (m, 1H), 1.01-0.97 (m, 6H). MS (M+1): 516.

Compound 10-2: (S)-3-(4-((1-((6-(2-chloro-4-(trifluoromethyl)phenyl)pyridin-3-yl)ox)-3-methylbutan-2-yl)aminobenzamido)propanoic Acid

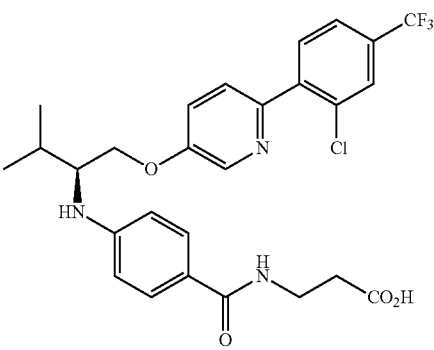 [SMILES: CC(C)[C@@H](COc1ccc(-c2ccc(C(F)(F)F)cc2Cl)nc1)Nc1ccc(C(=O)NCCC(=O)O)cc1]

White solid. $^1$HNMR (400 MHz, DMSO-$d_6$): δ 8.40 (d, J=3 Hz, 1H), 8.06-8.05 (m, 1H), 7.94-7.92 (m, 1H), 7.88 (s, 1H), 7.68-7.60 (m, 3H), 7.53-7.49 (m, 1H), 6.69-6.66 (m, 2H), 6.10-6.04 (m, 1H), 6.13 (d, J=8.8 Hz, 1H), 4.22-4.12 (m, 2H), 3.70-3.67 (m, 1H), 3.44-3.39 (m, 2H), 2.48 (t, J=7 Hz, 2H), 2.09-2.03 (m, 1H), 1.02-0.98 (m, 6H). MS (M+1): 550.

Compound 10-3: (S)-3-(4-((1-((6-(2-fluoro-4-(trifluoromethyl)phenyl)pyridin-3-yl)oxy)-3-methylbutan-2-yl)amino)benzamido)propanoic Acid

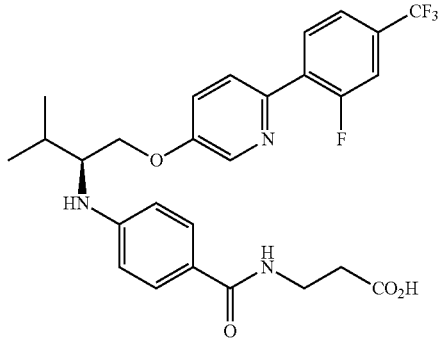 [SMILES: CC(C)[C@@H](COc1ccc(-c2ccc(C(F)(F)F)cc2F)nc1)Nc1ccc(C(=O)NCCC(=O)O)cc1]

White solid. ¹HNMR (400 MHz, DMSO-d$_6$): δ 12.18 (brs, 1H), 8.43 (d, J=3 Hz, 1H), 8.14-8.04 (m, 2H), 7.81-7.73 (m, 2H), 7.66-7.60 (m, 3H), 7.52 (dd, J=8.8, 2.5 Hz, 1H), 6.67 (d, J=8.8 Hz, 2H), 6.13 (d, J=8.8 Hz, 1H), 6.55-6.59 (m, 2H), 6.09 (d, J=8.8 Hz, 1H), 4.22-4.12 (m, 2H), 3.72-3.65 (m, 1H), 3.45-3.40 (m, 2H), 2.48 (t, J=7 Hz, 2H), 2.09-2.01 (m, 1H), 1.02-0.97 (m, 6H). MS (M+1): 534.

Compound 10-5: (S)-3-(4-((1-((6-(3,5-dichlorophenyl)pyridin-3-yl)oxy)-3-methylbutan-2-yl)amino)benzamido)propenoic Acid

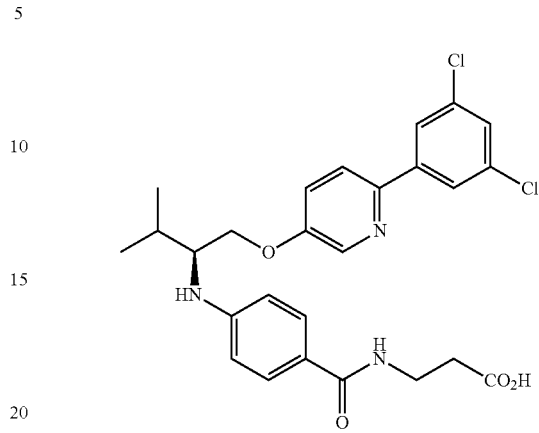

White solid. ¹HNMR (400 MHz, DMSO-d$_6$): δ 8.35 (d, J=3 Hz, 1H), 8.04-8.02 (m, 4H), 7.60-7.57 (m, 3H), 7.51-7.48 (m, 1H), 6.66 (d, J=8.8 Hz, 2H), 6.12 (d, J=8.8 Hz, 1H), 4.21-4.09 (m, 2H), 3.69-3.66 (m, 1H), 3.43-3.38 (m, 2H), 2.47 (t, J=7 Hz, 2H), 2.07-2.03 (m, 1H), 1.01-0.97 (m, 6H). MS (M+1): 516.

Compound 10-4: (S)-3-(4-((1-((6-(2,4-dichlorophenyl)pyridin-3-yl)oxy)-3-methylbutan-2-yl)amino)benzamido)propanoic Acid

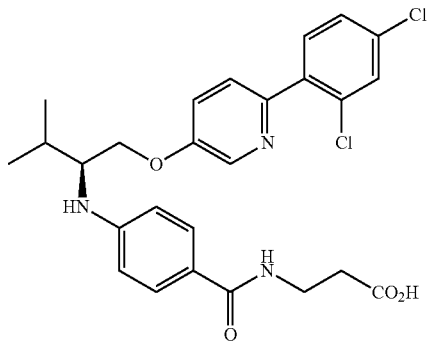 [SMILES: CC(C)[C@@H](COc1ccc(-c2ccc(Cl)cc2Cl)nc1)Nc1ccc(C(=O)NCCC(=O)O)cc1]

¹H NMR (400 MHz, DMSO-d$_6$): δ 8.36 (d, J=3 Hz, 1H), 8.04 (t, J=5.4 Hz, 1H), 7.69 (d, J=3 Hz, 1H), 7.61-7.56 (m, 4H), 7.51-7.47 (m, 2H), 6.67 (d, J=8.8 Hz, 2H), 6.12 (d, J=8.8 Hz, 1H), 4.21-4.02 (m, 2H), 3.69-3.66 (m, 1H), 3.44-3.39 (m, 2H), 2.47 (t, J=7 Hz, 2H), 2.07-2.02 (m, 1H), 1.02-0.97 (m, 6H). MS (M+1): 516.

Compound 10-6: (S)-3-(4-((1-((6-(benzofuran-2-yl)pyridin-3-yl)oxy)-3-methylbutan-2-yl)amino)benzamido)propanoic Acid

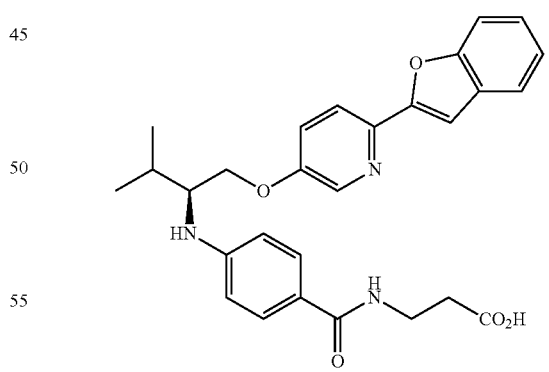

White solid. ¹HNMR (400 MHz, DMSO-d$_6$): δ 8.36 (d, J=3 Hz, 1H), 8.05 (t, J=5.4 Hz, 1H), 7.88 (d, J=8.8 Hz, 1H), 7.67 (d, J=7.8 Hz, 1H), 7.63-7.60 (m, 3H), 7.52 (dd, J=7.8, 3 Hz, 1H), 7.38 (s, 1H), 7.33 (dt, J=7.8, 1.9 Hz, 1H), 7.26 (dt, J=7.8, 1.9 Hz, 1H), 6.67 (d, J=8.8 Hz, 2H), 6.12 (d, J=8.8 Hz, 1H), 4.22-4.01 (m, 2H), 3.70-3.67 (m, 1H), 3.44-3.39 (m, 2H), 2.48 (t, J=7 Hz, 2H), 2.09-2.02 (m, 1H), 1.02-0.97 (m, 6H). MS (M+1): 488.

Compound 10-7: (S)-3-(4-((1-((6-(2,4-dichlorophenyl)pyridin-3-yl)oxy)hexan-2-yl)amino)benzamido)propanoic Acid

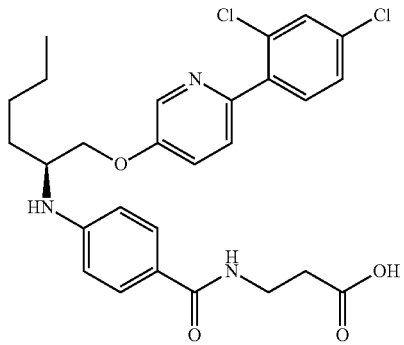 [SMILES: CCCC[C@@H](COc1ccc(-c2ccc(Cl)cc2Cl)nc1)Nc1ccc(C(=O)NCCC(=O)O)cc1]

$^1$H NMR (400 MHz, CDCl$_3$): δ 8.38 (d, J=2.9 Hz, 1H), 7.59 (d, J=8.8 Hz, 2H), 7.52 (d, J=8.8 Hz, 1H), 7.43-7.47 (m, 2H), 7.28 (dd, J=8.3, 2.4 Hz, 1H), 7.21-7.26 (m, 1H), 6.79 (br. s., 1H), 6.58 (d, J=8.3 Hz, 2H), 4.00-4.11 (m, 2H), 3.79 (dd, J=7.3, 5.9 Hz, 1H), 3.65 (d, J=5.4 Hz, 2H), 2.55-2.66 (m, 2H), 1.76-1.86 (m, 1H), 1.56-1.69 (m, 1H), 1.30-1.50 (m, 4H), 0.84-0.94 (t, J=7.1 Hz, 3H). MS (M+1): 530.

Compound 10-9: (S)-3-(4-((1-((6-(4-(trifluoromethyl)phenyl)pyridin-3-yl)oxy)hexan-2-yl)amino)benzamido)propanoic Acid

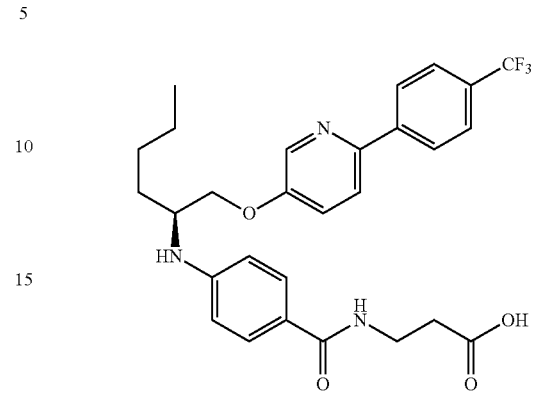

$^1$H NMR (400 MHz, CDCl$_3$): δ 8.33-8.42 (m, 1H), 7.96 (d, J=7.8 Hz, 2H), 7.53-7.71 (m, 5H), 7.24 (dt, J=5.9, 2.9 Hz, 1H), 6.81 (t, J=5.9 Hz, 1H), 6.54-6.62 (m, 2H), 4.01-4.09 (m, 2H), 3.78 (dd, J=7.3, 5.9 Hz, 1H), 3.65 (q, J=5.9 Hz, 2H), 2.63 (t, J=5.9 Hz, 2H), 1.75-1.85 (m, 1H), 1.57-1.69 (m, 1H), 1.30-1.48 (m, 4H), 0.88 (t, J=7.1 Hz, 3H). MS (M+1): 530.

Compound 10-8: (S)-3-(4-((1-((6-(2-fluoro-4-(trifluoromethyl)phenyl)pyridin-3-yl)oxy)hexan-2-yl)amino)benzamido)propanoic Acid

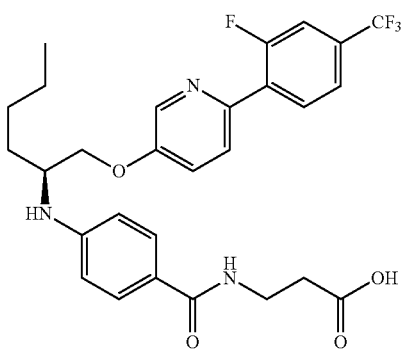 [SMILES: CCCC[C@@H](COc1ccc(-c2ccc(C(F)(F)F)cc2F)nc1)Nc1ccc(C(=O)NCCC(=O)O)cc1]

$^1$H NMR (400 MHz, CDCl$_3$): δ 8.40 (d, J=2.9 Hz, 3H), 7.99 (t, J=8.1 Hz, 3H), 7.70 (d, J=8.8 Hz, 1H), 7.59 (d, J=8.8 Hz, 2H), 7.45 (d, J=8.3 Hz, 1H), 7.37 (d, J=10.8 Hz, 1H), 7.20-7.26 (m, 1H), 6.89 (dt, J=11.4, 5.3 Hz, 1H), 6.52-6.62 (m, 2H), 4.00-4.07 (m, 2H), 3.78 (br. s., 1H), 3.64 (d, J=5.9 Hz, 2H), 2.61 (br. s., 2H), 1.74-1.86 (m, 1H), 1.55-1.68 (m, 1H), 1.28-1.46 (m, 4H), 0.87 (t, J=6.8 Hz, 3H). MS (M+1): 548.

Compound 10-10: (S)-3-(4-((1-((6-(3,5-dichlorophenyl)pyridin-3-yl)oxy)hexan-2-yl)amino)benzamido)propanoic Acid

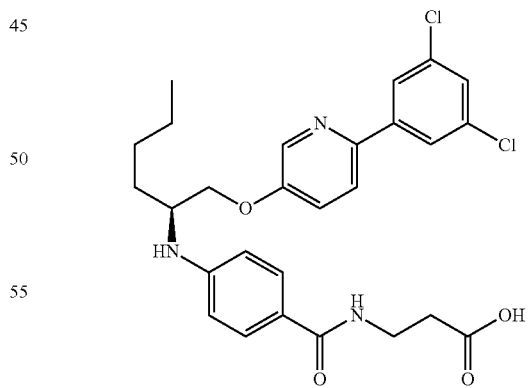

$^1$H NMR (400 MHz, CDCl$_3$): δ 8.33 (d, J=2.9 Hz, 1H), 7.75 (d, J=2.0 Hz, 2H), 7.57 (dd, J=13.2, 8.8 Hz, 3H), 7.30 (t, J=1.7 Hz, 1H), 7.20 (dd, J=8.8, 2.9 Hz, 1H), 6.77 (t, J=5.9 Hz, 1H), 6.57 (d, J=8.8 Hz, 2H), 4.00-4.07 (m, 2H), 3.78 (dd, J=7.3, 5.9 Hz, 1H), 3.62-3.69 (m, 2H), 2.63 (t, J=5.6 Hz, 2H), 1.74-1.87 (m, 1H), 1.57-1.68 (m, 1H), 1.30-1.48 (m, 4H), 0.86-0.91 (t, J=7.1 Hz, 3H). MS (M+1): 530.

Compound 10-11: (S)-3-(4-((1-((6-(2-chloro-4-(trifluoromethyl)phenyl)pyridin-3-yl)oxy)hexan-2-yl)amino)benzamido)propanoic Acid

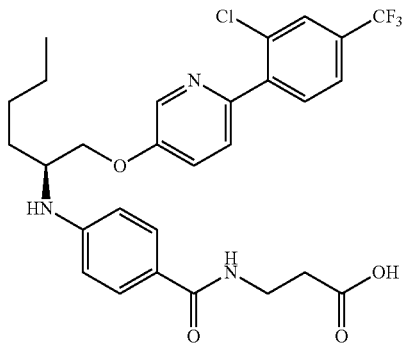

¹H NMR (400 MHz, CDCl₃): δ 8.39 (d, J=2.4 Hz, 1H), 7.47-7.76 (m, 6H), 7.19-7.28 (m, 1H), 6.77-6.97 (m, 1H), 6.57 (dd, J=8.6, 2.2 Hz, 2H), 3.96-4.12 (m, 2H), 3.78 (m, 1H), 3.62 (m, 2H), 2.58 (m, 2H), 1.72-1.85 (m, 1H), 1.54-1.69 (m, 1H), 1.27-1.51 (m, 4H), 0.88 (t, J=6.8 Hz, 3H). MS (M+1): 564.

Compound 10-13: 3-(4-(((2S,3S)-1-((6-(benzofuran-2-yl)pyridin-3-yl)oxy)-3-methylpentan-2-yl)amino)benzamido)propanoic Acid

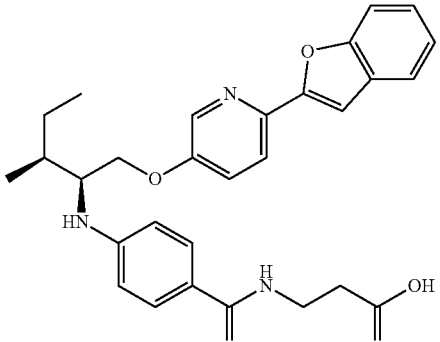

¹H NMR (400 MHz, CDCl₃): δ 8.32 (d, J=2.9 Hz, 1H), 7.76 (d, J=8.8 Hz, 1H), 7.57 (t, J=7.8 Hz, 3H), 7.48 (d, J=8.3 Hz, 1H), 7.15-7.31 (m, 4H), 6.91 (br. s., 1H), 6.54 (d, J=8.3 Hz, 2H), 4.00-4.12 (m, 2H), 3.52-3.75 (m, 3H), 2.64 (d, J=4.9 Hz, 2H), 1.73-1.87 (m, 1H), 1.48-1.67 (m, 1H), 1.10-1.23 (m, 1H), 0.95 (d, J=5.9 Hz, 3H), 0.90 (t, J=7.3 Hz, 3H). MS (M+1): 502.

Compound 10-12: (S)-3-(4-((1-((6-(benzofuran-2-yl)pyridin-3-yl)oxy)hexan-2-yl)amino)benzamido)propanoic Acid

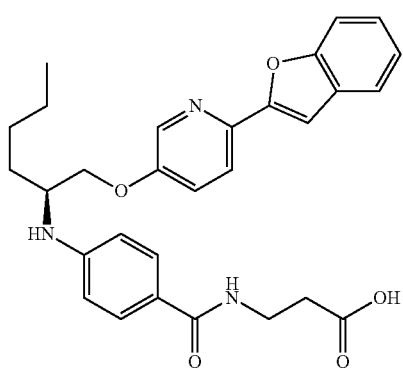 [SMILES: CCCC[C@@H](COc1ccc(-c2cc3ccccc3o2)nc1)Nc1ccc(C(=O)NCCC(=O)O)cc1]

¹H NMR (400 MHz, CDCl₃): δ 8.28-8.39 (m, 1H), 7.76 (td, J=8.2, 4.2 Hz, 1H), 7.44-7.66 (m, 4H), 7.11-7.34 (m, 4H), 6.80-7.00 (m, 1H), 6.47-6.59 (m, 2H), 3.92-4.02 (m, 2H), 3.56-3.78 (m, 3H), 2.63 (br. s., 2H), 1.66-1.84 (m, 1H), 1.48-1.66 (m, 1H), 1.23-1.40 (m, 4H), 0.80-0.89 (m, 3H). MS (M+1): 502.

Compound 10-14: 3-(4-(((2S,3S)-1-((6-(2-fluoro-4-(trifluoromethyl)phenyl)pyridin-3-yl)oxy)-3-methylpentan-2-yl)amino)benzamido)propanoic Acid

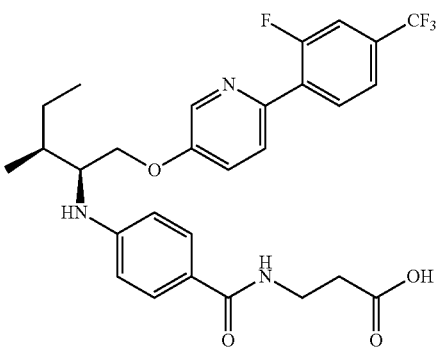 [SMILES: CC[C@H](C)[C@@H](COc1ccc(-c2ccc(C(F)(F)F)cc2F)nc1)Nc1ccc(C(=O)NCCC(=O)O)cc1]

¹H NMR (400 MHz, CDCl₃): δ 8.39 (d, J=2.9 Hz, 1H), 8.00 (t, J=7.8 Hz, 1H), 7.66-7.74 (m, 1H), 7.58 (d, J=8.8 Hz, 2H), 7.46 (d, J=8.3 Hz, 1H), 7.37 (d, J=10.8 Hz, 1H), 7.17-7.27 (m, 1H), 6.76-6.89 (m, 1H), 6.57 (d, J=8.3 Hz, 2H), 4.04-4.17 (m, 2H), 3.59-3.69 (m, 3H), 2.62 (t, J=5.1 Hz, 2H), 1.78-1.91 (m, 1H), 1.57-1.71 (m, 1H), 1.16-1.29 (m, 1H), 0.98 (d, J=6.4 Hz, 3H), 0.92 (t, J=7.3 Hz, 3H). MS (M+1): 548. HPLC 99%.

Compound 10-15: 3-(4-(((2S,3S)-1-((6-(2,4-dichlorophenyl)pyridin-3-yl)oxy)-3-methylpentan-2-yl)amino)benzamido)propanoic Acid

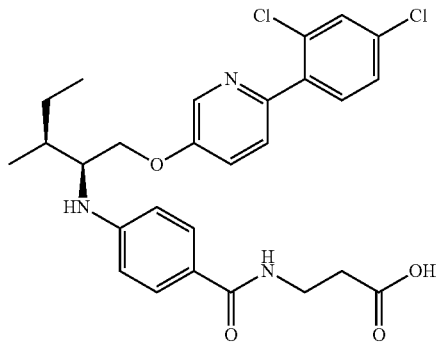 [SMILES: CC[C@H](C)[C@@H](COc1ccc(-c2ccc(Cl)cc2Cl)nc1)Nc1ccc(C(=O)NCCC(=O)O)cc1]

¹H NMR (400 MHz, CDCl₃): δ 8.36 (d, J=2.9 Hz, 1H), 7.58 (d, J=8.8 Hz, 2H), 7.52 (d, J=8.8 Hz, 1H), 7.43-7.47 (m, 2H), 7.29 (dd, J=8.3, 2.0 Hz, 1H), 7.22 (dd, J=8.8, 2.9 Hz, 1H), 6.76 (t, J=5.4 Hz, 1H), 6.58 (d, J=8.8 Hz, 2H), 4.07-4.17 (m, 2H), 3.60-3.69 (m, 3H), 2.62 (t, J=5.6 Hz, 2H), 1.80-1.91 (m, 1H), 1.65 (ddd, J=13.6, 7.5, 3.9 Hz, 1H), 1.19-1.29 (m, 1H), 1.00 (d, J=6.8 Hz, 3H), 0.93 (t, J=7.3 Hz, 3H). MS (M+1): 530. HPLC 99%.

Compound 10-17: (S)-3-(4-((4-methyl-1-((6-(4-(trifluoromethyl)phenyl)pyridin-3-yl)oxy)pentan-2-yl)amino)benzamido)propanoic Acid

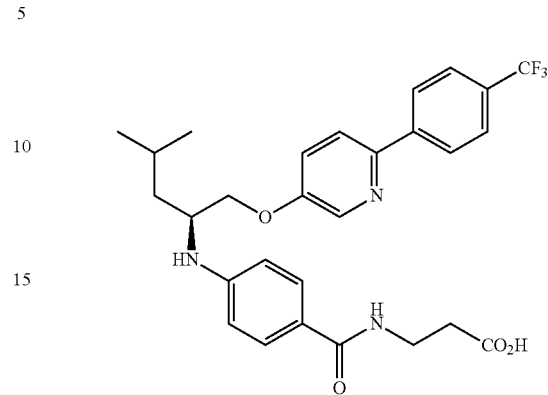

White solid. ¹HNMR (400 MHz, DMSO-d₆): δ 8.38 (d, J=1.9 Hz, 1H), 8.22 (d, J=7.8 Hz, 2H), 8.05-7.97 (m, 2H), 7.79 (d, J=7.8 Hz, 2H), 7.60 (d, J=8.8 Hz, 2H), 7.51-7.48 (m, 1H), 6.65 (d, J=8.8 Hz, 2H), 6.11 (d, J=8.8 Hz, 1H), 4.13-4.02 (m, 2H), 3.70-3.63 (m, 1H), 3.50-3.45 (m, 2H), 2.64 (t, J=6.8 Hz, 2H), 2.10-1.99 (m, 1H), 1.02-0.97 (m, 6H). MS (M+1): 530.

Compound 10-16: 3-(4-(((2S,3S)-1-((6-(2-chloro-4-(trifluoromethyl)phenyl)pyridin-3-yl)oxy)-3-methylpentan-2-yl)amino)benzamido)propanoic Acid

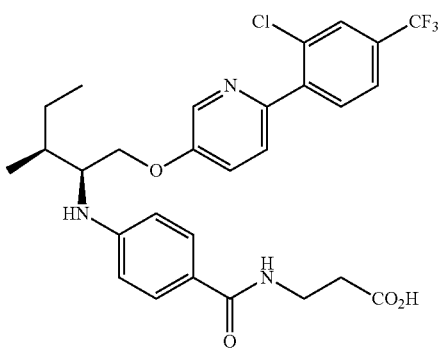 [SMILES: CC[C@H](C)[C@@H](COc1ccc(-c2ccc(C(F)(F)F)cc2Cl)nc1)Nc1ccc(C(=O)NCCC(=O)O)cc1]

¹H NMR (400 MHz, CDCl₃): δ 8.38 (d, J=2.9 Hz, 1H), 7.70 (d, J=1.0 Hz, 1H), 7.62-7.68 (m, 1H), 7.53-7.62 (m, 4H), 7.24 (dt, J=5.5, 2.9 Hz, 1H), 6.77 (t, J=5.6 Hz, 1H), 6.58 (d, J=8.8 Hz, 2H), 4.07-4.18 (m, 2H), 3.62-3.69 (m, 3H), 2.62 (t, J=5.6 Hz, 2H), 1.86 (qd, J=6.4, 3.4 Hz, 1H), 1.65 (ddd, J=13.6, 7.5, 3.9 Hz, 1H), 1.18-1.30 (m, 1H), 1.00 (d, J=6.8 Hz, 3H), 0.93 (t, J=7.3 Hz, 3H). MS (M+1): 564. HPLC 99%.

Compound 10-18: (S)-3-(4-((1-((6-(2-chloro-4-(trifluoromethyl)phenyl)pyridin-3-yl)oxy)-4-methylpentan-2-yl)amino)benzamido)propanoic Acid

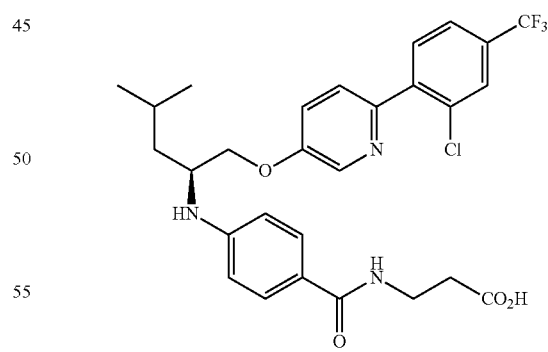

White solid. ¹H-NMR (400 MHz, DMSO-d₆): δ 8.39 (d, J=1.9 Hz, 1H), 8.04 (t, J=5.4 Hz, 1H), 7.96 (s, 1H), 7.82-7.76 (m, 2H), 7.68 (d, J=8.8 Hz, 1H), 7.60 (d, J=8.8 Hz, 2H), 7.52-7.49 (m, 1H), 6.65 (d, J=8.8 Hz, 2H), 6.12 (d, J=8.8 Hz, 1H), 4.08 (d, J=4.9 Hz, 2H), 3.91-3.85 (m, 1H), 3.42-3.37 (m, 2H), 2.47 (t, J=6.8 Hz, 2H), 1.81-1.76 (m, 1H), 1.58-1.54 (m, 2H), 0.96 (d, J=6.4 Hz, 3H), 0.88 (d, J=6.4 Hz, 3H). MS (M+1): 564.

Compound 10-19: (S)-3-(4-((1-((6-(2,4-dichlorophenyl)pyridin-3-yl)oxy)-4-methylpentan-2-yl)amino)benzamido)propanoic Acid

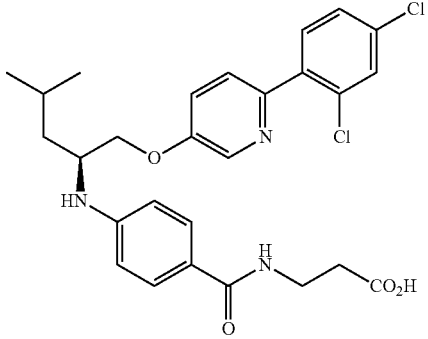 [SMILES: CC(C)C[C@@H](COc1ccc(-c2ccc(Cl)cc2Cl)nc1)Nc1ccc(C(=O)NCCC(=O)O)cc1]

White solid. $^1$H-NMR (400 MHz, DMSO-$d_6$): δ 8.36 (d, J=1.9 Hz, 1H), 8.04 (t, J=5.6 Hz, 1H), 7.70 (d, J=1.9 Hz, 1H), 7.61-7.56 (m, 4H), 7.52-7.45 (m, 2H), 6.64 (d, J=8.8 Hz, 2H), 6.11 (d, J=8.8 Hz, 1H), 4.08 (d, J=4.9 Hz, 2H), 3.89-3.85 (m, 2H), 3.42-3.37 (m, 2H), 2.45 (t, J=6.8 Hz, 2H), 1.80-1.75 (m, 1H), 1.58-1.53 (m, 2H), 0.95 (d, J=6.4 Hz, 3H), 0.88 (d, J=6.4 Hz, 3H). MS (M+1): 530.

Compound 11-2: (S)-3-(6-((1-((6-(benzofuran-2)pyridin-3-yl)oxy)-3-methylbutan-2-yl)amino)nicotinamido)propanoic Acid

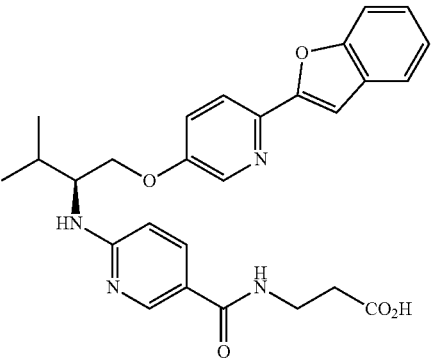 [SMILES: CC(C)[C@@H](COc1ccc(-c2cc3ccccc3o2)nc1)Nc1ccc(C(=O)NCCC(=O)O)cn1]

White solid. $^1$HNMR (400 MHz, DMSO-$d_6$): δ 8.49-8.48 (m, 1H), 8.37 (m, 1H), 8.21 (t, J=5.6 Hz, 1H), 7.88 (d, J=7.8 Hz, 1H), 7.79-7.76 (m, 1H), 7.68-7.56 (m, 3H), 7.38-7.24 (m, 3H), 7.08 (d, J=8.8 Hz, 1H), 6.58 (d, J=8.8 Hz, 1H), 4.31 (brs, 1H), 4.19-4.18 (m, 2H), 2.48 (t, J=6.8 Hz, 2H), 2.09-2.05 (m, 1H), 0.99-0.96 (m, 6H). MS (M+1): 489.

Example 12: Synthesis of Compounds 12-1 to 12-11

Compound 12-1: (S)-3-(4-((4-methyl-1-((2-(3-methyl-4-(trifluoromethyl)-1H-pyrazol-1-yl)pyrimidin-5-yl)oxy)pentan-2-yl)amino)benzamido)propanoic Acid Example 11: Synthesis of Compounds 11-1 to 11-2

Compound 11-1: (S)-3-(6-((1-((6-(2-chloro-4-(trifluoromethyl)phenyl)pyridin-3-yl)oxy)-3-methylbutan-2-yl)amino)nicotinamido)propanoic Acid

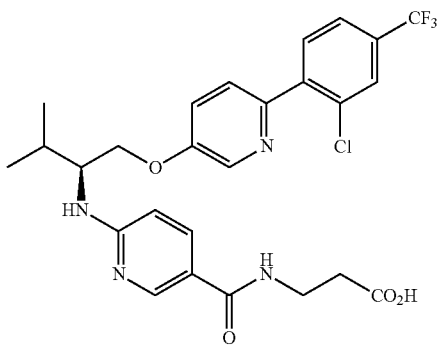

White solid. HNMR (400 MHz, DMSO-$d_6$): δ 8.47 (d, J=1.9 Hz, 1H), 8.42 (d, J=3 Hz, 1H), 8.19 (t, J=5.6 Hz, 1H), 7.96 (s, 1H), 7.82-7.76 (m, 3H), 7.69 (d, J=8.8 Hz, 1H), 7.58-7.55 (m, 1H), 7.08 (d, J=8.8 Hz, 1H), 6.58 (d, J=8.8 Hz, 1H), 4.31 (brs, 1H), 4.20-4.19 (m, 2H), 3.34-3.39 (m, 2H), 2.47 (t, J=6.8 Hz, 2H), 2.11-2.06 (m, 1H), 1.00-0.97 (m, 6H). MS (M+1): 551.

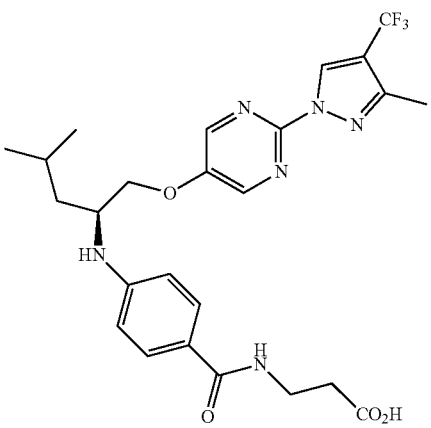 [SMILES: Cc1nn(-c2ncc(OC[C@H](CC(C)C)Nc3ccc(C(=O)NCCC(=O)O)cc3)cn2)cc1C(F)(F)F]

White solid. $^1$HNMR (400 MHz, DMSO-$d_6$): δ 8.94 (s, 1H), 8.59 (s, 2H), 8.04 (t, J=5.4 Hz, 1H), 8.04 (t, J=5.6 Hz, 1H), 7.59 (d, J=8.8 Hz, 2H), 6.63 (d, J=8.8 Hz, 2H), 6.12 (d, J=8.8 Hz, 1H), 4.16 (d, J=5.4 Hz, 2H), 3.89-3.86 (m, 1H), 3.42-3.37 (m, 2H), 2.46 (t, J=6.8 Hz, 2H), 1.80-1.75 (m, 1H), 1.57-1.52 (m, 2H), 0.95 (d, J=6.4 Hz, 3H), 0.87 (d, J=6.4 Hz, 3H). MS (M+1): 535.

Compound 12-2: (S)-3-(4-((1-((2-(benzofuran-2-yl)pyrimidin-5-yl)oxy)-3-methylbutan-2-yl)amino)benzamido)propanoic Acid

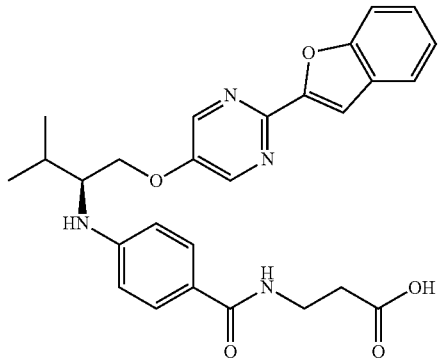 [SMILES: CC(C)[C@@H](COc1cnc(-c2cc3ccccc3o2)nc1)Nc1ccc(C(=O)NCCC(=O)O)cc1]

¹H NMR (400 MHz, DMSO-d₆): δ 8.64 (s, 2H), 8.04 (t, J=5.4 Hz, 1H), 7.74 (d, J=7.3 Hz, 1H), 7.67 (d, J=8.8 Hz, 1H), 7.55-7.63 (m, 3H), 7.37-7.43 (m, 1H), 7.27-7.34 (m, 1H), 6.66 (d, J=8.8 Hz, 2H), 6.14 (d, J=8.8 Hz, 1H), 4.32 (dd, J=10.0, 4.2 Hz, 1H), 4.23 (dd, J=9.8, 6.4 Hz, 1H), 3.71 (dd, J=8.8, 4.4 Hz, 1H), 2.44-2.48 (m, 2H), 2.04 (dd, J=13.2, 6.4 Hz, 1H), 1.09 (t, J=7.1 Hz, 2H), 0.99 (d, J=9.3 Hz, 3H), 1.01 (d, J=9.3 Hz, 3H); MS (M+1): 489.

Compound 12-4: 3-(4-(((2S,3S)-1-((6-(2-fluoro-4-(trifluoromethylphenyl)pyridin-3-yl)oxy)-3-methylpentan-2-yl)amino)benzamido)propanoic Acid

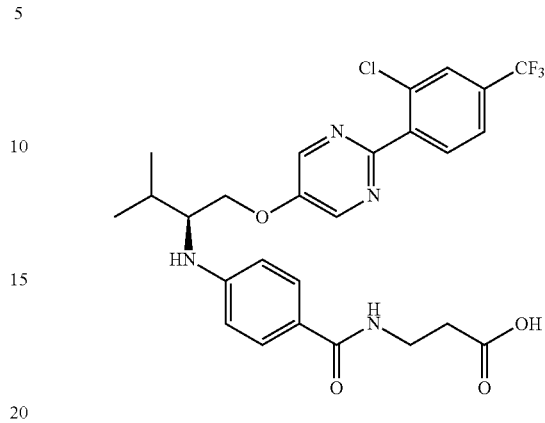

¹H NMR (400 MHz, DMSO-d₆): δ 8.70 (s, 2H), 7.96-8.06 (m, 2H), 7.87-7.92 (m, 1H), 7.81-7.87 (m, 1H), 7.57-7.60 (m, J=8.8 Hz, 2H), 6.63-6.69 (m, J=8.8 Hz, 2H), 6.14 (d, J=8.8 Hz, 1H), 4.33 (dd, J=10.0, 4.2 Hz, 1H), 4.24 (dd, J=10.3, 6.4 Hz, 1H), 3.67-3.75 (m, 1H), 3.37-3.43 (m, 2H), 2.44-2.48 (m, 2H), 2.00-2.10 (m, 1H), 1.00 (d, J=9.8 Hz, 3H), 1.01 (d, J=9.8 Hz, 3H). MS (M+1): 551.

Compound 12-3: (S)-3-(4-((1-((2-(benzofuran-2-yl)pyrimidin-5-yl)oxy)-4-methylpentan-2-yl)amino)benzamido)propanoic Acid

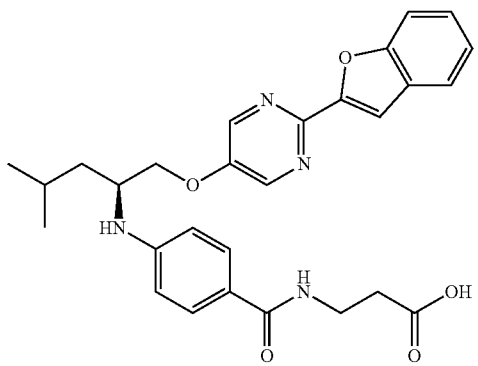 [SMILES: CC(C)C[C@@H](COc1cnc(-c2cc3ccccc3o2)nc1)Nc1ccc(C(=O)NCCC(=O)O)cc1]

¹H NMR (400 MHz, DMSO-d₆): δ 8.63 (s, 2H), 8.03-8.06 (m, 1H), 7.74 (d, J=7.3 Hz, 1H), 7.64-7.69 (m, 1H), 7.57-7.62 (m, 3H), 7.37-7.43 (m, 1H), 7.28-7.33 (m, 1H), 6.65 (d, J=9.3 Hz, 2H), 6.13 (d, J=8.8 Hz, 1H), 4.19 (d, J=4.9 Hz, 2H), 3.84-3.94 (m, 1H), 3.37-3.44 (m, 2H), 2.44-2.48 (m, 2H), 1.73-1.84 (m, 1H), 1.55 (dt, J=8.3, 5.4 Hz, 2H), 0.96 (d, J=6.8 Hz, 3H), 0.88 (d, J=6.8 Hz, 3H). MS (M+1): 503.

Compound 12-5: (S)-3-(4-((1-((2-(2-chloro-4-(trifluoromethyl)phenyl)pyrimidin-5-yl)oxy)hexan-2-yl)amino)benzamido)propanoic Acid

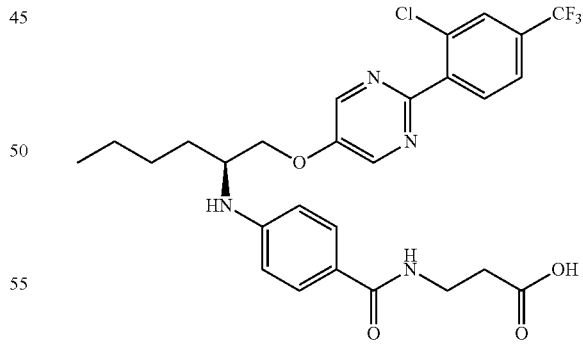

¹H NMR (400 MHz, DMSO-d₆): δ 8.70 (s, 2H), 8.01-8.07 (m, 1H), 7.98 (s, 1H), 7.90 (d, J=7.8 Hz, 1H), 7.83 (dd, J=8.1, 1.2 Hz, 1H), 7.57-7.62 (m, J=8.8 Hz, 2H), 6.61-6.65 (m, J=8.8 Hz, 2H), 6.16 (d, J=8.3 Hz, 1H), 4.22 (d, J=5.4 Hz, 2H), 3.84 (d, J=4.9 Hz, 1H), 3.38-3.43 (m, 2H), 2.45-2.48 (m, 2H), 1.73 (dd, J=9.0, 4.2 Hz, 1H), 1.53-1.64 (m, 1H), 1.41-1.47 (m, 1H), 1.32 (d, J=6.8 Hz, 3H), 0.88 (t, J=7.1 Hz, 3H). MS (M+1): 565.

Compound 12-6: (S)-3-(4-((1-((2-(2,4-dichlorophenyl)pyrimidin-5-yl)oxy)-3-methylbutan-2-yl)amino)benzamido)propanoic Acid

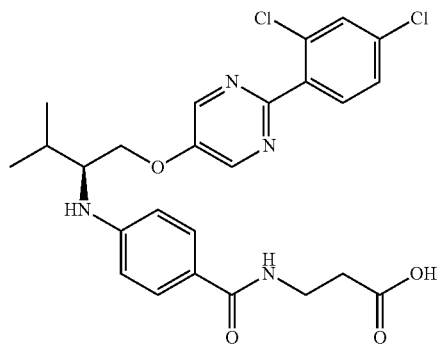 [SMILES: CC(C)[C@@H](COc1cnc(-c2ccc(Cl)cc2Cl)nc1)Nc1ccc(C(=O)NCCC(=O)O)cc1]

¹H NMR (400 MHz, DMSO-d₆): δ 8.66 (s, 2H), 7.99-8.07 (m, 2H), 7.67-7.75 (m, 2H), 7.56-7.62 (m, J=8.3 Hz, 2H), 7.51-7.56 (m, 1H), 6.62-6.69 (m, J=8.8 Hz, 2H), 4.31 (dd, J=9.8, 4.4 Hz, 1H), 4.22 (dd, J=10.3, 6.4 Hz, 1H), 3.39-3.43 (m, 4H), 2.44-2.48 (m, 2H), 2.04 (dq, J=13.2, 6.7 Hz, 1H), 1.01 (d, J=6.8 Hz, 3H), 0.99 (d, J=6.8 Hz, 3H). MS (M+1): 517.

Compound 12-7: (S)-3-(4-((1-((2-(2,4-dichlorophenyl)pyrimidin-5-yl)oxy)hexan-2-yl)amino)benzamido)propanoic Acid

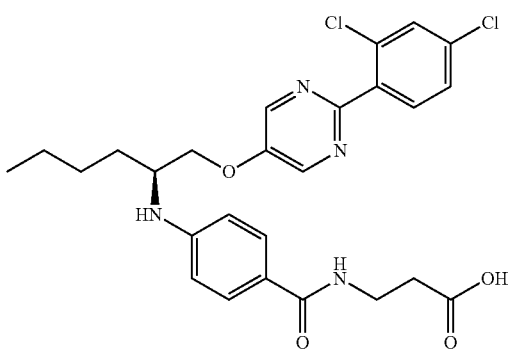 [SMILES: CCCC[C@@H](COc1cnc(-c2ccc(Cl)cc2Cl)nc1)Nc1ccc(C(=O)NCCC(=O)O)cc1]

¹H NMR (400 MHz, DMSO-d₆): δ 8.66 (s, 2H), 8.04 (s, 2H), 7.69-7.74 (m, 2H), 7.56-7.62 (m, J=8.8 Hz, 2H), 7.52-7.56 (m, 1H), 6.61-6.65 (m, J=9.3 Hz, 2H), 4.21 (d, J=5.4 Hz, 2H), 3.82-3.85 (m, 1H), 3.37-3.40 (m, 2H), 2.44-2.48 (m, 2H), 1.69-1.77 (m, 1H), 1.59 (td, J=9.2, 5.1 Hz, 1H), 1.1-1.50 (m, 1H), 1.30-1.37 (m, 3H), 0.86-0.89 (m, 3H). MS (M+1): 531.

Compound 12-8: 3-(4-(((2S)-1-((2-(2-chloro-4-(trifluoromethyl)phenyl)pyrimidin-5-yl)oxy)-3-methylpentan-2-yl)amino)benzamido)propanoic Acid

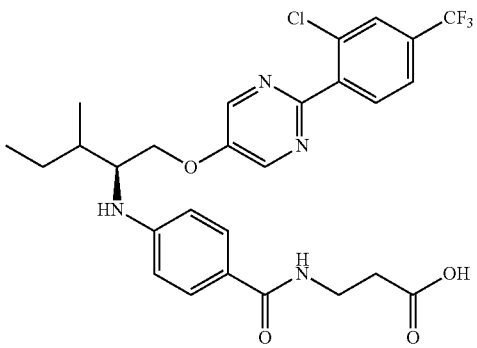 [SMILES: CCC(C)[C@@H](COc1cnc(-c2ccc(C(F)(F)F)cc2Cl)nc1)Nc1ccc(C(=O)NCCC(=O)O)cc1]

¹H NMR (400 MHz, DMSO-d₆): δ 8.01-8.05 (m, 2H), 7.90 (d, J=8.3 Hz, 1H), 7.83 (dd, J=8.3, 1.5 Hz, 1H), 7.55-7.63 (m, J=8.8 Hz, 2H), 6.59-6.68 (m, J=8.8 Hz, 2H), 6.19 (d, J=8.8 Hz, 1H), 4.35 (dd, J=10.3, 3.4 Hz, 1H), 4.25 (dd, J=10.3, 6.4 Hz, 1H), 3.69-3.79 (m, 1H), 3.40-3.44 (m, 2H), 2.44-2.48 (m, 2H), 1.75-1.85 (m, 1H), 1.68-1.57 (m, 1H), 1.25-1.32 (m, 1H), 0.97 (d, J=6.8 Hz, 3H), 0.91 (t, J=7.3 Hz, 3H). MS (M+1): 565. HPLC: 97.2%.

Compound 12-9: (S)-3-(4-((1-((2-(2-chloro-4-(trifluoromethyl)phenyl)pyrimidin-5-yl)oxy)-4-methylpentan-2-yl)amino)benzamido)propanoic Acid

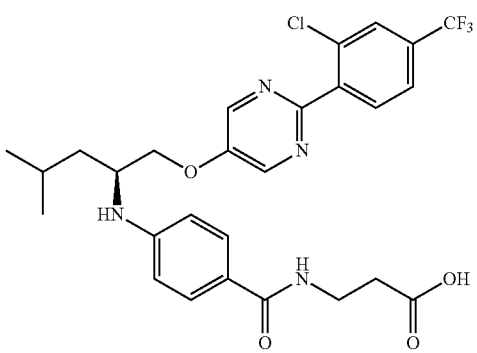 [SMILES: CC(C)C[C@@H](COc1cnc(-c2ccc(C(F)(F)F)cc2Cl)nc1)Nc1ccc(C(=O)NCCC(=O)O)cc1]

¹H NMR (400 MHz, DMSO-d₆): δ 7.96-8.05 (m, 2H), 7.86-7.92 (m, 1H), 7.78-7.86 (m, 1H), 7.52-7.65 (m, J=8.8 Hz, 2H), 6.58-6.69 (m, J=8.8 Hz, 2H), 6.12 (d, J=8.3 Hz, 1H), 4.20 (d, J=4.9 Hz, 2H), 3.94-3.82 (m, 1H), 3.39-3.44 (m, 2H), 2.44-2.48 (m, 2H), 1.71-1.86 (m, 1H), 1.46-1.63 (m, 2H), 0.96 (d, J=6.4 Hz, 3H), 0.88 (d, J=6.4 Hz, 3H). MS (M+1): 565. HPLC: 93.5%.

Compound 12-10: 3-(4-(((2S)-1-((2-(2,4-dichlorophenyl)pyrimidin-5-yl)oxy)-3-methylpentan-2-yl)amino)benzamido)propanoic Acid

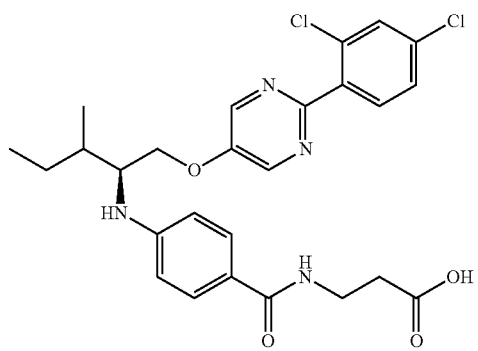 [SMILES: CCC(C)[C@@H](COc1cnc(-c2ccc(Cl)cc2Cl)nc1)Nc1ccc(C(=O)NCCC(=O)O)cc1]

¹H NMR (400 MHz, DMSO-d$_6$): δ 8.02 (s, 1H), 7.69-7.74 (m, 2H), 7.56-7.61 (m, J=8.8 Hz, 2H), 7.53 (dd, J=8.3, 2.0 Hz, 1H), 6.61-6.65 (m, J=8.8 Hz, 2H), 6.19 (d, J=8.8 Hz, 1H), 4.34 (dd, J=10.3, 3.9 Hz, 1H), 4.23 (dd, J=10.3, 6.4 Hz, 1H), 3.69-3.77 (m, 1H), 3.39-3.44 (m, 2H), 2.44-2.48 (m, 2H), 1.75-1.83 (m, 1H), 1.55-1.65 (m, 1H), 1.24-1.32 (m, 1H), 0.97 (d, J=6.8 Hz, 3H), 0.91 (t, J=7.3 Hz, 3H). MS (M+1): 531. HPLC: 92.1%.

Compound 12-11: (S)-3-(4-((1-((2-(2,4-dichlorophenyl)pyrimidin-5-yl)oxy)-4-methylpentan-2-yl)amino)benzamido)propanoic Acid

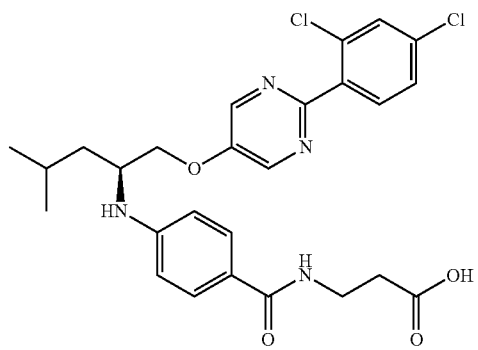 [SMILES: CC(C)C[C@@H](COc1cnc(-c2ccc(Cl)cc2Cl)nc1)Nc1ccc(C(=O)NCCC(=O)O)cc1]

¹H NMR (400 MHz, DMSO-d$_6$): δ 8.01-8.04 (m, 1H), 7.66-7.74 (m, 2H), 7.55-7.63 (m, J=8.8 Hz, 2H), 7.53 (dd, J=8.3, 2.0 Hz, 1H), 6.60-6.68 (m, J=8.3 Hz, 2H), 6.12 (d, J=8.3 Hz, 1H), 4.18 (d, I=4.9 Hz, 2H), 3.82-3.95 (m, 1H), 3.37-3.43 (m, 2H), 2.44-2.48 (m, 2H), 1.72-1.84 (m, 1H), 1.47-1.63 (m, 2H), 0.96 (d, J=6.8 Hz, 3H), 0.88 (d, J=6.8 Hz, 3H). MS (M+1): 531. HPLC: 94.3%.

Example 13: Synthesis of Compounds 13-1 to 13-14

Compound 13-1: 3-(4-(((2S,3S)-1-(4-(benzofuran-2-yl)-3-methoxyphenoxy)-3-methylpentan-2-yl)amino)benzamido)propanoic Acid

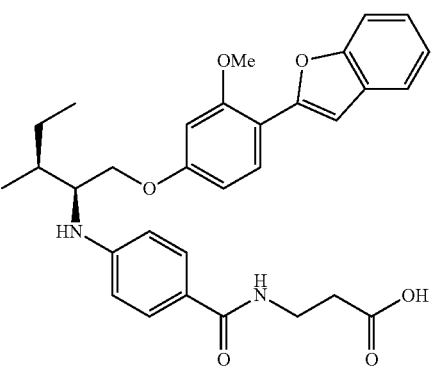 [SMILES: CC[C@H](C)[C@@H](COc1ccc(-c2cc3ccccc3o2)c(OC)c1)Nc1ccc(C(=O)NCCC(=O)O)cc1]

¹H NMR (400 MHz, CDCl$_3$): δ 7.92 (d, J=8.3 Hz, 1H), 7.58 (d, J=8.3 Hz, 2H), 7.51-7.55 (m, 1H), 7.45 (d, J=7.8 Hz, 1H), 7.15-7.23 (m, 3H), 6.68 (br. s., 1H), 6.57 (d, J=8.8 Hz, 2H), 6.53 (dd, J=8.6, 2.2 Hz, 1H), 6.49 (d, J=2.0 Hz, 1H), 4.02-4.10 (m, 2H), 3.91 (s, 3H), 3.64 (dd, J=10.3, 5.9 Hz, 3H), 2.65 (br. s., 2H), 1.85 (m, 1H), 1.63 (m, 1H), 1.22-1.29 (m, 1H), 0.99 (d, J=6.8 Hz, 3H), 0.93 (t, J=7.3 Hz, 3H). MS (M+1): 531.

Compound 13-2: 3-(4-(((2S,3S)-1-((2',4'-dichloro-2-methoxy-[1,1'-biphenyl]-4-yl)oxy)-3-methylpentan-2-yl)amino)benzamido)propanoic Acid

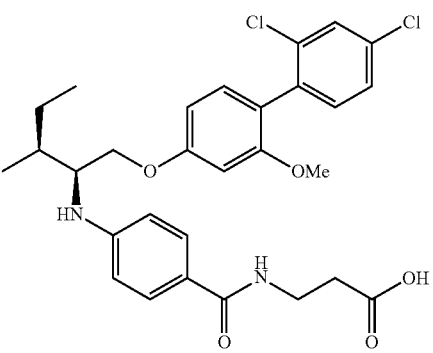 [SMILES: CC[C@H](C)[C@@H](COc1ccc(-c2ccc(Cl)cc2Cl)c(OC)c1)Nc1ccc(C(=O)NCCC(=O)O)cc1]

¹H NMR (400 MHz, CDCl$_3$): δ 7.58 (d, J=8.8 Hz, 2H), 7.42 (d, J=2.4 Hz, 1H), 7.20-7.24 (m, 1H), 7.16 (d, J=7.8 Hz, 1H), 7.02 (d, J=8.8 Hz, 1H), 6.68-6.76 (m, 1H), 6.58 (d, J=8.3 Hz, 2H), 6.48 (dq, J=4.3, 2.3 Hz, 2H), 4.02-4.09 (m, 2H), 3.70 (s, 3H), 3.65 (dd, J=12.2, 5.9 Hz, 3H), 2.65 (br. s., 2H), 1.83-1.92 (m, 1H), 1.65 (br. s., 1H), 1.20-1.30 (m, 1H), 1.00 (d, J=6.8 Hz, 3H), 0.94 (t, J=7.3 Hz, 3H). MS (M+1): 559. HPLC 95%.

Compound 13-3: 3-(4-(((2S,3S)-1-((2'-chloro-2-methoxy-4'-(trifluoromethyl)-[1,1'-biphenyl]-4-yl)oxy)-3-methylpentan-2-yl)amino)benzamido)propanoic Acid

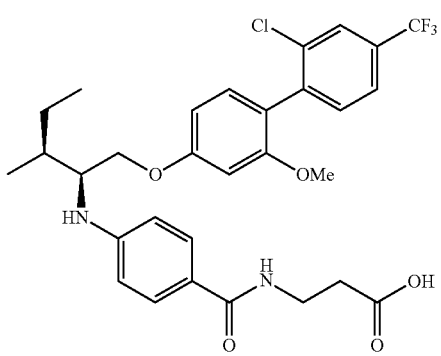 [SMILES: CC[C@H](C)[C@@H](COc1ccc(-c2ccc(C(F)(F)F)cc2Cl)c(OC)c1)Nc1ccc(C(=O)NCCC(=O)O)cc1]

$^1$H NMR (400 MHz, CDCl$_3$): δ 7.68 (d, J=1.0 Hz, 1H), 7.59 (d, J=8.3 Hz, 2H), 7.49 (dd, J=8.1, 1.2 Hz, 1H), 7.36 (d, J=8.3 Hz, 1H), 7.04 (d, J=9.3 Hz, 1H), 6.70-6.78 (m, 1H), 6.59 (d, J=8.8 Hz, 2H), 6.48-6.52 (m, 2H), 4.05-4.10 (m, 2H), 3.71 (s, 3H), 3.62-3.69 (m, 3H), 2.66 (br. s., 2H), 1.88 (d, J=5.4 Hz, 1H), 1.66 (br. s., 1H), 1.23-1.29 (m, 1H), 1.01 (d, J=6.8 Hz, 3H), 0.95 (t, J=7.6 Hz, 3H). MS (M+1): 593. HPLC 94%.

Compound 13-5: (S)-3-(4-((1-(4-(benzofuran-2-yl)-3-methoxyphenoxy)-3-methylbutan-2-yl)amino)benzamido)propanoic Acid $^1$H NMR (400 MHz, CDCl$_3$): δ 7.92 (d, J=8.3 Hz, 1H), 7.58 (d, J=8.8 Hz, 2H), 7.50-7.55 (m, 1H), 7.45 (d, J=7.8 Hz, 1H), 7.13-7.24 (m, 3H), 6.70 (t, J=6.1 Hz, 1H), 6.58 (d, J=8.8 Hz, 2H), 6.54 (dd, J=8.8, 2.4 Hz, 1H), 6.49 (d, J=2.4 Hz, 1H), 4.05 (d, J=4.4 Hz, 2H), 3.91 (s, 3H), 3.63-3.70 (m, 2H), 3.57 (d, J=6.4 Hz, 1H), 2.65 (t, J=5.9 Hz, 2H), 2.12 (m, 1H), 1.02 (dd, J=6.8, 2.0 Hz, 6H). MS (M+1): 517.

Compound 13-4: 3-(4-(((2S,3S)-1-((2'-fluoro-2-methoxy-4'-(trifluoromethyl)-[1,1'-biphenyl]-4-oxy)-3-methylpentan-2-yl)amino)benzamido)propanoic Acid

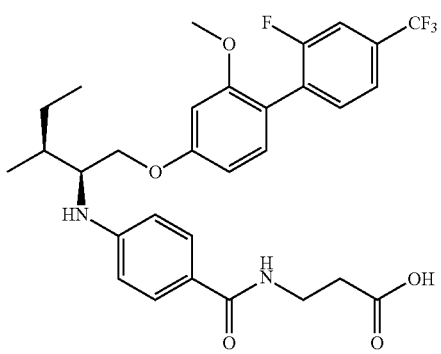 [SMILES: CC[C@H](C)[C@@H](COc1ccc(-c2ccc(C(F)(F)F)cc2F)c(OC)c1)Nc1ccc(C(=O)NCCC(=O)O)cc1]

$^1$H NMR (400 MHz, CDCl$_3$): δ 7.59 (d, J=8.3 Hz, 2H), 7.37-7.44 (m, 2H), 7.34 (d, J=10.3 Hz, 1H), 7.12 (d, J=8.8 Hz, 1H), 6.80-6.72 (m, 1H), 6.58 (d, J=8.8 Hz, 2H), 6.51 (dq, J=4.5, 2.3 Hz, 2H), 4.04-4.12 (m, 2H), 3.73 (s, 3H), 3.65 (dd, J=10.8, 6.4 Hz, 1H), 2.68-2.62 (m, 2H), 1.82-1.92 (m, 1H), 1.61-1.70 (m, 1H), 1.28-1.22 (m, 1H), 1.00 (d, J=6.8 Hz, 3H), 0.94 (t, J=7.3 Hz, 3H). MS (M+1): 577. HPLC 94%.

Compound 13-6: (S)-3-(4-((1-((2'-chloro-2-methoxy-4'-(trifluoromethyl)-[1,1'-biphenyl]-4-yl)oxy)-3-methylbutan-2-yl)amino)benzamido)propanoic Acid

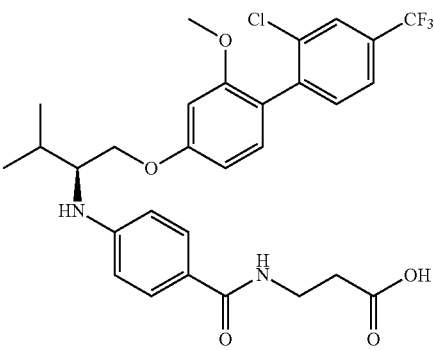 [SMILES: COc1cc(OC[C@@H](Nc2ccc(C(=O)NCCC(=O)O)cc2)C(C)C)ccc1-c1ccc(C(F)(F)F)cc1Cl]

$^1$H NMR (400 MHz, CDCl$_3$): δ 7.67 (d, J=1.0 Hz, 1H), 7.59 (d, J=8.8 Hz, 2H), 7.49 (dd, J=8.1, 1.2 Hz, 1H), 7.35 (d, J=7.8 Hz, 1H), 7.04 (d, J=8.8 Hz, 1H), 6.71 (br. s., 1H), 6.59 (d, J=8.8 Hz, 2H), 6.45-6.53 (m, 2H), 4.06 (dd, J=4.4, 2.4 Hz, 2H), 3.71 (s, 3H), 3.63-3.69 (m, 2H), 3.58 (d, J=6.4 Hz, 1H), 2.65 (t, J=5.6 Hz, 2H), 2.14 (d, J=6.8 Hz, 1H), 1.04 (d, J=6.8 Hz, 6H). MS (M+1): 579. HPLC 99%.

Compound 13-7: (S)-3-(4-((1-((2',4'-dichloro-2-methoxy-[1,1'-biphenyl]-4-yl)oxy)-3-methylbutan-2-yl)amino)benzamido)propanoic Acid

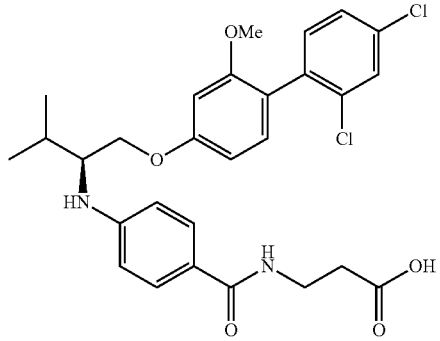 [SMILES: COc1cc(OC[C@@H](Nc2ccc(C(=O)NCCC(=O)O)cc2)C(C)C)ccc1-c1ccc(Cl)cc1Cl]

¹H NMR (400 MHz, CDCl₃): δ 7.58 (d, J=8.8 Hz, 2H), 7.42 (d, J=2.0 Hz, 1H), 7.19-7.26 (m, 1H), 7.12-7.18 (m, 1H), 6.98-7.06 (m, 1H), 6.75 (br. s., 1H), 6.58 (d, J=8.8 Hz, 2H), 6.48 (dq, J=4.3, 2.3 Hz, 2H), 4.05 (dd, J=4.2, 2.7 Hz, 2H), 3.70 (s, 3H), 3.62-3.68 (m, 2H), 3.60-3.53 (m, 1H), 2.65 (t, J=5.6 Hz, 2H), 2.19-2.09 (m, 1H), 1.03 (d, J=6.8 Hz, 6H). MS (M+1): 545. HPLC 93%.

Compound 13-9: (S)-3-(4-((1-((2',4'-dichloro-2-methoxy-[1,1'-biphenyl]-4-yl)oxy)hexan-2-yl)amino)benzamido)propanoic Acid

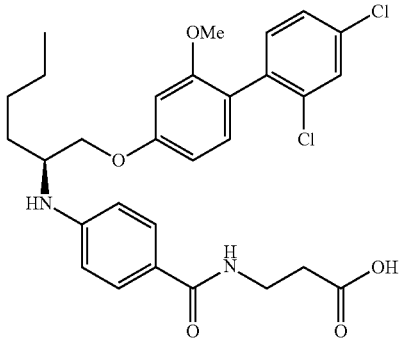

¹H NMR (400 MHz, CDCl₁): δ 7.59 (d, J=8.3 Hz, 2H), 7.43 (d, J=2.0 Hz, 1H), 7.21-7.24 (m, 1H), 7.15-7.18 (m, 1H), 7.02 (d, J=8.3 Hz, 1H), 6.69 (t, J=5.9 Hz, 1H), 6.59 (d, J=8.8 Hz, 2H), 6.47-6.52 (m, 2H), 4.01 (t, J=4.9 Hz, 2H), 3.73-3.79 (m, 1H), 3.71 (s, 3H), 3.67 (q, J=5.9 Hz, 2H), 2.66 (t, J=5.9 Hz, 2H), 1.77-1.87 (m, 1H), 1.58-1.68 (m, 1H), 1.32-1.47 (m, 4H), 0.90 (t, J=7.1 Hz, 3H). MS (M+1): 559. HPLC 95%.

Compound 13-8: (S)-3-(4-((1-((2'-fluoro-2-methoxy-4'-(trifluoromethyl)-[1,1'-biphenyl]-4-yl)oxy)-3-methylbutan-2-yl)amino)benzamido)propanoic Acid

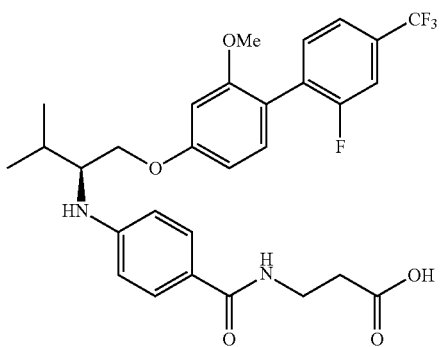 [SMILES: COc1cc(OC[C@@H](Nc2ccc(C(=O)NCCC(=O)O)cc2)C(C)C)ccc1-c1ccc(C(F)(F)F)cc1F]

¹H NMR (400 MHz, CDCl₃): δ 7.59 (d, J=8.8 Hz, 2H), 7.37-7.44 (m, 2H), 7.33 (d, J=9.8 Hz, 1H), 7.10-7.14 (m, 1H), 6.72-6.83 (m, 1H), 6.59 (d, J=8.8 Hz, 2H), 6.51 (dq, J=4.5, 2.3 Hz, 2H), 4.05 (dd, J=4.2, 1.7 Hz, 2H), 3.73 (s, 3H), 3.66 (q, J=5.9 Hz, 2H), 3.61-3.55 (m, 1H), 2.65 (t, J=5.4 Hz, 2H), 2.19-2.09 (m, 1H), 1.03 (dd, J=6.8, 1.5 Hz, 61H). MS (M+1): 563. HPLC 97%.

Compound 13-10: (S)-3-(4-((1-((2-methoxy-4'-(trifluoromethyl)-[1,1'-biphenyl]-4-yl)oxy)-3-methylbutan-2-yl)amino)benzamido)propanoic Acid ¹H NMR (400 MHz, CDCl₃): δ 7.53-7.62 (m, 6H), 7.16-7.20 (m, 1H), 6.75 (br. s., 1H), 6.59 (d, J=8.8 Hz, 2H), 6.49-6.53 (m, 2H), 4.02-4.09 (m, 2H), 3.75 (s, 3H), 3.66 (d, J=5.4 Hz, 2H), 3.54-3.60 (m, 1H), 2.65 (br. s., 2H), 2.09-2.19 (m, 1H), 1.03 (dd, J=6.8, 1.5 Hz, 6H). MS (M+1): 545. HPLC 96%.

113

Compound 13-11: (S)-3-(4-((1-((2-methoxy-4'-(trifluoromethyl)-[,1'-biphenyl]-4-yl)oxy)hexan-2-yl)amino)benzamido)propanoic Acid

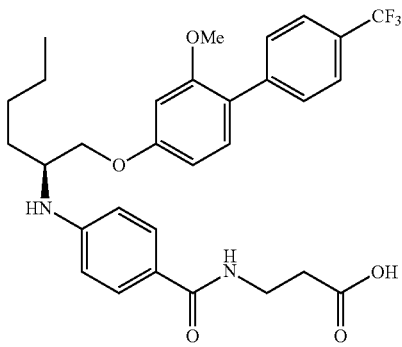 [SMILES: CCCC[C@@H](COc1ccc(-c2ccc(C(F)(F)F)cc2)c(OC)c1)Nc1ccc(C(=O)NCCC(=O)O)cc1]

$^1$H NMR (400 MHz, CDCl$_3$): δ 7.53-7.64 (m, 6H), 7.14-7.23 (m, 1H), 6.69 (br. s., 1H), 6.59 (d, J=8.8 Hz, 2H), 6.48-6.55 (m, 2H), 4.02 (t, J=4.6 Hz, 2H), 3.76 (s, 3H), 3.68 (q, J=5.9 Hz, 2H), 2.67 (t, J=5.6 Hz, 2H), 1.77-1.88 (m, 1H), 1.56-1.70 (m, 1H), 1.29-1.49 (m, 4H), 0.90 (t, J=7.1 Hz, 3H). MS (M+1): 559.

Compound 13-12: 3-(4-(((2S,3S)-1-(3-methoxy-4-(5-phenyl-1,3,4-oxadiazol-2-yl)phenoxy)-3-methylpentan-2-yl)amino)benzamido)propanoic Acid

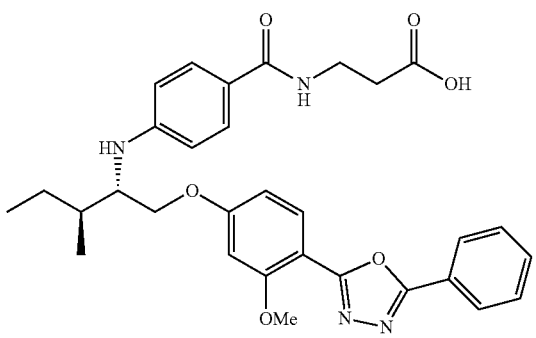 [SMILES: CC[C@H](C)[C@@H](COc1ccc(-c2nnc(-c3ccccc3)o2)c(OC)c1)Nc1ccc(C(=O)NCCC(=O)O)cc1]

$^1$H NMR (400 MHz, CDCl$_3$): δ 8.07 (dd, J=2.4, 7.3 Hz, 2H), 7.87 (d, J=8.3 Hz, 1H), 7.59 (d, J=8.8 Hz, 2H), 7.54-7.43 (m, 3H), 6.86 (t, J=5.9 Hz, 1H), 6.61-6.49 (m, 3H), 6.46 (d, J=2.0 Hz, 1H), 4.15-4.05 (m, 2H), 3.85 (s, 3H), 3.69-3.61 (m, 3H), 2.64 (t, J=5.6 Hz, 2H), 1.87-1.80 (m, 1H), 1.68-1.59 (m, 1H), 1.30-1.25 (m, 1H), 1.00 (d, J=6.8 Hz, 3H), 0.93 (t, J=7.3 Hz, 3H). MS (M+1): 559. HPLC 98%.

114

Compound 13-13: 3-(4-(((2S,3S)-1-(4-(5-(tert-butyl)-1,3,4-oxadiazol-2-yl)-3-methoxyphenoxy)-3-methylpentan-2-yl)amino)benzamido)propanoic Acid

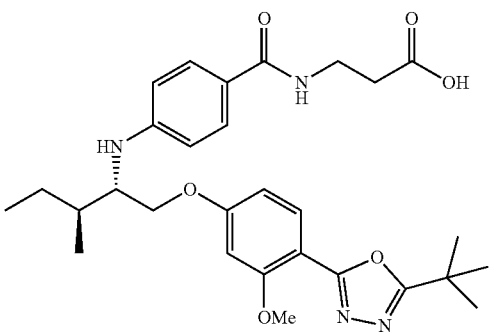 [SMILES: CC[C@H](C)[C@@H](COc1ccc(-c2nnc(C(C)(C)C)o2)c(OC)c1)Nc1ccc(C(=O)NCCC(=O)O)cc1]

$^1$H NMR (400 MHz, CDCl$_3$): δ 7.73 (d, J=8.8 Hz, 1H), 7.57 (d, J=8.8 Hz, 2H), 6.84-6.75 (m, 1H), 6.54 (d, J=8.3 Hz, 3H), 6.43-6.37 (m, 1H), 4.18-4.13 (m, 1H), 4.07-4.03 (m, 1H), 3.7$ (s, 3H), 3.71-3.59 (m, 3H), 2.68-2.61 (m, 2H), 1.89-1.77 (m, 1H), 1.70-1.57 (m, 1H), 1.43 (s, 9H), 1.31-1.26 (m, 1H), 1.00 (d, J=6.8 Hz, 3H), 0.94 (t, J=7.6 Hz, 3H). MS (M+1): 539.

Compound 13-14: (S)-3-(4-((1-((2'-fluoro-2-methoxy-4'-(trifluoromethyl)-[1,1'-biphenyl]-4-yl)oxy)hexan-2-yl)amino)benzamido)propanoic Acid

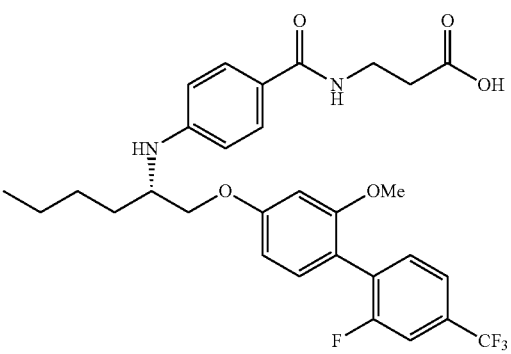 [SMILES: CCCC[C@@H](COc1ccc(-c2ccc(C(F)(F)F)cc2F)c(OC)c1)Nc1ccc(C(=O)NCCC(=O)O)cc1]

$^1$H NMR (400 MHz, CDCl$_3$): δ 7.60 (d, J=8.8 Hz, 2H), 7.45-7.38 (m, 2H), 7.34 (d, J=9.8 Hz, 1H), 7.13 (d, J=8.3 Hz, 1H), 6.72-6.64 (m, 1H), 6.59 (d, J=8.3 Hz, 2H), 6.54-6.49 (m, 2H), 4.02 (t, J=4.9 Hz, 2H), 3.85-3.76 (m 1H), 3.75 (s, 3H), 3.71-3.64 (m, 2H), 2.67 (t, J=5.9 Hz, 2H), 1.88-1.79 (m, 1H), 1.70-1.58 (m, 1H), 1.48-1.33 (m, 4H), 0.90 (t, J=7.1 Hz, 3H). MS (M+1): 577.

Example 14: Synthesis of Compounds 14-1 to 14-2

Compound 14-1: (S)-3-(6-((1-(4-(benzofuran-2-yl)-3-methoxyphenoxy)-3-methylbutan-2-yl)amino)nicotinamido)propanoic Acid

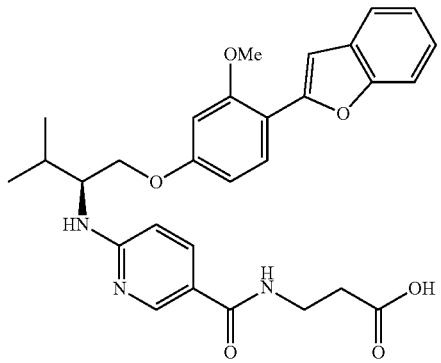 [SMILES: COc1cc(OC[C@@H](Nc2ccc(C(=O)NCCC(=O)O)cn2)C(C)C)ccc1-c1cc2ccccc2o1]

$^1$H NMR (400 MHz, CDCl$_3$): δ 8.19 (d, J=8.8 Hz, 1H), 8.11-8.06 (m, 1H), 7.90 (d, J=8.3 Hz, 1H), 7.77-7.70 (m, 1H), 7.51 (d, J=7.3 Hz, 1H), 7.43 (d, J=7.8 Hz, 1H), 7.22-7.10 (m, 3H), 6.74 (d, J=9.3 Hz, 1H), 6.53 (dd, J=2.0, 8.8 Hz, 1H), 6.45 (d, J=2.0 Hz, 1H), 4.23-4.04 (m, 2H), 3.89 (s, 3H), 3.77-3.62 (m, 3H), 2.55 (d, J=4.4 Hz, 2H), 2.22-2.08 (m, 1H), 1.11-1.02 (m, 6H). S (M+1): 518. HPLC 99%.

Compound 14-2: (S)-3-(6-((1-((2'-fluoro-2-methoxy-4'-(trifluoromethyl)-[1,1'-biphenyl]-4-yl)oxy)hexan-2-yl)amino)nicotinamido)propanoic Acid

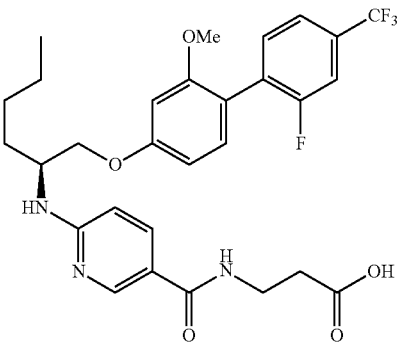 [SMILES: CCCC[C@@H](COc1ccc(-c2ccc(C(F)(F)F)cc2F)c(OC)c1)Nc1ccc(C(=O)NCCC(=O)O)cn1]

$^1$H NMR (400 MHz, CDCl$_3$): δ 8.26-8.15 (m, 2H), 7.82-7.75 (m, 1H), 7.43-7.36 (m, 2H), 7.32 (d, J=9.8 Hz, 1H), 7.11 (d, J=7.8 Hz, 1H), 6.78 (d, J=9.3 Hz, 1H), 6.52-6.47 (m, 2H), 4.06 (dd, J=2.4, 4.9 Hz, 2H), 3.95 (d, J=3.4 Hz, 1H), 3.73 (s, 3H), 3.68 (d, J=3.9 Hz, 2H), 2.59-2.49 (m, 2H), 1.86-1.78 (m, 1H), 1.76-1.66 (m, 1H), 1.51-1.35 (m, 4H), 0.90 (t, J=6.8 Hz, 3H). MS (M+1): 578. HPLC 98%.

Reaction Scheme III illustrates the general procedures that can be used to synthesize the following compounds of the formula (I) of the present disclosure.

Reaction Scheme III

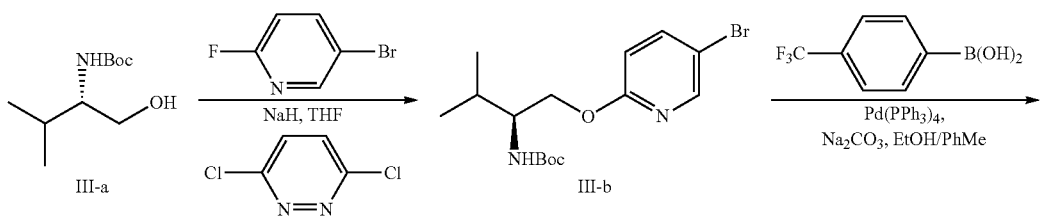

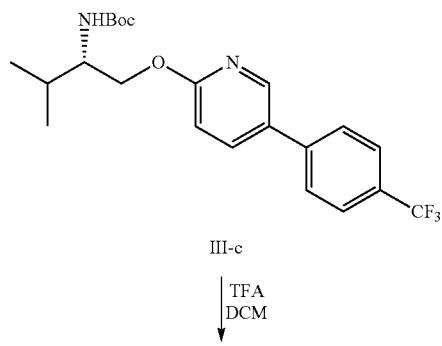

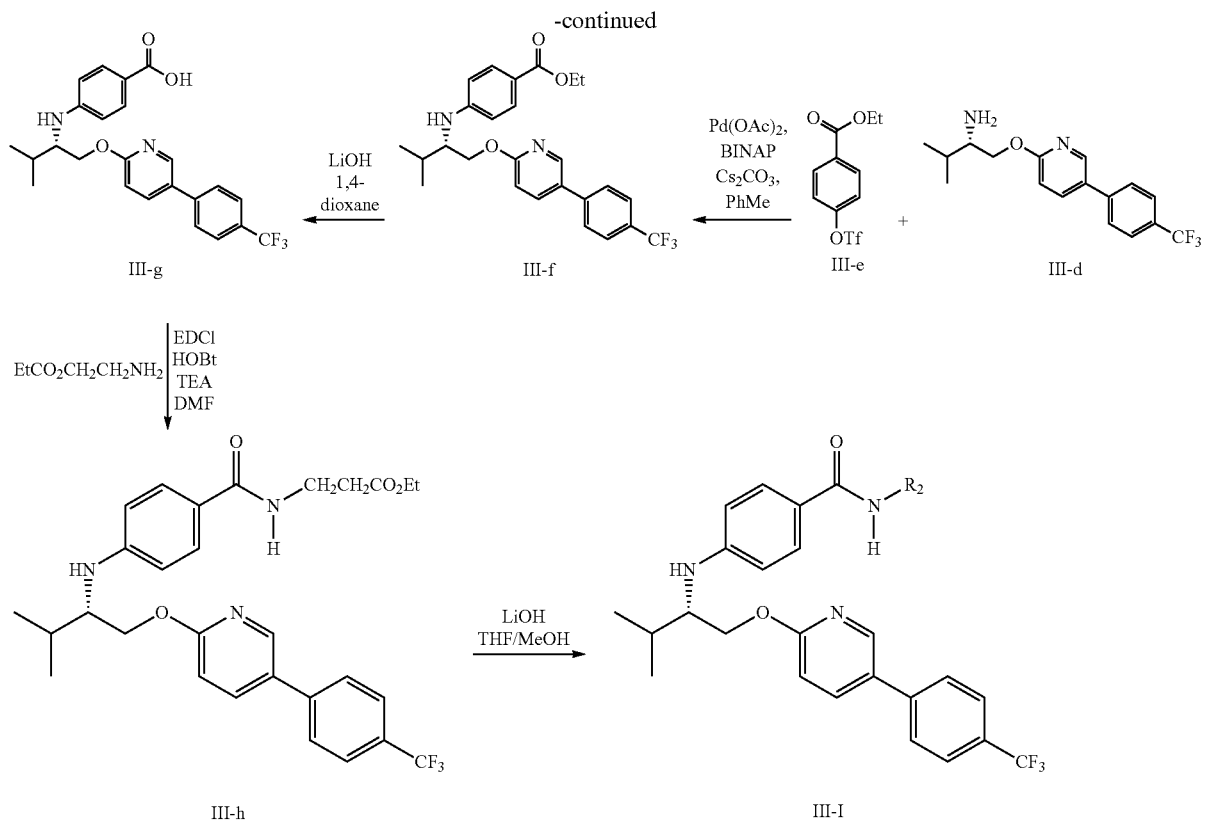

Step I

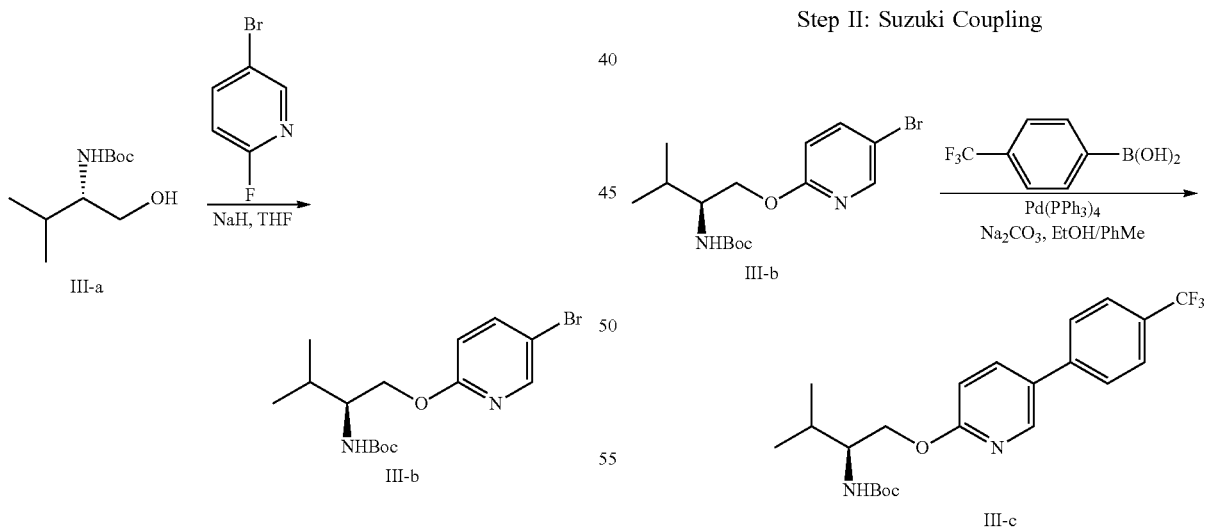

To a suspension of sodium hydride (2.08 g, 52 mmol) in dry THF (20 mL) was added (S)-tert-butyl 1-hydroxy-3-methylbutan-2-ylcarbamate (9.75 g, 48 mmol) in dry THF (60 mL) at 0° C. The reaction mixture was stirred for 20 mins and then 5-bromo-2-fluoropyridine (7.04 g, 20 mmol) in dry THF (50 mL) was added. After stirring at RT overnight, ice-water (100 mL) was poured into the mixture, then the mixture was extracted with EA. The organic solvent was removed by rotary evaporation. The crude reaction product was purified by column to give(S)-tert-butyl 1-(5-bromopyridin-2-yloxy)-3-methylbutan-2-ylcarbamate as a white solid (7.4 g, 58%).

Step II: Suzuki Coupling

A solution of(S)-tert-butyl 1-(5-bromopyridin-2-yloxy)-3-methylbutan-2-ylcarbamate (3.7 g, 10.3 mmol), (4-(trifluoromethyl)phenyl)boronic acid (2.34 g, 12.36 mmol), $Na_2CO_3$ (2M, 12 mL) in EtOH/PhMe (12 mL/40 mL) were purged with nitrogen for 30 min. $Pd(PPh_3)_4$ (0.57 g, 0.5 mmol) was added and heated at 110° C. for 12 h. The reaction mixture was cooled and extracted with EtOAc. The organic layer was dried over $MgSO_4$ and concentrated in vacuo. The residue was purified by silica gel chromatography to afford (S)-tert-butyl 3-methyl-1-(5-(4-(trifluoromethyl) phenyl)pyridin-2-yloxy)butan-2-ylcarbamate (3.8 g, 87%).

Step II: Deprotection

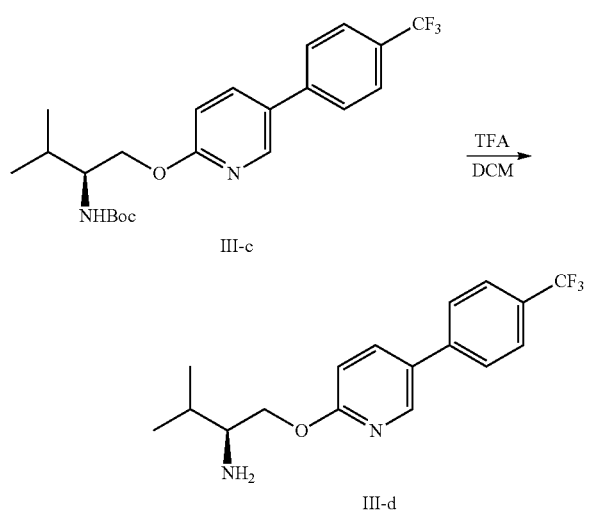

III-c

III-d

The compound (S)-tert-butyl 3-methyl-1-(5-(4-(trifluoromethyl)phenyl)pyridin-2-yloxy)butan-2-ylcarbamate (3.8 g, 8.95 mmol) was suspended in trifluoroacetic acid (10 mL, 134 mmol) in anhydrous dichloromethane (90 mL) at room temperature for 12 h. After reaction, excess trifluoroacetic acid was neutralized by dropwised addition of $Na_2CO_{3(aq)}$ until pH=10. Then it was extracted with $CH_2Cl_2$. The combined organic layer was dried with anhydrous $MgSO_4$ and concentrated in vacuo to give crude product, Compound III-d.

Step IV: Pd-Coupling

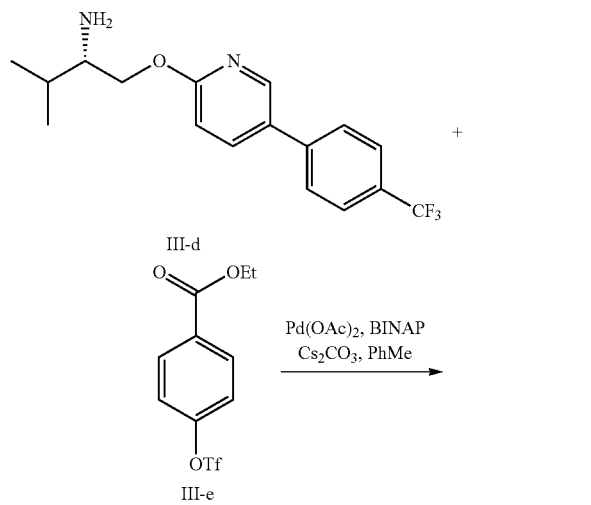

III-d

III-e

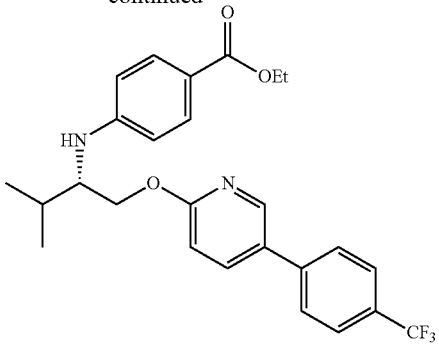

III-f

Pd(OAc)$_2$ (0.18 g, 0.8 mmol), BINAP (1 g, 1.6 mmol), cesium carbonate (1.95 g, 6 mmol), (S)-3-methyl-1-(5-(4-(trifluoromethyl)phenyl)pyridin-2-yloxy)butan-2-amine (1.3 g, 4 mmol), and ethyl 4-(trifluoromethylsulfonyloxy) benzoate (1.43 g, 4.8 mmol) in 40 mL PhMe were purged with nitrogen for 30 min. The mixture was stirred in an oil bath at 100° C. for 18 h. Cool the mixture to ambient temperature, dilute with EtOAc, filter through Celite washing with EtOAc. The mixture was washed with water and brine, dried the organic layer over Na$_2$SO$_4$, and concentrate to obtain the crude mixture. The residue was purified by silica gel chromatography to afford (S)-ethyl 4-(3-methyl-1-(5-(4-(trifluoromethyl)phenyl)pyridin-2-yloxy)butan-2-ylamino)benzoate (1.8 g, 95%).

Step V: Hydrolysis

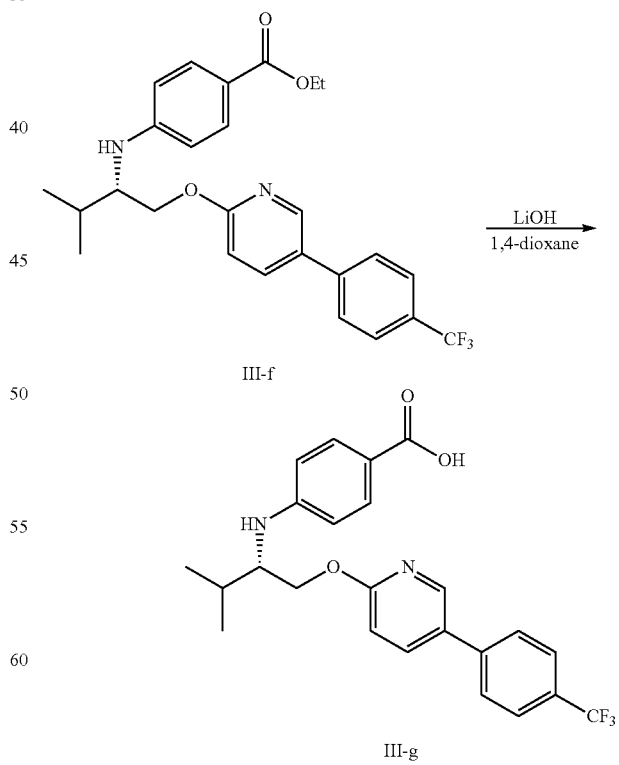

III-f

III-g (S)-ethyl 4-(3-methyl-1-(5-(4-(trifluoromethyl)phenyl) pyridin-2-yloxy)butan-2-ylamino)benzoate (1.8 g, 4 mmol)

was dissolved in 1,4-dioxane (40 mL) followed by addition of LiOH (20 mL). The reaction mixture was stirred in an oil bath at 100° C. for overnight. The reaction was monitored by TLC. With completion of the reaction, the solvent was removed by rotary evaporation and HCl (1.0 M, 15 mL) was added to the mixture. The white solid was collected by suction filtration and afford(S)-4-(3-methyl-1-(5-(4-(trifluoromethyl)phenyl)pyridin-2-yloxy)butan-2-ylamino)benzoic acid (1.7 g, 100%).

Step VI: Amidation

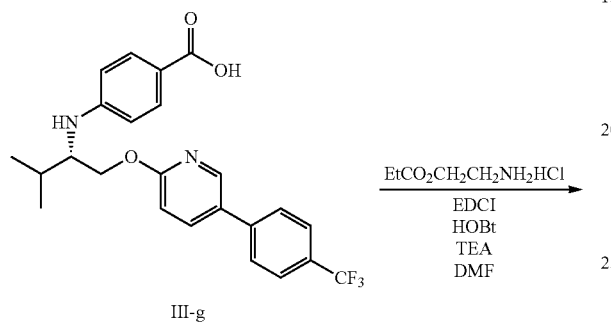

Step VII: Hydrolysis (Optional)

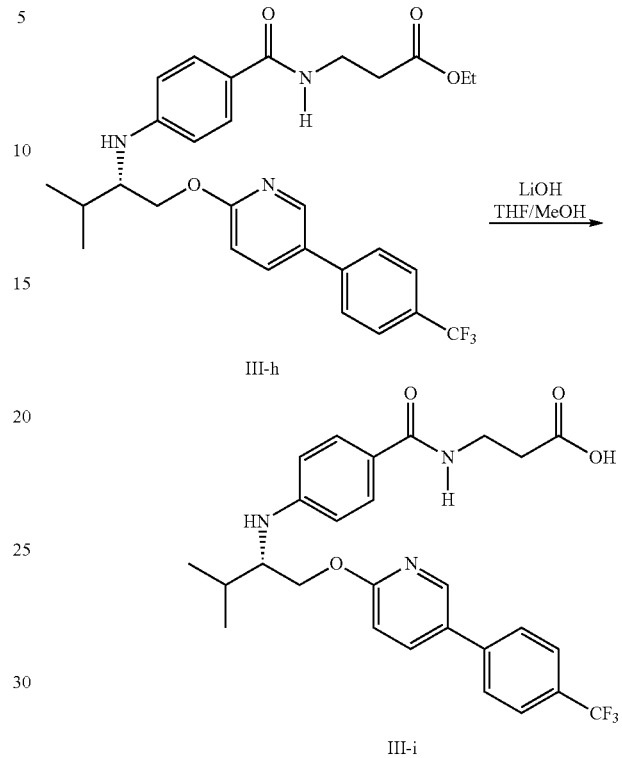

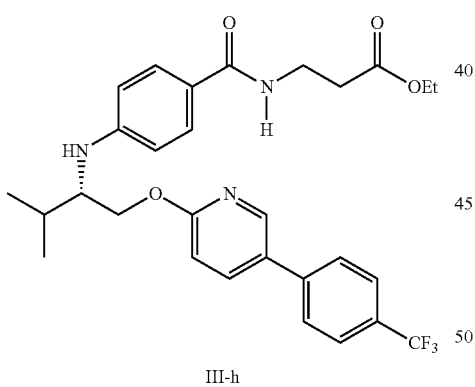

The compound (S)-4-(3-methyl-1-(5-(4-(trifluoromethyl)phenyl)pyridin-2-yloxy)butan-2-ylamino)benzoic acid (0.66 g, 1.5 mmol), (EtCO$_2$CH$_2$CH$_2$)NH$_2$HCl, EDCI (0.58 g), and HOBt (0.3 g) were dissolved in DMF (9 mL) followed by addition of TEA (0.4 mL). The mixture was stirred overnight at room temperature. Monitored by TLC, the mixture was added water, aqueous NaHCO$_3$ and extracted with EA. The organic layer was dried with MgSO$_4$, and then the solvent was removed by rotary evaporation. The residue was purified by silica gel chromatography to afford Compound III-h (0.8 g, 100%).

Compound III-h (0.8 g, 1.47 mmol) was dissolved in THF/MeOH (7.5/7.5 mL) followed by addition of LiOH (7.5 mL). The reaction mixture was stirred at RT for overnight. The reaction was monitored by TLC. With completion of the reaction, the solvent was removed by rotary evaporation and HCl (1.0 M, 5 mL) was added to the mixture. The white solid was collected by suction filtration and afforded Compound III-i (0.4 g, 53%).

Example 15: Synthesis of Compounds 15-1 to 15-37

Compound 15-1: (S)—N-((2H-tetrazol-5-yl)methyl)-4-((2-((5-(benzofuran-2-yl)pyridin-2-yl)oxy)-1-phenylethyl)amino)benzamide

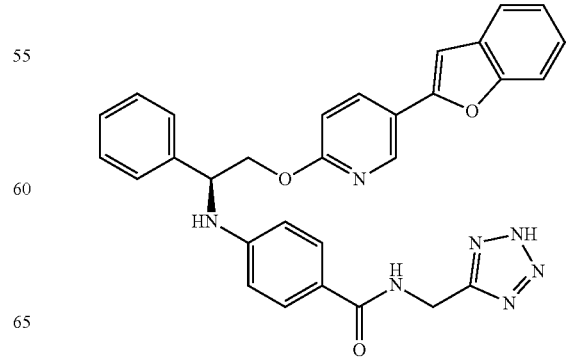

¹H NMR (400 MHz, DMSO-d₆): δ 8.69-8.76 (m, 2H), 8.22 (dd, J=8.8, 2.4 Hz, 1H), 7.58-7.67 (m, 4H), 7.50 (d, J=7.3 Hz, 2H), 7.24-7.42 (m, 6H), 7.06 (d, J=7.8 Hz, 1H), 6.98 (d, J=8.8 Hz, 1H), 6.62 (d, J=8.3 Hz, 2H), 4.96-5.03 (m, 1H), 4.67 (d, J=5.4 Hz, 2H), 4.50-4.62 (m, 2H). MS (M+1): 532.

Compound 15-2: (S)—N-((1H-tetrazol-5-yl)methyl)-4-((3-methyl-1-((5-(4-(trifluoromethyl)phenyl)pyridin-2-yl)oxy)butan-2-yl)amino)benzamide

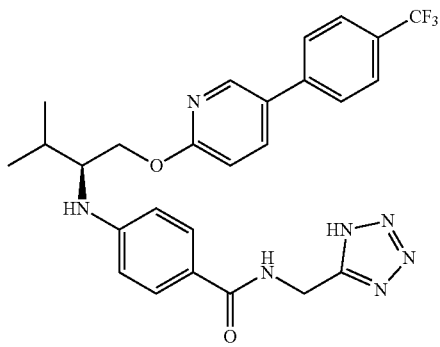 [SMILES: CC(C)[C@@H](COc1ccc(-c2ccc(C(F)(F)F)cc2)cn1)Nc1ccc(C(=O)NCc2nnn[nH]2)cc1]

White solid. ¹H-NMR (400 MHz, DMSO-d₆): δ 8.69 (t, J=5.5 Hz, 1H), 8.56 (d, J=2.5 Hz, 1H), 8.08 (dd, J=8.8, 2.5 Hz, 1H), 7.90 (d, J=8.8 Hz, 2H), 7.81 (d, J=8.8 Hz, 2H), 7.64 (d, J=8.8 Hz, 2H), 6.90 (d, J=8.8 Hz, 1H), 6.70 (d, J=8.8 Hz, 2H), 6.18 (d, J=8.8 Hz, 1H), 4.67 (d, J=6 Hz, 2H), 4.42-4.33 (m, 2H), 3.76-3.70 (m, 1H), 2.05-1.91 (m, 1H), 1.02-0.97 (m, 6H). MS (M+1): 526.

Compound 15-3: (S)-3-(4-((1-((5-(benzofuran-2-yl)pyridin-2-yl)oxy)-3-methylbutan-2-yl)amino)benzamido)propanoic Acid

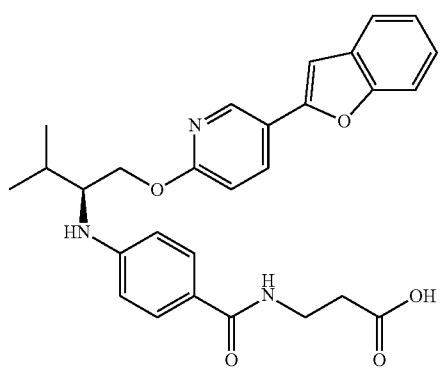 [SMILES: CC(C)[C@@H](COc1ccc(-c2cc3ccccc3o2)cn1)Nc1ccc(C(=O)NCCC(=O)O)cc1]

¹H NMR (400 MHz, DMSO-d₆): δ 8.72 (d, J=2.4 Hz, 1H), 8.17 (dd, J=8.6, 2.7 Hz, 1H), 8.06 (t, J=5.4 Hz, 1H), 7.54-7.70 (m, 4H), 7.20-7.35 (m, 2H), 6.90 (d, J=8.8 Hz, 1H), 6.68 (d, J=8.3 Hz, 2H), 6.09 (d, J=8.8 Hz, 1H), 4.30-4.46 (m, 2H), 3.64-3.76 (m, 1H), 3.42 (q, J=6.8 Hz, 2H), 2.48 (t, J=6.8 Hz, 2H), 2.06-1.96 (m, 1H), 0.92-1.07 (m, 6H). MS (M+1): 488.

Compound 15-4: (S)-3-(4-((2-((5-(4-(tert-butyl))pyridin-2-yl)oxy)-phenyl)pyridin-2-yl)oxy)-1-phenylethyl)amino) benzamido)propanoic Acid

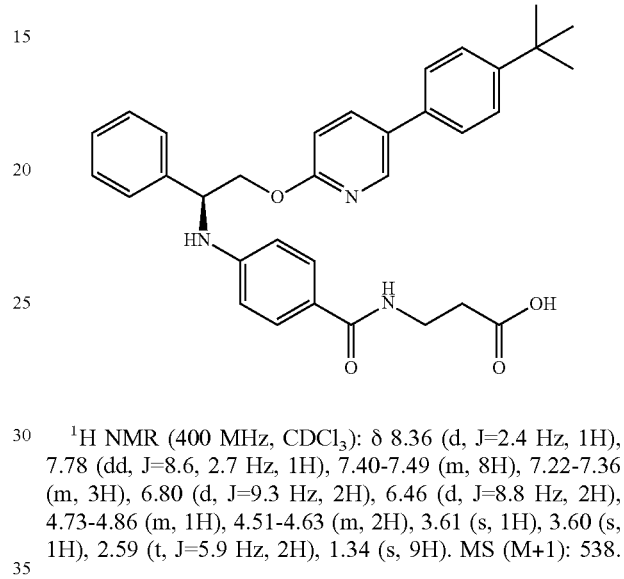

¹H NMR (400 MHz, CDCl₃): δ 8.36 (d, J=2.4 Hz, 1H), 7.78 (dd, J=8.6, 2.7 Hz, 1H), 7.40-7.49 (m, 8H), 7.22-7.36 (m, 3H), 6.80 (d, J=9.3 Hz, 2H), 6.46 (d, J=8.8 Hz, 2H), 4.73-4.86 (m, 1H), 4.51-4.63 (m, 2H), 3.61 (s, 1H), 3.60 (s, 1H), 2.59 (t, J=5.9 Hz, 2H), 1.34 (s, 9H). MS (M+1): 538.

Compound 15-5: (S)-3-(4-((2-((5-(benzofuran-2-yl)pyridin-2-yl)oxy)-1-phenylethyl)amino) benzamido) propanoic Acid

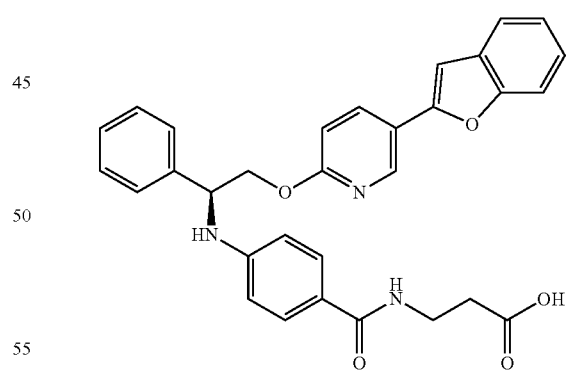

¹H NMR (400 MHz, DMSO-d₆): δ 12.14 (br. s., 1H), 8.74 (d, J=2.4 Hz, 1H), 8.20 (ddt, J=8.6, 4.4, 2.3 Hz, 1H), 8.03 (dd, J=7.1, 4.6 Hz, 1H), 7.48-7.66 (m, 6H), 7.23-7.40 (m, 6H), 6.93-7.05 (m, 2H), 6.57-6.64 (m, 2H), 4.93-5.01 (m, 1H), 4.49-4.61 (m, 2H), 4.00-4.05 (m, 1H), 3.25-3.49 (m, 4H), 2.42-2.53 (m, 3H), 1.98 (s, 1H), 1.1-1.32 (m, 1H). MS (M+1): 522.

Compound 15-6: (R)-3-(4-(((S)-2-((5-(4-(tert-butyl)phenyl)pyridin-2-yl)oxy)-1-phenylethyl) amino)benzamido)-2-hydroxypropanoic Acid

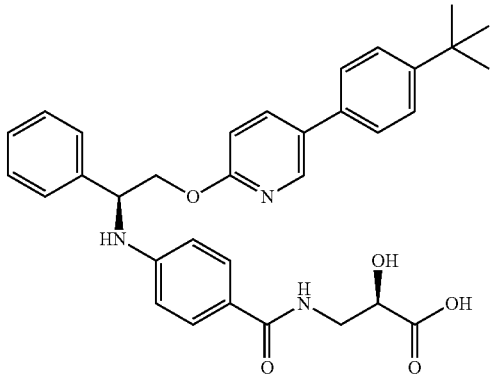 [SMILES: CC(C)(C)c1ccc(-c2ccc(OC[C@@H](Nc3ccc(C(=O)NC[C@@H](O)C(=O)O)cc3)c3ccccc3)nc2)cc1]

¹H NMR (400 MHz, CDCl₃): δ 8.37 (br. s., 1H), 7.79 (d, J=7.3 Hz, 1H), 7.39-7.57 (m, 8H), 7.13-7.39 (m, 4H), 6.62-6.88 (m, 2H), 6.46 (d, J=7.8 Hz, 2H), 4.83 (br. s., 1H), 4.48-4.70 (m, 2H), 4.30 (br. s., 1H), 3.85 (d, J=13.7 Hz, 1H), 3.73 (d, J=13.7 Hz, 1H), 1.34 (s, 9H). MS (M+1): 554.

Compound 15-8: (R)-2-hydroxy-3-(4-(((S)-3-methyl-1-((5-(4-(trifluoromethyl)phenyl)pyridin-2-yl)oxy)butan-2-yl)amino)benzamido)propanoic Acid

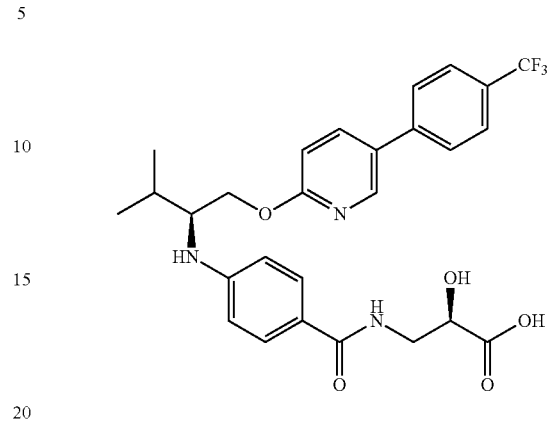

White solid. ¹H-NMR (400 MHz, DMSO-d₆): δ 8.54 (d, J=2.5 Hz, 1H), 8.15 (brs, 1H), 8.07-8.04 (m, 1H), 7.88 (d, J=8.8 Hz, 2H), 7.78 (d, J=8.8 Hz, 2H), 7.67 (d, J=8.8 Hz, 2H), 6.88 (d, J=8.8 Hz, 1H), 6.68 (d, J=8.8 Hz, 2H), 6.17 (d, J=8.8 Hz, 1H), 4.40-4.32 (m, 2H), 4.04 (pseudo-brs, 1H), 3.72-3.66 (m, 2H), 3.42-3.37 (m, 1H), 2.03-1.97 (m, 1H), 1.00-0.95 (m, 6H). MS (M+1): 532.

Compound 15-7: (S)-3-(4-((3-methyl-1-((5-(4-(trifluoromethyl)phenyl)pyridin-2-yl)oxy)butan-2-yl)amino)benzamido)propanoic Acid

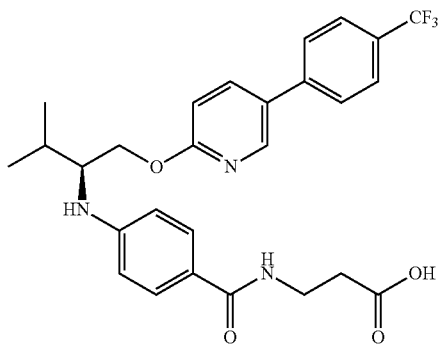 [SMILES: CC(C)[C@@H](COc1ccc(-c2ccc(C(F)(F)F)cc2)cn1)Nc1ccc(C(=O)NCCC(=O)O)cc1]

White solid. ¹H-NMR (400 MHz, DMSO-d₆): δ 8.56 (d, J=3 Hz, 1H), 8.07-8.04 (m, 2H), 7.88 (d, J=8.8 Hz, 2H), 7.79 (d, J=8.8 Hz, 2H), 7.59 (d, J=8.8 Hz, 2H), 6.89 (d, J=8.8 Hz, 1H), 6.67 (d, J=8.8 Hz, 2H), 6.10 (d, J=8.8 Hz, 1H), 4.40-4.32 (m, 2H), 3.86-3.67 (m, 11H), 3.41 (quartet, J=8 Hz, 2H), 2.45 (t, J=8 Hz, 2H), 2.06-1.98 (m, 1H), 1.01-0.96 (m, 6H). MS (M+1): 516.

Compound 15-9: (S)-3-(4-((1-((5-(2-chloro-4-(trifluoromethyl)phenyl)pyridin-2-yl)oxy)-3-methylbutan-2-yl)amino)benzamido)propanoic Acid

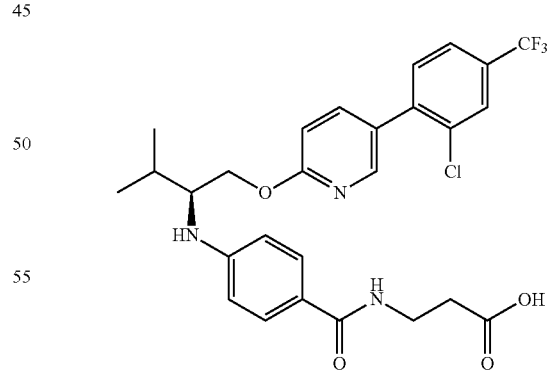

White solid. ¹H-NMR (400 MHz, DMSO-d₆): δ 8.27 (d, J=2 Hz, 1H), 8.10 (brs, 1H), 7.99 (d, J=0.9 Hz, 1H), 7.90-7.78 (m, 3H), 7.68 (d, J=8.3 Hz, 1H), 7.58 (d, J=8.8 Hz, 2H), 6.69 (d, J=8.8 Hz, 1H), 6.67 (d, J=8.8 Hz, 2H), 6.09 (d, J=8.8 Hz, 1H), 4.40-4.33 (m, 2H), 3.75-3.68 (m, 1H), 3.40-3.35 (m, 2H), 3.38 (t, J=6.8 Hz, 2H), 2.05-1.95 (m, 1H), 1.01-0.96 (m, 6H). MS (M+1): 551.

Compound 15-10: (S)-3-(4-((1-((5-(2-chloro-4-(trifluoromethyl)phenyl)pyridin-2-yl)oxy)-4-methylpentan-2-yl)amino)benzamido)propanoic Acid

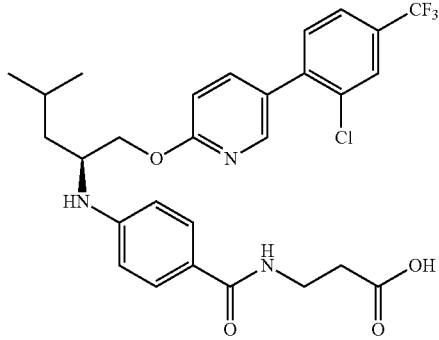

White solid. ¹H-NMR (400 MHz, DMSO-d$_6$): δ 8.26 (d, J=2.4 Hz, 1H), 8.03-7.98 (m, 3H), 7.85 (dd, J=8.8, 2.4 Hz, 1H), 7.80 (d, J=8 Hz, 1H), 7.68 (d, J=8 Hz, 1H), 7.59 (d, J=8.8 Hz, 1H), 6.90 (d, J=8.8 Hz, 2H), 6.66 (d, J=8.8 Hz, 2H), 6.06 (d, J=8.8 Hz, 1H), 4.36-4.32 (m, 1H), 4.24-4.20 (m, 1H), 3.91-3.88 (m, 1H), 3.40-3.35 (m, 2H), 2.46 (t, J=7 Hz, 2H), 1.79-1.74 (m, 1H), 1.54-1.50 (m, 2H), 0.94 (d, J=6.8 Hz, 3H), 0.85 (d, J=6.8 Hz, 3H). MS (M+1): 564.

Compound 15-12: 3-(4-(((2S,3S)-3-methyl-1-((5-(4-(trifluoromethyl)phenyl)pyridin-2-yl)oxy)pentan-2-yl)amino)benzamido)propanoic Acid

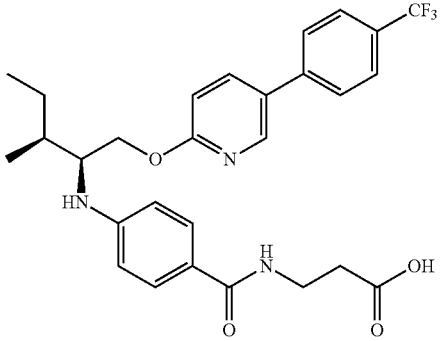

White solid. ¹HNMR (400 MHz, DMSO-d$_6$): δ 8.57 (d, J=2.5 Hz, 1H), 8.09 (dd, J=8.4, 2.5 Hz, 1H), 8.10-8.07 (m, 2H), 7.90 (d, J=7.8 Hz, 2H), 7.80 (d, J=7.8 Hz, 2H), 7.58 (d, J=8.8 Hz, 2H), 6.91 (d, J=8.8 Hz, 1H), 6.67 (d, J=8.8 Hz, 2H), 6.05 (d, J=8.4 Hz, 1H), 4.38-4.34 (m, 1H), 4.23-4.19 (m, 1H), 3.91-3.88 (m, 1H), 3.39-3.35 (m, 2H), 2.38-2.33 (m, 2H), 1.80-1.75 (m, 1H), 1.54-1.50 (m, 1H), 0.94 (d, J=6.4 Hz, 3H), 0.84 (d, J=6.4 Hz, 3H). MS (M+1): 530.

Compound 15-11: (S)-3-(4-((4-methyl-1-((5-(4-(trifluoromethyl)phenyl)pyridin-2-yl)oxy)pentan-2-yl)amino)benzamido)propanoic Acid

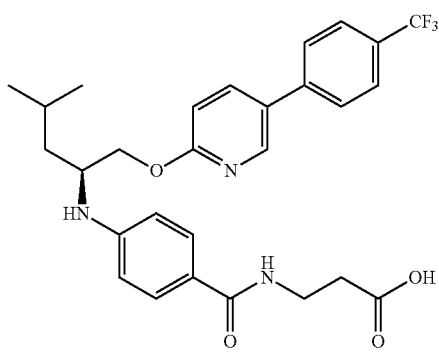 [SMILES: CC(C)C[C@@H](COc1ccc(-c2ccc(C(F)(F)F)cc2)cn1)Nc1ccc(C(=O)NCCC(=O)O)cc1]

White solid. ¹HNMR (400 MHz, DMSO-d$_6$): δ 8.56 (d, J=2.5 Hz, 1H), 8.09 (dd, J=8.4, 2.5 Hz, 1H), 8.02 (t, J=5.4 Hz, 1H), 7.90 (d, J=8.4 Hz, 2H), 7.80 (d, J=8.4 Hz, 2H), 7.60 (d, J=8.8 Hz, 2H), 6.91 (d, J=8.4 Hz, 1H), 6.68 (d, J=8.8 Hz, 2H), 6.06 (d, J=8.4 Hz, 1H), 438-4.34 (m, 1H), 4.24-4.20 (m, 1H), 3.92-3.86 (m, 1H), 3.43-3.38 (m, 2H), 2.46 (t, J=7 Hz, 2H), 1.81-1.74 (m, 1H), 1.54-1.50 (m, 2H), 0.94 (d, J=6.3 Hz, 3H), 0.84 (d, J=6.3 Hz, 3H). MS (M+1): 530.

Compound 15-13: 3-(4-(((2S,3S)-1-((5-(2-chloro-4-(trifluoromethyl)phenyl)pyridin-2-yl)oxy)-3-methylpentan-2-yl)amino)benzamido)propanoic Acid

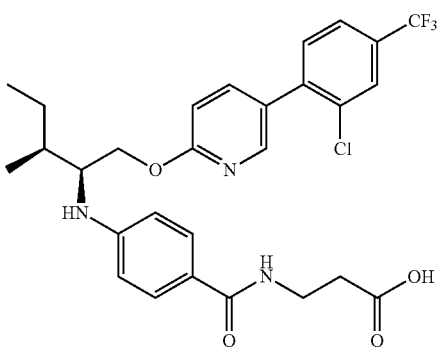 [SMILES: CC[C@H](C)[C@@H](COc1ccc(-c2ccc(C(F)(F)F)cc2Cl)cn1)Nc1ccc(C(=O)NCCC(=O)O)cc1]

White solid. ¹HNMR (400 MHz, DMSO-d$_6$): δ 8.26 (d, J=2.5 Hz, 1H), 8.00-7.95 (m, 2H), 7.85 (dd, J=8.4, 2.5 Hz, 1H), 7.80 (d, J=8.4 Hz, 1H), 7.68 (d, J=8.3 Hz, 1H), 7.60 (d, J=8.3 Hz, 2H), 6.90 (d, J=8.3 Hz, 1H), 6.66 (d, J=8.3 Hz, 2H), 6.05 (d, J=8.3 Hz, 1H), 4.36-4.32 (m, 1H), 4.24-4.20 (m, 1H), 3.91-3.88 (m, 1H), 3.42-3.40 (m, 2H), 2.37 (brs, 2H), 1.80-1.74 (m, 1H), 1.54-1.50 (m, 1H), 0.94 (d, J=6.4 Hz, 3H), 0.84 (d, J=6.4 Hz, 3H). MS (M+1): 564.

Compound 15-14: 3-(4-(((2S,3S)-1-((5-(2-fluoro-4-(trifluoromethyl)phenyl)pyridin-2-yl)oxy)-3-methyl-pentan-2-yl)amino)benzamido)propanoic Acid

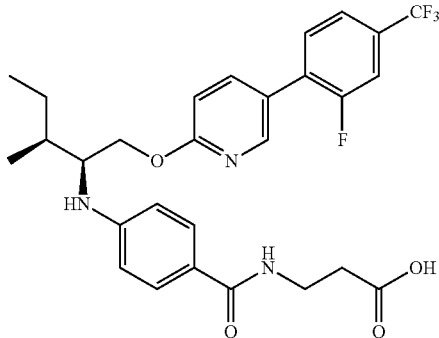 [SMILES: CC[C@H](C)[C@@H](COc1ccc(-c2ccc(C(F)(F)F)cc2F)cn1)Nc1ccc(C(=O)NCCC(=O)O)cc1]

White solid. ¹HNMR (400 MHz, DMSO-d$_6$): δ 8.41 (brs, 1H), 8.15-8.07 (m, 1H), 7.97-7.94 (m, 1H), 7.83-7.79 (m, 2H), 7.68-7.66 (m, 1H), 7.59-7.57 (m, 2H), 6.93 (d, J=8.3 Hz, 1H), 6.67 (d, J=8.3 Hz, 2H), 6.05 (d, J=8.3 Hz, 1H), 4.38-4.34 (m, 1H), 4.24-4.20 (m, 1H), 3.91-3.86 (m, 1H), 3.43-3.34 (m, 2H), 2.39-2.33 (m, 2H), 1.79-1.74 (m, 1H), 1.54-1.50 (m, 1H), 0.94 (d, J=6.4 Hz, 3H), 0.83 (d, J=6.4 Hz, 3H). MS (M+1): 548.

Compound 15-16: (S)-3-(4-((1-((5-(2-fluoro-4-(trifluoromethyl)phenyl)pyridin-2-yl)oxy)-4-methylpentan-2-yl)amino)benzamido)propanoic Acid

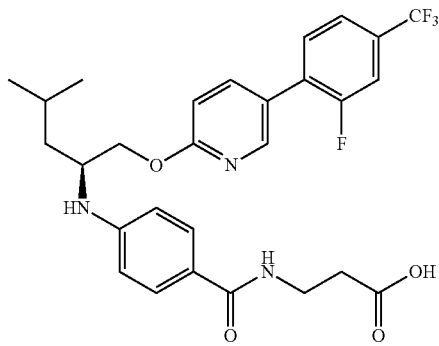

White solid. 1HNMR (400 MHz, DMSO-d$_6$): δ 8.41 (s, 1H), 8.03 (t, J=5.4 Hz, 1H), 7.85 (dt, J=8.4, 1.9 Hz, 1H), 7.94-7.79 (m, 2H), 7.68 (d, J=8.4 Hz, 1H), 7.60 (d, J=8.8 Hz, 2H), 6.93 (d, J=8.8 Hz, 1H), 6.67 (d, J=8.8 Hz, 2H), 6.08 (d, J=8.8 Hz, 1H), 4.38-4.34 (m, 1H), 4.24-4.20 (m, 1H), 3.92-3.86 (m, 1H), 3.34-3.38 (m, 2H), 2.46 (t, J=7 Hz, 2H), 1.81-1.74 (m, 1H), 1.54-1.50 (m, 2H), 0.94 (d, J=6.8 Hz, 3H), 0.84 (d, J=6.8 Hz, 3H). MS (M+1): 548.

Compound 15-15: 3-(4-(((2S,3S)-1-((5-(benzofuran-2-yl)pyridin-2-yl)oxy)-3-methylpentan-2-yl)amino)benzamido)propanoic Acid

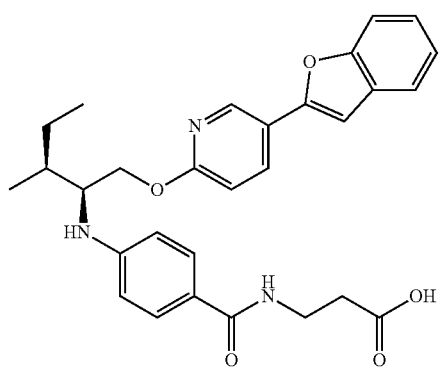 [SMILES: CC[C@H](C)[C@@H](COc1ccc(-c2cc3ccccc3o2)cn1)Nc1ccc(C(=O)NCCC(=O)O)cc1]

¹H NMR (400 MHz, DMSO-d$_6$): δ 8.72 (d, J=2.4 Hz, 1H), 8.18 (dd, J=8.8, 2.4 Hz, 1H), 8.03 (t, J=5.6 Hz, 1H), 7.50-7.71 (m, 4H), 7.19-7.35 (m, 2H), 6.90 (d, J=8.8 Hz, 1H), 6.64 (d, J=8.8 Hz, 2H), 6.15 (d, J=8.8 Hz, 1H), 4.27-4.52 (m, 2H), 3.75 (dt, J=13.0, 6.2 Hz, 1H), 3.38-3.45 (m, 2H), 2.45-2.50 (m, 2H), 1.69-1.84 (m, 1H), 1.51-1.68 (m, 1H), 1.18-1.37 (m, 1H), 0.95 (d, J=6.8 Hz, 3H), 0.90 (t, J=7.3 Hz, 2H). MS (M+1): 502.

Compound 15-17: (S)-3-(4-((1-((5-(2,4-dichlorophenyl)pyridin-2-yl)oxy)-3-methylbutan-2-yl)amino)benzamido)propanoic Acid

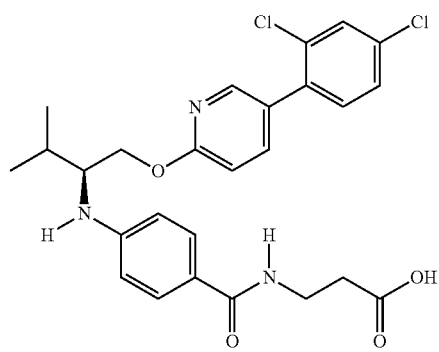 [SMILES: CC(C)[C@@H](COc1ccc(-c2ccc(Cl)cc2Cl)cn1)Nc1ccc(C(=O)NCCC(=O)O)cc1]

¹H NMR (400 MHz, CDCl$_3$): δ 8.13 (d, J=2.0 Hz, 2H), 7.61 (dd, J=8.3, 2.4 Hz, 1H), 7.55 (d, J=8.3 Hz, 2H), 7.46 (d, J=2.0 Hz, 1H), 7.23-7.29 (m, 1H), 7.18-7.22 (m, 1H), 6.80 (t, J=5.6 Hz, 1H), 6.72 (d, J=8.8 Hz, 1H), 6.57 (d, J=8.8 Hz, 2H), 4.43-4.49 (m, 1H), 4.32-4.38 (m, 1H), 3.59-3.70 (m, 3H), 2.62 (t, J=5.6 Hz, 2H), 1.98-2.13 (m, 1H), 1.01 (t, J=6.4 Hz, 6H). MS (M+1): 516.

Compound 15-18: (S)-2-(4-((1-((5-(2-chloro-4-(fluoromethyl)phenyl)pyridin-2-yl)oxy)-4-methylpentan-2-yl)amino)benzamido)ethane-1-sulfonic Acid

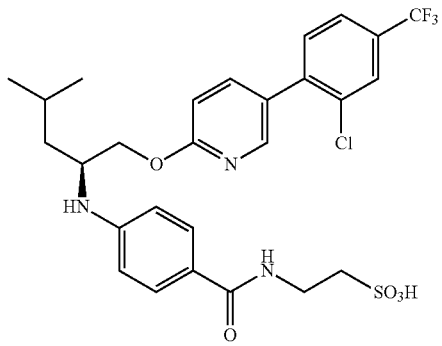 [SMILES: CC(C)C[C@@H](COc1ccc(-c2ccc(C(F)(F)F)cc2Cl)cn1)Nc1ccc(C(=O)NCCS(=O)(=O)O)cc1]

White solid. ¹HNMR (400 MHz, DMSO-d$_6$): δ 8.27 (d, J=2.5 Hz, 1H), 8.08 (t, J=4.9 Hz, 1H), 7.99 (s, 1H), 7.85 (dd, J=8.8, 2.4 Hz, 2H), 7.69 (d, J=8 Hz, 1H), 7.53 (d, J=8 Hz, 2H), 6.91 (d, J=8.8 Hz, 1H), 6.67 (d, J=8.8 Hz, 2H), 6.09 (d, J=8.8 Hz, 1H), 4.36-4.33 (m, 1H), 4.25-4.21 (m, 1H), 3.92-3.85 (m, 1H), 3.50-3.45 (m, 2H), 2.64 (t, J=7 Hz, 2H), 1.81-1.74 (m, 1H), 1.55-1.50 (m, 2H), 0.94 (d, J=6.8 Hz, 3H), 0.85 (d, J=6.8 Hz, 3H). MS (M+1): 600.

Compound 15-20: 3-(4-(((2S,3S)-1-((5-(2,4-difluorophenyl)pyridin-2-yl)oxy)-3-methylpentan-2-yl)amino)benzamido)propanoic Acid

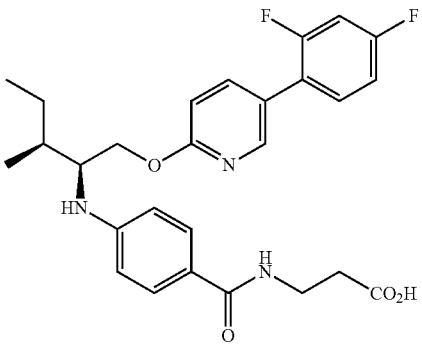

¹H NMR (400 MHz, CDCl$_3$): δ 8.23 (s, 1H), 7.67 (dt, J=8.8, 2.0 Hz, 1H), 7.55 (d, J=8.3 Hz, 2H), 7.31 (td, J=8.6, 6.4 Hz, 1H), 6.82-6.97 (m, 2H), 6.67-6.80 (m, 2H), 6.56 (d, J=8.8 Hz, 2H), 4.33-4.51 (m, 3H), 3.61-3.74 (m, 3H), 2.64 (t, J=5.9 Hz, 2H), 1.74-1.86 (m, 1H), 1.59-1.70 (m, 1H), 1.17-1.30 (m, 1H), 0.98 (d, J=6.8 Hz, 3H), 0.93 (t, J=7.3 Hz, 3H). MS (M+1): 498.

Compound 15-19: (S)-3-(4-((4-methyl-1-((5-(6-(trifluoromethyl)pyridazin-3-yl)pyridin-2-yl)oxy)pentan-2-yl)amino)benzamido)propanoic Acid

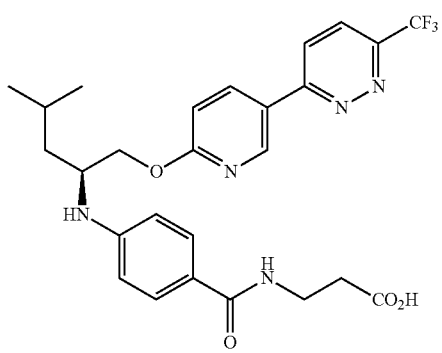 [SMILES: CC(C)C[C@@H](COc1ccc(-c2ccc(C(F)(F)F)nn2)cn1)Nc1ccc(C(=O)NCCC(=O)O)cc1]

White solid. H-NMR (400 MHz, DMSO-d$_6$): δ 9.05 (d, J=2.4 Hz, 1H), 8.58-8.54 (m, 2H), 8.34 (d, J=8.8 Hz, 1H), 8.04 (t, J=5.6 Hz, 1H), 7.60 (d, J=8.8 Hz, 2H), 7.01 (d, J=8.8, 3 Hz, 1H), 6.68 (d, J=8.8 Hz, 2H), 6.10 (d, J=8.8 Hz, 1H), 4.43-4.26 (m, 2H), 3.96-3.89 (m, 1H), 3.42-3.37 (m, 2H), 2.46 (t, J=6.8 Hz, 2H), 1.82-1.75 (m, 1H), 1.59-1.48 (m, 2H), 0.95 (d, J=6.4 Hz, 3H), 0.85 (d, J=6.4 Hz, 3H). MS (M+1): 532.

Compound 15-21: 2-(4-(((2S,3S)-1-((5-(2,4-difluorophenyl)pyridin-2-yl)oxy)-3-methylpentan-2-yl)amino)benzamido)ethane-1-sulfonic Acid

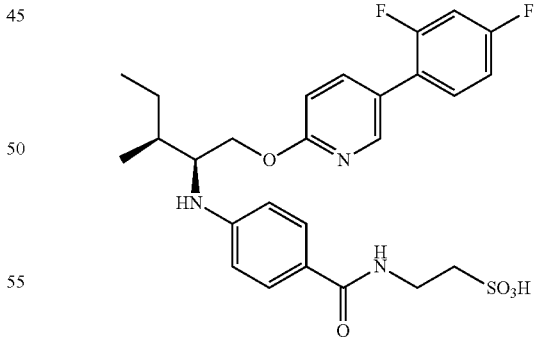

¹H NMR (400 MHz, DMSO-d$_6$): δ 8.31 (s, 1H), 8.08 (t, J=5.1 Hz, 1H), 7.81-7.87 (m, 1H), 7.49-7.64 (m, 3H), 7.29-7.43 (m, 1H), 7.12-7.27 (m, 1H), 6.87 (d, J=9.3 Hz, 1H), 6.64 (d, J=8.8 Hz, 2H), 6.16 (d, J=8.8 Hz, 1H), 4.26-4.47 (m, 2H), 3.73 (dd, J=7.8, 5.4 Hz, 1H), 3.43-3.54 (m, 2H), 2.66 (t, J=6.8 Hz, 2H), 1.71-1.80 (m, 1H), 1.60 (ddd, J=13.3, 7.5, 4.2 Hz, 1H), 1.17-1.31 (m, 1H), 0.94 (d, J=6.8 Hz, 3H), 0.90 (t, J=7.3 Hz, 3H). MS (M+1): 534.

Compound 15-22: (S)-3-(4-((1-((5-(benzofuran-2-yl)pyridin-2-yl)oxy)hexan-2-yl)amino)benzamido) propanoic Acid

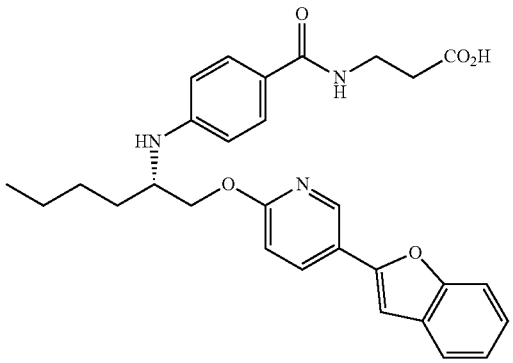 [SMILES: CCCC[C@@H](COc1ccc(-c2cc3ccccc3o2)cn1)Nc1ccc(C(=O)NCCC(=O)O)cc1]

$^1$H NMR (400 MHz, CDCl$_3$): δ 8.61 (d, J=2.4 Hz, 1H), 7.95 (dt, J=8.7, 2.0 Hz, 1H), 7.43-7.62 (m, 4H), 7.14-7.31 (m, 2H), 6.80-6.98 (m, 2H), 6.75 (d, J=8.8 Hz, 1H), 6.57 (d, J=8.3 Hz, 2H), 4.36-4.47 (m, 1H), 4.27 (dd, J=10.5, 4.6 Hz, 1H), 3.76 (d, J=4.9 Hz, 1H), 3.64 (d, J=5.9 Hz, 2H), 2.62 (t, J=5.1 Hz, 2H), 1.67-1.78 (m, 1H), 1.48-1.63 (m, 1H), 1.25-1.45 (m, 4H), 0.86 (t, J=6.8 Hz, 3H). MS (M+1): 502.

Compound 15-23: (S)-2-(4-((1-((5-(benzofuran-2-yl)pyridin-2-yl)oxy)hexan-2-yl)amino)benzamido) ethane-1-sulfonic Acid

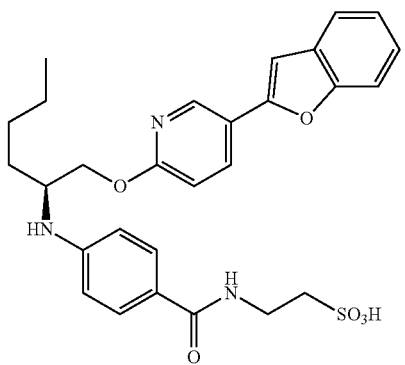 [SMILES: CCCC[C@@H](COc1ccc(-c2cc3ccccc3o2)cn1)Nc1ccc(C(=O)NCCS(=O)(=O)O)cc1]

$^1$H NMR (400 MHz, DMSO-d$_6$): δ 8.72 (d, J=2.4 Hz, 1H), 8.20 (dd, J=8.3, 2.4 Hz, 1H), 7.54-7.67 (m, 4H), 7.39 (s, 1H), 7.19-7.35 (m, 2H), 6.93 (d, J=8.8 Hz, 1H), 6.86 (br. s., 2H), 6.76 (d, J=6.8 Hz, 2H), 4.39 (dd, J=10.8, 5.4 Hz, 1H), 4.24 (dd, J=10.8, 5.9 Hz, 1H), 3.77-3.86 (m, 1H), 3.51 (t, J=7.1 Hz, 2H), 2.66-2.75 (m, 2H), 1.65-1.78 (m, 1H), 1.58 (td, J=8.7, 4.2 Hz, 1H), 1.19-1.45 (m, 4H), 0.84 (t, J=7.1 Hz, 3H). MS (M+1): 538.

Compound 15-24: (S)-3-(4-((1-((5-(2,4-dichlorophenyl)pyridin-2-yl)oxy)hexan-2-yl)amino)benzamido) propanoic Acid

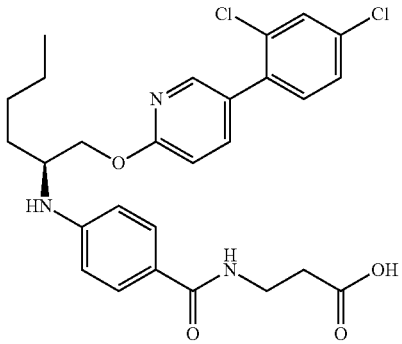 [SMILES: CCCC[C@@H](COc1ccc(-c2ccc(Cl)cc2Cl)cn1)Nc1ccc(C(=O)NCCC(=O)O)cc1]

$^1$H NMR (400 MHz, CDCl$_3$): δ 8.13 (d, J=2.0 Hz, 1H), 7.62 (dd, J=8.8, 2.4 Hz, 1H), 7.56 (d, J=8.3 Hz, 2H), 7.45 (d, J=2.0 Hz, 1H), 7.23-7.29 (m, 1H), 7.18-7.22 (m, 1H), 6.90 (t, J=5.9 Hz, 1H), 6.75 (d, J=8.8 Hz, 1H), 6.57 (d, J=8.8 Hz, 2H), 4.42 (dd, J=10.8, 4.9 Hz, 1H), 4.28 (dd, J=10.3, 4.9 Hz, 1H), 3.78 (m, J=6.1 Hz, 1H), 3.63 (q, J=5.9 Hz, 2H), 2.61 (t, J=5.9 Hz, 2H), 1.69-1.80 (m, 1H), 1.52-1.62 (m, 1H), 1.28-1.44 (m, 4H), 0.86 (t, J=7.1 Hz, 3H). MS (M+1): 530.

Compound 15-25: (S)-3-(4-((1-((5-(2-chlor-4-(trifluoromethyl)phenyl)pyridin-2-yl)oxy)hexan-2-yl) amino)benzamido)propanoic Acid

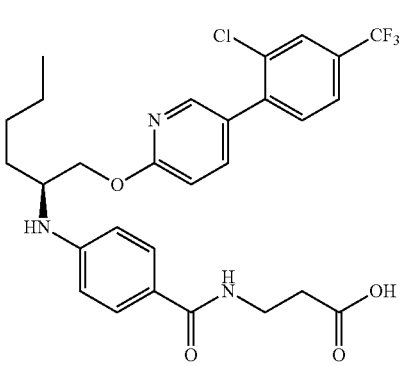 [SMILES: CCCC[C@@H](COc1ccc(-c2ccc(C(F)(F)F)cc2Cl)cn1)Nc1ccc(C(=O)NCCC(=O)O)cc1]

$^1$H NMR (400 MHz, CDCl$_3$): δ 8.18 (d, J=2.0 Hz, 1H), 7.71 (d, J=1.0 Hz, 1H), 7.67 (dd, J=8.3, 2.4 Hz, 1H), 7.52-7.60 (m, 3H), 7.40 (d, J=7.8 Hz, 1H), 6.88 (t, J=5.9 Hz, 1H), 6.78 (d, J=8.3 Hz, 1H), 6.58 (d, J=8.8 Hz, 2H), 4.44 (dd, J=10.8, 4.9 Hz, 1H), 4.30 (dd, J=10.8, 4.9 Hz, 1H), 3.76-3.83 (m, 1H), 3.64 (q, J=5.9 Hz, 2H), 2.62 (t, J=5.9 Hz, 2H), 1.69-1.81 (m, 1H), 1.53-1.65 (m, 1H), 1.30-1.48 (m, 4H), 0.87 (t, J=7.1 Hz, 3H). MS (M+1): 564.

Compound 15-26: (S)-3-(4-((1-((5-(2-fluoro-4-(trif-luoromethyl)phenyl)pyridin-2-yl)oxy)hexan-2-yl)amino)benzamido)propanoic Acid

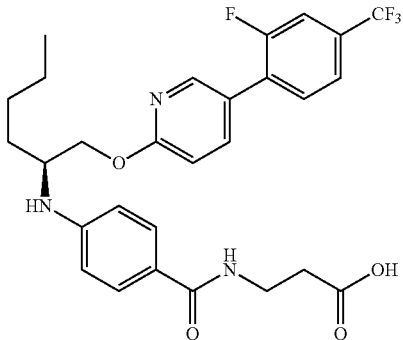

¹H NMR (400 MHz, CDCl₃): δ 8.30 (d, J=1.5 Hz, 1H), 7.74 (dt, J=8.7, 2.0 Hz, 1H), 7.57 (d, J=8.3 Hz, 2H), 7.43-7.51 (m, 2H), 7.39 (d, J=10.3 Hz, 1H), 6.90 (t, J=5.9 Hz, 1H), 6.79 (d, J=8.3 Hz, 1H), 6.58 (d, J=8.8 Hz, 2H), 4.44 (dd, J=10.8, 4.9 Hz, 1H), 4.29 (dd, J=10.8, 5.4 Hz, 1H), 3.79 (t, J=6.4 Hz, 1H), 3.64 (q, J=5.5 Hz, 2H), 2.61 (t, J=5.6 Hz, 2H), 1.71-1.81 (m, 1H), 1.52-1.63 (m, 1H), 1.24-1.48 (m, 4H), 0.86 (t, J=7.3 Hz, 3H). MS (M+1): 548. HPLC: 97%.

Compound 15-27: (S)-3-(4-((1-(4'-(trifluoromethyl)-[1,1'-biphenyl]-4-yl)-2-((5-(trifluoromethyl)pyridin-2-yl)oxy)ethyl)amino)benzamido)propanoic Acid

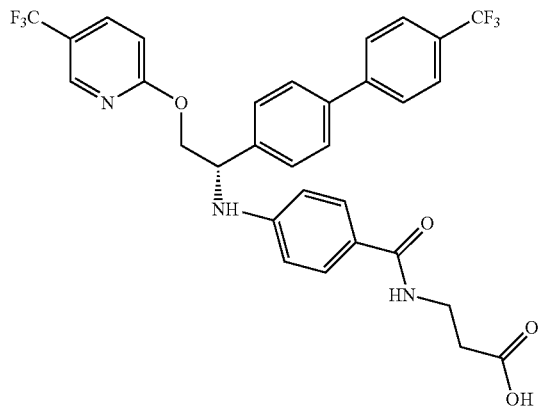 [SMILES: O=C(O)CCNC(=O)c1ccc(N[C@H](COc2ccc(C(F)(F)F)cn2)c2ccc(-c3ccc(C(F)(F)F)cc3)cc2)cc1]

¹H NMR (400 MHz, DMSO-d₆): δ 12.13 (br. s., 1H), 8.57-8.63 (m, 1H), 8.07 (dd, J=8.8, 2.4 Hz, 1H), 8.01 (t, J=5.6 Hz, 1H), 7.84-7.93 (m, J=7.8 Hz, 2H), 7.75-7.83 (m, J=8.3 Hz, 2H), 7.68-7.75 (m, J=8.3 Hz, 2H), 7.59-7.67 (m, J=8.8 Hz, 2H), 7.48-7.58 (m, J=8.8 Hz, 2H), 6.97-7.08 (m, 2H), 6.56-6.65 (m, J=8.8 Hz, 2H), 4.99-5.11 (m, 1H), 4.53-4.66 (m, 2H), 3.35-3.43 (m, 2H), 2.44 (t, J=7.1 Hz, 2H). MS (M+1): 618.

Compound 15-28: (S)-2-(4-((2-((5-(benzofuran-2-yl)pyridin-2-yl)oxy)-1-(4'-(trifluoromethyl)-[1,1'-biphenyl]-4-yl)ethyl)amino)benzamido)ethane-1-sulfonic Acid

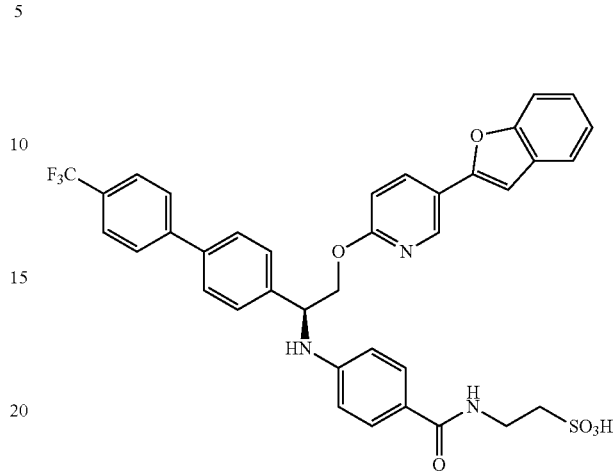

¹H NMR ((400 MHz, DMSO-d₆): δ 8.75 (d, J=2.4 Hz, 1H), 8.22 (dd, J=8.8, 2.4 Hz, 1H), 8.08 (t, J=5.1 Hz, 1H), 7.84-7.92 (m, J=8.3 Hz, 2H), 7.76-7.83 (m, J=8.8 Hz, 2H), 7.70-7.76 (m, 2H), 7.60-7.67 (m, 4H), 7.44-7.53 (m, J=8.8 Hz, 2H), 7.41 (s, 1H), 7.21-7.36 (m, 2H), 7.05 (d, J=7.3 Hz, 1H), 7.01 (d, J=8.8 Hz, 1H), 6.58-6.68 (m, J=8.8 Hz, 2H), 5.00-5.11 (m, 1H), 4.52-4.67 (m, 2H), 3.44 (q, J=6.4 Hz, 2H), 2.60 (t, J=7.1 Hz, 2H). MS (M+1): 702. HPLC purity: 98%.

Compound 15-29: (S)-3-(4-((2-((5-(benzofuran-2-yl)pyridin-2-yl)oxy)-1-(4'-(trifluoromethyl)-[1,1'-biphenyl]-4-yl)ethyl)amino)benzamido)propanoic Acid

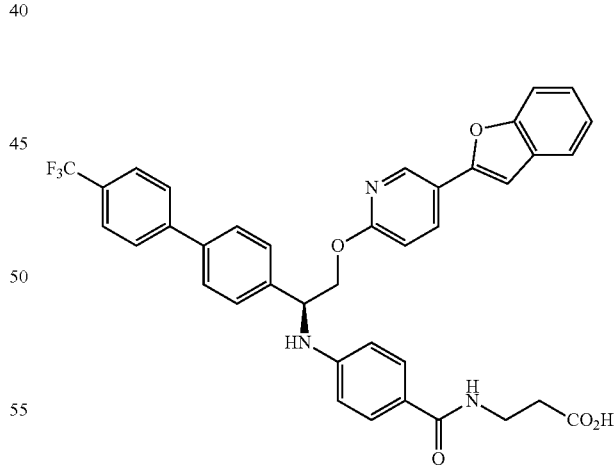

¹H NMR ((400 MHz, DMSO-d₆): δ 12.13 (br. s., 1H), 8.75 (d, J=2.4 Hz, 1H), 8.23 (dd, J=8.8, 2.4 Hz, 1H), 8.02 (t, J=5.4 Hz, 1H), 7.84-7.92 (m, J=7.8 Hz, 2H), 7.76-7.82 (m, J=8.3 Hz, 2H), 7.69-7.76 (m, 2H), 7.59-7.67 (m, 4H), 7.51-7.58 (m, J=8.8 Hz, 2H), 7.41 (s, 1H), 7.22-7.36 (m, 2H), 6.96-7.08 (m, 2H), 6.56-6.67 (m, J=8.8 Hz, 2H), 5.06 (q, J=6.8 Hz, 1H), 4.52-4.64 (m, 2H), 3.35-3.41 (m, 2H), 2.44 (t, J=7.3 Hz, 2H). MS (M+1): 666. HPLC purity: 99%.

Compound 15-30: (S)-3-(4-((2-((5-(5-(tert-butyl)-1,3,4-oxadiazol-2-yl)pyridin-2-yl)oxy)-1-(4'-(trifluoromethyl)-[1,1'-biphenyl]-4-yl)ethyl)amino)benzamido)propanoic Acid Compound 15-32: (S)-3-(4-((2-((5-(5-(tert-butyl)-1,3,4-oxadiazol-2-yl)pyridin-2-yl)oxy)-1-(2'-fluoro-4'-(trifluoromethyl)-[1,1'-biphenyl]-4-yl)ethyl)amino)benzamido)propanoic Acid

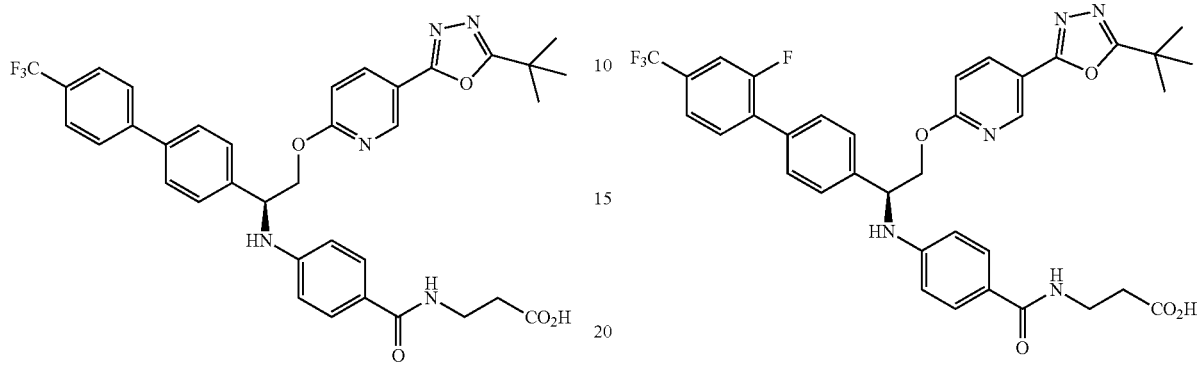

$^1$H NMR (400 MHz, CDCl$_3$): δ 8.80 (d, J=2.4 Hz, 1H), 8.23-8.14 (m, 1H), 7.63 (s, 4H), 7.57-7.48 (m, 6H), 6.85 (d, J=8.8 Hz, 1H), 6.79-6.69 (m, 1H), 6.50 (d, J=8.3 Hz, 2H), 4.94-4.84 (m, 1H), 4.73-4.58 (m, 2H), 3.65-3.54 (m, 2H), 2.63-2.53 (m, 2H), 1.46 (s, 9H). MS (M+1): 674.

$^1$H NMR (400 MHz, CDCl$_3$): δ 8.79 (d, J=2.4 Hz, 1H), 8.22-8.14 (m, 1H), 7.55-7.46 (m, 7H), 7.46-7.41 (m, 1H), 7.40-7.34 (m, 1H), 6.85 (d, J=8.8 Hz, 1H), 6.81-6.71 (m, 1H), 6.50 (d, J=8.8 Hz, 2H), 4.94-4.82 (m, 1H), 4.75-4.57 (m, 2H), 3.65-3.52 (m, 2H), 2.64-2.51 (m, 2H), 1.45 (s, 9H). MS (M+1): 692. HPLC 96.4%.

Compound 15-31: Ethyl (S)-3-(4-((2-((5-(5-(tert-butyl)-1,3,4-oxadiazol-2-yl)pyridin-2-yl)oxy)-1-(2'-fluoro-4'-(trifluoromethyl)-[1,1'-biphenyl]-4-yl)ethyl)amino)benzamido)propanoate Compound 15-33: Ethyl (S)-3-(4-((2-((5-(5-(tert-butyl)-1,3,4-oxadiazol-2-yl)pyridin-2-yl)oxy)-1-(2',4'-dichloro-[1,1'-biphenyl]-4-yl)ethyl)amino)benzamido)propanoate

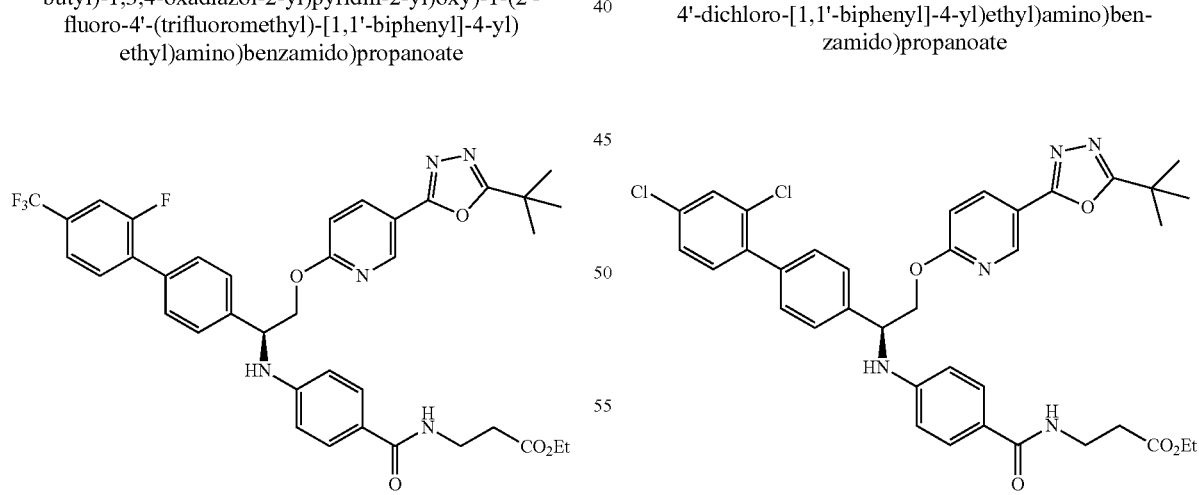

$^1$H NMR (400 MHz, CDCl$_3$): δ 8.81 (d, J=2.4 Hz, 1H), 8.24-8.18 (m, 1H), 7.59-7.48 (m, 7H), 7.48-7.36 (m, 2H), 6.88 (d, J=8.8 Hz, 1H), 6.66-6.56 (m, 1H), 6.53 (d, J=8.8 Hz, 2H), 5.33-5.25 (m, 1H), 4.95-4.87 (m, 1H), 4.75-4.59 (m, 2H), 4.11 (q, J=7.1 Hz, 2H), 3.63 (q, J=5.9 Hz, 2H), 2.56 (t, J=5.9 Hz, 2H), 1.47 (s, 9H), 1.22 (t, J=7.3 Hz, 3H). MS (M+1): 720. HPLC 97.8%.

$^1$H NMR (400 MHz, CDCl$_3$): δ 8.81 (s, 1H), 8.26-8.16 (m, 1H), 7.57-7.43 (m, 5H), 7.39 (d, J=8.3 Hz, 2H), 7.32-7.20 (m, 2H), 6.88 (d, J=9.3 Hz, 1H), 6.64-6.57 (m, 1H), 6.54 (d, J=8.8 Hz, 2H), 5.26-5.19 (m, 1H), 4.96-4.86 (m, 1H), 4.78-4.61 (m, 2H), 4.12 (d, J=6.8 Hz, 2H), 3.67-3.59 (m, 2H), 2.56 (s, 2H), 1.47 (s, 9H), 1.23 (t, J=7.1 Hz, 3H). MS (M+1): 702.

Compound 15-34: (S)-3-(4-((2-((5-(5-(tert-butyl)-1,3,4-oxadiazol-2-yl)pyridin-2-yl)oxy)-1-(2',4'-dichloro-[1,1'-biphenyl]-4-yl)ethyl)amino)benzamido)propanoic Acid

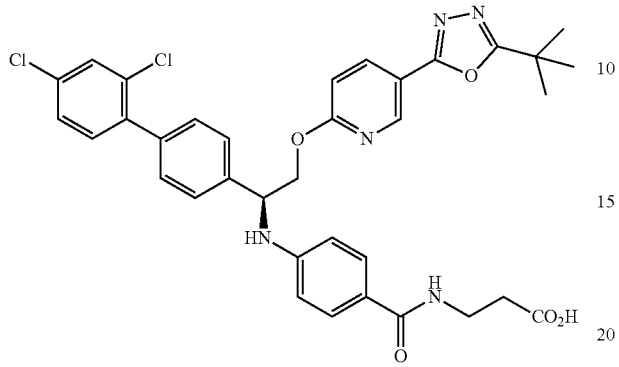

$^1$H NMR (400 MHz, CDCl$_3$): δ 8.80 (d, J=2.0 Hz, 1H), 8.26-8.12 (m, 1H), 7.54-7.45 (m, 5H), 7.38 (d, J=8.3 Hz, 2H), 7.25-7.23 (m, 2H), 6.86 (d, J=8.8 Hz, 1H), 6.64-6.59 (m, 1H), 6.52 (d, J=8.3 Hz, 2H), 4.92-4.88 (m, 1H), 4.74-4.62 (m, 2H), 3.67-3.61 (m, 2H), 2.63 (s, 2H), 1.47 (s, 9H). MS (M+1): 674.

Compound 15-36: Ethyl (S)-3-(4-((1-((5-(benzo[d]thiazol-2-yl)pyridin-2-yl)oxy)-3-methylbutan-2-yl)amino)benzamido)propanoate

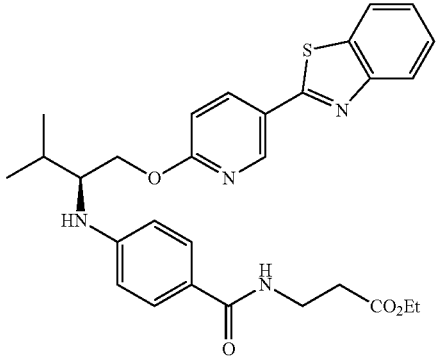

White solid. $^1$H-NMR (DMSO-d$_6$, 400 MHz): δ 8.81 (d, J=1.6 Hz, 1H), 8.27 (dd, J=8.8, 2.9 Hz, 1H), 8.04 (d, J=8.3 Hz, 1H), 7.89 (d, J=8.3 Hz, 1H), 7.60 (d, J=8.8 Hz, 2H), 7.51-7.46 (m, 1H), 7.47-7.36 (m, 1H), 6.80 (d, J=8.8 Hz, 1H), 6.63 (d, J=8.8 Hz, 2H), 4.57 (dd, J=11.2, 5.8 Hz, 1H), 4.43 (dd, J=10.7, 5.4 Hz, 1H), 4.22 (d, J=8.8 Hz, 1H), 4.15 (q, J=8.8 Hz, 2H), 3.71-3.66 (m, 3H), 2.61 (t, J=6.8 Hz, 2H), 2.12-2.08 (m, 1H), 1.28 (t, J=6.8 Hz, 3H), 1.06 (t, J=6.8 Hz, 3H), 0.82 (t, J=6.8 Hz, 3H). MS (M+1): 533.

Compound 15-35: (S)-2-(4-((2-((5-(benzofuran-2-yl)pyridin-2-yl)oxy)-1-(4-(5-methoxypyrimidin-2-yl)phenyl)ethyl)amino)benzamido)ethane-1-sulfonic Acid

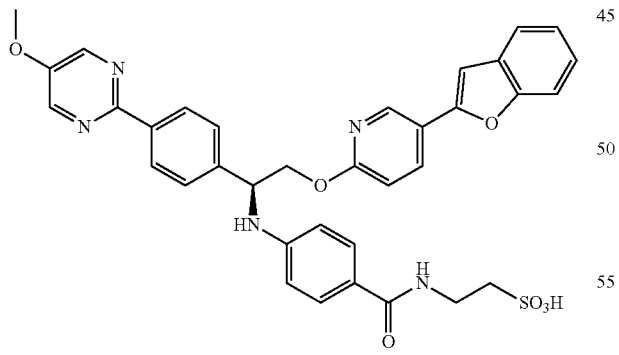

$^1$H NMR (400 MHz, DMSO-d$_6$): δ 12.29 (br. s., 1H), 8.74 (d, J=2.4 Hz, 1H), 8.63 (s, 2H), 8.27 (d, J=8.3 Hz, 2H), 8.22 (dd, J=8.3, 2.4 Hz, 1H), 8.08 (t, J=5.4 Hz, 1H), 7.57-7.67 (m, 4H), 7.44-7.53 (m, J=8.8 Hz, 2H), 7.39-7.43 (m, 1H), 7.21-7.34 (m, 2H), 7.10 (d, J=7.3 Hz, 1H), 6.99 (d, J=9.3 Hz, 1H), 6.58-6.66 (m, J=8.8 Hz, 2H), 4.99-5.08 (m, 1H), 4.52-4.67 (m, 2H), 3.94 (s, 3H), 3.40-3.49 (m, 2H), 2.61-2.79 (m, 2H), MS (M+1): 666.

Compound 15-37: (S)-3-(4-((1-((5-(benzo[d]thiazol-2-yl)pyridin-2-yl)oxy)-3-methylbutan-2-yl)amino)benzamido)propanoic Acid

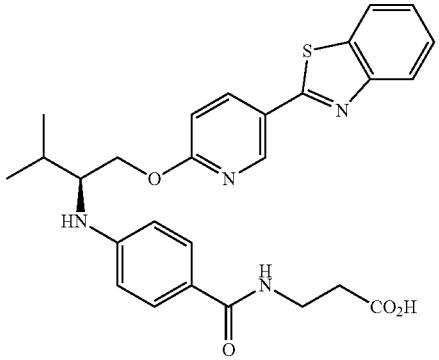

White solid. $^1$H-NMR (DMSO-d$_6$, 400 MHz): δ 8.87 (d, J=1.9 Hz, 1H), 8.34 (dd, J=8.8, 5.4 Hz, 1H), 8.14 (d, J=8.8 Hz, 1H), 8.05-8.02 (m, 2H), 7.59-7.44 (m, 4H), 6.95 (d, J=8.8 Hz, 1H), 6.67 (d, J=8.8 Hz, 2H), 6.09 (d, J=8.8 Hz, 1H), 4.46-4.37 (m, 3H), 3.75-3.69 (m, 2H), 2.46 (t, J=6.8 Hz, 2H), 2.05-2.00 (m, 1H), 1.01-0.97 (m, 6H). MS (M+1): 505.

Example 16: Synthesis of Compounds 16-1 to 16-2

Compound 16-1: (S)-3-(6-((1-((5-(2,4-dichlorophenyl)pyridin-2-yl)oxy)-3-methylbutan-2-yl)amino)nicotinamido)propanoic Acid

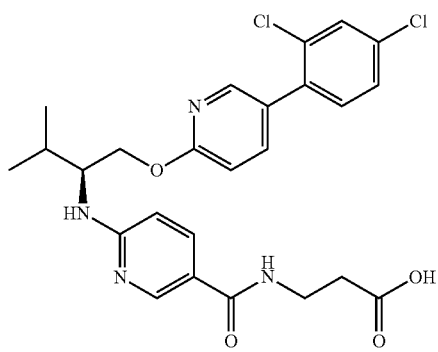 [SMILES: CC(C)[C@@H](COc1ccc(-c2ccc(Cl)cc2Cl)cn1)Nc1ccc(C(=O)NCCC(=O)O)cn1]

$^1$H NMR (400 MHz, CDCl$_3$): δ 8.09-8.21 (m, 4H), 7.78 (t, J=4.9 Hz, 1H), 7.57-7.61 (m, 1H), 7.44 (d, J=2.0 Hz, 1H), 7.23-7.29 (m, 1H), 7.19 (d, J=8.3, 1H), 6.78 (d, J=9.3 Hz, 1H), 6.67 (d, J=8.8 Hz, 1H), 4.51-4.57 (m, 1H), 4.42 (dd, J=11.2, 7.3 Hz, 1H), 3.80 (br. s., 1H), 3.63-3.71 (m, 2H), 2.54 (dd, J=7.1, 4.2 Hz, 2H), 2.05-2.18 (m, 1H), 1.07 (t, J=6.4 Hz, 6H). MS (M+1): 517.

Compound 16-2: (S)-3-(6-((1-((5-(benzofuran-2-yl)pyridin-2-yl)oxy)-3-methylbutan-2-yl)amino)nicotinamido)propanoic Acid

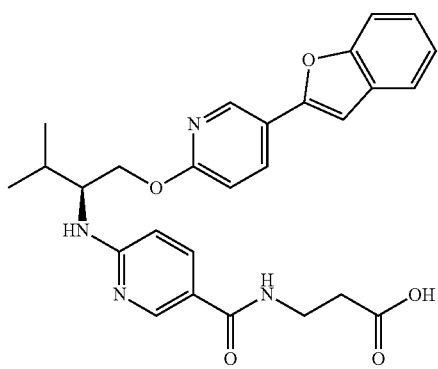 [SMILES: CC(C)[C@@H](COc1ccc(-c2cc3ccccc3o2)cn1)Nc1ccc(C(=O)NCCC(=O)O)cn1]

$^1$H NMR (400 MHz, DMSO-d$_6$): δ 8.71 (d, J=2.0 Hz, 1H), 8.44 (d, J=2.4 Hz, 1H), 8.18 (dd, J=8.8, 2.4 Hz, 2H), 7.72-7.80 (m, 1H), 7.59-7.67 (m, 2H), 7.38 (s, 1H), 7.23-7.34 (m, 2H), 7.04 (d, J=8.3 Hz, 1H), 6.91 (d, J=8.8 Hz, 1H), 6.55 (d, J=8.8 Hz, 1H), 4.40-4.51 (m, 1H), 4.25-4.40 (m, 2H), 3.37-3.43 (m, 2H), 2.45 (d, J=7.1 Hz, 2H), 1.99-2.07 (m, 1H), 0.97 (dd, J=6.8, 4.4 Hz, 6H). MS (M+1): 489.

Example 17: Synthesis of Compounds 17-1 to 17-12

Compound 17-1: (S)-3-(4-((1-((6-(2,4-difluorophenyl)pyridazin-3-yl)oxy)-4-methylpentan-2-yl)amino)benzamido)propanoic Acid

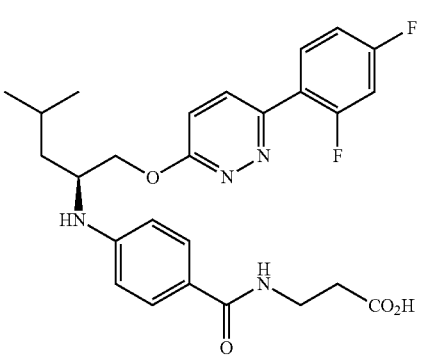 [SMILES: CC(C)C[C@@H](COc1ccc(-c2ccc(F)cc2F)nn1)Nc1ccc(C(=O)NCCC(=O)O)cc1]

White solid. $^1$H-NMR (400 MHz, DMSO-d$_6$): δ 8.06-7.89 (m, 3H), 7.62-7.58 (m, 2H), 7.43-7.38 (m, 1H), 7.28-7.23 (m, 2H), 6.68 (d, J=8.8 Hz, 2H), 6.12 (d, J=8.8 Hz, 1H), 4.54-4.40 (m, 2H), 4.03-3.96 (m, 1H), 3.42-3.39 (m, 2H), 2.48 (t, J=7 Hz, 2H), 1.82-1.75 (m, 1H), 1.59-1.53 (m, 2H), 0.94 (d, J=6.8 Hz, 3H), 0.85 (d, J=6.8 Hz, 3H). MS (M+1): 499.

Compound 17-2: (S)-3-(4-((1-((6-(2,4-dichlorophenyl)pyridazin-3-yl)oxy)-4-methylpentan-2-yl)amino)benzamido)propanoic Acid

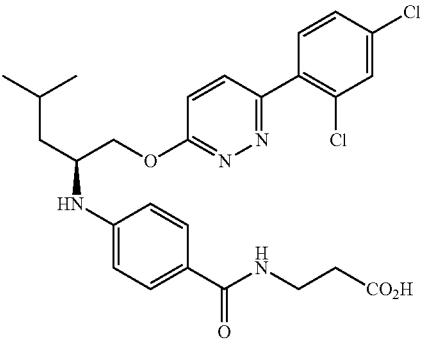 [SMILES: CC(C)C[C@@H](COc1ccc(-c2ccc(Cl)cc2Cl)nn1)Nc1ccc(C(=O)NCCC(=O)O)cc1]

White solid. $^1$HNMR (400 MHz, DMSO-d$_6$): δ 8.04 (t, J=5.4 Hz, 1H), 7.86 (d, J=8.8 Hz, 1H), 7.79 (d, J=2.0 Hz, 1H), 7.64 (d, J=8.8 Hz, 1H), 7.58 (d, J=8.8 Hz, 3H), 7.27 (d, J=8.8 Hz, 1H), 6.66 (d, J=8.8 Hz, 2H), 6.12 (d, J=8.8 Hz, 1H), 4.53-4.40 (m, 1H), 4.03-3.96 (m, 1H), 3.34-3.38 (m, 2H), 2.46 (t, J=7 Hz, 2H), 1.80-1.77 (m, 1H), 1.57-1.52 (m, 2H), 0.95 (d, J=6.8 Hz, 3H), 0.86 (d, J=6.8 Hz, 3H). MS (M+1): 531.

Compound 17-3: 3-(4-(((2S,3S)-3-methyl-1-((6-(4-(trifluoromethyl)phenyl)pyridazin-3-yl)oxy)pentan-2-yl)amino)benzamido)propanoic Acid

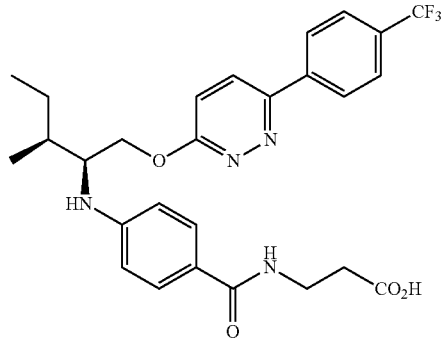 [SMILES: CC[C@H](C)[C@@H](COc1ccc(-c2ccc(C(F)(F)F)cc2)nn1)Nc1ccc(C(=O)NCCC(=O)O)cc1]

White solid. 1HNMR (400 MHz, DMSO-d$_6$): δ 8.28 (d, J=8.3 Hz, 2H), 8.24 (d, J=9.3 Hz, 1H), 8.02 (t, J=5.4 Hz, 1H), 7.89 (d, J=8.3 Hz, 2H), 7.58 (d, J=8.8 Hz, 2H), 7.29 (d, J=8.8 Hz, 1H), 6.63 (d, J=8.8 Hz, 2H), 6.21 (d, J=8.8 Hz, 1H), 4.67-4.52 (m, 2H), 3.84-3.81 (m, 1H), 3.42-3.37 (m, 2H), 2.46 (t, J=7 Hz, 2H), 2.03-1.97 (m, 1H), 1.79-1.76 (m, 1H), 1.63-1.60 (m, 1H), 0.97 (d, J=6.8 Hz, 3H), 0.92 (t, J=6.8 Hz, 3H). MS (M+1): 531.

Compound 17-5: 3-(4-(((2S,3S)-1-((6-(2-fluoro-4-(trifluoromethyl)phenyl)pyridazin-3-yl)oxy)-3-methylpentan-2-yl)amino)benzamido)propanoic Acid

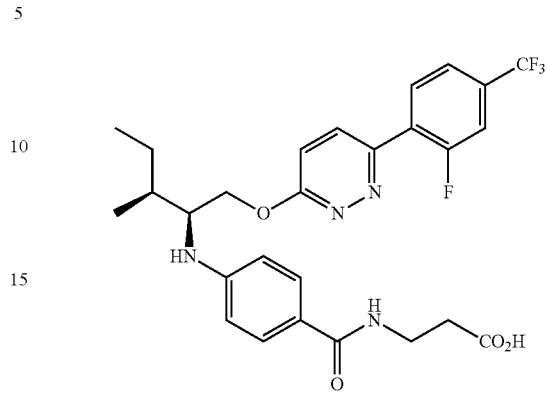

White solid. $^1$H-NMR (400 MHz, DMSO-d$_6$): δ 8.12 (t, J=8.4 Hz, 1H), 8.04-7.99 (m, 2H), 7.87 (d, J=8.8 Hz, 1H), 7.80-7.75 (m, 1H), 7.56 (d, J=8.8 Hz, 2H), 7.31 (d, J=8.8 Hz, 2H), 6.20 (d, J=8.8 Hz, 1H), 4.67-4.53 (m, 2H), 3.85-3.82 (m, 1H), 3.42-3.39 (m, 2H), 2.46 (t, J=7 Hz, 2H), 1.80-1.78 (m, 1H), 1.78-1.62 (m, 1H), 0.97 (d, J=6.8 Hz, 3H), 0.91 (t, J=6.8 Hz, 3H). MS (M+1): 549.

Compound 17-4: 3-(4-(((2S,3S)-1-((6-(2-chloro-4-(trifluoromethyl)phenyl)pyridazin-3-yl)oxy)-3-methylpentan-2-yl)amino)benzamido)propanoic Acid

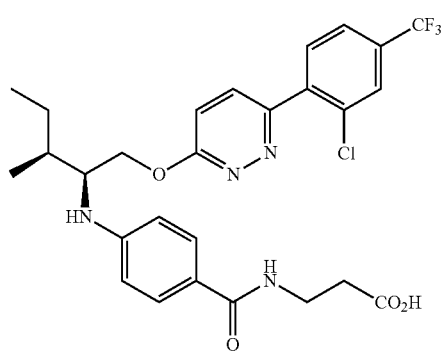 [SMILES: CC[C@H](C)[C@@H](COc1ccc(-c2ccc(C(F)(F)F)cc2Cl)nn1)Nc1ccc(C(=O)NCCC(=O)O)cc1]

White solid. 1HNMR (400 MHz, DMSO-d$_6$): δ 8.05-8.01 (m, 2H), 7.94-7.82 (m, 3H), 7.58 (d, J=8.8 Hz, 2H), 7.30 (d, J=8.8 Hz, 1H), 6.64 (d, J=8.8 Hz, 1H), 6.21 (d, J=8.8 Hz, 1H), 4.66.4.53 (m, 2H), 3.85-3.82 (m, 1H), 3.42-3.37 (m, 2H), 2.45 (t, J=7 Hz, 2H), 2.03-1.97 (m, 1H), 1.79-1.65 (m, 1H), 1.65-1.60 (m, 1H), 0.98 (d, J=6.8 Hz, 3H), 0.92 (t, J=6.8 Hz, 3H). MS (M+1): 565.

Compound 17-6: 3-(4-(((2S,3S)-1-((6-(2,4-difluorophenyl)pyridazin-3-yl)oxy)-3-methylpentan-2-yl)amino)benzamido)propanoic Acid

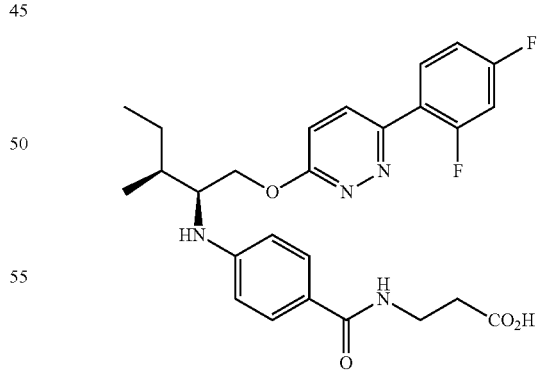

White solid. $^1$H-NMR (400 MHz, DMSO-d$_6$): δ 8.03 (t, J=5.4 Hz, 1H), 7.97-7.89 (m, 2H), 7.58 (d, J=8.8 Hz, 2H), 7.46-7.41 (m, 1H), 7.26 (d, J=8.8 Hz, 2H), 6.63 (d, J=8.8 Hz, 2H), 6.20 (d, J=8.8 Hz, 1H), 4.65-4.51 (m, 2H), 3.84-3.80 (m, 1H), 3.42-3.37 (m, 2H), 2.46 (t, J=7 Hz, 2H), 1.80-1.77 (m, 1H), 1.65-1.60 (m, 1H), 0.97 (d, J=6.8 Hz, 3H), 0.91 (t, J=6.8 Hz, 3H). MS (M+1): 499.

Compound 17-7: (S)-3-(4-((4-methyl-1-((6-(4-(trifluoromethyl)phenyl)pyridazin-3-yl)oxy)pentan-2-yl)amino)benzamido)propanoic Acid

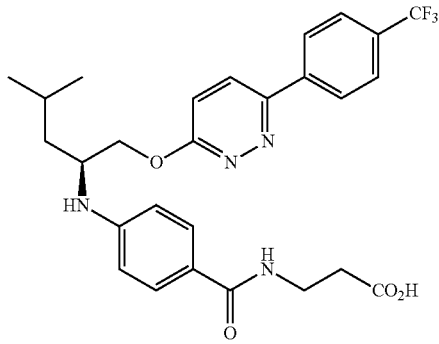 [SMILES: CC(C)C[C@@H](COc1ccc(-c2ccc(C(F)(F)F)cc2)nn1)Nc1ccc(C(=O)NCCC(=O)O)cc1]

White solid. ¹HNMR (400 MHz, DMSO-d$_6$): δ 8.30-8.24 (m, 3H), 8.04 (t, J=5.4 Hz, 1H), 7.89 (d, J=8.8 Hz, 2H), 7.59 (d, J=8.8 Hz, 2H), 7.31 (d, J=8.8 Hz, 1H), 6.67 (d, J=8.8 Hz, 2H), 6.12 (d, J=8.8 Hz, 1H), 4.55-4.41 (m, 2H), 3.99-3.96 (m, 1H), 3.42-3.39 (m, 2H), 2.46 (t, J=7 Hz, 2H), 1.81-1.76 (m, 1H), 1.57-1.53 (m, 2H), 0.95 (d, J=6.8 Hz, 3H), 0.86 (d, J=6.8 Hz, 3H). MS (M+1): 531.

Compound 17-9: (S)-3-(4-((1-(6-(2-fluoro-4-(trifluoromethyl)phenyl)pyridazin-3-yl)oxy)-3-methylbutan-2-yl)amino)benzamido)propanoic Acid

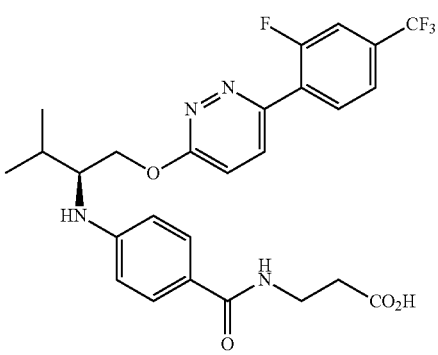

¹H NMR (400 MHz, CDCl$_3$): δ 7.58 (dd, J=8.8, 2.0 Hz, 3H), 7.43-7.51 (m, 1H), 6.82-7.03 (m, 1H), 6.54-6.66 (m, 3H), 4.44-4.93 (m, 2H), 3.74-3.84 (m, 1H), 3.71 (q, J=6.0 Hz, 2H), 2.66-2.75 (m, 2H), 2.00-2.15 (m, 1H), 1.09 (t, J=7.2 Hz, 3H), 1.06 (t, J=7.2 Hz, 3H). MS (M+1): 535.

Compound 17-8: (S)-3-(4-((1-((6-(benzofuran-2-yl)pyridazin-3-yl)oxy)-3-methylbutan-2-yl)amino)benzamido)propanoic Acid

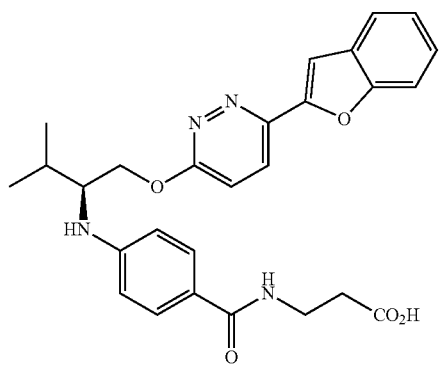 [SMILES: CC(C)[C@@H](COc1ccc(-c2cc3ccccc3o2)nn1)Nc1ccc(C(=O)NCCC(=O)O)cc1]

¹H NMR (400 MHz, CDCl$_3$): δ 7.26-7.97 (m, 9H), 6.58 (t, J=8.8 Hz, 2H), 4.48-4.82 (m, 2H), 3.67 (d, J=5.4 Hz, 4H), 2.62-2.72 (m, 2H), 0.99-1.11 (m, 6H). MS (M+1): 489.

Compound 17-10: (S)-3-(4-((1-((6-(4-fluorophenyl)pyridazin-3-yl)oxy)-3-methylbutan-2-yl)amino)benzamido)propanoic Acid

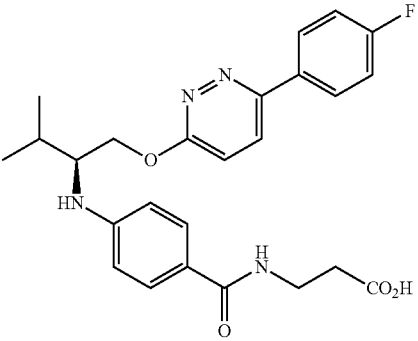 [SMILES: CC(C)[C@@H](COc1ccc(-c2ccc(F)cc2)nn1)Nc1ccc(C(=O)NCCC(=O)O)cc1]

¹H NMR (400 MHz, CDCl$_3$): δ 7.85-8.01 (m, 2H), 7.67 (s, 1H), 7.55 (d, J=8.8 Hz, 2H), 7.09-7.20 (m, 2H), 6.93 (d, J=9.3 Hz, 1H), 6.60 (s, 2H), 4.57-4.79 (m, 1H), 3.61-3.96 (m, 2H), 2.64-2.73 (m, 1H), 1.24 (s, 2H), 0.94-1.14 (m, 6H). MS (M+1): 467.

Compound 17-11: (S)-3-(4-((1-((6-(2,4-difluorophenyl)pyridazin-3-yl)oxy)-3-methylbutan-2-yl)amino)benzamido)propanoic Acid

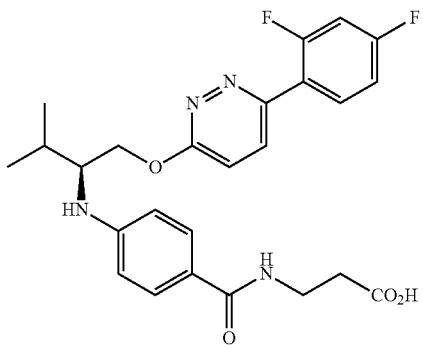 [SMILES: CC(C)[C@@H](COc1ccc(-c2ccc(F)cc2F)nn1)Nc1ccc(C(=O)NCCC(=O)O)cc1]

$^1$H NMR (400 MHz, CDCl$_3$): δ 7.98-8.13 (m, 1H), 7.76 (dd, J=9.3, 2.0 Hz, 1H), 7.50-7.60 (m, 2H), 6.87-7.10 (m, 3H), 6.52-6.65 (m, 2H), 4.56-4.83 (m, 1H), 3.59-3.87 (m, 3H), 2.58-2.75 (m, 2H), 1.24 (t, J=7.10 Hz, 2H), 0.95-1.13 (m, 6H). MS (M+1): 485.

Compound 17-12: (S)-3-(4-((1-((6-(4-(tert-buty)phenyl)pyridazin-3-yl)oxy)-3-methylbutan-2-yl)amino)benzamido)propanoic Acid

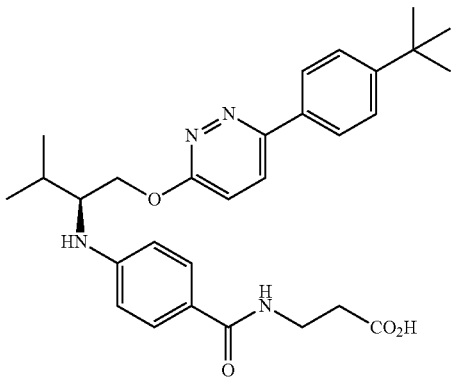 [SMILES: CC(C)[C@@H](COc1ccc(-c2ccc(C(C)(C)C)cc2)nn1)Nc1ccc(C(=O)NCCC(=O)O)cc1]

$^1$H NMR (400 MHz, CDCl$_3$): δ 7.89-7.95 (m, 2H), 7.82-7.89 (m, 1H), 7.74 (d, J=9.2 Hz, 1H), 7.55-7.61 (m, 2H), 7.45-7.55 (m, 3H), 6.94 (d, J=9.2 Hz, 1H), 6.70 (t, J=6.0 Hz, 1H), 6.56-6.64 (m, 2H), 4.77 (dd, J=11.2, 6.8 Hz, 1H), 4.63 (dd, J=11.2, 4.4 Hz, 1H), 3.74-3.82 (m, 2H), 3.70 (q, J=6.0 Hz, 2H), 2.66-2.72 (m, 2H), 1.99-2.15 (m, 1H), 1.38 (s, 9H), 1.00-1.10 (m, 6H). MS (M+1): 505.

Example 18: Synthesis of Compounds 18-1 to 18-9

Compound 18-1: (S)-3-(4-((1-((5-(benzofuran-2-yl)-6-methylpyridin-2-yl)oxy)hexan-2-yl)amino)benzamido)propanoic Acid

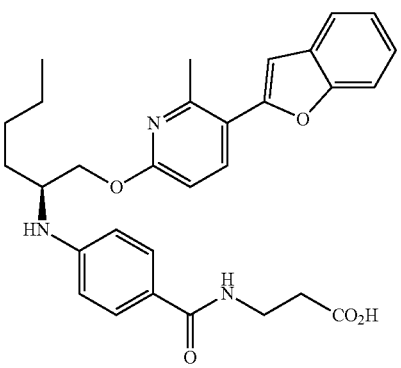 [SMILES: CCCC[C@@H](COc1ccc(-c2cc3ccccc3o2)c(C)n1)Nc1ccc(C(=O)NCCC(=O)O)cc1]

$^1$H NMR (400 MHz, CDCl$_3$): δ 7.99 (d, J=8.3 Hz, 1H), 7.53-7.62 (m, 3H), 7.48 (d, J=7.8 Hz, 1H), 7.19-7.31 (m, 2H), 6.80 (s, 1H), 6.64 (dd, J=8.3, 3.9 Hz, 3H), 4.48-4.57 (m, 1H), 4.25 (dd, J=10.8, 5.4 Hz, 1H), 3.74-3.83 (m, 1H), 3.67 (d, J=5.4 Hz, 2H), 2.69 (s, 3H), 2.66 (br. s., 2H), 1.69-1.82 (m, 1H), 1.57 (d, J=8.3 Hz, 1H), 1.30-1.46 (m, 4H), 0.81-0.92 (t, J=7.1 Hz, 3H). MS (M+1): 516. HPLC 99%.

Compound 18-2: (S)-3-(4-((1-((5-(2-chloro-4-(trifluoromethyl)phenyl)-6-methylpyridin-2-yl)oxy)hexan-2-yl)amino)benzamido)propanoic Acid

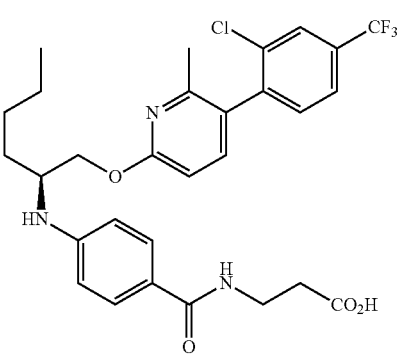 [SMILES: CCCC[C@@H](COc1ccc(-c2ccc(C(F)(F)F)cc2Cl)c(C)n1)Nc1ccc(C(=O)NCCC(=O)O)cc1]

$^1$H NMR (400 MHz, CDCl$_3$): δ 7.73 (d, J=1.5 Hz, 1H), 7.53-7.60 (m, 3H), 7.28-7.35 (m, 2H), 6.66-6.71 (m, 1H), 6.59-6.66 (m, 3H), 4.46-4.54 (m, 1H), 4.21-4.29 (m, 1H), 3.76-3.84 (m, 1H), 3.67 (q, J=5.9 Hz, 2H), 2.65 (t, J=5.6 Hz, 2H), 2.23 (s, 3H), 1.71-1.85 (m, 1H), 1.53-1.64 (m, 1H), 1.31-1.49 (m, 4H), 0.89 (t, J=7.3 Hz, 3H). MS (M+1): 578. HPLC 99%.

Compound 18-3: 3-(4-(((2S,3S)-1-((5-(2-chloro-4-(trifluoromethyl)phenyl)-6-methylpyridin-2-yl)oxy)-3-methylpentan-2-yl)amino)benzamido)propanoic Acid

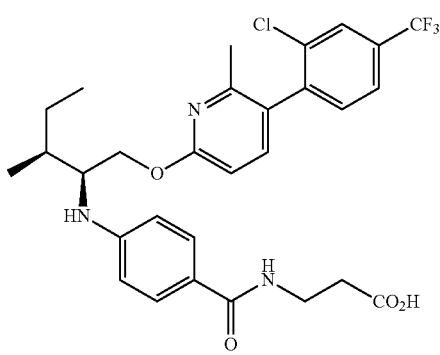 [SMILES: CC[C@H](C)[C@@H](COc1ccc(-c2ccc(C(F)(F)F)cc2Cl)c(C)n1)Nc1ccc(C(=O)NCCC(=O)O)cc1]

¹H NMR (400 MHz, CDCl₃): δ 7.72 (d, J=1.0 Hz, 1H), 7.52-7.60 (m, 3H), 7.26-7.35 (m, 2H), 6.70 (s, 1H), 6.54-6.63 (m, 3H), 4.47 (dd, J=10.8, 5.4 Hz, 1H), 4.33-4.43 (m, 1H), 3.62-3.76 (m, 3H), 2.65 (t, J=5.6 Hz, 2H), 2.22 (s, 3H), 1.78-1.88 (m, 1H), 1.59-1.71 (m, 1H), 1.23-1.32 (m, 1H), 1.00 (d, J=6.8 Hz, 3H), 0.95 (t, J=7.3 Hz, 3H). MS (M+1): 578. HPLC 94%.

Compound 18-5: 3-(4-(((2S,3S)-1-((5-(2,4-dichlorophenyl)-6-methylpyridin-2-yl)oxy)-3-methylpentan-2-yl)amino)benzamido)propanoic Acid

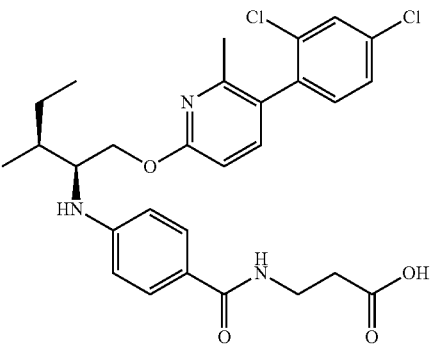

¹H NMR (400 MHz, CDCl₃): δ 7.56 (d, J=8.3 Hz, 2H), 7.47 (d, J=2.0 Hz, 1H), 7.25-7.30 (m, 2H), 7.11 (d, J=7.8 Hz, 1H), 6.68 (t, J=5.9 Hz, 1H), 6.53-6.61 (m, 3H), 4.43-4.53 (m, 1H), 4.33-4.42 (m, 1H), 3.63-3.74 (m, 3H), 2.65 (t, J=5.9 Hz, 2H), 2.22 (s, 3H), 1.87-1.79 (m, 1H), 1.71-1.62 (m, 1H), 1.24-1.30 (m, 1H), 1.00 (d, J=6.8 Hz, 3H), 0.95 (t, J=7.3 Hz, 3H). MS (M+1): 544. HPLC 95%.

Compound 18-4: 3-(4-(((2S,3S)-1-((5-(benzofuran-2-yl)-6-methylpyridin-2-yl)oxy)-3-methylpentan-2-yl)amino)benzamido)propanoic Acid

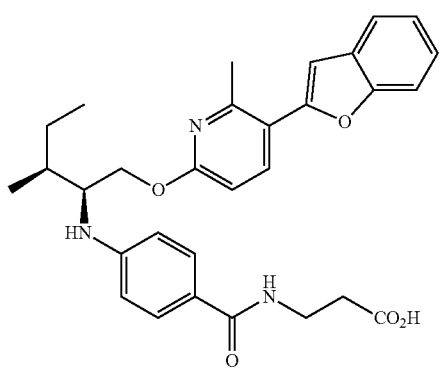 [SMILES: CC[C@H](C)[C@@H](COc1ccc(-c2cc3ccccc3o2)c(C)n1)Nc1ccc(C(=O)NCCC(=O)O)cc1]

¹H NMR (400 MHz, CDCl₃): δ 7.97 (d, J=8.3 Hz, 1H), 7.53-7.61 (m, 3H), 7.45-7.50 (m, 1H), 7.19-7.30 (m, 2H), 6.80 (s, 1H), 6.65 (s, 1H), 6.60 (dd, J=11.0, 8.6 Hz, 3H), 4.45-4.55 (m, 1H), 4.37-4.43 (m, 1H), 3.68 (dq, J=17.7, 5.7 Hz, 3H), 2.68 (s, 1H), 2.65 (t, J=5.6 Hz, 2H), 1.77-1.88 (m, 1H), 1.60-1.72 (m, 1H), 1.23-1.32 (m, 1H), 0.99 (d, J=6.8 Hz, 3H), 0.95 (t, J=7.3 Hz, 3H). MS (M+1): 516. HPLC 99%.

Compound 18-6: 3-(4-(((2S,3S)-1-((5-(2-fluoro-4-(trifluoromethyl)phenyl)-6-methylpyridin-2-yl)oxy)-3-methylpentan-2-yl)amino)benzamido)propanoic Acid

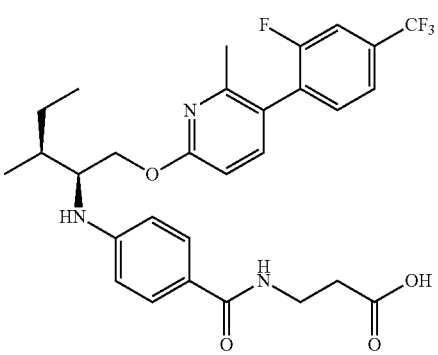 [SMILES: CC[C@H](C)[C@@H](COc1ccc(-c2ccc(C(F)(F)F)cc2F)c(C)n1)Nc1ccc(C(=O)NCCC(=O)O)cc1]

¹H NMR (400 MHz, CDCl₃): δ 7.56 (d, J=7.8 Hz, 2H), 7.45 (d, J=7.8 Hz, 1H), 7.30-7.41 (m, 3H), 6.75-6.67 (m, 1H), 6.58 (d, J=8.3 Hz, 3H), 4.44-4.51 (m, 1H), 4.36-4.42 (m, 1H), 3.63-3.74 (m, 3H), 2.69-2.60 (m, 2H), 2.31 (s, 3H), 1.78-1.87 (m, 1H), 1.66 (ddd, J=13.3, 7.5, 4.2 Hz, 1H), 1.24-1.29 (m, 1H), 0.99 (d, J=6.8 Hz, 3H), 0.94 (t, J=7.3 Hz, 3H). MS (M+1): 562. HPLC 97%.

Compound 18-7: (S)-3-(4-((1-((5-(2-chloro-4-(trifluoromethyl)phenyl)-6-methylpyridin-2-)oxy)-4-methylpentan-2-yl)amino)benzamido)propanoic Acid

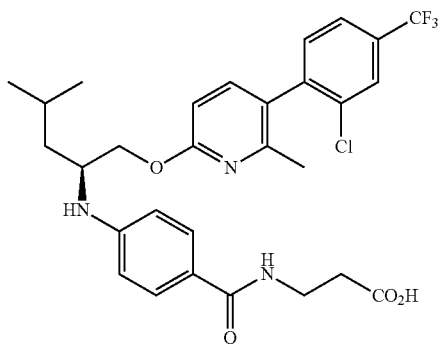 [SMILES: Cc1nc(OC[C@H](CC(C)C)Nc2ccc(C(=O)NCCC(=O)O)cc2)ccc1-c1ccc(C(F)(F)F)cc1Cl]

White solid. $^1$H-NMR ((400 MHz, DMSO-$d_6$): δ 8.04 (t, J=5.6 Hz, 1H), 8.01 (s, 1H), 7.80 (d, J=8.8 Hz, 1H), 7.59 (d, J=8.8 Hz, 3H), 7.51 (d, J=8.8 Hz, 1H), 6.73-6.70 (m, 3H), 6.07 (d, J=8.8 Hz, 1H), 4.40-4.36 (m, 1H), 4.13-4.08 (m, 1H), 3.90-3.89 (m, 1H), 2.46 (t, J=6.8 Hz, 2H), 2.19 (s, 3H), 1.80-1.75 (m, 1H), 1.54-1.51 (m, 2H), 0.94 (d, J=6.3 Hz, 3H), 0.83 (d, J=6.3 Hz, 3H). MS (M+1): 578.

Compound 18-8: (S)-3-(4-((1-((5-(2,4-dichlorophenyl)-6-methylpyridin-2-yl)oxy)-4-methylpentan-2-yl)amino)benzamido)propanoic Acid

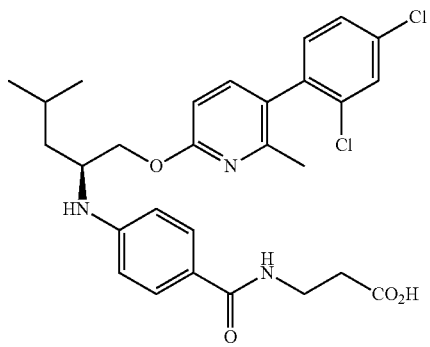 [SMILES: Cc1nc(OC[C@H](CC(C)C)Nc2ccc(C(=O)NCCC(=O)O)cc2)ccc1-c1ccc(Cl)cc1Cl]

White solid. $^1$H-NMR ((400 MHz, DMSO-$d_6$): δ 8.04 (t, J=5.6 Hz, 1H), 7.75 (s, 1H), 7.59 (d, J=8.8 Hz, 2H), 7.52-7.44 (m, 2H), 7.39-7.36 (m, 1H), 6.72-6.68 (m, 3H), 6.07 (d, J=8.8 Hz, 1H), 4.40-4.35 (m, 1H), 4.13-4.05 (m, 1H), 3.90-3.88 (m, 1H), 2.46 (t, J=6.8 Hz, 2H), 2.18 (s, 3H), 1.81-1.75 (m, 1H), 1.53-1.50 (m, 2H), 0.94 (d, J=6.3 Hz, 3H), 0.83 (d, J=6.3 Hz, 3H). MS (M+1): 544.

Compound 18-9: (S)-3-(4-((1-((5-(benzofuran-2-yl)-6-methylpyridin-2-yl)oxy)-4-methylpentan-2-yl)amino)benzamido)propanoic Acid

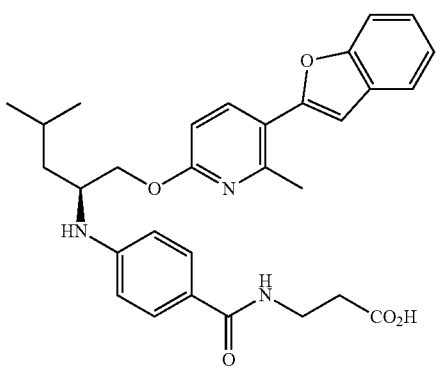 [SMILES: Cc1nc(OC[C@H](CC(C)C)Nc2ccc(C(=O)NCCC(=O)O)cc2)ccc1-c1cc2ccccc2o1]

White solid. $^1$H-NMR (400 MHz, DMSO-$d_6$): δ 8.10-8.04 (m, 2H), 7.68 (d, J=7.8 Hz, 1H), 7.61 (d, J=8.8 Hz, 3H), 7.34-7.25 (m, 2H), 7.16 (s, 1H), 6.78 (d, J=7.8 Hz, 1H), 6.72 (d, J=8.8 Hz, 2H), 6.08 (d, J=8.8 Hz, 1H), 4.45-4.41 (m, 1H), 4.15-4.11 (m, 1H), 3.91-3.86 (m, 1H), 2.47 (t, J=6.8 Hz, 2H), 1.98 (s, 3H), 1.81-1.75 (m, 1H), 1.54-1.50 (m, 2H), 0.94 (d, J=6.3 Hz, 3H), 0.82 (d, J=6.3 Hz, 3H). MS (M+1): 516.

Reaction Scheme IV illustrates the general procedures that can be used to synthesize the following compounds of the formula (I) of the present disclosure.

Reaction Scheme IV

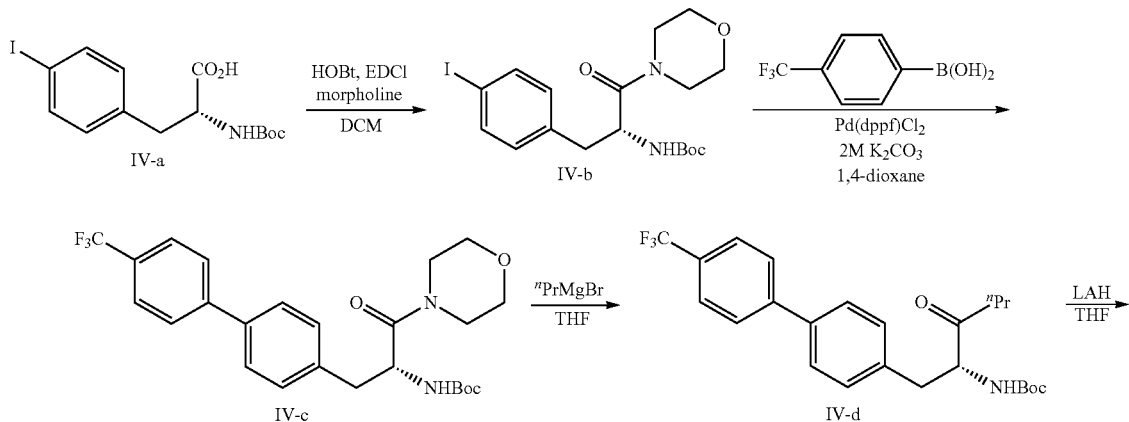

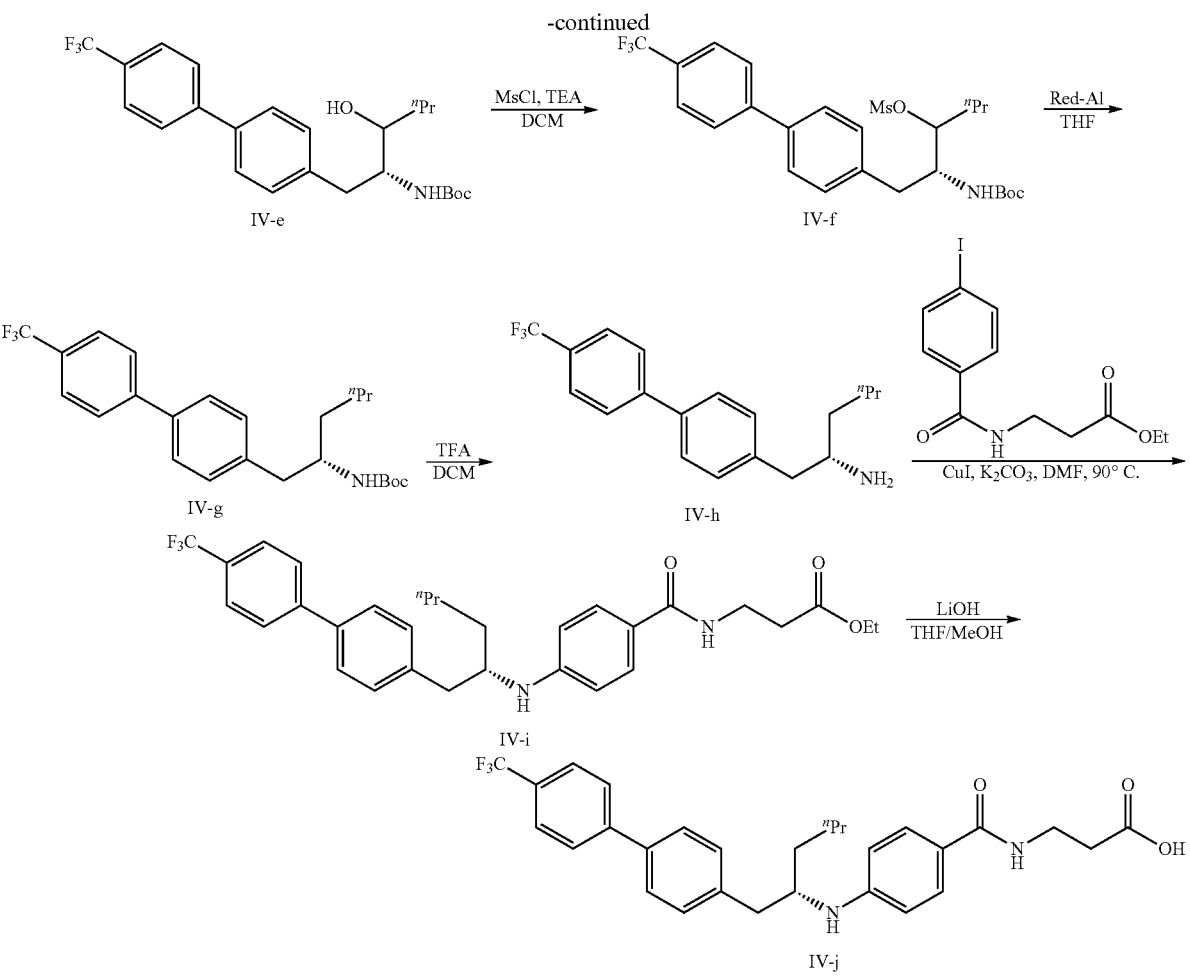

tert-butyl (R)-(3-(4-iodophenyl)-1-morpholino-1-oxopropan-2-yl)carbamate

Step I: Amide Formation

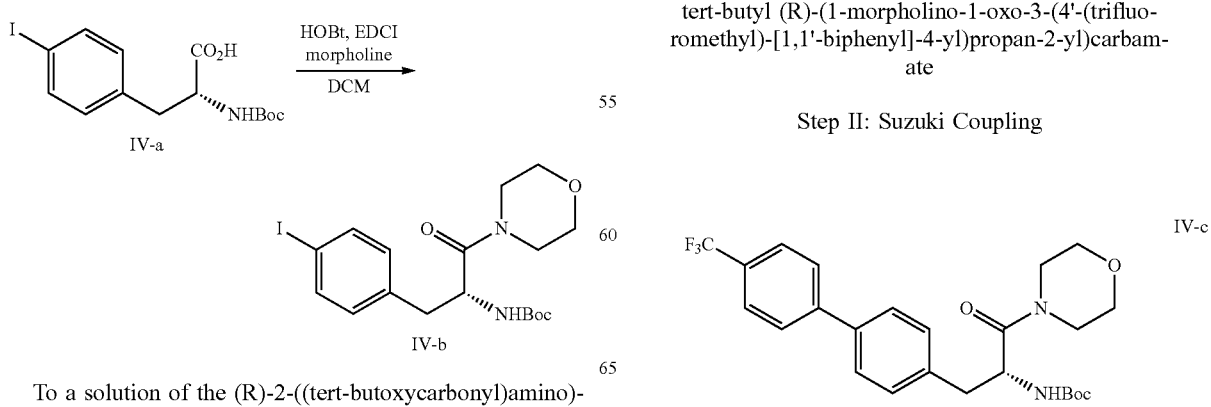

To a solution of the (R)-2-((tert-butoxycarbonyl)amino)-3-(4-iodophenyl)propanoic acid (20 g, 51.1 mmol) in DCM (200 mL) was combined with morpholine (8.9 ml, 102.2 mmol), EDC.HCl (11.8 g, 102.2 mmol), HOBt (8.30 g, 61.3 mmol), and triethylamine (14.2 mL, 102.2 mmol). The resulting solution was stirred overnight at room temperature. The reaction was then quenched by the addition of water (100 mL). The resulting mixture was washed with 1M HCl (2×100 mL) and saturated NaHCO₃ (1×100 mL), then dried over anhydrous MgSO₄ and concentrated in vacuo and purified by flash column chromatography on silica gel to yield tert-butyl (R)-(3-(4-iodophenyl)-1-morpholino-1-oxopropan-2-yl)carbamate (20.5 g, 87%) as a white solid.

tert-butyl (R)-(1-morpholino-1-oxo-3-(4'-(trifluoromethyl)-[1,1'-biphenyl]-4-yl)propan-2-yl)carbamate Step II: Suzuki Coupling To a degassing solution of tert-butyl (R)-(3-(4-iodophenyl)-1-morpholino-1-oxopropan-2-yl)carbamate (18.3 g, 42.2 mmol), (4-(trifluoromethyl)phenyl)boronic acid (9.60 g, 50.6 mmol), Pd(dppf)Cl$_2$ (3.1 g, 4.2 mmol), and 2M K$_2$CO$_3$ (65 mL, 126.7 mmol) in 1,4-dioxane (200 mL) was heated at 90° C. for 18 h. The reaction mixture was cooled, poured into water, and extracted with EtOAc. The combined organic layers were dried over MgSO$_4$ and concentrated in vacuo. Purification of the residue by silica gel chromatography to afford tert-butyl (R)-(1-morpholino-1-oxo-3-(4'-(trifluoromethyl)-[1,1'-biphenyl]-4-yl)propan-2-yl)carbamate (18 g, 90%).

tert-butyl (R)-(3-oxo-1-(4'-(trifluoromethyl)-[1,1'-biphenyl]-4-yl)hexan-2-yl)carbamate Step III: Formation of Tertibutyl

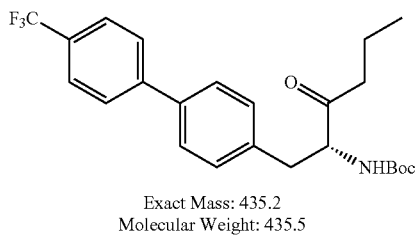

Exact Mass: 435.2
Molecular Weight: 435.5

To a stirred solution of amide (R)-(1-oxo-1-(piperidin-1-yl)-3-(4'-(trifluoromethyl) [1,1'-biphenyl]-4-yl)propan-2-yl)carbamate (5 g, 10.4 mmol) in THF (60 mL), was added dropwise a solution of n-Propylmagnesium chloride (26 mL, 52.2 mmol, 2 M in THF) at 0° C. The mixture was stirred for 1 h. at 0° C. and 1 h at rt. Then an aqueous solution of HCl (1 M, 100 mL) was carefully added at 0° C. The aqueous layer was extracted with EA (3×100 mL). The organic phases were combined, washed with water (100 mL), brine (100 mL), dried over MgSO$_4$, filtered and concentrated under vacuum. The residue was purified by flash column chromatography on silica gel to give tert-butyl (R)-(3-oxo-1-(4'-(trifluoromethyl)-[1,1'-biphenyl]-4-yl)hexan-2-yl)carbamate (3.3 g, 73%).

tert-butyl ((2R)-3-hydroxy-1-(4'-(trifluoromethyl)-[1,1'-biphenyl]-4-yl)hexan-2-yl)carbamate Step IV: Reduction

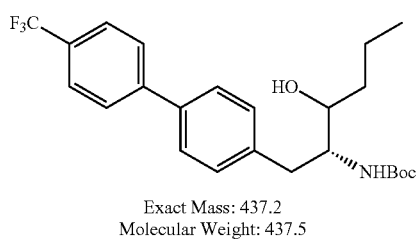

Exact Mass: 437.2
Molecular Weight: 437.5

To a stirred solution of tert-butyl (R)-(3-oxo-1-(4'-(trifluoromethyl)-[1,1'-biphenyl]-4-yl)hexan-2-yl)carbamate (2.0 g, 4.45 mmol) in THF (20 mL), was added LAH (0.17 g, 4.45 mmol) at 0° C. The mixture was stirred for 2 h at 0° C. The cooled reaction mixture was slowly quenched with saturated sodium sulfate solution (0.3 mL) and 1M-NaOH (0.3 mL). The precipitated solids were filtered off and washed with DCM (50 mL). The filtrate was concentrated under vacuum. The residue was purified by flash column chromatography on silica gel to give tert-butyl ((2R)-3-hydroxy-1-(4'-(trifluoromethyl)-[1,1'-biphenyl]-4-yl)hexan-2-yl)carbamate (1.33 g, 68%).

(2R)-2-((tert-butoxycarbonyl)amino)-1-(4'-(trifluoromethyl)-[1,1'-biphenyl]-4-yl)hexan-3-yl methanesulfonate Step V: Mesylation

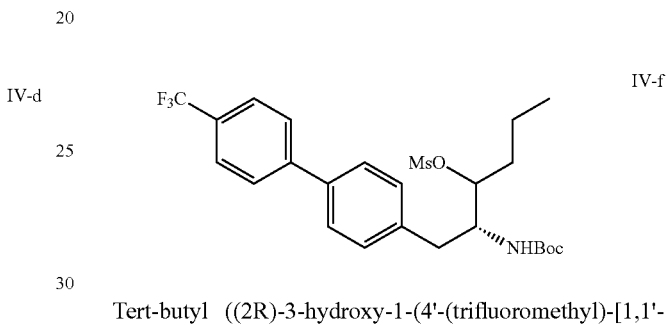

Tert-butyl ((2R)-3-hydroxy-1-(4'-(trifluoromethyl)-[1,1'-biphenyl]-4-yl) hexan-2-yl)carbamate (0.68 g, 1.7 mmol) was dissolved in anhydrous DCM (5 mL) and Et$_3$N (0.47 mL, 3.3 mmol) was added to the solution. A solution of methanesulfonyl chloride (0.14 mL, 1.8 mmol) was added drop wised to the mixture. The reaction mixture was stirred for 3 h. The mixture was poured to the cold water and white solid was precipitated to give crude product (2R)-2-((tert-butoxycarbonyl)amino)-1-(4'-(trifluoromethyl)-[1,1'-biphenyl]-4-yl)hexan-3-yl methanesulfonate (0.85 g, in qualitatively yield), which was of suitable purity to use directly in next reaction.

tert-butyl (S)-(1-(4'-(trifluoromethyl)-[1,1'-biphenyl]-4-yl)hexan-2-yl)carbamate Step VI: Reductive Elimination

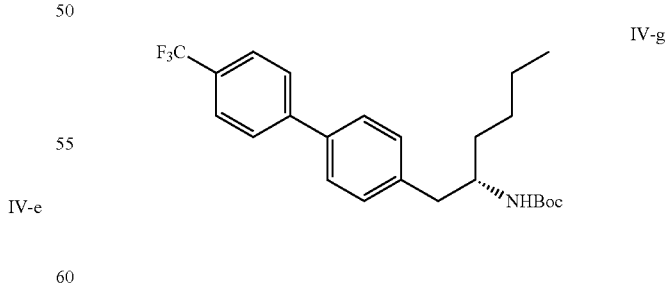

(2R)-2-((tert-butoxycarbonyl)amino)-1-(4'-(trifluoromethyl)-[1,1'-biphenyl]-4-yl)hexan-3-yl methanesulfonate (0.8 g, 1.64 mmol) was dissolved in anhydrous THF (10 mL), was added Red-Al (1.4 mL, 4.92 mmol, 3.5 M in THF) at 0° C. The mixture was stirred for 3 h at 0° C. The cooled reaction mixture was slowly quenched with saturated sodium sulfate solution (0.3 mL) and 1M-NaOH (0.3 mL). The precipitated solids were filtered off and washed with DCM (50 mL). The filtrate was concentrated under vacuum. The residue was purified by flash column chromatography on silica gel to give tert-butyl (S)-(1-(4'-(trifluoromethyl)-[1,1'-biphenyl]-4-yl)hexan-2-yl) carbamate (0.22 g, 33%).

(S)-1-(4'-(trifluoromethyl)-[1,1'-biphenyl]-4-yl)hexan-2-amine

Step VII: Deprotection

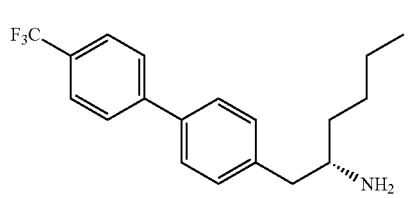

IV-h

Tert-butyl (S)-(1-(4'-(trifluoromethyl)-[1,1'-biphenyl]-4-yl)hexan-2-yl) carbamate (235 mg, 0.56 mmol) was suspended in trifluoroacetic acid (1.3 mL, 16.86 mmol) in anhydrous dichloromethane (5 mL) at room temperature for 2 h. After reaction, excess trifluoroacetic acid was neutralized by dropwise addition of $Na_2CO_{3(aq)}$ until pH=10. Then it was extracted with $CH_2Cl_2$. The combined organic layer was dried with anhydrous $MgSO_4$ and concentrated in vacuo to give crude product. It was further purified by silica gel flash column chromatography using dichloromethane and methanol as eluant to give (S)-1-(4'-(trifluoromethyl)-[1,1'-biphenyl]-4-yl) hexan-2-amine (220 mg, in qualitatively yield).

ethyl (S)-3-(4-((1-(4'-(trifluoromethyl)-[1,1'-biphenyl]-4-yl)hexan-2-yl)amino)benzamido)propanoate Step VIII: Ullmann Reaction

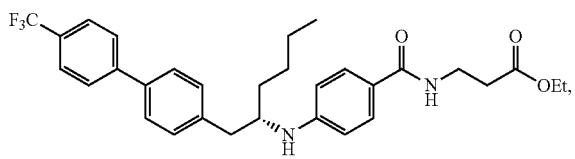

IV-i

A seal tube was charged with CuI (13 mg, 0.068 mmol), $K_2CO_3$ (207 mg, 1.5 mmol), (S)-1-(4'-(trifluoromethyl)-[1,1'-biphenyl]-4-yl) hexan-2-amine (220 mg, 0.68 mmol), ethyl 3-(4-iodobenzamido)propanoate (260 mg, 0.75 mmol) and DMF (6 mL). The seal tube was fitted with a septum and purged with nitrogen. Next, the test tube was capped and stirred in an oil bath at 90° C. for 24 h. Cool the mixture to ambient temperature, dilute with EtOAc, filter through a pad of silica gel or through Celite washing with EtOAc, and evaporate the solvent to obtain the crude mixture. Alternatively, partition the reaction mixture between brine or saturated aqueous $NaHCO_3$ and EtOAc, dry the organic layer over $Na_2SO_4$, and concentrate to obtain the crude mixture. The residue was purified by silica gel chromatography to afford ethyl (S)-3-(4-((1-(4'-(trifluoromethyl)-[1,1'-biphenyl]-4-yl)hexan-2-yl)amino)benzamido)propanoate (39 mg, 11%).

(S)-5-oxo-5-(4-((1-(4'-(trifluoromethyl)-[1,1'-biphenyl]-4-yl)hexan-2-yl)amino)phenyl)pentanoic acid Step IX. Hydrolysis

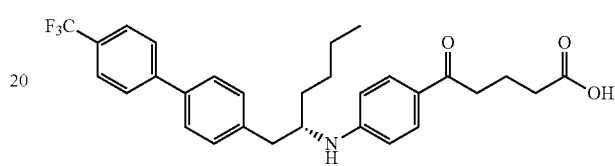

IV-j

Ester Compound IV-i (50 mg, 0.09 mmol) was dissolved in MeOH (2 mL)/THF (2 mL) followed by addition of LiOH (2.0 M, 0.5 mL). The reaction mixture was stirred at room temperature for overnight. The reaction was monitored by TLC. With completion of the reaction, the solvent was removed by rotary evaporation and HCl (2.0 M, 5 mL) was added to the mixture. The aqueous layer was extracted with EA (3×100 mL). The organic phases were combined, dried over $Na_2SO_4$, filtered and concentrated under vacuum to give the corresponding acid IV-j, (S)-3-(4-(1-(4'-(trifluoromethyl)biphenyl-4-yl)hexan-2-ylamino)benzamido)propanoic acid (42 mg, 88%). Exact Mass: 512.2; m/z: 512.23 (100.0%), 513.23 (32.6%), 514.24 (4.9%).

Compound 19-1: (R)-3-(4-((1-(4'-(trifluoromethyl)-[1,1'-biphenyl]-4-yl)hexan-2-yl)amino)benzamido)propanoic Acid

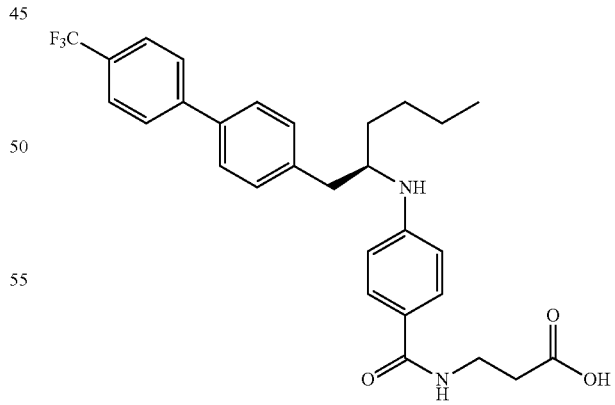

$^1$H NMR (400 MHz, DMSO-$d_6$): δ 8.01 (t, J=5.6 Hz, 1H), 7.84-7.88 (m, J=8.3 Hz, 2H), 7.76-7.80 (m, J=8.3 Hz, 2H), 7.64 (d, J=8.3 Hz, 2H), 7.56-7.60 (m, J=8.8 Hz, 2H), 7.33-7.39 (m, J=8.3 Hz, 2H), 6.58 (d, J=8.8 Hz, 2H), 6.04 (d, J=8.8 Hz, 1H), 3.61-3.72 (m, 1H), 3.36-3.43 (m, 2H), 2.75-2.86 (m, 2H), 2.46 (t, J=7.3 Hz, 2H), 1.47-1.56 (m,

1H), 1.36-1.47 (m, 2H), 1.21-1.31 (m, 3H), 0.82 (t, J=7.1 Hz, 3H). MS (M+1): 513.

Compound 19-2: (S)-3-(4-((1-(2',4'-dichloro-[1,1'-biphenyl]-4-yl)propan-2-yl)amino)benzamido)propanoic Acid

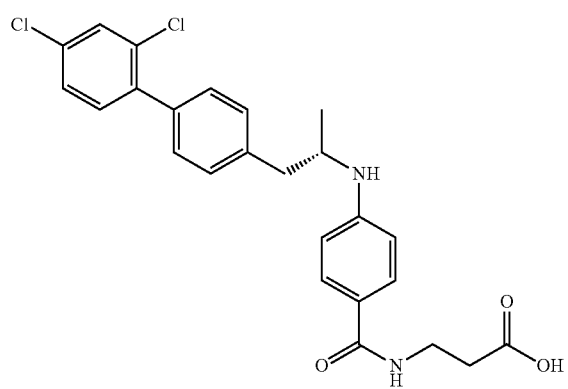 [SMILES: C[C@@H](Cc1ccc(-c2ccc(Cl)cc2Cl)cc1)Nc1ccc(C(=O)NCCC(=O)O)cc1]

$^1$H NMR (400 MHz, DMSO-d$_6$): δ 8.04 (d, J=2.4 Hz, 1H), 7.57-7.63 (m, 2H), 7.48 (dd, J=8.3, 2.0 Hz, 1H), 7.41 (d, J=8.3 Hz, 1H), 7.35 (s, 2H), 7.15-7.31 (m, 2H), 6.59 (t, J=9.3 Hz, 2H), 3.66-3.83 (m, 1H), 3.40 (d, J=6.4 Hz, 2H), 2.82-2.95 (m, 1H), 2.57-2.73 (m, 1H), 2.44-2.49 (m, 2H), 1.04-1.15 (m, 3H). MS (M+1): 471.

Compound 19-3: (S)-3-(4-((1-(4'-(trifluoromethyl)-[1,1'-biphenyl]-4-yl)propan-2-yl)amino)benzamido) propanoic Acid

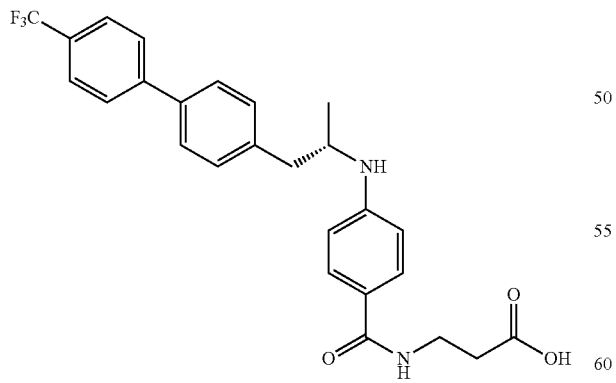

$^1$H NMR (400 MHz, DMSO-d$_6$): δ 7.86-7.89 (m, J=8.3 Hz, 2H), 7.77-7.81 (m, J=8.3 Hz, 2H), 7.66 (d, J=8.3 Hz, 2H), 7.59-7.63 (m, J=8.8 Hz, 2H), 7.38 (d, J=8.3 Hz, 2H), 6.57-6.64 (m, J=8.8 Hz, 2H), 3.74-3.83 (m, 1H), 3.43 (br. s., 2H), 2.91 (dd, J=13.2, 5.9 Hz, 1H), 2.71 (dd, J=13.7, 6.8 Hz, 1H), 2.44-2.49 (m, 2H), 1.12 (d, J=6.4 Hz, 3H). MS (M+1): 471.

Compound 19-4: (S)-3-(4-((1-(4'-(tert-butyl)-[1,1'-biphenyl]-4-yl)propan-2-yl)amino)benzamido)propanoic Acid

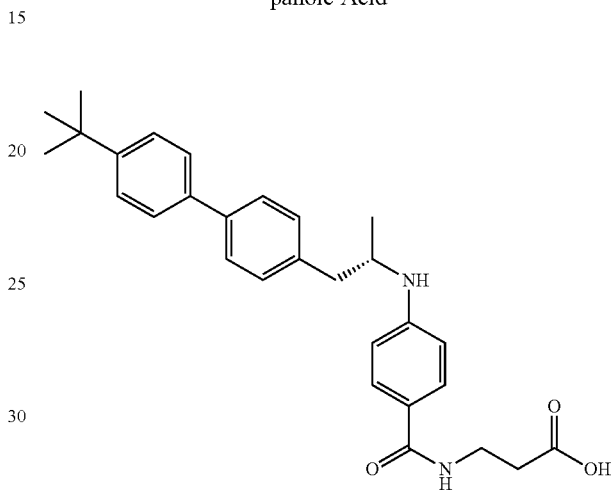

$^1$H NMR (400 MHz, DMSO-d$_6$): δ 7.60 (d, J=8.8 Hz, 2H), 7.55 (dd, J=8.3, 2.4 Hz, 4H), 7.45 (d, J=8.3 Hz, 2H), 7.31 (d, J=8.3 Hz, 2H), 6.60 (d, J=8.3 Hz, 2H), 3.65-3.35 (m, 1H), 3.40 (d, J=5.9 Hz, 2H), 2.75-2.65 (m, 1H), 2.69 (d, J=6.8 Hz, 1H), 2.45-2.48 (m, 2H), 1.31 (s, 9H), 1.11 (d, J=6.4 Hz, 3H). MS (M+1): 459.

Compound 19-5: (R)-3-(4-((1-(4-(benzofuran-2-yl)phenyl)-4-methylpentan-2-yl)amino)benzamido) propanoic Acid

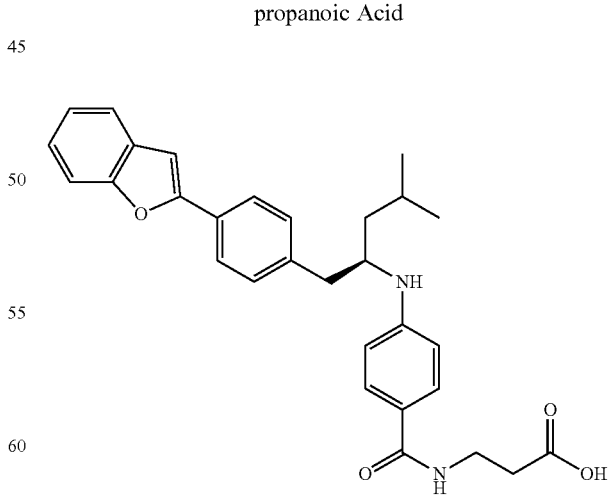

$^1$H NMR (400 MHz, DMSO-d$_6$): δ 8.04 (s, 1H), 7.82 (d, J=8.3 Hz, 2H), 7.64 (dd, J=7.8, 1.5 Hz, 1H), 7.58 (d, J=8.8 Hz, 2H), 7.25-7.37 (m, 5H), 6.60 (d, J=8.8 Hz, 2H), 3.75-3.65 (m, 1H), 3.39 (d, J=5.4 Hz, 2H), 2.78 (s, 2H), 2.46 (t,

J=7.1 Hz, 2H), 1.22-1.31 (m, 3H), 0.88 (d, J=6.4 Hz, 3H), 0.78 (d, J=6.4 Hz, 3H). MS (M+1): 485.

Compound 19-6: (R)-3-(4-((1-(4-(benzofuran-2-yl)phenyl)heptan-2-yl)amino)benzamido)propanoic Acid

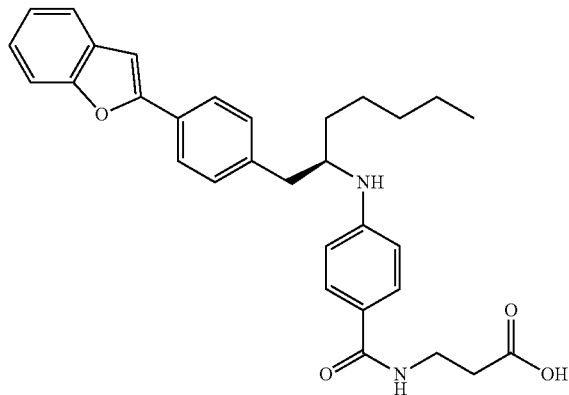 [SMILES: CCCCC[C@H](Cc1ccc(-c2cc3ccccc3o2)cc1)Nc1ccc(C(=O)NCCC(=O)O)cc1]

$^1$H NMR (400 MHz, DMSO-d$_6$): δ 8.04 (s, 1H), 7.81 (d, J=7.8 Hz, 2H), 7.56-7.65 (m, 5H), 7.34-7.36 (m, 3H), 7.23-7.32 (m, 3H), 6.58 (d, J=8.8 Hz, 2H), 3.67 (br. s., 1H), 3.38-3.41 (m, 2H), 2.79 (t, J=5.6 Hz, 2H), 2.46 (t, J=7.1 Hz, 2H), 1.47 (br. s., 1H), 1.38-1.44 (m, 2H), 1.17-1.26 (m, 6H), 0.78-0.85 (m, 4H). MS (M+1): 499.

Compound 19-7: (R)-3-(4-((1-(4'-(tert-butyl)-[1,1'-biphenyl]-4-yl)hexan-2-yl)amino)benzamido)propanoic Acid

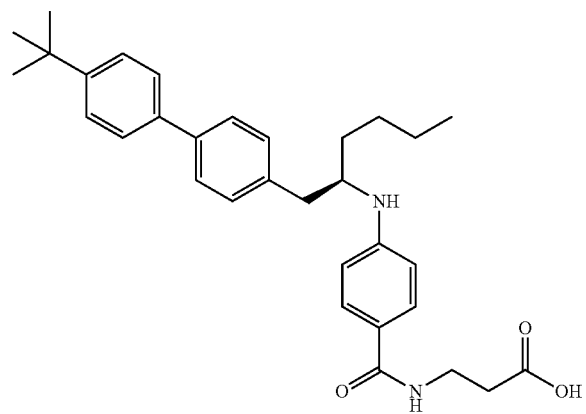 [SMILES: CCCC[C@H](Cc1ccc(-c2ccc(C(C)(C)C)cc2)cc1)Nc1ccc(C(=O)NCCC(=O)O)cc1]

$^1$H NMR (400 MHz, DMSO-d$_6$): δ 7.52-7.59 (m, 6H), 7.43-7.46 (m, 2H), 7.29 (d, J=8.3 Hz, 2H), 6.58 (d, J=8.8 Hz, 2H), 3.68-3.60 (m, 1H), 3.42-3.36 (m, 2H), 1.82-1.72 (m, 2H), 2.46 (s, 2H), 1.30-1.31 (m, 9H), 1.52-1.36 (m, 3H), 1.22-1.26 (m, 3H), 0.80-0.85 (m, 3H). MS (M+1): 501.

Compound 19-8: (R)-3-(4-((1-(4'-(tert-butyl)-[1,1'-biphenyl]-4-yl)-4-methylpentan-2-yl)amino)benzamido)propanoic Acid

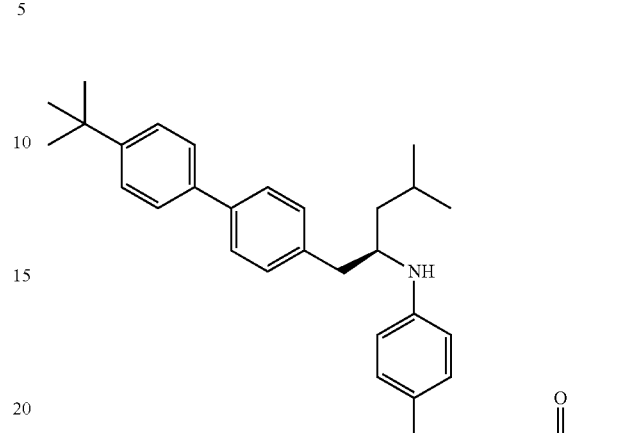

$^1$H NMR (400 MHz, DMSO-d$_6$): δ 7.52-7.60 (m, 7H), 7.45 (d, J=8.8 Hz, 2H), 7.27 (d, J=8.3 Hz, 2H), 6.60 (d, J=8.8 Hz, 2H), 3.40 (d, J=5.4 Hz, 2H), 2.76 (s, 2H), 2.46 (t, J=7.1 Hz, 2H), 1.74-1.83 (m, 1H), 1.45-1.35 (m, 1H), 1.31 (s, 9H), 0.88 (d, J=6.8 Hz, 3H), 0.78 (d, J=6.4 Hz, 3H). MS (M+1): 501.

Compound 19-9: (S)-3-(4-((1-(4'-(trifluoromethoxy)-[1,1'-biphenyl]-4-yl)heptan-2-yl)amino)benzamido)propanoic Acid

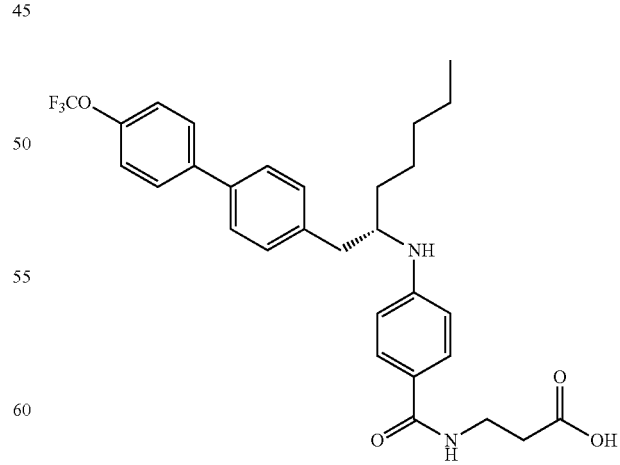

$^1$H NMR (400 MHz, DMSO-d$_6$): δ 7.74 (d, J=8.8 Hz, 2H), 7.58 (dd, J=8.3, 5.9 Hz, 4H), 7.41 (d, J=8.3 Hz, 2H), 7.32 (d, J=7.8 Hz, 2H), 6.59 (d, J=8.8 Hz, 2H), 6.03 (d, J=8.3 Hz,

1H), 3.60-3.69 (m, 1H), 3.41 (br. s., 2H), 2.72-2.85 (m, 2H), 2.43-2.48 (m, 2H), 1.36-1.52 (m, 3H), 1.21-1.34 (m, 5H), 0.81 (t, J=6.6 Hz, 3H). MS (M+1): 543.

Compound 19-10: (S)-3-(4-((5-methyl-1-(4'-(trifluoromethyl)-[1,1'-biphenyl]-4-yl)hexan-2-yl)amino)benzamido)propanoic Acid

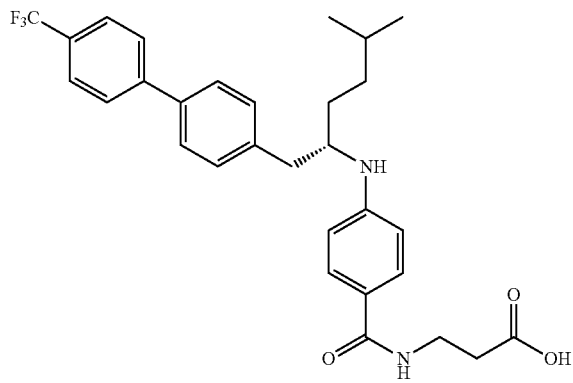 [SMILES: CC(C)CC[C@@H](Cc1ccc(-c2ccc(C(F)(F)F)cc2)cc1)Nc1ccc(C(=O)NCCC(=O)O)cc1]

$^1$H NMR (400 MHz, DMSO-d$_6$): δ 7.81-7.88 (m, 4H), 7.78 (t, J=7.6 Hz, 2H), 7.55-7.67 (m, 6H), 3.41-3.47 (m, 5H), 2.79 (br. s., 1H), 2.44-2.47 (m, 1H), 1.38-1.57 (m, 3H), 1.22 (br. s., 2H), 0.81 (d, J=6.8 Hz, 6H). MS (M+1): 527.

Compound 19-11: (S)-3-(4-((1-(4-(benzofuran-2-yl)phenyl)hexan-2-yl)amino)benzamido)propanoic Acid

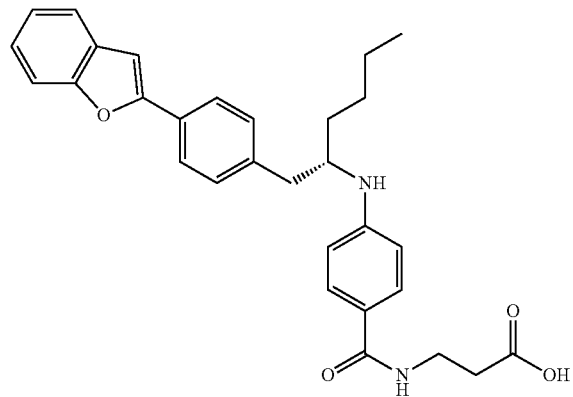 [SMILES: CCCC[C@@H](Cc1ccc(-c2cc3ccccc3o2)cc1)Nc1ccc(C(=O)NCCC(=O)O)cc1]

$^1$H NMR (400 MHz, DMSO-d$_6$): δ 7.99-8.06 (m, 3H), 7.76-7.94 (m, 2H), 7.54-7.68 (m, 3H), 7.20-7.44 (m, 4H), 6.58 (d, J=8.3 Hz, 1H), 3.35-3.42 (m, 5H), 2.79 (br. s., 1H), 2.41-2.48 (m, 1H), 1.61-1.79 (m, 1H), 1.32-1.61 (m, 3H), 1.19-1.32 (m, 4H), 0.77-0.89 (m, 3H); MS (M+1): 485.

Compound 19-12: (S)-3-(4-((1-(4'-(tert-butyl)-[1,1'-biphenyl]-4-yl)-3-propoxypropan-2-yl)amino)benzamido)propanoic Acid

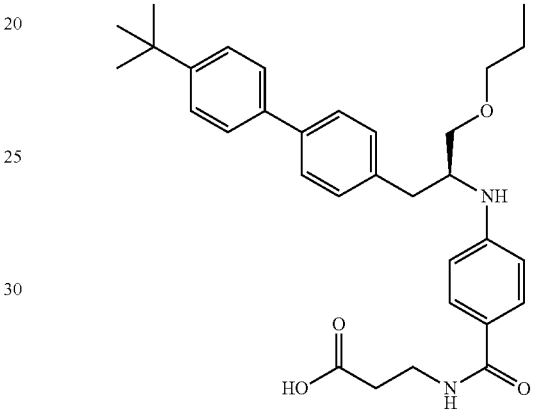

$^1$H NMR (400 MHz, Acetone-d$_6$): δ 7.68 (d, J=8.0 Hz, 2H), 7.52-7.61 (m, 4H), 7.48 (d, J=8.0 Hz, 2H), 7.36 (d, J=8.0 Hz, 2H), 6.71 (d, J=8.0 Hz, 2H), 3.85-4.01 (m, 1H), 3.55-3.63 (m, 2H), 3.47 (dd, J=4.9, 2.4 Hz, 2H), 3.36-3.43 (m, 2H), 3.02 (d, J=6.4 Hz, 1H), 2.93 (d, J=6.8 Hz, 1H), 2.60 (t, J=6.8 Hz, 2H), 1.53-1.64 (m, 2H), 1.34 (s, 9H), 0.93 (t, J=7.3 Hz, 3H). MS (M+1): 517.

Compound 19-13: (S)-3-(4-((1-propoxy-3-(4'-(trifluoromethyl)-[1,1'-biphenyl]-4-yl)propan-2-yl)amino)benzamido)propanoic Acid

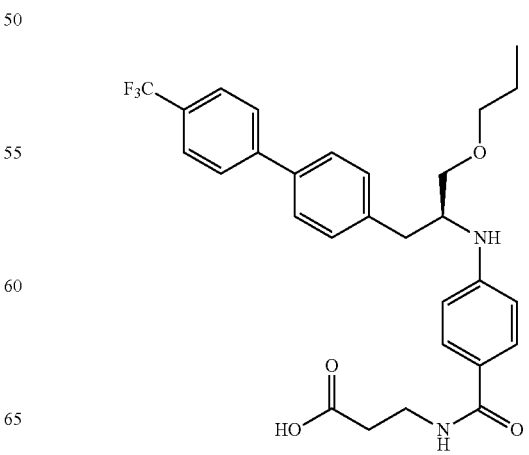

¹H NMR (400 MHz, Acetone-d₆): δ 7.86 (d, J=8.0 Hz, 2H), 7.77 (d, J=8.0 Hz, 2H), 7.68 (d, J=8.0 Hz, 2H), 7.65 (d, J=8.0 Hz, 2H), 7.43 (d, J=8.0 Hz, 2H), 6.71 (d, J=8.0 Hz, 2H), 3.89-4.01 (m, 1H), 3.59 (t, J=8.0 Hz, 2H), 3.44-3.51 (m, 2H), 3.37-3.43 (t, J=8.0 Hz, 2H), 3.04-3.11 (m, 1H), 2.91-2.98 (m, 1H), 2.61 (t, J=6.6 Hz, 2H), 1.52-1.65 (m, 2H), 0.93 (t, J=7.3 Hz, 3H). MS (M+1): 528.

Compound 19-14: (S)-3-(4-((1-propoxy-3-(4'-(trifluoromethoxy)-[1,1'-biphenyl]-4-yl)propan-2-yl)amino)benzamido)propanoic Acid

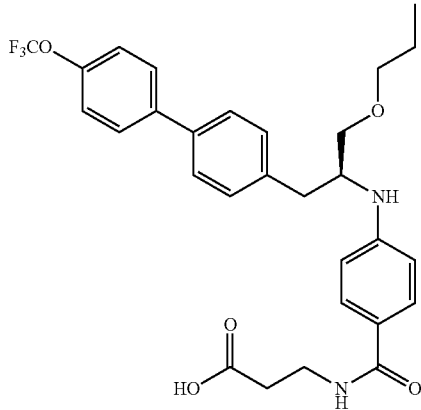 [SMILES: CCCOC[C@H](Cc1ccc(-c2ccc(OC(F)(F)F)cc2)cc1)Nc1ccc(C(=O)NCCC(=O)O)cc1]

¹H NMR (400 MHz, Acetone-d₆): δ 7.75 (d, J=8.0 Hz, 2H), 7.68 (d, J=8.0 Hz, 2H), 7.59 (d, J=8.0 Hz, 2H), 7.36-7.44 (m, 4H), 6.70 (d, J=8.0 Hz, 2H), 3.88-4.00 (m, 1H), 3.59 (t, J=6.8 Hz, 2H), 3.43-3.51 (m, 2H), 3.37-3.43 (m, 2H), 3.02-3.10 (m, 1H), 2.89-2.97 (m, 1H), 2.61 (t, J=6.8 Hz, 2H), 1.52-1.63 (m, 2H), 0.93 (t, J=7.6 Hz, 3H). MS (M+1): 545.

Compound 19-15: (S)-3-(4-((1-(2',4'-dichloro-[1,1'-biphenyl]-4-yl)-3-propoxypropan-2-yl)amino)benzamido)propanoic Acid

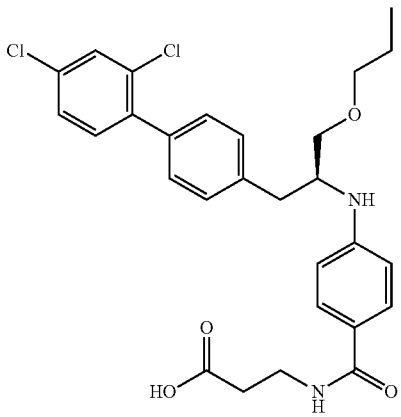 [SMILES: CCCOC[C@H](Cc1ccc(-c2ccc(Cl)cc2Cl)cc1)Nc1ccc(C(=O)NCCC(=O)O)cc1]

¹H NMR (400 MHz, Acetone-d₆): δ 7.87 (d, J=8.0 Hz, 2H), 7.56 (d, J=4.0 Hz, 1H), 7.33-7.45 (m, 6H), 6.69 (d, J=8.0 Hz, 2H), 3.95 (m, 1H), 3.59 (t, J=6.8 Hz, 2H), 3.44-3.52 (m, 2H), 3.38-3.44 (m, 2H), 3.03-3.11 (m, 1H), 2.90-2.97 (m, 1H), 2.61 (t, J=6.8 Hz, 2H), 1.53-1.64 (m, 2H), 0.92 (t, J=8.0 Hz, 3H). MS (M+1): 529.

Compound 19-16: (S)-3-(4-((1-propoxy-3-(2',4',6'-trimethyl-[1,1'-biphenyl]-4-yl)propan-2-yl)amino)benzamido)propanoic Acid

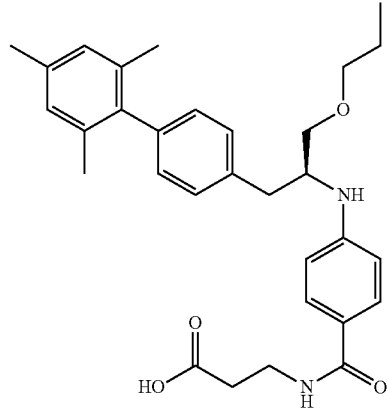 [SMILES: CCCOC[C@H](Cc1ccc(-c2c(C)cc(C)cc2C)cc1)Nc1ccc(C(=O)NCCC(=O)O)cc1]

¹H NMR (400 MHz, Acetone-d₆): δ 7.65 (d, J=8.8 Hz, 2H), 7.43 (br. s., 1H), 7.36 (d, J=7.8 Hz, 2H), 7.01 (d, J=7.8 Hz, 2H), 6.89 (s, 21H), 6.67 (d, J=8.8 Hz, 2H), 3.94 (br. s., 1H), 3.55-3.64 (m, 21H), 3.45-3.53 (m, 2H), 3.41 (t, J=6.4 Hz, 2H), 3.05 (m, 1H), 2.92 (m, 1H), 2.61 (t, J=6.8 Hz, 2H), 2.27 (s, 3H), 1.92 (s, 6H), 1.58 (q, J=6.8 Hz, 2H), 0.93 (t, J=7.3 Hz, 3H). MS (M+1): 503.

Compound 19-17: (R)-3-(4-((1-(4'-(tert-butyl)-[1,1'-biphenyl]-4-yl)-3-isobutoxypropan-2-yl)amino)benzamido)propanoic Acid

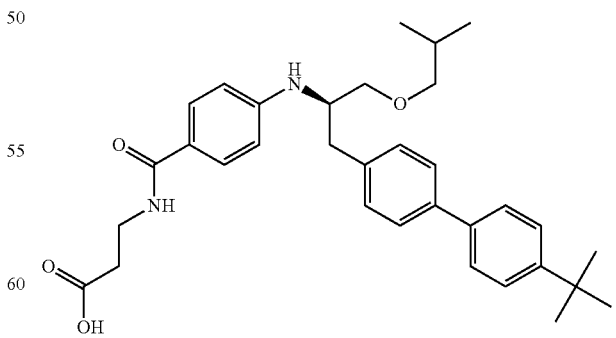

¹H NMR (400 MHz, Acetone-d₆): δ 7.68 (d, J=8.8 Hz, 2H), 7.54-7.59 (m, 4H), 7.48 (d, J=8.8 Hz, 2H), 7.36 (d, J=8.8 Hz, 2H), 6.71 (d, J=8.8 Hz, 2H), 3.90-3.98 (m, 1H), 3.58 (t, J=6.8 Hz, 3H), 3.44-3.49 (m, 2H), 3.22 (d, J=6.8 Hz, 2H), 3.03 (m, 1H), 2.82 (m, 1H), 2.61 (t, J=6.8 Hz, 3H), 1.86 (m, 1H), 1.34 (s, 9H), 0.92 (dd, J=6.8, 2.4 Hz, 6H). MS (M+1): 531.

2H), 2.94 (dd, J=13.7, 6.8 Hz, 2H), 2.60 (t, J=6.8 Hz, 2H), 1.86 (dt, J=13.2, 6.6 Hz, 1H), 0.89-0.95 (m, 6H); MS (M+1): 559.

Compound 19-18: (R)-3-(4-(1-isobutoxy-3-(4'-(trifluoromethyl)-[1,1'-biphenyl]-4-yl)propan-2-yl)amino)benzamido)propanoic Acid Compound 19-20: (R)-3-(4-((1-(2',4'-dichloro-[1,1'-biphenyl]-4-yl)-3-isobutoxypropan-2-yl)amino)benzamido)propanoic Acid

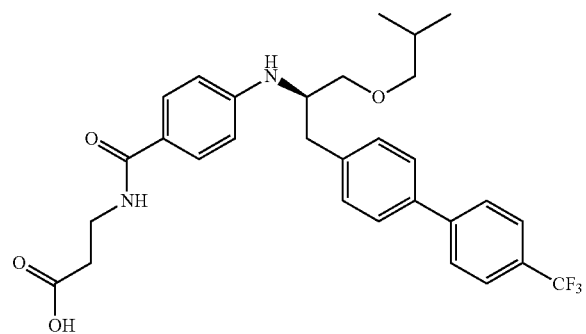 [SMILES: CC(C)COC[C@@H](Cc1ccc(-c2ccc(C(F)(F)F)cc2)cc1)Nc1ccc(C(=O)NCCC(=O)O)cc1]

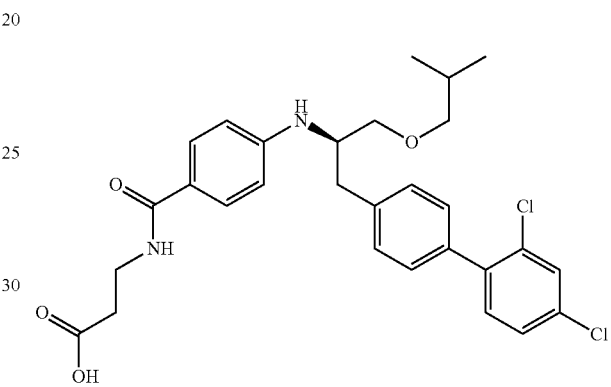

¹H NMR (400 MHz, Acetone-d₆): δ 7.86 (d, J=7.8 Hz, 2H), 7.77 (d, J=7.8 Hz, 2H), 7.64-7.69 (m, 4H), 7.43 (d, J=7.8 Hz, 2H), 6.71 (d, J=8.3 Hz, 2H), 3.96 (m, J=4.9 Hz, 1H), 3.59 (t, J=6.4 Hz, 2H), 3.42-3.52 (m, 2H), 3.22 (d, J=6.4 Hz, 2H), 3.09 (m, 1H), 2.91 (m, 1H), 2.61 (t, J=6.6 Hz, 2H), 1.86 (m, 1H), 0.92 (dd, J=6.4, 2.4 Hz, 6H); MS (M+1): 543.

¹H NMR (400 MHz, Acetone-d₆): δ 7.68 (d, J=8.0 Hz, 2H), 7.57 (d, J=2.0 Hz, 2H), 7.41-7.45 (m, 1H), 7.32-7.41 (m, 5H), 6.70 (d, J=8.0 Hz, 2H), 3.89-4.03 (m, 1H), 3.60 (t, J=6.8 Hz, 2H), 3.44-3.53 (m, 2H), 3.18-3.26 (m, 2H), 3.05-3.11 (m, 1H), 2.94 (m, 1H), 2.62 (t, J=6.8 Hz, 2H), 1.86 (m, 1H), 0.91 (dd, J=6.6, 2.2 Hz, 6H); MS (M+1): 543.

Compound 19-19: (R)-3-(4-((1-isobutoxy-3-(4'-(trifluoromethoxy)-[1,1'-biphenyl]-4-yl)propan-2-yl)amino)benzamido)propanoic Acid Compound 19-21: (R)-3-(4-((1-(4-(benzofuran-2-yl)phenyl)-3-isobutoxypropan-2-yl)amino)benzamido)propanoic Acid

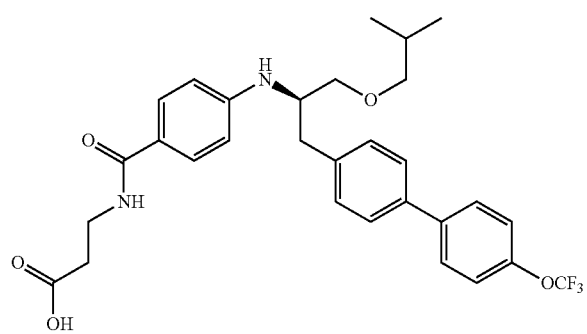 [SMILES: CC(C)COC[C@@H](Cc1ccc(-c2ccc(OC(F)(F)F)cc2)cc1)Nc1ccc(C(=O)NCCC(=O)O)cc1]

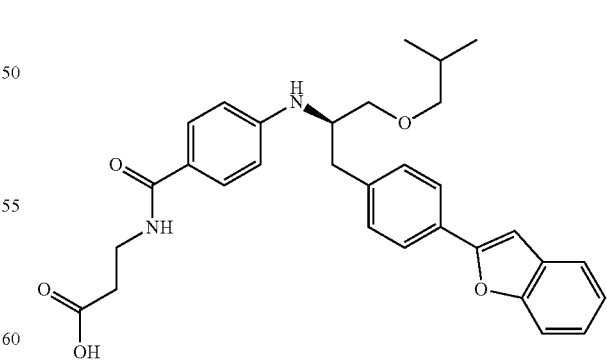

¹H NMR (400 MHz, Acetone-d₆): δ 7.73-7.79 (m, 2H), 7.65-7.71 (m, 2H), 7.57-7.63 (m, 2H), 7.45 (br. s., 1H), 7.37-7.43 (m, 4H), 6.70 (d, J=8.8 Hz, 2H), 5.23-5.41 (m, 1H), 3.95 (br. s., 1H), 3.55-3.64 (m, 2H), 3.47 (dd, J=4.9, 1.5 Hz, 2H), 3.22 (d, J=6.8 Hz, 2H), 3.07 (dd, J=13.7, 6.8 Hz, ¹H NMR (400 MHz, Acetone-d₆): δ 7.83-7.87 (m, 2H), 7.66-7.70 (m, 2H), 7.61-7.64 (m, 1H), 7.52-7.57 (m, 1H), 7.44-7.50 (m, 1H), 7.42 (d, J=8.3 Hz, 2H), 7.27-7.33 (m, 1H), 7.21-7.26 (m, 2H), 6.68-6.74 (m, 2H), 5.09-5.55 (m, 1H), 3.97 (br. s., 1H), 3.56-3.62 (m, 2H), 3.47 (d, J=4.4 Hz, 2H), 3.22 (d, J=6.8 Hz, 2H), 3.04-3.12 (m, 1H), 2.91-2.98 (m, 1H), 2.61 (t, J=6.6 Hz, 2H), 1.81-1.93 (m, 1H), 0.90-0.95 (m, 6H). MS (M+1): 515.

2H), 6.67-6.74 (m, 5H), 5.35 (d, J=4.9 Hz, 2H), 3.95 (br. s., 1H), 3.55-3.62 (m, 2H), 3.44-3.51 (m, 2H), 3.37-3.43 (m, 2H), 3.07 (dd, J=13.7, 6.8 Hz, 1H), 2.90-2.98 (m, 1H), 2.61 (t, J=6.6 Hz, 2H), 1.53-1.64 (m, 2H), 0.93 (t, J=7.3 Hz, 3H). MS (M+1): 529.

Compound 19-22: (S)-3-(4-((1-propoxy-3-(4'-(trifluoromethyl)-[1,1'-biphenyl]-4-yl)propan-2-yl)amino)benzamido)propanoic Acid

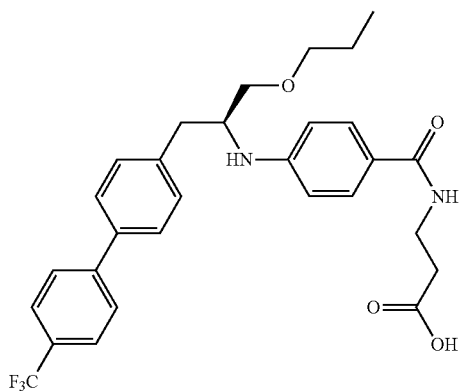 [SMILES: CCCOC[C@H](Cc1ccc(-c2ccc(C(F)(F)F)cc2)cc1)Nc1ccc(C(=O)NCCC(=O)O)cc1]

$^1$H NMR (400 MHz, Acetone-$d_6$): δ 7.84-7.88 (m, 2H), 7.75-7.80 (m, 5H), 7.63-7.71 (m, 10H), 7.45-7.51 (m, 1H), 7.43 (d, J=8.3 Hz, 2H), 6.67-6.73 (m, 2H), 5.35 (br. s., 1H), 3.96 (br. s., 1H), 3.55-3.63 (m, 2H), 3.43-3.52 (m, 2H), 3.36-3.43 (m, 2H), 3.03-3.13 (m, 1H), 2.94 (dd, J=13.7, 6.8 Hz, 1H), 2.61 (t, J=6.6 Hz, 2H), 1.58 (sxt, J=7.0 Hz, 2H), 0.93 (t, J=7.6 Hz, 3H). MS (M+1): 529.

Compound 19-23: (S)-3-(4-((1-propoxy-3-(3'-(trifluoromethyl)-[1,1'-biphenyl]-4-yl)propan-2-yl)amino)benzamido)propanoic Acid

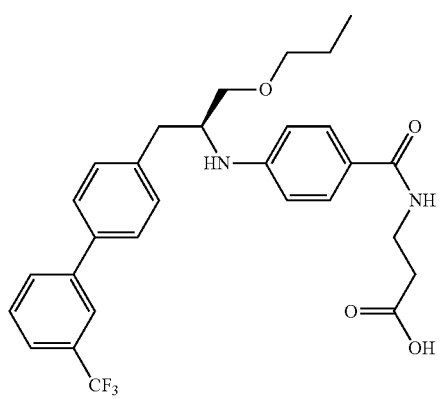 [SMILES: CCCOC[C@H](Cc1ccc(-c2cccc(C(F)(F)F)c2)cc1)Nc1ccc(C(=O)NCCC(=O)O)cc1]

$^1$H NMR (400 MHz, Acetone-$d_6$): δ 7.89-7.97 (m, 2H), 7.62-7.72 (m, 14H), 7.45-7.50 (m, 1H), 7.43 (d, J=8.3 Hz, Compound 19-24: (S)-3-(4-((1-propoxy-3-(4'-(trifluoromethoxy)-[1,1'-biphenyl]-4-yl)propan-2-yl)amino)benzamido)propanoic Acid

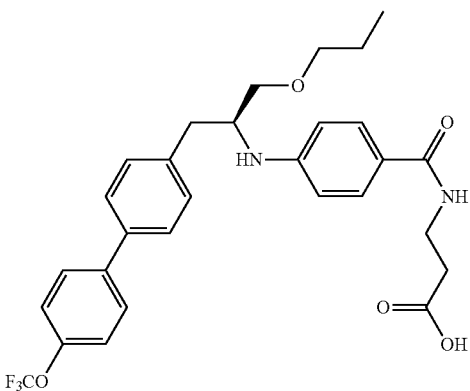 [SMILES: CCCOC[C@H](Cc1ccc(-c2ccc(OC(F)(F)F)cc2)cc1)Nc1ccc(C(=O)NCCC(=O)O)cc1]

$^1$H NMR (400 MHz, Acetone-$d_6$): δ 7.73-7.79 (m, 2H), 7.64-7.71 (m, 2H), 7.57-7.62 (m, 2H), 7.43-7.50 (m, 1H), 7.35-7.43 (m, 4H), 6.67-6.73 (m, 2H), 5.24-5.42 (m, 1H), 3.90-4.00 (m, 1H), 3.55-3.62 (m, 2H), 3.47 (dd, J=4.9, 2.9 Hz, 2H), 3.41 (td, J=6.6, 1.0 Hz, 2H), 3.03-3.08 (m, 2H), 2.93 (dd, J=13.7, 6.8 Hz, 2H), 2.60 (t, J=6.8 Hz, 2H), 1.54-1.63 (m, 2H), 0.93 (t, J=7.3 Hz, 3H); MS (M+1): 545.

Compound 19-25: (S)-3-(4-((1-propoxy-3-(3'-(trifluoromethoxy)-[1,1'-biphenyl]-4-yl)propan-2-yl)amino)benzamido)propanoic Acid

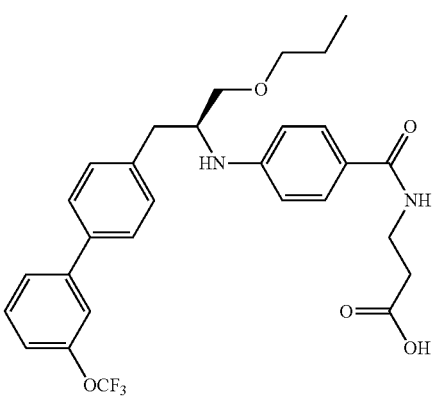 [SMILES: CCCOC[C@H](Cc1ccc(-c2cccc(OC(F)(F)F)c2)cc1)Nc1ccc(C(=O)NCCC(=O)O)cc1]

$^1$H NMR (400 MHz, Acetone-$d_6$): δ 7.65-7.70 (m, 3H), 7.60-7.64 (m, 2H), 7.55-7.60 (m, 2H), 7.46 (br. s., 1H), 7.42

(d, J=8.3 Hz, 2H), 7.27-7.33 (m, 1H), 6.70 (d, J=8.8 Hz, 2H), 5.24-5.42 (m, 1H), 3.95 (d, J=5.9 Hz, 1H), 3.56-3.62 (m, 2H), 3.44-3.50 (m, 2H), 3.38-3.43 (m, 2H), 3.07 (dd, J=13.7, 6.4 Hz, 1H), 2.94 (dd, J=13.7, 6.8 Hz, 1H), 2.60 (t, J=6.8 Hz, 2H), 1.53-1.64 (m, 2H), 0.93 (t, J=7.3 Hz, 3H). MS (M+1): 545.

2H), 6.83-6.87 (m, 1H), 6.68-6.73 (m, 2H), 5.11-5.54 (m, 1H), 3.94 (d, J=3.9 Hz, 1H), 3.56-3.62 (m, 2H), 3.44-3.50 (m, 2H), 3.41 (t, J=6.4 Hz, 2H), 3.04 (dd, J=13.7, 6.4 Hz, 1H), 2.88-2.94 (m, 1H), 2.61 (t, J=6.8 Hz, 2H), 1.54-1.63 (m, 2H), 0.93 (t, J=7.3 Hz, 3H). MS (M+1): 501.

Compound 19-26: (S)-3-(4-((1-(4-(benzofuran-2-yl)phenyl)-3-propoxypropan-2-yl)amino)benzamido)propanoic Acid Compound 19-28: (S)-3-(4-((1-isobutoxy-3-(3'-(trifluoromethyl)-[1,1'-biphenyl]-4-yl)propan-2-yl)amino)benzamido)propanoic Acid

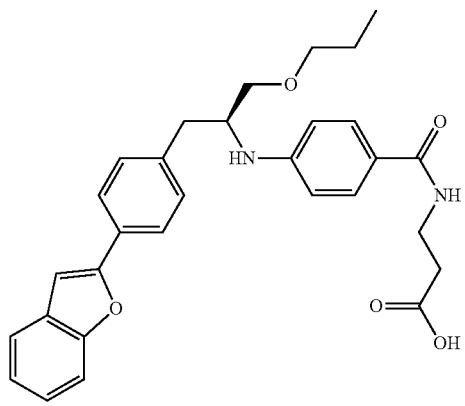 [SMILES: CCCOC[C@H](Cc1ccc(-c2cc3ccccc3o2)cc1)Nc1ccc(C(=O)NCCC(=O)O)cc1]

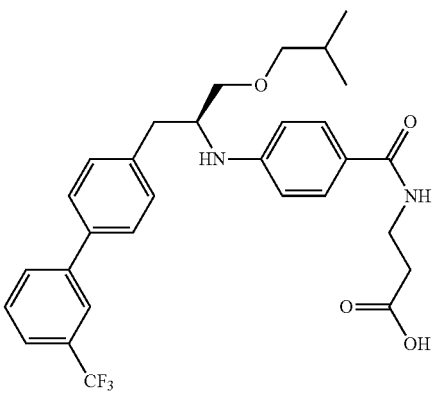

¹H NMR (400 MHz, Acetone-d₆): δ 7.83-7.87 (m, 2H), 7.66-7.70 (m, 4H), 7.61-7.65 (m, 1H), 7.52-7.58 (m, 1H), 7.42 (d, J=8.3 Hz, 3H), 7.28-7.33 (m, 1H), 7.21-7.26 (m, 2H), 6.68-6.73 (m, 2H), 5.14-5.51 (m, 1H), 3.87-4.05 (m, 1H), 3.55-3.62 (m, 2H), 3.47 (dd, J=4.9, 2.0 Hz, 2H), 3.38-3.44 (m, 2H), 3.04-3.10 (m, 1H), 2.94 (dd, J=13.7, 6.8 Hz, 1H), 2.61 (t, J=6.8 Hz, 2H), 1.53-1.64 (m, 2H), 0.91-0.97 (m, 3H). MS (M+1): 501.

¹H NMR (400 MHz, Acetone-d₆): δ 7.90-7.97 (m, 2H), 7.63-7.72 (m, 6H), 7.40-7.52 (m, 3H), 6.68-6.73 (m, 2H), 5.19-5.49 (m, 1H), 3.97 (d, J=4.9 Hz, 1H), 3.56-3.62 (m, 2H), 3.43-3.51 (m, 2H), 3.19-3.26 (m, 2H), 3.09 (dd, J=13.7, 6.4 Hz, 1H), 2.95 (dd, J=13.4, 6.6 Hz, 1H), 2.60 (t, J=6.8 Hz, 2H), 1.87 (dt, J=13.3, 6.8 Hz, 1H), 0.92 (dd, J=6.6, 2.7 Hz, 6H). MS (M+1): 543.

Compound 19-27: (S)-3-(4-((1-(4-(1H-indol-2-yl)phenyl)-3-propoxypropan-2-yl)amino)benzamido)propanoic Acid Compound 19-29: (S)-3-(4-((1-isobutoxy-3-(2'-(trifluoromethyl)-[1,1'-biphenyl]-4-yl)propan-2-yl)amino)benzamido)propanoic Acid

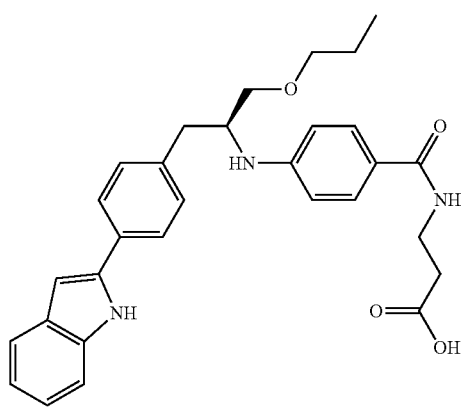 [SMILES: CCCOC[C@H](Cc1ccc(-c2cc3ccccc3[nH]2)cc1)Nc1ccc(C(=O)NCCC(=O)O)cc1]

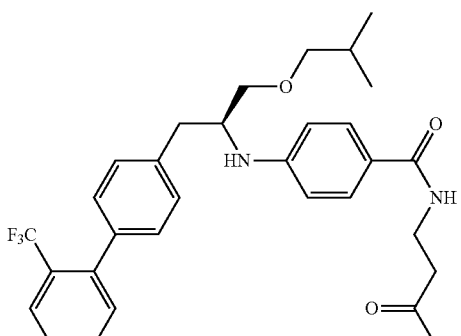

¹H NMR (400 MHz, Acetone-d₆): 10.59 (br. s., 1H), 7.75-7.78 (m, 2H), 7.66-7.70 (m, 2H), 7.54 (d, J=7.8 Hz, 1H), 7.41-7.49 (m, 1H), 7.34-7.40 (m, 3H), 6.98-7.11 (m, ¹H NMR (400 MHz, Acetone-d₆): δ 7.80 (d, J=7.8 Hz, 1H), 7.65-7.70 (m, 6H), 7.56-7.60 (m, 2H), 7.47 (br. s., 2H), 7.37 (d, J=7.8 Hz, 5H), 7.25 (d, J=7.8 Hz, 4H), 6.68-6.74 (m, 2H), 5.34 (br. s., 1H), 3.96 (br. s., 1H), 3.57-3.62 (m, 2H), 3.48 (d, J=4.4 Hz, 2H), 3.22 (d, J=6.4 Hz, 2H), 3.08 (dd, J=13.7, 6.4 Hz, 1H), 2.92-2.99 (m, 1H), 2.61 (t, J=6.6 Hz, 2H), 1.86 (dt, J=13.3, 6.8 Hz, 1H), 0.92 (dd, J=6.8, 2.9 Hz, 6H). MS (M+1): 543.

Compound 19-30: (S)-3-(4-((1-isobutoxy-3-(3'-(trifluoromethoxy)-[1,1'-biphenyl]-4-yl)propan-2-yl)amino)benzamido)propanoic Acid

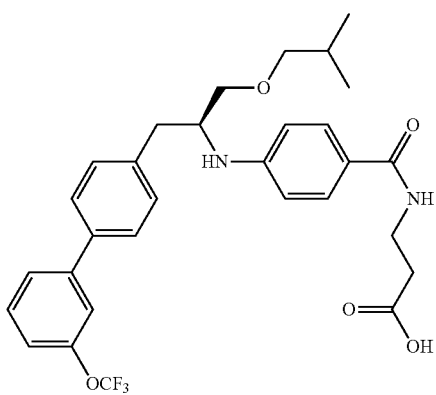

$^1$H NMR (400 MHz, Acetone-d$_6$): δ 7.65-7.71 (m, 3H), 7.60-7.64 (m, 2H), 7.54-7.60 (m, 2H), 7.47 (t, J=5.4 Hz, 1H), 7.42 (d, J=8.3 Hz, 2H), 7.30 (ddd, J=9.3, 2.4, 1.0 Hz, 1H), 6.66-6.73 (m, 2H), 5.34 (d, J=8.3 Hz, 1H), 3.96 (br. s., 1H), 3.59 (q, J=6.4 Hz, 2H), 3.43-3.50 (m, 2H), 3.23 (d, J=1.0 Hz, 2H), 3.08 (dd, J=13.7, 6.4 Hz, 5H), 2.94 (dd, J=13.4, 6.6 Hz, 3H), 2.60 (t, J=6.8 Hz, 2H), 1.86 (dt, J=13.3, 6.8 Hz, 1H), 0.92 (dd, J=6.8, 2.4 Hz, 6H); MS (M+1): 559.

Compound 19-31: (S)-3-(4-((1-isobutoxy-3-(3',4',5'-trifluoro-[1,1'-biphenyl]-4-yl)propan-2-yl)amino)benzamido)propanoic Acid

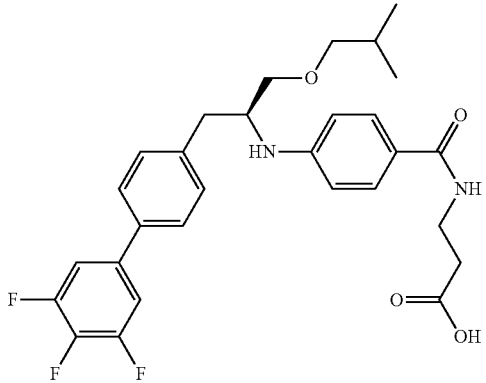 [SMILES: CC(C)COC[C@H](Cc1ccc(-c2cc(F)c(F)c(F)c2)cc1)Nc1ccc(C(=O)NCCC(=O)O)cc1]

$^1$H NMR (400 MHz, Acetone-d$_6$): δ 7.65-7.70 (m, 2H), 7.57-7.64 (m, 2H), 7.43-7.52 (m, 3H), 7.39-7.43 (m, 2H), 6.66-6.72 (m, 2H), 5.34 (br. s., 1H), 3.96 (br. s., 1H), 3.55-3.63 (m, 2H), 3.42-3.51 (m, 2H), 3.17-3.26 (m, 2H), 3.08 (dd, J=13.7, 6.4 Hz, 1H), 2.93 (dd, J=13.7, 6.8 Hz, 1H), 2.60 (t, J=6.8 Hz, 2H), 1.86 (dt, J=13.4, 6.5 Hz, 1H), 0.88-0.94 (m, 6H). MS (M+1): 529.

Compound 19-32: (S)-3-(4-((1-(4-(benzofuran-2-yl)phenyl)-3-isobutoxypropan-2-yl)amino)benzamido)propanoic Acid

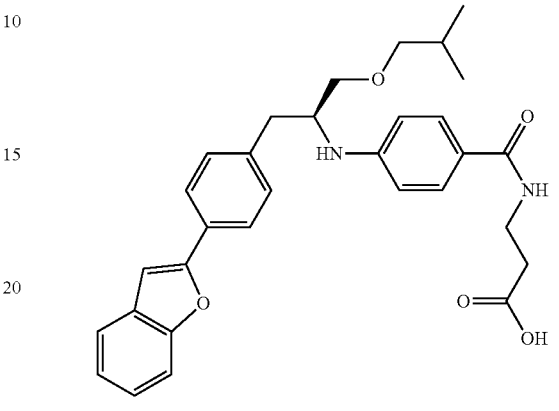

$^1$H NMR (400 MHz, Acetone-d$_6$): δ 7.81-7.88 (m, 2H), 7.65-7.70 (m, 2H), 7.60-7.65 (m, 1H), 7.51-7.58 (m, 1H), 7.43 (d, J=8.3 Hz, 3H), 7.29 (dd, J=7.8, 1.5 Hz, 1H), 7.20-7.27 (m, 2H), 6.65-6.77 (m, 2H), 5.24-5.41 (m, 1H), 3.89-4.05 (m, 1H), 3.55-3.62 (m, 2H), 3.43-3.51 (m, 2H), 3.23 (d, J=5.9 Hz, 2H), 3.06 (d, J=6.4 Hz, 1H), 2.97 (d, J=6.4 Hz, 1H), 2.61 (t, J=6.8 Hz, 2H), 1.80-1.94 (m, 1H), 0.92 (dd, J=6.4, 2.4 Hz, 6H). MS (M+1): 515.

Compound 19-33: (S)-3-(4-((1-isobutoxy-3-(4'-(trifluoromethoxy)-[1,1'-biphenyl]-4-yl)propan-2-yl)amino)benzamido)propanoic Acid

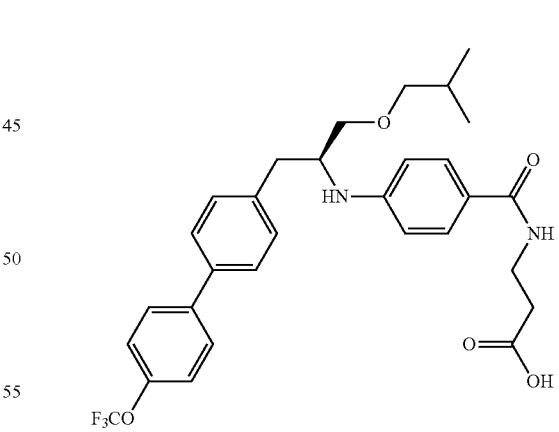

$^1$H NMR (400 MHz, Acetone-d$_6$): δ 7.73-7.78 (m, 2H), 7.64-7.70 (m, 2H), 7.56-7.62 (m, 2H), 7.37-7.44 (m, 4H), 6.66-6.74 (m, 2H), 3.95 (s, 1H), 3.58 (t, J=6.8 Hz, 2H), 3.43-3.51 (m, 2H), 3.22 (d, J=5.9 Hz, 2H), 3.04-3.12 (m, 1H), 2.94 (dd, J=13.7, 6.8 Hz, 1H), 2.61 (t, J=6.8 Hz, 2H), 1.80-1.92 (m, 1H), 0.92 (dd, J=6.8, 2.4 Hz, 6H). MS (M+1): 559.

175

Compound 19-34: (S)-3-(4-((1-isobutoxy-3-(4'-(trifluoromethyl)-[1,1'-biphenyl]-4-yl)propan-2-yl)amino)benzamido)propanoic Acid

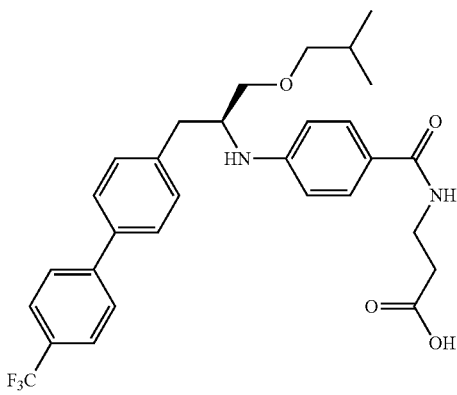 [SMILES: CC(C)COC[C@H](Cc1ccc(-c2ccc(C(F)(F)F)cc2)cc1)Nc1ccc(C(=O)NCCC(=O)O)cc1]

176

$^1$H NMR (400 MHz, Acetone-$d_6$): δ 7.83-7.90 (m, 2H), 7.73-7.81 (m, 2H), 7.63-7.70 (m, 4H), 7.44 (d, J=8.3 Hz, 3H), 6.68-6.74 (m, 2H), 5.33 (br. s., 1H), 3.97 (br. s., 1H), 3.55-3.63 (m, 2H), 3.43-3.52 (m, 2H), 3.19-3.26 (m, 2H), 3.09 (dd, J=13.7, 6.4 Hz, 1H), 2.95 (dd, J=13.7, 6.8 Hz, 1H), 2.61 (t, J=6.8 Hz, 2H), 1.87 (dt, J=13.3, 6.8 Hz, 1H), 0.92 (dd, J=6.4, 2.4 Hz, 6H). MS (M+1): 543.

Reaction Scheme V illustrates the general procedures that can be used to synthesize the following compounds of the formula (I) of the present disclosure.

Reaction Scheme V

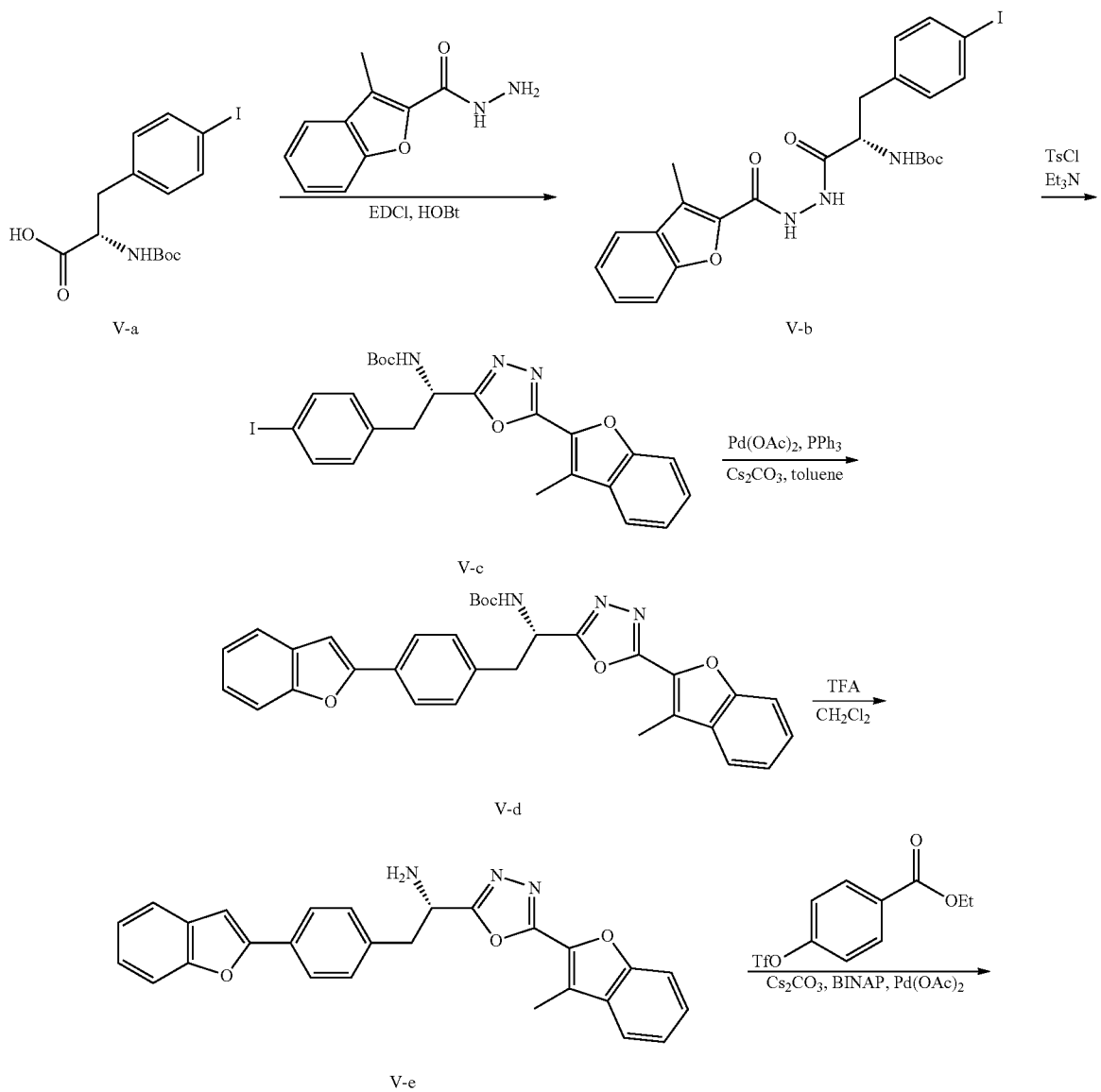

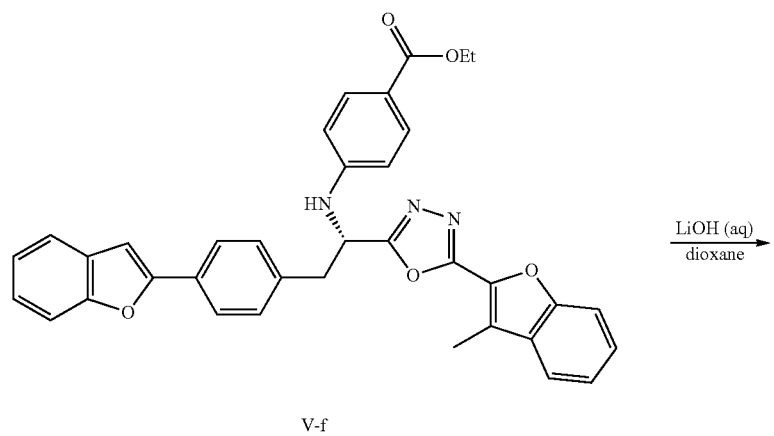
V-f
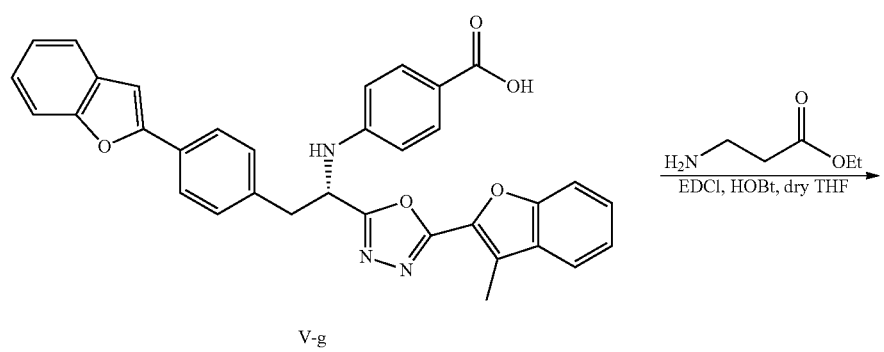
V-g
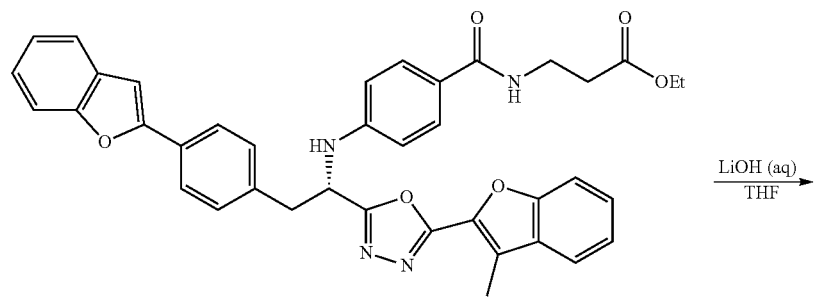
V-h
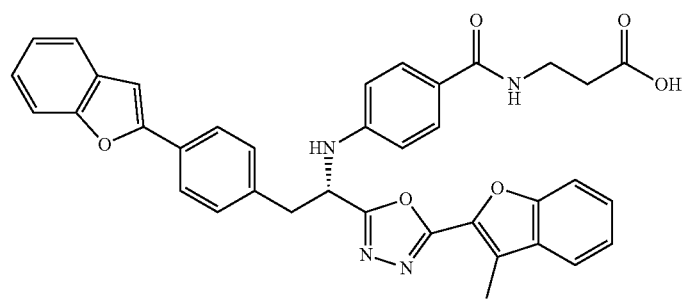
V-i

Step I: Preparation of (S)-tert-butyl-(3-(4-iodophenyl)-1-(2-(3-methylbenzofuran-2-carbonyl)hydrazinyl)-1-oxopropan-2-yl)carbamate

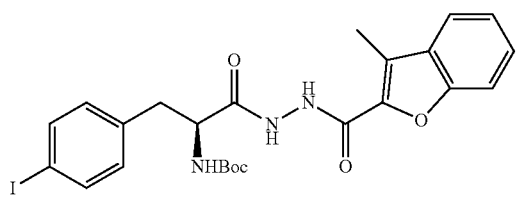

V-b

To a Solution of 3-methylbenzofuran-2-carbohydrazide, (S)-2-(tert-butoxycarbonylamino)-3-(4-iodophenyl)propanoic acid, EDCI and HOBt in DMF. The reaction was stirred at room temperature for overnight then concentrated in vacuo. Water was added to the residue and the aqueous layer was extracted with ethyl acetate. It was further concentrated in vacuo to give a residue. Purification of the crude oil residue by column chromatography (hexane/EtOAc 100:20) afforded pale white solid product(S)-tert-butyl 3-(4-iodophenyl)-1-(2-(3-methylbenzofuran-2-carbonyl)hydrazinyl)-1-oxopropan-2-ylcarbamate.

Step II: Preparation of (S)-tert-butyl 2-(4-iodophenyl)-1-(5-(3-methylbenzofuran-2-yl)-1,3,4-oxadiazol-2-yl)ethylcarbamate

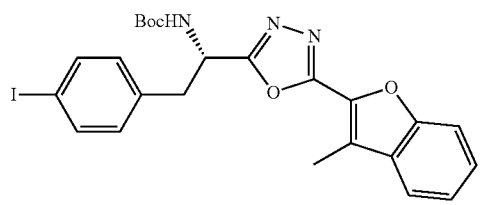

V-c (S)-tert-butyl 3-(4-iodophenyl)-1-(2-(3-methylbenzofuran-2-cabonyl)hydrazinyl)-1-oxopropan-2-yl)carbamate (16.90 g, 30 mmol), TsCl (1.5 equiv), and TEA (3 equiv) were mixed in ACN (50 ml) was stirred at room temperature for 10 mins. To this reaction solution, concentrated to remove methanol and extracted with EtOAc. The organic layer was washed with water and dried over anhydrous magnesium sulfate. It was filtered, the solvent evaporated under reduced pressure. The crude product of (S)-tert-butyl 2-(4-iodophenyl)-1-(5-(3-methylbenzofuran-2-yl)-1,3,4-oxadiazol-2-yl)ethylcarbamate obtained (9.93 g, 61% yield) as brown oil, and was used without any further purification in the successive step.

Step III. Preparation of (S)-tert-butyl-(2-(4-(benzofuran-2-yl)phenyl)-1-(5-(3-methylbenzofuran-2-yl)-1,3,4-oxadiazol-2-yl)ethyl)carbamate

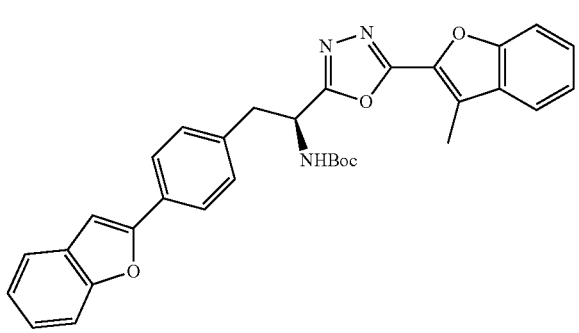

V-d

A solution of (S)-tert-butyl 2-(4-iodophenyl)-1-(5-(3-methylbenzofuran-2-yl)-1,3,4-oxadiazol-2-yl)ethylcarbamate (8.5 g, 15.5 mmol), 2-benzofuranylboronic acid (3.02 g, 18.6 mmol), palladium acetate(II) (0.36 g, 1.6 mmol), triphenylphosphine (0.81 g, 3.2 mmol) in EtOH/PhMe (20 mL/40 mL) were purged with nitrogen for 30 min. $K_2CO_3$ (7.50 g, 54.25 mmol) in 20 mL $H_2O$ was added and purged with nitrogen for another 10 min. The mixture was heated at 90° C. for 12 h. The reaction mixture was cooled and extracted with EtOAc. The organic layer was dried over $MgSO_4$ and concentrated in vacuo. The residue was purified by silica gel chromatography to afford (S)-tert-butyl 2-(4-(benzofuran-2-yl)phenyl)-1-(5-(3-methylbenzofuran-2-yl)-1,3,4-oxadiazol-2-yl)ethylcarbamate (3.09 g, 37%) as a white solid.

Step IV. Preparation of (S)-2-(4-(benzofuran-2-yl)phenyl)-1-(5-(3-methylbenzofuran-2-yl)-1,3,4-oxadiazol-2-yl)ethan-1-amine

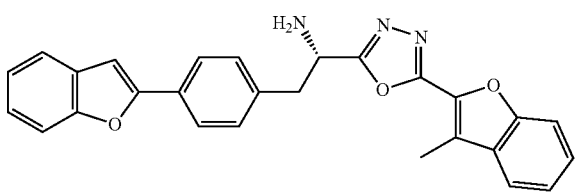

V-e

The compound (S)-tert-butyl 2-(4-(benzofuran-2-yl)phenyl)-1-(5-(3-methylbenzofuran-2-yl)-1,3,4-oxadiazol-2-yl) ethylcarbamate (3.09 g, 5.7 mmol) was suspended in trifluoroacetic acid (6.6 mL, 86.25 mmol) in anhydrous dichloromethane (30 mL) at room temperature for 2 h. After reaction, excess trifluoroacetic acid was neutralized by dropwised addition of $NaHCO_{3(aq)}$ until pH=10. Then it was extracted with CH₂Cl₂. The combined organic layer was dried with anhydrous MgSO₄ and concentrated in vacuo to give crude product (S)-2-(4-(benzofuran-2-yl)phenyl)-1-(5-(3-methylbenzofuran-2-yl)-1,3,4-oxadiazol-2-yl)ethanamine.

Step V: Preparation of ethyl (S)-4-((2-(4-(benzofuran-2-yl)phenyl)-1-(5-(3-methylbenzofuran-2-yl)-1,3,4-oxadiazol-2-yl)ethyl)amino)benzoate V-f

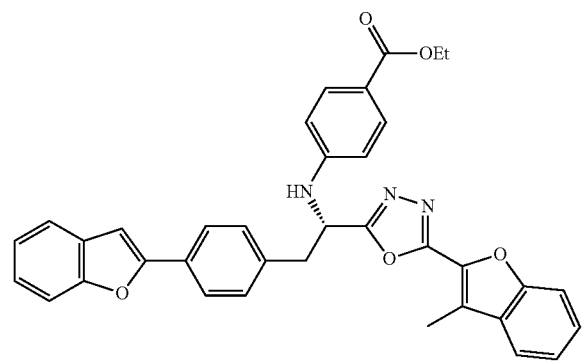

To a degassing solution of (S)-2-(4-(benzofuran-2-yl)phenyl)-1-(5-(3-methylbenzofuran-2-yl)-1,3,4-oxadiazol-2-yl)ethan-1-amine (1.74 g, 4 mmol), BINAP (1 g, 1.6 mmol), cesium carbonate (1.95 g, 6 mmol) and ethyl 3-(4-(((trifluoromethyl)sulfonyl)oxy)benzamido)propanoate (1.78 g, 4.8 mmol) in 40 mL PhMe were purged with nitrogen for 30 min then added Pd(OAc)₂ (0.18 g, 0.8 mmol). The mixture was stirred in an oil bath at 100° C. for 18 h. Cool the mixture to ambient temperature, dilute with EtOAc, filter through Celite washing with EtOAc. The mixture was washed with water and brine, dried the organic layer over Na₂SO₄, and concentrate to obtain the crude mixture. The residue was purified by silica gel chromatography to afford (S)-4-((2-(4-(benzofuran-2-yl) phenyl)-1-(5-(3-methylbenzofuran-2-yl)-1,3,4-oxadiazol-2-yl)ethyl)amino) benzoate.

Step VI: Preparation of(S)-4-((2-(4-(benzofuran-2-yl)phenyl)-1-(5-(3-methylbenzofuran-2-yl)-1,3,4-oxadiazol-2-yl)ethyl)amino)benzoic Acid V-g

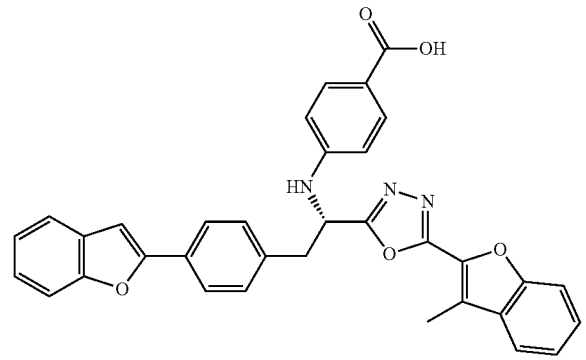

Ethyl (S)-4-((2-(4-(benzofuran-2-yl)phenyl)-1-(5-(3-methylbenzofuran-2-yl)-1,3,4-oxadiazol-2-yl)ethyl)amino) benzoate (1.00 g, 1.67 mmol) was dissolved in dioxane (20 mL) followed by addition of 2M/LiOH$_{(aq)}$ 20 mL. The reaction mixture was heat to reflux for overnight. The reaction was monitored by TLC. With completion of the reaction, the solvent was removed by rotary evaporation and was added HCl$_{(aq)}$ to pH4-5. The mixture cpd. was extracted with EtOAc. The combined organic layer was dried with anhydrous Na₂SO₄ and concentrated in vacuo to give brown oil product (S)-4-((2-(4-(benzofuran-2-yl)phenyl)-1-(5-(3-methylbenzofuran-2-yl)-1,3,4-oxadiazol-2-yl)ethyl)amino) benzoic acid (0.74 g, 77%).

Step VII: Preparation of ethyl (S)-3-(4-((2-(4-(benzofuran-2-yl)phenyl)-1-(5-(3-methylbenzofuran-2-yl)-1,3,4-oxadiazol-2-yl)ethyl)amino)benzamido) propanoate V-h

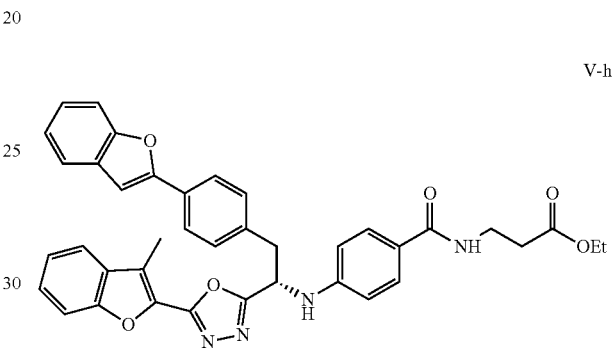

A solution of (S)-4-((2-(4-(benzofuran-2-yl)phenyl)-1-(5-(3-methylbenzofuran-2-yl)-1,3,4-oxadiazol-2-yl)ethyl) amino)benzoic acid, f-alanine ethyl ester:HCl, EDCI, Et₃N and HOBt in dry THF. The reaction was stirred at room temperature for overnight then concentrated in vacuo. Water was added to the residue and the aqueous layer was extracted with ethyl acetate. It was further concentrated in vacuo to give a residue. Purification of the crude oil residue by column chromatography (hexane/EtOAc 100:40) afforded colorness oil product, Compound V-h (0.65 g, 48%).

Step VII: Preparation of (S)-3-(4-(2-(4-(benzofuran-2-yl)phenyl)-1-(5-(3-methylbenzofuran-2-yl)-1,3,4-oxadiazol-2-yl)ethylamino)benzamido)propanoic Acid V-i

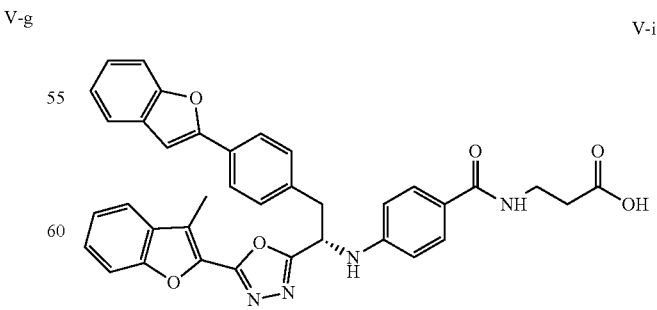

Compound V-h (0.66 g, 1.00 mmol) was dissolved in THF (20 mL) followed by addition of 2M/LiOH(aq) 20 mL. The reaction mixture stirred at room temperature for overnight.

The reaction was monitored by TLC. With completion of the reaction, the solvent was removed by rotary evaporation and was added HCl(aq) to pH4-5. The mixture cpd. was extracted with EtOAc. The combined organic layer was dried with anhydrous $Na_2SO_4$ and concentrated in vacuo to give brown oil product, Compound V-i.

Compound 20-1: (S)-3-(4-((2-(4-(benzofuran-2-yl)phenyl)-1-(5-(4-(tert-butyl)phenyl)-1,3,4-oxadiazol-2-yl)ethyl)amino)benzamido)propanoic Acid

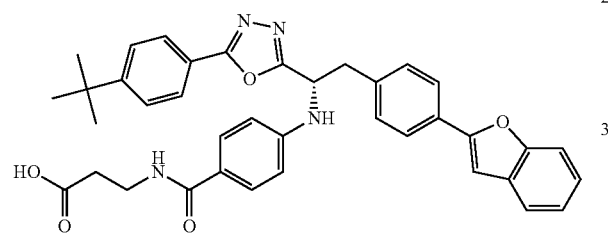

$^1$H NMR (400 MHz, DMSO-d$_6$): δ 8.10 (s, 1H), 7.84 (d, J=8.4 Hz, 2H), 7.81 (d, J=8.4 Hz, 2H), 7.55-7.66 (m, 6H), 7.47 (d, J=8.4 Hz, 2H), 7.37 (s, 1H), 7.22-7.32 (m, 2H), 6.98 (d, J=8.4 Hz, 1H), 6.75 (d, J=8.8 Hz, 2H), 5.30-5.32 (m, 1H), 3.35-3.43 (m, 4H), 2.43 (t, J=4.0 Hz, 2H), 1.28 (s, 9H). MS (M+1): 629.

Compound 20-2: 3-(4-(((1S)-2-methyl-1-(5-(3-methylbenzofuran-2-yl)-1,3,4-oxadiazol-2-yl)butyl)amino)benzamido)propanoic Acid

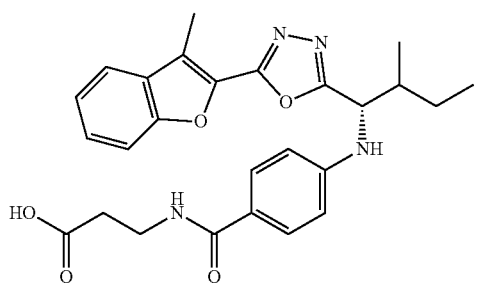 [SMILES: CCC(C)[C@H](Nc1ccc(C(=O)NCCC(=O)O)cc1)c1nnc(-c2oc3ccccc3c2C)o1]

$^1$H NMR (400 MHz, DMSO-d$_6$): δ 8.10 (t, J=5.4 Hz, 1H), 7.77 (d, J=7.8 Hz, 1H), 7.58-7.69 (m, 3H), 7.45-7.50 (m, 1H), 7.33-7.39 (m, 1H), 6.69-6.80 (m, 2H), 4.77-4.91 (m, 1H), 3.54 (t, J=7.2 Hz, 2H), 2.54 (d, J=3.2 Hz, 2H), 2.45 (t, J=7.2 Hz, 2H), 2.09-2.30 (m, 1H), 1.41-1.49 (m, 1H), 1.09 (d, J=6.4 Hz, 2H), 0.83-0.97 (m, 6H). MS (M+1): 477.

Compound 20-3: 3-(4-(((1S)-1-(5-(4-(tert-butyl)phenyl)-1,3,4-oxadiazol-2-yl)-2-methylbutyl)amino)benzamido)propanoic Acid

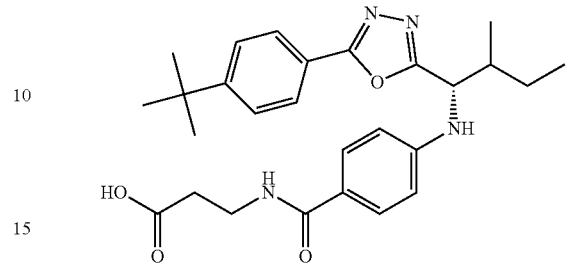

$^1$H NMR (400 MHz, CDCl$_3$): δ 7.89 (d, J=8.4 Hz, 2H), 7.56 (d, J=8.8 Hz, 2H), 7.39-7.50 (m, 2H), 6.97 (s, 1H), 6.65 (d, J=8.8 Hz, 2H), 4.67-4.81 (m, 1H), 3.63 (d, J=6.0 Hz, 2H), 2.60 (t, J=6.0 Hz, 2H), 2.02-2.16 (m, 1H), 1.15-1.39 (m, 10H), 1.08 (d, J=6.8 Hz, 2H), 0.76-1.01 (m, 6H). MS (M+1): 479.

Compound 20-4: (S)-3-(4-((1-(5-(4-(tert-butyl)phenyl)-1,3,4-oxadiazol-2-yl)-2-methylpropyl)amino)benzamido)propanoic Acid

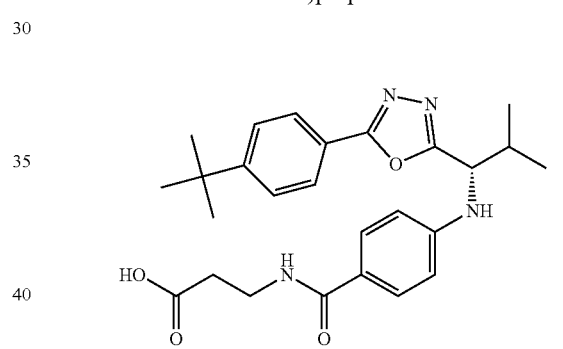

$^1$H NMR (400 MHz, CDCl$_3$): δ 7.87-7.92 (m, 2H), 7.58 (d, J=8.8 Hz, 2H), 7.41-7.51 (m, 2H), 7.24 (s, 1H), 6.68 (d, J=8.8 Hz, 2H), 4.67 (d, J=6.8 Hz, 1H), 3.66 (d, J=5.4 Hz, 2H), 2.63 (t, J=5.6 Hz, 2H), 1.31 (s, 9H), 1.12 (d, J=6.8 Hz, 3H), 0.98 (d, J=6.8 Hz, 3H). MS (M+1): 465.

Compound 20-5: (S)-3-(4-((1-(5-(4-(tert-butyl)phenyl)-1,3,4-oxadiazol-2-yl)-2-(2',4',6'-trimethyl-[1,1'-biphenyl]-4-yl)ethyl)amino)benzamido)propanoic Acid

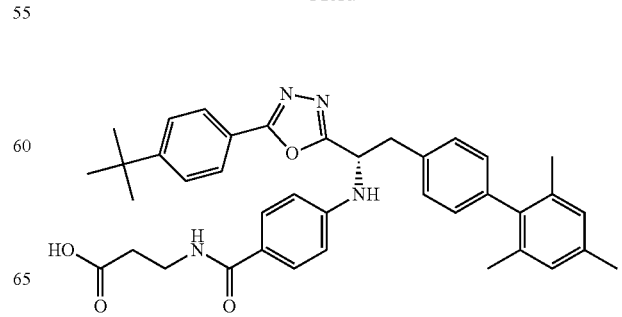

¹H NMR (400 MHz, DMSO-d₆): δ 10.42 (s, 1H), 10.35 (s, 1H), 8.08 (s, 1H), 7.84 (d, J=8.3 Hz, 2H), 7.47-7.60 (m, 4H), 7.32-7.47 (m, J=7.8 Hz, 2H), 6.95-7.04 (m, J=7.8 Hz, 2H), 6.88 (s, 2H), 6.63 (d, J=8.8 Hz, 2H), 6.53 (d, J=8.8 Hz, 1H), 3.18 (br. s., 3H), 2.39-2.54 (m, 4H), 2.24 (s, 3H), 1.88 (s, 6H), 1.30 (s, 9H). S (M+1): 631.

s., 2H), 3.19-3.43 (m, 2H), 2.98-3.19 (m, 2H), 2.55 (s, 3H). MS (M+1): 661.

Example 21: Synthesis of Compounds 21-1 to 21-3

Compound 21-1: (S)-3-(4-((1-(5-(4-(tert-butyl)phenyl)-1,2,4-oxadiazol-3-yl)hexan-2-yl)amino)benzamido)propanoic Acid Compound 20-6: (S)-3-(4-((1-(5-(3-methylbenzofuran-2-yl)-1,3,4-oxadiazol-2-yl)-2-(4'-(trifluoromethyl)-[1,1'-biphenyl]-4-yl)ethyl)amino)benzamido)propanoic Acid

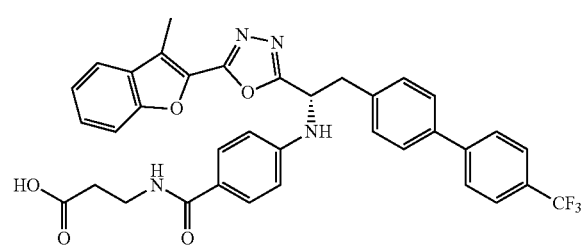 [SMILES: Cc1c(-c2nnc([C@H](Cc3ccc(-c4ccc(C(F)(F)F)cc4)cc3)Nc3ccc(C(=O)NCCC(=O)O)cc3)o2)oc2ccccc12]

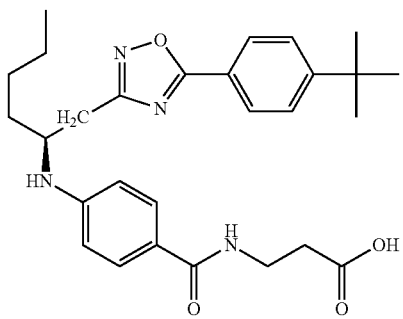 [SMILES: CCCC[C@@H](Cc1noc(-c2ccc(C(C)(C)C)cc2)n1)Nc1ccc(C(=O)NCCC(=O)O)cc1]

¹H NMR (400 MHz, DMSO-d₆): δ 10.41 (s, 1H), 8.10 (t, J=5.6 Hz, 1H), 7.88 (d, J=6.0 Hz, 2H), 7.72-7.80 (m, 3H), 7.48-7.69 (m, 8H), 7.36 (t, J=8.0 Hz, 1H), 6.65 (d, J=8.8 Hz, 2H), 6.55 (d, J=8.8 Hz, 1H), 4.36 (td, J=9.2, 4.0 Hz, 1H), 3.30-3.46 (m, 2H), 3.23 (dd, J=12.0, 8.0 Hz, 1H), 3.05 (m, 1H), 2.55 (s, 3H), 2.45-2.49 (m, 2H). MS (M+1): 655.

¹H NMR (400 MHz, CDCl₃): δ 8.00 (d, J=8.0 Hz, 2H), 7.56 (d, J=8.0 Hz, 2H), 7.51 (d, J=8.8 Hz, 2H), 6.81 (s, 1H), 6.58 (d, J=8.0 Hz, 2H), 3.92 (m, 1H), 3.65 (m, 2H), 2.99 (t, J=6.0 Hz, 2H), 2.63 (t, J=6.0 Hz, 2H), 1.56 (m, 2H), 1.19-1.42 (m, 13H), 0.78-1.01 (m, 4H). MS (M+1): 493.

Compound 20-7: (S)-2-(4-((1-(5-(3-methylbenzofuran-2-yl)-1,3,4-oxadiazol-2-yl)-2-(4'-(trifluoromethyl)-[1,1'-biphenyl]-4-yl)ethyl)amino)benzamido)ethane-1-sulfonic Acid Compound 21-2: 3-(4-(((2R)-1-(5-(4-(tert-butyl)phenyl)-1,2,4-oxadiazol-3-yl)-3-methylpentan-2-yl)amino)benzamido)propanoic Acid

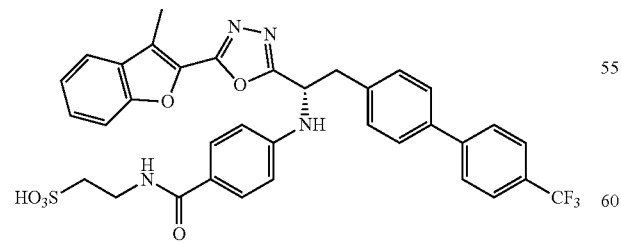

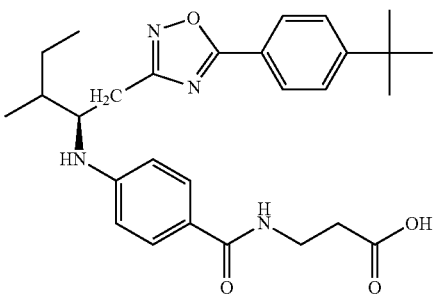 [SMILES: CCC(C)[C@@H](Cc1noc(-c2ccc(C(C)(C)C)cc2)n1)Nc1ccc(C(=O)NCCC(=O)O)cc1]

¹H NMR (400 MHz, DMSO-d₆): δ 10.43 (s, 1H), 8.15 (d, J=8.8 Hz, 1H), 7.98 (dd, J=8.6, 2.7 Hz, 2H), 7.84-7.91 (m, 3H), 7.65-7.81 (m, 8H), 7.48-7.63 (m, 1H), 6.76-6.91 (d, J=8.8 Hz, 2H), 6.65-6.74 (m, 1H), 4.54 (br. s., 1H), 4.39 (br.

¹H NMR (400 MHz, CDCl₃): δ 7.95-7.99 (m, 2H), 7.39-7.56 (m, 4H), 7.24 (s, 1H), 6.55 (d, J=8.8 Hz, 3H), 3.82-3.99 (m, 1H), 3.64 (s, 2H), 2.89-3.03 (m, 2H), 2.64 (t, J=5.9 Hz, 2H), 1.32 (s, 9H), 1.24 (s, 2H), 0.80-1.04 (m, 6H). MS (M+1): 493

Compound 21-3: (R)-3-(4-((1-(5-(4-(tert-butyl)phenyl)-1,2,4-oxadiazol-3-yl)-3-methylbutan-2-yl)amino)benzamido)propanoic Acid

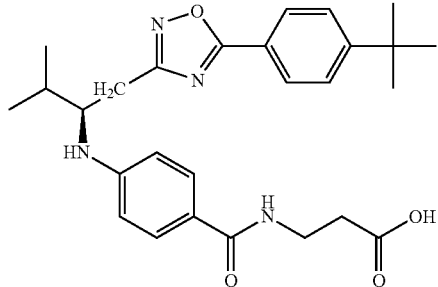 [SMILES: CC(C)[C@@H](Cc1noc(-c2ccc(C(C)(C)C)cc2)n1)Nc1ccc(C(=O)NCCC(=O)O)cc1]

$^1$H NMR (400 MHz, CDCl$_3$): δ 7.97 (d, J=8.4 Hz, 3H), 7.37-7.60 (m, 4H), 6.55 (d, J=8.4 Hz, 2H), 3.74-3.90 (m, 1H), 3.57-3.73 (m, 2H), 2.89-3.04 (m, 2H), 2.62 (m, 2H), 1.83-1.99 (m, 1H), 1.15-1.38 (m, 13H), 0.98 (m, 6H). MS (M+1): 479.

Reaction Scheme VI illustrates the general procedures that can be used to synthesize the following compounds of the formula (I) of the present disclosure.

Reaction Scheme VI

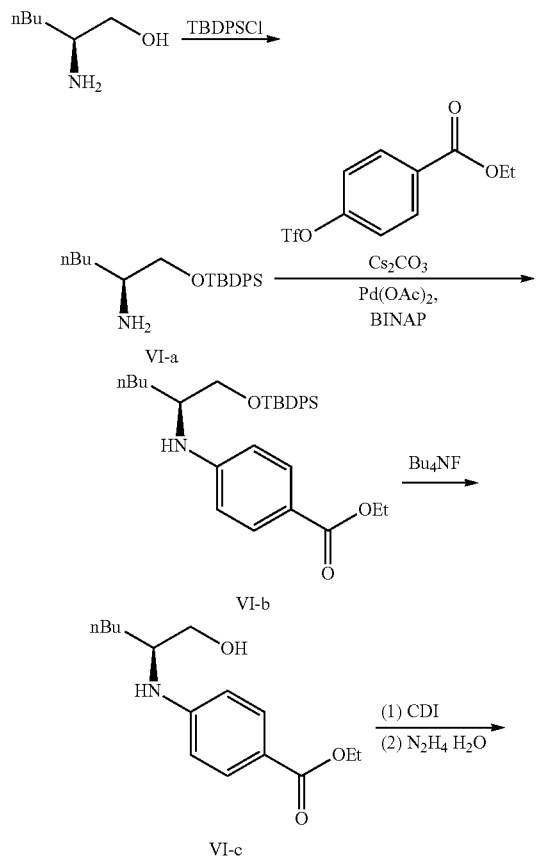

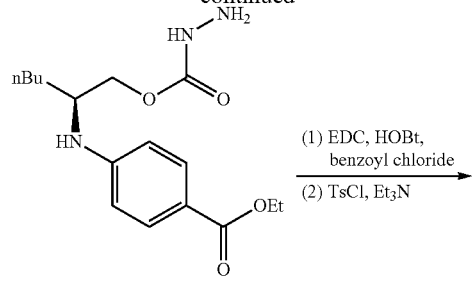

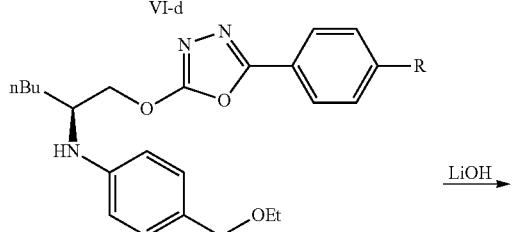

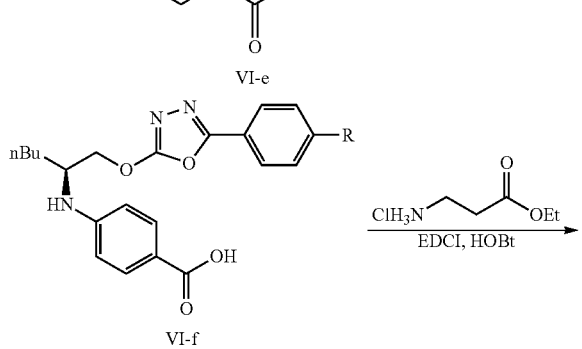

Step I: OH Protection

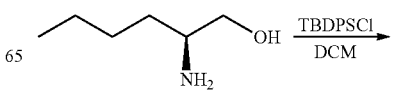

-continued

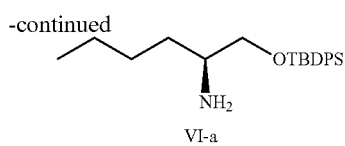

VI-a

L-Norleucinol (10.40 g, 88 mmol) was dissolved in anhydrous DCM (150 mL), TBDPSCl (48.78 g, 117 mmol) and Et₃N (26 mL, 195 mmol) was added to the solution. The reaction mixture was stirred overnight. The aqueous phase extracted with CH₂Cl₂. Drying by MgSO₄ and concentration to give a crude product. Purification of the crude oil residue by column chromatography (EA:Hex=15:100) afforded colorless oil product, Compound VI-a.

Step II: Pd-Coupling

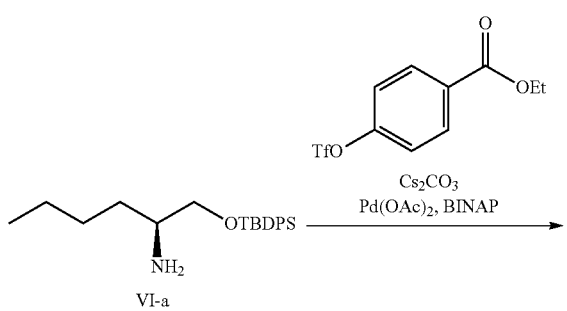

VI-b

To a solution of Pd(OAc)₂ (0.22 g, 1 mmol), BINAP (1.24 g, 2 mmol), Cesium carbonate (6.51 g, 20 mmol), ethyl 4-(trifluoromethylsulfonyloxy)benzoate (3.57 g, 12 mmol), and L-Norleucinol-TBDPS, Compound VI-a (3.55 g, 10 mmol) in 100 mL toluene were purged with nitrogen for 30 min. The mixture was stirred in an oil bath at 90° C. overnight. Cool the mixture to ambient temperature, dilute with EtOAc, filter through Celite washing with EtOAc. The mixture was washed with water and brine, dried the organic layer over MgSO₄, and concentrate to obtain the crude mixture. The residue was purified by silica gel chromatography to give brown oil product, Compound VI-b.

Step III: Deprotection

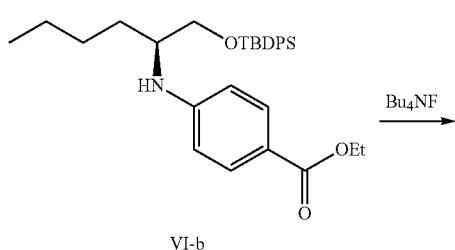

VI-b

-continued

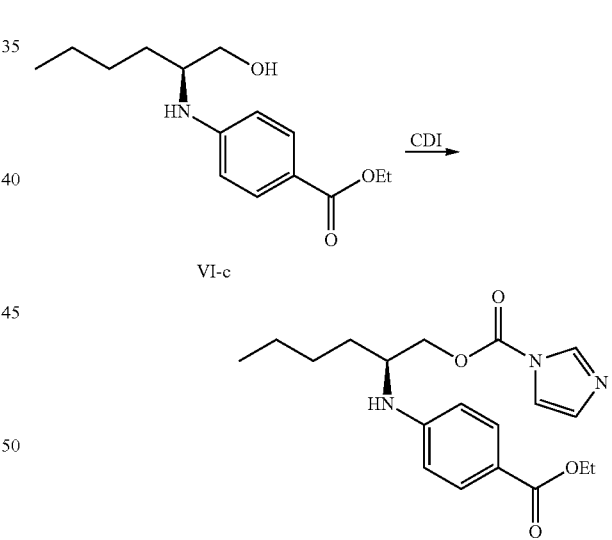

VI-c

To a solution of SM, Compound VI-b (9.2 g, 17.1 mmol) in THF (20 mL) was added TBAF (52 mL, 52 mmol, 1M in THF) at room temperature. The mixture was stirred overnight, diluted with water, and extracted with ethyl acetate. The combined organic layers were washed with brine and dried over MgSO₄. Solvent was carefully removed under vacuum. The residue was purified by flash column chromatography on silica gel (EA:Hex=15:100) to give 4.24 g (93%) of a light yellow liquid, Compound VI-c.

$^1$H NMR (400 MHz, CDCl₃): δ 7.80-7.84 (m, 2H), 6.54-6.58 (m, 2H), 4.08-4.12 (m, 1H), 3.70-3.74 (m, 1H), 3.56-3.61 (m, 1H), 1.45-1.65 (m, 2H), 1.27-1.37 (m, 6H), 0.84-0.91 (m, 3H).

Step IV

VI-c'

To a clean oven-dried 250 mL flask with a magnetic stirring bar was charged with 1,1-carbonyldiimidazole (3.40 g, 21 mmol) and 20 mL THF under nitrogen. The flask was cooled in a ice-water bath. A solution of alcohol, Compound VI-c (2.79 g, 10.5 mmol) in 20 mL THF was added slowly and stirred for 0.5 h. Most solvent was removed in vacuo by a rotavaporator and the crude product 4.6 g (122%) of a yellow liquid (Compound VI-c'), no further purification to use directly in next reaction.

Step V: Synthesis of (S)-2-(4-(ethoxycarbonyl)phenylamino)hexyl hydrazinecarboxylate

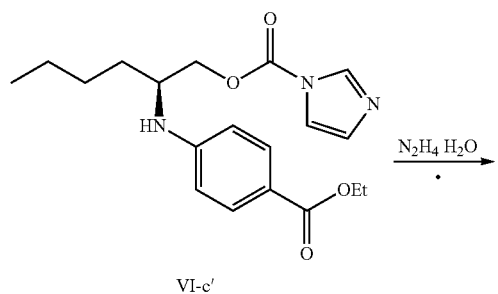

VI-c'

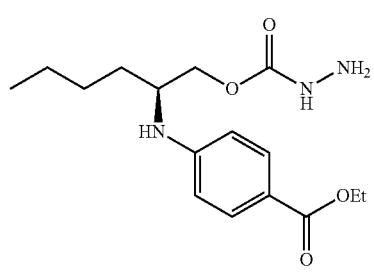

VI-d

To a solution of hydrazine hydrate (1.05 g, 21 mmol) was added dropwise to a solution of Compound VI-c' (4.6 g. 10.5 mmol) in THF (100 mL). The reaction mixture was stirred at room temperature for 0.5 hr. The mixture was concentrated and extracted with EA to obtain white solid crude product, Compound VI-d (3.7 g, 109%). No further purification to use directly in next reaction.

Step VI. Synthesis of (S)-2-(4-(ethoxycarbonyl)phenylamino)hexyl 2-(4-tert-butylbenzoyl)hydrazinecarboxylate

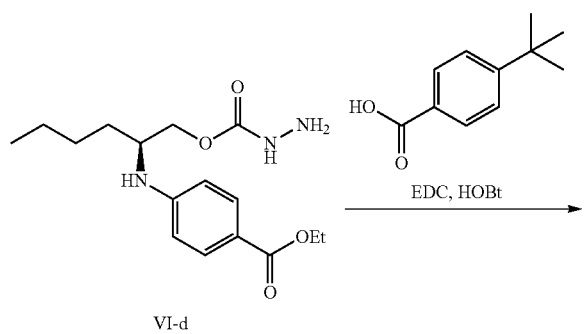

VI-d

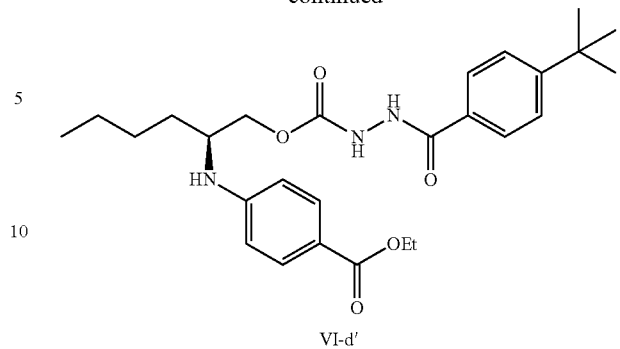

VI-d'

To a Solution of Compound VI-d (1.90 g, 5.88 mmol), tert-butylbenzoic acid (1.15 g, 6.47 mmol), EDCI (1.69 g, 8.81 mmol) and HOBt (1.35 g, 8.81 mmol) in 20 mL DMF. The reaction was stirred at room temperature for overnight then concentrated in vacuo. Water was added to the residue and the aqueous layer was extracted with ethyl acetate. It was further concentrated in vacuo to give a residue. Purification of the crude oil residue by column chromatography (EA:Hex=25:100) afforded colorless oil product, Compound VI-d' (2.2 g, 75%).

Step VII. Annulations

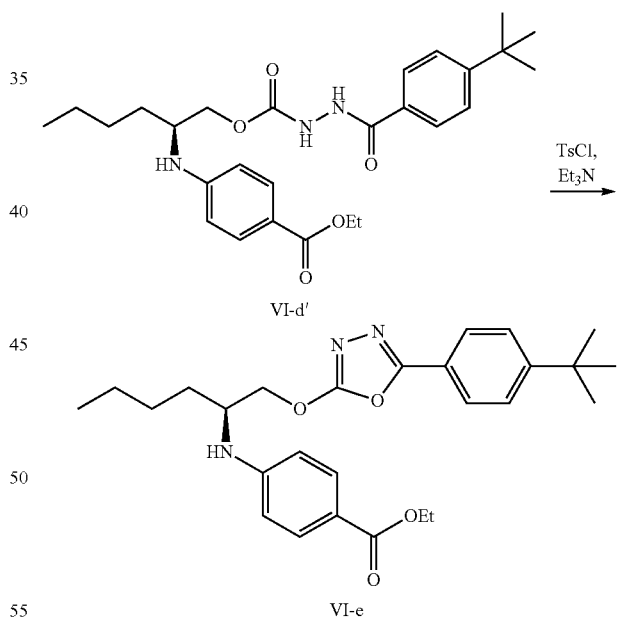

Compounds VI-d' (2.20 g, 4.42 mmol), TsCl (1.34, 13.26 mmol), and TEA (2 mL, 13.26 mmol) were mixed in ACN (20 mL) was stirred at room temperature for 1 hr. To this reaction solution, concentrated to remove methanol and extracted with EtOAc. The organic layer was washed with water and dried over anhydrous magnesium sulfate. It was filtered, the solvent evaporated under reduced pressure. Purification of the crude oil residue by column chromatography (EA:Hex=20:100) afforded colorless oil product, Compound VI-e.

Step VIII: Hydrolysis

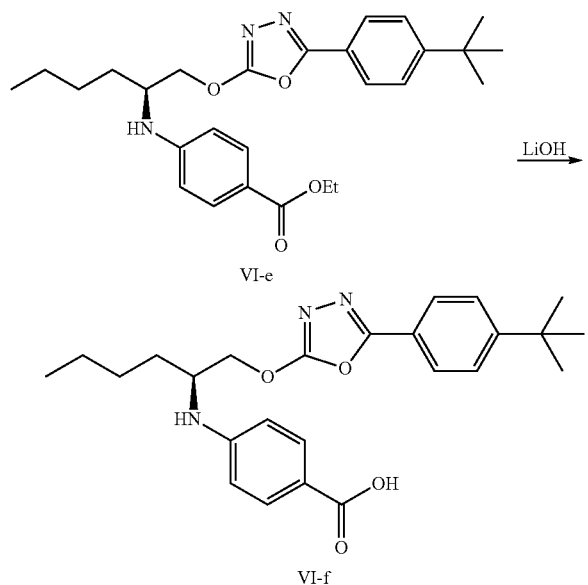

Compound VI-e (2.05 g, 4.42 mmol) was dissolved in dioxane (20 mL) followed by addition of 2M/LiOH(aq) 20 mL. The reaction mixture was heat to 60° C. for 1 hr. The reaction was monitored by TLC. With completion of the reaction, the solvent was removed by rotary evaporation and was added $HCl_{(aq)}$ to pH4-5. The mixture cpd. was extracted with EtOAc. The combined organic layer was dried with anhydrous $MgSO_4$ and concentrated in vacuo to give white solid crude, Compound VI-f (1.50 g, 78%, two steps yield).

Step IX: Amidation

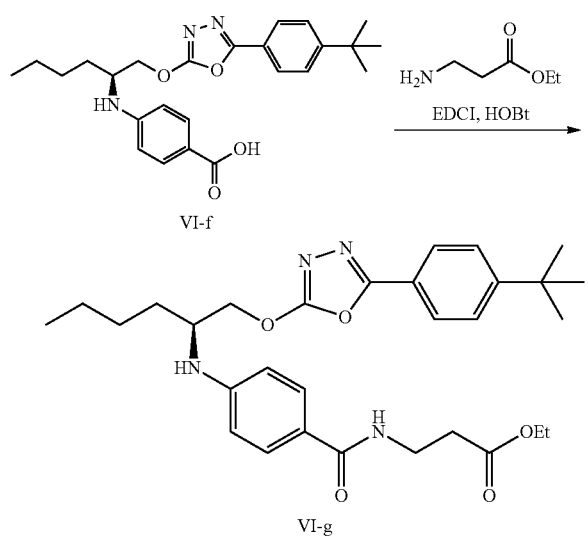

A solution of Compound VI-f, f-alanine ethyl ester hydrochloride, EDCI, $Et_3N$ and HOBt in dry THF. The reaction was stirred at room temperature for overnight then concentrated in vacuo. Water was added to the residue and the aqueous layer was extracted with ethyl acetate. It was further concentrated in vacuo to give a residue. Purification of the crude oil residue by column chromatography (EA:Hex=60:100) afforded colorless oil product, Compound VI-g.

Step X. Hydrolysis

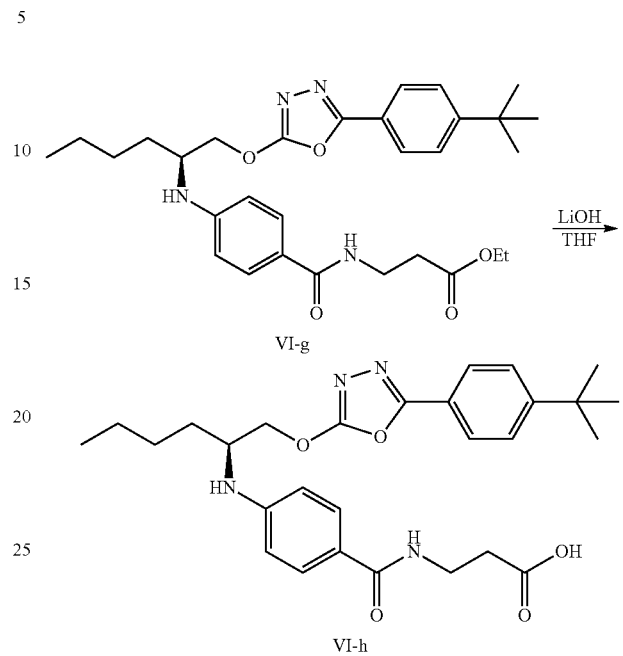

Compound VI-g (1.84 g, 3.43 mmol) was dissolved in THF (20 mL) followed by addition of 2M/LiOH(aq) 20 mL. The reaction mixture stirred at room temperature for overnight. The reaction was monitored by TLC. With completion of the reaction, the solvent was removed by rotary evaporation and was added $HCl_{(aq)}$ to pH4-5. The mixture cpd. was extracted with EtOAc. The combined organic layer was dried with anhydrous $MgSO_4$ and concentrated in vacuo to give brown oil product, Compound VI-h.

Example 22: Synthesis of Compounds 22-1 to 22-20

Compound 22-1:3-(4-(((2S,3S)-1-((5-(2-fluoro-4-(trifluoromethyl)phenyl)-1,3,4-oxadiazol-2-yl)oxy)-3-methylpentan-2-yl)amino)benzamido)propanoic Acid

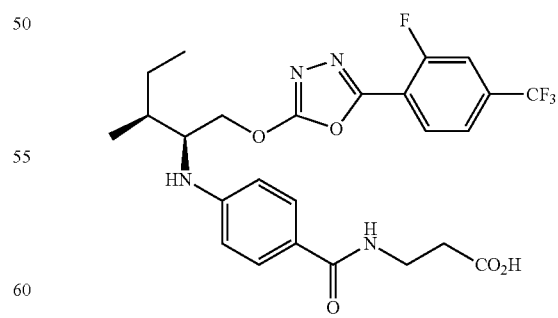

$^1$H NMR (400 MHz, DMSO-$d_6$): δ10.37 (d, J=2.0 Hz, 1H), 8.47 (m, 1H), 7.82-7.95 (m, 4H), 7.70-7.82 (m, 2H), 7.59-7.70 (m, 1H), 4.85 (dt, J=7.6, 4.0 Hz, 1H), 4.41-4.57 (m, 2H), 3.41-3.55 (m, 2H), 2.51-2.55 (m, 2H), 1.78-1.92 (m, 1H), 1.28-1.46 (m, 1H), 1.07-1.28 (m, 1H), 0.81-0.96 (m, 3H), 0.75 (d, J=6.8 Hz, 3H). MS (M+1): 539.

Compound 22-2: (S)-3-(4-((1-((5-(4-(trifluoromethoxy)phenyl)-1,3,4-oxadiazol-2-yl)oxy)hexan-2-yl)amino)benzamido)propanoic Acid

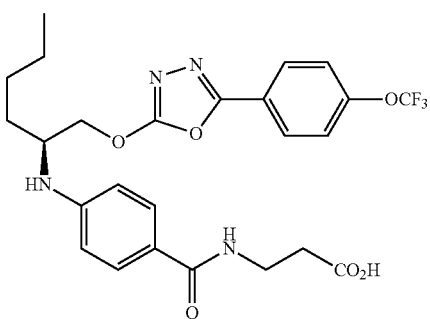 [SMILES: CCCC[C@@H](COc1nnc(-c2ccc(OC(F)(F)F)cc2)o1)Nc1ccc(C(=O)NCCC(=O)O)cc1]

¹H NMR (400 MHz, DMSO-d$_6$): δ10.40 (s, 1H), 8.40-8.56 (m, 1H), 7.92 (d, J=8.8 Hz, 2H), 7.85 (s, 4H), 7.43 (d, J=7.6 Hz, 2H), 4.63-4.86 (m, 1H), 4.48-4.61 (m, 1H), 4.24-4.44 (m, 1H), 2.52 (m, 2H), 1.46-1.75 (m, 2H), 1.07-1.39 (m, 4H), 0.82 (t, J=6.8 Hz, 3H). MS (M+1): 537.

Compound 22-3: (S)-3-(4-((1-((5-(2-fluoro-4-(trifluoromethyl)phenyl)-1,3,4-oxadiazol-2-yl)oxy)hexan-2-yl)amino)benzamido)propanoic Acid

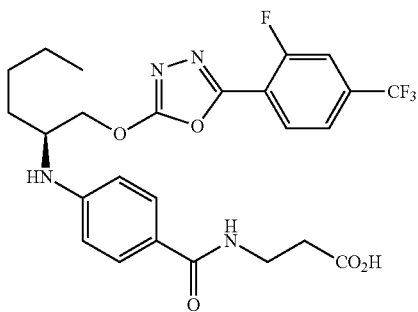 [SMILES: CCCC[C@@H](COc1nnc(-c2ccc(C(F)(F)F)cc2F)o1)Nc1ccc(C(=O)NCCC(=O)O)cc1]

¹H NMR (400 MHz, DMSO-d$_6$): δ 10.41 (d, J=2.0 Hz, 1H), 8.47 (t, J=5.6 Hz, 1H), 7.74-7.89 (m, 6H), 7.62-7.69 (m, 1H), 4.68-4.79 (m, 1H), 4.52-4.67 (m, 1H), 4.34-4.43 (m, 1H), 3.43-3.52 (m, 2H), 2.51-2.57 (m, 2H), 1.46-1.71 (m, 2H), 1.11-1.36 (m, 4H), 0.78-0.90 (m, 3H). MS (M+1): 539.

Compound 22-4: (S)-3-(4-((1-((5-(benzofuran-2-yl)-1,3,4-oxadiazol-2-yl)oxy)hexan-2-yl)amino)benzamido)propanoic Acid

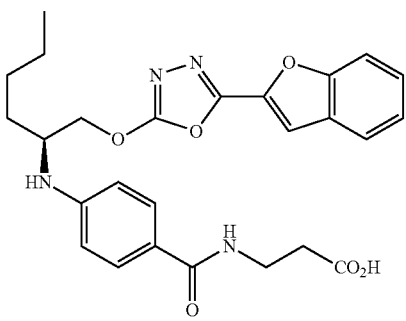 [SMILES: CCCC[C@@H](COc1nnc(-c2cc3ccccc3o2)o1)Nc1ccc(C(=O)NCCC(=O)O)cc1]

¹H NMR (400 MHz, DMSO-d$_6$): δ10.28 (s, 1H), 8.47 (t, J=5.6 Hz, 1H), 7.82-7.91 (m, 6H), 7.76 (d, J=7.8 Hz, 2H), 7.67 (d, J=8.3 Hz, 2H), 7.54 (s, 1H), 7.45 (ddd, J=8.4, 7.2, 1.5 Hz, 1H), 7.28-7.37 (m, 2H), 4.79 (br. s., 1H), 4.60 (t, J=8.1 Hz, 1H), 4.42 (dd, J=8.6, 3.2 Hz, 1H), 3.44-3.50 (m, 3H), 1.49-1.75 (m, 3H), 1.26 (td, J=14.3, 6.6 Hz, 6H), 0.83 (t, J=6.8 Hz, 3H). MS (M+1): 493.

Compound 22-5: (S)-3-(4-((1-((5-(4-(trifluoromethyl)phenyl)-1,3,4-oxadiazol-2-yl)oxy)hexan-2-yl)amino)benzamido)propanoic Acid

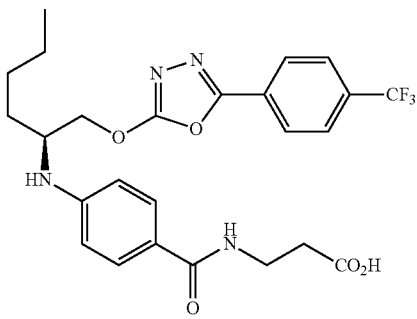 [SMILES: CCCC[C@@H](COc1nnc(-c2ccc(C(F)(F)F)cc2)o1)Nc1ccc(C(=O)NCCC(=O)O)cc1]

¹H NMR (400 MHz, DMSO-d$_6$): δ10.51 (s, 1H), 8.50 (t, J=5.4 Hz, 2H), 8.00 (d, J=7.8 Hz, 4H), 7.79-7.90 (m, 12H), 4.72-4.83 (m, 2H), 4.57 (t, J=7.8 Hz, 2H), 4.37 (dd, J=8.6, 3.2 Hz, 2H), 3.43-3.48 (m, 6H), 1.51-1.74 (m, 4H), 1.13-1.40 (m, 111H), 0.77-0.89 (m, 8H). MS (M+1): 521.

Compound 22-6: (S)-3-(4-((1-((5-(2,4-dichlorophenyl)-1,3,4-oxadiazol-2-yl)oxy)hexan-2-yl)amino)benzamido)propanoic Acid

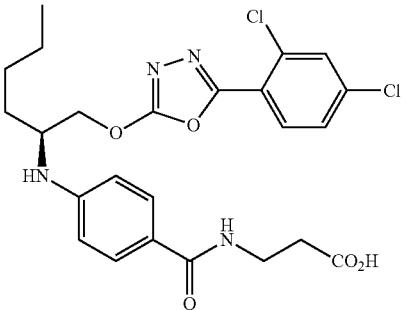 [SMILES: CCCC[C@@H](COc1nnc(-c2ccc(Cl)cc2Cl)o1)Nc1ccc(C(=O)NCCC(=O)O)cc1]

¹H NMR (400 MHz, DMSO-d$_6$): δ10.37 (s, 1H), 8.47 (t, J=5.4 Hz, 1H), 7.79-7.91 (m, 4H), 7.42-7.48 (m, 2H), 4.57 (t, J=8.1 Hz, 1H), 3.42-3.49 (m, 4H), 1.13-1.40 (m, 7H), 0.73-0.91 (m, 5H). MS (M+1): 522.

Compound 22-7: 3-(4-(((2S,3 S)-1-((5-(benzofuran-2-yl)-1,3,4-oxadiazol-2-yl)oxy)-3-methylpentan-2-yl)amino)benzamido)propanoic Acid

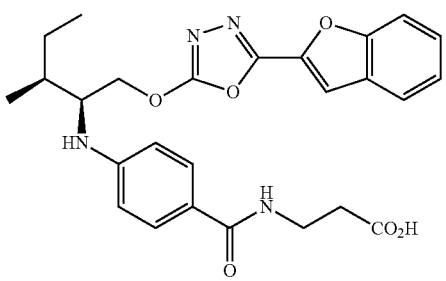 [SMILES: CC[C@H](C)[C@@H](COc1nnc(-c2cc3ccccc3o2)o1)Nc1ccc(C(=O)NCCC(=O)O)cc1]

¹H NMR (400 MHz, Acetone-d₆): δ 9.42 (s, 1H), 7.94-7.99 (m, 2H), 7.88-7.94 (m, 2H), 7.83 (br. s., 1H), 7.76 (d, J=7.8 Hz, 1H), 7.60 (dd, J=8.3, 1.0 Hz, 1H), 7.42-7.51 (m, 2H), 7.29-7.37 (m, 1H), 4.89-4.97 (m, 1H), 4.58-4.72 (m, 2H), 3.61-3.69 (m, 2H), 2.62-2.69 (m, 2H), 1.43-1.56 (m, 1H), 1.23-1.36 (m, 1H), 0.98 (t, J=7.3 Hz, 3H), 0.86 (d, J=6.8 Hz, 3H). MS (M+1): 493.

Compound 22-8: 3-(4-(((2S)-3-methyl-1-((5-(4-(trifluoromethoxy)phenyl)-1,3,4-oxadiazol-2-yl)oxy)pentan-2-yl)amino)benzamido)propanoic Acid

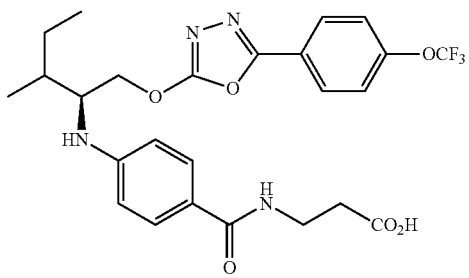 [SMILES: CCC(C)[C@@H](COc1nnc(-c2ccc(OC(F)(F)F)cc2)o1)Nc1ccc(C(=O)NCCC(=O)O)cc1]

¹H NMR (400 MHz, DMSO-d₆): δ10.35 (s, 1H), 8.46 (t, J=4.0 Hz, 1H), 7.93 (d, J=8.0 Hz, 2H), 7.87 (s, 4H), 7.43 (d, J=8.0 Hz, 2H), 4.85 (m, 1H), 4.39-4.54 (m, 2H), 3.47 (m, 2H), 2.45-2.58 (m, 2H), 1.77-1.90 (m, 1H), 1.30-1.44 (m, 1H), 1.12-1.22 (m, 1H), 0.84-0.96 (d, J=8.0 Hz, 3H), 0.76 (d, J=8.0 Hz, 3H). MS (M+1): 537.

Compound 22-9: 3-(4-(((2S)-1-((5-(4-(tert-butyl)phenyl)-1,3,4-oxadiazol-2-yl)oxy)-3-methylpentan-2-yl)amino)benzamido)propanoic Acid

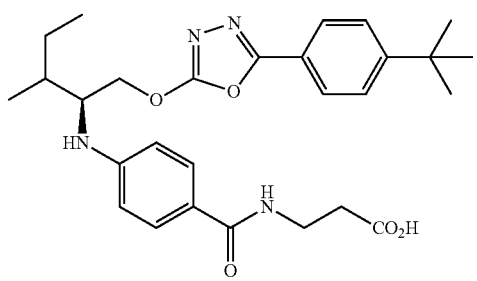 [SMILES: CCC(C)[C@@H](COc1nnc(-c2ccc(C(C)(C)C)cc2)o1)Nc1ccc(C(=O)NCCC(=O)O)cc1]

¹H NMR (400 MHz, DMSO-d₆): δ10.07 (s, 1H), 8.46 (s, 1H), 7.87 (s, 4H), 7.74 (d, J=8.0 Hz, 2H), 7.45 (d, J=8.0 Hz, 2H), 4.83-4.85 (m, 1H), 4.44-4.47 (m, 2H), 3.46-3.49 (m, 2H), 2.50-2.55 (m, 2H), 1.77-1.94 (m, 1H), 1.32-1.46 (m, 1H), 1.30 (s, 9H), 1.07-1.25 (m, 1H), 0.90 (t, J=8.0 Hz, 3H), 0.76 (d, J=8.0 Hz, 3H). MS (M+1): 509.

Compound 22-10: 3-(4-(((2S,3S)-3-methyl-1-((5-(4-(trifluoromethyl)phenyl)-1,3,4-oxadiazol-2-yl)oxy)pentan-2-yl)amino)benzamido)propanoic Acid

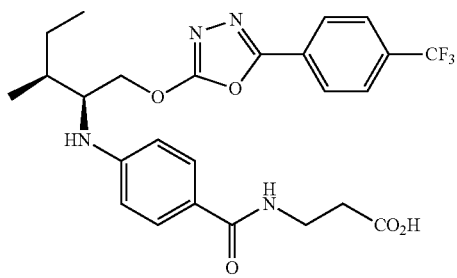 [SMILES: CC[C@H](C)[C@@H](COc1nnc(-c2ccc(C(F)(F)F)cc2)o1)Nc1ccc(C(=O)NCCC(=O)O)cc1]

¹H NMR (400 MHz, DMSO-d₆): δ10.48 (s, 1H), 8.48 (s, 1H), 8.00 (d, J=7.8 Hz, 2H), 7.87 (s, 4H), 7.82 (d, J=8.3 Hz, 4H), 4.81-4.90 (m, 1H), 4.42-4.54 (m, 2H), 3.46 (d, J=5.9 Hz, 3H), 1.78-1.90 (m, 1H), 1.38 (s, 1H), 1.12-1.23 (m, 1H), 0.90 (t, J=7.3 Hz, 3H), 0.76 (d, J=6.8 Hz, 3H). MS (M+1): 521

Compound 22-11: 3-(4-(((2S,3S)-1-((5-(2,4-dichlorophenyl)-1,3,4-oxadiazol-2-yl)oxy)-3-methylpentan-2-yl)amino)benzamido)propanoic Acid

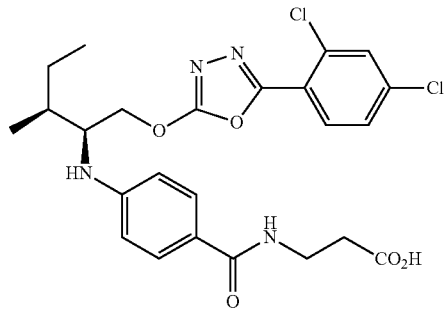 [SMILES: CC[C@H](C)[C@@H](COc1nnc(-c2ccc(Cl)cc2Cl)o1)Nc1ccc(C(=O)NCCC(=O)O)cc1]

¹H NMR (400 MHz, DMSO-d₆): δ10.33 (s, 1H), 8.47 (t, J=5.4 Hz, 2H), 7.80-7.91 (m, 7H), 7.45 (s, 3H), 4.84 (dt, J=7.6, 3.5 Hz, 1H), 4.43-4.55 (m, 3H), 1.08-1.46 (m, 3H), 0.88-0.92 (m, 3H), 0.74 (d, J=6.8 Hz, 3H). MS (M+1): 522.

Compound 22-12: (S)-3-(4-((1-((5-(benzofuran-2-yl)-1,3,4-oxadiazol-2-yl)oxy)-3-methylbutan-2-yl)amino)benzamido)propanoic Acid

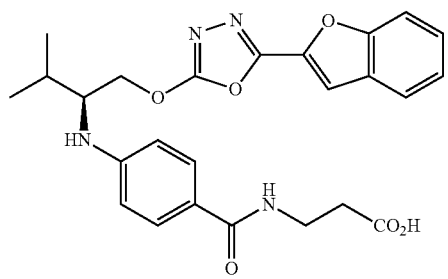 [SMILES: CC(C)[C@@H](COc1nnc(-c2cc3ccccc3o2)o1)Nc1ccc(C(=O)NCCC(=O)O)cc1]

¹H NMR (400 MHz, DMSO-d₆): δ10.26 (s, 1H), 8.48 (t, J=5.4 Hz, 2H), 7.83-7.93 (m, 8H), 7.76 (d, J=7.3 Hz, 2H), 7.67 (d, J=8.3 Hz, 2H), 7.53 (d, J=1.0 Hz, 2H), 7.45 (td, J=7.7, 1.2 Hz, 2H), 7.29-7.37 (m, 2H), 4.76-4.85 (m, 1H), 4.49-4.58 (m, 2H), 3.44-3.50 (m, 2H), 2.11 (d, J=3.4 Hz, 1H), 0.92 (d, J=6.8 Hz, 3H), 0.78 (d, J=6.8 Hz, 3H). MS (M+1): 479.

Compound 22-13: (S)-3-(4-((3-methyl-1-((5-(4-(trifluoromethyl)phenyl)-1,3,4-oxadiazol-2-yl)oxy)butan-2-yl)amino)benzamido)propanoic Acid

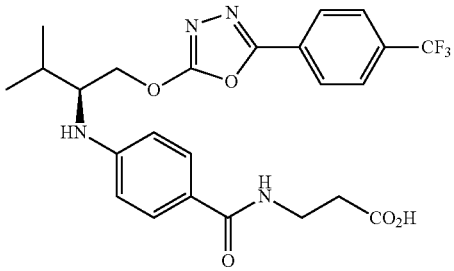 [SMILES: CC(C)[C@@H](COc1nnc(-c2ccc(C(F)(F)F)cc2)o1)Nc1ccc(C(=O)NCCC(=O)O)cc1]

¹H NMR (400 MHz, DMSO-d₆): δ10.49 (s, 1H), 8.52 (t, J=5.4 Hz, 2H), 8.00 (d, J=8.3 Hz, 5H), 7.84-7.92 (m, 9H), 7.82 (d, J=8.3 Hz, 5H), 4.74-4.83 (m, 2H), 4.48 (d, J=5.9 Hz, 5H), 3.42-3.48 (m, 6H), 2.46 (t, J=7.1 Hz, 5H), 2.11 (td, J=6.8, 3.4 Hz, 2H), 0.91 (d, J=7.3 Hz, 6H), 0.78 (d, J=6.8 Hz, 3H). MS (M+1): 507.

Compound 22-14: (S)-3-(4-((1-((5-(2,4-dichlorophenyl)-1,3,4-oxadiazol-2-yl)oxy)-3-methylbutan-2-yl)amino)benzamido)propanoic Acid

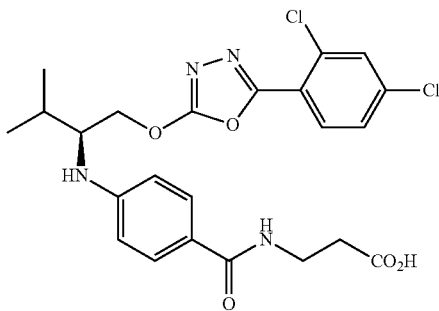 [SMILES: CC(C)[C@@H](COc1nnc(-c2ccc(Cl)cc2Cl)o1)Nc1ccc(C(=O)NCCC(=O)O)cc1]

¹H NMR (400 MHz, DMSO-d₆): δ8.05 (t, J=5.4 Hz, 1H), 7.85-7.92 (m, 2H), 7.83 (d, J=8.3 Hz, 3H), 7.62-7.65 (m, 2H), 7.61 (d, J=8.3 Hz, 2H), 7.57 (d, J=8.8 Hz, 3H), 7.22-7.43 (m, 9H), 7.10 (d, J=8.8 Hz, 1H), 4.12 (d, J=8.3 Hz, 1H), 3.79 (dd, J=13.9, 6.6 Hz, 2H), 2.98 (d, J=7.8 Hz, 3H), 2.46 (t, J=7.3 Hz, 3H), 1.00 (d, J=6.4 Hz, 4H), 0.90 (d, J=6.4 Hz, 3H). MS (M+1): 508.

Compound 22-15: (S)-3-(4-((3-methyl-1-((5-(4-(trifluoromethoxy)phenyl)-1,3,4-oxadiazol-2-yl)oxy)butan-2-yl)amino)benzamido)propanoic Acid

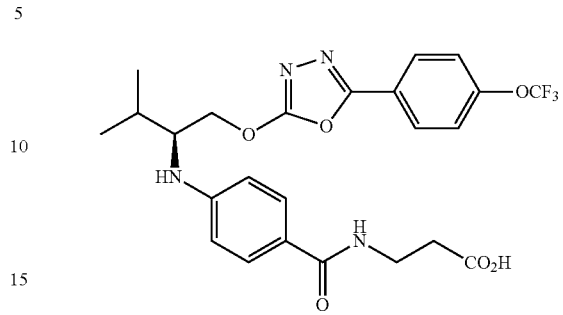

¹H NMR (400 MHz, DMSO-d₆): δ12.19 (br. s., 1H), 10.35 (s, 1H), 8.46 (m, 1H), 7.82-7.95 (m, 6H), 7.43 (d, J=8.0 Hz, 2H), 4.70-4.81 (m, 1H), 4.47 (m, 2H), 3.40-3.62 (m, 2H), 2.51-2.55 (m, 2H), 2.06-2.19 (m, 1H), 0.91 (d, J=6.8 Hz, 3H), 0.78 (d, J=6.8 Hz, 3H). MS (M+1): 523.

Compound 22-16: (S)-3-(4-((1-((5-(4-(tert-butyl)phenyl)-1,3,4-oxadiazol-2-yl)oxy)-3-methylbutan-2-yl)amino)benzamido)propanoic Acid

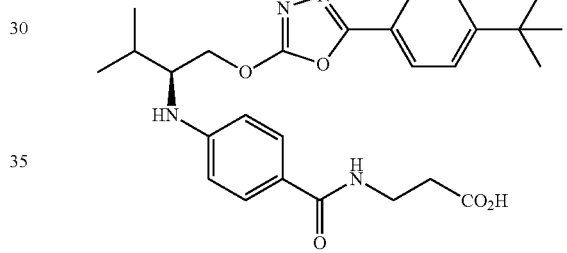

¹H NMR (400 MHz, DMSO-d₆): δ10.08 (s, 1H), 8.46 (s, 1H), 7.87-7.92 (m, 4H), 7.74 (d, J=8.4 Hz, 2H), 7.42-7.56 (m, 2H), 4.76-4.77 (m, 1H), 4.46-4.47 (m, 2H), 3.46-3.48 (m, 2H), 2.50-2.57 (m, 2H), 1.30 (s, 9H), 0.91 (d, J=6.8 Hz, 3H), 0.78 (d, J=6.8 Hz, 3H). MS (M+1): 495.

Compound 22-17: (S)-3-(4-((1-((5-(2-fluor-4-(trifluoromethyl)phenyl)-1,3,4-oxadiazol-2-yl)oxy)-3-methylbutan-2-yl)amino)propanoic Acid

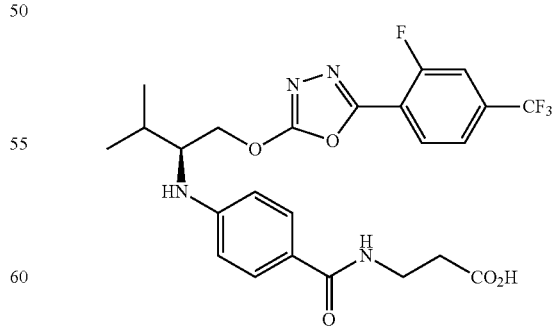

¹H NMR (400 MHz, DMSO-d₆): δ10.38 (s, 1H), 8.47 (t, J=5.6 Hz, 1H), 7.74-7.91 (m, 6H), 7.62-7.69 (m, 1H), 4.67-4.81 (m, 1H), 4.42-4.62 (m, 2H), 3.37-3.59 (m, 2H), 2.46-2.55 (m, 2H), 1.98-2.16 (m, 1H), 0.89-0.96 (d, J=6.4 Hz, 3H), 0.76 (d, J=6.4 Hz, 3H). MS (M+1): 525.

Compound 22-18: (S)-3-(4-((1-((5-(4-(tert-butyl)phenyl)-1,3,4-oxadiazol-2-yl)oxy)hexan-2-yl)amino)benzamido)propanoic Acid

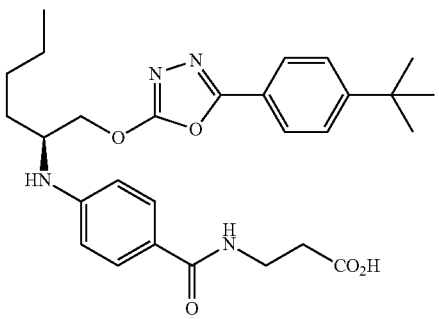 [SMILES: CCCC[C@@H](COc1nnc(-c2ccc(C(C)(C)C)cc2)o1)Nc1ccc(C(=O)NCCC(=O)O)cc1]

$^1$H NMR (400 MHz, DMSO-$d_6$): δ12.21 (br. s., 1H), 10.12 (s, 1H), 8.47 (t, J=5.6 Hz, 1H), 7.87 (s, 4H), 7.76 (d, J=8.4 Hz, 2H), 7.45 (d, J=8.4 Hz, 2H), 4.74 (m, 1H), 4.54 (m, 1H), 4.35 (m, 1H), 3.40-3.59 (m, 2H), 3.35 (m, 1H), 2.44-2.61 (m, 2H), 1.58-1.66 (m, 1H), 1.16-1.29 (m, 13H), 0.83 (t, J=6.8 Hz, 3H). MS (M+1): 509.

Compound 22-19: 3-(4-(((2S,3S)-1-((5-(2-chloro-4-(trifluoromethyl)phenyl)-1,3,4-oxadiazol-2-yl)oxy-3-methylpentan-2-yl)amino)benzamido)propanoic Acid

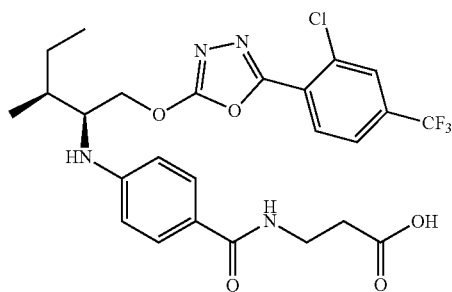 [SMILES: CC[C@H](C)[C@@H](COc1nnc(-c2ccc(C(F)(F)F)cc2Cl)o1)Nc1ccc(C(=O)NCCC(=O)O)cc1]

$^1$H NMR (400 MHz, CDCl$_3$): δ 7.72-7.85 (m, 3H), 7.60-7.70 (m, 3H), 7.50-7.59 (m, 2H), 4.60 (dt, J=7.8, 3.9 Hz, 1H), 4.49 (t, J=8.0 Hz, 1H), 4.32-4.37 (m, 1H), 3.65 (t, J=6.0 Hz, 2H), 2.64 (t, J=6.0 Hz, 2H), 1.84-1.97 (m, 1H), 1.09-1.34 (m, 2H), 0.83-0.96 (t, J=8.0 Hz, 3H), 0.78 (d, J=6.8 Hz, 3H). MS (M+1): 555.

Compound 22-20: Methyl 3-(4-(((2S,3S)-1-((5-(2-fluoro-4-(trifluoromethyl)phenyl)-1,3,4-oxadiazol-2-yl) oxy)-3-methylpentan-2-yl)amino)benzamido)propanoate $^1$H NMR (400 MHz, CDCl$_3$): δ 8.24 (t, J=7.6 Hz, 1H), 7.75 (d, J=8.8 Hz, 2H), 7.65 (d, J=8.0 Hz, 2H), 7.49 (dd, J=8.0, 1.2 Hz, 1H), 7.36 (d, J=8.0 Hz, 1H), 7.29 (dd, J=8.0 Hz, 8.0 Hz, 1H), 4.56-4.59 (m, 1H), 4.50 (t, J=8.4 Hz, 1H), 4.37 (dd, J=8.0, 4.0 Hz, 1H), 3.66 (s, 3H), 3.63 (t, J=6.4 Hz, 2H), 2.62 (t, J=6.4 Hz, 2H), 1.85-1.99 (m, 1H), 1.23-1.36 (m, 1H), 1.09-1.23 (m, 1H), 0.91 (t, J=8.0 Hz, 3H), 0.78 (d, J=6.8 Hz, 3H). MS (M+1): 553.

Reaction Scheme VII illustrates the general procedures that can be used to synthesize the following compounds of the formula (I) of the present disclosure.

Reaction Scheme VII

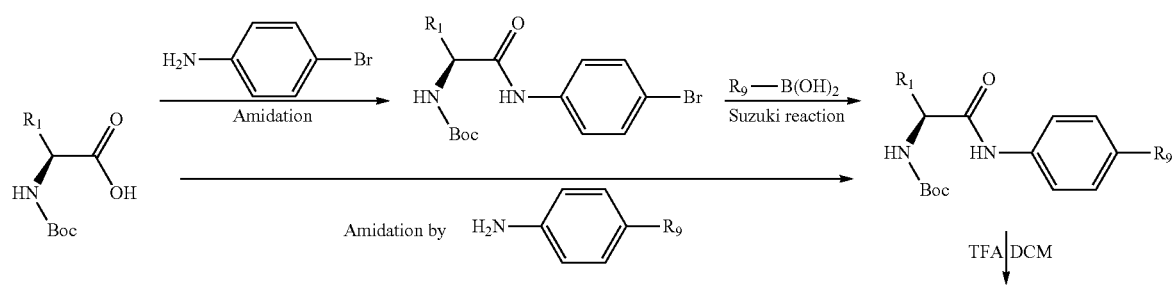

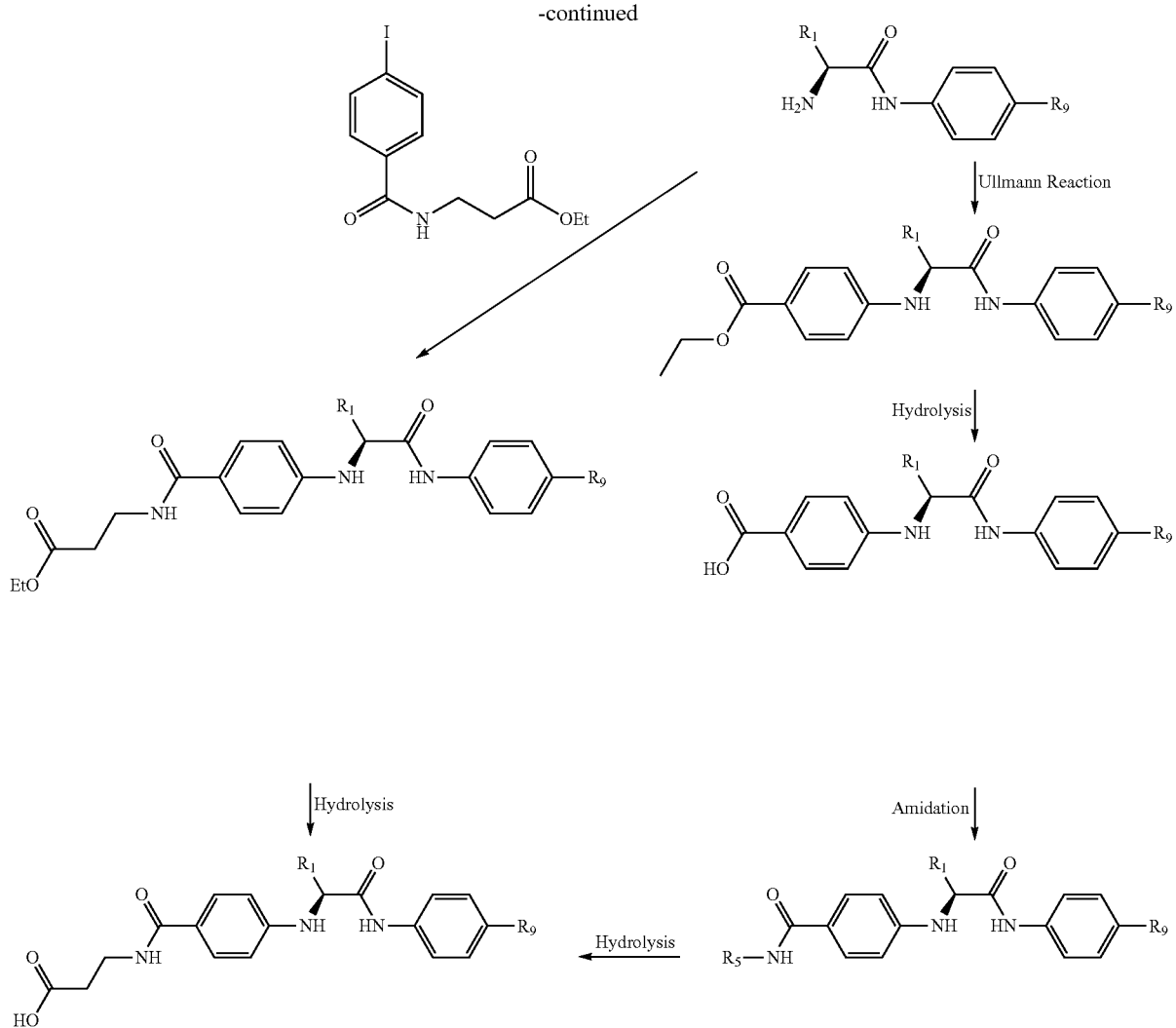
Herein, Reaction Scheme VII' as one example of Reaction Scheme VII illustrates the general procedures that can be used to synthesize the following compounds of the formula (I) of the present disclosure.
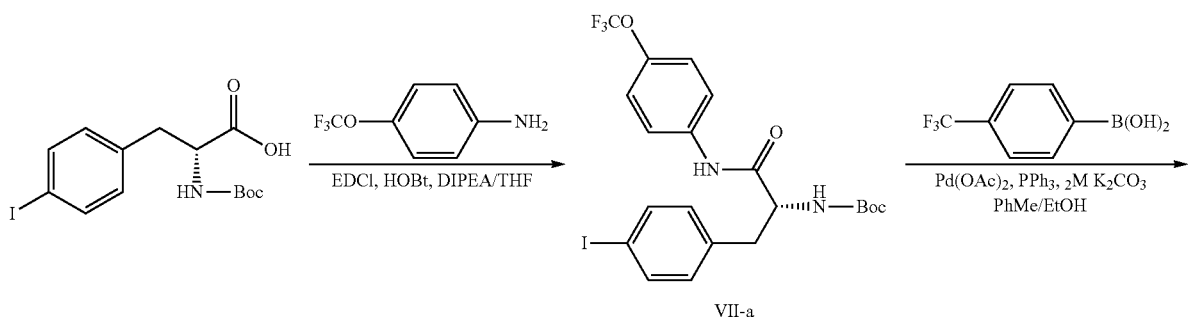

-continued
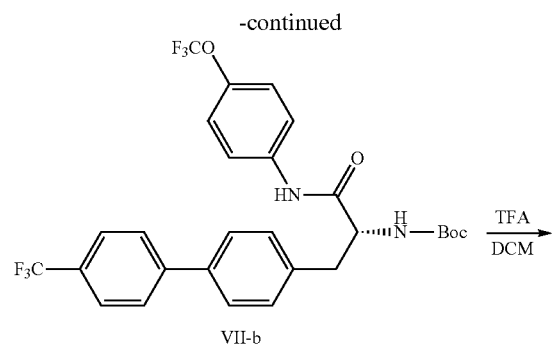
VII-b
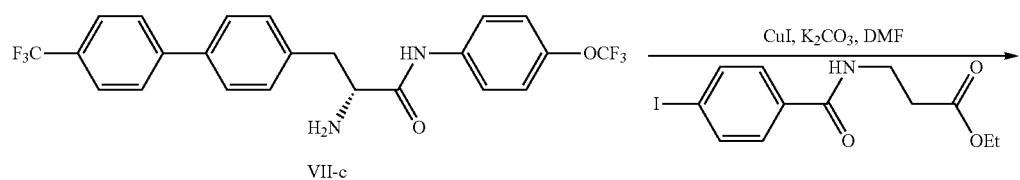
VII-c
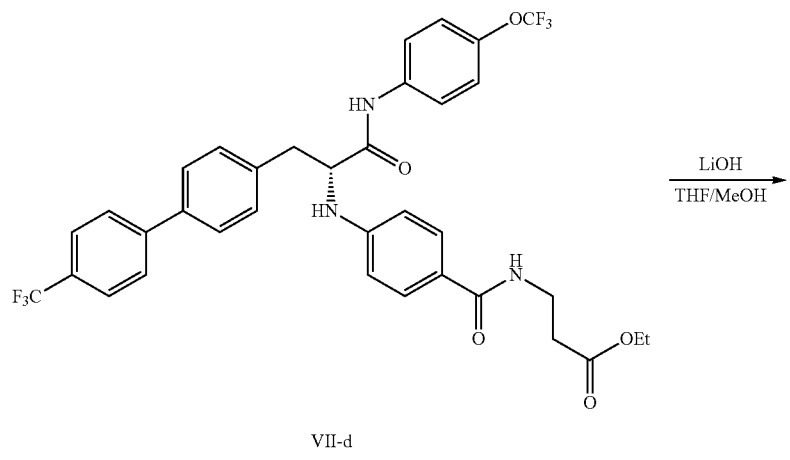
VII-d
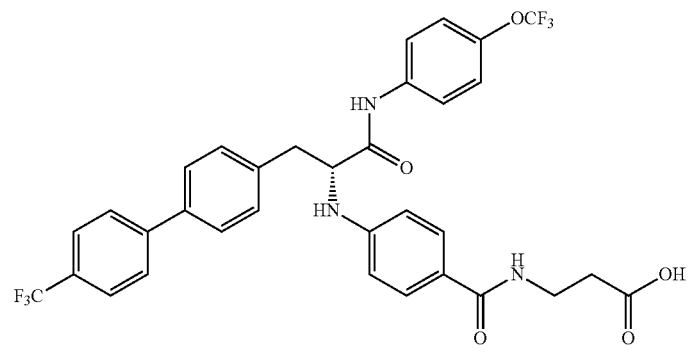
VII-e

Step I: Synthesis of (R)-tert-butyl 3-(4-iodophenyl)-1-oxo-1-(4-(trifluoromethoxy)phenylamino) propan-2-ylcarbamate

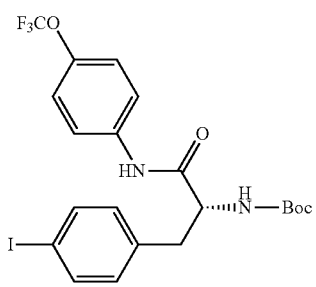

VII-a

To a mixture of (R)-2-((tert-butoxycarbonyl)amino)-3-(4-iodophenyl)propanoic acid (3.91 g, 10 mmol), EDCI (2.30 g, 12 mmol) and HOBt (1.51 g, 11 mmol) in anhydrous THF (50 ml) was added and stirred at 0° C. for 30 min. 4-(trifluoromethoxy)benzenamine (2.13 g, 12 mmol) and N-Ethyldiisopropylamine (3.48 ml, 20 mmol) were added to the mixture and the reaction was stirred at room temperature for 16 hours. The reaction mixture was washed with 1N HCl and then saturated NaHCO₃. The organic layer was dried over anhydrous sodium sulfate and concentrated in vacuo. The crude product was purified by column chromatography (silica gel, ethyl acetate:hexane 1:4) to give the desired product, Compound VII-a. Colorless liquid, yield 4.4 g, 80%.

Step II. Synthesis of tert-butyl (R)-(1-oxo-3-(4'-(trifluoromethyl)-[1,1'-biphenyl]-4-yl)-1-((4-(trifluoromethyl)phenyl)amino)propan-2-yl)carbamate

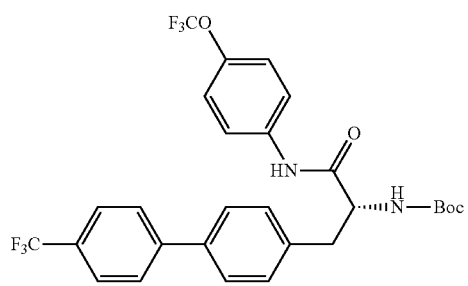

VII-b

A solution of tert-butyl (R)-(3-(4-iodophenyl)-1-oxo-1-((4-(trifluoromethyl) phenyl)amino)propan-2-yl)carbamate (1.50 g, 2.81 mmol), 4-trifluoromethylphenyl boronic acid (640 mg, 3.37 mmol), palladium acetate(II) (65 mg, 0.28 mmol), triphenylphosphate (150 mg, 0.56 mmol) and 2M K₂CO₃ (5 mL, 9.83 mmol) in EtOH/PhMe (1 mL/6 mL) was heated at 90° C. for 18 h. The reaction mixture was cooled, poured into half-saturated NaHCO₃(aq), and extracted with EtOAc. The combined organic layers were dried over MgSO₄ and concentrated in vacuo. The residue was purified by silica gel chromatography to afford the tert-butyl (R)-(1-oxo-3-(4'-(trifluoromethyl)-[1,1'-biphenyl]-4-yl)-1-((4-(trifluoromethyl)phenyl)amino)propan-2-yl)carbamate (871 mg, 56.2%).

Step III: Synthesis of (R)-2-amino-3-(4'-(trifluoromethyl)-[1,1'-biphenyl]-4-yl)-N-(4-(trifluoromethyl)phenyl)propanamide

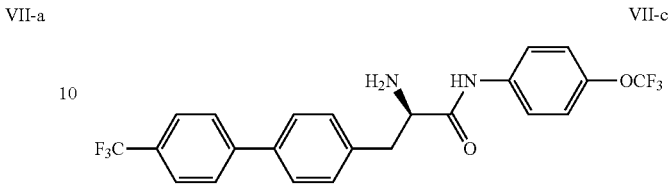

VII-c

The compound tert-butyl (R)-(1-oxo-3-(4'-(trifluoromethyl)-[1,1'-biphenyl]-4-yl)-1-((4-(trifluoromethyl)phenyl)amino)propan-2-yl)carbamate (871 mg, 1.58 mmol) was suspended in trifluoroacetic acid (1.8 mL, 23.65 mmol) in anhydrous dichloromethane (20 mL) at room temperature for overnight. After reaction, excess trifluoroacetic acid was neutralized by dropwise addition of Na₂CO₃(aq) until pH=10. Then it was extracted with CH₂Cl₂. The combined organic layer was dried with anhydrous MgSO₄ and concentrated in vacuo to give crude product. It was further purified by silica gel flash column chromatography using dichloromethane and methanol as eluent to give compound (R)-2-amino-3-(4'-(trifluoromethyl)-[1,1'-biphenyl]-4-yl)-N-(4-(trifluoromethyl)phenyl)propanamide (695.2 m, 97.5%).

Step IV: Synthesis of ethyl (R)-3-(4-((1-oxo-3-(4'-(trifluoromethyl)-[1,1'-biphenyl]-4-yl)-1-((4-(trifluoromethyl)phenyl)amino)propan-2-yl)amino)benzamido)propanoate

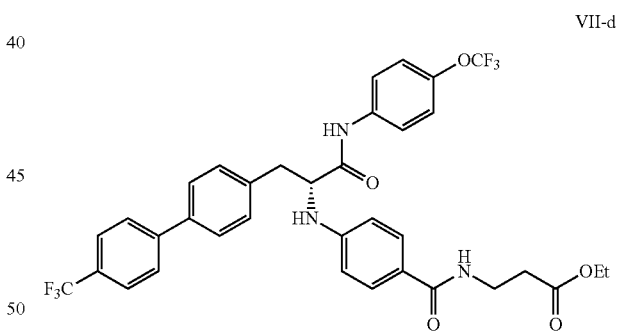

VII-d

A seal tube was charged with CuI (21 mg, 0.11 mmol, 10 mol %), K₂CO₃ (465 mg, 3.36 mmol), ethyl 3-(4-iodobenzamido)propanoate (430 mg, 1.23 mmol), and (R)-2-amino-3-(4'-(trifluoromethyl)-[1,1'-biphenyl]-4-yl)-N-(4-(trifluoromethyl)phenyl)propanamide (506 mg, 1.12 mmol). The seal tube was fitted with a septum and purged with nitrogen before added DMF (1.5 mL). Next, the test tube was capped and stirred in an oil bath at 100° C. for 2 d. The reaction mixture was cooled to room temperature and filtered, washing well with ethyl acetate. The filtrate (25 mL) was washed with NH₄Cl and the acid extracts were washed with EtOAc. The organic layers were dried over MgSO₄, filtered, and concentrated. It was further purified by silica gel flash column chromatography using dichloromethane and methanol as eluent to give compound ethyl (R)-3-(4-((1-oxo-3-

(4'-(trifluoromethyl)-[1,1'-biphenyl]-4-yl)-1-((4-(trifluoromethyl)phenyl)amino)propan-2-yl)amino)benzamido)propanoate (385 mg, 51.3%).

Step V: Synthesis of (R)-3-(4-((1-oxo-3-(4'-(trifluoromethyl)-[1,1'-biphenyl]4-yl)-1-((4-(trifluoromethyl)phenyl)amino)propan-2-yl)amino)benzamido)propanoic Acid

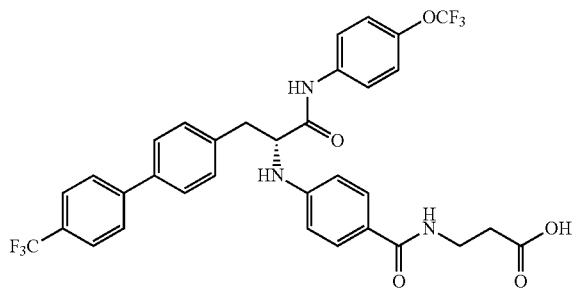

VII-e

Ethyl (R)-3-(4-((1-oxo-3-(4'-(trifluoromethyl)-[1,1'-biphenyl]-4-yl)-1-((4-(trifluoromethyl)phenyl)amino)propan-2-yl)amino)benzamido)propanoate (100 mg, 0.15 mmol) was dissolved in MeOH (2 mL)/THF (2 mL) followed by addition of LiOH (2.0 M, 1.0 mL). The reaction mixture was stirred at room temperature for overnight. The reaction was monitored by TLC. With completion of the reaction, the solvent was removed by rotary evaporation and HCl (2.0 M, 5 mL) was added to the mixture. The white solid was collected by suction filtration and air-dried to give the corresponding acid to yield title compound (R)-3-(4-((1-oxo-3-(4'-(trifluoromethyl)-[1,1'-biphenyl]-4-yl)-1-((4-(trifluoromethyl)phenyl)amino)propan-2-yl)amino)benzamido)propanoic acid (51.9 mg, 58%).

Example 23: Synthesis of Compounds 23-1 to 23-35

Compound 23-1: (S)-3-(4-((1-((2',4'-dichloro-[1,1'-biphenyl]-4-yl)amino)-4-methyl-1-oxopentan-2-yl)amino)benzamido)propanoic Acid

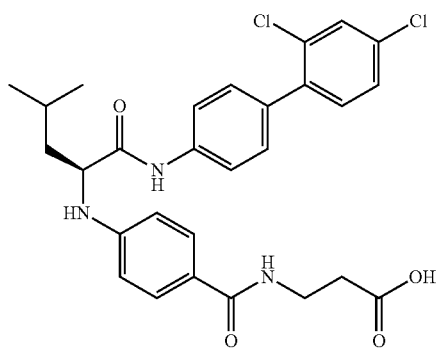 [SMILES: CC(C)C[C@H](Nc1ccc(C(=O)NCCC(=O)O)cc1)C(=O)Nc1ccc(-c2ccc(Cl)cc2Cl)cc1]

The mass data of this compound is listed in the following Table 23.

Compound 23-2: (S)-3-(4-((1-((2',4'-dichloro-[1,1'-biphenyl]-4-yl)amino)-1-oxo-3-phenylpropan-2-yl)amino)benzamido)propanoic Acid

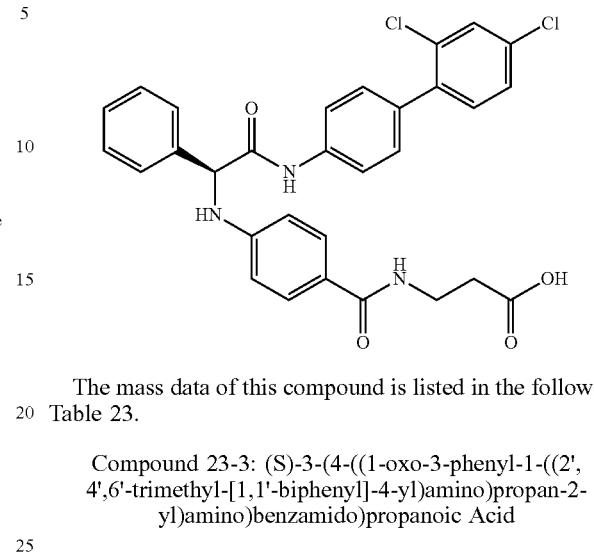

The mass data of this compound is listed in the following Table 23.

Compound 23-3: (S)-3-(4-((1-oxo-3-phenyl-1-((2',4',6'-trimethyl-[1,1'-biphenyl]-4-yl)amino)propan-2-yl)amino)benzamido)propanoic Acid

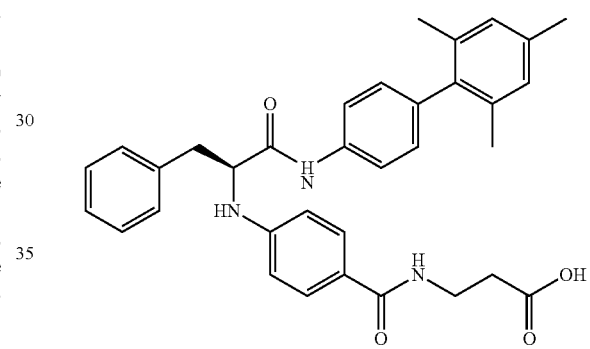

The mass data of this compound is listed in the following Table 23.

Compound 23-4: (S)-3-(4-((4-methyl-1-oxo-1-((4'-(trifluoromethyl)-[1,1'-biphenyl]-4-yl)amino)pentan-2-yl)amino)benzamido)propanoic Acid

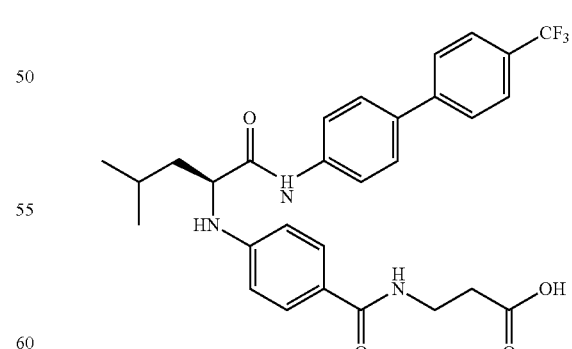

$^1$H NMR (400 MHz, DMSO-$d_6$): δ11.78-12.46 (m, 1H), 10.03-10.42 (m, 1H), 8.00-8.09 (m, 1H), 7.85 (s, 2H), 7.79 (s, 2H), 7.72 (d, J=5.9 Hz, 4H), 7.59 (s, 2H), 6.67 (d, J=8.8 Hz, 2H), 6.35-6.43 (m, 1H), 4.05-4.18 (m, 1H), 3.36-3.42 (m, 2H), 2.45 (s, 2H), 1.56-1.85 (m, 3H), 0.98 (d, J=6.4 Hz, 3H), 0.92 (d, J=6.4 Hz, 3H). MS (M+1): 542.

Compound 23-5: (S)-3-(4-((1-((4-(benzofuran-2-yl)phenyl)amino)-4-methyl-1-oxopentan-2-yl)amino)benzamido)propanoic Acid

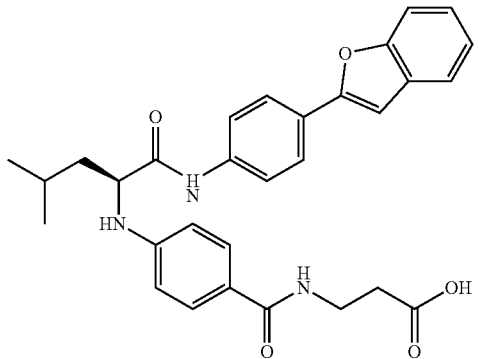

The mass data of this compound is listed in the following Table 23.

Compound 23-6: Ethyl (S)-3-(4-((1-((4-(benzofuran-2-yl)phenyl)amino)-4-methyl-1-oxopentan-2-yl)amino)benzamido)propanoate

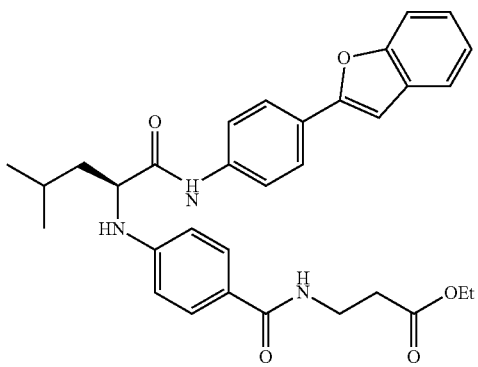 [SMILES: CCOC(=O)CCNC(=O)c1ccc(N[C@@H](CC(C)C)C(=O)Nc2ccc(-c3cc4ccccc4o3)cc2)cc1]

The mass data of this compound is listed in the following Table 23.

Compound 23-7: Ethyl (S)-3-(4-((1-((4-(benzofuran-2-yl)phenyl)amino)-1-oxo-3-phenylpropan-2-yl)amino)benzamido)propanoate

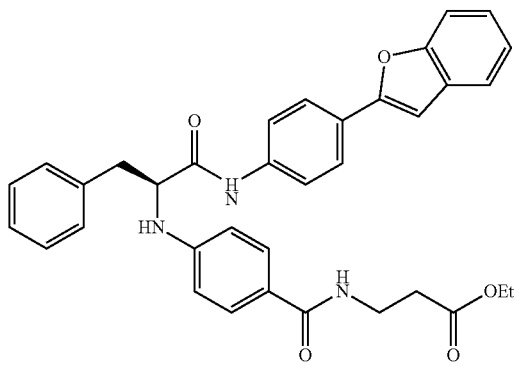 [SMILES: CCOC(=O)CCNC(=O)c1ccc(N[C@@H](Cc2ccccc2)C(=O)Nc2ccc(-c3cc4ccccc4o3)cc2)cc1]

The mass data of this compound is listed in the following Table 23.

Compound 23-8: (S)-3-(4-((1-((4-(benzofuran-2-yl)phenyl)amino)-1-oxo-3-phenylpropan-2-yl)amino)benzamido)propanoic Acid

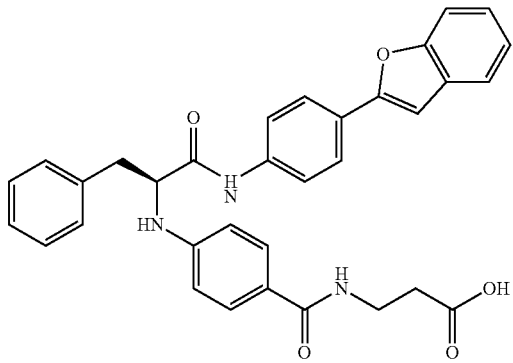 [SMILES: O=C(O)CCNC(=O)c1ccc(N[C@@H](Cc2ccccc2)C(=O)Nc2ccc(-c3cc4ccccc4o3)cc2)cc1]

$^1$H NMR (400 MHz, DMSO-$d_6$): δ10.32 (s, 1H), 8.05 (t, J=5.6 Hz, 1H), 7.82-7.88 (m, 4H), 7.69 (d, J=8.8 Hz, 2H), 7.55-7.65 (m, 4H), 7.34-7.39 (m, 2H), 7.16-7.32 (m, 6H), 6.66 (d, J=8.8 Hz, 3H), 6.58 (d, J=8.8 Hz, 2H), 4.37 (d, J=5.9 Hz, 1H), 3.00-3.17 (m, 2H), 2.44 (t, J=7.1 Hz, 2H). MS (M+1): 548.

Compound 23-9: Ethyl (S)-3-(4-((1-((4-(benzofuran-2-yl)phenyl)amino)-3-(4-fluorophenyl)-1-oxopropan-2-yl)amino)benzamido)propanoate

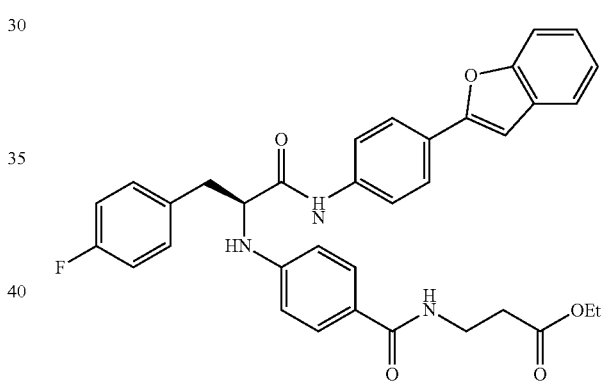

The mass data of this compound is listed in the following Table 23.

Compound 23-10: (S)-3-(4-((1-((4-(benzofuran-2-yl)phenyl)amino)-3-(4-fluorophenyl)-1-oxopropan-2-yl)amino)benzamido)propanoic Acid

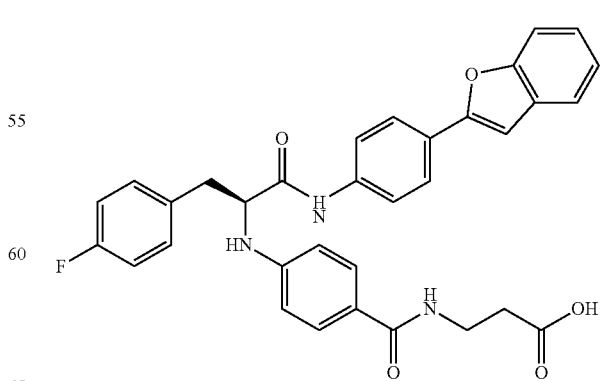

The mass data of this compound is listed in the following Table 23.

Compound 23-11: Ethyl (S)-3-(4-((1-((4-(benzo[b]thiophen-2-yl)phenyl)amino)-4-methyl-1-oxopentan-2-yl)amino)benzamido)propanoate

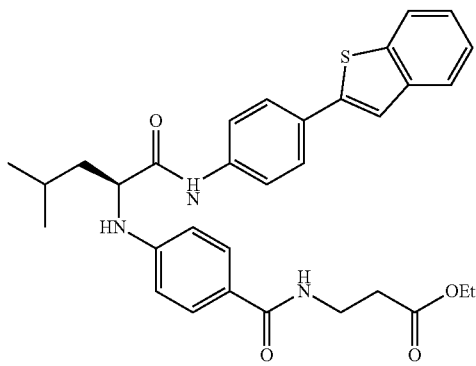 [SMILES: CCOC(=O)CCNC(=O)c1ccc(N[C@@H](CC(C)C)C(=O)Nc2ccc(-c3cc4ccccc4s3)cc2)cc1]

The mass data of this compound is listed in the following Table 23.

Compound 23-12: (S)-3-(4-((1-((4-(benzo[b]thiophen-2-yl)phenyl)amino)-4-methyl-1-oxopentan-2-yl)amino)benzamido)propanoic Acid

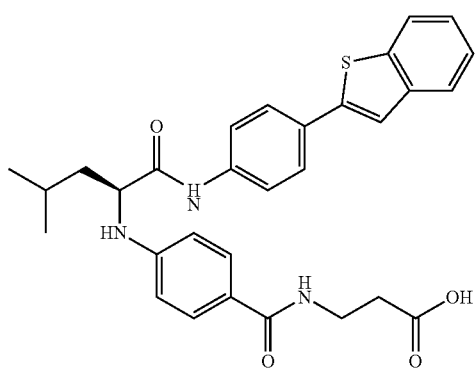

¹H NMR (400 MHz, DMSO-d₆): δ10.25 (s, 1H), 8.05 (s, 1H), 7.94 (d, J=7.8 Hz, 1H), 7.81 (d, J=7.3 Hz, 1H), 7.69-7.78 (m, 5H), 7.60 (d, J=8.8 Hz, 3H), 7.36 (dd, J=7.6, 1.2 Hz, 1H), 7.34 (dd, J=7.6, 1.2 Hz, 1H), 6.67 (d, J=8.8 Hz, 3H), 6.39 (d, J=8.3 Hz, 1H), 4.05-4.17 (m, 1H), 3.37-3.41 (m, 3H), 2.45 (t, J=7.1 Hz, 3H), 1.55-1.86 (m, 4H), 0.98 (d, J=6.4 Hz, 3H), 0.92 (d, J=6.4 Hz, 3H). MS (M+1): 530.

Compound 23-13: Ethyl (S)-3-(4-((1-((4-(benzofuran-2-yl)phenyl)amino)-3-(naphthalen-1-yl)-1-oxopropan-2-yl)amino)benzamido)propanoate

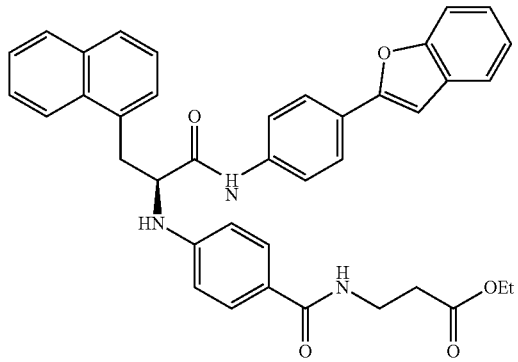 [SMILES: CCOC(=O)CCNC(=O)c1ccc(N[C@@H](Cc2cccc3ccccc23)C(=O)Nc2ccc(-c3cc4ccccc4o3)cc2)cc1]

Compound 23-14: (S)-3-(4-((1-((2',4'-dichloro-[1,1'-biphenyl]-4-yl)amino)-1-oxo-3-phenylpropan-2-yl)amino)benzamido)propanoic Acid

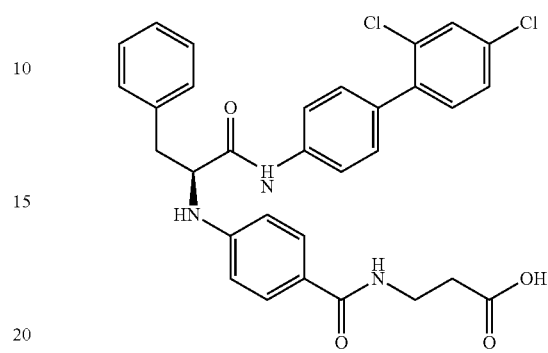

The mass data of this compound is listed in the following Table 23.

Compound 23-15: Ethyl (S)-3-(4-((1-((2',4'-dichloro-[1,1'-biphenyl]-4-yl)amino)-1-oxo-3-phenylpropan-2-yl)amino)benzamido)propanoate

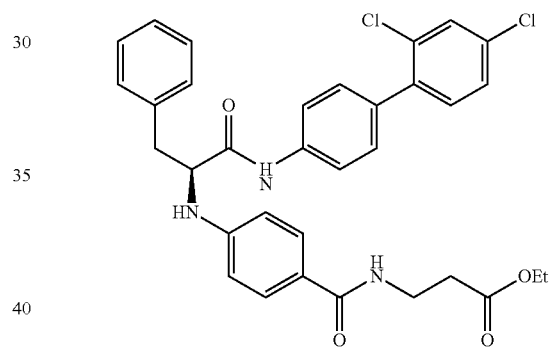

The mass data of this compound is listed in the following Table 23.

Compound 23-16: (R)-3-(4-((1-((4-(benzofuran-2-yl)phenyl)amino)-4-methyl-1-oxopentan-2-yl)amino) benzamido)propanoic Acid

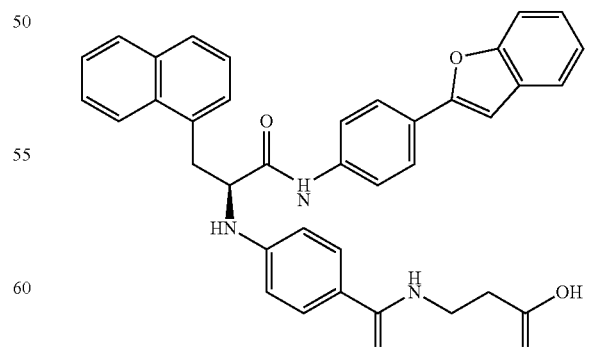

¹H NMR (400 MHz, DMSO-d₆): δ 8.83 (s, 1H), 8.29 (t, J=5.6 Hz, 2H), 7.74-7.86 (m, 7H), 7.56-7.64 (m, 4H), 7.21-7.30 (m, 9H), 7.12-7.17 (m, 3H), 3.41-3.48 (m, 4H), 3.00-3.17 (m, 2H), 2.44 (t, J=6.8 Hz, 2H). MS (M+1): 598.

Compound 23-17: Ethyl (S)-3-(4-((1-((4-(tert-butyl)phenyl)amino)-3-(naphthalen-1-yl)-1-oxopropan-2-yl)amino)benzamido)propanoate

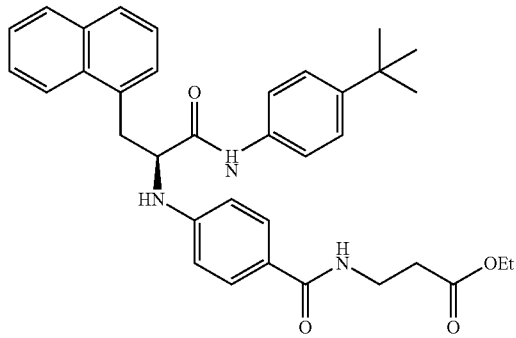 [SMILES: CCOC(=O)CCNC(=O)c1ccc(N[C@@H](Cc2cccc3ccccc23)C(=O)Nc2ccc(C(C)(C)C)cc2)cc1]

The mass data of this compound is listed in the following Table 23.

Compound 23-18: (S)-3-(4-((1-((4-(tert-butyl)phenyl)amino)-3-(naphthalen-1-yl)-1-oxopropan-2-yl)amino)benzamido)propanoic Acid

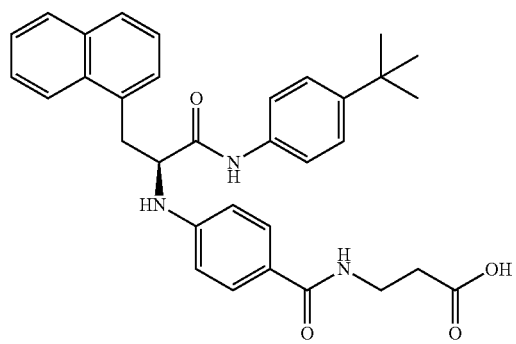 [SMILES: CC(C)(C)c1ccc(NC(=O)[C@H](Cc2cccc3ccccc23)Nc2ccc(C(=O)NCCC(=O)O)cc2)cc1]

The mass data of this compound is listed in the following Table 23.

Compound 23-19: Ethyl (S)-3-(4-((1-((4-(tert-butyl)phenyl)amino)-3-(naphthalen-2-yl)-1-oxopropan-2-yl)amino)benzamido)propanoate

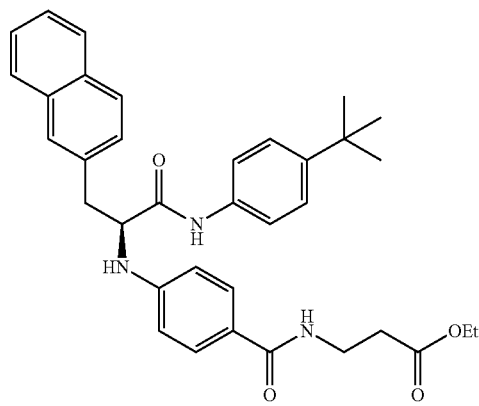 [SMILES: CCOC(=O)CCNC(=O)c1ccc(N[C@@H](Cc2ccc3ccccc3c2)C(=O)Nc2ccc(C(C)(C)C)cc2)cc1]

The mass data of this compound is listed in the following Table 23.

Compound 23-20: (S)-3-(4-((1-((4-(tert-butyl)phenyl)amino)-3-(naphthalen-2-yl)-1-oxopropan-2-yl)amino)benzamido)propanoic Acid

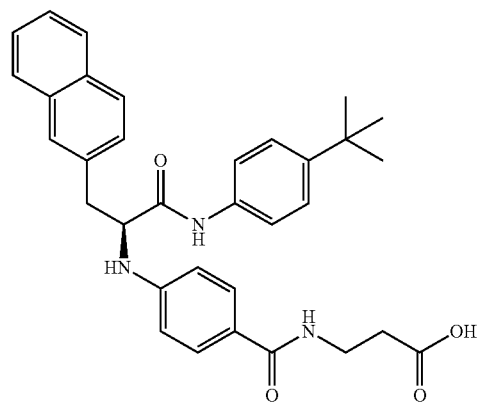 [SMILES: CC(C)(C)c1ccc(NC(=O)[C@H](Cc2ccc3ccccc3c2)Nc2ccc(C(=O)NCCC(=O)O)cc2)cc1]

$^1$H NMR (400 MHz, DMSO-$d_6$): δ10.40-10.71 (m, 1H), 8.24-8.51 (m, 1H), 7.69-7.93 (m, 6H), 7.50-7.55 (m, 4H), 7.40-7.49 (m, 6H), 725 (d, J=8.8 Hz, 3H), 7.03-7.14 (m, 1H), 6.68 (d, J=8.8 Hz, 3H), 4.34-4.46 (m, 1H), 2.13 (s, 3H), 1.22 (s, 9H). MS (M+1): 538.

Compound 23-21: Ethyl (S)-3-(4-((1-((4-(benzofuran-2-yl)phenyl)amino)-3-(naphthalen-2-yl)-1-oxopropan-2-yl)amino)benzamido)propanoate

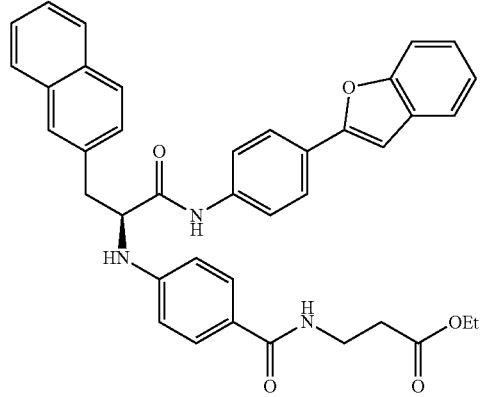 [SMILES: CCOC(=O)CCNC(=O)c1ccc(N[C@@H](Cc2ccc3ccccc3c2)C(=O)Nc2ccc(-c3cc4ccccc4o3)cc2)cc1]

The mass data of this compound is listed in the following Table 23.

Compound 23-22: (S)-3-(4-((1-((4-(benzofuran-2-yl)phenyl)amino)-3-(naphthalen-2-yl)-1-oxopropan-2-yl)amino)benzamido)propanoic Acid

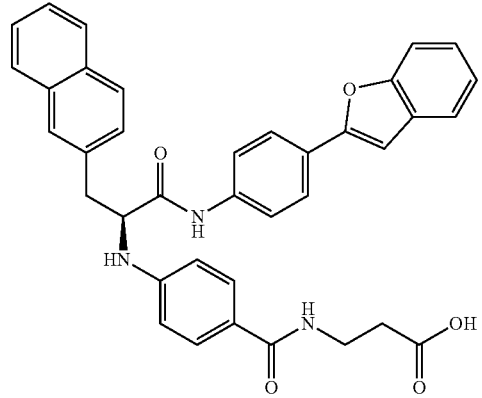 [SMILES: O=C(O)CCNC(=O)c1ccc(N[C@@H](Cc2ccc3ccccc3c2)C(=O)Nc2ccc(-c3cc4ccccc4o3)cc2)cc1]

The mass data of this compound is listed in the following Table 23.

Compound 23-23: (S)-3-(4-((1-oxo-3-phenyl-1-((2'-(trifluoromethyl)-[1,1'-biphenyl]-4-yl)amino)propen-2-yl)amino)benzamido)propanoic Acid

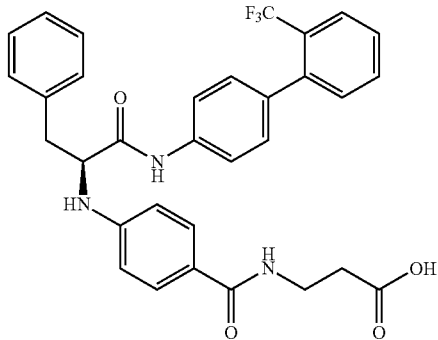 [SMILES: O=C(O)CCNC(=O)c1ccc(N[C@@H](Cc2ccccc2)C(=O)Nc2ccc(-c3ccccc3C(F)(F)F)cc2)cc1]

The mass data of this compound is listed in the following Table 23.

Compound 23-24: (S)-2-(4-((1-((4-(benzofuran-2-yl)phenyl)amino)-1-oxo-3-phenylpropan-2-yl)amino) benzamido)ethane-1-sulfonic Acid

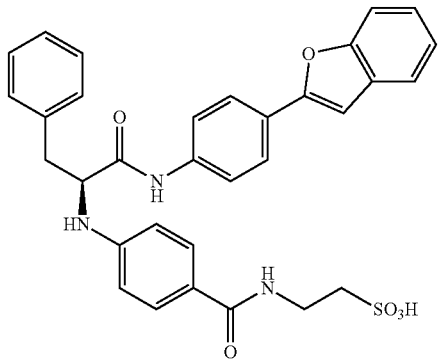 [SMILES: O=C(NCCS(=O)(=O)O)c1ccc(N[C@@H](Cc2ccccc2)C(=O)Nc2ccc(-c3cc4ccccc4o3)cc2)cc1]

$^1$H NMR (400 MHz, DMSO-d$_6$): δ 10.29 (s, 1H), 7.92-8.28 (m, 1H), 7.80-7.90 (m, 2H), 7.65-7.73 (m, 2H), 7.57-7.65 (m, 2H), 7.52 (d, J=8.8 Hz, 2H), 7.33-7.38 (m, 2H), 7.16-7.32 (m, 6H), 6.67 (d, J=8.8 Hz, 2H), 4.37 (dd, J=8.1, 6.1 Hz, 1H), 3.42-3.49 (m, 2H), 2.97-3.20 (m, 2H), 2.63 (t, J=7.1 Hz, 2H). MS (M+1): 584.

Compound 23-25: (S)-3-(4-((1-((tert-butyl)phenyl)amino)-1-oxo-3-(2',4',6'-trimethyl-[1,1'-biphenyl]-4-yl)propan-2-yl)amino)benzamido)propanoic Acid

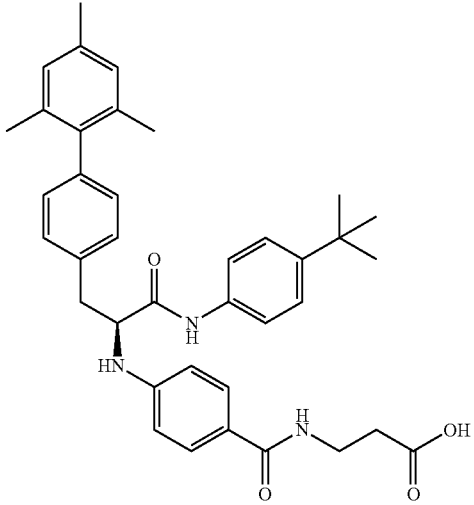 [SMILES: Cc1cc(C)c(-c2ccc(C[C@H](Nc3ccc(C(=O)NCCC(=O)O)cc3)C(=O)Nc3ccc(C(C)(C)C)cc3)cc2)c(C)c1]

Compound 23-26: (S)-2-(4-((1-((4-(tert-butyl)phenyl)amino)-1-oxo-3-(2',4',6'-trimethyl-[1,1'-biphenyl]-4-yl)propan-2-yl)amino)benzamido)ethane-1-sulfonic Acid

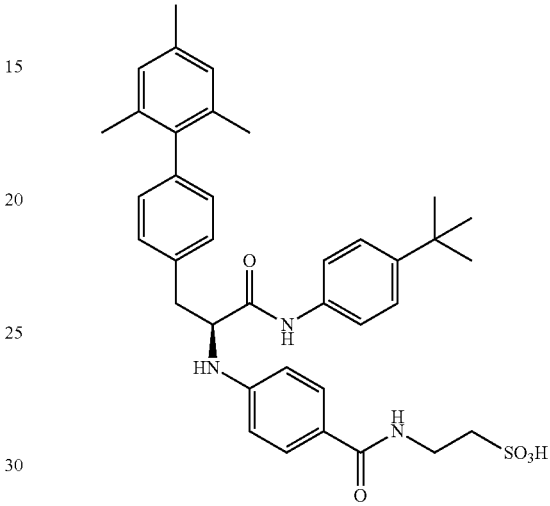

$^1$H NMR (400 MHz, DMSO-d$_6$): δ 9.93 (s, 1H), 7.87-8.30 (m, 1H), 7.51 (d, J=8.8 Hz, 3H), 7.34-7.44 (m, 5H), 7.22-7.30 (m, 3H), 6.98 (d, J=7.8 Hz, 3H), 6.87 (s, 3H), 6.69 (d, J=8.8 Hz, 3H), 4.39 (s, 2H), 3.46 (t, J=7.1 Hz, 3H), 3.10 (d, J=7.3 Hz, 3H), 2.61-2.66 (m, 3H), 2.23 (s, 4H), 1.82 (s, 8H), 1.23 (s, 13H). MS (M+1): 642.

Compound 23-27: Ethyl (S)-3-(4-((1-((4-(benzofuran-2-yl)phenyl)amino)-3-(1H-indol-3-yl)-1-oxopropan-2-yl)amino)benzamido)propanoate

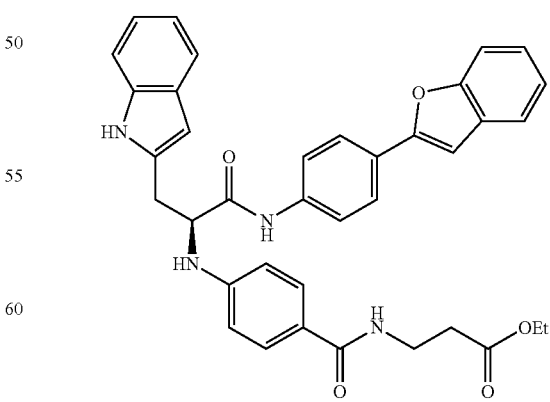

The mass data of this compound is listed in the following Table 23.

Compound 23-28: Methyl (S)-3-(4-((1-((4-(1H-indol-2-yl)phenyl)amino)-4-methyl-1-oxopentan-2-yl)amino)benzamido)propanoate

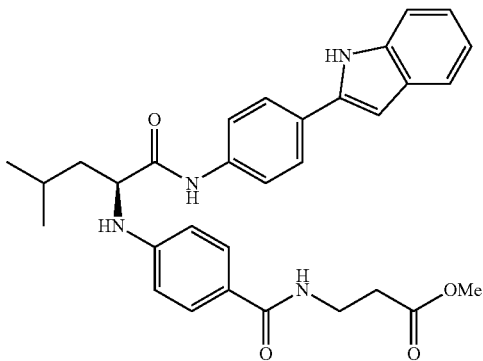 [SMILES: COC(=O)CCNC(=O)c1ccc(N[C@@H](CC(C)C)C(=O)Nc2ccc(-c3cc4ccccc4[nH]3)cc2)cc1]

The mass data of this compound is listed in the following Table 23.

Compound 23-29: (S)-3-(4-((1-((4-(1H-indol-2-yl)phenyl)amino)-4-methyl-1-oxopentan-2-yl)amino)benzamido)propanoic Acid

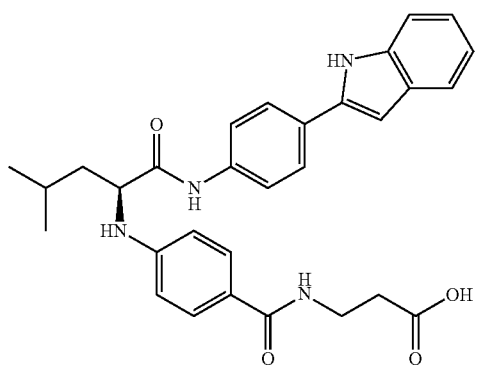 [SMILES: CC(C)C[C@H](Nc1ccc(C(=O)NCCC(=O)O)cc1)C(=O)Nc1ccc(-c2cc3ccccc3[nH]2)cc1]

The mass data of this compound is listed in the following Table 23.

Compound 23-30: 3-(4-(((2S,3S)-1-((6-methoxynaphthalen-2-yl)amino)-3-methyl-1-oxopentan-2-yl)amino)benzamido)propanoic Acid

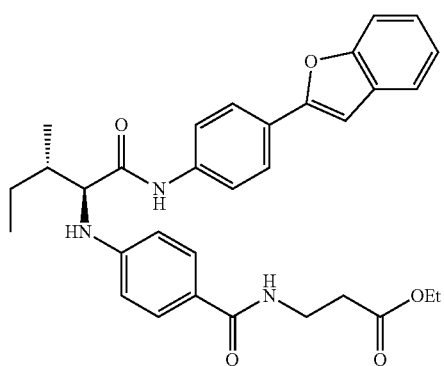 [SMILES: CCOC(=O)CCNC(=O)c1ccc(N[C@H](C(=O)Nc2ccc(-c3cc4ccccc4o3)cc2)[C@@H](C)CC)cc1]

$^1$H NMR 400 MHz, DMSO-$d_6$): δ10.29 (s, 1H), 8.07 (t, 1H), 7.83-7.89 (m, 2H), 7.71-7.76 (m, 2H), 7.55-7.65 (m, 4H), 7.21-7.32 (m, 3H), 6.71 (d, 2H), 6.35 (d, 1H), 4.04 (q, 2H), 3.89 (t, 1H), 3.41 (t, 2H), 1.85-1.95 (m, 1H), 1.63-1.72 (m, 1H), 1.25-1.36 (m, 1H), 1.15 (t, 3H), 0.98 (d, 3H), 0.88 (t, 3H). MS (M+1): 542.

Compound 23-31: 3-(4-(((2S,3S)-1-((4-(benzofuran-2-yl)phenyl)amino)-3-methyl-1-oxopentan-2-yl)amino)benzamido)propanoic Acid

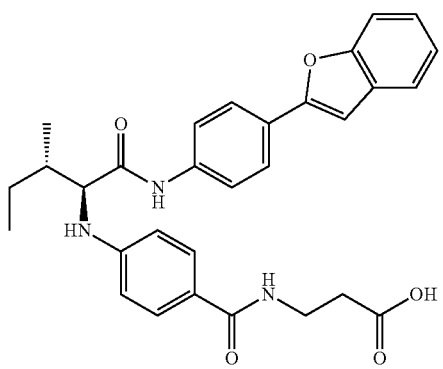 [SMILES: CC[C@H](C)[C@H](Nc1ccc(C(=O)NCCC(=O)O)cc1)C(=O)Nc1ccc(-c2cc3ccccc3o2)cc1]

The mass data of this compound is listed in the following Table 23.

Compound 23-32: Ethyl (S)-3-(4-((1-((4-(benzofuran-2-yl)phenyl)amino)-3-methyl-1-oxobutan-2-yl)amino)benzamido)propanoate

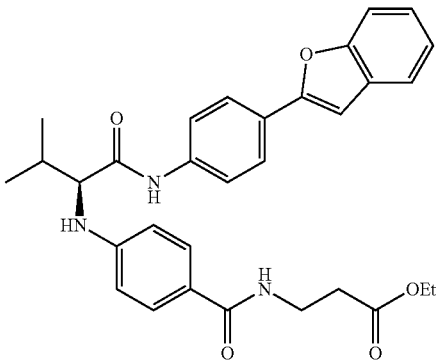 [SMILES: CCOC(=O)CCNC(=O)c1ccc(N[C@H](C(=O)Nc2ccc(-c3cc4ccccc4o3)cc2)C(C)C)cc1]

The mass data of this compound is listed in the following Table 23.

Compound 23-33: (S)-3-(4-((1-((4-(benzofuran-2-yl)phenyl)amino)-3-methyl-1-oxobutan-2-yl)amino)benzamido)propanoic Acid

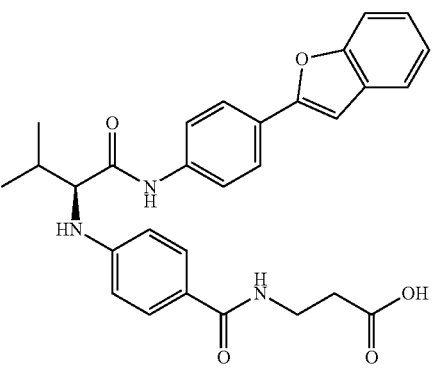 [SMILES: CC(C)[C@H](Nc1ccc(C(=O)NCCC(=O)O)cc1)C(=O)Nc1ccc(-c2cc3ccccc3o2)cc1]

The mass data of this compound is listed in the following Table 23.

Compound 23-34: (S)-2-(4-((1-((4-(benzofuran-2-yl)phenyl)amino)-3-methyl-1-oxobutan-2-yl)amino)benzamido)ethane-1-sulfonic Acid

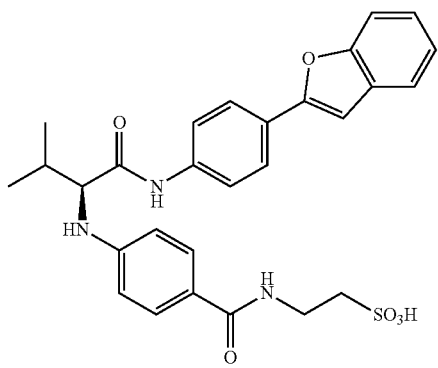 [SMILES: CC(C)[C@H](Nc1ccc(C(=O)NCCS(=O)(=O)O)cc1)C(=O)Nc1ccc(-c2cc3ccccc3o2)cc1]

The mass data of this compound is listed in the following Table 23.

Compound 23-35: (S)-3-(4-((1-((4-(benzofuran-2-yl)phenyl)amino)-1-oxohexan-2-yl)amino)benzamido) propanoic Acid

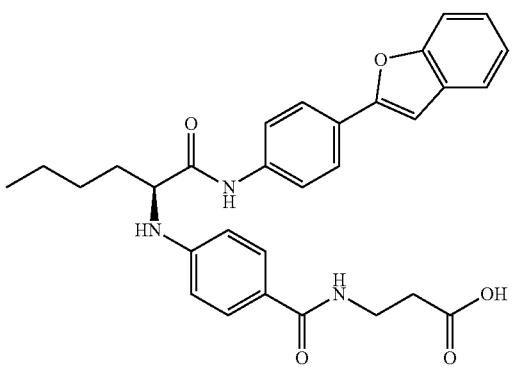 [SMILES: CCCC[C@H](Nc1ccc(C(=O)NCCC(=O)O)cc1)C(=O)Nc1ccc(-c2cc3ccccc3o2)cc1]

$^1$H NMR (400 MHz, Acetone-d$_6$): δ 9.52 (s, 1H), 7.86 (d, J=8.0 Hz, 2H), 7.79 (d, J=8.0 Hz, 2H), 7.70 (d, J=8.0 Hz, 2H), 7.61 (d, J=8.0 Hz, 1H), 7.54 (d, J=8.0 Hz, 1H), 7.29 (t, J=8.0 Hz, 1H), 7.23 (t, J=8.0 Hz, 1H), 7.19 (s, 1H), 6.74 (d, J=8.0 Hz, 2H), 5.73 (s, 1H), 3.98-4.12 (m, 1H), 3.53-3.63 (m, 2H), 2.60 (d, J=8.0 Hz, 2H), 1.84-1.95 (m, 2H), 1.46-1.59 (m, 2H), 1.34-1.43 (m, 2H), 0.91 (t, J=7.3 Hz, 3H). MS (M+1): 514.

Example 24: Synthesis of Compounds 24-1 to 24-28

Compound 24-1: Ethyl (R)-3-(4-((1-((4-(benzofuran-2-yl)phenyl)amino)-4-methyl-1-oxopentan-2-yl)amino)benzamido)propenoate

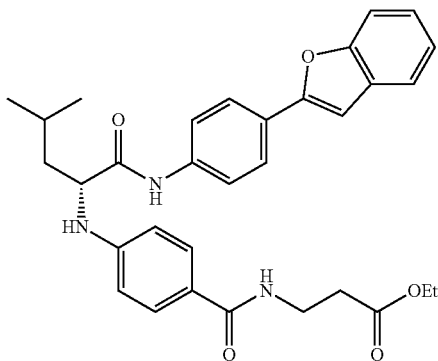 [SMILES: CCOC(=O)CCNC(=O)c1ccc(N[C@H](CC(C)C)C(=O)Nc2ccc(-c3cc4ccccc4o3)cc2)cc1]

The mass data of this compound is listed in the following Table 24.

Compound 24-2: (R)-3-(4-((1-((4-(benzofuran-2-yl)phenyl)amino)-4-methyl-1-oxopentan-2-yl)amino)benzamido)propanoic Acid

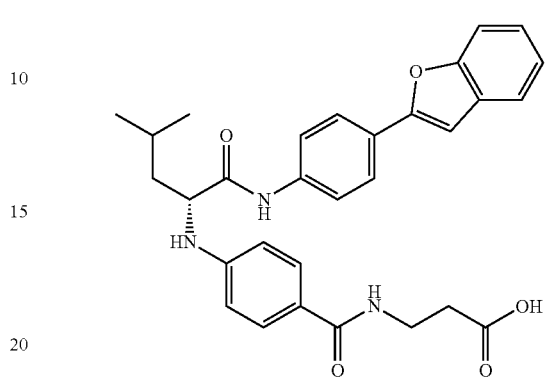

$^1$H NMR (400 MHz, DMSO-d$_6$): δ10.26 (s, 1H), 7.96-8.14 (m, 1H), 7.86 (d, J=8.8 Hz, 2H), 7.74 (d, J=8.8 Hz, 2H), 7.63 (dd, J=7.8, 1.5 Hz, 1H), 7.57-7.61 (m, 3H), 7.20-7.34 (m, 3H), 6.67 (d, J=8.8 Hz, 2H), 6.34-6.45 (m, 1H), 4.05-4.19 (m, 1H), 3.38 (d, J=5.9 Hz, 3H), 2.45 (t, J=7.3 Hz, 2H), 1.56-1.86 (m, 3H), 0.98 (d, J=6.4 Hz, 3H), 0.92 (d, J=6.8 Hz, 3H). MS (M+1): 514.

Compound 24-3: Ethyl (R)-3-(4-((1-oxo-3-phenyl-1-((4-(trifluoromethyl)phenyl)amino)propan-2-yl)amino)benzamido)propanoate

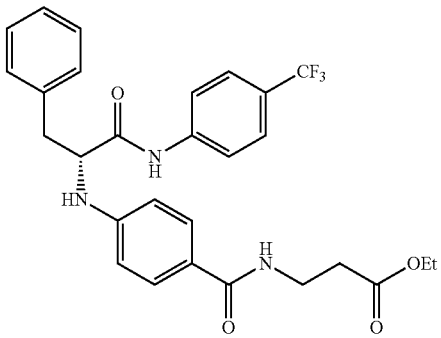 [SMILES: CCOC(=O)CCNC(=O)c1ccc(N[C@H](Cc2ccccc2)C(=O)Nc2ccc(C(F)(F)F)cc2)cc1]

The mass data of this compound is listed in the following Table 24.

Compound 24-4: (S)-3-(4-((1-oxo-3-phenyl-1-((4-(trifluoromethyl)phenyl)amino)propan-2-yl)amino)benzamido)propanoic Acid

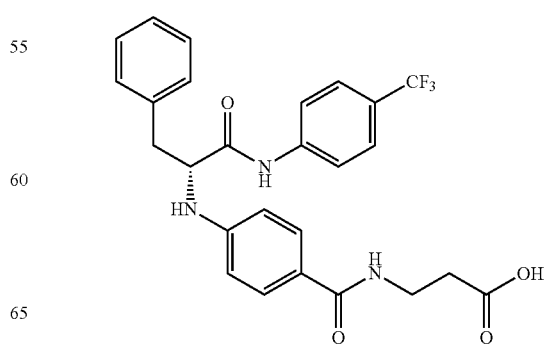

¹H NMR (400 MHz, DMSO-d₆): δ10.44 (s, 1H), 8.04 (s, 2H), 7.70-7.79 (m, 4H), 7.63-7.69 (m, 4H), 7.57 (d, J=8.8 Hz, 4H), 7.31-7.38 (m, 4H), 7.27 (t, J=7.6 Hz, 4H), 7.19 (d, J=7.3 Hz, 2H), 6.64 (d, J=8.8 Hz, 4H), 6.59 (d, J=8.8 Hz, 2H), 4.28-4.44 (m, 1H), 3.37 (d, J=5.9 Hz, 2H), 2.99-3.16 (m, 2H), 2.44 (t, J=7.1 Hz, 2H). MS (M+1): 500.

Compound 24-5: Ethyl (S)-3-(4-((1-oxo-3-phenyl-1-((4-(trifluoromethyl)phenyl)amino)propan-2-yl)amino)benzamido)propanoate

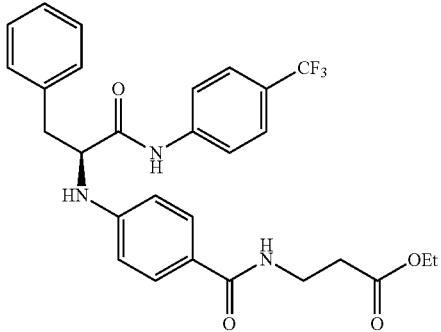 [SMILES: CCOC(=O)CCNC(=O)c1ccc(N[C@@H](Cc2ccccc2)C(=O)Nc2ccc(C(F)(F)F)cc2)cc1]

The mass data of this compound is listed in the following Table 24.

Compound 24-6: (S)-3-(4-((1-oxo-3-phenyl-1-((4-(trifluoromethyl)phenyl)amino)propan-2-yl)amino)benzamido)propanoic Acid

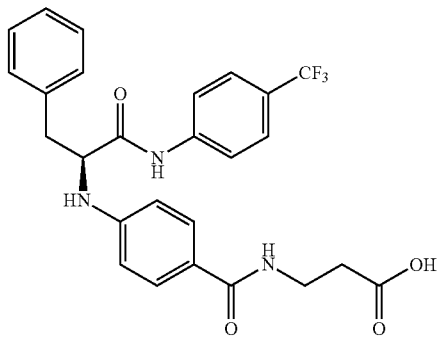 [SMILES: O=C(O)CCNC(=O)c1ccc(N[C@@H](Cc2ccccc2)C(=O)Nc2ccc(C(F)(F)F)cc2)cc1]

¹H NMR (400 MHz, DMSO-d₆): δ11.91-12.33 (m, 1H), 10.21-10.61 (m, 1H), 7.92-8.11 (m, 1H), 7.71-7.79 (m, 2H), 7.62-7.69 (m, 2H), 7.53-7.61 (m, 2H), 7.23-7.37 (m, 4H), 7.15-7.22 (m, 1H), 6.61-6.69 (m, 2H), 6.53-6.61 (m, 1H), 4.30-4.43 (m, 1H), 3.34-3.41 (m, 2H), 3.07-3.17 (m, 1H), 2.97-3.07 (m, 1H), 2.62-2.74 (m, 1H), 2.40-2.47 (m, 2H). MS (M+1): 500.

Compound 24-7: Ethyl 3-(4-(((2S,3S)-1-((6-methoxynaphthalen-2-yl)amino)-3-methyl-1-oxopentan-2-yl)amino)benzamido)propanoate

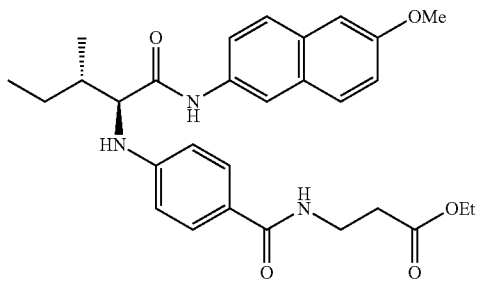 [SMILES: CCOC(=O)CCNC(=O)c1ccc(N[C@H](C(=O)Nc2ccc3cc(OC)ccc3c2)[C@@H](C)CC)cc1]

The mass data of this compound is listed in the following Table 24.

Compound 24-8: 3-(4-(((2S,3S)-1-((6-methoxynaphthalen-2-yl)amino)-3-methyl-1-oxopentan-2-yl)amino)benzamido)propanoic Acid

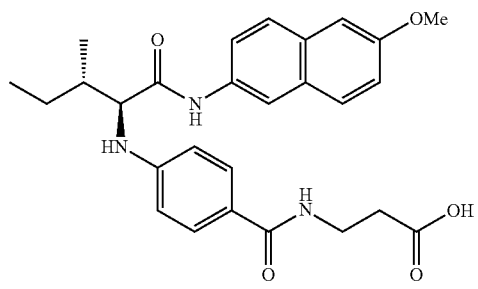 [SMILES: CC[C@H](C)[C@H](Nc1ccc(C(=O)NCCC(=O)O)cc1)C(=O)Nc1ccc2cc(OC)ccc2c1]

¹H NMR (400 MHz, DMSO-d₆): δ12.12 (s, 1H), 10.16 (s, 2H), 8.15 (d, J=1.5 Hz, 2H), 8.03 (t, J=5.6 Hz, 2H), 7.74 (dd, J=12.7, 8.8 Hz, 4H), 7.52-7.64 (m, 7H), 7.25 (d, J=2.4 Hz, 2H), 7.12 (dd, J=8.8, 2.4 Hz, 2H), 6.72 (d, J=8.8 Hz, 4H), 6.32 (d, J=8.8 Hz, 2H), 3.90 (t, J=8.6 Hz, 1H), 3.34-3.43 (m, 2H), 2.45 (t, J=7.1 Hz, 2H), 1.84-1.99 (m, 1H), 1.60-1.75 (m, 1H), 1.22-1.39 (m, 1H), 0.98 (d, J=6.8 Hz, 3H), 0.90 (t, J=7.6 Hz, 3H). MS (M+1): 478.

Compound 24-9: Ethyl (R)-3-(4-((4-methyl-1-oxo-1-((4-(trifluoromethyl)phenyl)amino)pentan-2-yl)amino)benzamido)propanoate

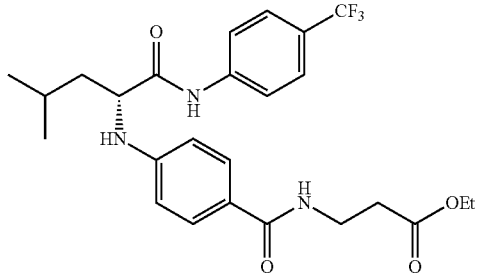 [SMILES: CCOC(=O)CCNC(=O)c1ccc(N[C@H](CC(C)C)C(=O)Nc2ccc(C(F)(F)F)cc2)cc1]

The mass data of this compound is listed in the following Table 24.

Compound 24-10: (R)-3-(4-((4-methyl-1-oxo-1-((4-(trifluoromethyl)phenyl)amino)pentan-2-yl)amino)benzamido)propanoic Acid

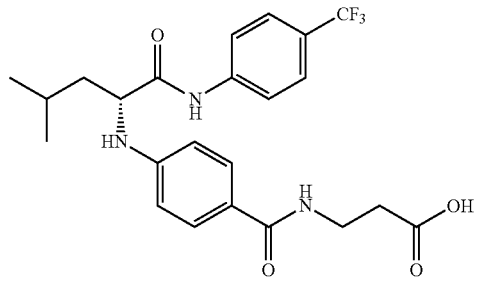 [SMILES: CC(C)C[C@@H](Nc1ccc(C(=O)NCCC(=O)O)cc1)C(=O)Nc1ccc(C(F)(F)F)cc1]

¹H NMR (400 MHz, DMSO-d₆): δ10.45 (s, 1H), 8.05 (s, 2H), 7.81 (d, J=8.8 Hz, 4H), 7.66 (d, J=8.8 Hz, 4H), 7.59 (d, J=8.8 Hz, 4H), 6.65 (d, J=8.8 Hz, 4H), 6.42 (d, J=8.3 Hz, 2H), 4.11 (s, 2H), 3.35-3.41 (m, 5H), 2.44 (t, J=7.3 Hz, 4H), 1.56-1.84 (m, 6H), 0.97 (d, J=6.4 Hz, 6H), 0.90 (d, J=6.4 Hz, 3H). MS (M+1): 466.

Compound 24-11: Ethyl (S)-3-(4-((1-(isopropylamino)-3-(naphthalen-1-yl)-1-oxopropan-2-yl)amino)benzamido)propanoate

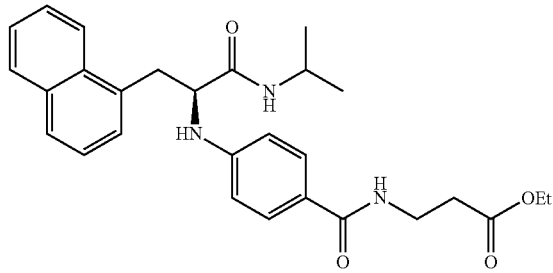 [SMILES: CCOC(=O)CCNC(=O)c1ccc(N[C@@H](Cc2cccc3ccccc23)C(=O)NC(C)C)cc1]

The mass data of this compound is listed in the following Table 24.

Compound 24-12: (S)-3-(4-((1-(isopropylamino)-3-(naphthalen-1-yl)-1-oxopropan-2-yl)amino)benzamido)propanoic Acid

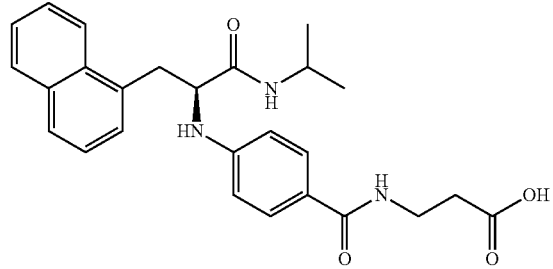 [SMILES: CC(C)NC(=O)[C@H](Cc1cccc2ccccc12)Nc1ccc(C(=O)NCCC(=O)O)cc1]

¹H NMR (400 MHz, DMSO-d₆): δ11.85-12.36 (m, 1H), 8.15 (d, J=8.3 Hz, 2H), 8.05 (t, J=5.6 Hz, 2H), 7.91 (d, J=6.8 Hz, 2H), 7.79 (d, J=7.8 Hz, 4H), 7.49-7.60 (m, 7H), 7.38-7.46 (m, 4H), 6.58 (d, J=8.8 Hz, 4H), 4.19 (br. s., 2H), 3.75 (dd, J=14.2, 6.8 Hz, 2H), 3.42-3.52 (m, 2H), 3.35-3.40 (m, 5H), 2.45 (t, J=7.1 Hz, 4H), 0.96 (d, J=6.8 Hz, 5H), 0.78 (d, J=6.4 Hz, 3H). MS (M+1): 448.

Compound 24-13: Ethyl (S)-3-(4-((1-(isopropylamino)-3-(naphthalen-2-yl)-1-oxopropan-2-yl)amino)benzamido)propanoate

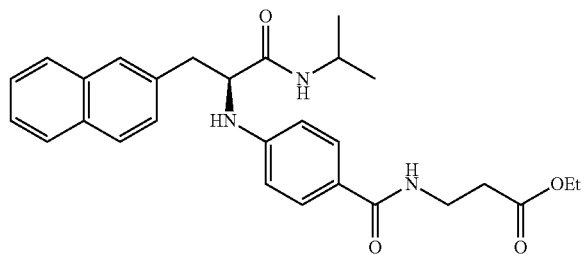 [SMILES: CCOC(=O)CCNC(=O)c1ccc(N[C@@H](Cc2ccc3ccccc3c2)C(=O)NC(C)C)cc1]

The mass data of this compound is listed in the following Table 24.

Compound 24-14: (S)-3-(4-((1-(isopropylamino)-3-(naphthalen-2-yl)-1-oxopropan-2-yl)amino)benzamido)propanoic Acid

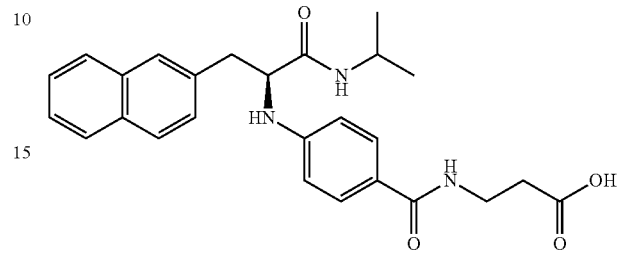

¹H NMR (400 MHz, DMSO-d₆): δ 8.04 (s, 1H), 7.72-7.89 (m, 9H), 7.56 (d, J=8.8 Hz, 2H), 7.41-7.51 (m, 3H), 6.60 (d, J=8.8 Hz, 2H), 6.31-6.44 (m, 1H), 4.12-4.26 (m, 1H), 3.69-3.84 (m, 1H), 3.38 (d, J=5.4 Hz, 2H), 3.10 (d, J=2.0 Hz, 2H), 2.45 (t, J=7.1 Hz, 2H), 0.98 (d, J=6.8 Hz, 3H), 0.81 (d, J=6.8 Hz, 3H). MS (M+1): 448.

Compound 24-15: Ethyl (R)-3-(4-((3-(4'-(tert-butyl)-[1,1'-biphenyl]-4-yl)-1-oxo-1-((4-(trifluoromethyl)phenyl)amino)propan-2-yl)amino)benzamido)propanoate

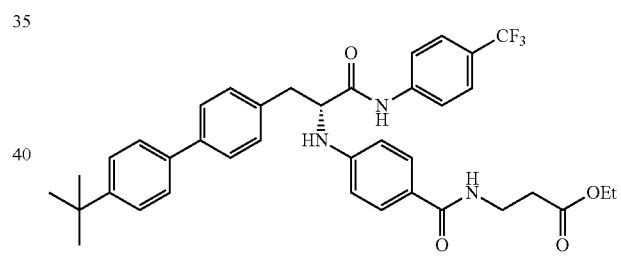

The mass data of this compound is listed in the following Table 24.

Compound 24-16: (R)-3-(4-((3-(4'-(tert-butyl)-[1,1'-biphenyl]-4-yl)-1-oxo-1-((4-(trifluormethyl)phenyl)amino)propan-2-yl)amino)benzamido)propanoic Acid

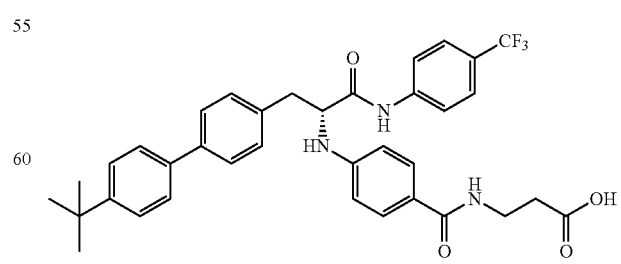

The mass data of this compound is listed in the following Table 24.

Compound 24-17: Ethyl (R)-3-(4-((3-(2',4'-dichloro-[1,1'-biphenyl]-4-yl)-1-oxo-1-((4-(trifluoromethyl)phenyl)amino)propan-2-yl)amino)benzamido)propanoate

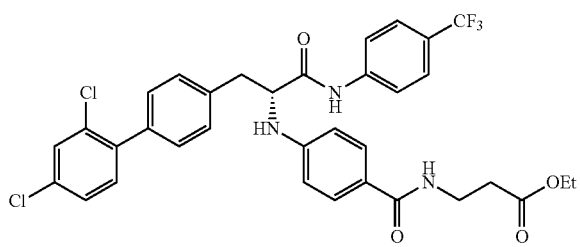 [SMILES: CCOC(=O)CCNC(=O)c1ccc(N[C@H](Cc2ccc(-c3ccc(Cl)cc3Cl)cc2)C(=O)Nc2ccc(C(F)(F)F)cc2)cc1]

The mass data of this compound is listed in the following Table 24.

Compound 24-18: (R)-3-(4-((3-(2',4'-dichloro-[1,1'-biphenyl]-4-yl)-1-oxo-1-((4-(trifluoromethyl)phenyl)amino)propan-2-yl)amino)benzamido)propanoic Acid

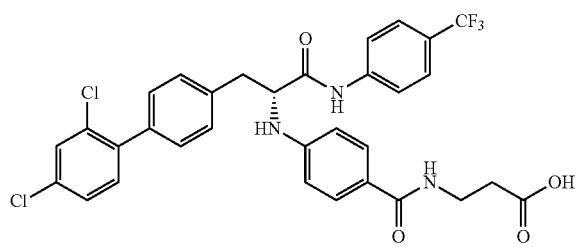

The mass data of this compound is listed in the following Table 24.

Compound 24-19: Ethyl (R)-3-(4-((3-(4-(benzofuran-2-yl)phenyl)-1-oxo-1-((4-(trifluoromethyl)phenyl)amino)propan-2-yl)amino)benzamido)propanoate

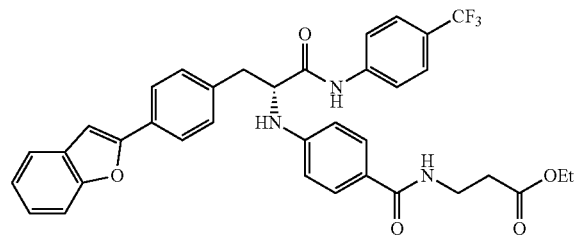 [SMILES: CCOC(=O)CCNC(=O)c1ccc(N[C@H](Cc2ccc(-c3cc4ccccc4o3)cc2)C(=O)Nc2ccc(C(F)(F)F)cc2)cc1]

The mass data of this compound is listed in the following Table 24.

Compound 24-20: (R)-3-(4-((3-(4-(benzofuran-2-yl)phenyl)-1-oxo-1-((4-(trifluoromethyl)phenyl)amino)propan-2-yl)amino)benzamido)propanoic Acid

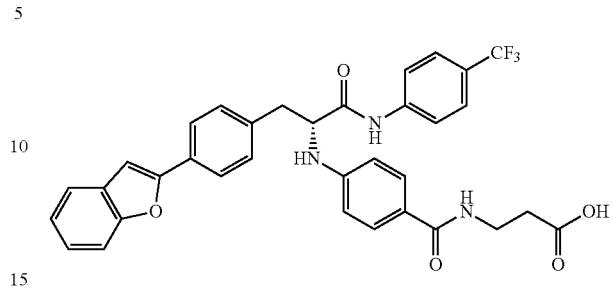

The mass data of this compound is listed in the following Table 24.

Compound 24-21: Ethyl (R)-3-(4-((3-(4-(benzofuran-2-yl)phenyl)-1-(isopropylamino)-1-oxopropan-2-yl)amino)benzamido)propanoate

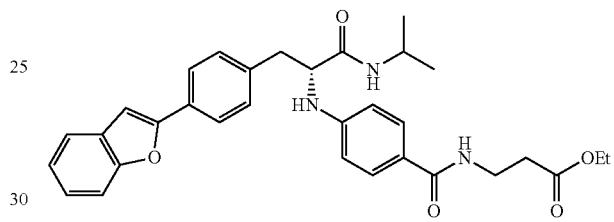

The mass data of this compound is listed in the following Table 24.

Compound 24-22: (R)-3-(4-((3-(4-(benzofuran-2-yl)phenyl)-1-(isopropylamino)-1-oxopropan-2-yl)amino)benzamido)propanoic Acid

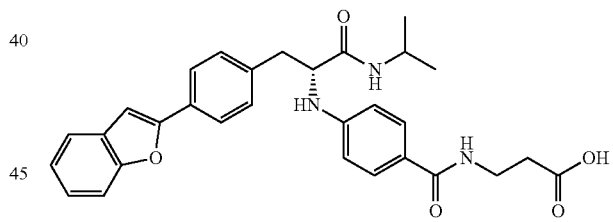

The mass data of this compound is listed in the following Table 24.

Compound 24-23: Ethyl (R)-3-(4-((3-(4-(benzofuran-2-yl)phenyl)-1-((3,5-difluorophenyl)amino)-1-oxopropan-2-yl)amino)benzamido)propanoate

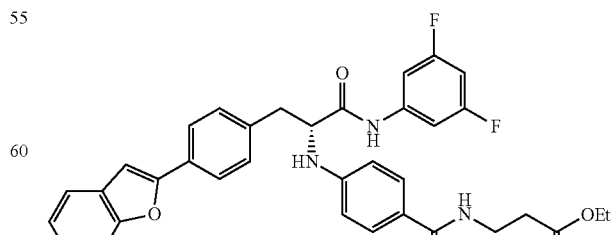

The mass data of this compound is listed in the following Table 24.

Compound 24-24: (R)-3-(4-((3-(4-(benzofuran-2-yl)phenyl)-1-((3,5-difluorophenyl)amino)-1-oxopropan-2-yl)amino)benzamido)propanoic Acid

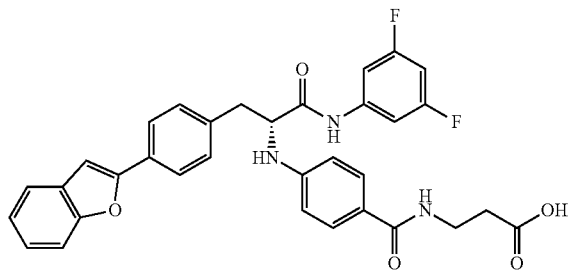 [SMILES: O=C(O)CCNC(=O)c1ccc(N[C@H](Cc2ccc(-c3cc4ccccc4o3)cc2)C(=O)Nc2cc(F)cc(F)c2)cc1]

The mass data of this compound is listed in the following Table 24.

Compound 24-25: Ethyl (R)-3-(4-((3-(4'-(tert-butyl)-[1,1'-biphenyl]-4-yl)-1-oxo-1-((4-(trifluoromethoxy)phenyl)amino)propan-2-yl)amino)benzamido)propanoate

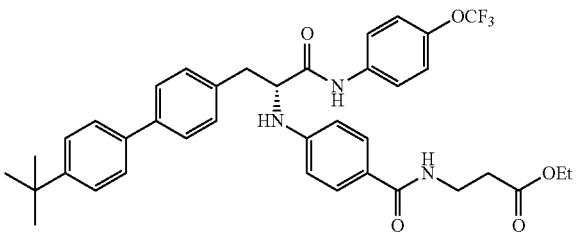 [SMILES: CCOC(=O)CCNC(=O)c1ccc(N[C@H](Cc2ccc(-c3ccc(C(C)(C)C)cc3)cc2)C(=O)Nc2ccc(OC(F)(F)F)cc2)cc1]

The mass data of this compound is listed in the following Table 24.

Compound 24-26: (R)-3-(4-((3-(4'-(tat-butyl)-[1,1'-biphenyl]-4-yl)-1-oxo-1-((4-(trifluoromethoxy)phenyl)amino)propan-2-yl)amino)benzamido)propanoic Acid

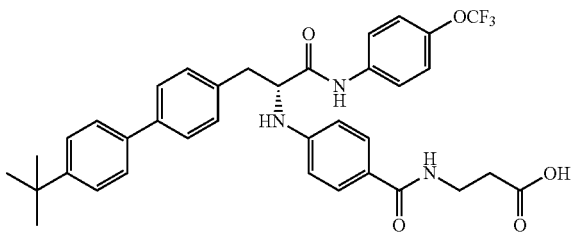 [SMILES: CC(C)(C)c1ccc(-c2ccc(C[C@@H](Nc3ccc(C(=O)NCCC(=O)O)cc3)C(=O)Nc3ccc(OC(F)(F)F)cc3)cc2)cc1]

The mass data of this compound is listed in the following Table 24.

Compound 24-27: Ethyl (R)-3-(4-((1-oxo-1-((4-(trifluoromethoxy)phenyl)amino)-3-(4'-(trifluoromethyl)-[1,1'-biphenyl]-4-yl)propan-2-yl)amino)benzamido)propanoate

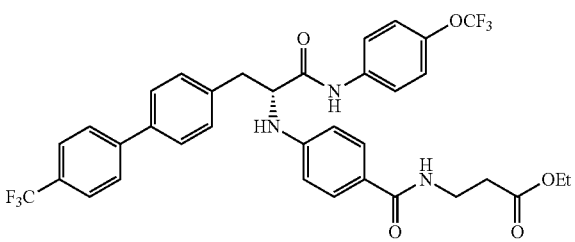 [SMILES: CCOC(=O)CCNC(=O)c1ccc(N[C@H](Cc2ccc(-c3ccc(C(F)(F)F)cc3)cc2)C(=O)Nc2ccc(OC(F)(F)F)cc2)cc1]

The mass data of this compound is listed in the following Table 24.

Compound 24-28: (R)-3-(4-((1-oxo-1-((4-(trifluoromethoxy)phenyl)amino)-3-(4'-(trifluoromethyl)-[1,1'-biphenyl]-4-yl)propan-2-yl)amino)benzamido) propanoic Acid

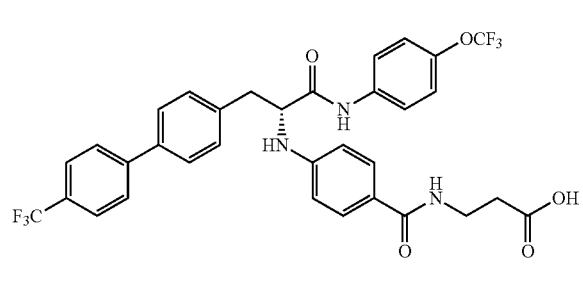 [SMILES: O=C(O)CCNC(=O)c1ccc(N[C@H](Cc2ccc(-c3ccc(C(F)(F)F)cc3)cc2)C(=O)Nc2ccc(OC(F)(F)F)cc2)cc1]

The mass data of this compound is listed in the following Table 24.

In EXAMPLES 1-24, the detail synthesized procedures of some compounds are not repeated again if the synthesized procedures thereof are similar to those of the forgoing compounds.

Example 25: Evaluation of Compounds of Formula (I) in In Vitro Assays

Glucagon cAMP Inhibition Assay

Downstream secondary messenger cAMP induced by glucagon was detected by Cisbio cAMP Dynamic 2 kit. Testing compounds were each prepared as a dimethyl sulfoxide (DMSO) solution at the concentration of 10 mM. To evaluate the potency of compounds in inhibiting the cAMP production, glucagon receptor (GCGR) overexpressed CHO-K1 cells or human primary hepatocytes were treated with compounds with a serial dilution. The cells were re-suspended in Hank's Balanced Salt solution (HBSS) contained 0.1% (w/v) bovine serum albumin and 800 nM 3-isobutyl-1-methylxanthine (IBMX) and seeded into low volume, 384 wells white plate. The diluted compounds were then added into the plate for 30 minutes pre-incubation where the final DMSO concentration was 1%. The cells were stimulated with glucagon at the concentration equaled to EC50 (an indicium of the concentration of a drug that gives half-maximal response) for 30 minutes at room temperature. After incubation, lysis buffer contain cAMP antibody and fluorescence acceptor were added into each well for additional 60 minutes incubation. Results were recorded by Molecular Devices SpectraMax Paradigm with the HTRF Detection Cartridges and the $IC_{50}$ value of each compound in inhibiting the cAMP production was calculated with non-linear regression based on the amount of cAMP production.

$I^{125}$-Glucagon Binding Assay

The binding affinity of each compound was evaluated by a competition assay with $I^{125}$-glucagon. GCGR membrane fractions were obtained from GCGR overexpressed CHO-K1 cells as a stock of 1 mg/ml concentration. To evaluate the $IC_{50}$ of compounds binding to GCGR, GCGR membrane fractions were treated with compounds with a serial dilution. The membrane fractions were diluted to 7.5 microgram per well in 70 microliter assay buffer contained 50 mM Tris pH 7.4 and 0.5% (w/v) bovine serum albumin and added into 96 wells plate. The membrane fractions were then mixed with 10 microliter diluted compounds. After 5 minutes pre-incubation, 20 microliter $I^{125}$ labeled glucagon (Perkin Elmer) was added into each well at the final concentration of 0.0625 nM. The assay mixtures were incubated at 25° C. for 30 minutes and then transferred onto the Millipore Multi-Screen GF/B Plate coated with 0.5% (w/v) Polyethylene-imine. The filter plate was washed with wash buffer contained 50 mM Tris pH 7.4 for 2 times, 300 microliter each time. The residual isotope was detected by Hidex CHAMELEON V micro-beta counter and the $IC_{50}$ value of each compound binding to GCGR was calculated with non-linear regression.

The compounds prepared in EXAMPLES 1-24 were tested in two in vitro assays described below. The results are shown in Tables 1-24 shown below.

TABLE 1

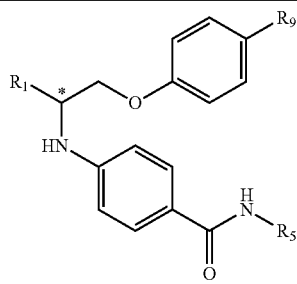

*indicium of chirality

| Compound | $R_1$ | $R_9$ | $R_5$ | Chirality | $IC_{50}^{binding}$ (nM)$^a$ | $IC_{50}^{cAMP}$ (nM) |
|---|---|---|---|---|---|---|
| 1-1 | isopropyl | Benzofuranyl | Ethyl propionate | S | 802.5 | 1177 |
| 1-2 | isopropyl | Benzofuranyl | Propanoic acid | S | 207 | 195.6 |
| 1-3 | 2-butyl | 4-tert-butyl phenyl | Propanoic acid | S | 319 | 884.4 |
| 1-4 | 2-butyl | Benzofuranyl | Propionic acid | S | 184 | 528 |
| 1-5 | 2-butyl | 4-(trifluoro-methyl)phenyl | Propionic acid | S | 213 | 839 |
| 1-6 | 2-butyl | 4-Trifluoro-methoxy phenyl | Propionic acid | S | 228 | 1078 |
| 1-7 | 2-butyl | 2,4-dichloro phenyl | Propionic acid | S | 139 | 494.8 |
| 1-8 | 2-butyl | Benzofuranyl | 5-methyl-1H-tertazole | S | 98 | 3305 |
| 1-9 | 2-butyl | Benzofuranyl | (R)-2-hydroxy-propanoic acid | S | 260 | 3600 |
| 1-10 | n-butyl | Benzofuranyl | Propionic acid | S | 122 | 629.8 |
| 1-11 | n-butyl | Trimethyl benzene | Propionic acid | S | 150 | 320.3 |
| 1-12 | isopropyl | N,N-dimethylaniline | Propanoic acid | S | 224 | 414.3 |
| 1-13 | 2-butyl | 2,4-dichloro phenyl | 5-methyl-1H-tertazole | S | 141 | 1730 |
| 1-14 | 2-butyl | 2,4-dichloro phenyl | (R)-2-hydroxy-propanoic acid | S | 112 | 3553 |
| 1-15 | n-butyl | 4-(trifluoro-methyl)phenyl | Propanoic acid | S | 211 | 338.8 |
| 1-16 | n-butyl | 4-(trifluoro-methyl)phenyl | 5-methyl-1H-tertazole | S | 52 | 948.8 |
| 1-17 | n-butyl | 2,4-dichloro phenyl | Propanoic acid | S | 34 | 864.4 |
| 1-18 | n-butyl | 2,4-dichloro phenyl | 5-methyl-1H-tertazole | S | 31 | 1564 |
| 1-19 | n-butyl | 2-chloro-4-(trifluoromethyl) phenyl | Propanoic acid | S | 11 | 93 |
| 1-20 | n-butyl | 2-chloro-4-(trifluoromethyl) phenyl | 5-methyl-1H-tertazole | S | 96 | 524 |
| 1-21 | isopropyl | N,N-dimethylaniline | (R)-2-hydroxy-propanoic acid | S | >30000 | >30000 |
| 1-22 | isopropyl | 2-chloro-4-(trifluoromethyl) phenyl | Propanoic acid | S | 70 | 14.2 |
| 1-23 | Phenyl | Benzofuranyl | Propionic acid | — | 148 | 39.8 |
| 1-24 | isopropyl | 4-(trifluoro-methyl)pyridine | Propanoic acid | S | 134 | 187.5 |

TABLE 1-continued

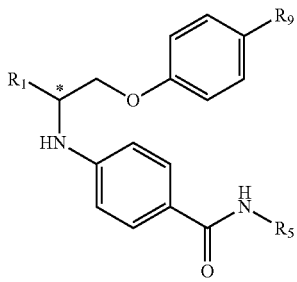

*indicium of chirality

| Compound | R$_1$ | R$_9$ | R$_5$ | Chirality | IC$_{50}^{binding}$ (nM)$^a$ | IC$_{50}^{cAMP}$ (nM) |
|---|---|---|---|---|---|---|
| 1-25 | isopropyl | 2-fluoro-4-(trifluoromethyl)phenyl | Propanoic acid | S | 44 | 90.4 |
| 1-26 | 2-butyl | 2,4-difluorophenyl | Propanoic acid | S | N/A | 213 |
| 1-27 | n-butyl | 2-fluoro-4-(trifluoromethyl)phenyl | Propanoic acid | S | 108 | 96.5 |
| 1-28 | Phenyl | 4-(trifluoromethyl)phenyl | Propanoic acid | — | 150 | 287.7 |
| 1-29 | isopropyl | 6-(trifluoromethyl)pyridazine | Propanoic acid | S | 2791 | >30000 |
| 1-30 | isopropyl | Benzo[d]thiazol-2-yl | Ethyl propionate | S | 7626 | 1214 |
| 1-31 | isopropyl | benzo[d]thiazole | Methyl propanoate | S | 5771 | 83 |
| 1-32 | isopropyl | Benzo[d]thiazol-2-yl | Propanoic acid | S | 57 | 152 |
| 1-33 | isopropyl | 2-fluoro-4-(trifluoromethyl)phenyl | Ethanesulfonic acid | S | 1900 | 3767 |
| 1-34 | isopropyl | Benzofuranyl | Propanoic acid | R | 113 | 238.7 |
| 1-35 | isopropyl | 2-chloro-4-(trifluoromethyl)phenyl | Propanoic acid | R | 145 | 209.3 |
| 1-36 | t-butyl | 2,4-dichlorophenyl | Propanoic acid | S | 141 | 243 |
| 1-37 | isopropyl | 2-chloro-N,N-dimethylaniline | Propanoic acid | S | 372 | 376 |
| 1-38 | 2-butyl | 2-chloro-4-methoxyphenyl | Propanoic acid | S | 172 | 203 |
| 1-39 | isopropyl | Imidazo[1,2-a]pyridin-2-yl | Propanoic acid | S | 3812 | 17895 |
| 1-40 | t-butyl | Benzofuranyl | Propanoic acid | S | 195 | 235.3 |
| 1-41 | isopropyl | furo[3,2-b]pyridin-2-yl | Propanoic acid | S | 227 | 1403 |
| 1-42 | t-butyl | 2-chloro-4-(trifluoromethyl)phenyl | Propanoic acid | S | 234 | 298 |
| 1-43 | isopropyl | 5-(trifluoromethyl)-1,3,4-oxadiazol-2-yl | Propanoic acid | S | 583 | >30000 |
| 1-44 | 2-butyl | 5-(trifluoromethyl)-1,3,4-oxadiazol-2-yl | Propanoic acid | S | 388 | 10000 |
| 1-45 | 2-butyl | 5-(tert-butyl)-1,3,4-oxadiazol-2-yl | Propanoic acid | S | 1522 | 11981 |
| 1-46 | 2-butyl | 5-phenyl-1,3,4-oxadiazol-2-yl | Propanoic acid | S | 601 | 5441 |
| 1-47 | isopropyl | benzo[d]oxazole | Ethyl propanoate | S | >30000 (56%) | 170 |
| 1-48 | isopropyl | benzo[d]oxazole | Propanoic acid | S | 138 | 546 |
| 1-49 | n-butyl | 2-(tert-butyl)-1,3,4-oxadiazole | Propanoic acid | S | 7200 | 7065 |
| 1-50 | n-butyl | 5-phenyl-1,3,4-oxadiazole | Propanoic acid | S | 715 | 1622 |
| 1-51 | isopropyl | Benzo[d]thiazol-2-yl | Ethyl propanoate | R | >30 uM | 197 |

TABLE 1-continued

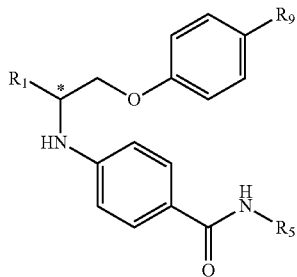

*indicium of chirality

| Compound | $R_1$ | $R_9$ | $R_5$ | Chirality | $IC_{50}^{binding}$ (nM)[a] | $IC_{50}^{cAMP}$ (nM) |
|---|---|---|---|---|---|---|
| 1-52 | isopropyl | Benzo[d]thiazol-2-yl | Propanoic acid | R | 89 | 377 |
| 1-53 | isopropyl | benzo[d]oxazole | Ethyl propanoate | R | 24480 | 90 |
| 1-54 | isopropyl | benzo[d]oxazole | Propanoic acid | R | 95 | 213 |

[a] the number in pathenthesis represents the percentage of inhibition when a compound was administered at the concentration of 30 μM.

TABLE 2

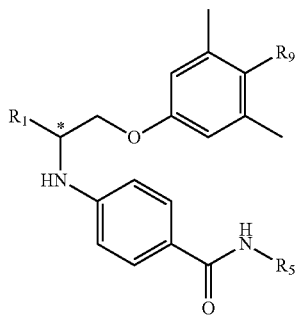

*indicium of chirality

| Compound | $R_1$ | $R_9$ | $R_5$ | Chirality | $IC_{50}^{binding}$ (nM) | $IC_{50}^{cAMP}$ (nM) |
|---|---|---|---|---|---|---|
| 2-1 | Benzyl | 4-(trifluoromethyl)phenyl | Propanoic acid | R | 266 | 322.9 |
| 2-2 | Benzyl | 4-Trifluoromethoxy phenyl | Propanoic acid | R | 377.5 | 474.8 |
| 2-3 | isobutyl | 4-Trifluoromethoxy phenyl | Propionic acid | S | 465 | 493 |
| 2-4 | isopropyl | 4-(trifluoromethyl)phenyl | Propionic acid | S | 91 | 245.8 |
| 2-5 | isopropyl | 4-tert-butyl phenyl | Propanoic acid | S | 347 | 352 |
| 2-6 | 2-butyl | 4-tert-butyl phenyl | Propanoic acid | S | 67 | 448 |
| 2-7 | 2-butyl | Benzofuranyl | Propanoic acid | S | 158 | 468 |
| 2-8 | 2-butyl | 4-(trifluoromethoxy)phenyl | Propanoic acid | S | 627 | 602 |
| 2-9 | 2-butyl | 2,4-dichloro phenyl | Propanoic acid | S | 60 | 447.6 |
| 2-10 | 2-butyl | 4-(trifluoromethyl)phenyl | Propanoic acid | S | 90 | 241.4 |
| 2-11 | isopropyl | 2-chloro-4-(trifluoromethyl)phenyl | Propanoic acid | S | 872 | 277.2 |

TABLE 2-continued

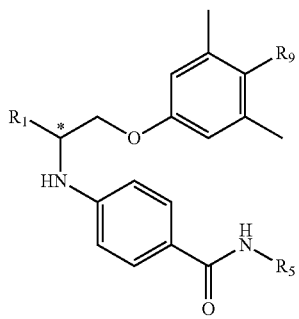

*indicium of chirality

| Compound | $R_1$ | $R_9$ | $R_5$ | Chirality | $IC_{50}^{binding}$ (nM) | $IC_{50}^{cAMP}$ (nM) |
|---|---|---|---|---|---|---|
| 2-12 | n-butyl | Benzofuranyl | Propanoic acid | S | 108 | 62.8 |
| 2-13 | n-butyl | Benzofuranyl | 5-methyl-1H-tertazole | S | 167 | 148.5 |

TABLE 3

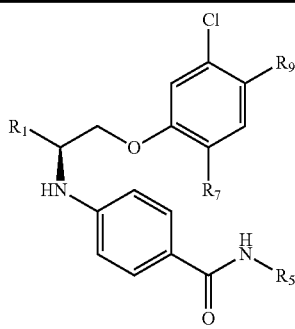

| Compound | $R_1$ | $R_9$ | $R_5$ | $R_7$ | $IC_{50}^{binding}$ (nM) | $IC_{50}^{cAMP}$ (nM) |
|---|---|---|---|---|---|---|
| 3-1 | 2-butyl | Benzofuranyl | 5-methyl-1H-tertazole | H | 217 | 1822 |
| 3-2 | isopropyl | 2-chloro-4-(trifluoromethyl)phenyl | (R)-2-hydroxybutanoic acid | H | 135 | >10000 |
| 3-3 | isopropyl | 2-chloro-4-(trifluoromethyl)phenyl | 5-methyl-1H-tertazole | H | 86 | 1250 |
| 3-4 | isopropyl | 2-chloro-4-(trifluoromethyl)phenyl | Propanoic acid | H | 17 | 313.6 |
| 3-5 | isopropyl | Benzofuranyl | 5-methyl-1H tertazole | H | 117 | 1863 |
| 3-6 | isopropyl | Benzofuranyl | (R)-2-hydroxybutanoic acid | H | 184 | 9291 |
| 3-7 | isopropyl | Benzofuranyl | Propanoic acid | H | 103 | 363.5 |
| 3-8 | n-butyl | 2-chloro-4-(trifluoromethyl)phenyl | Propanoic acid | H | 26 | 35 |
| 3-9 | n-butyl | 2-chloro-4-(trifluoromethyl)phenyl | 5-methyl-1H tertazole | H | 37 | 528.1 |
| 3-10 | n-butyl | Benzofuranyl | Propanoic acid | H | 20 | 88.7 |
| 3-11 | n-butyl | Benzofuranyl | 5-methyl-1H-tertazole | H | 149 | 672.8 |
| 3-12 | n-butyl | 2,4-dichloro phenyl | Propanoic acid | H | 30 | 28.1 |
| 3-13 | n-butyl | 2,4-dichloro phenyl | 5-methyl-1H-tertazole | H | 92 | 279.9 |
| 3-14 | isopropyl | Benzofuranyl | Propanoic acid | Cl | 58 | 115.4 |

TABLE 3-continued

[Structure: chlorophenyl ether linked via OCH(R1)CH2 to NH-phenyl-C(=O)NH-R5, with R9 on chlorophenyl and R7 substituent]

| Compound | R₁ | R₉ | R₅ | R₇ | IC₅₀$^{binding}$ (nM) | IC₅₀$^{cAMP}$ (nM) |
|---|---|---|---|---|---|---|
| 3-15 | Phenyl | 2-chloro-4-(trifluoromethyl)phenyl | Propanoic acid | H | 97 | 330.4 |
| 3-16 | n-butyl | 4-(trifluoromethyl)phenyl | Propanoic acid | H | 51 | 367.7 |
| 3-17 | n-butyl | 4-(trifluoromethyl)phenyl | 5-methyl-1H tertazole | H | 111 | 105 |
| 3-18 | isopropyl | Benzofuranyl | Ethanesulfonic acid | H | 836 | >30000 |
| 3-19 | 2-butyl | Benzofuranyl | Propanoic acid | Cl | 64 | 130 |
| 3-20 | 2-butyl | 2-chloro-4-(trifluoromethyl)phenyl | Propanoic acid | Cl | 73 | 44 |
| 3-21 | 2-butyl | 2-fluoro-4-(trifluoromethyl)phenyl | Propanoic acid | Cl | 295 | 653 |
| 3-22 | n-butyl | 2-fluoro-4-(trifluoromethyl)phenyl | Propanoic acid | H | 83 | 54 |
| 3-23 | t-butyl | Benzofuranyl | Proparioic acid | H | 156 | 293 |
| 3-24 | t-butyl | 2-fluoro-4-(trifluoromethyl)phenyl | Propanoic acid | H | 53 | 80 |

TABLE 4

[Structure: R2O-CH2-CH(R1)-NH linked to pyridine/aromatic ring with A1 and A3 as ring atoms, C(=O)NH-R5]

| Compound | R₁ | R₂ | R₅ | A₁ | A₃ | IC₅₀$^{binding}$ (nM) | IC₅₀$^{cAMP}$ (nM) |
|---|---|---|---|---|---|---|---|
| 4-1 | isopropyl | 4-(trifluoromethyl)-1,1'-biphenyl | Propanoic acid | N | C | 369 | 626.9 |
| 4-2 | isopropyl | 2-phenylbenzofuran | Propanoic acid | N | C | 90 | 121.3 |
| 4-3 | 2-butyl | 2,4-dichloro-biphenyl | Propanoic acid | N | C | 610 | 414 |
| 4-4 | 2-butyl | 2-(tert-butyl)-5-phenyl-1,3,4-oxadiazole | Propanoic acid | N | C | 2395 | >30000 |
| 4-5 | 2-butyl | 2,5-diphenyl-1,3,4-oxadiazole | Propanoic acid | N | C | 708 | 11200 |

TABLE 5

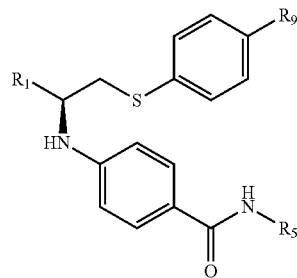

| Compound | R₁ | R₉ | R₅ | IC₅₀ binding (nM) | IC₅₀ cAMP (nM) |
|---|---|---|---|---|---|
| 5-1 | isopropyl | Benzofuranyl | Propanoic acid | 2041 | 14405 |
| 5-2 | 2-butyl | 4-(trifluoromethyl)phenyl | Propanoic acid | 1193 | 2465 |
| 5-3 | 2-butyl | Benzofuranyl | Propanoic acid | 400 | 946.9 |

TABLE 6

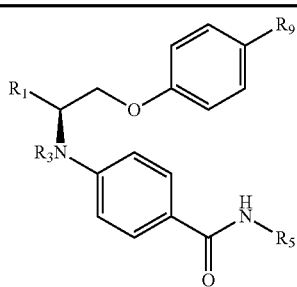

| Compound | R₁ | R₉ | R₃ | R₅ | IC₅₀ binding (nM) | IC₅₀ cAMP (nM) |
|---|---|---|---|---|---|---|
| 6-1 | isopropyl | Benzofuranyl | Methyl | Propanoic acid | 391 | 204.2 |
| 6-2 | isopropyl | Benzofuranyl | n-ethyl | Propanoic acid | 645 | 164.3 |
| 6-3 | Ethoxymethyl | Benzofuranyl | H | Propanoic acid | 479 | 3859 |

TABLE 7

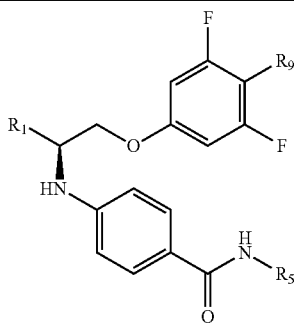

| Compound | R₁ | R₉ | R₅ | IC₅₀ binding (nM) | IC₅₀ cAMP (nM) |
|---|---|---|---|---|---|
| 7-1 | isopropyl | Benzofuranyl | Propanoic acid | 93 | 495 |
| 7-2 | isopropyl | 2-chloro-4-(trifluoromethyl)phenyl | Propanoic acid | 177 | 201 |
| 7-3 | isopropyl | 4-(trifluoromethyl)phenyl | Propanoic acid | 107 | 140 |
| 7-4 | isopropyl | 2-fluoro-4-(trifluoromethyl)phenyl | Propanoic acid | 182 | 165 |

TABLE 7-continued

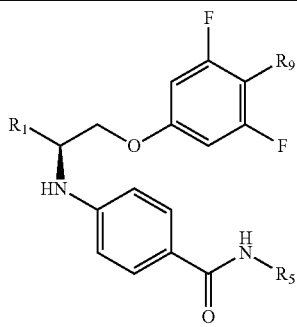

| Compound | R₁ | R₉ | R₅ | IC₅₀ binding (nM) | IC₅₀ cAMP (nM) |
|---|---|---|---|---|---|
| 7-5 | isobutyl | 2-chloro-4-(trifluoromethyl)phenyl | Propanoic acid | 75 | 811 |
| 7-6 | isobutyl | 4-(trifluoromethyl)phenyl | Propanoic acid | 144 | 371 |
| 7-7 | isobutyl | 2-fluoro-4-(trifluoromethyl)phenyl | Propanoic acid | 307 | 689 |
| 7-8 | isobutyl | 2,4-dichlorophenyl | Propanoic acid | 49 | 329 |

TABLE 7-continued

| Compound | R₁ | R₉ | R₅ | IC₅₀$^{binding}$ (nM) | IC₅₀$^{cAMP}$ (nM) |
|---|---|---|---|---|---|
| 7-9 | isobutyl | 3,5-dichlorophenyl | Propanoic acid | 262 | 816 |
| 7-10 | isobutyl | Benzofuranyl | Propanoic acid | 145 | 730.9 |
| 7-11 | isopropyl | 2,4-dichlorophenyl | Propanoic acid | 74 | 209 |

TABLE 8

| Compound | R₁ | R₉ | R₅ | IC₅₀$^{binding}$ (nM) | IC₅₀$^{cAMP}$ (nM) |
|---|---|---|---|---|---|
| 8-1 | isopropyl | 2-fluoro-4-(trifluoromethyl)phenyl | Propanoic acid | 112 | 61.9 |
| 8-2 | isopropyl | 2-fluoro-4-(trifluoromethyl)phenyl | Ethanesulfonic acid | 1713 | 12144 |
| 8-3 | isopropyl | Benzofuranyl | Propanoic acid | 83 | 84.4 |
| 8-4 | isopropyl | Benzofuranyl | Ethanesulfonic acid | 1720 | 10292 |
| 8-5 | isopropyl | 2-chloro-4-(trifluoromethyl)phenyl | Propanoic acid | 75 | 85 |
| 8-6 | isobutyl | 2-fluoro-4-(trifluoromethyl)phenyl | Propanoic acid | 172 | 428 |
| 8-7 | 2-butyl | Benzofuranyl | Propanoic acid | 186 | 129 |
| 8-8 | 2-butyl | 2-chloro-4-(trifluoromethyl)phenyl | Propanoic acid | 277 | 500 |
| 8-9 | isopropyl | 2,4-dichlorophenyl | Propanoic acid | 145 | 365 |
| 8-10 | 2-butyl | 2-fluoro-4-(trifluoromethyl)phenyl | Propanoic acid | 186 | 353.2 |
| 8-11 | 2-butyl | 2,4-dichlorophenyl | Propanoic acid | 51 | 269.1 |
| 8-12 | isopropyl | 3,5-dichlorophenyl | Propanoic acid | 227 | 1243 |
| 8-13 | n-butyl | Benzofuranyl | Propanoic acid | 44 | 84 |
| 8-14 | 2-butyl | 4-(trifluoromethyl)phenyl | Propanoic acid | 251 | 250 |
| 8-15 | n-butyl | 2-chloro-4-(trifluoromethyl)phenyl | Propanoic acid | 59 | 129 |
| 8-16 | n-butyl | 2,4-dichlorophenyl | Propanoic acid | 89 | 135 |
| 8-17 | n-butyl | 2-fluoro-4-(trifluoromethyl)phenyl | Propanoic acid | 308 | 227.6 |
| 8-18 | n-butyl | 4-(trifluoromethyl)phenyl | Propanoic acid | 158 | 153.5 |
| 8-19 | isobutyl | 2,4-dichlorophenyl | Propanoic acid | 101 | 182 |
| 8-20 | isobutyl | Benzofuranyl | Propanoic acid | 83 | 234 |
| 8-21 | t-butyl | Benzofuranyl | Propanoic acid | 111 | 181 |
| 8-22 | t-butyl | 2,4-dichlorophenyl | Propanolc acid | 68 | 166.9 |
| 8-23 | t-butyl | 2-fluoro-4-(trifluoromethyl)phenyl | Propanoic acid | 81 | 89.46 |

TABLE 8-continued

| Compound | $R_1$ | $R_9$ | $R_5$ | $IC_{50}^{binding}$ (nM) | $IC_{50}^{cAMP}$ (nM) |
|---|---|---|---|---|---|
| 8-24 | n-butyl | 5-(trifluoromethyl)-1,3,4-oxadiazol-2-yl | Propanoic acid | 366 | 2701 |
| 8-25 | isopropyl | Benzo[d]thiazol-2-yl | Propanoic acid | 95 | 653 |

TABLE 9

| Compound | $R_1$ | $R_2$ | $A_1$ | $A_3$ | $IC_{50}^{binding}$ (nM) | $IC_{50}^{cAMP}$ (nM) |
|---|---|---|---|---|---|---|
| 9-1 | isopropyl | 2-phenylbenzofuran | N | N | 125 | 386.1 |
| 9-2 | 2-butyl | 2,4-dichloro-1,1'-biphenyl | N | N | 363 | 427 |
| 9-3 | isopropyl | 4-(trifluoromethyl)-1,1'-biphenyl | C | N | 120 | 487 |
| 9-4 | 2-butyl | 2,6-difluoro-4'-(trifluorometlyl)-1,1'-biphenyl | N | C | 1668 | 2300 |
| 9-5 | isopropyl | 2-(2-fluorophenyl)benzo[d]thiazole | N | C | 606 | 2408 |
| 9-6 | isopropyl | 4-((1-((1-(2,4-difluorophenyl)-1H-pyrazol-4-yl)oxy | C | C | 3650 | 5577 |

TABLE 10

| Compound | $R_1$ | $R_9$ | $R_5$ | $IC_{50}^{binding}$ (nM) | $IC_{50}^{cAMP}$ (nM) |
|---|---|---|---|---|---|
| 10-1 | isopropyl | 4-(trifluoromethyl)phenyl | Propanoic acid | 531 | 1959 |
| 10-2 | isopropyl | 2-chloro-4-(trifluoromethyl)phenyl | Propanoic acid | 255 | 1805 |
| 10-3 | isopropyl | 2-fluoro-4-(trifluoromethyl)phenyl | Propanoic acid | 511 | 1206 |

TABLE 10-continued

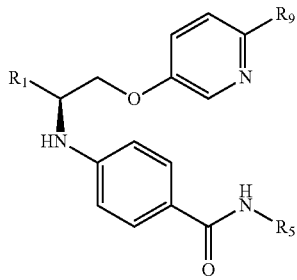

| Compound | $R_1$ | $R_9$ | $R_5$ | $IC_{50}^{binding}$ (nM) | $IC_{50}^{cAMP}$ (nM) |
|---|---|---|---|---|---|
| 10-4 | isopropyl | 2,4-dichlorophenyl | Propanoic acid | 445 | 4036 |
| 10-5 | isopropyl | 3,5-dichlorophenyl | Propanoic acid | 441 | 3690 |
| 10-6 | isopropyl | Benzofuranyl | Propanoic acid | 252 | 2650 |
| 10-7 | n-butyl | 2,4-dichlorophenyl | Propanoic acid | 319 | 732 |
| 10-8 | n-butyl | 2-fluoro-4-(trifluoromethyl)phenyl | Propanoic acid | 180 | 344 |
| 10-9 | n-butyl | 4-(trifluoromethyl)phenyl | Propanoic acid | 127 | 465 |
| 10-10 | n-butyl | 3,5-dichlorophenyl | Propanoic acid | 314 | 493 |
| 10-11 | n-butyl | 2-chloro-4-(trifluoromethyl)phenyl | Propanoic acid | 270 | 537.4 |
| 10-12 | n-butyl | Benzofuranyl | Propanoic acid | 181 | 791.6 |
| 10-13 | 2-butyl | Benzofuranyl | Propanoic acid | 224 | 863.9 |
| 10-14 | 2-butyl | 2-fluoro-4-(trifluoromethyl)phenyl | Propanoic acid | 306 | 497.1 |
| 10-15 | 2-butyl | 2,4-dichlorophenyl | Propanoic acid | 179 | 301 |
| 10-16 | 2-butyl | 2-chloro-4-(trifluoromethyl)phenyl | Propanoic acid | 141 | 272 |
| 10-17 | isobutyl | 4-(trifluoromethyl)phenyl | Propanoic acid | 542 | 847 |
| 10-18 | isobutyl | 2-chloro-4-(trifluoromethyl)phenyl | Propanoic acid | 234 | 880 |
| 10-19 | isobutyl | 2,4-dichlorophenyl | Propanoic acid | 301 | 1064 |

TABLE 11

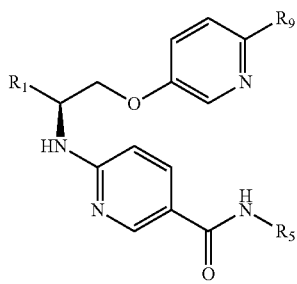

| Compound | $R_1$ | $R_9$ | $R_5$ | $IC_{50}^{binding}$ (nM) | $IC_{50}^{cAMP}$ (nM) |
|---|---|---|---|---|---|
| 11-1 | isopropyl | 2-chloro-4-(trifluoromethyl)phenyl | Propanoic acid | 1736 | 8711 |
| 11-2 | isopropyl | Benzofuranyl | Propanoic acid | 926 | 14398 |

TABLE 12

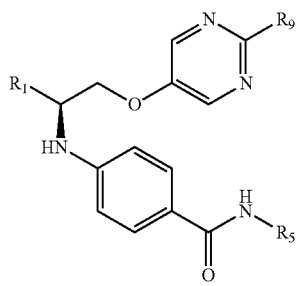

| Compound | $R_1$ | $R_9$ | $R_5$ | $IC_{50}^{binding}$ (nM) | $IC_{50}^{cAMP}$ (nM) |
|---|---|---|---|---|---|
| 12-1 | isobutyl | 3-methyl-4-(trifluoromethyl)-1H-pyrazol-1-yl | Propanoic acid | 674 | 14170 |
| 12-2 | isopropyl | Benzofuranyl | Propanoic acid | 266 | 6849 |
| 12-3 | isobutyl | Benzofuranyl | Propanoic acid | 608 | >30000 |
| 12-4 | isopropyl | 2-chloro-4-(trifluromethyl)phenyl | Propanoic acid | 539 | 9828 |
| 12-5 | n-butyl | 2-chloro-4-(trifluromethyl)phenyl | Propanoic acid | 451 | 2357 |
| 12-6 | isopropyl | 2,4-dichlorophenyl | Propanoic acid | 1667 | >30000 |
| 12-7 | n-butyl | 2,4-dichlorophenyl | Propanoic acid | 888 | 3868 |
| 12-8 | 2-butyl | 2-chloro-4-(trifluromethyl)phenyl | Propanoic acid | 331 | 2719 |
| 12-9 | isobutyl | 2-chloro-4-(trifluromethyl)phenyl | Propanoic acid | 501 | 19185 |
| 12-10 | 2-butyl | 2,4-dichlorophenyl | Propanoic acid | 337 | 890 |
| 12-11 | isobutyl | 2,4-dichlorophenyl | Propanoic acid | 233 | 3585 |

TABLE 13

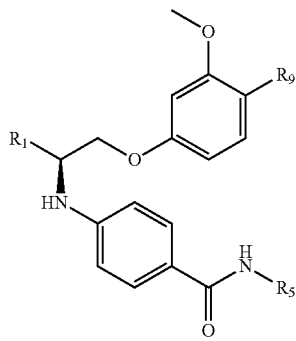

| Compound | $R_1$ | $R_9$ | $R_5$ | $IC_{50}^{binding}$ (nM) | $IC_{50}^{cAMP}$ (nM) |
|---|---|---|---|---|---|
| 13-1 | 2-butyl | Benzofuranyl | Propanoic acid | 46 | 157 |
| 13-2 | 2-butyl | 2,4-dichlorophenyl | Propanoic acid | 92 | 254 |
| 13-3 | 2-butyl | 2-chloro-4-(trifluoromethyl)phenyl | Propanoic acid | 57 | 71 |
| 13-4 | 2-butyl | 2-fluoro-4-(trifluoromethyl)phenyl | Propanoic acid | 68 | 131 |
| 13-5 | isopropyl | Benzofuranyl | Propanoic acid | 111 | 112 |
| 13-6 | isopropyl | 2-chloro-4-(trifluoromethyl)phenyl | Propanoic acid | 89 | 97 |
| 13-7 | isopropyl | 2,4-dichlorophenyl | Propanoic acid | 95 | 139 |
| 13-8 | isopropyl | 2-fluoro-4-(trifluoromethyl)phenyl | Propanoic acid | 79 | 77.8 |
| 13-9 | n-butyl | 2,4-dichlorophenyl | Propanoic acid | 54 | 219 |
| 13-10 | isproopyl | 4-(trifluoromethyl)phenyl | Propanoic acid | 92 | 246 |

TABLE 13-continued

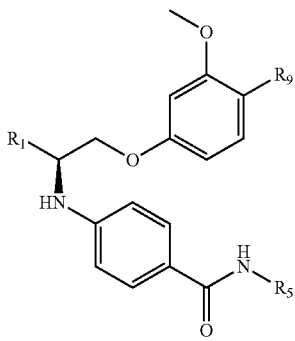

| Compound | $R_1$ | $R_9$ | $R_5$ | $IC_{50}^{binding}$ (nM) | $IC_{50}^{cAMP}$ (nM) |
|---|---|---|---|---|---|
| 13-11 | n-butyl | 4-(trifluoromethyl)phenyl | Propanoic acid | 47 | 118 |
| 13-12 | 2-butyl | 5-phenyl-1,3,4-oxadiazol-2-yl | Propanoic acid | 608 | 23347 |
| 13-13 | 2-butyl | 5-(tert-butyl)-1,3,4-oxadiazol-2-yl | Propanoic acid | 883 | 300000 |
| 13-14 | n-butyl | 2-fluoro-4-(trifluoromethyl)phenyl | Propanoic acid | 15 | 66 |

TABLE 14

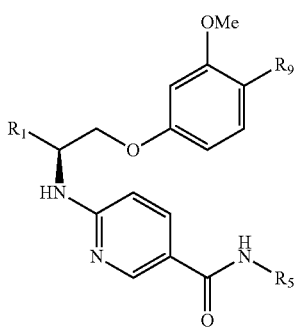

| Compound | $R_1$ | $R_9$ | $R_5$ | $IC_{50}^{binding}$ (nM) | $IC_{50}^{cAMP}$ (nM) |
|---|---|---|---|---|---|
| 14-1 | isopropyl | Benzofuranyl | Propanoic acid | 750 | 1232 |
| 14-2 | n-butyl | 2-fluoro-4-(trifluoromethyl)phenyl | Propanoic acid | 74 | 508 |

TABLE 15

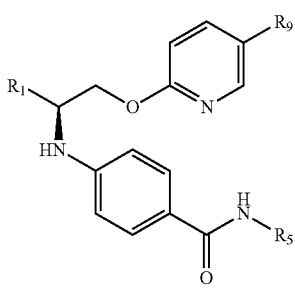

| Compound | $R_1$ | $R_9$ | $R_5$ | $IC_{50}^{binding}$ (nM) | $IC_{50}^{cAMP}$ (nM) |
|---|---|---|---|---|---|
| 15-1 | Phenyl | Benzofuranyl | 5-methyl-1H-tertazole | 388 | 7356 |

TABLE 15-continued

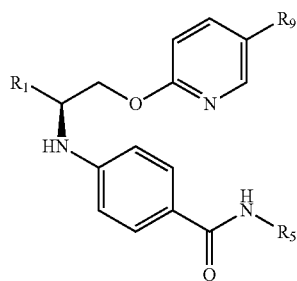

| Compound | R₁ | R₉ | R₅ | IC$_{50}^{binding}$ (nM) | IC$_{50}^{cAMP}$ (nM) |
|---|---|---|---|---|---|
| 15-2 | Isopropyl | 4-(trifluoromethyl)phenyl | 5-methyl-1H-tertazole | 390 | 1543 |
| 15-3 | Isopropyl | Benzofuranyl | Propanoic acid | 51 | 111 |
| 15-4 | Phenyl | 4-t-butylphenyl | Propanoic acid | 626 | 3241 |
| 15-5 | Phenyl | Benzofuranyl | Propanoic acid | 706 | 2067 |
| 15-6 | Phenyl | 4-t-butylphenyl | (R)-2-hydroxypropanoic acid | 172 | >30000 |
| 15-7 | Isopropyl | 4-(trifluoromethyl)phenyl | Propanoic acid | 753 | 258.8 |
| 15-8 | Isopropyl | 4-(trifluoromethyl)phenyl | (R)-2-hydroxypropanoic acid | 3302 | >30000 |
| 15-9 | Isopropyl | 2-chloro-4-(trifluoromethyl)phenyl | Propanoic acid | 330 | 81.5 |
| 15-10 | Isobutyl | 2-chloro-4-(trifluoromethyl)phenyl | Propanoic acid | 80 | 198.4 |
| 15-11 | Isobutyl | 4-(trifluoromethyl)phenyl | Propanoic acid | 210 | 284.7 |
| 15-12 | 2-butyl | 4-(trifluoromethyl)phenyl | Propanoic acid | 376 | 294 |
| 15-13 | 2-butyl | 2-chloro-4-(trifluoromethyl)phenyl | Propanoic acid | 98 | 123 |
| 15-14 | 2-butyl | 2-fluoro-4-(trifluoromethyl)phenyl | Propanoic acid | 379 | 280.6 |
| 15-15 | 2-butyl | Benzofuranyl | Propanoic acid | 207 | 32.73 |
| 15-16 | Isobutyl | 2-fluoro-4-(trifluoromethyl)phenyl | Propanoic acid | 669 | 999 |
| 15-17 | Isopropyl | 2,4-dichlorophenyl | Propanoic acid | 216 | 196 |
| 15-18 | Isobutyl | 2-chloro-4-(trifluoromethyl)phenyl | Ethanesulfonic acid | 1306 | >30000 |
| 15-19 | Isobutyl | 6-(trifluoromethyl)pyridazin-3-yl | Propanoic acid | 2990 | >30000 |
| 15-20 | 2-butyl | 2,4-difluorophenyl | Propanoic acid | 382 | 1255 |
| 15-21 | 2-butyl | 2,4-difluorophenyl | Ethanesulfonic acid | 5280 | >30000 |
| 15-22 | n-butyl | Benzofuranyl | Propanoic acid | 89 | 168 |
| 15-23 | n-butyl | Benzofuranyl | Ethanesulfonic acid | 453 | >30000 |
| 15-24 | n-butyl | 2,4-dichlorophenyl | Propanoic acid | 301 | 293.9 |
| 15-25 | n-butyl | 2-chloro-4-(trifluoromethyl)phenyl | Propanoic acid | 218 | 245 |

TABLE 15-continued

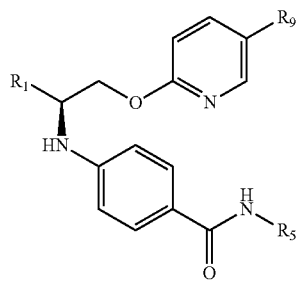

| Compound | R₁ | R₉ | R₅ | IC₅₀$^{binding}$ (nM) | IC₅₀$^{cAMP}$ (nM) |
|---|---|---|---|---|---|
| 15-26 | n-butyl | 2-fluoro-4-(trifluoromethyl)phenyl | Propanoic acid | 228 | 206.6 |
| 15-27 | 4'-(trifluoromethyl)-[1,1'-biphenyl]-4-yl | trifluoromethyl | Propanoic acid | 101 | 316 |
| 15-28 | 4'-(trifluoromethyl)-[1,1'-biphenyl]-4-yl | Benzofuranyl | Ethanesulfonic acid | 100 | 11647 |
| 15-29 | 4'-(trifluoromethyl)-[1,1'-biphenyl]-4-yl | Benzofuranyl | Propanoic acid | 20 | 107 |
| 15-30 | 4'-(trifluoromethyl)-1,1'-biphenyl | 2-(tert-butyl)-1,3,4-oxadiazole | Propanoic acid | 1997 | 18257 |
| 15-31 | 2-fluoro-4-(trifluoromethyl)-1,1'-biphenyl | 2-(tert-butyl)--1,3,4-oxadiazole | Ethyl propionate | >30000 | >30000 |
| 15-32 | 2-fluoro-4-(trifluoromethyl)-1,1'-biphenyl | 2-(tert-butyl)--1,3,4-oxadiazole | Propanoic acid | 151 | 809 |
| 15-33 | 2,4-dichloro-1,1'-biphenyl | 2-(tert-butyl)--1,3,4-oxadiazole | Ethyl propionate | >30000 | >30000 |
| 15-34 | 2,4-dichloro-1,1'-biphenyl | 2-(tert-butyl)--1,3,4-oxadiazole | Propanoic acid | 2999 | 4558 |
| 15-35 | 5-methoxy-2-phenylpyrimidine | Benzofuranyl | Ethanesulfonic acid | 584 | >30000 |
| 15-36 | Isopropyl | Benzo[d]thiazol-2-yl | Ethyl propionate | >30 uM | 1973 |
| 15-37 | Isopropyl | Benzo[d]thiazol-2-yl | Propanoic acid | 468 | 1609 |

TABLE 16

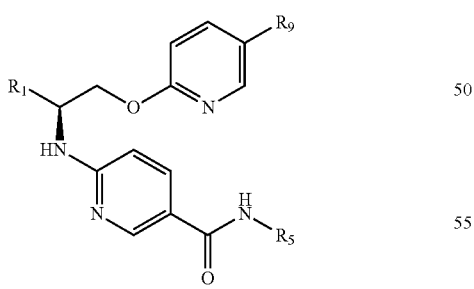

| Compound | R₁ | R₉ | R₅ | IC₅₀$^{binding}$ (nM) | IC₅₀$^{cAMP}$ (nM) |
|---|---|---|---|---|---|
| 16-1 | isopropyl | 2,4-dichlorophenyl | Propanoic acid | 215 | 357.2 |
| 16-2 | isopropyl | Benzofuranyl | Propanoic acid | 528 | 239.3 |

TABLE 17

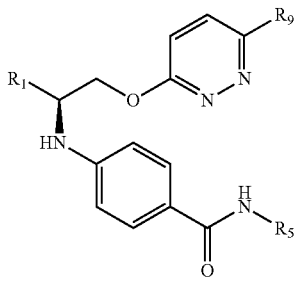

| Compound | R₁ | R₉ | R₅ | $IC_{50}^{binding}$ (nM) | $IC_{50}^{cAMP}$ (nM) |
|---|---|---|---|---|---|
| 17-1 | isobutyl | 2,4-difluorophenyl | Propanoic acid | 2259 | 4239 |
| 17-2 | isobutyl | 2,4-dichlorophenyl | Propanoic acid | 139 | 716 |
| 17-3 | 2-butyl | 4-(trifluoromethyl)phenyl | Propanoic acid | 989 | 1307 |
| 17-4 | 2-butyl | 2-chloro-4-(trifluoromethyl)phenyl | Propanoic acid | 609 | 1266 |
| 17-5 | 2-butyl | 2-fluoro-4-(trifluoromethyl)phenyl | Propanoic acid | 769 | 3332 |
| 17-6 | 2-butyl | 2,4-difluorophenyl | Propanoic acid | 445 | 10157 |
| 17-7 | isobutyl | 4-(trifluoromethyl)phenyl | Propanoic acid | 1318 | 7647 |
| 17-8 | isopropyl | Benzofuranyl | Propanoic acid | 2045 | 10741 |
| 17-9 | isopropyl | 2-fluoro-4-(trifluoromethyl)phenyl | Propanoic acid | 2600 | 11597 |
| 17-10 | isopropyl | 4-fluorophenyl | Propanoic acid | 2295 | >30000 |
| 17-11 | isopropyl | 2,4-difluorophenyl | Propanoic acid | 1013 | >30000 |
| 17-12 | isopropyl | 4-t-butylphenyl | Propanoic acid | 20000 | 6494 |

TABLE 18

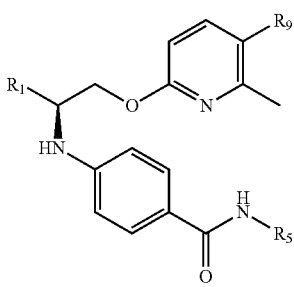

| Compound | R₁ | R₉ | R₅ | $IC_{50}^{binding}$ (nM) | $IC_{50}^{cAMP}$ (nM) |
|---|---|---|---|---|---|
| 18-1 | n-butyl | Benzofuranyl | Propanoic acid | 386 | 250 |
| 18-2 | n-butyl | 2-chloro-4-(trifluoromethyl)phenyl | Propanoic acid | 42 | 49 |
| 18-3 | 2-butyl | 2-chloro-4-(trifluoromethyl)phenyl | Propanoic acid | 62 | 75 |
| 18-4 | 2-butyl | Benzofuranyl | Propanoic acid | 203 | 151 |
| 18-5 | 2-butyl | 2,4-dichlorophenyl | Propanoic acid | 165 | 151 |
| 18-6 | 2-butyl | 2-fluoro-4-(trifluoromethyl)phenyl | Propanoic acid | 179 | 204 |
| 18-7 | isobutyl | 2-chloro-4-(trifluoromethyl)phenyl | Propanoic acid | 74 | 80 |
| 18-8 | isobutyl | 2,4-dichlorophenyl | Propanoic acid | 49 | 122.5 |
| 18-9 | isobutyl | Benzofuranyl | Propanoic acid | 207 | 429.9 |

TABLE 19

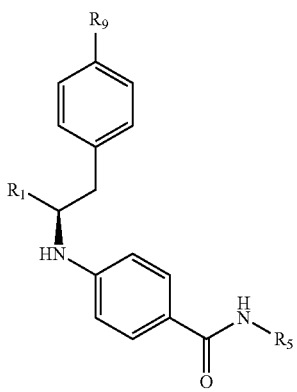

| Compound | $R_1$ | $R_9$ | $R_5$ | $IC_{50}^{binding}$ (nM) | $IC_{50}^{cAMP}$ (nM) |
|---|---|---|---|---|---|
| 19-1 | n-butyl | 4-(trifluoromethyl)phenyl | Propanoic acid | 109 | 393.8 |
| 19-2 | Methyl | 2,4-dichlorophenyl | Propanoic acid | 6316 | 5186 |
| 19-3 | Methyl | 4-(trifluoromethyl)phenyl | Propanoic acid | 2728 | 2719 |
| 19-4 | Methyl | 4-t-butylphenyl | Propanoic acid | 1633 | 3488 |
| 19-5 | Isobutyl | Benzofuranyl | Propanoic acid | 163 | 1082 |
| 19-6 | n-pentyl | Benzofuranyl | Propanoic acid | 158 | 632 |
| 19-7 | n-butyl | 4-t-butylphenyl | Propanoic acid | 299 | 731 |
| 19-8 | Isobutyl | 4-t-butylphenyl | Propanoic acid | 152 | 877 |
| 19-9 | n-pentyl | 4-(trifluoromethoxy)phenyl | Propanoic acid | 151 | 76.8 |
| 19-10 | Isopentyl | 4-(trifluoromethyl)phenyl | Propanoic acid | 194.9 | 373 |
| 19-11 | n-butyl | Benzofuranyl | Propanoic acid | 283 | 259.9 |
| 19-12 | 1-methoxypropyl | 4-t-butylphenyl | Propanoic acid | 763 | 1788 |
| 19-13 | 1-methoxypropyl | 4-(trifluoromethyl)phenyl | Propanoic acid | 621 | 740 |
| 19-14 | 1-methoxypropyl | 4-(trifluoromethoxy)phenyl | Propanoic acid | 444 | 787 |
| 19-15 | 1-methoxypropyl | 2,4-dichlorophenyl | Propanoic acid | 2671 | 2029 |
| 19-16 | 1-methoxypropyl | 2,4,6-trimethyl | Propanoic acid | 3698 | 1729 |
| 19-17 | 3-isobutoxypropan-2-yl | 4-t-butylphenyl | Propanoic acid | 1044 | 1225 |
| 19-18 | 1-isobutoxy | 4-(trifluoromethyl)phenyl | Propanoic acid | 688 | 916.8 |
| 19-19 | 1-methoxy-2-methylpropyl | 4-(trifluoromethoxy)phenyl | Propanoic acid | 317 | 582.5 |
| 19-20 | 1-methoxy-2-methylpropyl | 2,4-dichlorophenyl | Propanoic acid | 1151 | 822.4 |
| 19-21 | 1-methoxy-2-methylpropyl | Benzofuranyl | Propanoic acid | 269 | 437.3 |
| 19-22 | 1-methoxypropyl | 4-(trifluoromethyl)phenyl | Propanoic acid | 745 | 986.5 |
| 19-23 | 1-methoxypropyl | 3-(trifluoromethyl)phenyl | Propanoic acid | 1310 | 1126 |
| 19-24 | 1-methoxypropyl | 4-(trifluoromethoxy)phenyl | Propanoic acid | 512 | 630.4 |
| 19-25 | 1-methoxypropyl | 3-(trifluoromethyl)phenyl | Propanoic acid | 1282 | 1513 |
| 19-26 | 1-methoxypropyl | Benzofuranyl | Propanoic acid | 592 | 902.8 |
| 19-27 | 1-methoxypropyl | 2H-indole | Propanoic acid | 455 | 4952 |
| 19-28 | 1-methoxy-2-methylpropyl | 3-(trifluoromethyl)phenyl | Propanoic acid | 872 | 726 |
| 19-29 | 1-methoxy-2-methylpropyl | 2-(trifluoromethyl)phenyl | Propanoic acid | 2117 | 871 |
| 19-30 | 1-methoxy-2-methylpropyl | 4-(trifluoromethoxy)phenyl | Propanoic acid | 548 | 1104 |
| 19-31 | 1-methoxy-2-methylpropyl | 3,4,5-trifluorobenzene | Propanoic acid | 500 | 1341 |
| 19-32 | 1-methoxy-2-methylpropyl | Benzofuranyl | Propanoic acid | 483 | 1017 |

TABLE 19-continued

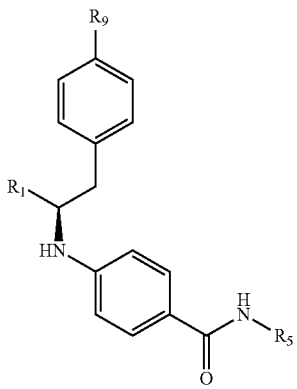

| Compound | $R_1$ | $R_9$ | $R_5$ | $IC_{50}^{binding}$ (nM) | $IC_{50}^{cAMP}$ (nM) |
|---|---|---|---|---|---|
| 19-33 | 1-methoxy-2-methylpropyl | 4-(trifluoromethoxy)phenyl | Propanoic acid | 284 | 472 |
| 19-34 | 1-methoxy-2-methylpropyl | 4-(trifluoromethyl)phenyl | Propanoic acid | 380 | 487 |

TABLE 20

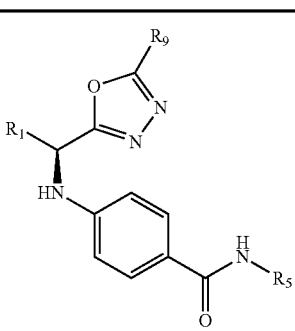

| Compound | $R_1$ | $R_9$ | $R_5$ | $IC_{50}^{binding}$ (nM) | $IC_{50}^{cAMP}$ (nM) |
|---|---|---|---|---|---|
| 20-1 | 2-(4-methylphenyl)benzofuranyl | 4-t-butylphenyl | Propanoic acid | 201 | 1403 |
| 20-2 | 2-butyl | 3-methylbenzofuranyl | Propanoic acid | 974 | 22191 |
| 20-3 | 2-butyl | Benzofuranyl | Propanoic acid | 801 | 9163 |
| 20-4 | Isopropyl | 4-t-butylphenyl | Propanoic acid | 1041 | 4853 |
| 20-5 | 4'-methyl-2,4,6-trimethyl-1,1'-biphenyl | 4-t-butylphenyl | Propanoic acid | 4855 | >30000 |
| 20-6 | 4-methyl-4'-(trifluoromethyl)-1,1'-bipehnyl | 3-methylbenzofuranyl | Propanoic acid | 2678 | >30000 |
| 20-7 | 4-methyl-4'-(triflouromethyl)-1,1'-bipehnyl | 3-methylbenzofuranyl | Ethanesulfonic acid | >30000 | >30000 |

TABLE 21

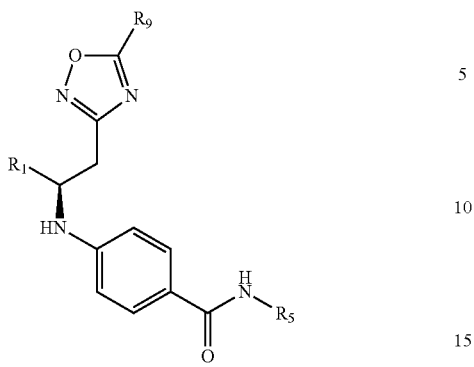

| Compound | R₁ | R₉ | R₅ | IC₅₀$^{binding}$ (nM) | IC₅₀$^{cAMP}$ (nM) |
|---|---|---|---|---|---|
| 21-1 | n-butyl | 4-t-butylphenyl | Propanoic acid | 803 | 170.4 |
| 21-2 | 2-butyl | 4-t-butylphenyl | Propanoic acid | 637 | 1242 |
| 21-3 | isopropyl | 4-t-butylphenyl | Propanoic acid | 1128 | 5436 |

TABLE 22

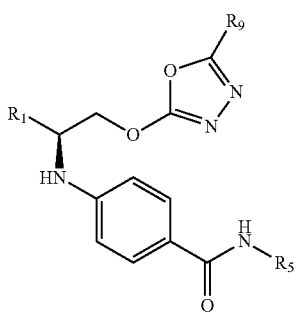

| Compound | R₁ | R₉ | R₅ | IC₅₀$^{binding}$ (nM) | IC₅₀$^{cAMP}$ (nM) |
|---|---|---|---|---|---|
| 22-1 | 2-butyl | 2-fluoro-4-(trifluoromethyl)phenyl | Propanoic acid | 62 | >30000 |
| 22-2 | n-butyl | 4-(trifluoromethoxy)phenyl | Propanoic acid | 1432 | >30000 |
| 22-3 | n-butyl | 2-fluoro-4-(trifluoromethyl)phenyl | Propanoic acid | 13581 | >30000 |
| 22-4 | n-butyl | Benzofuranyl | Propanoic acid | >30000 | >30000 |
| 22-5 | n-butyl | 4-(trifluoromethoxy)phenyl | Propanoic acid | >30000 | >30000 |
| 22-6 | n-butyl | 2,4-dichlorophenyl | Propanoic acid | >30000 | >30000 |
| 22-7 | 2-butyl | Benzofuranyl | Propanoic acid | >30000 | >30000 |
| 22-8 | 2-butyl | 4-(trifluoromethxoy)phenyl | Propanoic acid | >30000 | N/A |
| 22-9 | 2-butyl | 4-t-butylphenyl | Propanoic acid | >30000 | N/A |
| 22-10 | 2-butyl | 4-(trifluoromethyl)phenyl | Propanoic acid | >30000 | >30000 |
| 22-11 | 2-butyl | 2,4-dichlorophenyl | Propanoic acid | >30000 | >30000 |
| 22-12 | isopropyl | Benzofuranyl | Propanoic acid | >30000 | >30000 |
| 22-13 | isopropyl | 4-(trifluoromethyl)phenyl | Propanoic acid | >30000 | >30000 |
| 22-14 | isopropyl | 2,4-dichlorophenyl | Propanoic acid | >30000 | >30000 |
| 22-15 | isopropyl | 4-(trifluoromethoxy)phenyl | Propanoic acid | >30000 | >30000 |
| 22-16 | isopropyl | 4-t-butylphenyl | Propanoic acid | >30000 | >30000 |
| 22-17 | isopropyl | 2-fluoro-4-(trifluoromethyl)phenyl | Propanoic acid | >30000 | >30000 |
| 22-18 | n-butyl | 4-t-butylphenyl | Propanoic acid | >30000 | >30000 |
| 22-19 | 2-butyl | 2-chloro-4-(trifluoromethyl)phenyl | Propanoic acid | >30000 | >30000 |
| 22-20 | 2-butyl | 2-fluoro-4-(trifluoromethyl)phenyl | Methyl propionate | >30000 | >30000 |

TABLE 23

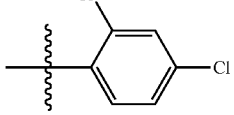

| Compound | R₁ | R₉ | R₁₁ | IC₅₀$^{binding}$ (nM) | IC₅₀$^{cAMP}$ (nM) | LC-MS Data |
|---|---|---|---|---|---|---|
| 23-1 | Isobutyl | 2,4-dichlorophenyl | CO$_2$H | 87 | 3600 | 542 |
| 23-2 | Benzyl | 2,4-dichlorophenyl | CO$_2$H | 462 | 5200 | 576 |
| 23-3 | Benzyl | 2,4,6-trimethylphenyl | CO$_2$H | 388 | 5800 | 550 |
| 23-4 | Isopropyl | 4-(trifluoromethyl)phenyl | CO$_2$H | 269 | 3200 | 542 |
| 23-5 | Isobutyl | benzofuran-2-yl | CO$_2$H | 80 | 3500 | 514 |
| 23-6 | Isobutyl | benzofuran-2-yl | CO$_2$Et | 2507 | 181 | 542 |
| 23-7 | Benzyl | benzofuran-2-yl | CO$_2$Et | 4274 | 64.3 | 576 |
| 23-8 | Benzyl | benzofuran-2-yl | CO$_2$H | >10 uM | 2000 | 548 |
| 23-9 | 4-fluorobenzyl | benzofuran-2-yl | CO$_2$Et | 1939 | 2600 | 594 |

TABLE 23-continued
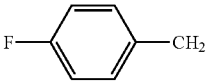
| Compound | R₁ | R₉ | R₁₁ | IC₅₀$^{binding}$ (nM) | IC₅₀$^{cAMP}$ (nM) | LC-MS Data |
|---|---|---|---|---|---|---|
| 23-10 | 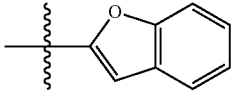 [SMILES: *c1cc2ccccc2o1] 4-F-C₆H₄-CH₂ | 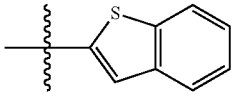 [SMILES: *c1cc2ccccc2s1] 2-benzofuranyl | CO₂H | 61 | 1900 | 566 |
| 23-11 | Isobutyl | 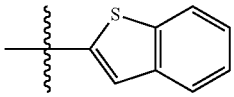 [SMILES: *c1cc2ccccc2s1] 2-benzothienyl | CO₂Et | >10 uM | 6800 | 558 |
| 23-12 | Isobutyl | 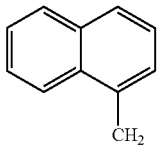 2-benzothienyl | CO₂H | 375 | 4100 | 530 |
| 23-13 | 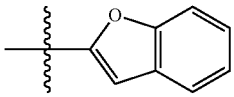 [SMILES: *c1cc2ccccc2o1] 1-naphthyl-CH₂ | 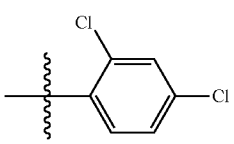 [SMILES: *c1ccc(Cl)cc1Cl] 2-benzofuranyl | CO₂Et | >10 uM | >10 uM | 626 |
| 23-14 | Benzyl | 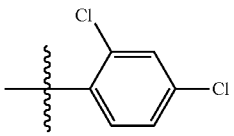 [SMILES: *c1ccc(Cl)cc1Cl] 2,4-diCl-C₆H₃ | CO₂H | >10 uM | >10 uM | 576 |
| 23-15 | Benzyl | 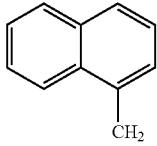 2,4-diCl-C₆H₃ | CO₂Et | >10 uM | 6300 | 604 |
| 23-16 | 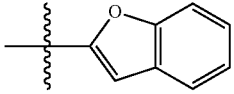 [SMILES: *c1cc2ccccc2o1] 1-naphthyl-CH₂ | 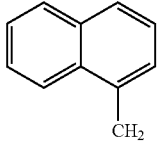 2-benzofuranyl | CO₂H | 3011 | 1193 | 598 |
| 23-17 | 1-naphthyl-CH₂ | tBu | CO₂Et | >10 uM | 7400 | 566 |

TABLE 23-continued
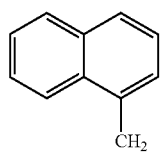
| Compound | R₁ | R₉ | R₁₁ | IC₅₀$^{binding}$ (nM) | IC₅₀$^{cAMP}$ (nM) | LC-MS Data |
|---|---|---|---|---|---|---|
| 23-18 | 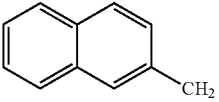 | tBu | CO₂H | 1870 | 4700 | 538 |
| 23-19 | 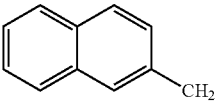 | tBu | CO₂Et | >10 uM | 5400 | 566 |
| 23-20 | 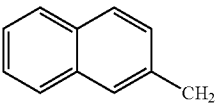 | tBu | CO₂H | 724 | 4700 | 538 |
| 23-21 | 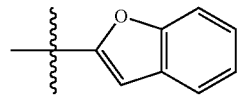 [SMILES: *c1cc2ccccc2o1] | 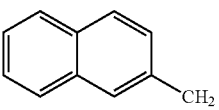 | CO₂Et | >10 uM | >10 uM | 626 |
| 23-22 | 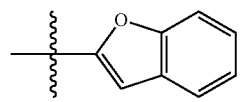 | 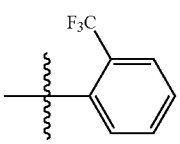 [SMILES: *c1ccccc1C(F)(F)F] | CO₂H | >10 uM | 32100 | 598 |
| 23-23 | Benzyl | 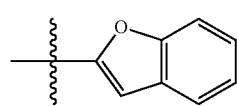 | CO₂H | 4147 | 5800 | 576 |
| 23-24 | Benzyl | 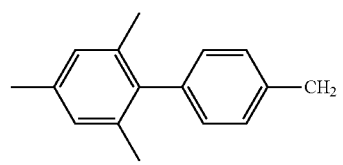 | SO₃H | >10 uM | >10 uM | 584 |
| 23-25 |  | tBu | CO₂H | 458 | 3100 | 606 |

TABLE 23-continued
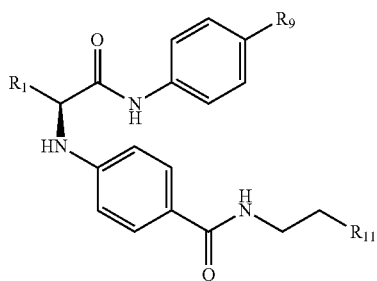
| Compound | R₁ | R₉ | R₁₁ | IC₅₀$^{binding}$ (nM) | IC₅₀$^{cAMP}$ (nM) | LC-MS Data |
|---|---|---|---|---|---|---|
| 23-26 | 2,4,6-trimethylbiphenyl-CH₂ | tBu | SO₃H | NA | 39300 | 642 |
| 23-27 | (1H-indol-3-yl)-CH₂ | | 2-benzofuranyl | CO₂Et | NA | 34600 | 615 |
| 23-28 | Isobutyl | | 2-(1H-indolyl) | CO₂Me | 6941 | 179 | 527 |
| 23-29 | Isobutyl | | 2-(1H-indolyl) | CO₂H | 141 | >10 uM | 513 |
| 23-30 | sec-Butyl | | 2-benzofuranyl | CO₂Et | 1477 | 25.2 | 542 |
| 23-31 | sec-Butyl | | 2-benzofuranyl | CO₂H | 294 | 4145 | 514 |
| 23-32 | Isopropyl | | 2-benzofuranyl | CO₂Me | 5184 | 92.8 | 514 |
| 23-33 | Isopropyl | | 2-benzofuranyl | CO₂H | 1007 | 1633 | 500 |
| 23-34 | Isopropyl | | 2-benzofuranyl | SO₃H | 2566 | 75611 | 536 |

TABLE 23-continued

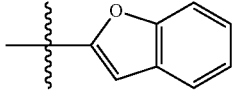 [SMILES: *c1cc2ccccc2o1]

| Compound | R$_1$ | R$_9$ | R$_{11}$ | IC$_{50}^{binding}$ (nM) | IC$_{50}^{cAMP}$ (nM) | LC-MS Data |
|---|---|---|---|---|---|---|
| 23-35 | n-butyl | 2-benzofuranyl | CO$_2$H | 186 | 15397 | 514 |

TABLE 24

*indicium of chirality

| Compound | R$_1$ | R$_2$ | R$_{11}$ | R/S | IC$_{50}^{binding}$ (nM) | IC$_{50}^{cAMP}$ (nM) | LC-MS Data |
|---|---|---|---|---|---|---|---|
| 24-1 | isobutyl | 4-(2-benzofuranyl)phenyl | CO$_2$Et | R | >10 uM | 1500 | 542 |
| 24-2 | isobutyl | 4-(2-benzofuranyl)phenyl | CO$_2$H | R | 311 | 598.6 | 514 |
| 24-3 | benzyl | 4-CF$_3$-phenyl | CO$_2$Et | R | >10 uM | 208 | 528 |
| 24-4 | benzyl | 4-CF$_3$-phenyl | CO$_2$H | R | 6020 | >10 uM | 500 |
| 24-5 | benzyl | 4-CF$_3$-phenyl | CO$_2$Et | S | >10 uM | 5800 | 528 |

TABLE 24-continued

*indicium of chirality

| Compound | R₁ | R₂ | R₁₁ | R/S | IC₅₀$^{binding}$ (nM) | IC₅₀$^{cAMP}$ (nM) | LC-MS Data |
|---|---|---|---|---|---|---|---|
| 24-6 | benzyl | 4-CF₃-phenyl | CO₂H | S | 7397 | >10 uM | 500 |
| 24-7 | sec-Butyl | 6-OMe-naphthyl | CO₂Et | S | 11369 | 217 | 506 |
| 24-8 | sec-Butyl | 6-OMe-naphthyl | CO₂H | S | 1026 | >10 uM | 478 |
| 24-9 | isobutyl | 4-CF₃-phenyl | CO₂H | R | >10 uM | 1059 | 494 |
| 24-10 | isobutyl | 4-CF₃-phenyl | CO₂Et | R | 5821 | 30780 | 466 |
| 24-11 | 1-naphthylmethyl | isopropyl | CO₂Et | S | — | >10 uM | 476 |
| 24-12 | 1-naphthylmethyl | isopropyl | CO₂H | S | — | >10 uM | 448 |
| 24-13 | 2-naphthylmethyl | isopropyl | CO₂Et | S | — | >10 uM | 476 |

TABLE 24-continued

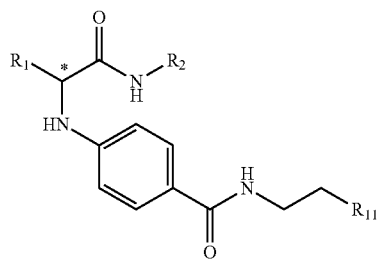

*indicium of chirality

| Compound | R₁ | R₂ | R₁₁ | R/S | IC₅₀$^{binding}$ (nM) | IC₅₀$^{cAMP}$ (nM) | LC-MS Data |
|---|---|---|---|---|---|---|---|
| 24-14 | 2-naphthyl-CH₂ | isopropyl | CO₂H | S | — | >10 uM | 448 |
| 24-15 | 4'-tBu-biphenyl-4-CH₂ | 4-CF₃-phenyl | CO₂Et | R | 578 | 7988 | 660 |
| 25-16 | 4'-tBu-biphenyl-4-CH₂ | 4-CF₃-phenyl | CO₂H | R | 126 | 252.4 | 632 |
| 24-17 | 2,4-diCl-biphenyl-4'-CH₂ | 4-CF₃-phenyl | CO₂Et | S | >30 uM | 167.1 | 672 |
| 24-18 | 2,4-diCl-biphenyl-4'-CH₂ | 4-CF₃-phenyl | CO₂H | S | 239.5 | 1510 | 644 |
| 24-19 | 2-(benzofuran-2-yl)phenyl-4-CH₂ | 4-CF₃-phenyl | CO₂Et | R | 1366 | 538.4 | 644 |
| 24-20 | 2-(benzofuran-2-yl)phenyl-4-CH₂ | 4-CF₃-phenyl | CO₂H | R | 192.7 | 1947 | 616 |
| 24-21 | 2-(benzofuran-2-yl)phenyl-4-CH₂ | isopropyl | CO₂Et | R | 4097 | >10 uM | 542 |
| 24-22 | 2-(benzofuran-2-yl)phenyl-4-CH₂ | isopropyl | CO₂H | R | 17625 | 9522 | 514 |

TABLE 24-continued

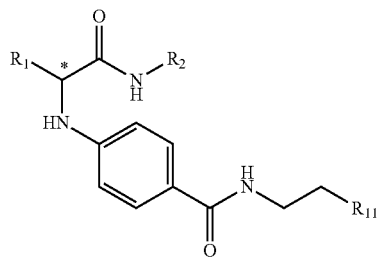

*indicium of chirality

| Compound | R₁ | R₂ | R₁₁ | R/S | IC₅₀$^{binding}$ (nM) | IC₅₀$^{cAMP}$ (nM) | LC-MS Data |
|---|---|---|---|---|---|---|---|
| 24-23 | benzofuran-2-yl-phenyl-CH₂– | 3,5-difluorophenyl | CO₂Et | R | 168.5 | 9529 | 612 |
| 24-24 | benzofuran-2-yl-phenyl-CH₂– | 3,5-difluorophenyl | CO₂H | R | 1215 | 214 | 584 |
| 24-25 | tBu-biphenyl-CH₂– | 4-OCF₃-phenyl | CO₂Et | R | 225.6 | >10 uM | 676 |
| 24-26 | tBu-biphenyl-CH₂– | 4-OCF₃-phenyl | CO₂H | R | 45.7 | 831.3 | 648 |
| 24-27 | F₃C-biphenyl-CH₂– | 4-OCF₃-phenyl | CO₂Et | R | 1281 | 318.5 | 688 |
| 24-28 | F₃C-biphenyl-CH₂– | 4-OCF₃-phenyl | CO₂H | R | 46.5 | 1540 | 660 |

Shown in Tables 1-24 are the structures and in vitro activities of 390 exemplary compounds of formula (I). All 390 compounds were found to bind to glucagon receptor and inhibit the level of glucagon downstream cAMP to various degrees as indicated by their IC₅₀ values (IC₅₀ being the concentration of an inhibitor where the response or binding is reduced by half) included in the above tables.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present disclosure, and without departing from the spirit and scope thereof can make various changes and modifications of the disclosure to adapt it to various usages and conditions. Thus, other embodiments are also within the claims.

What is claimed is:

1. A compound of formula (I):

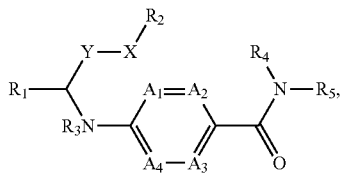

or a pharmaceutically acceptable salt thereof,
wherein
each of $A_1$, $A_2$, $A_3$ and $A_4$ independently is $CR_6$;
X is —O— or —S—;
Y is —$CH_2$—;
$R_1$ is $C_{1-6}$ alkyl, $C_{1-6}$ alkoxy, aryl, heteroaryl, $C_{3-12}$ cycloalkyl, $C_{1-12}$ heterocycloalkyl, or —($C_{1-6}$ alkyl)-($C_{3-12}$ cycloalkyl); the $C_{1-6}$ alkyl being optionally substituted with one to three moieties selected from the group consisting of halo, hydroxyl, $C_{1-6}$ alkoxy, aryl and heteroaryl; each of the $C_{1-6}$ alkoxy, aryl, heteroaryl, $C_{3-12}$ cycloalkyl, and $C_{1-12}$ heterocycloalkyl being optionally substituted with one to three moieties selected from the group consisting of halo, aryl, $C_{1-6}$ alkyl optionally substituted with one to three halo and $C_{1-6}$ alkoxy optionally substituted with one to three halo; the heteroaryl being optionally fused with one aryl moiety; and the aryl being optionally substituted with heteroaryl or heteroaryl fused with one aryl moiety;
$R_2$ is

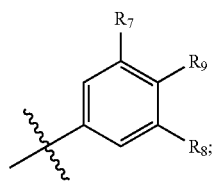

$R_3$ is H;
$R_4$ is H;
$R_5$ is tetrazolyl, —$CH_2$-tetrazolyl, —$CH_2CH_2CO_2R_{10}$, —$CH_2CH(OH)CO_2H$, or —$(CH_2)_2SO_3H$;
$R_6$ is H;
$R_7$ is F, Cl, methoxy, ethoxy, propoxy or isobutoxy;
$R_8$ is H;
$R_9$ is H, halo, $C_{1-6}$ alkyl, $C_{1-6}$ alkoxy, $C_{3-12}$ cycloalkyl, aryl or heteroaryl; the $C_{1-6}$ alkyl being optionally substituted with one to three halo; each of the $C_{1-6}$ alkoxy, $C_{3-12}$ cycloalkyl, aryl and heteroaryl being optionally substituted with one to three moieties selected from the group consisting of halo, aryl, $C_{1-6}$ alkyl optionally substituted with one to three halo, $C_{1-6}$ alkoxy optionally substituted with one to three halo, amino, and CN; and the heteroaryl being optionally fused with one aryl moiety or one heteroaryl moiety; and
$R_{10}$ is H or $C_{1-6}$ alkyl.

2. The compound or the pharmaceutically acceptable salt thereof of claim 1, wherein $R_1$ is methyl, ethyl, n-propyl, i-propyl, 2-butyl, n-butyl, i-butyl, t-butyl, n-pentyl, isopentyl, methoxy, ethoxymethyl, 1-methoxypropyl, 1-methoxy-2-methylpropyl, ethoxy, n-propoxy, i-propoxy, 3-isobutoxy-propan-2-yl, 2-butoxy, n-butoxy, i-butoxy, t-butoxy, phenyl, benzyl, biphenyl, naphthyl, benzofuranyl or indolyl; each of the methyl, ethyl, n-propyl, i-propyl, 2-butyl, n-butyl, i-butyl, t-butyl, n-pentyl and isopentyl, is optionally substituted with one to three moieties selected from the group consisting of F, Cl, methoxy, ethoxy, n-propoxy, i-propoxy, 2-butoxy, n-butoxy, i-butoxy, t-butoxy, phenyl, biphenyl and naphthyl; each of the methoxy, ethoxy, n-propoxy, i-propoxy, 2-butoxy, n-butoxy, i-butoxy and t-butoxy is optionally substituted with one to three F or Cl; each of the phenyl, biphenyl and naphthyl is optionally substituted with one to three moieties selected from the group consisting of F, Cl, methyl, ethyl, n-propyl, i-propyl, 2-butyl, n-butyl, i-butyl, t-butyl, trifluoromethyl, benzofuranyl and methoxy substituted pyrimidyl; and indolyl is optionally substituted with one to three moieties selected from the group consisting of F, Cl, methyl, ethyl, n-propyl, i-propyl, 2-butyl, n-butyl, i-butyl, t-butyl, and trifluoromethyl.

3. The compound or the pharmaceutically acceptable salt thereof of claim 1, wherein $R_5$ is tetrazolyl, —$CH_2$-tetrazolyl, —$CH_2CH_2CO_2H$, —$CH_2CH_2CO_2Et$, —$CH_2CH_2CO_2Me$, —$CH_2CH(OH)CO_2H$, or —$(CH_2)_2SO_3H$.

4. The compound or the pharmaceutically acceptable salt thereof of claim 1, wherein $R_9$ is methyl, ethyl, n-propyl, i-propyl, 2-butyl, n-butyl, i-butyl, t-butyl, methoxy, ethoxy, n-propoxy, i-propoxy, 2-butoxy, n-butoxy, i-butoxy, t-butoxy, phenyl, biphenyl, naphthyl, pyridinyl, pyridazinyl, benzofuranyl, benzothiazolyl, imidazopyridinyl, oxadiazol, benzooxazol, pyrazol or indolyl; each of the methyl, ethyl, n-propyl, i-propyl, 2-butyl, n-butyl, i-butyl and t-butyl is optionally substituted with one to three moieties selected from the group consisting of F and Cl; each of the methoxy, ethoxy, n-propoxy, i-propoxy, 2-butoxy, n-butoxy, i-butoxy and t-butoxy is optionally substituted with one to three F, Cl or amino; each of the phenyl, biphenyl, naphthyl, pyridinyl, pyridazinyl, benzofuranyl, benzothiazolyl, imidazopyridinyl, oxadiazol, benzooxazol, pyrazol and indolyl is optionally substituted with one to three moieties selected from the group consisting of F, Cl, methyl, ethyl, n-propyl, i-propyl, 2-butyl, n-butyl, i-butyl, t-butyl, methoxy, ethoxy, n-propoxy, i-propoxy, 2-butoxy, n-butoxy, i-butoxy, t-butoxy, —$CF_3$, —$OCF_3$ and phenyl.

5. The compound or the pharmaceutically acceptable salt thereof of claim 1, which is represented by the following formula (II):

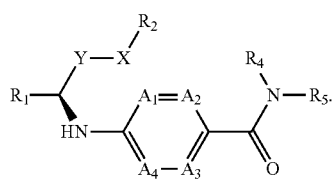

6. A compound or a pharmaceutically acceptable salt thereof, selected from the group consisting of Ethyl(S)-3-(4-((1-(4-(benzofuran-2-yl)phenoxy)-3-methylbutan-2-yl)amino)benzamido) propanoate, (S)-3-(4-((1-(4-(benzofuran-2-yl)phenoxy)-3-methylbutan-2-yl)amino) benzamido)propanoic acid, 3-(4-(((2S,3S)-1-((4'-(tert-butyl)-[1,1'-biphenyl]-4-yl)oxy)-3-methylpentan-2-yl) amino)benzamido)propanoic acid, 3-(4-(((2S,3 S)-1-(4-(benzofuran-2-yl)phenoxy)-3-methylpentan-2-yl)amino) benzamido)propanoic acid, 3-(4-(((2S)-3-methyl-1-((4'-

(trifluoromethyl)-[1,1'-biphenyl]-4-yl)oxy)pentan-2-yl) amino)benzamido)propanoic acid, 3-(4-(((2S,3 S)-3-methyl-1-((4'-(trifluoromethoxy)-[1,1'-biphenyl]-4-yl)oxy) pentan-2-yl)amino)benzamido)propanoic acid, 3-(4-(((2S,3 S)-1-((2',4'-dichloro-[1,1'-biphenyl]-4-yl)oxy)-3-methylpentan-2-yl)amino)benzamido)propanoic acid, N-((1H-tetrazol-5-yl)methyl)-4-(((2S,3S)-1-(4-(benzofuran-2-yl)phenoxy)-3-methylpentan-2-yl)amino)benzamide, (R)-3-(4-(((2S,3 S)-1-(4-(benzofuran-2-yl)phenoxy)-3-methylpentan-2-yl)amino)benzamido)-2-hydroxypropanoic acid, (S)-3-(4-((1-(4-(benzofuran-2-yl)phenoxy)hexan-2-yl) amino)benzamido) propanoic acid, (S)-3-(4-((1-((4'-(tert-butyl)-[1,1'-biphenyl]-4-yl)oxy)hexan-2-yl)amino)benzamido)propanoic acid, (S)-3-(4-((1-((4'-(dimethylamino)-[1,1'-biphenyl]-4-yl)oxy)-3-methylbutan-2-yl)amino) benzamido)propanoic acid, N-((1H-tetrazol-5-yl)methyl)-4-(((2S,3S)-1-((2',4'-dichloro-[1,1'-biphenyl]-4-yl)oxy)-3-methylpentan-2-yl)amino)benzamide, (R)-3-(4-(((2S,3 S)-1-((2',4'-dichloro-[1,1'-biphenyl]-4-yl)oxy)-3-methylpentan-2-yl)amino)benzamido)-2-hydroxypropanoic acid, (S)-3-(4-((1-((4'-(trifluoromethyl)-[1,1'-biphenyl]-4-yl)oxy) hexan-2-yl)amino)benzamido)propanoic acid, (S)—N-((1H-tetrazol-5-yl)methyl)-4-((1-((4'-(trifluoromethyl)-[1, 1'-biphenyl]-4-yl)oxy)hexan-2-yl)amino)benzamide, (S)-3-(4-((1-((2',4'-dichloro-[1,1'-biphenyl]-4-yl)oxy)hexan-2-yl) amino)benzamido)propanoic acid, (S)—N-((1H-tetrazol-5-yl)methyl)-4-((1-((2',4'-dichloro-[1,1'-biphenyl]-4-yl)oxy) hexan-2-yl)amino)benzamide, (S)-3-(4-((1-((2'-chloro-4'-(trifluoromethyl)-[1,1'-biphenyl]-4-yl)oxy)hexan-2-yl) amino)benzamido)propanoic acid, (S)—N-((1H-tetrazol-5-yl)methyl)-4-((1-((2'-chloro-4'-(trifluoromethyl)-[1,1'-biphenyl]-4-yl)oxy)hexan-2-yl)amino)benzamide, (R)-3-(4-(((S)-1-((4'-(dimethylamino)-[1,1'-biphenyl]-4-yl)oxy)-3-methylbutan-2-yl)amino)benzamido)-2-hydroxypropanoic acid, (S)-3-(4-((1-((2'-chloro-4'-(trifluoromethyl)-[1,1'-biphenyl]-4-yl)oxy)-3-methylbutan-2-yl)amino)benzamido) propanoic acid, 3-(4-((2-(4-(benzofuran-2-yl)phenoxy)-1-phenylethyl)amino)benzamido) propanoic acid, (S)-3-(4-((3-methyl-1-(4-(5-(trifluoromethyl)pyridin-2-yl)phenoxy) butan-2-yl)amino)benzamido)propanoic acid, (S)-3-(4-((1-((2'-fluoro-4'-(trifluoromethyl)-[1,1'-biphenyl]-4-yl)oxy)-3-methylbutan-2-yl)amino)benzamido)propanoic acid, 3-(4-(((2S,3 S)-1-((2',4'-difluoro-[1,1'-biphenyl]-4-yl)oxy)-3-methylpentan-2-yl)amino)benzamido)propanoic acid, (S)-3-(4-((1-((2'-fluoro-4'-(trifluoromethyl)-[1,1'-biphenyl]-4-yl) oxy)hexan-2-yl)amino)benzamido)propanoic acid, 3-(4-((1-phenyl-2-((4'-(trifluoromethyl)-[1,1'-biphenyl]-4-yl)oxy) ethyl)amino) benzamido)propanoic acid, (S)-3-(4-((3-methyl-1-(4-(6-(trifluoromethyl)pyridazin-3-yl)phenoxy) butan-2-yl)amino)benzamido)propanoic acid, Ethyl (S)-3-(4-((1-(4-(benzo[d]thiazol-2-yl)phenoxy)-3-methylbutan-2-yl)amino)benzamido)propan oate, Methyl (S)-3-(4-((1-(4-(benzo[d]thiazol-2-yl)phenoxy)-3-methylbutan-2-yl)amino) benzamido)propanoate, (S)-3-(4-((1-(4-(benzo[d]thiazol-2-yl)phenoxy)-3-methylbutan-2-yl)amino)benzamido)propanoic acid, (S)-2-(4-((1-((2'-fluoro-4'-(trifluoromethyl)-[1, 1'-biphenyl]-4-yl)oxy)-3-methylbutan-2-yl)amino) benzamido)ethane-1-sulfonic acid, (R)-3-(4-((1-(4-(benzofuran-2-yl)phenoxy)-3-methylbutan-2-yl)amino) benzamido) propanoic acid, (R)-3-(4-((1-((2'-chloro-4'-(trifluoromethyl)-[1,1'-biphenyl]-4-yl)oxy)-3-methylbutan-2-yl)amino)benzamido)propanoic acid, (S)-3-(4-((1-(2',4'-dichloro-[1,1'-biphenyl]-4-yl)oxy)-3,3-dimethylbutan-2-yl) amino)benzamido)propanoic acid, (S)-3-(4-((1-((2'-chloro-4'-(dimethylamino)-[1,1'-biphenyl]-4-yl)oxy)-3-methylbutan-2-yl)amino)benzamido)propanoic acid, 3-(4-(((2S,3 S)-1-((2'-chloro-4'-methoxy-[1,1'-biphenyl]-4-yl) oxy)-3-methylpentan-2-yl)amino)benzamido)propanoic acid, (S)-3-(4-((1-(4-(imidazo[1,2-a]pyridin-2-yl)phenoxy)-3-methylbutan-2-yl)amino)benzamido) propanoic acid, (S)-3-(4-((1-(4-(benzofuran-2-yl)phenoxy)-3,3-dimethylbutan-2-yl)amino)benzamido)propanoic acid, (S)-3-(4-((1-(4-(furo[3,2-b]pyridin-2-yl)phenoxy)-3-methylbutan-2-yl) amino)benzamido)propanoic acid, (S)-3-(4-((1-((2'-chloro-4'-(trifluoromethyl)-[1,1'-biphenyl]-4-yl)oxy)-3,3-dimethylbutan-2-yl) amino)benzamido)propanoic acid, 3-(4-((3-methyl-1-(4-(5-(trifluoromethyl)-1,3,4-oxadiazol-2-yl)phenoxy)butan-2-yl)amino)benzamido)propanoic acid, 3-(4-((3-methyl-1-(4-(5-(trifluoromethyl)-1,3,4-oxadiazol-2-yl)phenoxy) pentan-2-yl)amino)benzamido)propanoic acid, 3-(4-(((2S,3 S)-1-(4-(5-(tert-butyl)-1,3,4-oxadiazol-2-yl)phenoxy)-3-methylpentan-2-yl)amino)benzamido)propanoic acid, 3-(4-(((2S,3 S)-3-methyl-1-(4-(5-phenyl-1,3,4-oxadiazol-2-yl)phenoxy)pentan-2-yl)amino)benzamido) propanoic acid, Ethyl (S)-3-(4-((1-(4-(benzo[d]oxazol-2-yl)phenoxy)-3-methylbutan-2-yl)amino)benzamido)propan oate, (S)-3-(4-((1-(4-(benzo[d]oxazol-2-yl)phenoxy)-3-methylbutan-2-yl)amino)benzamido)propanoic acid, (S)-3-(4-((1-(4-(5-(tert-butyl)-1,3,4-oxadiazol-2-yl)phenoxy) hexan-2-yl)amino)benzamido)propanoic acid, (S)-3-(4-((1-(4-(5-phenyl-1,3,4-oxadiazol-2-yl)phenoxy)hexan-2-yl) amino) benzamido)propanoic acid, Ethyl (R)-3-(4-((1-(4-(benzo[d]thiazol-2-yl)phenoxy)-3-methylbutan-2-yl)amino) benzamido)propanoate, (R)-3-(4-((1-(4-(benzo[d]thiazol-2-yl)phenoxy)-3-methylbutan-2-yl)amino)benzamido)propanoic acid, Ethyl (R)-3-(4-((1-(4-(benzo[d]oxazol-2-yl) phenoxy)-3-methylbutan-2-yl)amino)benzamido)propan oate, (R)-3-(4-((1-(4-(benzo[d]oxazol-2-yl)phenoxy)-3-methylbutan-2-yl)amino)benzamido)propanoic acid, (R)-3-(4-((1-((2,6-dimethyl-4'-(trifluoromethyl)-[1,1'-biphenyl]-4-yl)oxy)-3-phenylpropan-2-yl)amino)benzamido) propanoic acid, (R)-3-(4-((1-((2,6-dimethyl-4'-(trifluoromethoxy)-[1,1'-biphenyl]-4-yl)oxy)-3-phenylpropan-2-yl)amino)benzamido)propanoic acid, (S)-3-(4-((1-((2,6-dimethyl-4'-(trifluoromethoxy)-[1,1'-biphenyl]-4-yl)oxy)-4-methylpentan-2-yl)amino) benzamido)propanoic acid, (S)-3-(4-((1-((2,6-dimethyl-4'-(trifluoromethyl)-[1,1'-biphenyl]-4-yl)oxy)-3-methylbutan-2-yl) amino)benzamido)propanoic acid, (S)-3-(4-((1-((4'-(tert-butyl)-2,6-dimethyl-[1,1'-biphenyl]-4-yl)oxy)-3-methylbutan-2-yl)amino)benzamido)propanoic acid, 3-(4-(((2S,3 S)-1-((4'-(tert-butyl)-2,6-dimethyl-[1,1'-biphenyl]-4-yl)oxy)-3-methylpentan-2-yl) amino)benzamido) propanoic acid, 3-(4-(((2S,3 S)-1-(4-(benzofuran-2-yl)-3,5-dimethylphenoxy)-3-methylpentan-2-yl)amino)benzamido) propanoic acid, 3-(4-(((2S,3 S)-1-((2,6-dimethyl-4'-(trifluoromethoxy)-[1,1'-biphenyl]-4-yl)oxy)-3-methylpentan-2-yl)amino)benzamido)propanoic acid, 3-(4-(((2S,3 S)-1-((2',4'-dichloro-2,6-dimethyl-[1,1'-biphenyl]-4-yl)oxy)-3-methylpentan-2-yl) amino)benzamido)propanoic acid, 3-(4-(((2S,3 S)-1-((2,6-dimethyl-4'-(trifluoromethyl)-[1,1'-biphenyl]-4-yl)oxy)-3-methylpentan-2-yl)amino)benzamido)propanoic acid, (S)-3-(4-((1-((2'-chloro-2,6-dimethyl-4'-(trifluoromethyl)-[1,1'-biphenyl]-4-yl)oxy)-3-methylbutan-2-yl)amino)benzamido)propanoic acid, (S)-3-(4-((1-(4-(benzofuran-2-yl)-3,5-dimethylphenoxy)hexan-2-yl)amino)benzamido)propanoic acid, (S)—N-((1H-tetrazol-5-yl)methyl)-4-((1-(4-(benzofuran-2-yl)-3,5-dimethylphenoxy)hexan-2-yl)amino)benzamide, N-((1H-tetrazol-5-yl)methyl)-4-(((2S,3S)-1-(4-(benzofuran-2-yl)-3-chlorophenoxy)-3-methyl pentan-2-yl)amino)benzamide, (R)-3-(4-(((S)-1-((2,2'-dichloro-4'-(trifluoromethyl)-[1,1'-biphenyl]-4-yl)oxy)-3-methylbutan-2-yl)amino)benzamido)-2-hydroxypropanoic acid, (S)—N-((1H-tetrazol-5- yl)methyl)-4-((1-((2,2'-dichloro-4'-(trifluoromethyl)-[1,1'-biphenyl]-4-yl)oxy)-3-methylbutan-2-yl)amino)benzamide, (S)-3-(4-((1-((2,2'-dichloro-4'-(trifluoromethyl)-[1,1'-biphenyl]-4-yl)oxy)-3-methylbutan-2-yl) amino)benzamido)propanoic acid, (S)—N-((1H-tetrazol-5-yl)methyl)-4-((1-(4-(benzofuran-2-yl)-3-chlorophenoxy)-3-methylbutan-2-yl) amino)benzamide, (R)-3-(4-(((S)-1-(4-(benzofuran-2-yl)-3-chlorophenoxy)-3-methylbutan-2-yl)amino)benzamido)-2-hydroxypropanoic acid, (S)-3-(4-((1-(4-(benzofuran-2-yl)-3-chlorophenoxy)-3-methylbutan-2-yl)amino)benzamido) propanoic acid, (S)-3-(4-((1-((2,2'-dichloro-4'-(trifluoromethyl)-[1,1'-biphenyl]-4-yl)oxy)hexan-2-yl) amino)benzamido)propanoic acid, (S)—N-((1H-tetrazol-5-yl)methyl)-4-((1-((2,2'-dichloro-4'-(trifluoromethyl)-[1,1'-biphenyl]-4-yl)oxy)hexan-2-yl)amino)benzamide, (S)-3-(4-((1-(4-(benzofuran-2-yl)-3-chlorophenoxy)hexan-2-yl) amino)benzamido)propanoic acid, (S)—N-((1H-tetrazol-5-yl)methyl)-4-((1-(4-(benzofuran-2-yl)-3-chlorophenoxy) hexan-2-yl)amino)benzamide, (S)-3-(4-((1-((2,2',4'-trichloro-[1,1'-biphenyl]-4-yl)oxy)hexan-2-yl)amino) benzamido)propanoic acid, (S)—N-((1H-tetrazol-5-yl)methyl)-4-((1-((2,2',4'-trichloro-[1,1'-biphenyl]-4-yl)oxy)hexan-2-yl) amino)benzamide, (S)-3-(4-((1-(4-(benzofuran-2-yl)-2,5-dichlorophenoxy)-3-methylbutan-2-yl)amino)benzamido) propanoic acid, 3-(4-((2-((2'-chloro-4'-(trifluoromethyl)-[1,1'-biphenyl]-4-yl)oxy)-1-phenylethyl)amino)benzamido) propanoic acid, (S)-3-(4-((1-((2-chloro-4'-(trifluoromethyl)-[1,1'-biphenyl]-4-yl)oxy)hexan-2-yl)amino)benzamido) propanoic acid, (S)—N-((1H-tetrazol-5-yl)methyl)-4-((1-((2-chloro-4'-(trifluoromethyl)-[1,1'-biphenyl]-4-yl)oxy) hexan-2-yl)amino)benzamide, (S)-2-(4-((1-(4-(benzofuran-2-yl)-3-chlorophenoxy)-3-methylbutan-2-yl)amino) benzamido)ethane-1-sulfonic acid, 3-(4-(((2S,3 S)-1-(4-(benzofuran-2-yl)-2,5-dichlorophenoxy)-3-methylpentan-2-yl)amino)benzamido)propanoic acid, 3-(4-(((2S,3 S)-3-methyl-1-((2,2',5-trichloro-4'-(trifluoromethyl)-[1,1'-biphenyl]-4-yl)oxy)pentan-2-yl)amino)benzamido) propanoic acid, 3-(4-(((2S,3 S)-1-((2,5-dichloro-2'-fluoro-4'-(trifluoromethyl)-[1,1'-biphenyl]-4-yl)oxy)-3-methylpentan-2-yl)amino)benzamido)propanoic acid, (S)-3-(4-((1-((2-chloro-2'-fluoro-4'-(trifluoromethyl)-[1,1'-biphenyl]-4-yl)oxy)hexan-2-yl)amino)benzamido) propanoic acid, (S)-3-(4-((1-(4-(benzofuran-2-yl)-3-chlorophenoxy)-3,3-dimethylbutan-2-yl)amino)benzamido) propanoic acid, (S)-3-(4-((1-((2-chloro-2'-fluoro-4'-(trifluoromethyl)-[1,1'-biphenyl]-4-yl)oxy)-3,3-dimethylbutan-2-yl)amino)benzamido)propanoic acid, (S)-3-(4-((1-((4-(benzofuran-2-yl)phenyl)thio)-3-methylbutan-2-yl)amino)benzamido)propanoic acid, 3-(4-(((2S,3S)-3-methyl-1-((4'-(trifluoromethyl)-[1,1'-biphenyl]-4-yl)thio) pentan-2-yl)amino) benzamido)propanoic acid, 3-(4-(((2S,3S)-1-((4-(benzofuran-2-yl)phenyl)thio)-3-methylpentan-2-yl)amino)benzamido)propanoic acid, (S)-3-(4-((1-(4-(benzofuran-2-yl)phenoxy)-3-methylbutan-2-yl)(methyl) amino)benzamido)propanoic acid, (S)-3-(4-((1-(4-(benzofuran-2-yl)phenoxy)-3-methylbutan-2-yl)(ethyl) amino)benzamido)propanoic acid, (S)-3-(4-((1-(4-(benzofuran-2-yl)phenoxy)-3-ethoxypropan-2-yl)amino) benzamido)propanoic acid, (S)-3-(4-((1-(4-(benzofuran-2-yl)-3,5-difluorophenoxy)-3-methylbutan-2-yl)amino)benzamido)propanoic acid, (S)-3-(4-((1-((2'-chloro-2,6-difluoro-4'-(trifluoromethyl)-[1,1'-biphenyl]-4-yl)oxy)-3-methylbutan-2-yl)amino)benzamido)propanoic acid, (S)-3-(4-((1-((2,6-difluoro-4'-(trifluoromethyl)-[1,1'-biphenyl]-4-yl)oxy)-3-methylbutan-2-yl) amino)benzamido) propanoic acid, (S)-3-(4-((3-methyl-1-((2,2',6-trifluoro-4'-(trifluoromethyl)-[1,1'-biphenyl]-4-yl)oxy)butan-2-yl)amino)benzamido)propanoic acid, (S)-3-(4-((1-((2'-chloro-2,6-difluoro-4'-(trifluoromethyl)-[1,1'-biphenyl]-4-yl)oxy)-4-methylpentan-2-yl)amino)benzamido)propanoic acid, (S)-3-(4-((1-((2,6-difluoro-4'-(trifluoromethyl)-[1,1'-biphenyl]-4-yl)oxy)-4-methylpentan-2-yl)amino)benzamido)propanoic acid, (S)-3-(4-((4-methyl-1-((2,2',6-trifluoro-4'-(trifluoromethyl)-[1,1'-biphenyl]-4-yl)oxy)pentan-2-yl)amino)benzamido)propanoic acid, (S)-3-(4-((1-((2',4'-dichloro-2,6-difluoro-[1,1'-biphenyl]-4-yl)oxy)-4-methylpentan-2-yl) amino)benzamido)propanoic acid, (S)-3-(4-((1-((3',5'-dichloro-2,6-difluoro-[1,1'-biphenyl]-4-yl)oxy)-4-methylpentan-2-yl)amino)benzamido)propanoic acid, (S)-3-(4-((1-(4-(benzofuran-2-yl)-3,5-difluorophenoxy)-4-methylpentan-2-yl)amino)benzamido)propanoic acid, (S)-3-(4-((1-((2',4'-dichloro-2,6-difluoro-[1,1'-biphenyl]-4-yl)oxy)-3-methylbutan-2-yl)amino) benzamido)propanoic acid, (S)-3-(4-((1-((2,2'-difluoro-4'-(trifluoromethyl)-[1,1'-biphenyl]-4-yl)oxy)-3-methylbutan-2-yl) amino)benzamido)propanoic acid, (S)-2-(4-((1-((2,2'-difluoro-4'-(trifluoromethyl)-[1,1'-biphenyl]-4-yl)oxy)-3-methylbutan-2-yl) amino)benzamido)ethane-1-sulfonic acid, (S)-3-(4-((1-(4-(benzofuran-2-yl)-3-fluorophenoxy)-3-methylbutan-2-yl)amino)benzamido)propanoic acid, (S)-2-(4-((1-(4-(benzofuran-2-yl)-3-fluorophenoxy)-3-methylbutan-2-yl) amino)benzamido)ethane-1-sulfonic acid, (S)-3-(4-((1-((2'-chloro-2-fluoro-4'-(trifluoromethyl)-[1,1'-biphenyl]-4-yl)oxy)-3-methylbutan-2-yl)amino)benzamido)propanoic acid, (S)-3-(4-((1-((2,2'-difluoro-4'-(trifluoromethyl)-[1,1'-biphenyl]-4-yl)oxy)-4-methylpentan-2-yl)amino)benzamido)propanoic acid, 3-(4-(((2S,3 S)-1-(4-(benzofuran-2-yl)-3-fluorophenoxy)-3-methylpentan-2-yl)amino)benzamido) propanoic acid, 3-(4-(((2S,3 S)-1-((2'-chloro-2-fluoro-4'-(trifluoromethyl)-[1,1'-biphenyl]-4-yl)oxy)-3-methylpentan-2-yl)amino)benzamido)propanoic acid, (S)-3-(4-((1-((2',4'-dichloro-2-fluoro-[1,1'-biphenyl]-4-yl)oxy)-3-methylbutan-2-yl)amino)benzamido)propanoic acid, 3-(4-(((2S,3 S)-1-((2,2'-difluoro-4'-(trifluoromethyl)-[1,1'-biphenyl]-4-yl)oxy)-3-methylpentan-2-yl)amino) benzamido)propanoic acid, 3-(4-(((2S,3 S)-1-((2',4'-dichloro-2-fluoro-[1,1'-biphenyl]-4-yl)oxy)-3-methylpentan-2-yl)amino)benzamido)propanoic acid, (S)-3-(4-((1-((3',5'-dichloro-2-fluoro-[1,1'-biphenyl]-4-yl)oxy)-3-methylbutan-2-yl)amino)benzamido)propanoic acid, (S)-3-(4-((1-(4-(benzofuran-2-yl)-3-fluorophenoxy)hexan-2-yl) amino)benzamido) propanoic acid, 3-(4-(((2S,3 S)-1-((2-fluoro-4'-(trifluoromethyl)-[1,1'-biphenyl]-4-yl)oxy)-3-methylpentan-2-yl)amino)benzamido)propanoic acid, (S)-3-(4-((1-((2'-chloro-2-fluoro-4'-(trifluoromethyl)-[1,1'-biphenyl]-4-yl)oxy)hexan-2-yl)amino)benzamido) propanoic acid, (S)-3-(4-((1-((2',4'-dichloro-2-fluoro-[1,1'-biphenyl]-4-yl)oxy)hexan-2-yl)amino)benzamido) propanoic acid, (S)-3-(4-((1-((2,2'-difluoro-4'-(trifluoromethyl)-[1,1'-biphenyl]-4-yl)oxy)hexan-2-yl) amino)benzamido)propanoic acid, (S)-3-(4-((1-((2-fluoro-4'-(trifluoromethyl)-[1,1'-biphenyl]-4-yl)oxy)hexan-2-yl) amino)benzamido)propanoic acid, (S)-3-(4-((1-((2',4'-dichloro-2-fluoro-[1,1'-biphenyl]-4-yl)oxy)-4-methylpentan-2-yl)amino)benzamido)propanoic acid, (S)-3-(4-((1-(4-(benzofuran-2-yl)-3-fluorophenoxy)-4-methylpentan-2-yl)amino)benzamido)propanoic acid, (S)-3-(4-((1-(4-(benzofuran-2-yl)-3-fluorophenoxy)-3,3-dimethylbutan-2-yl)amino)benzamido)propanoic acid, (S)-3-(4-((1-((2',4'-dichloro-2-fluoro-[1,1'-biphenyl]-4-yl)oxy)-3,3-dimethylbutan-2-yl)amino) benzamido)propanoic acid, (S)-3-(4-((1-((2,2'-difluoro-4'-(trifluoromethyl)-[1,1'-biphenyl]-4-yl)oxy)-3,3-dimethylbutan-2-yl)amino)benzamido) propanoic acid, (S)-3-(4-((1-(3-fluoro-4-(5-(trifluoromethyl)-1,3,4-oxadiazol-2-yl)phenoxy)hexan-2-yl)amino) benzamido)propanoic acid, (S)-3-(4-((1-(4-(benzo[d] thiazol-2-yl)-3-fluorophenoxy)-3-methylbutan-2-yl)amino) benzamido)propanoic acid, (S)-3-(4-((1-((1-(2,4-difluorophenyl)-1H-pyrazol-4-yl)oxy)-4-methylpentan-2-yl)amino)benzamido)propanoic acid, (S)-3-(4-((3-methyl-1-((6-(4-(trifluoromethyl)phenyl)pyridin-3-yl)oxy)butan-2-yl) amino)benzamido)propanoic acid, (S)-3-(4-((1-((6-(2-chloro-4-(trifluoromethyl)phenyl)pyridin-3-yl)oxy)-3-methylbutan-2-yl)amino)benzamido)propanoic acid, (S)-3-(4-((1-((6-(2-fluoro-4-(trifluoromethyl)phenyl)pyridin-3-yl)oxy)-3-methylbutan-2-yl)amino)benzamido)propanoic acid, (S)-3-(4-((1-((6-(2,4-dichlorophenyl)pyridin-3-yl)oxy)-3-methylbutan-2-yl)amino)benzamido)propanoic acid, (S)-3-(4-((1-((6-(3,5-dichlorophenyl)pyridin-3-yl)oxy)-3-methylbutan-2-yl)amino)benzamido)propanoic acid, (S)-3-(4-((1-((6-(benzofuran-2-yl)pyridin-3-yl)oxy)-3-methylbutan-2-yl)amino)benzamido)propanoic acid, (S)-3-(4-((1-((6-(2,4-dichlorophenyl)pyridin-3-yl)oxy)hexan-2-yl)amino) benzamido)propanoic acid, (S)-3-(4-((1-((6-(2-fluoro-4-(trifluoromethyl)phenyl)pyridin-3-yl)oxy)hexan-2-yl) amino)benzamido)propanoic acid, (S)-3-(4-((1-((6-(4-(trifluoromethyl)phenyl)pyridin-3-yl)oxy)hexan-2-yl) amino) benzamido)propanoic acid, (S)-3-(4-((1-((6-(3,5-dichlorophenyl)pyridin-3-yl)oxy)hexan-2-yl)amino) benzamido) propanoic acid, (S)-3-(4-((1-((6-(2-chloro-4-(trifluoromethyl)phenyl)pyridin-3-yl)oxy)hexan-2-yl) amino)benzamido)propanoic acid, (S)-3-(4-((1-((6-(benzofuran-2-yl)pyridin-3-yl)oxy)hexan-2-yl)amino) benzamido)propanoic acid, 3-(4-(((2S,3 S)-1-((6-(benzofuran-2-yl)pyridin-3-yl)oxy)-3-methylpentan-2-yl) amino)benzamido)propanoic acid, 3-(4-(((2S,3 S)-1-((6-(2-fluoro-4-(trifluoromethyl)phenyl)pyridin-3-yl)oxy)-3-methylpentan-2-yl)amino)benzamido)propanoic acid, 3-(4-(((2S,3 S)-1-((6-(2,4-dichlorophenyl)pyridin-3-yl)oxy)-3-methylpentan-2-yl)amino)benzamido)propanoic acid, 3-(4-(((2S,3 S)-1-((6-(2-chloro-4-(trifluoromethyl)phenyl) pyridin-3-yl)oxy)-3-methylpentan-2-yl)amino)benzamido) propanoic acid, (S)-3-(4-((4-methyl-1-((6-(4-(trifluoromethyl)phenyl)pyridin-3-yl)oxy)pentan-2-yl) amino)benzamido)propanoic acid, (S)-3-(4-((1-((6-(2-chloro-4-(trifluoromethyl)phenyl)pyridin-3-yl)oxy)-4-methylpentan-2-yl)amino)benzamido)propanoic acid, (S)-3-(4-((1-((6-(2,4-dichlorophenyl)pyridin-3-yl)oxy)-4-methylpentan-2-yl)amino)benzamido)propanoic acid, (S)-3-(4-((4-methyl-1-((2-(3-methyl-4-(trifluoromethyl)-1H-pyrazol-1-yl)pyrimidin-5-yl)oxy) pentan-2-yl)amino) benzamido)propanoic acid, (S)-3-(4-((1-((2-(benzofuran-2-yl)pyrimidin-5-yl)oxy)-3-methylbutan-2-yl)amino) benzamido) propanoic acid, (S)-3-(4-((1-((2-(benzofuran-2-yl)pyrimidin-5-yl)oxy)-4-methylpentan-2-yl)amino) benzamido)propanoic acid, 3-(4-(((2S,3 S)-1-((6-(2-fluoro-4-(trifluoromethyl)phenyl)pyridin-3-yl)oxy)-3-methylpentan-2-yl)amino)benzamido)propanoic acid, (S)-3-(4-((1-((2-(2-chloro-4-(trifluoromethyl)phenyl)pyrimidin-5-yl)oxy)hexan-2-yl)amino)benzamido)propanoic acid, (S)-3-(4-((1-((2-(2,4-dichlorophenyl)pyrimidin-5-yl)oxy)-3-methylbutan-2-yl)amino)benzamido)propanoic acid, (S)-3-(4-((1-((2-(2,4-dichlorophenyl)pyrimidin-5-yl)oxy)hexan-2-yl)amino)benzamido)propanoic acid, 3-(4-(((2S)-1-((2-(2-chloro-4-(trifluoromethyl)phenyl)pyrimidin-5-yl)oxy)-3-methylpentan-2-yl)amino)benzamido)propanoic acid, (S)-3-(4-((1-((2-(2-chloro-4-(trifluoromethyl)phenyl)pyrimidin-5-yl)oxy)-4-methylpentan-2-yl)amino)benzamido)propanoic acid, 3-(4-(((2S)-1-((2-(2,4-dichlorophenyl)pyrimidin-5-yl) oxy)-3-methylpentan-2-yl)amino)benzamido propanoic acid, (S)-3-(4-((1-((2-(2,4-dichlorophenyl)pyrimidin-5-yl) oxy)-4-methylpentan-2-yl)amino)benzamido)propanoic acid, 3-(4-(((2S,3 S)-1-(4-(benzofuran-2-yl)-3-methoxyphenoxy)-3-methylpentan-2-yl)amino)benzamido)propanoic acid, 3-(4-(((2S,3 S)-1-((2',4'-dichloro-2-methoxy-[1,1'-biphenyl]-4-yl)oxy)-3-methylpentan-2-yl)amino)benzamido) propanoic acid, 3-(4-(((2S,3 S)-1-((2'-chloro-2-methoxy-4'-(trifluoromethyl)-[1,1'-biphenyl]-4-yl)oxy)-3-methylpentan-2-yl)amino)benzamido)propanoic acid, 3-(4-(((2S,3 S)-1-((2'-fluoro-2-methoxy-4'-(trifluoromethyl)-[1,1'-biphenyl]-4-yl)oxy)-3-methylpentan-2-yl)amino)benzamido)propanoic acid, (S)-3-(4-((1-(4-(benzofuran-2-yl)-3-methoxyphenoxy)-3-methylbutan-2-yl)amino) benzamido) propanoic acid, (S)-3-(4-((1-((2'-chloro-2-methoxy-4'-(trifluoromethyl)-[1,1'-biphenyl]-4-yl)oxy)-3-methylbutan-2-yl)amino)benzamido)propanoic acid, (S)-3-(4-((1-((2',4'-dichloro-2-methoxy-[1,1'-biphenyl]-4-yl)oxy)-3-methylbutan-2-yl)amino)benzamido)propanoic acid, (S)-3-(4-((1-((2'-fluoro-2-methoxy-4'-(trifluoromethyl)-[1,1'-biphenyl]-4-yl)oxy)-3-methylbutan-2-yl)amino)benzamido) propanoic acid, (S)-3-(4-((1-((2',4'-dichloro-2-methoxy-[1,1'-biphenyl]-4-yl)oxy)hexan-2-yl)amino)benzamido) propanoic acid, (S)-3-(4-((1-((2-methoxy-4'-(trifluoromethyl)-[1,1'-biphenyl]-4-yl)oxy)-3-methylbutan-2-yl)amino)benzamido)propanoic acid, (S)-3-(4-((1-((2-methoxy-4'-(trifluoromethyl)-[1,1'-biphenyl]-4-yl)oxy) hexan-2-yl)amino)benzamido)propanoic acid, 3-(4-(((2S,3 S)-1-(3-methoxy-4-(5-phenyl-1,3,4-oxadiazol-2-yl)phenoxy)-3-methylpentan-2-yl)amino)benzamido)propanoic acid, 3-(4-(((2S,3 S)-1-(4-(5-(tert-butyl)-1,3,4-oxadiazol-2-yl)-3-methoxyphenoxy)-3-methylpentan-2-yl)amino)benzamido)propanoic acid, (S)-3-(4-((1-((2'-fluoro-2-methoxy-4'-(trifluoromethyl)-[1,1'-biphenyl]-4-yl)oxy)hexan-2-yl) amino)benzamido)propanoic acid, (S)—N-((2H-tetrazol-5-yl)methyl)-4-((2-((5-(benzofuran-2-yl)pyridin-2-yl)oxy)-1-phenylethyl) amino)benzamide, (S)—N-((1H-tetrazol-5-yl) methyl)-4-((3-methyl-1-((5-(4-(trifluoromethyl) phenyl) pyridin-2-yl)oxy)butan-2-yl)amino)benzamide, (S)-3-(4-((1-((5-(benzofuran-2-yl)pyridin-2-yl)oxy)-3-methylbutan-2-yl)amino)benzamido)propanoic acid, (S)-3-(4-((2-((5-(4-(tert-butyl)phenyl)pyridin-2-yl)oxy)-1-phenylethyl)amino) benzamido)propanoic acid, (S)-3-(4-((2-((5-(benzofuran-2-yl)pyridin-2-yl)oxy)-1-phenylethyl)amino) benzamido)propanoic acid, (R)-3-(4-(((S)-2-((5-(4-(tert-butyl)phenyl)pyridin-2-yl)oxy)-1-phenylethyl) amino)benzamido)-2-hydroxypropanoic acid, (S)-3-(4-((3-methyl-1-((5-(4-(trifluoromethyl)phenyl)pyridin-2-yl)oxy)butan-2-yl) amino)benzamido)propanoic acid, (R)-2-hydroxy-3-(4-(((S)-3-methyl-1-((5-(4-(trifluoromethyl)phenyl)pyridin-2-yl)oxy)butan-2-yl)amino)benzamido)propanoic acid, (S)-3-(4-((1-((5-(2-chloro-4-(trifluoromethyl)phenyl)pyridin-2-yl)oxy)-3-methylbutan-2-yl)amino)benzamido)propanoic acid, (S)-3-(4-((1-((5-(2-chloro-4-(trifluoromethyl)phenyl) pyridin-2-yl)oxy)-4-methylpentan-2-yl)amino)benzamido) propanoic acid, (S)-3-(4-((4-methyl-1-((5-(4-(trifluoromethyl)phenyl)pyridin-2-yl)oxy)pentan-2-yl)amino) benzamido)propanoic acid, 3-(4-(((2S,3 S)-3-methyl-1-((5-(4-(trifluoromethyl)phenyl)pyridin-2-yl)oxy)pentan-2-yl) amino)benzamido)propanoic acid, 3-(4-(((2S,3 S)-1-((5-(2-chloro-4-(trifluoromethyl)phenyl)pyridin-2-yl)oxy)-3-methylpentan-2-yl)amino)benzamido)propanoic acid, 3-(4-(((2S,3 S)-1-((5-(2-fluoro-4-(trifluoromethyl)phenyl) pyridin-2-yl)oxy)-3-methylpentan-2-yl)amino)benzamido) propanoic acid, 3-(4-(((2S,3 S)-1-((5-(benzofuran-2-yl) pyridin-2-yl)oxy)-3-methylpentan-2-yl)amino)benzamido) propanoic acid, (S)-3-(4-((1-((5-(2-fluoro-4-(trifluoromethyl)phenyl)pyridin-2-yl)oxy)-4-methylpentan-2-yl)amino)benzamido)propanoic acid, (S)-3-(4-((1-((5-(2, 4-dichlorophenyl)pyridin-2-yl)oxy)-3-methylbutan-2-yl) amino)benzamido)propanoic acid, (S)-2-(4-((1-((5-(2-chloro-4-(trifluoromethyl)phenyl)pyridin-2-yl)oxy)-4-methylpentan-2-yl)amino)benzamido)ethane-1-sulfonic acid, (S)-3-(4-((4-methyl-1-((5-(6-(trifluoromethyl) pyridazin-3-yl)pyridin-2-yl)oxy)pentan-2-yl)amino)benzamido)propanoic acid, 3-(4-(((2S,3 S)-1-((5-(2,4-difluorophenyl)pyridin-2-yl)oxy)-3-methylpentan-2-yl)amino) benzamido)propanoic acid, 2-(4-(((2S,3 S)-1-((5-(2,4-difluorophenyl)pyridin-2-yl)oxy)-3-methylpentan-2-yl) amino)benzamido)ethane-1-sulfonic acid, (S)-3-(4-((1-((5-(benzofuran-2-yl)pyridin-2-yl)oxy)hexan-2-yl)amino)benzamido)propanoic acid, (S)-2-(4-((1-((5-(benzofuran-2-yl)pyridin-2-yl)oxy)hexan-2-yl)amino)benzamido) ethane-1-sulfonic acid, (S)-3-(4-((1-((5-(2,4-dichlorophenyl) pyridin-2-yl)oxy)hexan-2-yl)amino)benzamido)propanoic acid, (S)-3-(4-((1-((5-(2-chloro-4-(trifluoromethyl)phenyl) pyridin-2-yl)oxy)hexan-2-yl)amino)benzamido)propanoic acid, (S)-3-(4-((1-((5-(2-fluoro-4-(trifluoromethyl)phenyl) pyridin-2-yl)oxy)hexan-2-yl)amino)benzamido)propanoic acid, (S)-3-(4-((1-(4'-(trifluoromethyl)-[1,1'-biphenyl]-4-yl)-2-((5-(trifluoromethyl)pyridin-2-yl)oxy)ethyl)amino)benzamido)propanoic acid, (S)-2-(4-((2-((5-(benzofuran-2-yl)pyridin-2-yl)oxy)-1-(4'-(trifluoromethyl)-[1,1'-biphenyl]-4-yl)ethyl)amino)benzamido)ethane-1-sulfonic acid, (S)-3-(4-((2-((5-(benzofuran-2-yl)pyridin-2-yl)oxy)-1-(4'-(trifluoromethyl)-[1,1'-biphenyl]-4-yl)ethyl)amino) benzamido)propanoic acid, (S)-3-(4-((2-((5-(5-(tert-butyl)-1,3,4-oxadiazol-2-yl)pyridin-2-yl)oxy)-1-(4'-(trifluoromethyl)-[1,1'-biphenyl]-4-yl)ethyl)amino) benzamido)propanoic acid, Ethyl (S)-3-(4-((2-((5-(5-(tert-butyl)-1,3,4-oxadiazol-2-yl)pyridin-2-yl)oxy)-1-(2'-fluoro-4'-(trifluoromethyl)-[1,1'-biphenyl]-4-yl)ethyl)amino) benzamido)propanoate, (S)-3-(4-((2-((5-(5-(tert-butyl)-1,3,4-oxadiazol-2-yl)pyridin-2-yl)oxy)-1-(2'-fluoro-4'-(trifluoromethyl)-[1,1'-biphenyl]-4-yl)ethyl)amino) benzamido)propanoic acid, Ethyl (S)-3-(4-((2-((5-(5-(tert-butyl)-1,3,4-oxadiazol-2-yl)pyridin-2-yl)oxy)-1-(2',4'-dichloro-[1,1'-biphenyl]-4-yl)ethyl)amino)benzamido) propanoate, (S)-3-(4-((2-((5-(5-(tert-butyl)-1,3,4-oxadiazol-2-yl)pyridin-2-yl)oxy)-1-(2',4'-dichloro-[1,1'-biphenyl]-4-yl)ethyl)amino)benzamido)propanoic acid, (S)-2-(4-((2-((5-(benzofuran-2-yl)pyridin-2-yl)oxy)-1-(4-(5-methoxypyrimidin-2-yl)phenyl)ethyl)amino)benzamido) ethane-1-sulfonic acid, Ethyl (S)-3-(4-((1-((5-(benzo[d]thiazol-2-yl)pyridin-2-yl)oxy)-3-methylbutan-2-yl) amino)benzamido)propanoate, (S)-3-(4-((1-((5-(benzo[d]thiazol-2-yl)pyridin-2-yl)oxy)-3-methylbutan-2-yl)amino) benzamido)propanoic acid, (S)-3-(4-((1-((6-(2,4-difluorophenyl)pyridazin-3-yl)oxy)-4-methylpentan-2-yl)amino)benzamido)propanoic acid, (S)-3-(4-((1-((6-(2,4-dichlorophenyl)pyridazin-3-yl)oxy)-4-methylpentan-2-yl)amino)benzamido)propanoic acid, 3-(4-(((2S,3 S)-3-methyl-1-((6-(4-(trifluoromethyl)phenyl)pyridazin-3-yl) oxy)pentan-2-yl)amino)benzamido)propanoic acid, 3-(4-(((2S,3 S)-1-((6-(2-chloro-4-(trifluoromethyl)phenyl) pyridazin-3-yl)oxy)-3-methylpentan-2-yl)amino) benzamido)propanoic acid, 3-(4-(((2S,3 S)-1-((6-(2-fluoro-4-(trifluoromethyl)phenyl)pyridazin-3-yl)oxy)-3-methylpentan-2-yl)amino)benzamido)propanoic acid, 3-(4-(((2S,3 S)-1-((6-(2,4-difluorophenyl)pyridazin-3-yl)oxy)-3-methylpentan-2-yl)amino)benzamido)propanoic acid, (S)-3-(4-((4-methyl-1-((6-(4-(trifluoromethyl)phenyl)pyridazin-3-yl)oxy)pentan-2-yl)amino)benzamido)propanoic acid, (S)-3-(4-((1-((6-(benzofuran-2-yl)pyridazin-3-yl)oxy)-3-methylbutan-2-yl)amino)benzamido) propanoic acid, (S)-3-(4-((1-((6-(2-fluoro-4-(trifluoromethyl)phenyl)pyridazin-3-yl)oxy)-3-methylbutan-2-yl) amino)benzamido)propanoic acid, (S)-3-(4-((1-((6-(4-fluorophenyl)pyridazin-3-yl)oxy)-3-methylbutan-2-yl)amino)benzamido)propanoic acid, (S)-3-(4-((1-((6-(2,4-difluorophenyl)pyridazin-3-yl)oxy)-3-methylbutan-2-yl)amino)benzamido)propanoic acid, (S)-3-(4-((1-((6-(4-(tert-butyl)phenyl)pyridazin-3-yl)oxy)-3-methylbutan-2-yl)amino)benzamido)propanoic acid, (S)-3-(4-((1-((5-(benzofuran-2-yl)-6-methylpyridin-2-yl)oxy) hexan-2-yl)amino)benzamido)propanoic acid, (S)-3-(4-((1-((5-(2-chloro-4-(trifluoromethyl)phenyl)-6-methylpyridin-2-yl)oxy)hexan-2-yl)amino)benzamido)propanoic acid, 3-(4-(((2S,3 S)-1-((5-(2-chloro-4-(trifluoromethyl)phenyl)-6-methylpyridin-2-yl)oxy)-3-methylpentan-2-yl)amino) benzamido)propanoic acid, 3-(4-(((2S,3 S)-1-((5-(benzofuran-2-yl)-6-methylpyridin-2-yl)oxy)-3-methylpentan-2-yl)amino)benzamido)propanoic acid, 3-(4-(((2S,3 S)-1-((5-(2,4-dichlorophenyl)-6-methylpyridin-2-yl)oxy)-3-methylpentan-2-yl)amino)benzamido)propanoic acid, 3-(4-(((2S,3 S)-1-((5-(2-fluoro-4-(trifluoromethyl)phenyl)-6-methylpyridin-2-yl)oxy)-3-methyl pentan-2-yl)amino) benzamido)propanoic acid, (S)-3-(4-((1-((5-(2-chloro-4-(trifluoromethyl)phenyl)-6-methylpyridin-2-yl)oxy)-4-methylpentan-2-yl)amino)benzamido)propanoic acid, (S)-3-(4-((1-((5-(2,4-dichlorophenyl)-6-methylpyridin-2-yl)oxy)-4-methylpentan-2-yl)amino) benzamido)propanoic acid, (S)-3-(4-((1-((5-(benzofuran-2-yl)-6-methylpyridin-2-yl) oxy)-4-methylpentan-2-yl)amino)benzamido)propanoic acid, (R)-3-(4-((1-(4'-(trifluoromethyl)-[1,1'-biphenyl]-4-yl) hexan-2-yl)amino)benzamido)propanoic acid, (S)-3-(4-((1-(2',4'-dichloro-[1,1'-biphenyl]-4-yl)propan-2-yl)amino)benzamido)propanoic acid, (S)-3-(4-((1-(4'-(trifluoromethyl)-[1,1'-biphenyl]-4-yl)propan-2-yl)amino)benzamido) propanoic acid, (S)-3-(4-((1-(4'-(tert-butyl)-[1,1'-biphenyl]-4-yl)propan-2-yl)amino)benzamido)propanoic acid, (R)-3-(4-((1-(4-(benzofuran-2-yl)phenyl)-4-methylpentan-2-yl) amino)benzamido)propanoic acid, (R)-3-(4-((1-(4-(benzofuran-2-yl)phenyl)heptan-2-yl)amino)benzamido) propanoic acid, (R)-3-(4-((1-(4'-(tert-butyl)-[1,1'-biphenyl]-4-yl)hexan-2-yl)amino)benzamido)propanoic acid, (R)-3-(4-((1-(4'-(tert-butyl)-[1,1'-biphenyl]-4-yl)-4-methylpentan-2-yl)amino)benzamido)propanoic acid, (S)-3-(4-((1-(4'-(trifluoromethoxy)-[1,1'-biphenyl]-4-yl)heptan-2-yl)amino)benzamido)propanoic acid, (S)-3-(4-((5-methyl-1-(4'-(trifluoromethyl)-[1,1'-biphenyl]-4-yl)hexan-2-yl)amino) benzamido)propanoic acid, (S)-3-(4-((1-(4-(benzofuran-2-yl)phenyl)hexan-2-yl)amino)benzamido)propanoic acid, (S)-3-(4-((1-(4'-(tert-butyl)-[1,1'-biphenyl]-4-yl)-3-propoxypropan-2-yl)amino)benzamido)propanoic acid, (S)-3-(4-((1-propoxy-3-(4'-(trifluoromethyl)-[1,1'-biphenyl]-4-yl)propan-2-yl)amino)benzamido)propanoic acid, (S)-3-(4-((1-propoxy-3-(4'-(trifluoromethoxy)-[1,1'-biphenyl]-4-yl) propan-2-yl)amino)benzamido)propanoic acid, (S)-3-(4-((1-(2',4'-dichloro-[1,1'-biphenyl]-4-yl)-3-propoxypropan-2-yl) amino)benzamido)propanoic acid, (S)-3-(4-((1-propoxy-3-(2',4',6'-trimethyl-[1,1'-biphenyl]-4-yl)propan-2-yl)amino) benzamido) propanoic acid, (R)-3-(4-((1-(4'-(tert-butyl)-[1,1'-biphenyl]-4-yl)-3-isobutoxypropan-2-yl)amino) benzamido)propanoic acid, (R)-3-(4-((1-isobutoxy-3-(4'-(trifluoromethyl)-[1,1'-biphenyl]-4-yl)propan-2-yl)amino) benzamido)propanoic acid, (R)-3-(4-((1-isobutoxy-3-(4'-(trifluoromethoxy)-[1,1'-biphenyl]-4-yl)propan-2-yl)amino) benzamido)propanoic acid, (R)-3-(4-((1-(2',4'-dichloro-[1,1'-biphenyl]-4-yl)-3-isobutoxypropan-2-yl)amino) benzamido)propanoic acid, (R)-3-(4-((1-(4-(benzofuran-2-yl)phenyl)-3-isobutoxypropan-2-yl)amino)benzamido) propanoic acid, (S)-3-(4-((1-propoxy-3-(4'-(trifluoromethyl)-[1,1'-biphenyl]-4-yl)propan-2-yl)amino benzamido)propanoic acid, (S)-3-(4-((1-propoxy-3-(3'-(trifluoromethyl)-[1,1'-biphenyl]-4-yl)propan-2-yl)amino) benzamido)propanoic acid, (S)-3-(4-((1-propoxy-3-(4'-(trifluoromethoxy)-[1,1'-biphenyl]-4-yl)propan-2-yl)amino) benzamido)propanoic acid, (S)-3-(4-((1-propoxy-3-(3'-(trifluoromethoxy)-[1,1'-biphenyl]-4-yl)propan-2-yl)amino) benzamido)propanoic acid, (S)-3-(4-((1-(4-(benzofuran-2-yl)phenyl)-3-propoxypropan-2-yl)amino)benzamido) propanoic acid, (S)-3-(4-((1-(4-(1H-indol-2-yl)phenyl)-3-propoxypropan-2-yl)amino)benzamido)propanoic acid, (S)-3-(4-((1-isobutoxy-3-(3'-(trifluoromethyl)-[1,1'-biphenyl]-4-yl)propan-2-yl)amino)benzamido)propanoic acid, (S)-3-(4-((1-isobutoxy-3-(2'-(trifluoromethyl)-[1,1'-biphenyl]-4-yl)propan-2-yl)amino)benzamido)propanoic acid, (S)-3-(4-((1-isobutoxy-3-(3'-(trifluoromethoxy)-[1,1'-biphenyl]-4-yl) propan-2-yl)amino)benzamido)propanoic acid, (S)-3-(4-((1-isobutoxy-3-(3',4',5'-trifluoro-[1,1'-biphenyl]-4-yl)propan-2-yl)amino)benzamido) propanoic acid, (S)-3-(4-((1-(4-(benzofuran-2-yl)phenyl)-3-isobutoxypropan-2-yl)amino) benzamido)propanoic acid, (S)-3-(4-((1-isobutoxy-3-(4'-(trifluoromethoxy)-[1,1'-biphenyl]-4-yl)propan-2-yl)amino) benzamido)propanoic acid, (S)-3-(4-((1-isobutoxy-3-(4'-(trifluoromethyl)-[1,1'-biphenyl]-4-yl)propan-2-yl)amino) benzamido)propanoic acid, (S)-3-(4-((2-(4-(benzofuran-2-yl)phenyl)-1-(5-(4-(tert-butyl)phenyl)-1,3,4-oxadiazol-2-yl) eth yl)amino)benzamido)propanoic acid, 3-(4-(((1S)-2-methyl-1-(5-(3-methylbenzofuran-2-yl)-1,3,4-oxadiazol-2-yl)butyl)amino)benzamido)propanoic acid, 3-(4-(((1S)-1-(5-(4-(tert-butyl)phenyl)-1,3,4-oxadiazol-2-yl)-2-methylbutyl)amino)benzamido)propanoic acid, (S)-3-(4-((1-(5-(4-(tert-butyl)phenyl)-1,3,4-oxadiazol-2-yl)-2-methylpropyl)amino)benzamido)propanoic acid, (S)-3-(4-((1-(5-(4-(tert-butyl)phenyl)-1,3,4-oxadiazol-2-yl)-2-(2',4',6'-trimethyl-[1,1'-biphenyl]-4-yl)ethyl)amino)benzamido) propanoic acid, (S)-3-(4-((1-(5-(3-methylbenzofuran-2-yl)-1,3,4-oxadiazol-2-yl)-2-(4'-(trifluoromethyl)-[1,1'-biphenyl]-4-yl)ethyl)amino)benzamido)propanoic acid, (S)-2-(4-((1-(5-(3-methylbenzofuran-2-yl)-1,3,4-oxadiazol-2-yl)-2-(4'-(trifluoromethyl)-[1,1'-biphenyl]-4-yl)ethyl) amino)benzamido)ethane-1-sulfonic acid, (S)-3-(4-((1-(5-(4-(tert-butyl)phenyl)-1,2,4-oxadiazol-3-yl)hexan-2-yl) amino)benzamido)propanoic acid, 3-(4-(((2R)-1-(5-(4-(tert-butyl)phenyl)-1,2,4-oxadiazol-3-yl)-3-methylpentan-2-yl) amino)benzamido)propanoic acid, (R)-3-(4-((1-(5-(4-(tert-butyl)phenyl)-1,2,4-oxadiazol-3-yl)-3-methylbutan-2-yl) amino)benzamido)propanoic acid, 3-(4-(((2S,3 S)-1-((5-(2-fluoro-4-(trifluoromethyl)phenyl)-1,3,4-oxadiazol-2-yl) oxy)-3-methyl pentan-2-yl)amino)benzamido)propanoic acid, (S)-3-(4-((1-((5-(4-(trifluoromethoxy)phenyl)-1,3,4-oxadiazol-2-yl)oxy)hexan-2-yl)amino)benzamido)propanoic acid, (S)-3-(4-((1-((5-(2-fluoro-4-(trifluoromethyl) phenyl)-1,3,4-oxadiazol-2-yl)oxy)hexan-2-yl)amino) benzamido)propanoic acid, (S)-3-(4-((1-((5-(benzofuran-2-yl)-1,3,4-oxadiazol-2-yl)oxy)hexan-2-yl)amino)benzamido) propanoic acid, (S)-3-(4-((1-((5-(4-(trifluoromethyl) phenyl)-1,3,4-oxadiazol-2-yl)oxy)hexan-2-yl)amino) benzamido)propanoic acid, (S)-3-(4-((1-((5-(2,4-dichlorophenyl)-1,3,4-oxadiazol-2-yl)oxy)hexan-2-yl) amino)benzamido) propanoic acid, 3-(4-(((2S,3 S)-1-((5-(benzofuran-2-yl)-1,3,4-oxadiazol-2-yl)oxy)-3-methylpentan-2-yl)amino)benzamido)propanoic acid, 3-(4-(((2S)-3-methyl-1-((5-(4-(trifluoromethoxy)phenyl)-1,3,4-oxadiazol-2-yl)oxy)pentan-2-yl)amino)benzamido propanoic acid, 3-(4-(((2S)-1-((5-(4-(tert-butyl)phenyl)-1,3,4-oxadiazol-2-yl)oxy)-3-methylpentan-2-yl)amino) benzamido)propanoic acid, 3-(4-(((2S,3 S)-3-methyl-1-((5-(4-(trifluoromethyl)phenyl)-1,3,4-oxadiazol-2-yl)oxy) pentan-2-yl)amino)benzamido)propanoic acid, 3-(4-(((2S,3 S)-1-((5-(2,4-dichlorophenyl)-1,3,4-oxadiazol-2-yl)oxy)-3-methylpentan-2-yl)amino)benzamido)propanoic acid, (S)-3-(4-((1-((5-(benzofuran-2-yl)-1,3,4-oxadiazol-2-yl)oxy)-3-methylbutan-2-yl)amino)benzamido)propanoic acid, (S)-3-(4-((3-methyl-1-((5-(4-(trifluoromethyl)phenyl)-1,3,4-oxadiazol-2-yl)oxy)butan-2-yl)amino)benzamido) propanoic acid, (S)-3-(4-((1-((5-(2,4-dichlorophenyl)-1,3,4-oxadiazol-2-yl)oxy)-3-methylbutan-2-yl)amino)benzamido) propanoic acid, (S)-3-(4-((3-methyl-1-((5-(4-(trifluoromethoxy)phenyl)-1,3,4-oxadiazol-2-yl)oxy)butan-2-yl)amino)benzamido)propanoic acid, (S)-3-(4-((1-((5-(4-(tert-butyl)phenyl)-1,3,4-oxadiazol-2-yl)oxy)-3-methylbutan-2-yl)amino)benzamido)propanoic acid, (S)-3-(4-((1-((5-(2-fluoro-4-(trifluoromethyl)phenyl)-1,3,4-oxadiazol-2-yl)oxy)-3-methylbutan-2-yl)amino)benzamido) propanoic acid, (S)-3-(4-((1-((5-(4-(tert-butyl)phenyl)-1,3,4-oxadiazol-2-yl)oxy)hexan-2-yl)amino)benzamido) propanoic acid, 3-(4-(((2S,3 S)-1-((5-(2-chloro-4-(trifluoromethyl)phenyl)-1,3,4-oxadiazol-2-yl)oxy)-3-methyl pentan-2-yl)amino)benzamido)propanoic acid, Methyl 3-(4-(((2S,3 S)-1-((5-(2-fluoro-4-(trifluoromethyl) phenyl)-1,3,4-oxadiazol-2-yl) oxy)-3-methylpentan-2-yl) amino)benzamido)propanoate, (S)-3-(4-((1-((2',4'-dichloro-[1,1'-biphenyl]-4-yl)amino)-4-methyl-1-oxopentan-2-yl) amino)benzamido)propanoic acid, (S)-3-(4-((1-((2',4'-dichloro-[1,1'-biphenyl]-4-yl)amino)-1-oxo-3-phenylpropan-2-yl)amino)benzamido)propanoic acid, (S)-3-(4-((1-oxo-3-phenyl-1-((2',4',6'-trimethyl-[1,1'-biphenyl]-4-yl)amino)propan-2-yl)amino)benzamido)propanoic acid, (S)-3-(4-((4-methyl-1-oxo-1-((4'-(trifluoromethyl)-[1,1'-biphenyl]-4-yl)amino)pentan-2-yl)amino)benzamido)propanoic acid, (S)-3-(4-((1-((4-(benzofuran-2-yl)phenyl) amino)-4-methyl-1-oxopentan-2-yl)amino)benzamido) propanoic acid, Ethyl (S)-3-(4-((1-((4-(benzofuran-2-yl)phenyl)amino)-4-methyl-1-oxopentan-2-yl)amino) benzamido)propanoate, Ethyl (S)-3-(4-((1-((4-(benzofuran-2-yl)phenyl)amino)-1-oxo-3-phenylpropan-2-yl)amino) benzamido)propanoate, (S)-3-(4-((1-((4-(benzofuran-2-yl) phenyl)amino)-1-oxo-3-phenylpropan-2-yl)amino) benzamido)propanoic acid, Ethyl (S)-3-(4-((1-((4-(benzofuran-2-yl)phenyl)amino)-3-(4-fluorophenyl)-1-oxopropan-2-yl)amino)benzamido)propanoate, (S)-3-(4-((1-((4-(benzofuran-2-yl)phenyl)amino)-3-(4-fluorophenyl)-1-oxopropan-2-yl)amino)benzamido)propanoic acid, Ethyl (S)-3-(4-((1-((4-(benzo[b]thiophen-2-yl)phenyl)amino)-4-methyl-1-oxopentan-2-yl)amino)benzamido)propanoate, (S)-3-(4-((1-((4-(benzo[b]thiophen-2-yl)phenyl)amino)-4-methyl-1-oxopentan-2-yl)amino)benzamido)propanoic acid, Ethyl (S)-3-(4-((1-((4-(benzofuran-2-yl)phenyl)amino)-3-(naphthalen-1-yl)-1-oxopropan-2-yl)amino)benzamido)propanoate, (S)-3-(4-((1-((2',4'-dichloro-[1,1'-biphenyl]-4-yl) amino)-1-oxo-3-phenylpropan-2-yl)amino)benzamido) propanoic acid, Ethyl (S)-3-(4-((1-((2',4'-dichloro-[1,1'-biphenyl]-4-yl)amino)-1-oxo-3-phenylpropan-2-yl)amino) benzamido)propanoate, (R)-3-(4-((1-((4-(benzofuran-2-yl) phenyl)amino)-4-methyl-1-oxopentan-2-yl)amino) benzamido)propanoic acid, Ethyl (S)-3-(4-((1-((4-(tert-butyl)phenyl)amino)-3-(naphthalen-1-yl)-1-oxopropan-2-yl)amino)benzamido)propanoate, (S)-3-(4-((1-((4-(tert-butyl)phenyl)amino)-3-(naphthalen-1-yl)-1-oxopropan-2-yl)amino)benzamido)propanoic acid, Ethyl (S)-3-(4-((1-((4-(tert-butyl)phenyl)amino)-3-(naphthalen-2-yl)-1-oxopropan-2-yl)amino)benzamido)propanoate, (S)-3-(4-((1-((4-(tert-butyl)phenyl)amino)-3-(naphthalen-2-yl)-1-oxopropan-2-yl)amino)benzamido)propanoic acid, Ethyl (S)-3-(4-((1-((4-(benzofuran-2-yl)phenyl)amino)-3-(naphthalen-2-yl)-1-oxopropan-2-yl)amino)benzamido)propanoate, (S)-3-(4-((1-((4-(benzofuran-2-yl)phenyl)amino)-3-(naphthalen-2-yl)-1-oxopropan-2-yl)amino)benzamido) propanoic acid, (S)-3-(4-((1-oxo-3-phenyl-1-((2'-(trifluoromethyl)-[1,1'-biphenyl]-4-yl)amino)propan-2-yl) amino)benzamido)propanoic acid, (S)-3-(4-((1-((4-(tert-butyl)phenyl)amino)-1-oxo-3-(2',4',6'-trimethyl-[1,1'-biphenyl]-4-yl)propan-2-yl)amino)benzamido)propanoic acid, Ethyl (S)-3-(4-((1-((4-(benzofuran-2-yl)phenyl) amino)-3-(1H-indol-3-yl)-1-oxopropan-2-yl)amino) benzamido)propanoate, Methyl (S)-3-(4-((1-((4-(1H-indol-2-yl)phenyl)amino)-4-methyl-1-oxopentan-2-yl)amino) benzamido) propanoate, (S)-3-(4-((1-((4-(1H-indol-2-yl) phenyl)amino)-4-methyl-1-oxopentan-2-yl)amino) benzamido) propanoic acid, 3-(4-(((2S,3 S)-1-((6-methoxynaphthalen-2-yl)amino)-3-methyl-1-oxopentan-2-yl)amino)benzamido)propanoic acid, 3-(4-(((2S,3 S)-1-((4-(benzofuran-2-yl)phenyl)amino)-3-methyl-1-oxopentan-2-yl)amino)benzamido)propanoic acid, Ethyl (S)-3-(4-((1-((4-(benzofuran-2-yl)phenyl)amino)-3-methyl-1-oxobutan-2-yl)amino)benzamido)propanoate, (S)-3-(4-((1-((4-(benzofuran-2-yl)phenyl)amino)-3-methyl-1-oxobutan-2-yl)amino)benzamido)propanoic acid, (S)-3-(4-((1-((4-(benzofuran-2-yl)phenyl)amino)-1-oxohexan-2-yl)amino) benzamido) propanoic acid, Ethyl (R)-3-(4-((1-((4-(benzofuran-2-yl)phenyl)amino)-4-methyl-1-oxopentan-2-yl)amino)benzamido)propanoate, (R)-3-(4-((1-((4-(benzofuran-2-yl)phenyl)amino)-4-methyl-1-oxopentan-2-yl)amino)benzamido)propanoic acid, Ethyl (R)-3-(4-((1-oxo-3-phenyl-1-((4-(trifluoromethyl)phenyl)amino)propan-2-yl)amino)benzamido)propanoate, (S)-3-(4-((1-oxo-3-phenyl-1-((4-(trifluoromethyl)phenyl)amino)propan-2-yl) amino)benzamido)propanoic acid, Ethyl (S)-3-(4-((1-oxo-3-phenyl-1-((4-(trifluoromethyl)phenyl)amino)propan-2-yl) amino)benzamido)propanoate, (S)-3-(4-((1-oxo-3-phenyl-1-((4-(trifluoromethyl)phenyl)amino)propan-2-yl)amino) benzamido)propanoic acid, Ethyl 3-(4-(((2S,3 S)-1-((6-methoxynaphthalen-2-yl)amino)-3-methyl-1-oxopentan-2-yl)amino)benzamido)propanoate, 3-(4-(((2S,3 S)-1-((6-methoxynaphthalen-2-yl)amino)-3-methyl-1-oxopentan-2-yl)amino)benzamido)propanoic acid, Ethyl (R)-3-(4-((4-methyl-1-oxo-1-((4-(trifluoromethyl)phenyl)amino)pentan-2-yl)amino)benzamido)propanoate, (R)-3-(4-((4-methyl-1-oxo-1-((4-(trifluoromethyl)phenyl)amino)pentan-2-yl) amino) benzamido) propanoic acid, Ethyl (S)-3-(4-((1-(isopropylamino)-3-(naphthalen-1-yl)-1-oxopropan-2-yl) amino)benzamido)propanoate, (S)-3-(4-((1-(isopropylamino)-3-(naphthalen-1-yl)-1-oxopropan-2-yl) amino)benzamido)propanoic acid, Ethyl (S)-3-(4-((1-(isopropylamino)-3-(naphthalen-2-yl)-1-oxopropan-2-yl) amino)benzamido)propanoate, (S)-3-(4-((1-(isopropylamino)-3-(naphthalen-2-yl)-1-oxopropan-2-yl) amino)benzamido)propanoic acid, Ethyl (R)-3-(4-((3-(4'-(tert-butyl)-[1,1'-biphenyl]-4-yl)-1-oxo-1-((4-(trifluoromethyl)phenyl)amino) propan-2-yl)amino) benzamido)propanoate, (R)-3-(4-((3-(4'-(tert-butyl)-[1,1'-biphenyl]-4-yl)-1-oxo-1-((4-(trifluoromethyl)phenyl) amino) propan-2-yl)amino)benzamido)propanoic acid, Ethyl (R)-3-(4-((3-(2',4'-dichloro-[1,1'-biphenyl]-4-yl)-1-oxo-1-((4-(trifluoromethyl)phenyl)amino)propan-2-yl) amino)benzamido)propanoate, (R)-3-(4-((3-(2',4'-dichloro-[1,1'-biphenyl]-4-yl)-1-oxo-1-((4-(trifluoromethyl)phenyl) amino)propan-2-yl)amino)benzamido)propanoic acid, Ethyl (R)-3-(4-((3-(4-(benzofuran-2-yl)phenyl)amino)-1-oxo-1-((4-(trifluoromethyl)phenyl)amino)propan-2-yl)amino)benzamido) propanoate, (R)-3-(4-((3-(4-(benzofuran-2-yl)phenyl)-1-oxo-1-((4-(trifluoromethyl)phenyl)amino)propan-2-yl) amino)benzamido)propanoic acid, Ethyl (R)-3-(4-((3-(4-(benzofuran-2-yl)phenyl)-1-(isopropylamino)-1-oxopropan-2-yl)amino)benzamido)propanoate, (R)-3-(4-((3-(4-(benzofuran-2-yl)phenyl)-1-(isopropylamino)-1-oxopropan-2-yl)amino)benzamido)propanoic acid, Ethyl (R)-3-(4-((3-(4-(benzofuran-2-yl)phenyl)-1-((3,5-difluorophenyl)amino)-1-oxopropan-2-yl)amino)benzamido)propanoate, (R)-3-(4-((3-(4-(benzofuran-2-yl)phenyl)-1-((3,5-difluorophenyl)amino)-1-oxopropan-2-yl)amino) benzamido)propanoic acid, Ethyl (R)-3-(4-((3-(4'-(tert-butyl)-[1,1'-biphenyl]-4-yl)-1-oxo-1-((4-(trifluoromethoxy) phenyl)amino)propan-2-yl)amino)benzamido)propanoate, (R)-3-(4-((3-(4'-(tert-butyl)-[1,1'-biphenyl]-4-yl)-1-oxo-1-((4-(trifluoromethoxy)phenyl)amino)propan-2-yl)amino) benzamido)propanoic acid, Ethyl (R)-3-(4-((1-oxo-1-((4-(trifluoromethoxy)phenyl)amino)-3-(4'-(trifluoromethyl)-[1,1'-biphenyl]-4-yl)propan-2-yl)amino)benzamido) propanoate, and (R)-3-(4-((1-oxo-1-((4-(trifluoromethoxy) phenyl)amino)-3-(4'-(trifluoromethyl)-[1,1'-biphenyl]-4-yl) propan-2-yl)amino)benzamido)propanoic acid.

7. The compound or the pharmaceutically acceptable salt thereof of claim 6, which is any one selected from the group consisting of (S)-3-(4-((1-(4-(benzofuran-2-yl)phenoxy)-3-methylbutan-2-yl)amino)benzamido)propanoic acid, N-((1H-tetrazol-5-yl)methyl)-4-(((2S,3S)-1-(4-(benzofuran-2-yl)phenoxy)-3-methylpentan-2-yl)amino)benzamide, (R)-3-(4-(((2S,3 S)-1-(4-(benzofuran-2-yl)phenoxy)-3-methylpentan-2-yl)amino)benzamido)-2-hydroxypropanoic acid, (S)-3-(4-((1-((4'-(dimethylamino)-[1,1'-biphenyl]-4-yl)oxy)-3-methylbutan-2-yl)amino) benzamido)propanoic acid, (S)—N-((1H-tetrazol-5-yl) methyl)-4-((1-((4'-(trifluoromethyl)-[1,1'-biphenyl]-4-yl) oxy)hexan-2-yl)amino)benzamide, (S)-3-(4-((1-((2',4'-dichloro-[1,1'-biphenyl]-4-yl)oxy)hexan-2-yl)amino) benzamido) propanoic acid, (S)—N-((1H-tetrazol-5-yl) methyl)-4-((1-((2',4'-dichloro-[1,1'-biphenyl]-4-yl)oxy) hexan-2-yl)amino)benzamide, (S)-3-(4-((1-((2'-chloro-4'-(trifluoromethyl)-[1,1'-biphenyl]-4-yl)oxy)hexan-2-yl) amino)benzamido)propanoic acid, (S)—N-((1H-tetrazol-5-yl)methyl)-4-((1-((2'-chloro-4'-(trifluoromethyl)-[1,1'-biphenyl]-4-yl)oxy)hexan-2-yl)amino)benzamide, (S)-3-(4-((1-((2'-chloro-4'-(trifluoromethyl)-[1,1'-biphenyl]-4-yl) oxy)-3-methylbutan-2-yl)amino)benzamido)propanoic acid, (S)-3-(4-((1-((2'-fluoro-4'-(trifluoromethyl)-[1,1'-biphenyl]-4-yl)oxy)-3-methylbutan-2-yl)amino)benzamido)propanoic acid, Ethyl (S)-3-(4-((1-(4-(benzo[d]thiazol-2-yl)phenoxy)-3-methylbutan-2-yl)amino)benzamido)propan oate, (S)-3-(4-((1-(4-(benzo[d]thiazol-2-yl)phenoxy)-3-methylbutan-2-yl)amino)benzamido)propanoic acid, (S)-3-(4-((1-(4-(benzo[d]oxazol-2-yl)phenoxy)-3-methylbutan-2-yl)amino) benzamido)propanoic acid, (R)-3-(4-((1-(4-(benzo[d] thiazol-2-yl)phenoxy)-3-methylbutan-2-yl)amino) benzamido)propanoic acid, (R)-3-(4-((1-(4-(benzo[d] oxazol-2-yl)phenoxy)-3-methylbutan-2-yl)amino) benzamido)propanoic acid, (S)-3-(4-((1-((2,6-dimethyl-4'-(trifluoromethyl)-[1,1'-biphenyl]-4-yl)oxy)-3-methylbutan-2-yl) amino)benzamido)propanoic acid, 3-(4-(((2S,3 S)-1-((4'-(tert-butyl)-2,6-dimethyl-[1,1'-biphenyl]-4-yl)oxy)-3-methylpentan-2-yl) amino)benzamido)propanoic acid, 3-(4-(((2S,3 S)-1-((2',4'-dichloro-2,6-dimethyl-[1,1'-biphenyl]-4-yl)oxy)-3-methylpentan-2-yl) amino)benzamido)propanoic acid, 3-(4-(((2S,3 S)-1-((2,6-dimethyl-4'-(trifluoromethyl)-[1,1'-biphenyl]-4-yl)oxy)-3-methylpentan-2-yl)amino)benzamido)propanoic acid, (R)-3-(4-(((S)-1-((2,2'-dichloro-4'-(trifluoromethyl)-[1,1'-biphenyl]-4-yl)oxy)-3-methylbutan-2-yl)amino)benzamido)-2-hydroxypropanoic acid, (S)—N-((1H-tetrazol-5-yl)methyl)-4-((1-((2,2'-dichloro-4'-

(trifluoromethyl)-[1,1'-biphenyl]-4-yl)oxy)-3-methylbutan-2-yl)amino)benzamide, (S)-3-(4-((1-((2,2'-dichloro-4'-(trifluoromethyl)-[1,1'-biphenyl]-4-yl)oxy)-3-methylbutan-2-yl) amino)benzamido)propanoic acid, (S)—N-((1H-tetrazol-5-yl)methyl)-4-((1-(4-(benzofuran-2-yl)-3-chlorophenoxy)-3-methylbutan-2-yl)amino)benzamide, (S)-3-(4-((1-((2,2'-dichloro-4'-(trifluoromethyl)-[1,1'-biphenyl]-4-yl)oxy)hexan-2-yl)amino)benzamido)propanoic acid, (S)—N-((1H-tetrazol-5-yl)methyl)-4-((1-((2,2'-dichloro-4'-(trifluoromethyl)-[1,1'-biphenyl]-4-yl)oxy)hexan-2-yl) amino)benzamide, (S)-3-(4-((1-(4-(benzofuran-2-yl)-3-chlorophenoxy)hexan-2-yl)amino)benzamido)propanoic acid, (S)-3-(4-((1-((2,2',4'-trichloro-[1,1'-biphenyl]-4-yl)oxy)hexan-2-yl)amino) benzamido)propanoic acid, (S)—N-((1H-tetrazol-5-yl)methyl)-4-((1-((2,2',4'-trichloro-[1,1'-biphenyl]-4-yl)oxy)hexan-2-yl) amino)benzamide, (S)-3-(4-((1-(4-(benzofuran-2-yl)-2,5-dichlorophenoxy)-3-methylbutan-2-yl)amino)benzamido)propanoic acid, 3-(4-((2-((2'-chloro-4'-(trifluoromethyl)-[1,1'-biphenyl]-4-yl)oxy)-1-phenylethyl)amino)benzamido)propanoic acid, 3-(4-(((2S,3 S)-1-(4-(benzofuran-2-yl)-2,5-dichlorophenoxy)-3-methylpentan-2-yl)amino)benzamido)propanoic acid, 3-(4-(((2S,3 S)-3-methyl-1-((2,2',5-trichloro-4'-(trifluoromethyl)-[1,1'-biphenyl]-4-yl)oxy)pentan-2-yl amino)benzamido)propanoic acid, (S)-3-(4-((1-((2-chloro-2'-fluoro-4'-(trifluoromethyl)-[1,1'-biphenyl]-4-yl)oxy)hexan-2-yl)amino)benzamido)propanoic acid, (S)-3-(4-((1-((2-chloro-2'-fluoro-4'-(trifluoromethyl)-[1,1'-biphenyl]-4-yl)oxy)-3,3-dimethylbutan-2-yl)amino)benzamido) propanoic acid, (S)-3-(4-((1-(4-(benzofuran-2-yl)-3,5-difluorophenoxy)-3-methylbutan-2-yl)amino)benzamido) propanoic acid, (S)-3-(4-((1-((2'-chloro-2,6-difluoro-4'-(trifluoromethyl)-[1,1'-biphenyl]-4-yl)oxy)-4-methylpentan-2-yl)amino)benzamido)propanoic acid, (S)-3-(4-((1-((2',4'-dichloro-2,6-difluoro-[1,1'-biphenyl]-4-yl)oxy)-4-methylpentan-2-yl)amino)benzamido)propanoic acid, (S)-3-(4-((1-((2',4'-dichloro-2,6-difluoro-[1,1'-biphenyl]-4-yl)oxy)-3-methylbutan-2-yl)amino) benzamido)propanoic acid, (S)-3-(4-((1-(4-(benzofuran-2-yl)-3-fluorophenoxy)-3-methylbutan-2-yl)amino)benzamido)propanoic acid, (S)-3-(4-((1-((2'-chloro-2-fluoro-4'-(trifluoromethyl)-[1,1'-biphenyl]-4-yl)oxy)-3-methylbutan-2-yl)amino)benzamido)propanoic acid, 3-(4-(((2S,3 S)-1-((2'-chloro-2-fluoro-4'-(trifluoromethyl)-[1,1'-biphenyl]-4-yl)oxy)-3-methylpentan-2-yl)amino)benzamido)propanoic acid, 3-(4-(((2S,3 S)-1-((2',4'-dichloro-2-fluoro-[1,1'-biphenyl]-4-yl)oxy)-3-methylpentan-2-yl)amino)benzamido)propanoic acid, (S)-3-(4-((1-(4-(benzofuran-2-yl)-3-fluorophenoxy)hexan-2-yl)amino)benzamido) propanoic acid, (S)-3-(4-((1-((2'-chloro-2-fluoro-4'-(trifluoromethyl)-[1,1'-biphenyl]-4-yl)oxy)hexan-2-yl)amino)benzamido)propanoic acid, (S)-3-(4-((1-((2',4'-dichloro-2-fluoro-[1,1'-biphenyl]-4-yl)oxy) hexan-2-yl)amino)benzamido)propanoic acid, (S)-3-(4-((1-(4-(benzofuran-2-yl)-3-fluorophenoxy)-4-methylpentan-2-yl)amino)benzamido)propanoic acid, (S)-3-(4-((1-((2',4'-dichloro-2-fluoro-[1,1'-biphenyl]-4-yl)oxy)-3,3-dimethylbutan-2-yl)amino) benzamido)propanoic acid, (S)-3-(4-((1-((2,2'-difluoro-4'-(trifluoromethyl)-[1,1'-biphenyl]-4-yl)oxy)-3,3-dimethylbutan-2-yl)amino)benzamido) propanoic acid, (S)-3-(4-((1-(4-(benzo[d]thiazol-2-yl)-3-fluorophenoxy)-3-methylbutan-2-yl)amino)benzamido) propanoic acid, 3-(4-(((2S,3 S)-1-(4-(benzofuran-2-yl)-3-methoxyphenoxy)-3-methylpentan-2-yl)amino)benzamido) propanoic acid, 3-(4-(((2S,3 S)-1-((2',4'-dichloro-2-methoxy-[1,1'-biphenyl]-4-yl)oxy)-3-methylpentan-2-yl) amino)benzamido)propanoic acid, 3-(4-(((2S,3 S)-1-((2'-chloro-2-methoxy-4'-(trifluoromethyl)-[1,1'-biphenyl]-4-yl) oxy)-3-methylpentan-2-yl)amino)benzamido)propanoic acid, 3-(4-(((2S,3 S)-1-((2'-fluoro-2-methoxy-4'-(trifluoromethyl)-[1,1'-biphenyl]-4-yl)oxy)-3-methylpentan-2-yl) amino)benzamido)propanoic acid, (S)-3-(4-((1-((2'-chloro-2-methoxy-4'-(trifluoromethyl)-[1,1'-biphenyl]-4-yl)oxy)-3-methylbutan-2-yl)amino)benzamido)propanoic acid, (S)-3-(4-((1-((2',4'-dichloro-2-methoxy-[1,1'-biphenyl]-4-yl)oxy)-3-methylbutan-2-yl)amino)benzamido)propanoic acid, (S)-3-(4-((1-((2'-fluoro-2-methoxy-4'-(trifluoromethyl)-[1,1'-biphenyl]-4-yl)oxy)-3-methylbutan-2-yl)amino)benzamido) propanoic acid, (S)-3-(4-((1-((2',4'-dichloro-2-methoxy-[1,1'-biphenyl]-4-yl)oxy)hexan-2-yl)amino)benzamido) propanoic acid, (S)-3-(4-((1-((2-methoxy-4'-(trifluoromethyl)-[1,1'-biphenyl]-4-yl)oxy)-3-methylbutan-2-yl)amino)benzamido)propanoic acid, (S)-3-(4-((1-((2-methoxy-4'-(trifluoromethyl)-[1,1'-biphenyl]-4-yl)oxy) hexan-2-yl)amino)benzamido)propanoic acid, (S)-3-(4-((1-((2'-fluoro-2-methoxy-4'-(trifluoromethyl)-[1,1'-biphenyl]-4-yl)oxy)hexan-2-yl)amino)benzamido)propanoic acid, (S)-3-(4-((1-((5-(benzofuran-2-yl)pyridin-2-yl)oxy)-3-methylbutan-2-yl)amino)benzamido)propanoic acid, (S)-3-(4-((3-methyl-1-((5-(4-(trifluoromethyl)phenyl)pyridin-2-yl)oxy)butan-2-yl)amino)benzamido)propanoic acid, (S)-3-(4-((1-((5-(2-chloro-4-(trifluoromethyl)phenyl)pyridin-2-yl)oxy)-3-methylbutan-2-yl)amino)benzamido)propanoic acid, (S)-3-(4-((1-((5-(2-chloro-4-(trifluoromethyl)phenyl)pyridin-2-yl)oxy)-4-methylpentan-2-yl)amino)benzamido) propanoic acid, 3-(4-(((2S,3 S)-1-((5-(2-chloro-4-(trifluoromethyl)phenyl)pyridin-2-yl)oxy)-3-methylpentan-2-yl)amino)benzamido)propanoic acid, (S)-3-(4-((1-((5-(benzofuran-2-yl)pyridin-2-yl)oxy)hexan-2-yl)amino) benzamido)propanoic acid, (S)-2-(4-((2-((5-(benzofuran-2-yl)pyridin-2-yl)oxy)-1-(4'-(trifluoromethyl)-[1,1'-biphenyl]-4-yl)ethyl)amino)benzamido)ethane-1-sulfonic acid, (S)-3-(4-((2-((5-(benzofuran-2-yl)pyridin-2-yl)oxy)-1-(4'-(trifluoromethyl)-[1,1'-biphenyl]-4-yl)ethyl)amino) benzamido)propanoic acid, (S)-3-(4-((1-((5-(2-chloro-4-(trifluoromethyl)phenyl)-6-methylpyridin-2-yl)oxy)hexan-2-yl)amino)benzamido)propanoic acid, 3-(4-(((2S,3 S)-1-((5-(2-chloro-4-(trifluoromethyl)phenyl)-6-methylpyridin-2-yl)oxy)-3-methylpentan-2-yl)amino)benzamido) propanoic acid, (S)-3-(4-((1-((5-(2-chloro-4-(trifluoromethyl)phenyl)-6-methylpyridin-2-yl)oxy)-4-methylpentan-2-yl)amino)benzamido)propanoic acid, (S)-3-(4-((1-((5-(2,4-dichlorophenyl)-6-methylpyridin-2-yl)oxy)-4-methylpentan-2-yl)amino)benzamido)propanoic acid, (R)-3-(4-((1-(4-(benzofuran-2-yl)phenyl)-4-methylpentan-2-yl)amino)benzamido)propanoic acid, 3-(4-(((2S,3S)-1-((5-(2-fluoro-4-(trifluoromethyl)phenyl)-1,3,4-oxadiazol-2-yl)oxy)-3-methyl pentan-2-yl)amino)benzamido)propanoic acid, (S)-3-(4-((1-((5-(4-(tert-butyl)phenyl)-1,3,4-oxadiazol-2-yl)oxy)hexan-2-yl)amino)benzamido)propanoic acid, (S)-3-(4-((1-((2',4'-dichloro-[1,1'-biphenyl]-4-yl) amino)-4-methyl-1-oxopentan-2-yl)amino)benzamido)propanoic acid, (S)-3-(4-((1-((4-(benzofuran-2-yl)phenyl)amino)-4-methyl-1-oxopentan-2-yl)amino)benzamido) propanoic acid and (S)-3-(4-((1-((4-(benzofuran-2-yl)phenyl)amino)-3-(4-fluorophenyl)-1-oxopropan-2-yl) amino)benzamido)propanoic acid.

8. A pharmaceutical composition comprising a compound or the pharmaceutically acceptable salt thereof of claim 1 or claim 6 and a pharmaceutically acceptable carrier.

9. A method for reducing the glycemic level in a subject, the method comprising administering to the subject in need thereof an effective amount of a compound or pharmaceutically acceptable salt of claim 1 or claim 6.

10. A method of alleviating disorders associated with glucagon, the method comprising administering to a subject in need thereof an effective amount of a compound or pharmaceutically acceptable salt of claim 1 or claim 6,
wherein the disorder is at least one of hyperglycemia, Type II diabetes, metabolic syndrome, impaired glucose tolerance, glucosuria, diabetic nephropathy, diabetic neuropathy, diabetic retinopathy, hyperinsulinemia, insulin resistance syndrome, cataracts, obesity dyslididemia, hypertension, and myocardial infarction.

* * * * *